United States Patent
Ammirante et al.

(10) Patent No.: US 11,873,283 B2
(45) Date of Patent: *Jan. 16, 2024

(54) SUBSTITUTED 3-((3-AMINOPHENYL)AMINO) PIPERIDINE-2,6-DIONE COMPOUNDS, COMPOSITIONS THEREOF, AND METHODS OF TREATMENT THEREWITH

(71) Applicant: Celgene Corporation, Summit, NJ (US)

(72) Inventors: Massimo Ammirante, San Diego, CA (US); Sogole Bahmanyar, Rancho Santa Fe, CA (US); Matthew D. Correa, San Diego, CA (US); Virginia Heather Sharron Grant, San Diego, CA (US); Joshua Hansen, San Diego, CA (US); Evan J. Horn, San Diego, CA (US); Timothy S. Kercher, Longmont, CO (US); Christopher Mayne, San Diego, CA (US); Mark A. Nagy, San Diego, CA (US); Rama Krishna Narla, San Diego, CA (US); Surendra Nayak, San Diego, CA (US); Stephen Norris, San Diego, CA (US); Patrick Papa, San Diego, CA (US); Veronique Plantevin-Krenitsky, San Francisco, CA (US); John J. Sapienza, San Diego, CA (US); Brandon W. Whitefield, San Diego, CA (US); Shuichan Xu, San Diego, CA (US)

(73) Assignee: Celgene Corporation, Summit, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/403,742

(22) Filed: Aug. 16, 2021

(65) Prior Publication Data

US 2023/0002321 A1 Jan. 5, 2023

Related U.S. Application Data

(62) Division of application No. 16/719,171, filed on Dec. 18, 2019, now Pat. No. 11,149,007.

(60) Provisional application No. 62/879,900, filed on Jul. 29, 2019, provisional application No. 62/782,298, filed on Dec. 19, 2018.

(51) Int. Cl.
    *C07D 211/94*     (2006.01)
    *C07D 233/30*     (2006.01)

(52) U.S. Cl.
    CPC .......... *C07D 211/94* (2013.01); *C07D 233/30* (2013.01)

(58) Field of Classification Search
    CPC .................................................. C07D 211/94
    See application file for complete search history.

(56) References Cited

U.S. PATENT DOCUMENTS

| | | | |
|---|---|---|---|
| 5,908,843 A | 6/1999 | Gante et al. | |
| 11,149,007 B2 * | 10/2021 | Ammirante | C07D 401/14 |
| 2008/0064876 A1 | 3/2008 | Muller et al. | |
| 2011/0306615 A1 | 12/2011 | Tachibana et al. | |
| 2013/0116269 A1 | 5/2013 | Ivachtchenko et al. | |
| 2014/0112922 A1 | 4/2014 | DeLisa et al. | |
| 2014/0356322 A1 | 12/2014 | Crews et al. | |
| 2015/0274738 A1 | 10/2015 | Gray et al. | |
| 2015/0291562 A1 | 10/2015 | Crew et al. | |
| 2016/0058872 A1 | 3/2016 | Crew et al. | |
| 2016/0096818 A1 | 4/2016 | Muller et al. | |
| 2016/0214972 A1 | 7/2016 | Jin et al. | |
| 2016/0272639 A1 | 9/2016 | Crew et al. | |
| 2017/0008904 A1 | 1/2017 | Crew et al. | |
| 2017/0065719 A1 | 3/2017 | Qian et al. | |
| 2018/0008587 A1 | 1/2018 | Bignan | |
| 2018/0085465 A1 | 3/2018 | Bradner et al. | |

(Continued)

FOREIGN PATENT DOCUMENTS

| | | |
|---|---|---|
| CN | 109422725 A | 3/2019 |
| CN | 109651256 A | 4/2019 |

(Continued)

OTHER PUBLICATIONS

Brinkmann et al., "Mechanisms of androgen receptor activation and function," J. Steroid *Biochem. Mol. Biol.*, 69:307-313 (1999).

(Continued)

*Primary Examiner* — Nizal S Chandrakumar
(74) *Attorney, Agent, or Firm* — Jones Day

(57) ABSTRACT

Provided herein are piperidine dione compounds having the following structure:

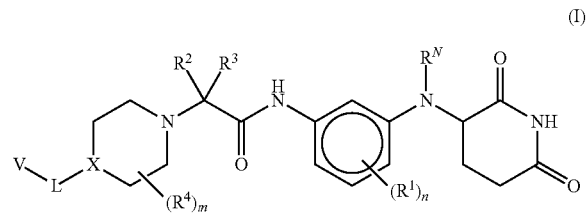

(I)

wherein $R^N$, $R^1$, $R^2$, $R^3$, $R^4$, L, V, m, and n are as defined herein, compositions comprising an effective amount of a piperidine dione compound, and methods for treating or preventing an androgen receptor mediated disease.

34 Claims, No Drawings

(56) References Cited

U.S. PATENT DOCUMENTS

| | | |
|---|---|---|
| 2018/0093990 A1 | 4/2018 | Gray et al. |
| 2018/0099940 A1 | 4/2018 | Crew et al. |
| 2018/0100001 A1 | 4/2018 | Verdine et al. |
| 2018/0179164 A1 | 6/2018 | Ivachtchenko et al. |
| 2018/0118733 A1 | 7/2018 | Harling et al. |
| 2018/0215731 A1 | 8/2018 | Crew et al. |
| 2018/0298021 A1 | 10/2018 | Bignan et al. |
| 2019/0071415 A1 | 3/2019 | Bradner et al. |
| 2019/0076542 A1 | 3/2019 | Phillips et al. |
| 2020/0199074 A1 | 6/2020 | Ammirante et al. |

FOREIGN PATENT DOCUMENTS

| | | |
|---|---|---|
| EP | 2894151 | 7/2015 |
| EP | 3897635 | 10/2021 |
| FR | 2768729 A1 | 3/1999 |
| FR | 2768728 A1 | 12/1999 |
| WO | WO 2007/044804 A2 | 4/2007 |
| WO | WO 2012/082837 A1 | 6/2012 |
| WO | WO 2014/120815 A1 | 8/2014 |
| WO | WO 2017/123542 | 7/2017 |
| WO | WO 2018/237026 A1 | 4/2018 |
| WO | WO 2018/089736 A1 | 5/2018 |
| WO | WO 2018/067764 A1 | 6/2018 |
| WO | WO 2018/098280 A1 | 12/2018 |
| WO | WO 2018/113584 A1 | 6/2019 |
| WO | WO 2019/106691 A1 | 6/2019 |
| WO | WO 2019/113006 A1 | 6/2019 |
| WO | WO 2019/228341 A1 | 12/2019 |

OTHER PUBLICATIONS

Chen et al., "Anti-androgens and androgen-depleting therapies in prostate cancer: new agents for an established target," *Lancet Oncol.*, 10:981-991 (2009).

Mills, Maintaining and reprogramming genomic androgen receptor activity in prostate cancer, *Nat. Rev. Cancer*, 14:187-198 (2014).

Murtha et al., "Androgen induction of a human prostate-specific kallikrein, hklk2: characterization of an androgen response element in the 5' promoter region of the gene," *Biochemistry*, 32:6459-6464 (1993).

Taplin, "Drug insight: role of the androgen receptor in the development and progression of prostate cancer," *Nat. Clin. Pract. Oncol.*, 4:236-244 (2007).

Tran et al., "Development of a second-generation antiandrogen for treatment of advanced prostate cancer," Science, 324:787-790 (2009).

Wirth et al., "Antiandrogens in the treatment of prostate cancer," *Eur. Urol.*, 51(2):306-313 (2007).

\* cited by examiner

SUBSTITUTED 3-((3-AMINOPHENYL)AMINO)PIPERIDINE-2,6-DIONE COMPOUNDS, COMPOSITIONS THEREOF, AND METHODS OF TREATMENT THEREWITH

RELATED APPLICATIONS

This application is a divisional of U.S. application Ser. No. 16/719,171, filed Dec. 18, 2019, which claims the benefit of U.S. Provisional Application Nos. 62/782,298, filed Dec. 19, 2018 and 62/879,900 filed Jul. 29, 2019, the disclosures of each of which are incorporated herein by reference in their entireties.

FIELD

Provided herein are certain 3-((3-aminophenyl)amino)piperidine-2,6-dione compounds, compositions comprising an effective amount of such compounds, and methods for treating or preventing androgen receptor mediated diseases, comprising administering an effective amount of such 3-((3-aminophenyl)amino)piperidine-2,6-dione compounds to a subject in need thereof. Also provided herein are the compounds and compositions for use in these methods.

BACKGROUND

Androgen receptor signaling is known to play a crucial role in the pathogenesis of prostate cancer and is involved in the development of other androgen receptor positive cancers (Chen Y et al., *Lancet Oncol*, 2009, 10:981-91; Mills I G, *Nat Rev Cancer*, 2014, 14:187-98; Taplin M E, *Nat Clin Pract Oncol*, 2007, 4:236-44; Wirth M P et al., *Eur Urol*, 2007, 51(2):306-13). The inhibition of androgen receptor signaling with anti-androgens that antagonize the androgen receptor has been used or proposed for the treatment of prostate cancer.

The androgen receptor normally resides in the cytoplasm bound to chaperones such as HSP90 (Brinkmann A O et al., *J Steroid Biochem Mol Biol*, 1999, 69:307-13). Upon binding of dihydrotestosterone (DHT) the androgen receptor changes its conformation and translocates to the nucleus, where it binds androgen responsive elements (AREs) driving the transcription of canonical targets such as KLK3 (also known as prostate specific antigen PSA), TMPRSS2 and KLK2 (Tran C et al., *Science*, 2009, 324:787-90; Murtha P et al., *Biochemistry* (Mosc.), 1993, 32:6459-64).

Prostate cancer (PCa) is one of the most frequently diagnosed non-cutaneous cancers among men in the US and is the second most common cause of cancer deaths with more than 200,000 new cases and over 30,000 deaths each year in the United States.

Androgen-deprivation therapy (ADT) is the standard of treatment for advanced PCa. Patients with advanced PCa undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

There remains a significant need for safe and effective methods of treating, preventing and managing AR mediated diseases, particularly for AR mediated diseases that are refractory to standard treatments, such as surgery, radiation therapy, chemotherapy and hormonal therapy, while reducing or avoiding the toxicities and/or side effects associated with conventional therapies.

Citation or identification of any reference in this section of this application is not to be construed as an admission that the reference is prior art to the present application.

SUMMARY

Provided herein are compounds having the following formula (I):

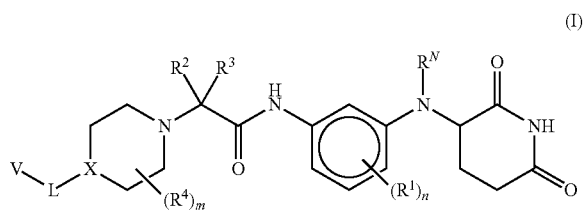

(I)

or a pharmaceutically acceptable salt, tautomer, isotopolog, or stereoisomer thereof, wherein $R^N$, $R^1$, $R^2$, $R^3$, $R^4$, X, L, V, m and n are as defined herein.

A compound of formula (I) or a pharmaceutically acceptable salt, tautomer, isotopolog, or stereoisomer thereof (each being referred to herein as a "Piperidine Dione Compound") is useful for treating or preventing androgen receptor mediated diseases in a subject.

In one aspect, provided herein are Piperidine Dione Compounds as described in the instant disclosure, such as, for example, in Table 1.

In one aspect, provided herein are pharmaceutical compositions comprising an effective amount of a compound as described herein, and a pharmaceutically acceptable carrier, excipient or vehicle. In one aspect, provided herein are pharmaceutical compositions comprising an effective amount of a Piperidine Dione Compound as described herein, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing androgen receptor mediated diseases in a subject, comprising administering to a subject in need thereof an effective amount of a compound as described herein; and a pharmaceutically acceptable carrier, excipient or vehicle. In one aspect, provided herein are methods for treating or preventing androgen receptor mediated diseases in a subject, comprising administering to a subject in need thereof an effective amount of a Piperidine Dione Compound as described herein; and a pharmaceutically acceptable carrier, excipient or vehicle. In another aspect, provided herein are compounds for use in methods of treatment of androgen receptor mediated diseases. In another aspect, provided herein are Piperidine Dione Compounds for use in methods of treatment of androgen receptor mediated diseases.

In another aspect provided herein are methods for preparing compounds as described herein. In another aspect provided herein are methods for preparing Piperidine Dione Compounds as described herein.

The present embodiments can be understood more fully by reference to the detailed description and examples, which are intended to exemplify non-limiting embodiments.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 carbon atoms. In some embodiments, the alkyl group is a saturated alkyl group. Representative saturated alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. In some embodiments, the alkyl group is an unsaturated alkyl group, also termed an alkenyl or alkynyl group. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C=C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); amino, alkylamino, cycloalkylamino, arylamino, heterocyclylamino, heteroarylamino, heterocycloalkylamino, cycloalkylalkylamino, aralkylamino, heterocyclylalkylamino, heteroaralkylamino, heterocycloalkylalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or —B(OH)2. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted. In some embodiments, the cycloalkyl group has 3 to 8 ring members, whereas in other embodiments the number of ring carbon atoms ranges from 3 to 5, 3 to 6, or 3 to 7. In some embodiments, the cycloalkyl groups are saturated cycloalkyl groups. Such saturated cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. In other embodiments, the cycloalkyl groups are unsaturated cycloalkyl groups. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d] oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups. A heteroaryl group can be substituted or unsubstituted.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

As used herein and unless otherwise specified, a "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopropylmethyl, cyclobutylmethyl, cyclopentylmethyl, cyclohexylmethyl, cyclopropylethyl, cyclobutylethyl, cyclopentylethyl, cyclohexylethyl, cyclopentylpropyl, cyclohexylpropyl and the like.

As used herein and unless otherwise specified, an "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and aralkyl groups wherein the aryl group is fused to a cycloalkyl group such as indan-4-yl ethyl.

As used herein and unless otherwise specified, a "heterocyclylalkyl" group is a radical of the formula: -alkyl-heterocyclyl, wherein alkyl and heterocyclyl are defined above. A "heteroarylalkyl" group is a radical of the formula: -alkyl-heteroaryl, wherein alkyl and heteroaryl are defined above. A "heterocycloalkylalkyl" group is a radical of the formula: -alkyl-heterocycloalkyl, wherein alkyl and heterocycloalkyl are defined above. Substituted heterocyclylalkyl groups may be substituted at the alkyl, the heterocyclyl, or both the alkyl and the heterocyclyl portions of the group. Representative heterocyclylalkyl groups include but are not limited to morpholin-4-yl ethyl, morpholin-4-yl propyl, furan-2-yl methyl, furan-3-yl methyl, pyridin-3-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —NH$_2$, —NH(R$^\#$), or —N(R$^\#$)$_2$, wherein each R$^\#$ is independently an alkyl, cycloalkyl, cycloalkylalkyl, aryl, aralkyl, heterocyclyl (e.g., heteroaryl or heterocycloalkyl), or heterocyclylalkyl (e.g., heteroarylalkyl or heterocycloalkylalkyl) group defined above, each of which is independently substituted or unsubstituted.

In one embodiment, an "amino" group is an "alkylamino" group, which is a radical of the formula: —NH-alkyl or —N(alkyl)$_2$, wherein each alkyl is independently defined above. The term "cycloalkylamino", "arylamino", "heterocyclylamino", "heteroarylamino", "heterocycloalkylamino", or the like, mirrors the above description for "alkylamino" where the term "alkyl" is replaced with "cycloalkyl", "aryl", "heterocyclyl", "heteroaryl", "heterocycloalkyl", or the like, respectively.

A "carboxy" group is a radical of the formula: —C(O)OH.

As used herein and unless otherwise specified, an "acyl" group is a radical of the formula: —C(O)(R$^\#$) or —C(O)H, wherein R$^\#$ is defined above. A "formyl" group is a radical of the formula: —C(O)H.

As used herein and unless otherwise specified, an "amido" group is a radical of the formula: —C(O)—NH$_2$, —C(O)—NH(R$^\#$), —C(O)—N(R$^\#$)$_2$, —NH—C(O)H, —NH—C(O)—(R$^\#$), —N(R$^\#$)—C(O)H, or —N(R$^\#$)—C(O)—(R$^\#$), wherein each R$^\#$ is independently defined above.

In one embodiment, an "amido" group is an "aminocarbonyl" group, which is a radical of the formula: —C(O)—NH$_2$, —C(O)—NH(R$^\#$), —C(O)—N(R$^\#$)$_2$, wherein each R$^\#$ is independently defined above.

In one embodiment, an "amido" group is an "acylamino" group, which is a radical of the formula: —NH—C(O)H, —NH—C(O)—(R$^\#$), —N(R$^\#$)—C(O)H, or —N(R$^\#$)—C(O)—(R$^\#$), wherein each R$^\#$ is independently defined above.

A "sulfonylamino" group is a radical of the formula: —NHSO$_2$(R$^\#$) or —N(alkyl)SO$_2$(R$^\#$), wherein each alkyl and R$^\#$ are defined above.

A "urea" group is a radical of the formula: —N(alkyl)C(O)N(R$^\#$)$_2$, —N(alkyl)C(O)NH(R$^\#$), —N(alkyl)C(O)NH$_2$, —NHC(O)N(R$^\#$)$_2$, —NHC(O)NH(R$^\#$), or —NH(CO)NH$_2$, wherein each alkyl and R$^\#$ are independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, the term "Piperidine Dione Compound" refers to compounds of formula (I) as well as to further embodiments provided herein. In one embodiment, an "Piperidine Dione Compound" is a compound set forth in Table 1. The term "Piperidine Dione Compound" includes pharmaceutically acceptable salts, tautomers, isotopologues, and stereoisomers of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride formic, and mesylate salts. Others are well known in the art, see for example, *Remington's Pharmaceutical Sciences*, 18$^{th}$ eds., Mack Publishing, Easton PA (1990) or *Remington: The Science and Practice of Pharmacy*, 19$^{th}$ eds., Mack Publishing, Easton PA (1995).

As used herein and unless otherwise indicated, the term "stereoisomer" or "stereoisomerically pure" means one stereoisomer of a Piperidine Dione Compound that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Piperidine Dione Compounds can have chiral centers and can occur as racemates, individual enantiomers or diastereomers, and mixtures thereof. All such isomeric forms are included within the embodiments disclosed herein, including mixtures thereof.

The use of stereoisomerically pure forms of such Piperidine Dione Compounds, as well as the use of mixtures of those forms, are encompassed by the embodiments disclosed herein. For example, mixtures comprising equal or unequal amounts of the enantiomers of a particular Piperidine Dione Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); Wilen, S.

H., *Tables of Resolving Agents and Optical Resolutions* p. 268 (E. L. Eliel, Ed., Univ. of Notre Dame Press, Notre Dame, IN, 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

It should also be noted the Piperidine Dione Compounds can include E and Z isomers, or a mixture thereof, and cis and trans isomers or a mixture thereof. In certain embodiments, the Piperidine Dione Compounds are isolated as either the E or Z isomer. In other embodiments, the Piperidine Dione Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

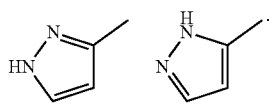

As readily understood by one skilled in the art, a wide variety of functional groups and other structures may exhibit tautomerism and all tautomers of compounds of formula (I) are within the scope of the present invention.

It should also be noted the Piperidine Dione Compounds can contain unnatural proportions of atomic isotopes at one or more of the atoms. For example, the compounds may be radiolabeled with radioactive isotopes, such as for example tritium (H), iodine-125 ($^{125}$I) sulfur-35 ($^{35}$S), or carbon-14 ($^{14}$C), or may be isotopically enriched, such as with deuterium (2H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the Piperidine Dione Compounds as described herein, whether radioactive or not, are intended to be encompassed within the scope of the embodiments provided herein. In some embodiments, there are provided isotopologues of the Piperidine Dione Compounds, for example, the isotopologues are deuterium, carbon-13, and/or nitrogen-15 enriched Piperidine Dione Compounds. As used herein, "deuterated", means a compound wherein at least one hydrogen (H) has been replaced by deuterium (indicated by D or $^2$H), that is, the compound is enriched in deuterium in at least one position.

It is understood that, independently of stereoisomerical or isotopic composition, each Piperidine Dione Compound referred to herein can be provided in the form of any of the pharmaceutically acceptable salts discussed herein. Equally, it is understood that the isotopic composition may vary independently from the stereoisomerical composition of each Piperidine Dione Compound referred to herein. Further, the isotopic composition, while being restricted to those elements present in the respective Piperidine Dione Compound or salt thereof, may otherwise vary independently from the selection of the pharmaceutically acceptable salt of the respective Piperidine Dione Compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is an androgen receptor mediated disease, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is an androgen receptor mediated disease, as described herein, or symptoms thereof.

The term "effective amount" in connection with a Piperidine Dione Compound means an amount capable of treating or preventing a disorder, disease or condition, or symptoms thereof, disclosed herein.

The terms "subject" and "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having an androgen receptor mediated disease, or a symptom thereof.

The term "androgen receptor" or "AR" or "NR3C4" as used herein refers to a nuclear hormone receptor activated by binding of the androgenic hormones, including testosterone or dihydrotestosterone. The term "androgen receptor" may refer to the nucleotide sequence or protein sequence of human androgen receptor (e.g., Entrez 367, Uniprot P10275, RefSeq NM_000044, or RefSeq NP_000035).

The term "AR-full length" (AR-FL) as used herein refers to AR protein that contains all four functional domains, including the N-terminal transactivation domain (NTD, exon 1), the DNA-binding domain (DBD, exons 2-3), the hinge domain (exon 4), and the C-terminal ligand binding domain (LBD, exons 4-8).

The term "castration resistant prostate cancer" (CRPC) refers to advanced prostate cancer that is worsening or progressing while the patient remains on androgen deprivation therapy or other therapies to reduce testosterone, or prostate cancer which is considered hormone refractory, hormone naive, androgen independent or chemical or surgical castration resistant. Castration resistant prostate cancer (CRPC) is an advanced prostate cancer that developed despite ongoing ADT and/or surgical castration. Castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix or abarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometriq®, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

Piperidine Dione Compounds

Provided herein are compounds having the following formula (I):

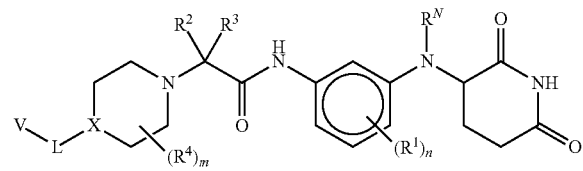

or a pharmaceutically acceptable salt, tautomer, isotopolog, or stereoisomer thereof,
wherein:
$R^N$ is H;
each $R^1$ is independently selected from halogen, CN, and $C_{1-3}$ alkyl;
$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
X is N;
L is —O($C_{1-6}$ alkyl)- or —($C_{1-9}$ alkyl)-;
n is 0-4;
m is 0-8;
V is

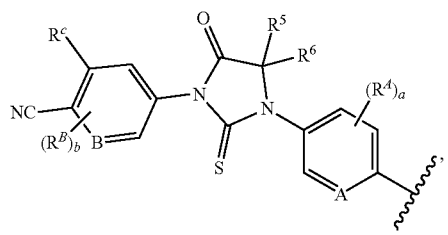

wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3; and
b is 0-2.

Provided herein are compounds having the following formula (I):

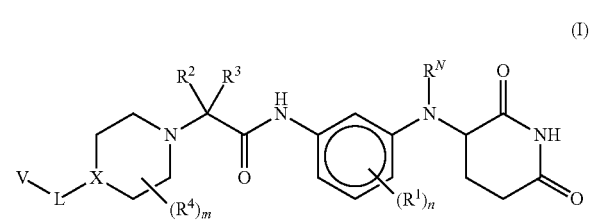

or a pharmaceutically acceptable salt, tautomer, isotopolog, or stereoisomer thereof,
wherein:
$R^N$ is H;
each $R^1$ is independently selected from halogen, CN, and $C_{1-3}$ alkyl;
$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
X is N;
L is —O($CH_2$)$_p$— or —($CH_2$)$_p$—;
n is 0-4;
m is 0-8;
p is 1-3;
V is

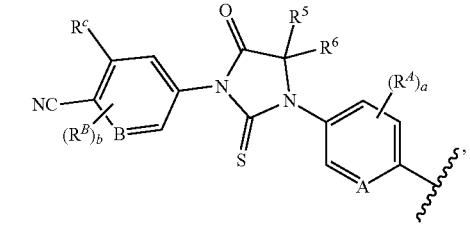

wherein
A is N, CH, or CR$^A$;
B is N, CH, or CR$^B$;
each R$^A$ is independently selected from halogen, substituted or unsubstituted C$_{1-6}$ alkyl, and substituted or unsubstituted C$_{3-6}$ cycloalkyl;
each R$^B$ is independently selected from halogen, and substituted or unsubstituted C$_{1-6}$ alkyl;
R$^C$ is halogen or CF$_3$;
R$^5$ and R$^6$ are C$_{1-3}$ alkyl, or R$^5$ and R$^6$, together with the carbon atom to which they are attached, form a substituted or unsubstituted C$_{3-5}$ cycloalkyl or a 3-5 membered heterocyclyl;
a is 0-3; and
b is 0-2.

In one embodiment of a compound of formula (I), the compound is

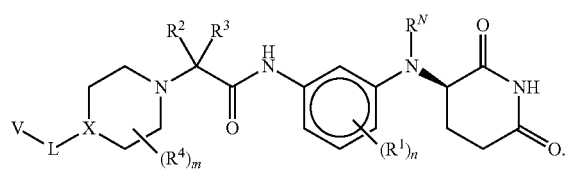

(IIa)

In another embodiment of a compound of formula (I), the compound is

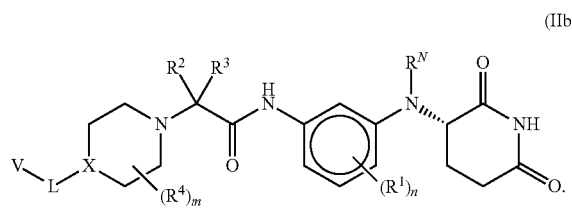

(IIb)

In some embodiments of compounds of formula (I), (IIa) and (IIb), each R$^1$ is independently selected from halogen, and C$_{1-3}$ alkyl. In some embodiments of compounds of formula (I), (IIa) and (IIb), each R$^1$ is independently selected from Cl, F, Br, CN, —CH$_3$, —CH$_2$CH$_3$, and isopropyl. In other embodiments, each R$^1$ is independently selected from Cl, F, CN, and —CH$_3$. In some other embodiments, each R$^1$ is independently selected from Cl, F, and CN.

In some embodiments of compounds of formula (I), n is 0. In other embodiments, n is 1 or 2.

In some embodiments of compounds of formula (I), the compound is

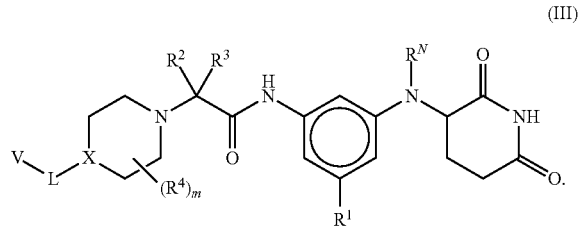

(III)

In other embodiments of compounds of formula (I), the compound is

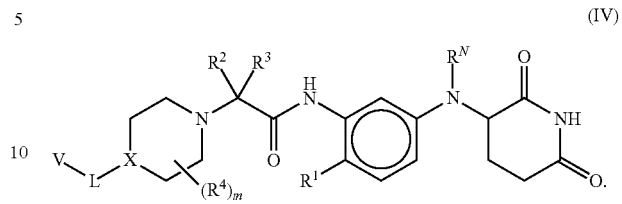

(IV)

In still other embodiments of compounds of formula (I), the compound is

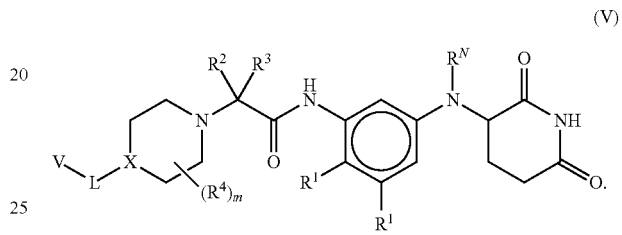

(V)

In some embodiments, the compound is a compound of formula (III), (IV) or (V), wherein each R$^1$ is independently selected from Cl, F, CN, and CH$_3$. In some such embodiments, the compound is a compound of formula (III), (IV) or (V), wherein R$^1$ is F or Cl. In some embodiments of compounds of formula (III), R$^1$ is F, Cl, or CN. In some embodiments of compounds of formula (IV), R$^1$ is F.

In some embodiments of compounds of formula (I), R$^2$ and R$^3$ are each independently selected from H, substituted or unsubstituted methyl, and ethyl, or R$^2$ and R$^3$ and the carbon to which they are attached form a substituted or unsubstituted cyclopropyl, cyclobutyl or cyclopentyl. In some such embodiments, R$^2$ and R$^3$ are each independently selected from H and methyl, or R$^2$ and R$^3$ and the carbon to which they are attached form an unsubstituted cyclopropyl. In some other embodiments, R$^2$ and R$^3$ are both H or methyl, or R$^2$ and R$^3$ and the carbon to which they are attached form an unsubstituted cyclopropyl. In some embodiments, R$^2$ and R$^3$ are H.

In some embodiments of compounds of formula (I), each R$^4$ is independently selected from substituted or unsubstituted methyl and ethyl, or two R$^4$ groups, together with the same carbon atom to which they are attached, form a substituted or unsubstituted cyclopropyl or cyclobutyl. In some embodiments, each R$^4$ is independently substituted or unsubstituted methyl, or two R$^4$ groups, together with the same carbon atom to which they are attached, form an unsubstituted cyclopropyl. In yet other embodiments, each R$^4$ is independently selected from methyl, CF$_3$, and CH$_2$OH, or two R$^4$ groups, together with the same carbon atom to which they are attached, form an unsubstituted cyclopropyl. In still other embodiments, R$^4$ is methyl. In some embodiments, R$^4$ is ethyl.

In some embodiments of compounds of formula (I), m is 0, 1, 2, 3 or 4. In some embodiments, m is 0, 1, or 2.

In some embodiments of compounds of formula (I), two R$^4$ groups together with the non-adjacent carbon atoms to which they are attached form an unsubstituted 4-7-membered heterocyclyl. In some such embodiments, the compound is

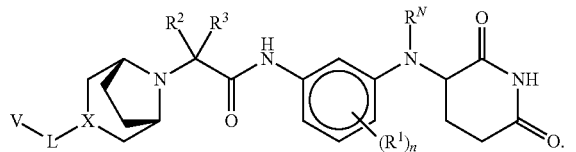

(VI)

In some such embodiments, the compound is

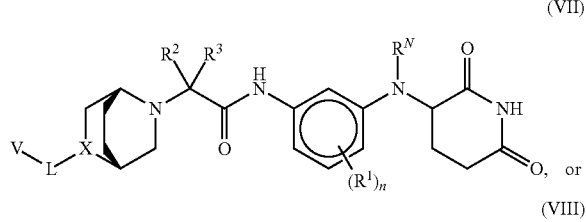

(VII)

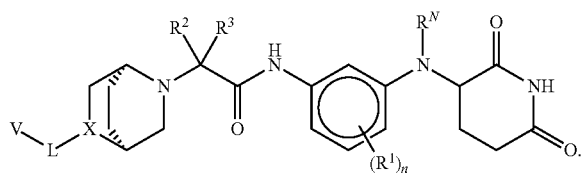

(VIII)

In some embodiments, the compound is

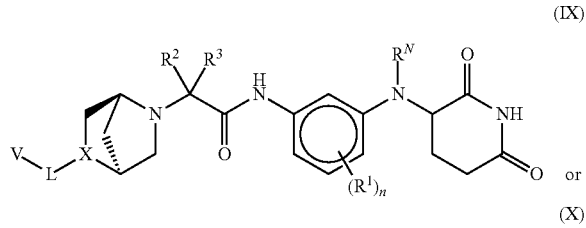

(IX)

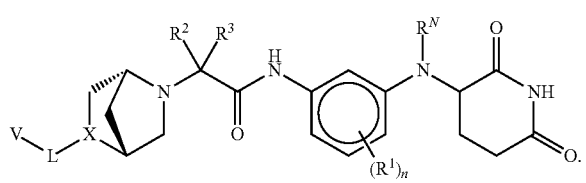

(X)

In some embodiments of compounds of formula (I), (IIa), (IIb), (III), (IV), (V), (VI), (VII), (VIII), (IX), and (X), exemplary L groups include, but are not limited to, —O(CH$_2$)(CH$_2$)—, —O(CH$_2$)(CH(CH$_3$))—, —O(CH$_2$)(C(CH$_3$)$_2$)—, —O(CH(CH$_3$))(CH$_2$)—, —O(C(CH$_3$)$_2$)(CH$_2$)—, —O(CH(CH$_3$))(CH(CH$_3$))—, —O(CH(CH$_3$))(C(CH$_3$)$_2$)—, —O(C(CH$_3$)$_2$)(CH(CH$_3$))—, —(CH$_2$)—, —(CH$_2$)(CH$_2$)—, —(CH$_2$)(CH$_2$)(CH$_2$)—, —(C(CH$_3$)$_2$)(C(CH$_3$)$_2$)—, —(CH(CH$_3$))—, —(C(CH$_3$)$_2$)—, —(CH(CH$_3$))(CH(CH$_3$))—, —(CH(CH$_3$))(C(CH$_3$)$_2$)—, —(C(CH$_3$)$_2$)(CH(CH$_3$))—, —(C(CH$_3$)$_2$)(C(CH$_3$)$_2$)—, —(CH$_3$)(CH$_3$)(CH(CH$_3$))—, —(CH$_2$)(CH(CH$_3$))(CH$_2$)—, —(CH(CH$_3$))(CH$_2$)(CH$_2$)—, —(CH$_2$)(CH$_2$)(C(CH$_2$)$_2$)—, —(CH$_2$)(C(CH$_2$)$_2$)(CH$_2$)—, —(C(CH$_2$)$_2$)(CH$_2$)(CH$_2$)—, —(CH$_2$)(CH(CH$_3$))(CH(CH$_3$))—, —(CH(CH$_3$))(CH(CH$_3$))(CH$_2$)—, —(CH(CH$_3$))(CH$_2$)(CH(CH$_3$))—, —(CH$_2$)(CH(CH$_3$))(C(CH$_3$)$_2$)—, —(CH(CH$_3$))(CH$_2$)(C(CH$_2$)$_2$)—, —(C(CH$_3$)$_2$)(CH$_2$)(C(CH$_3$)$_2$)—, —(CH$_2$)(C(CH$_3$)$_2$)(C(CH$_3$)$_2$)—, —(CH$_2$)(C(CH$_3$)$_2$)(CH(CH$_3$))—, —(CH(CH$_3$)(C(CH$_3$)$_2$)(CH$_2$)—, —(C(CH$_3$)$_2$)(CH(CH$_3$))(CH$_2$)—, —(C(CH$_3$)$_2$)(CH(CH$_3$))—, —(CH(CH$_3$)(C(CH$_3$)$_2$)(CH$_2$)—, —(C(CH$_3$)$_2$)(CH(CH$_3$))(CH$_2$)—, —(C(CH$_3$)$_2$)(CH(CH$_3$))—, —(C(CH$_3$))(CH(CH$_3$))(CH$_2$)—, —(CH(CH$_3$))(C(CH$_3$)$_2$)(CH$_2$)—, —(C(CH$_3$)$_2$)(CH$_2$)(CH(CH$_3$))—, —(CH(CH$_3$))(CH$_2$)(C(CH$_3$)$_2$)—, —(C(CH$_3$)$_2$)(C(CH$_3$)$_2$)(CH(CH$_3$))—, —(CH$_3$)(CH$_3$)(CH(CH$_3$))—, —(CH$_2$)(CH(CH$_3$))(CH$_2$)—, —(CH(CH$_3$))(CH$_2$)—, —(C(CH$_3$)$_2$)(CH$_2$)(CH$_2$)—, —(CH$_2$)(C(CH$_3$)$_2$)(CH$_2$)—, —(CH$_2$)(C(CH$_3$)$_2$)(C(CH$_3$)$_2$)—, —(CH$_2$)(C(CH$_3$)$_2$)(CH(CH$_3$))—, —(CH(CH$_3$)(C(CH$_3$)$_2$)(CH$_2$)—, —(C(CH$_3$)$_2$)(CH(CH$_3$))(CH$_2$)—, —(C(CH$_3$)$_2$)(CH(CH$_3$))—, —(C(CH$_3$)$_2$)(CH(CH$_3$))(CH(CH$_3$))—, and —(C(CH$_3$)$_2$)(C(CH$_3$)$_2$)—.

In some embodiments of compounds of formula (I), L is —O(CH$_2$)(CH$_2$)—, —O(CH$_2$)(CH(CH$_3$))—, —O(CH$_2$)(C(CH$_3$)$_2$)—, —O(CH(CH$_3$))(CH$_2$)—, O(CH(CH$_3$))(CH(CH$_3$))—, —O(CH(CH$_3$)(C(CH$_3$)$_2$)—, —O(C(CH$_3$)$_2$)(CH$_2$)—, —(CH$_2$)—, —(CH$_2$)(CH$_2$)—, or —(CH$_2$)(CH$_2$)(CH$_2$)—. In some embodiments of compounds of formula (I), L is —O(CH$_2$)(CH$_2$)—, —(CH$_2$)—, —(CH$_2$)(CH$_2$)—, or —(CH$_2$)(CH$_2$)(CH$_2$)—. In other embodiments, L is —O(CH$_2$)(CH$_2$)—, or —(CH$_2$)(CH$_2$)(CH$_2$)—. In still other embodiments, L is —O(CH$_2$)(CH$_2$)—. In some embodiments of compounds of formula (I), L is —O(CH$_2$)(CH$_2$)—, —O(CH$_2$)(CH(CH$_3$))—, —O(CH(CH$_3$))(CH$_2$)—, or —(CH$_2$)(CH$_2$)(CH$_2$)—.

In some embodiments of compounds of formula (I), A is CH. In some other embodiments of compounds of formula (I), B is CH. In some other embodiments, B is N.

In some embodiments of compounds of formula (I), a is 0, 1 or 2.

In some embodiments of compounds of formula (I), each $R^A$ is independently selected from Cl, Br, F, methyl, ethyl, n-propyl, isopropyl, n-butyl, isobutyl, sec-butyl, tert-butyl, n-pentyl, CH$_2$CH$_2$CH(CH$_3$)$_2$, CH(CH$_3$)CH(CH$_3$)$_2$, CF$_3$, CF(CH$_3$)$_2$, CF$_2$CH$_3$, CH$_2$CH$_2$F, CH$_2$CHF$_2$, CH$_2$CF$_3$, CH$_2$OH, CH(CH$_3$)OH, CH$_2$CH$_2$OH, CH(CH$_3$)CH$_2$OH, CH$_2$CH(CH$_3$)OH, cyclopropyl, cyclobutyl, and cyclopentyl. In some such embodiments, each $R^A$ is independently selected from Cl, Br, F, methyl, ethyl, n-propyl, isopropyl, isobutyl, sec-butyl, CF$_3$, CF$_2$CH$_3$, CH$_2$CH$_2$F, CH$_2$CHF$_2$, CH$_2$OH, CH(CH$_3$)OH, cyclopropyl, cyclobutyl, and cyclopentyl. In some embodiments wherein B is CH, each $R^A$ is independently selected from Cl, Br, F, methyl, ethyl, n-propyl, isopropyl, isobutyl, sec-butyl, CF$_3$, CF$_2$CH$_3$, CH$_2$CH$_2$F, CH$_2$CHF$_2$, cyclopropyl, cyclobutyl, and cyclopentyl. In other embodiments, wherein B is N, each $R^A$ is independently selected from Cl, F, methyl, ethyl, n-propyl, isopropyl, sec-butyl, CF$_2$CH$_3$, CH$_2$CH$_2$F, CH$_2$CHF$_2$, CH$_2$OH, CH(CH$_3$)OH, cyclopropyl, and cyclobutyl. In some such embodiments, each $R^A$ is independently selected from ethyl, isopropyl and cyclopropyl.

In some embodiments of compounds of formula (I), b is 0 or 1. In some embodiments of compounds of formula (I), $R^B$ is methyl. In some embodiments of compounds of formula (I), $R^C$ is CF$_3$ or Cl.

In some embodiments of compounds of formula (I), $R^5$ and $R^6$ are methyl, or $R^5$ and $R^6$, together with the carbon atom to which they are attached, form a cyclopropyl, cyclobutyl, tetrahydrofuranyl, or tetrahydropyranyl. In some embodiments, $R^5$ and $R^6$ are methyl, or $R^5$ and $R^6$, together with the carbon atom to which they are attached, form a cyclobutyl, or tetrahydrofuranyl. In some embodiments, $R^5$ and $R^6$ are methyl, or $R^5$ and $R^6$, together with the carbon atom to which they are attached, form a cyclobutyl, cyclopentyl, cyclohexyl, or tetrahydrofuranyl.

In some embodiments of compounds of formula (III), (IV) or (V), each $R^1$ is independently selected from Cl, F, CN, and CH$_3$, and $R^2$ and $R^3$ are H. In some such embodiments, each $R^4$ is independently selected from methyl, CF$_3$, and CH$_2$OH, or two R$^4$ groups, together with the same carbon atom to which they are attached, form an unsubstituted cyclopropyl. In some such embodiments, R$^4$ is methyl. In some such embodiments, R$^4$ is ethyl. In some other such embodiments, L is —O(CH$_2$)(CH$_2$)—, or —(CH$_2$)(CH$_2$)(CH$_2$)—. In some other such embodiments, L is —O(CH$_2$)(CH(CH$_3$))—, —O(CH(CH$_3$))(CH$_2$)—. In still other such embodiments, A is CH. In yet other such embodiments, B is CH, and each R$^A$ is independently selected from Cl, Br, F, methyl, ethyl, n-propyl, isopropyl, isobutyl, sec-butyl, CF$_3$, CF$_2$CH$_3$, CH$_2$CH$_2$F, CH$_2$CHF$_2$, cyclopropyl, cyclobutyl, and cyclopentyl. In other such embodiments, B is N, and each R$^A$ is independently selected from Cl, F, methyl, ethyl, n-propyl, isopropyl, sec-butyl, CF$_2$CH$_3$, CH$_2$CH$_2$F, CH$_2$CHF$_2$, CH$_2$OH, CH(CH$_3$)OH, and cyclopropyl. In some other such embodiments, each R$^A$ is ethyl, isopropyl or cyclopropyl. In still other such embodiments, R$^5$ and R$^6$ are methyl, or R$^5$ and R$^6$, together with the carbon atom to which they are attached, form a cyclobutyl, or tetrahydrofuranyl. In some embodiments, R$^5$ and R$^6$ are methyl, or R$^5$ and R$^6$, together with the carbon atom to which they are attached, form a cyclobutyl, cyclopentyl, cyclohexyl, or tetrahydrofuranyl.

In some embodiments of compounds of formula (I), (IIa), and (IIb),

R$^N$ is H;

each R$^1$ is independently selected from Cl, F, Br, CN, —CH$_3$, —CH$_2$CH$_3$, and isopropyl;

R$^2$ and R$^3$ are each independently selected from H, substituted or unsubstituted methyl and ethyl, or R$^2$ and R$^3$ and the carbon to which they are attached form a substituted or unsubstituted cyclopropyl, cyclobutyl or cyclopentyl;

each R$^4$ is independently selected from substituted or unsubstituted methyl or ethyl, or two R$^4$ groups, together with the same carbon atom or adjacent carbon atoms to which they are attached, form a substituted or unsubstituted cyclopropyl or cyclobutyl, or two R$^4$ groups together with the non-adjacent carbon atoms to which they are attached form a substituted or unsubstituted 4-7-membered heterocyclyl;

X is N;

L is —O(C$_{1-5}$ alkyl)- or —(C$_{1-5}$ alkyl)-;

n is 0-4;

m is 0-2;

V is

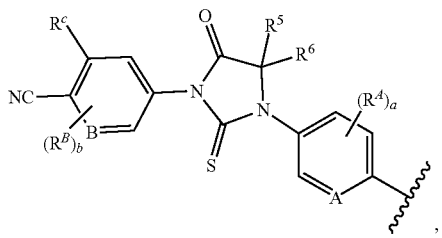

wherein

A is N, CH, or CR$^A$;

B is N, CH, or CR$^B$;

each R$^A$ is independently selected from Cl, Br, F, methyl, ethyl, n-propyl, isopropyl, n-butyl, isobutyl, sec-butyl, tert-butyl, n-pentyl, CH$_2$CH$_2$CH(CH$_3$)$_2$, CH(CH$_3$)CH(CH$_3$)$_2$, CF$_3$, CF$_2$CH$_3$, CH$_2$CH$_2$F, CH$_2$CHF$_2$, CH$_2$CF$_3$, CH$_2$OH, CH(CH$_3$)OH, CH$_2$CH$_2$OH, CH(CH$_3$)CH$_2$OH, CH$_2$CH(CH$_3$)OH, cyclopropyl, cyclobutyl, and cyclopentyl; each R$^B$ is independently selected from halogen, and methyl;

R$^C$ is halogen or CF$_3$;

R$^5$ and R$^6$ are methyl, or R$^5$ and R$^6$, together with the carbon atom to which they are attached, form a substituted or unsubstituted cyclobutyl, cyclopentyl, cyclohexyl, or tetrahydrofuranyl;

a is 0-3; and b is 0-2.

In some embodiments of compounds of formula (I), (IIa), and (IIb),

R$^N$ is H;

each R$^1$ is independently selected from Cl, F, Br, CN, —CH$_3$, —CH$_2$CH$_3$, and isopropyl;

R$^2$ and R$^3$ are each independently selected from H, substituted or unsubstituted methyl and ethyl, or R$^2$ and R$^3$ and the carbon to which they are attached form a substituted or unsubstituted cyclopropyl, cyclobutyl or cyclopentyl;

each R$^4$ is independently selected from substituted or unsubstituted methyl or ethyl, or two R$^4$ groups, together with the same carbon atom or adjacent carbon atoms to which they are attached, form a substituted or unsubstituted cyclopropyl or cyclobutyl, or two R$^4$ groups together with the non-adjacent carbon atoms to which they are attached form a substituted or unsubstituted 4-7-membered heterocyclyl;

X is N;

L is —O(CH$_2$)$_p$— or —(CH$_2$)$_p$—;

n is 0-4;

m is 0-2;

p is 1-3;

V is

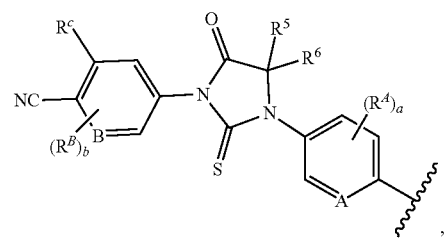

wherein

A is N, CH, or CR$^A$;

B is N, CH, or CR$^B$;

each R$^A$ is independently selected from Cl, Br, F, methyl, ethyl, n-propyl, isopropyl, n-butyl, isobutyl, sec-butyl, tert-butyl, n-pentyl, CH$_2$CH$_2$CH(CH$_3$)$_2$, CH(CH$_3$)CH(CH$_3$)$_2$, CF$_3$, CF$_2$CH$_3$, CH$_2$CH$_2$F, CH$_2$CHF$_2$, CH$_2$CF$_3$, CH$_2$OH, CH(CH$_3$)OH, CH$_2$CH$_2$OH, CH(CH$_3$)CH$_2$OH, CH$_2$CH(CH$_3$)OH, cyclopropyl, cyclobutyl, and cyclopentyl;

each R$^B$ is independently selected from halogen, and methyl;

R$^C$ is halogen or CF$_3$;

R$^5$ and R$^6$ are methyl, or R$^5$ and R$^6$, together with the carbon atom to which they are attached, form a substituted or unsubstituted cyclobutyl, or tetrahydrofuranyl;

a is 0-3; and b is 0-2.

In some embodiments of compounds of formula (III), (IV) and (V), $R^N$ is H;

each $R^1$ is independently selected from Cl, F, Br, CN, —CH$_3$, —CH$_2$CH$_3$, and isopropyl;

$R^2$ and $R^3$ are each independently selected from H, substituted or unsubstituted methyl and ethyl, or $R^2$ and $R^3$ and the carbon to which they are attached form a substituted or unsubstituted cyclopropyl, cyclobutyl or cyclopentyl;

each $R^4$ is independently selected from substituted or unsubstituted methyl or ethyl, or two $R^4$ groups, together with the same carbon atom or adjacent carbon atoms to which they are attached, form a substituted or unsubstituted cyclopropyl or cyclobutyl, or two $R^4$ groups together with the non-adjacent carbon atoms to which they are attached form a substituted or unsubstituted 4-7-membered heterocyclyl;

X is N;

L is —O(C$_{1-5}$ alkyl)- or —(C$_{1-5}$ alkyl)-;

n is 0-4;

m is 0, 1 or 2;

V is

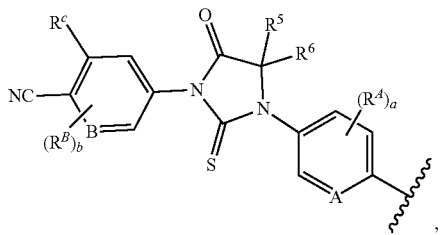

wherein

A is N, CH, or CR$^A$;

B is N, CH, or CR$^B$;

each $R^A$ is independently selected from Cl, Br, F, methyl, ethyl, n-propyl, isopropyl, n-butyl, isobutyl, sec-butyl, tert-butyl, n-pentyl, CH$_2$CH$_2$CH(CH$_3$)$_2$, CH(CH$_3$)CH(CH$_3$)$_2$, CF$_3$, CF$_2$CH$_3$, CH$_2$CH$_2$F, CH$_2$CHF$_2$, CH$_2$CF$_3$, CH$_2$OH, CH(CH$_3$)OH, CH$_2$CH$_2$OH, CH(CH$_3$)CH$_2$OH, CH$_2$CH(CH$_3$)OH, cyclopropyl, cyclobutyl, and cyclopentyl;

each $R^B$ is independently selected from halogen, and methyl;

$R^C$ is halogen or CF$_3$;

$R^5$ and $R^6$ are methyl, or $R^5$ and $R^6$, together with the carbon atom to which they are attached, form a substituted or unsubstituted cyclobutyl, cyclopentyl, cyclohexyl, or tetrahydrofuranyl;

a is 0-3; and b is 0-2.

In some embodiments of compounds of formula (III), (IV) and (V), $R^N$ is H;

each $R^1$ is independently selected from Cl, F, Br, CN, —CH$_3$, —CH$_2$CH$_3$, and isopropyl;

$R^2$ and $R^3$ are each independently selected from H, substituted or unsubstituted methyl and ethyl, or $R^2$ and $R^3$ and the carbon to which they are attached form a substituted or unsubstituted cyclopropyl, cyclobutyl or cyclopentyl;

each $R^4$ is independently selected from substituted or unsubstituted methyl or ethyl, or two $R^4$ groups, together with the same carbon atom or adjacent carbon atoms to which they are attached, form a substituted or unsubstituted cyclopropyl or cyclobutyl, or two $R^4$ groups together with the non-adjacent carbon atoms to which they are attached form a substituted or unsubstituted 4-7-membered heterocycle;

X is N;

L is —O(CH$_2$)$_p$— or —(CH$_2$)$_p$—;

n is 0-4;

m is 0, 1 or 2;

p is 1-3;

V is

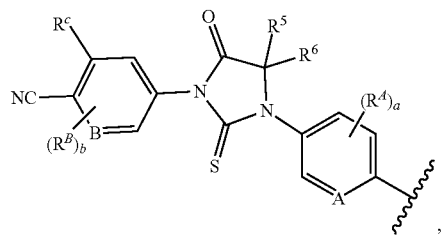

wherein

A is N, CH, or CR$^A$;

B is N, CH, or CR$^B$;

each $R^A$ is independently selected from Cl, Br, F, methyl, ethyl, n-propyl, isopropyl, n-butyl, isobutyl, sec-butyl, tert-butyl, n-pentyl, CH$_2$CH$_2$CH(CH$_3$)$_2$, CH(CH$_3$)CH(CH$_3$)$_2$, CF$_3$, CF$_2$CH$_3$, CH$_2$CH$_2$F, CH$_2$CHF$_2$, CH$_2$CF$_3$, CH$_2$OH, CH(CH$_3$)OH, CH$_2$CH$_2$OH, CH(CH$_3$)CH$_2$OH, CH$_2$CH(CH$_3$)OH, cyclopropyl, cyclobutyl, and cyclopentyl;

each $R^B$ is independently selected from halogen, and methyl;

$R^C$ is halogen or CF$_3$;

$R^5$ and $R^6$ are methyl, or $R^5$ and $R^6$, together with the carbon atom to which they are attached, form a substituted or unsubstituted cyclobutyl, or tetrahydrofuranyl;

a is 0-3; and b is 0-2.

Further embodiments provided herein include any combination of one or more of the particular embodiments set forth above.

In some embodiments of compounds of formula (I), the compound is a compound from Table 1.

Representative compounds of formula (I), (II), (III), (IV), (V), (VI), (VII), (VIII), (IX) or (X) are set forth in Table 1.

Piperidine Dione Compounds set forth in Table 1 were tested in the AR mediated assays described herein and were found to have activity therein. In one embodiment, the Piperidine Dione Compound is a compound as described herein, wherein the compound at a concentration of 1 μM leads to degradation of AR protein, by at least about 50% or more.

Methods for Making Piperidine Dione Compounds

The Piperidine Dione Compounds described herein can be made using conventional organic syntheses and commercially available starting materials, or the methods provided herein. By way of example and not limitation, Piperidine Dione Compounds of formula (I), wherein $R^N$, $R^1$, $R^2$, $R^3$, $R^4$, $R^5$, $R^6$, $R^A$, $R^B$, $R^c$, L, V, X, n, m, p, a and b are as defined herein, can be prepared as outlined in Schemes 1 to 8 shown below, as well as in the examples set forth herein. It should be noted that one skilled in the art would know how to modify the procedures set forth in the illustrative schemes and examples to arrive at the desired products.

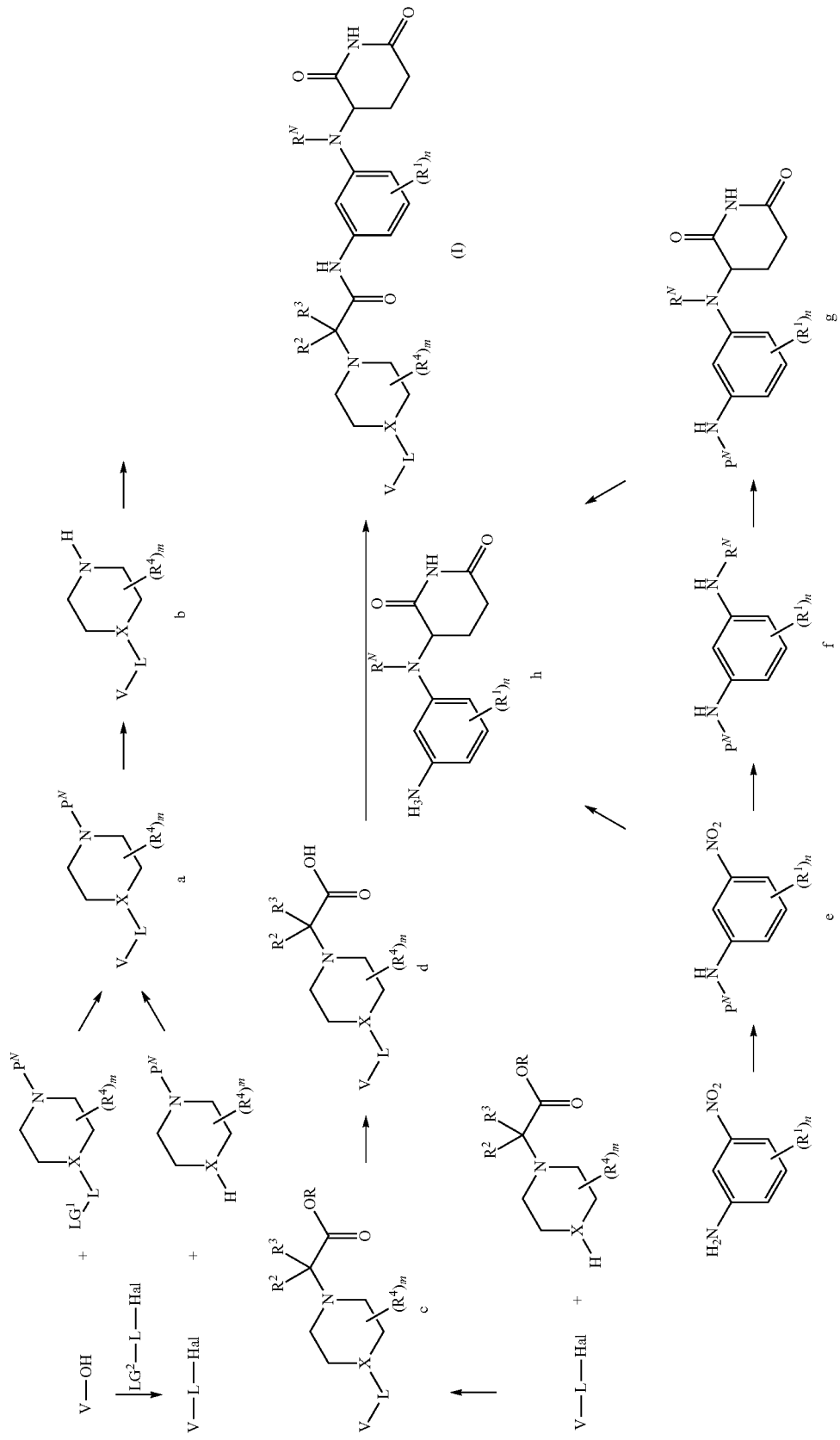

As shown in Scheme 1, Piperidine Dione Compounds of formula (I), wherein L is —O(C$_{1-6}$ alkyl)-, can be prepared starting by reacting the phenol (A is CH or CR$^4$) or pyridinone (A is N) derivative V—OH with the appropriately derivatized and N-protected piperazinyl (for example, wherein P$^N$ is Boc and the leaving group LG$^1$ is Br, Cl, OTs, or OMs), in the presence of a base, in a solvent (for example, CsCO$_3$ in DMF, or K$_2$CO$_3$ in acetonitrile), at elevated temperature (for example, between about 40° C. and about 70° C.) to provide intermediate a. Alternatively, when LG$^1$ is —OH, V—OH is treated under Mitsunobu conditions (for example, with PPh$_3$ and DIAD or DEAD, in a solvent such as THF, at room temperature) to provide intermediate a. In yet another approach, V—OH can first be reacted with LG$^2$-L-Hal, wherein Hal is Cl, Br, OMs or OTs, and wherein LG$^2$ is Br, Cl, OH, and, when LG$^2$ is Br or Cl, the reaction is performed in the presence of a base, such as CsCO$_3$ or K$_2$CO$_3$, in a solvent, such as DMF or NMP, at elevated temperature, for example, between about 40° C. and about 70° C.; or when LG$^2$ is OH, a Mitsunobu reaction is performed (using PPh$_3$ and DIAD or DEAD, in a solvent, such as THF, at room temperature) to generate V-L-Hal, which is reacted with the appropriately protected piperazinyl (in the presence of a base, such as CsCO$_3$ or K$_2$CO$_3$, in a solvent, such as DMF or NMP, at elevated temperature, such as between about 40° C. and about 70° C.), to provide intermediate a. Removal of the N-protecting group P$^N$ from intermediate a, (for example, when P$^N$ is Boc, by treatment with an acid in a solvent, for example, hydrochloric acid in dioxane or EtOAc, at room temperature, or with TFA in DCM, at room temperature), provides intermediate b. Reaction of intermediate b with Br—C(R$^2$)(R$^3$)COOR (wherein R is C$_{1-4}$ alkyl, for example, methyl, ethyl, or t-butyl), in the presence of a base, such as TEA, DBU, or DIEA, in a solvent, such as THF, NMP, or DMF, optionally at elevated temperature (for example, a temperature between about 20° C. and about 80° C.), optionally in the presence of NaI or KI, provides intermediate c. Alternatively, intermediate c is prepared by reaction of V-L-Hal (wherein Hal is Cl, Br, OMs, or OTs) with the appropriately derivatized 2-(piperazin-1-yl)acetate (wherein R is C$_{1-4}$ alkyl, for example, methyl, ethyl, or t-butyl) in the presence of a base, such as DIEA, TEA, or DBU, in a solvent, such as DMF or NMP, at room temperature. Deprotection of the carboxylate in intermediate c, wherein R is methyl or ethyl, by treatment with a base, such as LiOH or NaOH, in a solvent, such as THF/H$_2$O mixtures or dioxane/H$_2$O mixtures; or when R is t-butyl, by treatment with an acid in a solvent, such as HCl in dioxane/DCM mixtures or TFA in DCM, provides intermediate d.

Appropriately derivatized 3-((3-aminophenyl)amino)piperidine-2,6-diones h are prepared from R$^1$-derivatized 3-nitroanilines, which are protected with an amine protecting group P$^N$ (wherein when P$^N$ is, for example Boc, by treatment with Boc$_2$O in the presence of a base, such as TEA, DIEA or DBU, in a solvent, such as THF, NMP or DMF) to form intermediate e. The nitro group in intermediate e is reduced (by treatment with a reducing agent, for example H$_2$, in the presence of a catalyst, such as Pd/C, in a solvent, such as EtOH or MeOH; or Fe and NH$_4$Cl, in a solvent such as EtOH and H$_2$O) to provide the mono-protected derivatized dianiline intermediate f. Coupling of intermediate f with 3-bromopiperidine-2,6-dione in the presence of a base, in a solvent (for example, NaHCO$_3$, CsCO$_3$ or K$_2$CO$_3$, in DMF or NMP, at elevated temperature, for example between about 50° C. and about 80° C.; or DIEA in DMF or NMP, at elevated temperature, for example, about 150° C.), followed by removal of the protecting group P$^N$ (for example, when P$^N$ is Boc, treatment with an acid in a solvent, such as TFA in DCM; or treatment with HCl in dioxane or EtOAc) provides intermediate h. Alternatively, intermediate h is obtained via iron-catalyzed reductive coupling of intermediate e and 3-bromopiperidine-2,6-dione (for example, by reaction in the presence of Zn, TMSCl, FeCl$_2$*4H$_2$O, in a solvent, such as NMP, at elevated temperature, for example between about 80° C. to about 100° C.), followed by removal of the protecting group P$^N$ (for example, when P$^N$ is Boc, treatment with an acid in a solvent, such as TFA in DCM; or treatment with HCl in dioxane or EtOAc).

Coupling of intermediate d with intermediate h, for example in the presence of a coupling agent, such as HATU, HBTU, or EDC or DCC, optionally in combination with HOBt, in the presence of a base, such as DIEA, NMM, or TEA, in a solvent, such as DCM, DMF, or NMP, or mixtures thereof, provides compounds of formula (I), wherein L is —O(C$_{1-6}$ alkyl)-.

Scheme 2

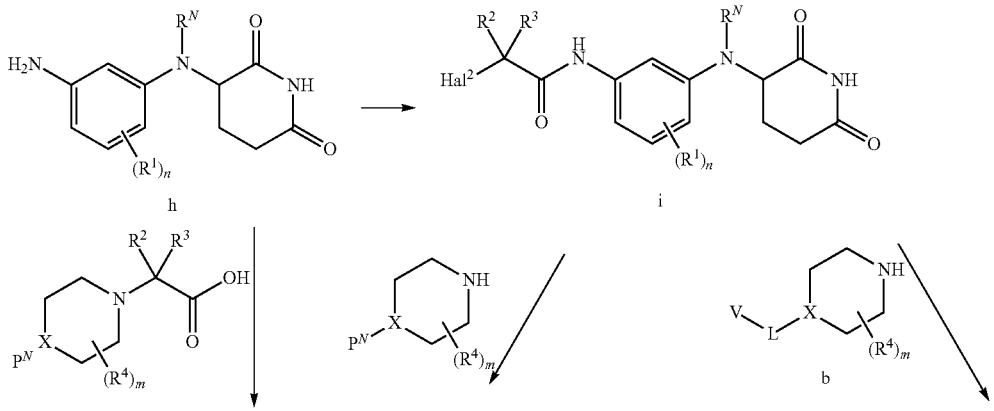

-continued

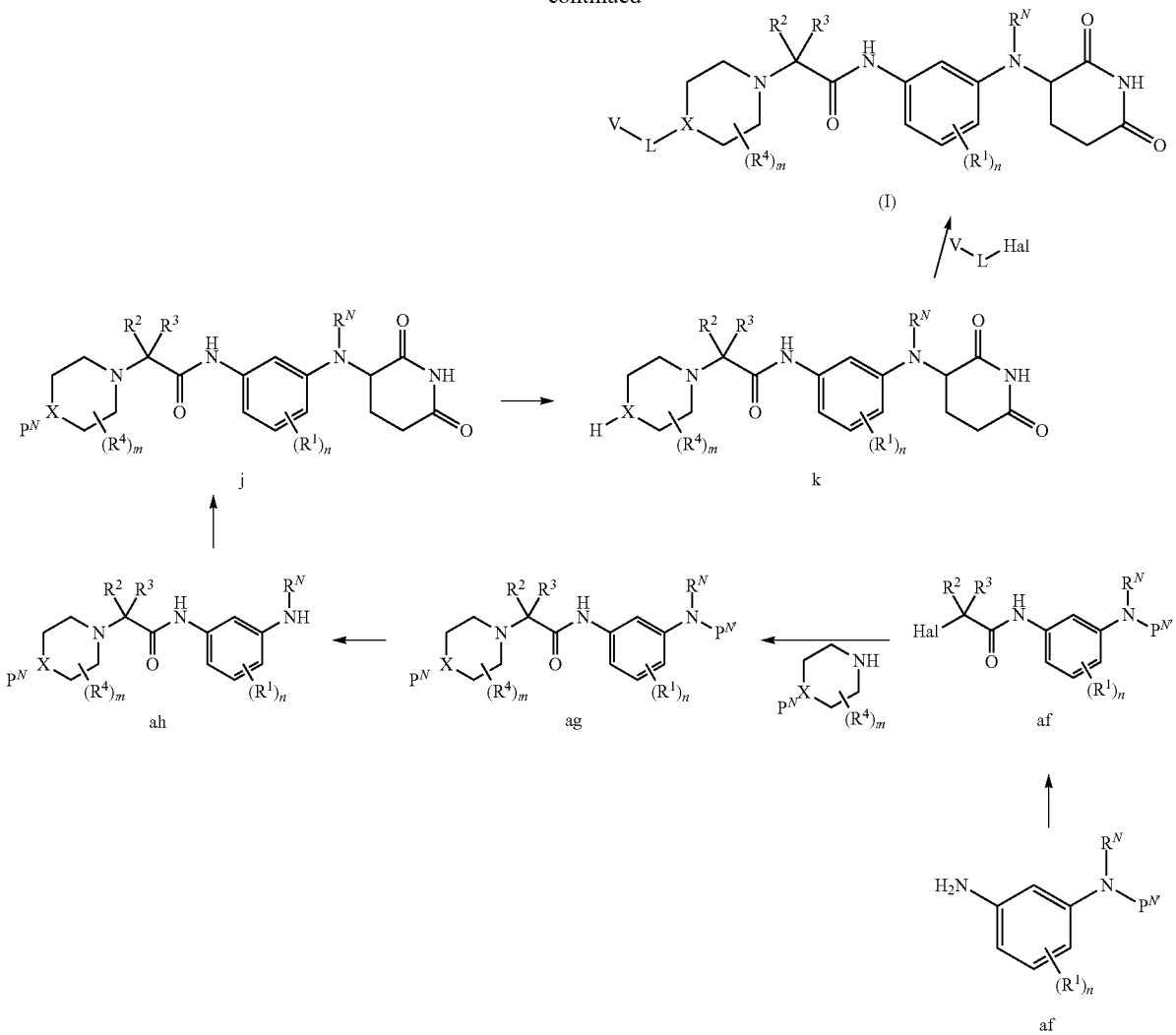

Alternate approaches to the synthesis of compounds of formula (I) are shown in Scheme 2. In one approach, the common intermediate h is reacted with $Hal^2-C(R^2)(R^3)COY$ (wherein $Hal^2$ is Cl or Br), in the presence of, when Y is OH, a coupling agent (for example HATU, HBTU, or EDC or DCC, optionally in combination with HOBt), and a base (for example DIEA, TEA, or NMM), in a solvent (for example, DCM, DMF, NMP or mixtures thereof); or in the presence of, when Y is Cl, a base, such as TEA or DIEA, in a solvent, such as DMF or NMP, at a temperature between about 0° C. and about 25° C., to provide intermediate i. Treatment of intermediate i with intermediate b, in the presence of a base, such as DIEA, TEA, or NMM, in a solvent, such as DMF or NMP, at elevated temperature, for example, between about 40° C. and about 60° C., optionally in the presence of NaI or KI, provides the target compounds of formula (I). In a second approach, intermediate h is coupled with an N-protected, appropriately derivatized 2-(piperazin-1-yl)acetic acid (wherein $P^N$ is, for example, Boc), by reaction in the presence of a coupling agent (for example, HATU, HBTU, or EDC or DCC, optionally in combination with HOBt), and a base (for example, DIEA, TEA or NMM), in a solvent (for example DCM, DMF, NMP or mixtures thereof) to provide intermediate j. Alternatively, intermediate j is prepared by reaction of intermediate i with an appropriately derivatized protected piperazine (wherein $P^N$ is, for example, Boc), in the presence of a base, such as DIEA, TEA, or NMM, in a solvent, such as DMF or NMP, at elevated temperature, for example, between about 40° C. and about 80° C., optionally in the presence of NaI or KI. In yet another approach, intermediate j is prepared starting by reacting intermediate ae (wherein $P^{N'}$ is, for example, Cbz) with $Hal-C(R^2)(R^3)COY$ (wherein Hal is Cl or Br), in the presence of, when Y is OH, a coupling agent (for example HATU, HBTU, or EDC or DCC, optionally in combination with HOBt), and a base (for example, DIEA, TEA, or NMM), in a solvent (for example, DCM, DMF, NMP, or mixtures thereof), to provide intermediate af. Treatment of intermediate af with an N-protected, appropriately functionalized piperazine (wherein $P^N$ is, for example, Boc), in the presence of a base, such as DIEA or TEA, in a solvent, such as DMF or NMP, at elevated temperature, for example, between about 60° C. and about 90° C., optionally in the presence of NaI or KI, provides intermediate ag. Intermediate ag is deprotected, for example with a reducing agent, such as $H_2$, when $P^{N'}$ is Cbz, in the presence of a catalyst (for example, Pd/C, Pt/C, or Pd(OH)$_2$), in a solvent, such as MeOH or EtOAc, to give intermediate ah. Coupling of intermediate ah with 3-bromopiperidine-2,6-dione in the presence of a base, in a solvent (for example, NaHCO$_3$, CsCO$_3$ or K$_2$CO$_3$, in DMF or NMP, at elevated temperature, for example between about 50° C. and about 80° C.; or DIEA in DMF or NMP, at elevated temperature, for example, at about 150° C.), provides intermediate j. Deprotection of intermediate j (when P$^N$ is Boc, by treatment with an acid in a solvent, for example, TFA in DCM, or HCl in dioxane/DCM or EtOAc), followed by reaction with V-L-Hal (wherein Hal is Cl, Br, OMs, or OTs) in the presence of a base, for example DIEA, TEA or NMM, in a solvent, for example DMF or NMP, at elevated temperature, for example between about 50° C. and about 70° C., provides compounds of formula (I).

temperature is between about 50° C. and about 80° C.), to provide intermediate n. When LG$^2$ is OH, a Mitsunobu reaction is performed (using PPh$_3$ and DIAD or DEAD, in a solvent, such as THF, at room temperature) to provide intermediate n. Alternatively, when A is N, appropriately derivatized 2-halo-5-nitropyridine is reacted with intermediate m, in the presence of a base, such as CsCO$_3$ or K$_2$CO$_3$, in a solvent, such as acetonitrile, DMF, THF, or NMP, at elevated temperature, for example between about 50° C. and about 70° C., to provide intermediate n. Reduction of the nitro group in intermediate n with a reducing agent, in a solvent, (for example, H$_2$ in EtOH, in the presence of a catalyst, for example, Pd/C; or Fe and NH$_4$Cl, in EtOH and Scheme 3

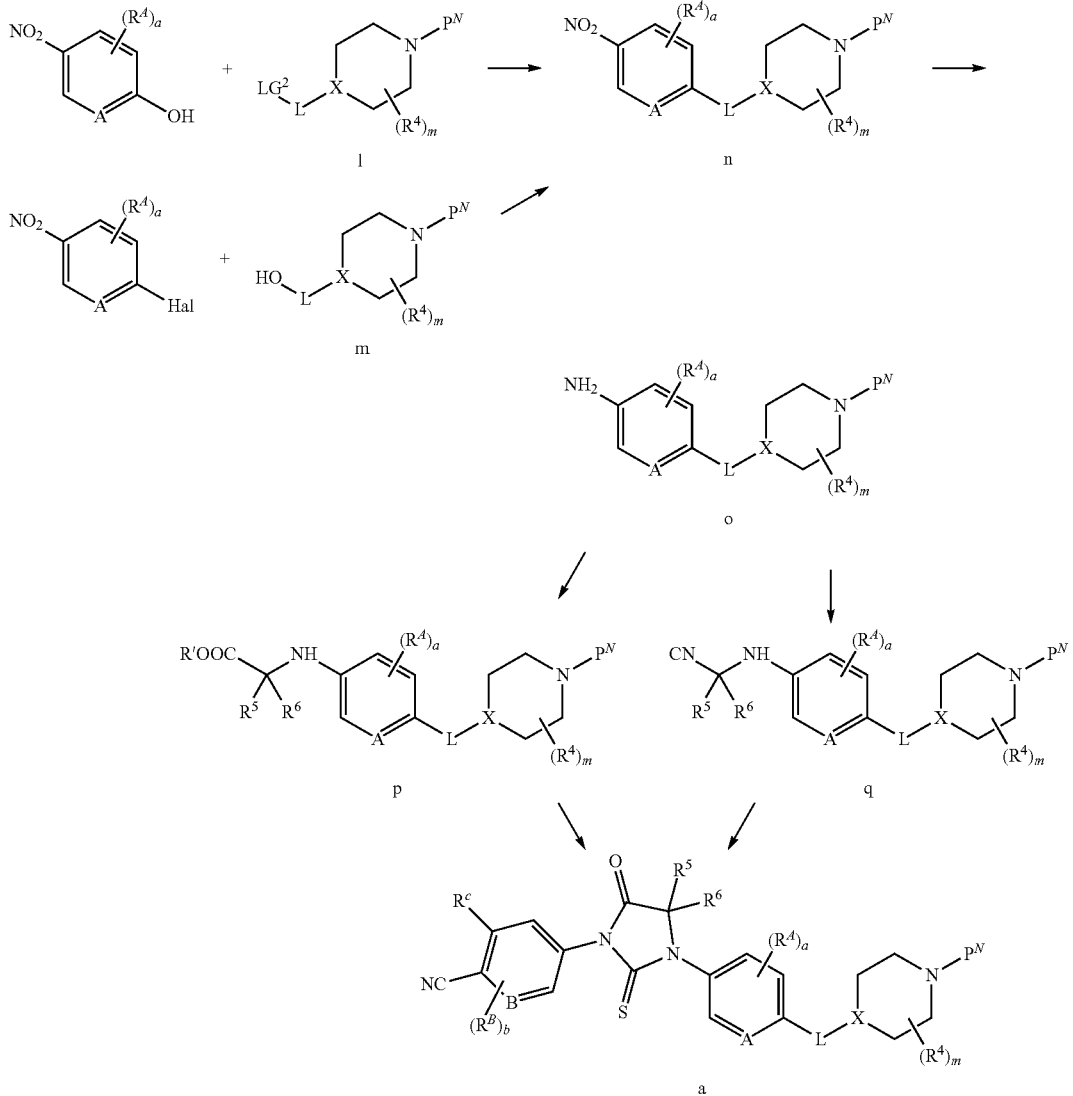

An alternate synthesis of intermediate a, wherein L is —O(C$_{1-6}$ alkyl)-, is shown in Scheme 3. Appropriately derivatized 4-nitrophenol or 5-nitropyridin-2-ol, is reacted with intermediate l (wherein LG$^2$ is Br, Cl or OH), and when LG$^2$ is Br or Cl, in the presence of a base, in a solvent, at elevated temperature (for example, the base is CsCO$_3$ or K$_2$CO$_3$, the solvent is acetonitrile, DMF or NMP, and the temperature is between about 50° C. and about 80° C.), to provide intermediate n. When LG$^2$ is OH, a Mitsunobu reaction is performed (using PPh$_3$ and DIAD or DEAD, in a solvent, such as THF, at room temperature) to provide intermediate n. Alternatively, when A is N, appropriately derivatized 2-halo-5-nitropyridine is reacted with intermediate m, in the presence of a base, such as CsCO$_3$ or K$_2$CO$_3$, in a solvent, such as acetonitrile, DMF, THF, or NMP, at elevated temperature, for example between about 50° C. and about 70° C., to provide intermediate n. Reduction of the nitro group in intermediate n with a reducing agent, in a solvent, (for example, H$_2$ in EtOH, in the presence of a catalyst, for example, Pd/C; or Fe and NH$_4$Cl, in EtOH and H$_2$O, at elevated temperature, for example about 80° C.) provides intermediate o. Reaction of intermediate o with R'OOC—C(R$^5$)(R$^6$)Hal (wherein Hal is Br or Cl and R' is C$_{1-3}$ alkyl) in the presence of a base (for example DIEA or TEA) at elevated temperature (for example, between 110° C. and about 130° C.) provides intermediate p. Reaction of intermediate p with an appropriately derivatized 4-isothiocyanatobenzonitrile or 5-isothiocyanatopicolinonitrile, in the presence of a base, such as TEA, in a solvent, such as EtOAc, at elevated temperature, for example, between about 70° C. and about 90° C., provides intermediates a, which can be further reacted to provide compounds of formula (I), wherein L is —O($C_{1-6}$ alkyl)-, as described in the schemes above.

Alternatively, reaction of intermediate o with CN—C($R^5$)($R^6$)OH in the presence of MgSO$_4$, at elevated temperature, for example between about 50° C. to about 70° C., provides intermediate q. Reagents CN—C($R^5$)($R^6$)OH can be formed by reaction of C(=O)($R^5$)($R^6$) with TMSCN and TMSOTf, in a solvent, such as DCM. Reaction of intermediate q, with an appropriately derivatized 4-isothiocyanatobenzonitrile or 5-isothiocyanatopicolinonitrile, in a solvent, such as DMF or DMA, followed by treatment with an acid, for example, HCl, in a solvent, such as MeOH or EtOH, at elevated temperature, for example between about 70° C. and about 80° C., provides intermediate a, to be used as described above to provide compounds of formula (I), wherein L is —O($C_{1-6}$ alkyl)-.

Synthesis of intermediates wherein $R^A$ is substituted or unsubstituted $C_{1-6}$ alkyl, or substituted or unsubstituted $C_{3-6}$ cycloalkyl, is shown in Schemes 4, 5 and 6.

or $CR^A$ and $P^O$ is a phenol protecting group, such as benzyl. Treatment of intermediate aw with $R^A$—B(OH)$_2$, in the presence of a catalyst and a base, for example Pd(dppf)$_2$Cl$_2$ and Cs$_2$CO$_3$, in a solvent, such as a toluene and water mixture, at elevated temperature, such as about 100° C., provides intermediate ax. The nitro group in intermediate ax can be selectively reduced to provide intermediate ay using a reducing agent, such as iron, in the presence of a Lewis acid, such as ammonium chloride, in a solvent, for example an EtOH and water mixture, at elevated temperature, such as about 60° C. The reaction of intermediate ay with CN—C($R^5$)($R^6$)OH in the presence of MgSO$_4$, at elevated temperature, for example between about 50° C. and about 70° C., provides intermediates az. Reaction of intermediate az, with an appropriately derivatized 4-isothiocyanatobenzonitrile (wherein B is CH or $CR^B$) or 5-isothiocyanatopicolinonitrile (wherein B is N), in a solvent, such as DMF or DMA, followed by treatment with an acid, for example, HCl, in a solvent, such as MeOH or EtOH, at elevated temperature, for example between about 70° C. and about 80° C., provides intermediate s. Removal of the protecting group $P^O$, as described above, provides compounds of formula V—OH, wherein $R^A$ is substituted or unsubstituted $C_{1-6}$ alkyl, or substituted or unsubstituted $C_{3-6}$ cycloalkyl.

Scheme 4

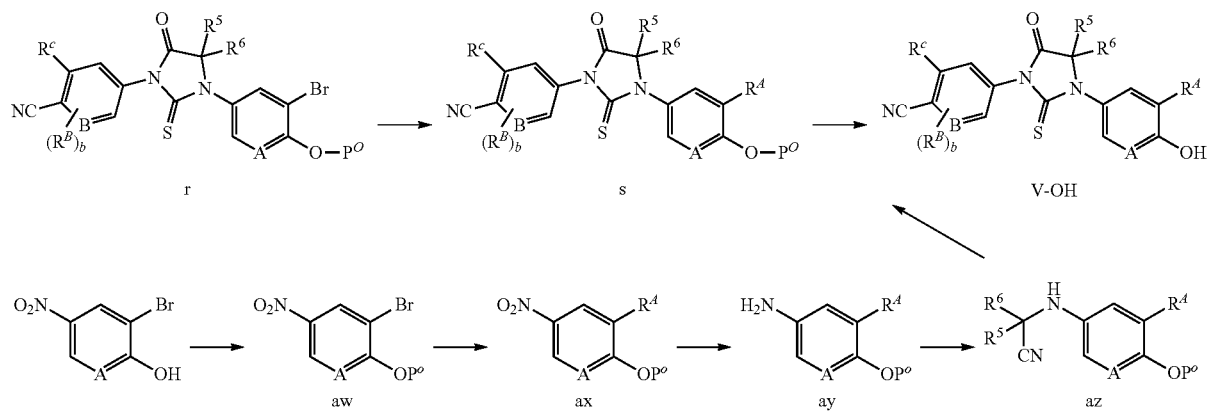

Intermediates r, wherein $P^O$ is a phenol protecting group, for example acetyl or benzyl, can be treated with $R^A$—Zn—Br, in the presence of a catalyst and a ligand, for example, CPhosPdG3 and CPhos in a solvent, for example, toluene, at lower temperature for example, between about 0° C. and about 25° C. to generate intermediates s. Removal of the protecting group $P^O$ (when $P^O$ is acetyl, by treatment with a base, such as K$_2$CO$_3$, in a solvent, such as MeOH or EtOH; or when $P^O$ is benzyl, by treatment with a reducing agent such as H$_2$, in the presence of a catalyst such as Pd/C, in a solvent, such as EtOH or MeOH, or by treatment with a dealkylating agent, such as BBr$_3$, in a solvent, such as DCM, at low temperature, for example about −70° C.), provides the intermediates V—OH, wherein $R^A$ is substituted or unsubstituted $C_{1-6}$ alkyl, or substituted or unsubstituted $C_{3-6}$ cycloalkyl, which can be used in the schemes above. Alternatively, intermediates s, wherein A is CH or $CR^A$, are formed starting by hydroxyl-protection of an appropriately derivatized phenol with an alkylating agent, such as bromomethylbenzene, in a solvent, such as acetonitrile, with a base, for example K$_2$CO$_3$, at elevated temperature, such as about 80° C., to provide intermediate aw, wherein A is CH Scheme 5

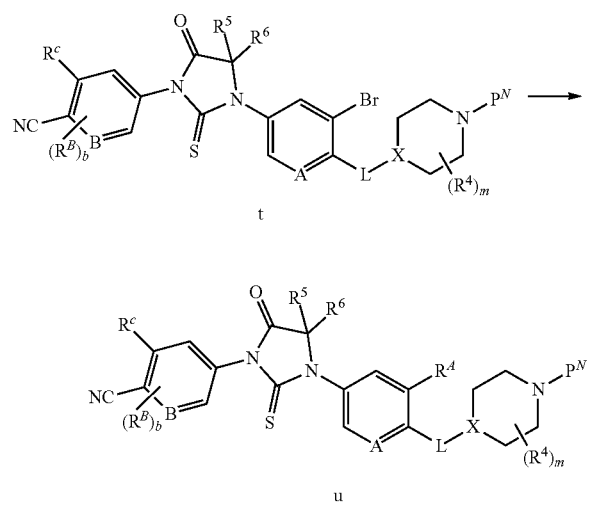

Alternatively, as shown in Scheme 5, $R^A$ can be incorporated by reaction of intermediate t with $R^A$—Zn—Br, in the presence of a catalyst and a ligand, for example, CPhosPdG3 and CPhos in a solvent, for example, toluene, at lower temperature for example, between about 0° C. and about 25° C. to generate intermediates u, wherein $R^A$ is substituted or unsubstituted $C_{1-6}$ alkyl, or substituted or unsubstituted $C_{3-6}$ cycloalkyl and which can be used similarly to intermediate a in the schemes above.

example at between about 50° C. and about 70° C., to provide intermediate v. Introduction of $R^A$ is achieved by reaction of intermediate v with a boronate $R^{A'}[B(OR^+)_2]_2$, (wherein $R^{A'}$ is substituted or unsubstituted $C_{2-6}$ alkenyl, substituted or unsubstituted cyclopropyl, or substituted or unsubstituted $C_{5-6}$ cycloalkenyl, and $R^+$ together with the boron atom and the atoms to which they are attached, forms a cyclic boronate, for example, 4,4,4',4',5,5,5',5'-octamethyl-2,2'-bi(1,3,2-dioxaborolane), in the presence of a palladium

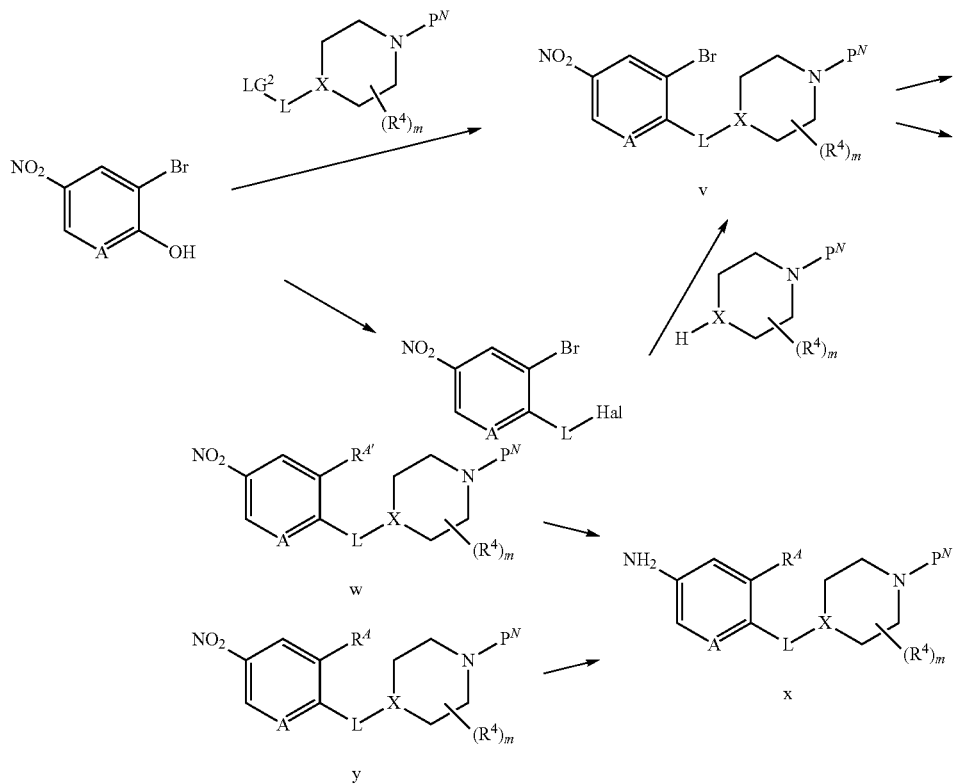

Scheme 6

Intermediates x, wherein L is —O($C_{1-6}$ alkyl)- and $R^A$ is as defined below, for use in the schemes above, can be prepared as shown in Scheme 6. In a first step, 2-bromo-4-nitrophenol or 3-bromo-5-nitropyridin-2-ol, is reacted with the appropriately derivatized and N-protected piperazinyl (for example, wherein $P^N$ is Boc and the leaving group $LG^3$ is Br, Cl, OTs, or OMs), in the presence of a base in a solvent (for example, $CsCO_3$ or $K_2CO_3$, in DMF, NMP, or acetonitrile), at elevated temperature (for example, between about 40° C. and about 70° C.) to provide intermediate v. Alternatively, when $LG^3$ is —OH, 2-bromo-4-nitrophenol or 3-bromo-5-nitropyridin-2-ol, is treated under Mitsunobu conditions (for example, with $PPh_3$ and DIAD or DEAD, in a solvent such as THF, at room temperature) to provide intermediate v. In yet another approach, 2-bromo-4-nitrophenol or 3-bromo-5-nitropyridin-2-ol, is reacted with Hal-L-Hal, wherein Hal is Br, in the presence of a base (such as $K_2CO_3$ or $CsCO_3$), in a solvent (such as acetonitrile or DMF), at elevated temperature, for example between about 80° C. and about 100° C., followed by coupling with the appropriately derivatized and protected piperazinyl, in the presence of a base, for example DIEA or TEA, in a solvent, for example DMF or NMP, at elevated temperature, for catalyst (for example $Pd(dppf)Cl_2$) and a base (such as $K_3PO_4$) in a solvent (such as a 1,4-dioxane/water mixtures), providing intermediate w, wherein $R^{A'}$ is substituted or unsubstituted $C_{2-6}$ alkenyl, substituted or unsubstituted cyclopropyl, or substituted or unsubstituted $C_{5-6}$ cycloalkenyl. Reduction of the nitro group and the $R^{A'}$ alkenyl or cycloalkenyl group in intermediate w, using a reducing agent, such as $H_2$, in the presence of a catalyst, such as Pd/C, in a solvent, such as MeOH or EtOH, at a temperature between about 20° C. and about 30° C., provides intermediates x, wherein $R^A$ is substituted or unsubstituted $C_{2-6}$ alkyl, substituted or unsubstituted cyclopropyl or substituted or unsubstituted $C_{5-6}$ cycloalkyl, that can be used in the schemes above to provide compounds of formula (I), wherein L is —O($C_{1-6}$ alkyl)- and $R^A$ is substituted or unsubstituted $C_{2-6}$ alkyl, substituted or unsubstituted cyclopropyl, or substituted or unsubstituted $C_{5-6}$ cycloalkyl. Alternatively, intermediate v is treated with $R^ABF_3^-K^+$, wherein $R^A$ is substituted or unsubstituted $C_{1-6}$ alkyl, in the presence of a catalyst and a ligand (for example, cataCXium® A Palladacycle Gen. 3 and butyldi-1-adamantylphosphine), in the presence of a base, such as $Cs_2CO_3$ or $K_2CO_3$, in a solvent, such as a toluene/water mixtures, at elevated temperature, for example, between about 90° C. and about 110° C., to provide intermediate y, wherein $R^A$ is substituted or unsubstituted $C_{1-6}$ alkyl. As before, reduction of the nitro group in intermediate y, using a reducing agent, such as $H_2$, in the presence of a catalyst, such as Pd/C, in a solvent, such as MeOH or EtOH, at a temperature between about 20° C. and about 30° C., provides intermediates x, wherein $R^A$ is substituted or unsubstituted $C_{1-6}$ alkyl, that can be used in the schemes above to provide compounds of formula (I), wherein L is —O($C_{1-6}$ alkyl)- and $R^A$ is substituted or unsubstituted $C_{1-6}$ alkyl.

Scheme 7

V-OH ⟶ V-OTf ⟶
aa

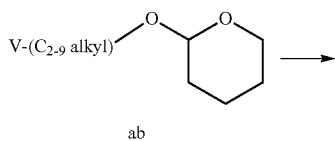
ab

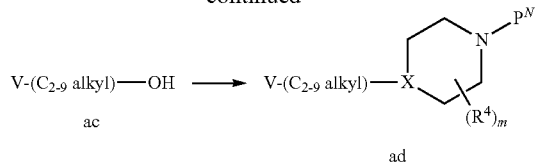
ac

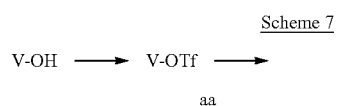
ad

Synthesis of intermediates ad, useful in the synthesis of compounds of formula (I) wherein L is —($C_{2-9}$ alkyl)-, is described in Scheme 7. Starting material V—OH is treated with $Tf_2O$, in the presence of a base, such as DIEA or TEA, in a solvent, such as DCM, to provide intermediate aa. Treatment of intermediate aa with THP-O—$C_{2-9}$ alkyl-zinc (II), in the presence of a catalyst and a ligand, for example, CPhosPdG3 and CPhos in a solvent, for example, toluene, at lower temperature for example, about 0° C., provides the THP protected intermediate ab. After THP removal (by treatment with an acid, such as TsOH, in a solvent, such as DCM/EtOH mixtures), intermediate ac is oxidized using an oxidizing agent (for example Dess-Martin periodinane (1,1,1-triacetoxy-1,1-dihydro-1,2-benziodoxol-3(1H)-one), in a solvent, such as DCM, at lower temperature, for example, about 0° C.), then coupled to the N-protected appropriately derivatized piperazinyl via reductive amination, using a reducing agent, for example, sodium triacetoxyborohydride, in a solvent, for example, MeOH, to provide intermediate ad, which can be used as described in Schemes 1 and 2 for intermediate a, to provide compounds of formula (I), wherein L is —($C_{2-9}$ alkyl)-.

Scheme 8

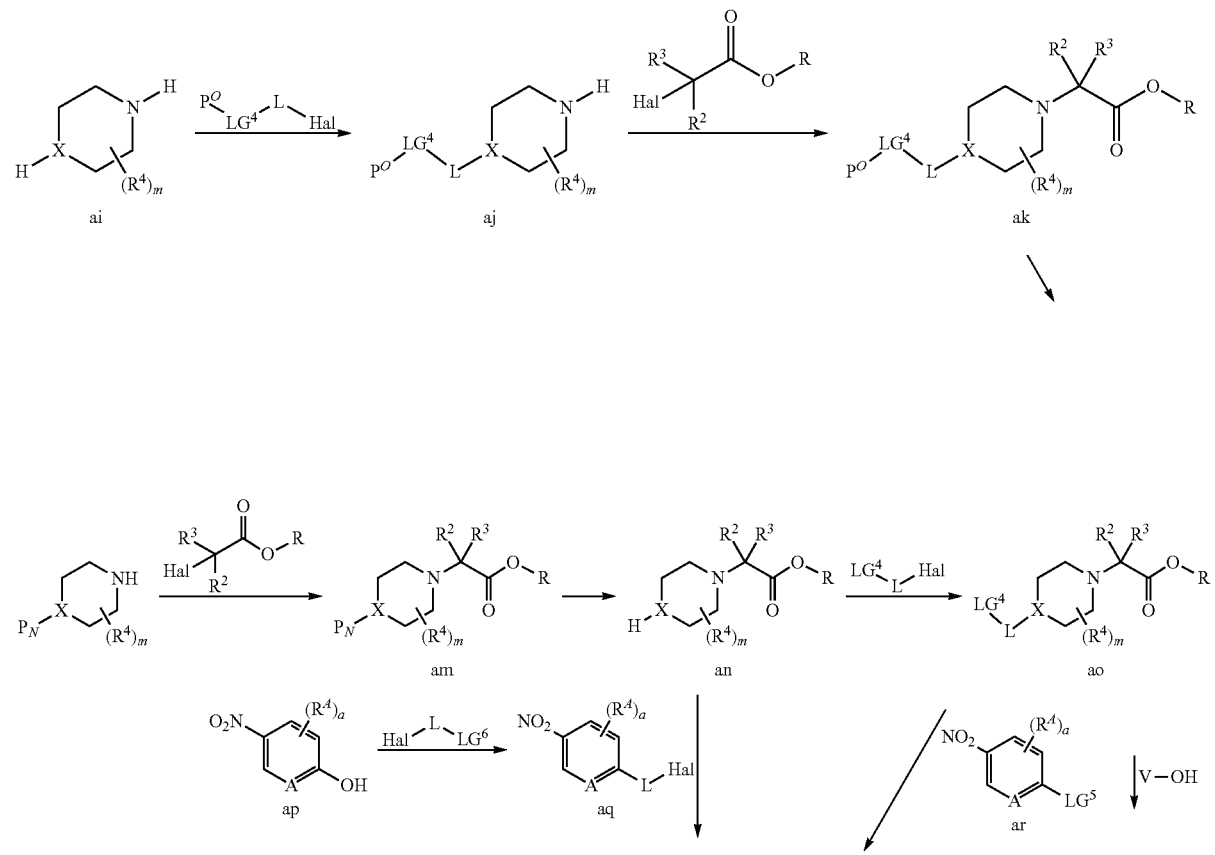

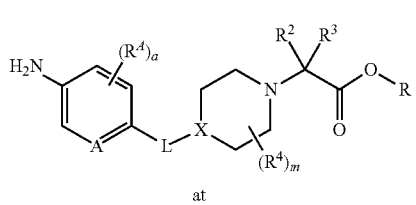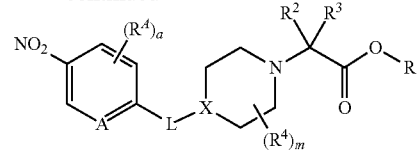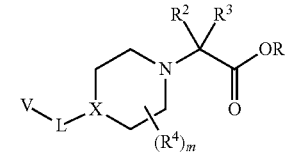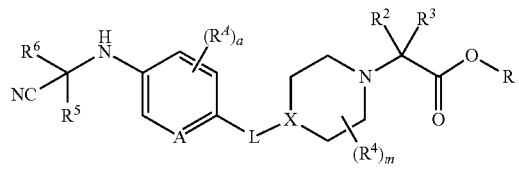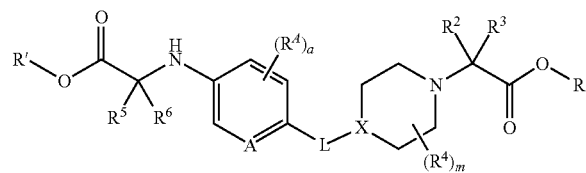

Intermediates c, wherein L is —O(C$_{1-6}$ alkyl)- or —(C$_{1-9}$ alkyl)-, can also be prepared as shown in Scheme 8. In one approach, an appropriately derivatized intermediate ai is reacted with an alkylating agent, such as an O-protected LG$^4$-L-Hal (for example, wherein the O-protecting group P$^O$ is benzyl, LG$^4$ is O, and Hal is Br or Cl), in the presence of a base in a solvent (for example, CsCO$_3$ in DMF, or K$_2$CO$_3$ in acetonitrile), at elevated temperature (for example, between about 40° C. and about 70° C.) to provide intermediate aj. Reaction of intermediate aj with Hal-C(R$^2$)(R$^3$)COOR (wherein R is C$_{1-4}$ alkyl, for example, methyl, ethyl, or t-butyl, and Hal is Cl or Br), in the presence of a base, such as TEA, DBU, or DIEA, in a solvent, such as THF, NMP, or DMF, optionally at elevated temperature (for example, a temperature between about 20° C. and about 80° C.), optionally in the presence of NaI or KI, provides intermediate ak. Removal of the O-protecting group P$^O$ in intermediate ak, wherein P$^O$ is benzyl, is achieved using a reducing agent, such as H$_2$, in the presence of a catalyst, such as Pd/C and Pd(OH)$_2$, in a solvent, such as MeOH or EtOH, at a temperature between about 20° C. and about 30° C., under increased pressure, for example a pressure level of 15 psi, provides intermediate ao.

Alternatively, the reaction of an appropriately derivatized, N-protected piperazyl with Hal-C(R$^2$)(R$^3$)COOR (wherein R is C$_{1-4}$ alkyl, for example, methyl, ethyl, or t-butyl, P$^N$ is an N-protecting group, such as Boc, and Hal is Br or Cl), in the presence of a base, such as TEA, DBU, or DIEA, in a solvent, such as THF, NMP, or DMF, optionally at elevated temperature (for example, a temperature between about 20° C. and about 80° C.), optionally in the presence of NaI or KI, provides intermediate am. Deprotection of intermediate am (when P$^N$ is Boc, by treatment with an acid in a solvent, for example, TFA in DCM, or HCl in dioxane/DCM, MeOH or EtOAc), followed by reaction with LG$^4$-L-Hal (wherein LG$^4$ is Br, Cl or OH, and Hal is Br or Cl) in the presence of a base, for example DIEA, TEA or NMM, in a solvent, for example DMF or NMP, at elevated temperature, for example between about 50° C. and about 70° C., provides intermediate ao.

Intermediate ao is reacted with the phenol derivative V—OH, wherein when LG$^4$ is —OH, the reaction is performed under Mitsunobu conditions (for example, in the presence of PPh$_3$ and DIAD or DEAD, in a solvent such as THF, at room temperature) to provide intermediate c. When the leaving group LG$^4$ in intermediate ao is Br, Cl, OTs, or OMs (prepared from the corresponding alcohol), the reaction with V—OH is performed in the presence of a base, in a solvent (for example, CsCO$_3$ in DMF, or K$_2$CO$_3$ in acetonitrile), at elevated temperature (for example, between about 40° C. and about 70° C.) to provide intermediate c.

Intermediate ao, wherein LG$^4$ is Br, Cl or OH, can also be treated with an appropriately derivatized 4-nitrophenol (wherein LG$^5$ is OH, and A is CH or CR$^A$) or 5-nitropyridin-2-ol (wherein LG$^5$ is OH, and A is N) (intermediate ar), in the presence of a base (for example, NaOtBu, CsCO$_3$ or K$_2$CO$_3$), in a solvent (for example, acetonitrile, DMF or NMP), at elevated temperature (for example, between about 0° C. and about 90° C.), to provide intermediate as. Alternatively, intermediate ao, wherein LG$^4$ is OH, is reacted with intermediate ar wherein LG$^5$ is OH, under Mitsunobu conditions (by reaction in the presence of PPh$_3$ and DIAD or DEAD, in a solvent, such as THF, at room temperature) to provide intermediate as. In yet a third approach, intermediate ao wherein LG$^4$ is OH is reacted with an appropriately derivatized 2-halo-5-nitropyridine (wherein LG$^5$ is F or Cl, and A is N), or 1-halo-4-nitrobenzene (wherein LG$^5$ is F or Cl and A is CH or CR$^A$) in the presence of a base, such as NaOtBu, CsCO$_3$ or K$_2$CO$_3$, in a solvent, such as acetonitrile, DMF, THF, or NMP, at elevated temperature, for example between about 0° C. and about 70° C., to provide intermediate as.

In still another approach, an appropriately derivatized 4-nitrophenol (wherein A is CH or CR$^A$) or 5-nitropyridin-2-ol (wherein A is N) (intermediate ap) can be reacted with LG$^6$-L-Hal (wherein LG$^6$ is Br or Cl, and Hal is Cl or Br), in the presence of a base (for example, NaOtBu, CsCO$_3$ or K$_2$CO$_3$), in a solvent (for example acetonitrile, DMF or NMP), at elevated temperature (for example between about 0° C. and about 90° C.), to provide intermediate aq. Intermediate ap can also be reacted with LG⁶-L-Hal, wherein LG⁶ is OH, under Mitsunobu conditions (using PPh₃ and DIAD or DEAD, in a solvent, such as THF, at room temperature) to provide intermediate aq. Intermediate aq can then be used to alkylate intermediate an, in the presence of a base, such as NaOtBu, CsCO₃ or K₂CO₃, in a solvent, such as acetonitrile, DMF, THF, or NMP, at elevated temperature, for example between about 0° C. and about 70° C., to provide intermediate as.

Reduction of the nitro group in intermediate as with a reducing agent, in a solvent, (for example, H₂ in MeOH or EtOH, in the presence of a catalyst, for example, Pd/C, under increased pressure, for example of 50 psi; or Fe and NH₄Cl, in EtOH and H₂O) at elevated temperature, for example about 80° C., provides intermediate at. Reaction of intermediate at with R'OOC—C(R⁵)(R⁶)Hal (wherein Hal is Br or Cl and R' is $C_{1-3}$ alkyl) in the presence of a base (for example NaHCO₃, DIEA or TEA) at elevated temperature (for example, between about 90° C. and about 130° C.) provides intermediate av. Reaction of intermediate av with an appropriately derivatized 4-isothiocyanatobenzonitrile (wherein B is CH or $CR^B$) or 5-isothiocyanatopicolinonitrile (wherein B is N), in the presence of a base, such as TEA, in a solvent, such as EtOAc, at elevated temperature, for example, between about 60° C. and about 90° C., again provides intermediates c wherein L is —O($C_{1-6}$ alkyl)-, which can be used as described above.

Alternatively, reaction of intermediate at with CN—C(R⁵)(R⁶)OH in the presence of MgSO₄, at elevated temperature, for example between about 50° C. and about 70° C., provides intermediate au. Reaction of intermediate au, with an appropriately derivatized 4-isothiocyanatobenzonitrile (wherein B is CH or $CR^B$) or 5-isothiocyanatopicolinonitrile (wherein B is N), in a solvent, such as DMF or DMA, followed by treatment with an acid, for example, HCl, in a solvent, such as MeOH or EtOH, at elevated temperature, for example between about 70° C. and about 80° C., again provides intermediate c wherein L is —O($C_{1-6}$ alkyl)-.

Intermediate as (when $R^A$ is Br) can also be used to obtain intermediate as wherein $R^A$ is substituted or unsubstituted $C_{2-6}$ alkyl, substituted or unsubstituted cyclopropyl or substituted or unsubstituted $C_{5-6}$ cycloalkyl, by reaction of intermediate as (when $R^A$ is Br) with a boronate $R^{A'}[B(OR^+)2]2$, (wherein $R^{A'}$ is substituted or unsubstituted $C_{2-6}$ alkenyl, substituted or unsubstituted cyclopropyl, or substituted or unsubstituted $C_{5-6}$ cycloalkenyl, and R⁺ together with the boron atom and the atoms to which they are attached, forms a cyclic boronate, for example, 4,4,4',4',5,5,5',5'-octamethyl-2,2'-bi(1,3,2-dioxaborolane), in the presence of a palladium catalyst (for example Pd(dppf)Cl₂) and a base (such as K₃PO₄) in a solvent (such as a 1,4-dioxane/water mixtures), providing intermediate as, wherein $R^A$ is substituted or unsubstituted $C_{2-6}$ alkenyl, substituted or unsubstituted cyclopropyl, or substituted or unsubstituted $C_{5-6}$ cycloalkenyl. Reduction of the nitro group and the $R^A$ alkenyl or cycloalkenyl group in intermediate as, using a reducing agent, such as H₂, in the presence of a catalyst, such as Pd/C, in a solvent, such as MeOH or EtOH, at a temperature between about 20° C. and about 30° C., provides intermediates at, wherein $R^A$ is substituted or unsubstituted $C_{2-6}$ alkyl, substituted or unsubstituted cyclopropyl or substituted or unsubstituted $C_{5-6}$ cycloalkyl, that can be used in the schemes above to provide compounds of formula (I), wherein L is —O($C_{1-6}$ alkyl)-.

In some embodiments, chiral separation (by standard methods and as described herein) of the enantiomers of compounds of formula (I) provides compounds of formula (IIa) and formula (IIb)

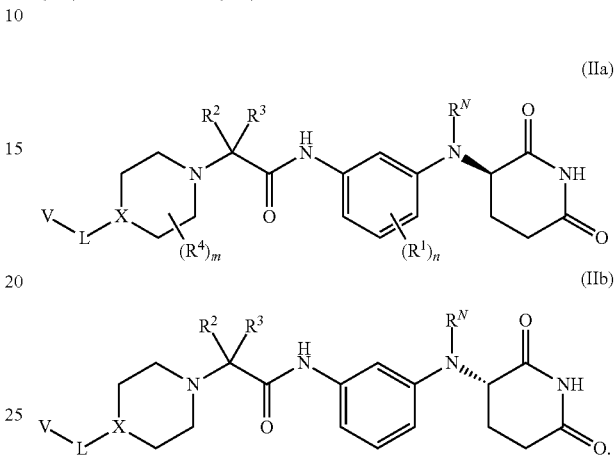

Alternatively, chiral separation by standard methods of intermediates h or i, used as described in the schemes above, provides compounds of formula (IIa) or (IIb).

The term "protected" with respect to amine and hydroxyl groups, refers to forms of these functionalities which are protected from undesirable reaction with a protecting group known to those skilled in the art, such as those set forth in Protective Groups in Organic Synthesis, Greene, T. W.; Wuts, P. G. M., John Wiley & Sons, New York, N.Y., (5th Edition, 2014), which can be added or removed using the procedures set forth therein.

In one aspect, provided herein are methods for preparing a compound of formula (I):

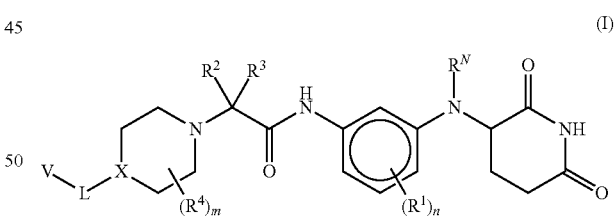

the methods comprising contacting a compound of formula (h)

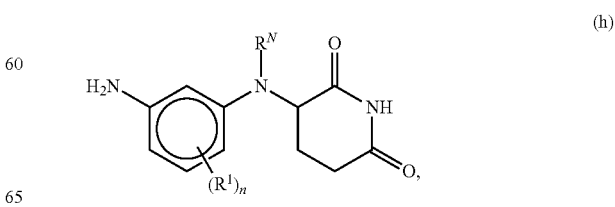

with a compound of formula (d)

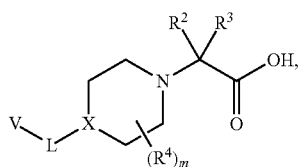

in the presence of a coupling agent, and a base, in a solvent, under conditions suitable to provide a compound of formula (I); wherein $R^N$ is H;

each $R^1$ is independently selected from halogen, CN, and $C_{1-3}$ alkyl;

$R^2$ and $R^3$ are each independently selected from H, and $C_{1-3}$ alkyl or $R^2$ and $R^3$ and the carbon to which they are attached form a substituted or unsubstituted $C_{3-6}$ cycloalkyl;

each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

X is N;

L is —O($C_{1-6}$ alkyl)- or —($C_{1-9}$ alkyl)-;

n is 0-4;

m is 0-8;

V is

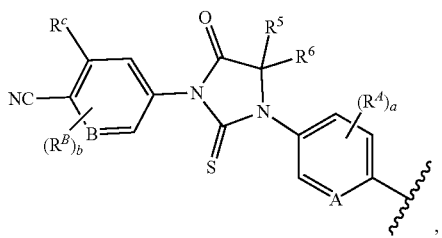

wherein

A is N, CH, or $CR^A$;

B is N, CH, or $CR^B$;

each $R^A$ is independently selected from halogen, substituted or unsubstituted $C_{1-6}$ alkyl, or substituted and unsubstituted $C_{3-6}$ cycloalkyl;

each $R^B$ is independently selected from halogen, and substituted or unsubstituted $C_{1-6}$ alkyl;

$R^C$ is halogen or $CF_3$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;

a is 0-3; and b is 0-2.

In one embodiment, the coupling agent is HATU, HBTU, EDC, or DCC, optionally in combination with HOBt. In one embodiment, the coupling agent is HATU. In another embodiment, the base is DIEA, NMM or TEA. In one embodiment, the base is DIEA. In another embodiment, the solvent is DCM, DMF, NMP, or mixtures thereof. In one embodiment the solvent is DMF.

In the following embodiments, the variables $R^N$, $R^1$, $R^2$, $R^3$, $R^4$, $R^5$, $R^6$, $R^A R^B$, $R^C$, L, V, A, B, n, m, p, a, and b are as defined herein, unless otherwise specified.

In some embodiments, the methods additionally comprise preparing a compound of formula (h)

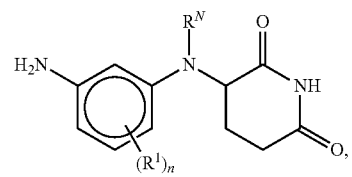

the methods comprising deprotecting a compound of formula (g)

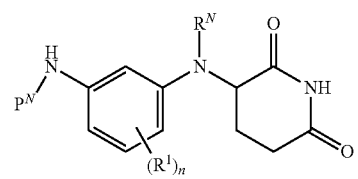

under conditions suitable to provide a compound of formula (h), wherein $P^N$ is an amine protecting group.

In some embodiments, $P^N$ is a Boc group. In some such embodiments, the deprotecting is performed by treatment with an acid, in a solvent. In some embodiments, acid is TFA and the solvent is DCM. In other embodiments, the acid is HCl, and the solvent is dioxane or EtOAc.

In some embodiments, the methods additionally comprise preparing a compound of formula (g)

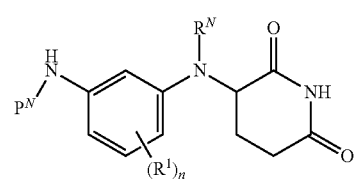

the methods comprising contacting a compound of formula (f)

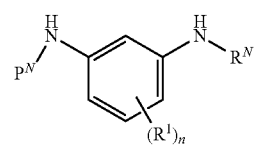

with 3-bromopiperidine-2,6-dione, in the presence of a base, in a solvent, at elevated temperature, under conditions suitable to provide a compound of formula (g).

In some such embodiments, the base is $NaHCO_3$, $CsCO_3$ or $K_2CO_3$ and the solvent is DMF or NMP. In one embodiment, base is NaHCO₃, and the solvent is DMF. In some such embodiments, the contacting is performed at a temperature of between about 50° C. and about 80° C. In other embodiments, the base is DIEA. In some such embodiments the solvent is DMF or NMP. In some such embodiments, the contacting is performed at a temperature of about 150° C.

In some embodiments, the methods additionally comprise preparing a compound of formula (f)

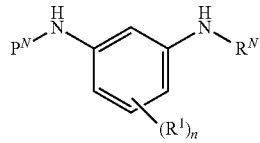

(f)

the methods comprising reduction of the nitro group in a compound of formula (e)

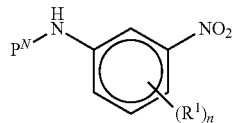

(e)

using a reducing agent, optionally in the presence of a catalyst, in a solvent, under conditions suitable to provide a compound of formula (f).

In some such embodiments, the reducing agent is H₂, and the catalyst is Pd/C. In some such embodiments, the solvent is EtOH or MeOH. In other embodiments, the reducing agent is Fe and NH₄Cl. In some such embodiments, the solvent is EtOH and H₂O.

In some embodiments, the methods additionally comprise preparing a compound of formula (e)

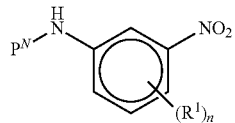

(e)

the methods comprising protecting a nitroaniline of formula

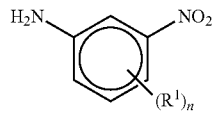

with an amine protecting group $P^N$, by reaction with a protecting agent in the presence of a base, in a solvent, under conditions suitable to provide a compound of formula (e).

In some such embodiments, amine protecting group $P^N$ is Boc and the protecting agent is Boc₂O. In some embodiments, the base is TEA, DIEA or DBU. In some embodiments, the base is TEA. In some such embodiments, the solvent is THF, NMP or DMF. In some embodiments, the solvent is THF.

In some other embodiments, the methods additionally comprise preparing a compound of formula (g)

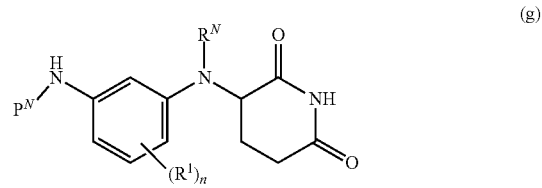

(g)

the methods comprising contacting a compound of formula (e)

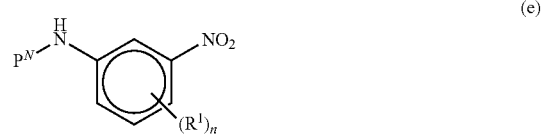

(e)

with 3-bromopiperidine-2,6-dione, in the presence of Zn, TMSCl, and FeCl₂*4H₂O, in a solvent, at elevated temperature, under conditions suitable to provide a compound of formula (g).

In some embodiments, the solvent is NMP. In some embodiments, the temperature is between about 80° C. to about 100° C.

In some embodiments, the methods additionally comprise preparing a compound of formula (d)

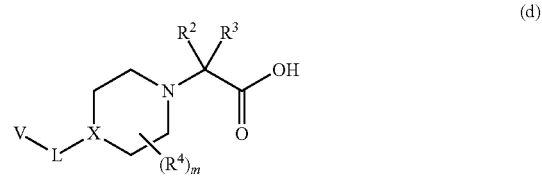

(d)

the methods comprising deprotecting a compound of formula (c)

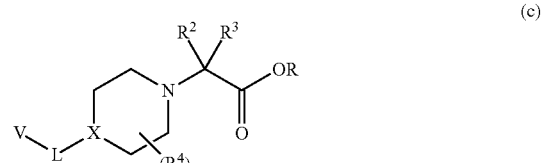

(c)

wherein R is $C_{1-4}$ alkyl, under conditions suitable to provide a compound of formula (d).

In some embodiments, wherein R is methyl or ethyl, the deprotecting is performed by treatment with a base, in a solvent. In some embodiments, the base is LiOH or NaOH. In other embodiments, the solvent is THF/H₂O mixtures or dioxane/H₂O mixtures. In other embodiments, wherein R is t-butyl, the deprotecting is performed by treatment with an acid in a solvent. In some such embodiments, the acid is HCl and the solvent is dioxane/DCM mixtures. In other embodiments, the acid is TFA and the solvent is DCM.

In some embodiments, the methods additionally comprise preparing a compound of formula (c)

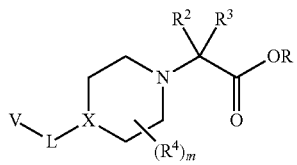
(c)

the methods comprising contacting a compound

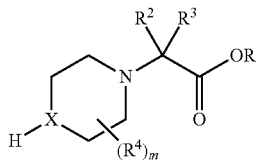

with V-L-Hal, wherein Hal is Cl, Br, OMs, or OTs, in the presence of a base, in a solvent under conditions suitable to provide a compound of formula (c).

In some embodiments, the base is DIEA, TEA, or DBU. In some embodiments, the base is DIEA. In other embodiments, the solvent is DMF or NMP. In some such embodiments, the solvent is DMF. In some embodiments, the contacting is at room temperature. In one embodiment, Hal is Cl or Br.

In some other embodiments, the methods additionally comprise preparing a compound of formula (c)

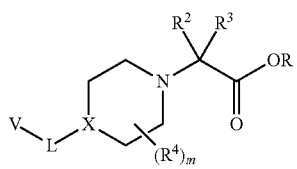
(c)

the methods comprising contacting a compound of formula (b)

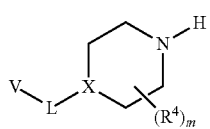
(b)

with Br—C($R^2$)($R^3$)COOR, in the presence of a base, in a solvent under conditions suitable to provide a compound of formula (c).

In some embodiments, the base is TEA, DBU, or DIEA. In some embodiments, the base is TEA. In other embodiments, the solvent is THF, NMP, or DMF. In some such embodiments, the solvent is THF. In some embodiments, the contacting is at elevated temperature, for example, a temperature between about 20° C. and about 80° C. In some embodiments, the contacting is in the presence of NaI or KI.

In some embodiments, the methods additionally comprise preparing a compound of formula (b)

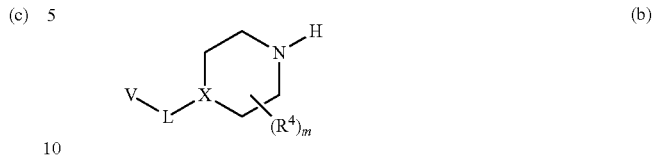
(b)

the methods comprising deprotecting a compound of formula (a)

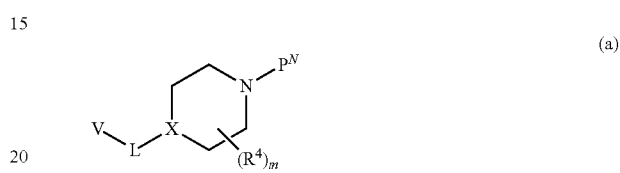
(a)

wherein $P^N$ is an amine protecting group, under conditions suitable to provide a compound of formula (b).

In some embodiments, the $P^N$ is Boc. In some such embodiments, the deprotecting is performed by treatment with an acid in a solvent. In some embodiments, the acid is HCl and the solvent is dioxane or EtOAc. In other embodiments, the acid is TFA and the solvent is DCM.

In some embodiments, the methods additionally comprise preparing a compound of formula (a)

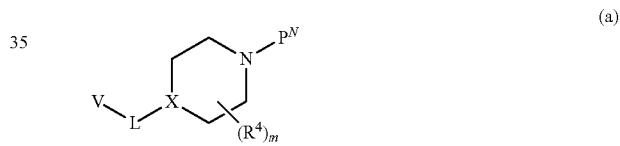
(a)

the methods comprising contacting a compound

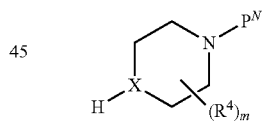

with V-L-Hal, wherein Hal is Cl, Br, OMs, or OTs, in the presence of a base, in a solvent, under conditions suitable to provide a compound of formula (a).

In some embodiments, the base is $CsCO_3$ or $K_2CO_3$. In some embodiments, the base is $CsCO_3$. In other embodiments, the solvent is DMF or NMP. In some such embodiments, the solvent is DMF. In some embodiments, the contacting is performed at elevated temperature, for example, a temperature between about 40° C. and about 70° C. In one embodiment, Hal is Cl or Br.

In some embodiments, the methods additionally comprise preparing a compound V-L-Hal, wherein L is —O($C_{1-6}$ alkyl)-, the methods comprising contacting a compound V—OH with $LG^2$-L-Hal, wherein $LG^2$ is a leaving group selected from Br, Cl, and OH, under conditions suitable to provide a compound V-L-Hal.

In some embodiments, wherein $LG^2$ is Br or Cl, the contacting is performed in the presence of a base, in a solvent. In some embodiments, the base is CsCO₃ or K₂CO₃. In some such embodiments, the base is CsCO₃. In other embodiments, the solvent is DMF or NMP. In some such embodiments, the solvent is DMF. In some embodiments, the contacting is performed at elevated temperature, for example, a temperature between about 40° C. and about 70° C. In other embodiments, LG² is OH, and the contacting is performed in the presence of PPh₃ and DIAD or DEAD, in a solvent. In some such embodiments, the solvent is THF. In some embodiments the contacting is performed at room temperature.

In some embodiments, the methods additionally comprise preparing a compound of formula (a)

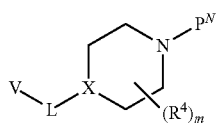
(a)

the methods comprising contacting a compound

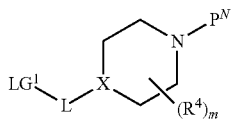

with V—OH, wherein LG¹ is a leaving group selected from OH, Br, Cl, OTs, and OMs, under conditions suitable to provide a compound of formula (a).

In some embodiments, LG¹ is Br, Cl, OTs, or OMs, and the contacting is performed in the presence of a base, in a solvent. In some such embodiments, the base is CsCO₃ and the solvent is DMF. In other embodiments, the base is K₂CO₃ and the solvent is acetonitrile. In some embodiments, the contacting is performed at elevated temperature. In some such embodiments, the temperature is between about 40° C. and about 70° C. In some embodiments, wherein LG¹ is —OH, and the contacting is performed in the presence of PPh₃ and DIAD or DEAD, in a solvent. In some such embodiments, the solvent is THF. In some embodiments, the contacting is performed at room temperature.

Also provided are methods of preparing compounds of formula (I)

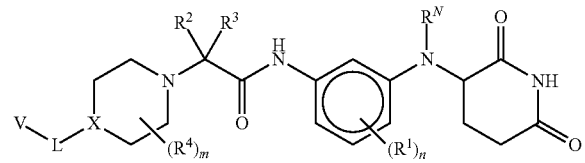
(I)

the methods comprising contacting a compound of formula (k)

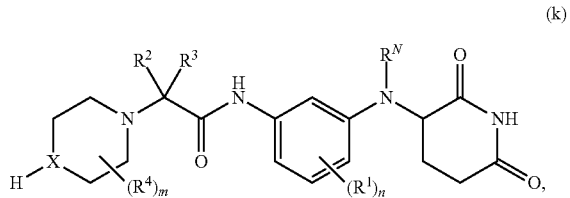
(k)

with V-L-Hal, wherein Hal is Br, Cl, OMs, or OTs, in the presence of a base, in a solvent, under conditions suitable to provide a compound of formula (I); wherein
R$^N$ is H;
each R¹ is independently selected from halogen, CN, and C$_{1-3}$ alkyl;
R² and R³ are each independently selected from H, and C$_{1-3}$ alkyl or R² and R³ and the carbon to which they are attached form a substituted or unsubstituted C$_{3-6}$ cycloalkyl;
each R⁴ is independently substituted or unsubstituted C$_{1-3}$ alkyl, or two R⁴ groups, together with the same carbon atom or adjacent carbon atoms to which they are attached, form a substituted or unsubstituted C$_{3-6}$ cycloalkyl, or two R⁴ groups together with the non-adjacent carbon atoms to which they are attached form a substituted or unsubstituted 4-7-membered heterocyclyl;
X is N;
L is —O(C$_{1-6}$ alkyl)- or —(C$_{1-9}$ alkyl)-;
n is 0-4;
m is 0-8;
V is

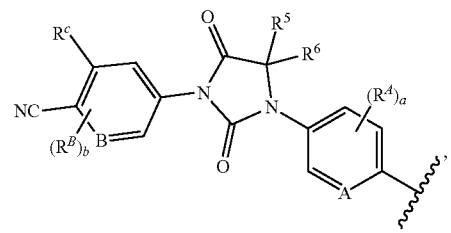

wherein
A is N, CH, or CR$^A$;
B is N, CH, or CR$^B$;
each R$^A$ is independently selected from halogen, substituted or unsubstituted C$_{1-6}$ alkyl, or substituted or unsubstituted C$_{3-6}$ cycloalkyl;
each R$^B$ is independently selected from halogen, or substituted or unsubstituted C$_{1-6}$ alkyl;
R$^C$ is halogen or CF₃;
R⁵ and R⁶ are C$_{1-3}$ alkyl, or R⁵ and R⁶, together with the carbon atom to which they are attached, form a substituted or unsubstituted C$_{3-6}$ cycloalkyl or a 3-6 membered heterocyclyl;
a is 0-3; and
b is 0-2.

In one embodiment, the base is DIEA, TEA or NMM. In one embodiment, the base is DIEA. In another embodiment, the solvent is DMF or NMP. In one embodiment, the contacting is performed at elevated temperature. In one such embodiment, the temperature is between about 50° C. and about 70° C. In one embodiment, Hal is Br or Cl.

In some embodiments, the methods additionally comprise preparing a compound of formula (k)

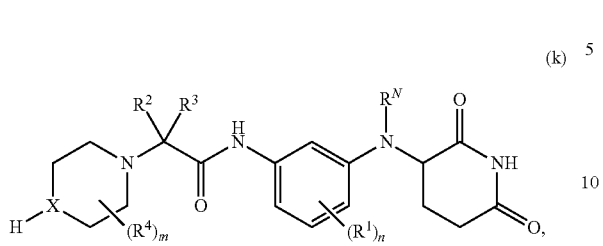

(k)

the methods comprising deprotecting a compound of formula (j)

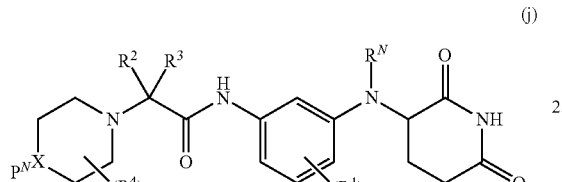

(j)

under conditions suitable to provide a compound of formula (k), wherein $P^N$ is an amine protecting group.

In some embodiments, $P^N$ is a Boc group. In some embodiments, the deprotecting is performed by treatment with an acid, in a solvent. In some such embodiments, the acid is TFA and the solvent is DCM. In other embodiments, the acid is HCl, and the solvent is dioxane/DCM or EtOAc.

In some embodiments, the methods additionally comprise preparing a compound of formula (j)

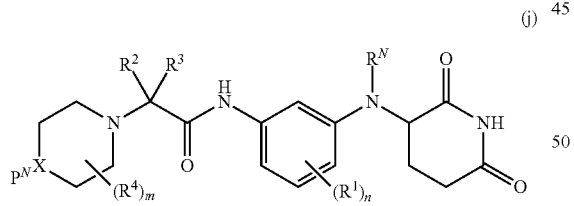

(j)

the methods comprising contacting a compound of formula (h)

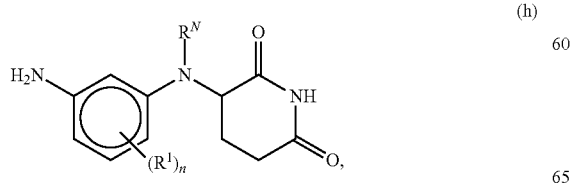

(h)

with a compound

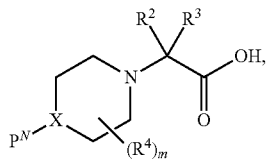

in the presence of a coupling agent, and a base, in a solvent, under conditions suitable to provide a compound of formula (j).

In one embodiment, the coupling agent is HATU, HBTU, EDC or DCC, optionally in combination with HOBt. In one embodiment, the coupling agent is HATU. In another embodiment, the base is DIEA, NMM or TEA. In one embodiment, the base is DIEA. In another embodiment, the solvent is DCM, DMF, NMP, or mixtures thereof. In one embodiment, the solvent is DMF.

Also provided are methods of preparing compounds of formula (I)

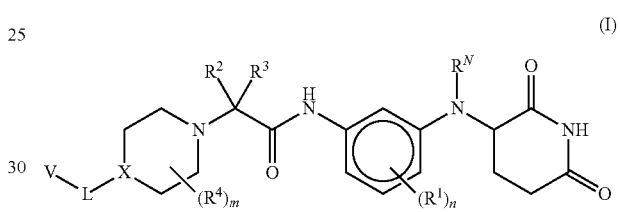

(I)

the methods comprising contacting a compound of formula (i)

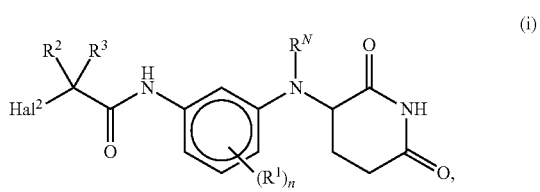

(i)

with a compound o formula

(b)

wherein $Hal^2$ is Br or Cl, in the presence of a base, in a solvent, under conditions suitable to provide a compound of formula (I); wherein
$R^N$ is H;
each $R^1$ is independently selected from halogen, CN, and $C_{1-3}$ alkyl;
$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;

X is N;

L is —O($C_{1-6}$ alkyl)- or ($C_{1-9}$ alkyl)-;

n is 0-4;

m is 0-8;

V is

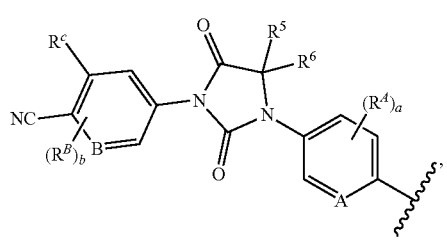

wherein

A is N, CH, or $CR^A$;

B is N, CH, or $CR^B$;

each $R^A$ is independently selected from halogen, substituted or unsubstituted $C_{1-6}$ alkyl, and substituted or unsubstituted $C_{3-6}$ cycloalkyl;

each $R^B$ is independently selected from halogen, or substituted and unsubstituted $C_{1-6}$ alkyl;

$R^C$ is halogen or $CF_3$;

$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;

a is 0-3; and b is 0-2.

In one embodiment, the base is DIEA, TEA or NMM. In one embodiment, the base is DIEA. In another embodiment, the solvent is DMF or NMP. In one embodiment, the contacting is performed at elevated temperature. In one such embodiment, the temperature is between about 40° C. and about 60° C. In one embodiment, the contacting is performed in the presence of NaI or KI.

In some embodiments, the methods additionally comprise preparing a compound of formula (i)

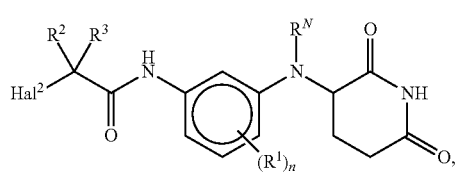

the methods comprising contacting a compound of formula (h)

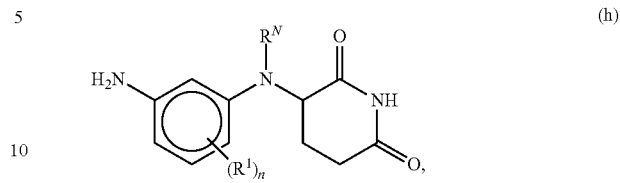

with $Hal^2$-C($R^2$)($R^3$)COY, wherein Y is OH or Cl, under conditions suitable to provide a compound of formula (i).

In some embodiments, wherein Y is OH, the contacting is performed in the presence of a coupling agent, and a base, in a solvent. In one embodiment, the coupling agent is HATU, HBTU, EDC or DCC, optionally in combination with HOBt. In one embodiment, the coupling agent is HATU. In some embodiments, the base is DIEA, TEA, or NMM. In one embodiment, the base is DIEA. In one embodiment, the solvent is DCM, DMF, NMP or mixtures thereof. In one embodiment, the solvent is DMF. In other embodiments, wherein Y is Cl, the contacting is performed in the presence of a base, in a solvent. In some such embodiments, the base is TEA or DIEA. In other embodiments, the solvent is DMF or NMP. In some embodiments, the contacting is performed at a temperature between about 0° C. and about 25° C.

In some embodiments, the methods additionally comprise preparing a compound of formula (j)

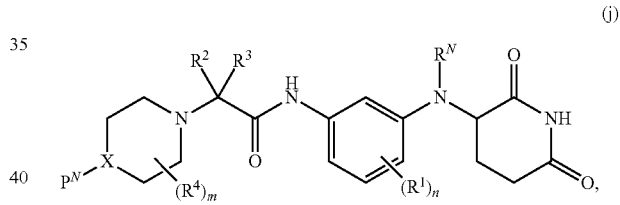

the methods comprising contacting a compound of formula (i)

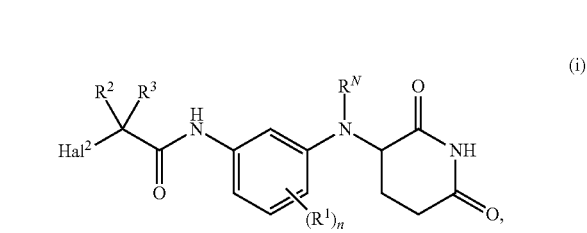

with compound

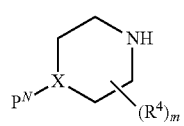

wherein $P^N$ is an amine protecting group, in the presence of a base, in a solvent, under conditions suitable to provide a compound of formula (j). In one embodiment, $P^N$ is Boc group.

In one embodiment, the base is DIEA, NMM or TEA. In one embodiment, the base is DIEA. In another embodiment, the solvent is DMF, NMP, or a mixture thereof. In one such embodiment, the contacting is performed at a temperature between about 40° C. and about 80° C. In one embodiment, the contacting is performed in the presence of NaI or KI.

In one embodiment, the methods provided herein comprise preparing a compound of formula (j)

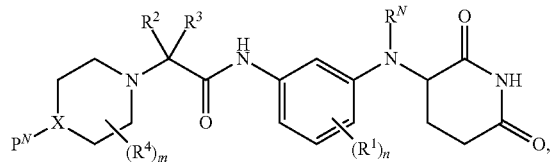

(j)

wherein $P^N$ is an amine protecting group, with 3-bromopiperidine-2,6-dione in the presence of a base, in a solvent under conditions suitable to provide a compound of formula (j). In one embodiment, $P^N$ is Boc group.

In one embodiment, the base is NaHCO₃, CsCO₃ or K₂CO₃. In another embodiment, the solvent is DMF, NMP, or a mixture thereof. In one such embodiment, the contacting is performed at a temperature between about 50° C. and about 80° C. In one embodiment, the base is NaHCO₃, CsCO₃ or K₂CO₃, the solvent is DMF or NMP, and the contacting is performed at a temperature between about 50° C. and about 80° C.

In one embodiment, the base is DIEA. In another embodiment, the solvent is DMF, NMP, or a mixture thereof. In one such embodiment, the contacting is performed at a temperature of about 150° C. In one embodiment, the base is DIEA, the solvent is DMF or NMP, and the contacting is performed at a temperature of about 150° C.

In one embodiment, the methods provided herein comprise preparing a compound of formula (j)

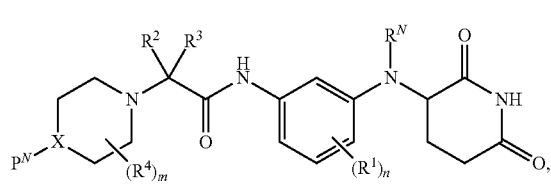

(j)

wherein the method comprises contacting compound (ah)

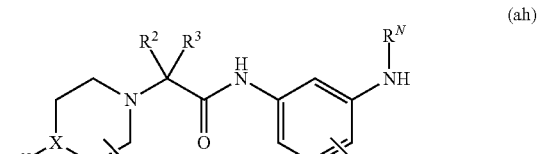

(ah)

with 3-bromopiperidine-2,6-dione in the presence of a base, in a solvent under conditions suitable to provide a compound of formula (j).

In one embodiment, the methods provided herein comprise preparing a compound of formula (ah)

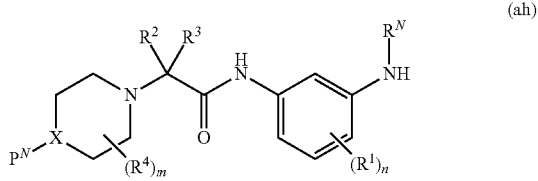

(ah)

wherein the method comprises deprotecting compound (ag)

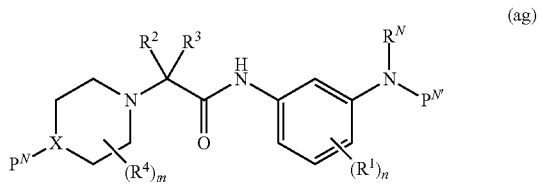

(ag)

with a reducing agent, under conditions suitable to provide a compound of formula (ah).

In one embodiment, the reducing agent is H₂. In one embodiment, PN' is Cbz, and the deprotecting is conducted in presence of a catalyst Pd/C, Pt/C, or Pd(OH)₂, in a solvent. In one embodiment, the solvent is MeOH or EtOAc.

In one embodiment, the methods provided herein comprise preparing a compound of formula (ag)

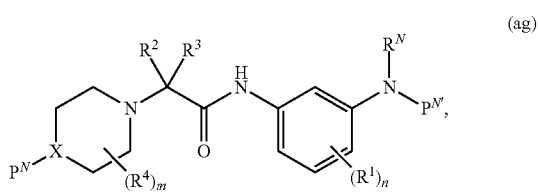

(ag)

wherein the method comprises contacting compound (ah)

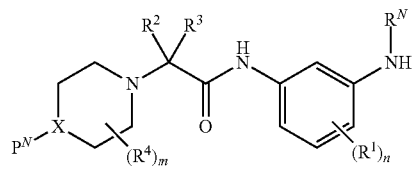

(ah)

wherein the method comprises contacting compound (af)

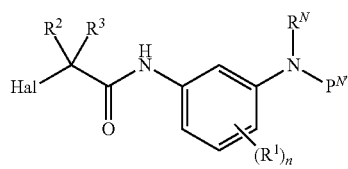
(af)

with an N-protected piperazine,

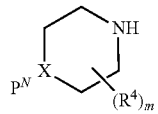

wherein $P^N$ is a protecting group, in the presence of a base in a solvent, under conditions suitable to provide a compound of formula (ag).

In one embodiment, $P^N$ is Boc group. In one embodiment, the base is DIEA or TEA. In another embodiment, the solvent is DMF or NMP. In one such embodiment, the contacting is performed at a temperature between about 60° C. and about 90° C. In one embodiment, the contacting is performed in the presence of NaI or KI.

In one embodiment, the methods provided herein comprise preparing a compound of formula (af),

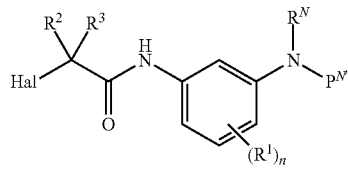
(af)

wherein the method comprises contacting compound (ae)

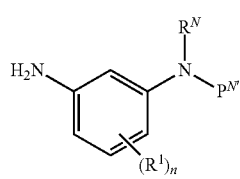
(ae)

with Hal$^2$-C(R$^2$)(R$^3$)COY, wherein Y is OH or Cl, under conditions suitable to provide a compound of formula (af).

In some embodiments, wherein Y is OH, the contacting is performed in the presence of a coupling agent, and a base, in a solvent. In one embodiment, the coupling agent is HATU, HBTU, EDC or DCC, optionally in combination with HOBt. In some embodiments, the base is DIEA, TEA, or NMM. In one embodiment, the solvent is DCM, DMF, NMP or a mixture thereof.

In other embodiments, wherein Y is Cl, the contacting is performed in the presence of a base, in a solvent. In some such embodiments, the base is TEA or DIEA. In other embodiments, the solvent is DMF or NMP. In some embodiments, the contacting is performed at a temperature between about 0° C. and about 25° C.

In some embodiments, the methods additionally comprise preparing a compound of formula (a)

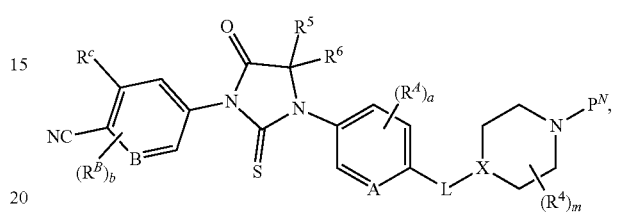
(a)

the methods comprising contacting a compound of formula (q)

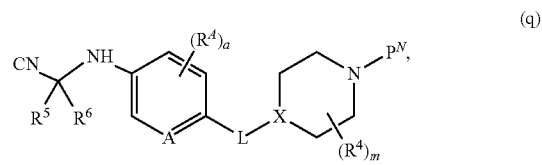
(q)

with a compound

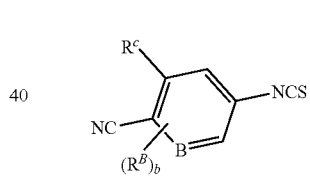

in a first solvent, followed by treatment with an acid, in a second solvent, under conditions suitable to provide a compound of formula (a), wherein L is —O(C$_{1-6}$ alkyl)-.

In some embodiments, the first solvent is DMF or DMA. In some embodiments, the acid is HCl. In some such embodiments, the second solvent is MeOH or EtOH. In some embodiments, the contacting with the acid is performed at elevated temperature. In some such embodiments, the temperature is between about 70° C. and about 80° C.

In some embodiments, the methods additionally comprise preparing a compound of formula (q)

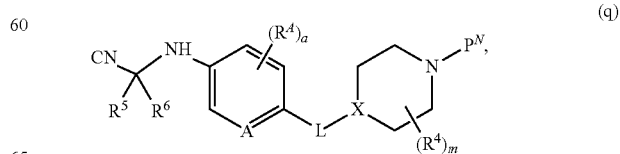
(q)

the methods comprising contacting a compound of formula (o)

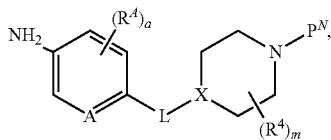
(o)

with CN—C(R$^5$)(R$^6$)OH, in the presence of a drying agent, under conditions suitable to provide a compound of formula (q).

In some embodiments, the drying agent is MgSO$_4$. In some embodiments, the contacting is performed at elevated temperature. In some such embodiments, the temperature is between about 50° C. and about 70° C.

In some embodiments, the methods additionally comprise preparing a compound of formula (a)

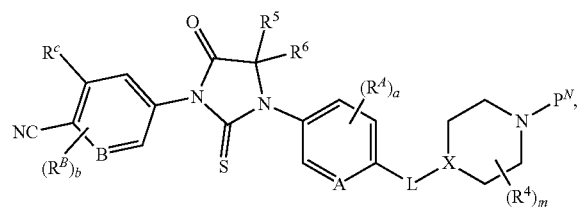
(a)

the methods comprising contacting a compound of formula (p)

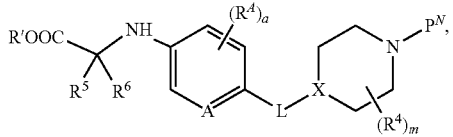
(p)

with a compound

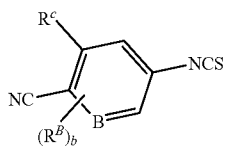

wherein R' is C$_{1-3}$ alkyl, in the presence of a base, in a solvent, under conditions suitable to provide a compound of formula (a), wherein L is —O(C$_{1-6}$ alkyl)-.

In some embodiments, the base is TEA. In other embodiments, the solvent is EtOAc. In some embodiments the contacting is performed at elevated temperature. In some such embodiments, the temperature is between about 70° C. and about 90° C.

In some embodiments, the methods additionally comprise preparing a compound of formula (p)

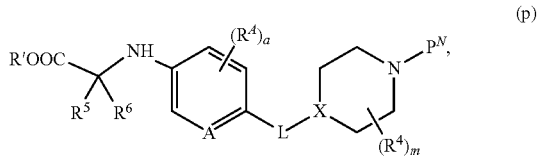
(p)

the methods comprising contacting a compound of formula (o)

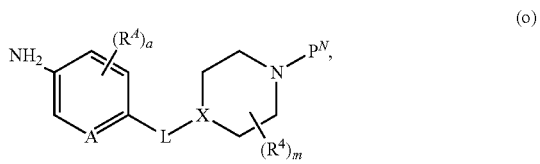
(o)

with R'OOC—C(R$^5$)(R$^6$)Hal, wherein Hal is Br or Cl, in the presence of a base, under conditions suitable to provide a compound of formula (p).

In some embodiments, Hal is Br. In some embodiments, the base is DIEA or TEA. In some embodiments the contacting is performed at elevated temperature. In some such embodiments, the temperature is between about 110° C. and about 130° C.

In some embodiments, the methods additionally comprise preparing a compound of formula (o)

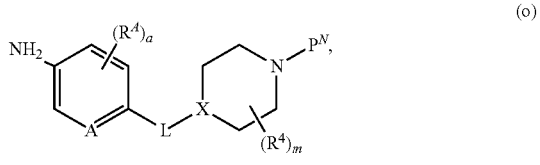
(o)

the methods comprising reducing a compound of formula (n)

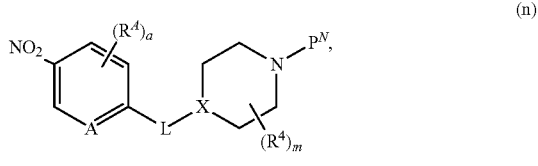
(n)

with a reducing agent, in a solvent, under conditions suitable to provide a compound of formula (o).

In some embodiments, the reducing agent is H$_2$. In some such embodiments, the contacting is performed in the presence of a catalyst. In some embodiments the catalyst is Pd/C. In some such embodiments, the solvent is EtOH. In other embodiments, the reducing agent is Fe and NH$_4$Cl. In some such embodiments, the solvent is EtOH and H$_2$O. In some such embodiments, the contacting is performed at elevated temperature. In some embodiments, the temperature is about 80° C.

In some embodiments, the methods additionally comprise preparing a compound of formula (n)

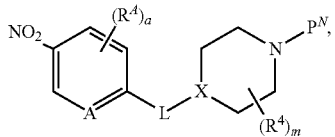 (n)

the methods comprising contacting a compound of formula (m)

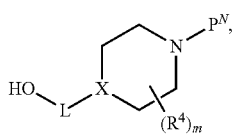 (m)

with a compound

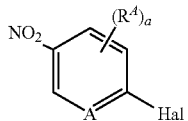

wherein A is N, in the presence of a base, in a solvent, under conditions suitable to provide a compound of formula (n), wherein A is N.

In some embodiments, the base is $CsCO_3$ or $K_2CO_3$. In some embodiments, the base is $K_2CO_3$. In some embodiments, the solvent is acetonitrile, DMF, THF, or NMP. In some embodiments, the solvent is acetonitrile. In some embodiments, the contacting is performed at elevated temperature. In some such embodiments, the temperature is between about 50° C. and about 70° C.

In some other embodiments, the methods additionally comprise preparing a compound of formula (n)

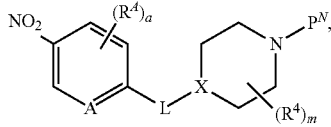 (n)

the methods comprising contacting a compound of formula (l)

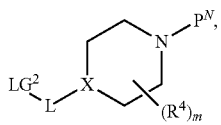 (l)

with a compound

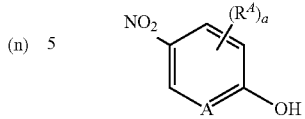

wherein $LG^2$ is Br, Cl or OH, under conditions suitable to provide a compound of formula (n), wherein A is N.

In some embodiments, $LG^2$ is Br or Cl, and the contacting is performed in the presence of a base, in a solvent. In some embodiments, the base is $CsCO_3$ or $K_2CO_3$. In some embodiments, the base is $CsCO_3$. In some embodiments, the solvent is acetonitrile, DMF or NMP. In some embodiments, the solvent is acetonitrile. In some embodiments, the contacting is performed at elevated temperature. In some embodiments the temperature is between about 50° C. and about 80° C. In some embodiments, Hal is Br, the base is $CsCO_3$, the solvent is DMF and the temperature is about 70° C. In other embodiments, Hal is Cl, the base is $K_2CO_3$, the solvent is acetonitrile, and the temperature is about 60° C. In some embodiments, $LG^2$ is OH, and the contacting is performed in the presence of $PPh_3$ and DIAD or DEAD, in a solvent. In some embodiments, the solvent is THF. In some embodiments the contacting is performed at room temperature.

In some embodiments, the methods additionally comprise preparing a compound of formula V—OH

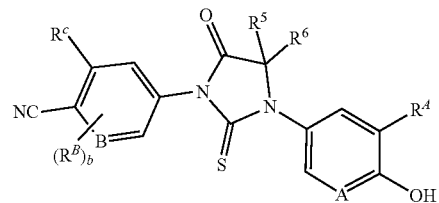

the methods comprising deprotecting a compound of formula (s)

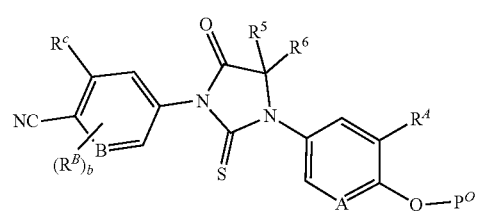 (s)

wherein $R^A$ is substituted or unsubstituted $C_{1-6}$ alkyl, or substituted or unsubstituted $C_{3-6}$ cycloalkyl and $P^O$ is a phenol protecting group, under conditions suitable to provide a compound of formula V—OH.

In some embodiments, $P^O$ is acetyl, and the deprotecting is performed by treatment with a base, in a solvent. In some such embodiments, the base is such as $K_2CO_3$. In some embodiments, the solvent is MeOH or EtOH. In other embodiments, $P^O$ is benzyl, and the deprotecting is performed by treatment with a reducing agent in a solvent. In some embodiments, the reducing agent is $H_2$, and the contacting is performed in the presence of a catalyst. In one embodiment, the catalyst is Pd/C. In some embodiments, the solvent is EtOH or MeOH.

In some embodiments, the methods additionally comprise preparing a compound of formula (s)

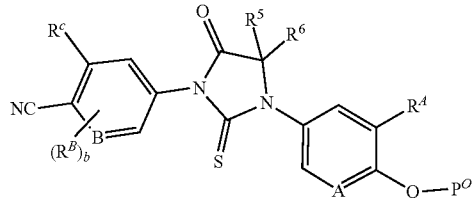
(s)

the methods comprising contacting a compound of formula (r)

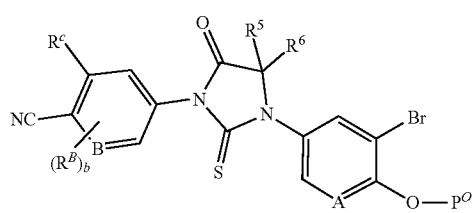
(r)

with $R^A$—Zn—Br, wherein $R^A$ is substituted or unsubstituted $C_{1-6}$ alkyl, or substituted or unsubstituted $C_{3-6}$ cycloalkyl, in the presence of a catalyst and a ligand, in a solvent, under conditions suitable to provide a compound of formula (s).

In some embodiments, the catalyst and the ligand are CPhosPdG3 and CPhos. In some embodiments, the solvent is toluene. In some embodiments, the contacting is performed at lower temperature. In some such embodiments, the temperature is between about 0° C. and about 25° C.

In some embodiments, the methods additionally comprise preparing a compound of formula (s)

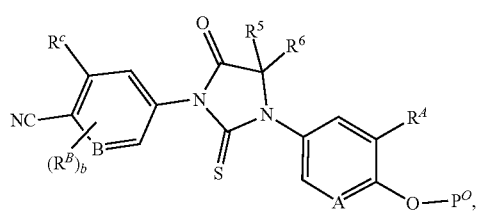
(s)

wherein A is CH or $CR^A$ and $P^O$ is a phenol protecting group, the methods comprising contacting a compound of formula (az)

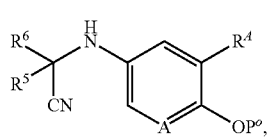
(az)

with compound

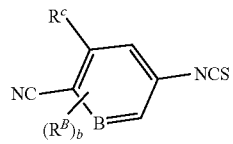

wherein B is CH, $CR^B$ or N, in a solvent, followed by treatment with an acid in a solvent, under conditions suitable to provide a compound of formula (s).

In one embodiment, $P^O$ is benzyl group. In one embodiment, the solvent is DMF or DMA. In one embodiment, the acid is HCl. In one embodiment, the acid is in a solvent, such as MeOH or EtOH. In one embodiment, the contacting is performed at a temperature between about 70° C. and about 80° C.

In one embodiment, provided herein is a method for preparing compound (az)

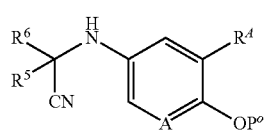
(az)

wherein the method comprises contacting compound (ay)

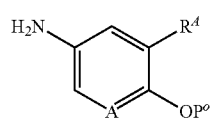
(ay)

with CN—$C(R^5)(R^6)$OH in the presence of MgSO$_4$, under conditions suitable to provide a compound of formula (az).

In one embodiment, the contacting is performed at a temperature between about 50° C. and about 70° C.

In one embodiment, provided herein is a method for preparing compound (ay)

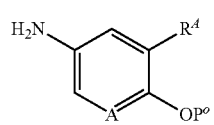
(ay)

wherein the method comprises contacting compound (ax)

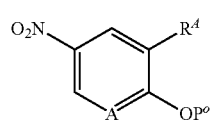
(ax)

with a reducing agent in the presence of a Lewis acid in a solvent, under conditions suitable to provide a compound of formula (ay).

In one embodiment, the reducing agent is iron. In one embodiment, the Lewis acid is ammonium chloride. In one embodiment, the solvent is an EtOH and water mixture. In one embodiment, the contacting is performed at a temperature of about 60° C.

In one embodiment, provided herein is a method for preparing compound (ax)

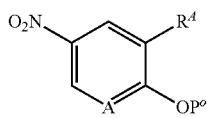

(ax)

wherein the method comprises contacting compound (aw)

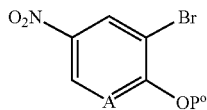

(aw)

with $R^A$—$B(OH)_2$, in the presence of a catalyst and a base in a solvent, under conditions suitable to provide a compound of formula (ax).

In one embodiment, the catalyst is $Pd(dppf)_2Cl_2$. In one embodiment, the base is $Cs_2CO_3$. In one embodiment, the solvent is a toluene and water mixture. In one embodiment, the contacting is performed at a temperature of about 100° C.

In one embodiment, provided herein is a method for preparing compound (aw)

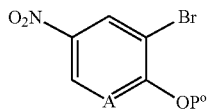

(aw)

wherein the method comprises contacting compound

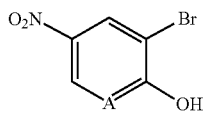

with an alkylating agent in a solvent with a base, under conditions suitable to provide a compound of formula (aw).

In one embodiment, the alkylating agent is bromomethylbenzene. In one embodiment, the solvent is acetonitrile. In one embodiment, the base is $K_2CO_3$. In one embodiment, the contacting is performed at a temperature of about 80° C.

In some embodiments, the methods additionally comprise preparing a compound of formula (u)

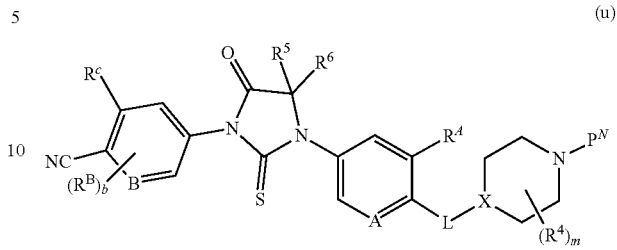

(u)

the methods comprising contacting a compound of formula (t)

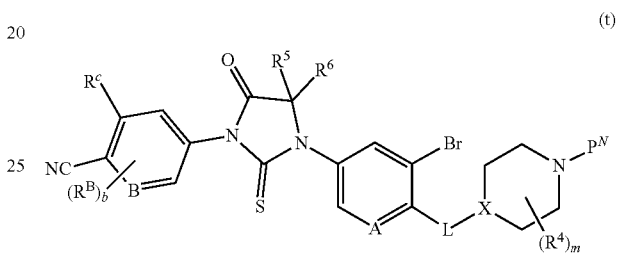

(t)

with $R^A$—Zn—Br, wherein $R^A$ is substituted or unsubstituted $C_{1-6}$ alkyl or substituted or unsubstituted $C_{3-6}$ cycloalkyl, in the presence of a catalyst and a ligand, in a solvent, under conditions suitable to provide a compound of formula (u).

In some embodiments, the catalyst and the ligand are CPhosPdG3 and CPhos. In some embodiments, the solvent is toluene. In some embodiments, the contacting is performed at lower temperature. In some such embodiments, the temperature is between about 0° C. and about 25° C.

In some embodiments, the methods additionally comprise preparing a compound of formula (x)

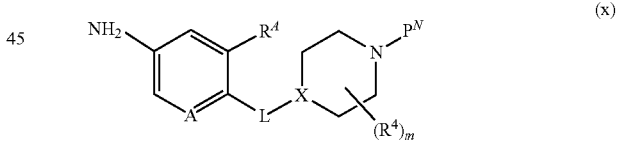

(x)

the methods comprising reducing a compound of formula (y)

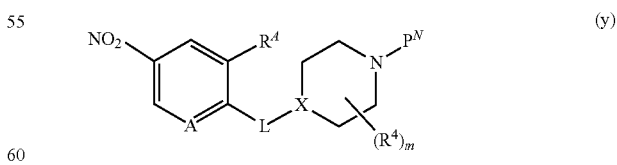

(y)

with a reducing agent, wherein L is —O($C_{1-6}$ alkyl)-, and $R^A$ is substituted or unsubstituted $C_{1-6}$ alkyl, in a solvent, under conditions suitable to provide a compound of formula (x).

In some embodiments, the reducing agent is $H_2$, in the presence of a catalyst. In some embodiments the catalyst is Pd/C. In some embodiments, the solvent is MeOH or EtOH. In some embodiments, the contacting is performed at a temperature between about 20° C. and about 30° C.

In some embodiments, the methods additionally comprise preparing a compound of formula (y)

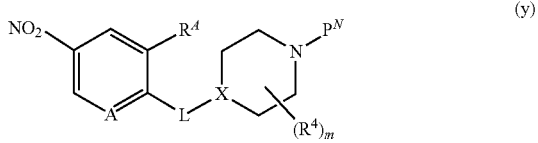

the methods comprising contacting a compound of formula (v)

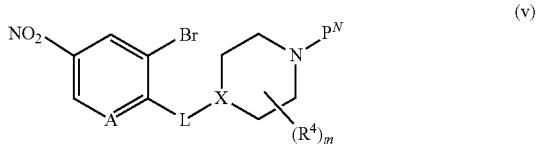

with $R^A BF_3^- K^+$, wherein $R^A$ is substituted or unsubstituted $C_{1-6}$ alkyl, in the presence of a catalyst and a ligand, in the presence of a base, in a solvent, under conditions suitable to provide a compound of formula (y).

In some embodiments the catalyst and the ligand are cataCXium® A Palladacycle Gen. 3 and butyldi-1-adamantylphosphine. In some embodiments, the base is $Cs_2CO_3$ or $K_2CO_3$. In some embodiments the base is $Cs_2CO_3$. In some embodiments, the solvent is a toluene/water mixture. In some embodiments, the contacting is performed at elevated temperature. In some embodiments, the temperature is between about 90° C. and about 110° C.

In some embodiments, the methods additionally comprise preparing a compound of formula (x)

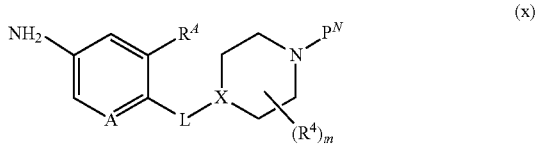

the methods comprising contacting a compound of formula (w)

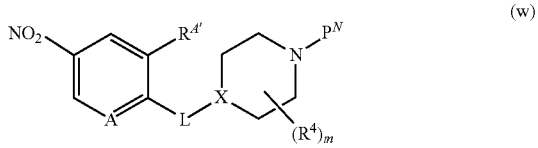

with a reducing agent, wherein L is —O($C_{1-6}$ alkyl)-, and $R^{A'}$ is substituted or unsubstituted $C_{2-6}$ alkenyl, substituted or unsubstituted cyclopropyl, or substituted or unsubstituted $C_{5-6}$ cycloalkenyl, in a solvent, under conditions suitable to provide a compound of formula (x), wherein $R^A$ is substituted or unsubstituted $C_{2-6}$ alkyl, substituted or unsubstituted cyclopropyl or substituted or unsubstituted $C_{5-6}$ cycloalkyl, under conditions suitable to provide a compound of formula (x).

In some embodiments, the reducing agent is $H_2$, in the presence of a catalyst. In some embodiments, the catalyst is Pd/C. In some embodiments, the solvent is MeOH or EtOH. In some embodiments, the contacting is performed at a temperature between about 20° C. and about 30° C.

In some embodiments, the methods additionally comprise preparing a compound of formula (w)

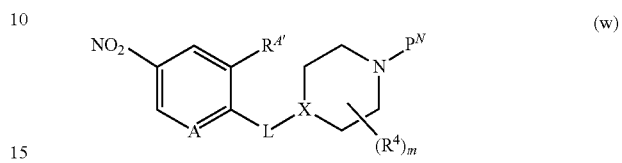

the methods comprising contacting a compound of formula (v)

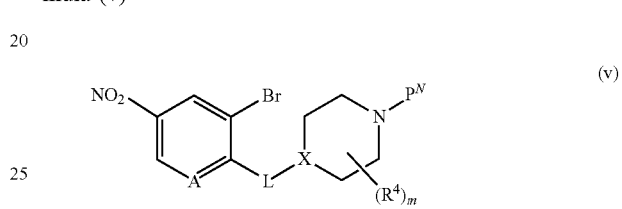

with $R^{A'}[B(OR^+)_2]_2$, wherein $R^{A'}$ is substituted or unsubstituted $C_{2-6}$ alkenyl, substituted or unsubstituted cyclopropyl, or substituted or unsubstituted $C_{5-6}$ cycloalkenyl, and $R^+$ together with the boron atom and the atoms to which they are attached, forms a cyclic boronate, for example, 4,4,4',4',5,5,5',5'-octamethyl-2,2'-bi(1,3,2-dioxaborolane, in the presence of a catalyst and a base, in a solvent, under conditions suitable to provide a compound of formula (w).

In some embodiments, the catalyst is Pd(dppf)$Cl_2$. In some embodiments, the base is $K_3PO_4$. In some embodiments, the solvent is a 1,4-dioxane/water mixture.

In some embodiments, the methods additionally comprise preparing a compound of formula (v)

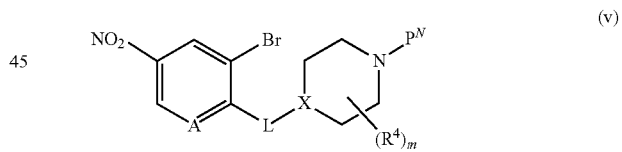

the methods comprising contacting a compound

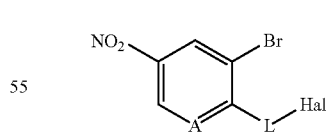

with a compound

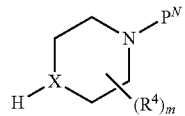

wherein Hal is Br, in the presence of a base, in a solvent, under conditions suitable to provide a compound of formula (v).

In some embodiments, the base is DIEA or TEA. In some embodiments, the solvent is DMF or NMP. In some embodiments, the contacting is performed at elevated temperature. In some embodiments, the temperature is between about 50° C. and about 70° C.

In some embodiments, the methods additionally comprise preparing a compound of formula

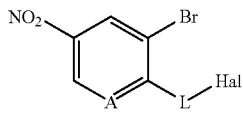

the methods comprising contacting a compound

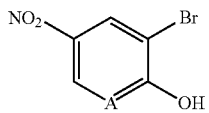

with Hal-L-Hal, wherein Hal is Br, in the presence of a base, in a solvent, under conditions suitable to provide a compound of formula

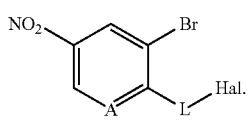

In some embodiments, the base is $K_2CO_3$ or $CsCO_3$. In some embodiments, the solvent is acetonitrile or DMF. In some embodiments, the contacting is performed at elevated temperature. In some embodiments, the temperature is between about 80° C. and about 100° C.

In some embodiments, the methods additionally comprise preparing a compound of formula (v)

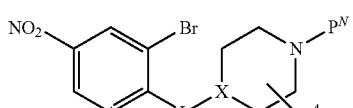

the methods comprising contacting a compound

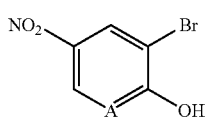

with a compound

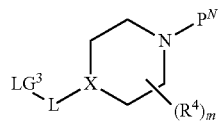

wherein $LG^3$ is OH, Br, Cl, OTs, or OMs, under conditions suitable to provide a compound of formula (v).

In some embodiments, $LG^3$ is Br, Cl, OTs, or OMs, and the contacting is performed in the presence of a base, in a solvent. In some embodiments, the base $CsCO_3$ or $K_2CO_3$. In some embodiments, the solvent is DMF, NMP, or acetonitrile. In some embodiments, the contacting is performed at elevated temperature. In some embodiments, the temperature is between about 40° C. and about 70° C. In other embodiments, $LG^3$ is —OH, and the contacting is performed in the presence of $PPh_3$ and DIAD or DEAD, in a solvent. In some embodiments, the solvent is THF. In some embodiments, the contacting is performed at room temperature.

In some embodiments, the methods additionally comprise preparing a compound of formula (ad)

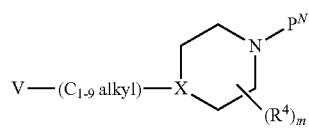

the methods comprising contacting a compound

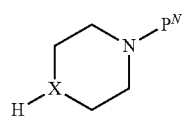

with V—($C_{1-9}$ alkyl)-C(=O)H, wherein $P^N$ is an amine protecting group, in the presence of a reducing agent, in a solvent, under conditions suitable to provide a compound of formula (ad).

In some embodiments, the reducing agent is sodium triacetoxyborohydride. In other embodiments, the solvent is MeOH.

In some embodiments, the methods additionally comprise preparing a compound of formula V—($C_{1-9}$ alkyl)-C(=O)H, the methods comprising contacting a compound of formula (ac)

V—($C_{2-9}$ alkyl)-OH (ac)

with an oxidizing agent, in a solvent, under conditions suitable to provide a compound of formula V—($C_{1-9}$ alkyl)-C(=O)H.

In some embodiments, the oxidizing agent is Dess-Martin periodinane (1,1,1-triacetoxy-1,1-dihydro-1,2-benziodoxol-3(1H)-one). In other embodiments, the solvent is DCM. In some embodiments, the contacting is performed at lower temperature. In one embodiment, the temperature is about 0° C.

In some embodiments, the methods additionally comprise preparing a compound of formula (ac)

V—($C_{2-9}$ alkyl)-OH (ac)

the methods comprising deprotecting a compound of formula (ab)

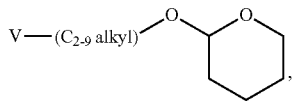
(ab)

under conditions suitable to provide a compound of formula (ac).

In some embodiments, the deprotection is performed by treatment with and acid in a solvent. In one embodiment, the acid is TsOH. In another embodiment, the solvent is a DCM/EtOH mixture.

In some embodiments, the methods additionally comprise preparing a compound of formula (ab)

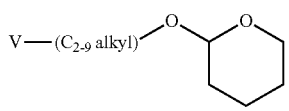
(ab)

the methods comprising contacting a compound of formula (aa)

V—OTf    (aa)

with THP-O($C_{2-9}$ alkyl)-zinc(II), in the presence of a catalyst and a ligand, in a solvent, under conditions suitable to provide a compound of formula (ab).

In some embodiments, the catalyst and a ligand are CPhosPdG3 and CPhos. In some embodiments, the solvent is toluene. In some embodiments, the contacting is performed at lower temperature. In some embodiments, the temperature is about 0° C.

In some embodiments, the methods additionally comprise preparing a compound of formula (aa)

V—OTf    (aa)

the methods comprising contacting V—OH with $Tf_2O$, in the presence of a base, in in a solvent, under conditions suitable to provide a compound of formula (aa).

In some embodiments, the base is DIEA or TEA. In other embodiments the solvent is DCM.

In one embodiment, provided herein is a method for preparing compound (ao)

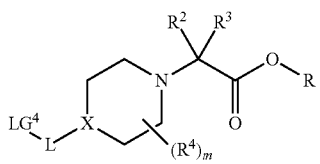
(ao)

wherein the method comprises contacting compound (ak)

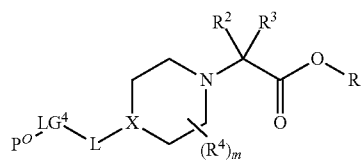
(ak)

where $P^O$ is an O-protecting group,
with a reducing agent in the presence of a catalyst, under conditions suitable to provide a compound of formula (ao).

In one embodiment, the contacting of compound (ak) with a reducing agent in the presence of a catalyst is in a solvent at a temperature between about 20° C. and about 30° C. under increased pressure.

In one embodiment, $P^O$ is benzyl group. In one embodiment, the reducing agent is $H_2$. In one embodiment, the catalyst is Pd/C or Pd(OH)$_2$. In one embodiment, the solvent is MeOH or EtOAc. In one embodiment, the pressure is increased to about 15 psi.

In one embodiment, the methods provided herein comprise preparing a compound of formula (ak),

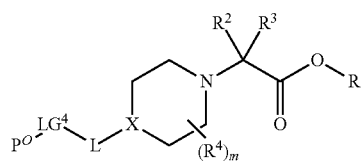
(ak)

wherein the method comprises contacting compound (aj)

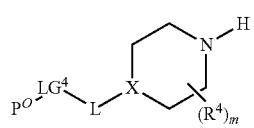
(aj)

with

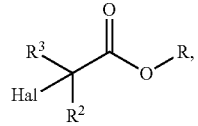

wherein R is alkyl and Hal is Cl or Br, under conditions suitable to provide a compound of formula (ak).

In some embodiments, R is $C_{1-4}$ alkyl. In one embodiment, R is methyl, ethyl, or t-butyl. In some embodiments, the contacting is performed in the presence of a base in a solvent. In some embodiments, the base is TEA, DBU or DIEA. In one embodiment, the solvent is THF, NMP, or DMF. In one embodiment, the contacting is conducted at a temperature between about 20° C. and about 80° C. In one embodiment, the contacting is conducted in the presence of NaI or KI.

In one embodiment, the methods provided herein comprise preparing a compound of formula (aj),

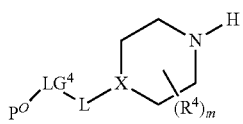
(aj)

wherein the method comprises contacting compound (ai)

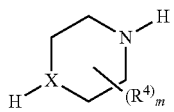
(ai)

with an alkylating agent

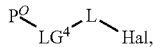

wherein $P^O$ is O-protecting group, under conditions suitable to provide a compound of formula (aj).

In one embodiment, $P^O$ is benzyl group, $LG^4$ is O, and Hal is Br or Cl. In one embodiment, the contacting is performed in the presence of a base in a solvent. In one embodiment, the contacting is performed in the presence of $CsCO_3$ in DMF, or $K_2CO_3$ in acetonitrile. In one embodiment, the contacting is conducted at an elevated temperature. In one embodiment, the temperature is between about 40° C. and about 70° C.

In one embodiment, provided herein is a method for preparing compound (ao)

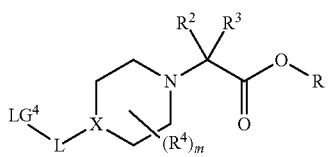
(ao)

wherein the method comprises contacting compound (an)

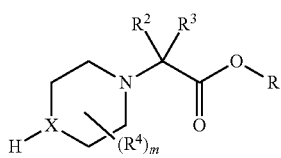
(an)

with $LG^4$-L-Hal, wherein $LG^4$ is Br, Cl or OH, and Hal is Br or Cl,
in the presence of a base in a solvent under conditions suitable to provide a compound of formula (ao).

In one embodiment, the base is DIEA, TEA or NMM. In one embodiment, the solvent is DMF or NMP. In one embodiment, the contacting is conducted at a temperature between about 50° C. and about 70° C.

In one embodiment, provided herein is a method for preparing compound (an)

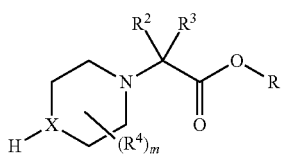
(an)

wherein the method comprises contacting compound (am)

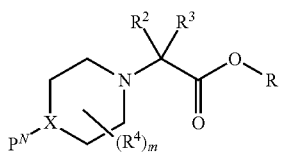
(am)

wherein $P^N$ is Boc group,
with an acid in a solvent, under conditions suitable to provide a compound of formula (an).

In one embodiment, the acid is TFA or HCl. In one embodiment the solvent is DCM, dioxane, MeOH or EtOH. In one embodiment, the acid and solvent is TFA in DCM, or HCl in dioxane/DCM, MeOH or EtOAc.

In one embodiment, the methods provided herein comprise preparing a compound of formula (am),

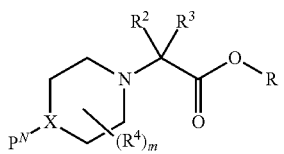
(am)

wherein the method comprises contacting N-protected piperazyl compound

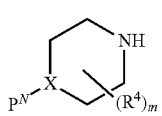

with

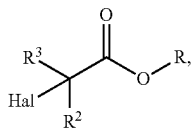

wherein $P^N$ is an N-protecting group, R is alkyl and Hal is Cl or Br, under conditions suitable to provide a compound of formula (am).

In one embodiment, $P^N$ is Boc group. In some embodiments, R is $C_{1-4}$ alkyl. In one embodiment, R is methyl, ethyl, or t-butyl. In some embodiments, the contacting is performed in the presence of a base in a solvent. In some embodiments, the base is TEA, DBU or DIEA. In one embodiment, the solvent is THF, NMP, or DMF. In one embodiment, the contacting is conducted at a temperature between about 20° C. and about 80° C. In one embodiment, the contacting is conducted in the presence of NaI or KI.

In one embodiment, the methods provided herein comprise preparing a compound of formula (c),

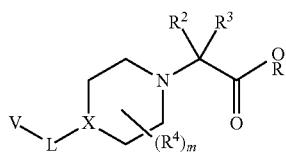

(c)

wherein the method comprises contacting compound (ao)

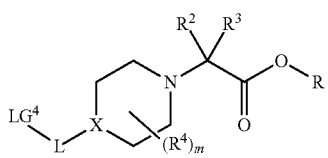

(ao)

with V—OH, wherein $LG^4$ is a leaving group, and R is alkyl, under conditions suitable to provide a compound of formula (c).

In one embodiment, $LG^4$ is —OH, and the contacting of (ao) with V—OH is conducted under Mitsunobu conditions, for example, in the presence of $PPh_3$ and DIAD or DEAD, in a solvent such as THF, at room temperature. In one embodiment, the leaving group $LG^4$ in compound (ao) is Br, Cl, OTs, or OMs, and the reaction with V—OH is performed in the presence of a base, in a solvent. In one embodiment, the base is $CsCO_3$ and the solvent is DMF. In one embodiment, the base is $K_2CO_3$ and the solvent is acetonitrile. In one embodiment, the reaction is conducted at an elevated temperature. In one embodiment, the reaction is conducted at a temperature between about 40° C. and about 70° C.

In one embodiment, the methods provided herein comprise preparing a compound of formula (as),

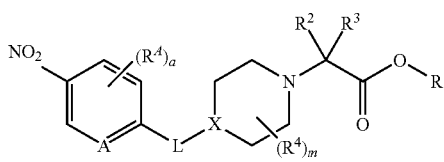

(as)

wherein the method comprises contacting compound (ao)

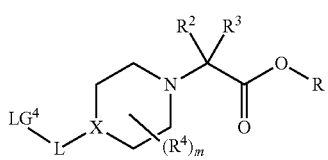

(ao)

with compound (ar)

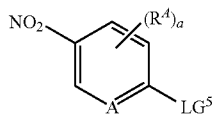

(ar)

wherein $LG^4$ is Br, Cl or OH, $LG^5$ is OH and A is CH or $CR^A$ or N, under conditions suitable to provide a compound of formula (as).

In one embodiment, $LG^4$ in compound (ao) is OH, and the reaction is performed in the presence of a base in a solvent. In one embodiment, the base is NaOtBu, $CsCO_3$ or $K_2CO_3$. In one embodiment, the solvent is acetonitrile, DMF or NMP. In one embodiment, the reaction is conducted at a temperature between about 0° C. and about 70° C.

In one embodiment, $LG^4$ in compound (ao) is OH, and the contacting of compound (ao) and compound (ar) is conducted under Mitsunobu conditions, for example, in the presence of $PPh_3$ and DIAD or DEAD, in a solvent such as THF, at room temperature to obtain compound (as).

In one embodiment, in compound (ao), $LG^4$ is OH; in compound (ar), $LG^5$ is F or Cl, and A is N; and the contacting of compound (ao) and compound (ar) is conducted in the presence of a base, in a solvent at a temperature between about 0° C. and about 70° C. to provide compound (as). In one embodiment, the base is NaOtBu, $CsCO_3$ or $K_2CO_3$. In one embodiment, the solvent is acetonitrile, DMF, THF or NMP.

In one embodiment, in compound (ao), $LG^4$ is OH; in compound (ar), $LG^5$ is F or Cl, and A is CH or $CR^A$; and the contacting of compound (ao) and compound (ar) is conducted in the presence of a base in a solvent at a temperature between about 0° C. and about 70° C. to provide compound (as). In one embodiment, the base is NaOtBu, $CsCO_3$ or $K_2CO_3$. In one embodiment, the solvent is acetonitrile, DMF, THE or NMP.

In one embodiment, the methods provided herein comprise preparing a compound of formula (as),

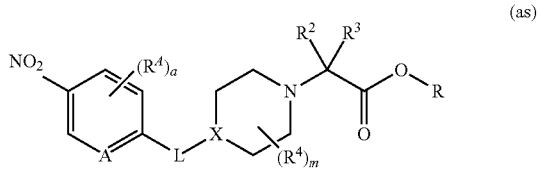

(as)

wherein the method comprises contacting compound (an)

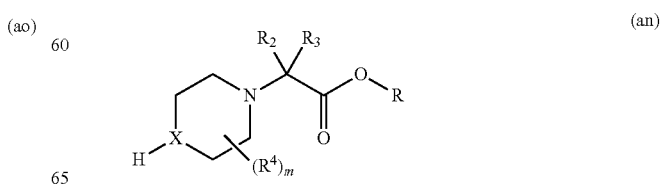

(an)

with compound (aq)

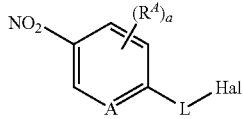
(aq)

in the presence of a base, in a solvent, under conditions suitable to provide a compound of formula (as).

In one embodiment, the base is NaOtBu, CsCO$_3$ or K$_2$CO$_3$. In one embodiment, the solvent is acetonitrile, DMF, THE or NMP. In one embodiment, the contacting is performed at a temperature between about 0° C. and about 70° C.

In one embodiment, the methods provided herein comprise preparing a compound of formula (aq),

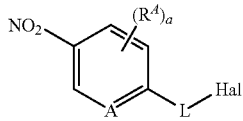
(aq)

wherein the method comprises contacting compound (ap)

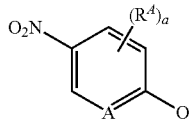
(ap)

wherein A is CH, CR$^{A'}$ or N;

with LG$^6$-L-Hal, in a solvent, under conditions suitable to provide a compound of formula (aq).

In one embodiment, LG$^6$ is Br or Cl, and Hal is Cl or Br, and the contacting is performed in the presence of a base. In some such embodiments, the base is NaOtBu, CsCO$_3$ or K$_2$CO$_3$. In one embodiment, the solvent is acetonitrile, DMF, THE or NMP. In one embodiment, the contacting is performed at a temperature between about 0° C. and about 90° C.

In one embodiment, LG$^6$ is OH, and the contacting is performed in the presence of PPh$_3$ and DIAD or DEAD. In one embodiment, the solvent is THF. In one embodiment, the contacting is performed at room temperature.

In some embodiments, the methods provided herein comprise preparing a compound of formula (c)

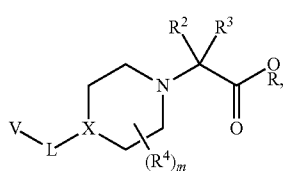
(c)

wherein L is —O(C$_{1-6}$ alkyl)-, the method comprising contacting a compound of formula (av)

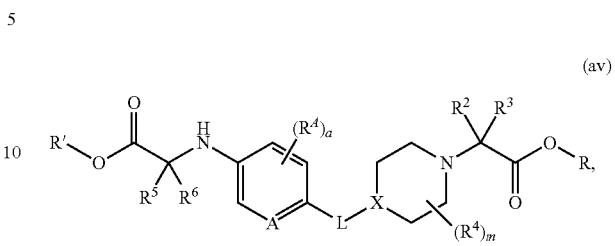
(av)

with compound

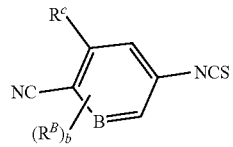

wherein B is CH, CR$^B$ or N, with base in a solvent, under conditions suitable to provide a compound of formula (c).

In one embodiment, the solvent is EtOAc. In one embodiment, the base is TEA. In one embodiment, the contacting is performed at a temperature between about 60° C. and about 90° C.

In some embodiments, the methods provided herein comprise preparing a compound of formula (av)

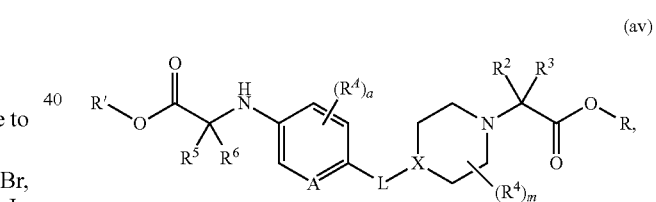
(av)

the methods comprising contacting a compound of formula (at)

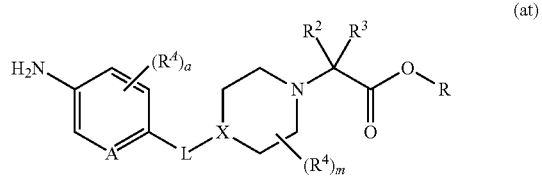
(at)

with R'OOC—C(R$^5$)(R$^6$)Hal, wherein Hal is Br or Cl and R' is C$_{1-3}$ alkyl, in presence of a base under conditions suitable to provide a compound of formula (av).

In one embodiment, the base is NaHCO$_3$, DIEA or TEA. In one embodiment, the contacting is conducted at a temperature of between about 90° C. and about 130° C.

In some embodiments, the methods provided herein comprise preparing a compound of formula (at)

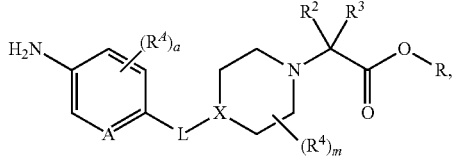

(at)

the methods comprising contacting a compound of formula (as)

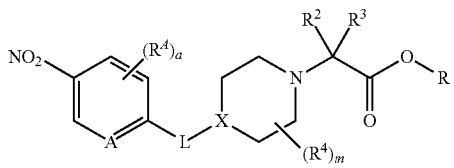

(as)

with a reducing agent, in a solvent in the presence of a catalyst under increased pressure, under conditions suitable to obtain a compound of formula (at).

In one embodiment, the reducing agent is H$_2$ in MeOH or EtOH. In one embodiment, the catalyst is Pd/C. In one embodiment, the pressure is about 50 psi. In one embodiment, the contacting is performed at a temperature of about 80° C.

In some embodiments, the methods provided herein comprise preparing a compound of formula (c)

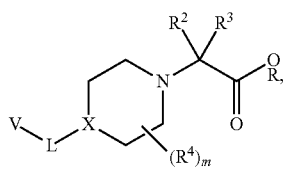

(c)

wherein L is —O(C$_{1-6}$ alkyl)-,
the methods comprising contacting a compound of formula (au)

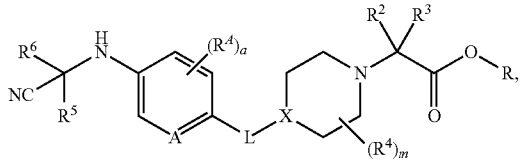

(au)

with compound

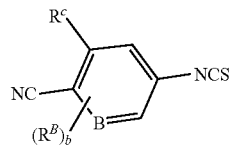

wherein B is CH, CR$^B$ or N, in a solvent, followed by treatment with an acid in a solvent, under conditions suitable to provide a compound of formula (c).

In one embodiment, the solvent is DMF or DMA. In one embodiment, the acid is HCl. In one embodiment, the acid is in a solvent, such as MeOH or EtOH. In one embodiment, the contacting is performed at a temperature between about 70° C. and about 80° C.

In some embodiments, the methods provided herein comprise preparing a compound of formula (at)

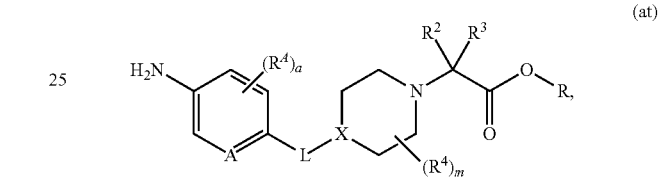

(at)

wherein R$^A$ is substituted or unsubstituted C$_{2-6}$ alkyl, substituted or unsubstituted cyclopropyl or substituted or unsubstituted C$_{5-6}$ cycloalkyl, and L is —O(C$_{1-6}$ alkyl)-,
the methods comprising contacting a compound of formula (as)

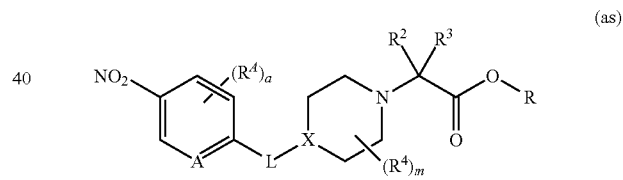

(as)

with a reducing agent, in a solvent in the presence of a catalyst, under conditions suitable to obtain a compound of formula (at).

In one embodiment, the reducing agent is H$_2$ in MeOH or EtOH. In one embodiment, the catalyst is Pd/C. In one embodiment, the contacting is performed at a temperature between about 20° C. and about 30° C.

In some embodiments, the methods provided herein comprise preparing a compound of formula (as)

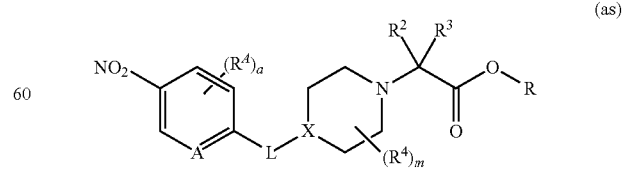

(as)

wherein R$^A$ is substituted or unsubstituted C$_{2-6}$ alkenyl, substituted or unsubstituted cyclopropyl, or substituted or unsubstituted C$_{5-6}$ cycloalkenyl;

the methods comprising contacting a compound of formula (as)

(as)

wherein $R^A$ is Br,
with a boronate $R^{A'}[B(OR^+)_2]_2$,
wherein $R^{A'}$ is substituted or unsubstituted $C_{2-6}$ alkenyl, substituted or unsubstituted cyclopropyl, or substituted or unsubstituted $C_{5-6}$ cycloalkenyl, and $R^+$ together with the boron atom and the atoms to which they are attached, forms a cyclic boronate, in the presence of a palladium catalyst and a base in a solvent, under conditions suitable to provide a compound of formula (as), wherein $R^A$ is substituted or unsubstituted $C_{2-6}$ alkenyl, substituted or unsubstituted cyclopropyl, or substituted or unsubstituted $C_{5-6}$ cycloalkenyl.

In one embodiment, the cyclic boronate is 4,4,4',4',5,5,5',5'-octamethyl-2,2'-bi(1,3,2-dioxaborolane). In one embodiment, the catalyst is Pd(dppf)$_2$Cl$_2$. In one embodiment, the base is K$_3$PO$_4$. In one embodiment, the solvent is a 1,4-dioxane/water mixture.

In one embodiment, provided herein are compounds having the following formula (V-L-Hal):

V-L-Hal or a pharmaceutically acceptable salt, tautomer, isotopolog, or stereoisomer thereof, where the variables are as described elsewhere herein.

In one embodiment, provided herein is a compound of formula (a), wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or CF$_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3;
b is 0-2
L is —O(C$_{1-6}$ alkyl)- or —(C$_{1-9}$ alkyl)-; and
Hal is Cl, Br, OMs or OTs;

In one embodiment, provided herein are compounds having the following formula (a):

(a)

or a pharmaceutically acceptable salt, tautomer, isotopolog, or stereoisomer thereof, where the variables are as described elsewhere herein.

In one embodiment, provided herein is a compound of formula (a), wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or CF$_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3;
b is 0-2
X is N;
L is —O(C$_{1-6}$ alkyl)- or —(C$_{1-9}$ alkyl)-;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
m is 0-8; and
$P^N$ is an amine protecting group.

In one embodiment, $P^N$ is tert-butyloxycarbonyl or carboxybenzyl.

In one embodiment, provided herein are compounds having the following formula (a1):

(a$_1$)

or a pharmaceutically acceptable salt, tautomer, isotopolog, or stereoisomer thereof, wherein $R^x$ is $C_{1-4}$ alkyl, and the remaining variables are as described elsewhere herein.

In one embodiment, provided herein is a compound of formula (a1), wherein
A is N, CH, or CR$^A$;
B is N, CH, or CR$^B$;
each R$^A$ is independently selected from halogen, substituted or unsubstituted C$_{1-6}$ alkyl, and substituted or unsubstituted C$_{3-6}$ cycloalkyl;
each R$^B$ is independently selected from halogen, and substituted or unsubstituted C$_{1-6}$ alkyl;
R$^C$ is halogen or CF$_3$;
R$^5$ and R$^6$ are C$_{1-3}$ alkyl, or R$^5$ and R$^6$, together with the carbon atom to which they are attached, form a substituted or unsubstituted C$_{3-6}$ cycloalkyl or a 3-6 membered heterocyclyl;
a is 0-3;
b is 0-2
X is N;
L is —O(C$_{1-6}$ alkyl)- or —(C$_{1-9}$ alkyl)-;
each R$^4$ is independently substituted or unsubstituted C$_{1-3}$ alkyl, or two R$^4$ groups, together with the same carbon atom or adjacent carbon atoms to which they are attached, form a substituted or unsubstituted C$_{3-6}$ cycloalkyl, or two R$^4$ groups together with the non-adjacent carbon atoms to which they are attached form a substituted or unsubstituted 4-7-membered heterocyclyl;
m is 0-8; and
R$^x$ is C$_{1-4}$ alkyl.

In one embodiment, provided herein are compounds having the following formula (b):

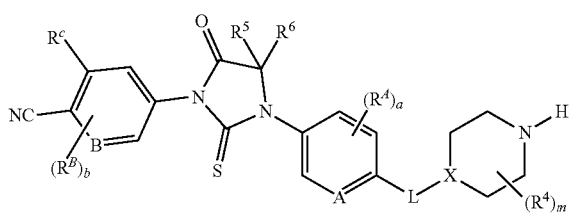

(b)

or a pharmaceutically acceptable salt, tautomer, isotopolog, or stereoisomer thereof, where the variables are as described elsewhere herein.

In one embodiment, provided herein is a compound of formula (b), wherein
A is N, CH, or CR$^A$;
B is N, CH, or CR$^B$;
each R$^A$ is independently selected from halogen, substituted or unsubstituted C$_{1-6}$ alkyl, and substituted or unsubstituted C$_{3-6}$ cycloalkyl;
each R$^B$ is independently selected from halogen, and substituted or unsubstituted C$_{1-6}$ alkyl;
R$^C$ is halogen or CF$_3$;
R$^5$ and R$^6$ are C$_{1-3}$ alkyl, or R$^5$ and R$^6$, together with the carbon atom to which they are attached, form a substituted or unsubstituted C$_{3-6}$ cycloalkyl or a 3-6 membered heterocyclyl;
a is 0-3;
b is 0-2
X is N;
L is —O(C$_{1-6}$ alkyl)- or —(C$_{1-9}$ alkyl)-;
each R$^4$ is independently substituted or unsubstituted C$_{1-3}$ alkyl, or two R$^4$ groups, together with the same carbon atom or adjacent carbon atoms to which they are attached, form a substituted or unsubstituted C$_{3-6}$ cycloalkyl, or two R$^4$ groups together with the non-adjacent carbon atoms to which they are attached form a substituted or unsubstituted 4-7-membered heterocyclyl; and
m is 0-8.

In one embodiment, provided herein are compounds having the following formula (c):

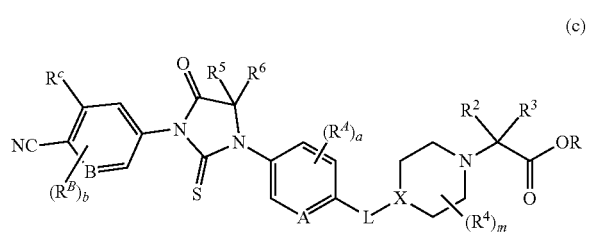

(c)

or a pharmaceutically acceptable salt, tautomer, isotopolog, or stereoisomer thereof, where the variables are as described elsewhere herein.

In one embodiment, provided herein is a compound of formula (c), wherein
A is N, CH, or CR$^A$;
B is N, CH, or CR$^B$;
each R$^A$ is independently selected from halogen, substituted or unsubstituted C$_{1-6}$ alkyl, and substituted or unsubstituted C$_{3-6}$ cycloalkyl;
each R$^B$ is independently selected from halogen, and substituted or unsubstituted C$_{1-6}$ alkyl;
R$^C$ is halogen or CF$_3$;
R$^5$ and R$^6$ are C$_{1-3}$ alkyl, or R$^5$ and R$^6$, together with the carbon atom to which they are attached, form a substituted or unsubstituted C$_{3-6}$ cycloalkyl or a 3-6 membered heterocyclyl;
a is 0-3;
b is 0-2
X is N;
L is —O(C$_{1-6}$ alkyl)- or —(C$_{1-9}$ alkyl)-;
each R$^4$ is independently substituted or unsubstituted C$_{1-3}$ alkyl, or two R$^4$ groups, together with the same carbon atom or adjacent carbon atoms to which they are attached, form a substituted or unsubstituted C$_{3-6}$ cycloalkyl, or two R$^4$ groups together with the non-adjacent carbon atoms to which they are attached form a substituted or unsubstituted 4-7-membered heterocyclyl;
m is 0-8;
R$^2$ and R$^3$ are each independently selected from H, and C$_{1-3}$ alkyl, or R$^2$ and R$^3$ and the carbon to which they are attached form a substituted or unsubstituted C$_{3-6}$ cycloalkyl; and
R is C$_{1-4}$ alkyl.

In one embodiment, provided herein are compounds having the following formula (d):

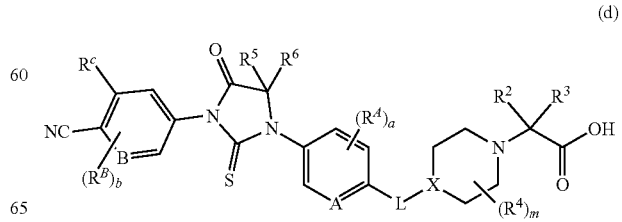

(d)

or a pharmaceutically acceptable salt, tautomer, isotopolog, or stereoisomer thereof, where the variables are as described elsewhere herein.

In one embodiment, provided herein is a compound of formula (d), wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3;
b is 0-2
X is N;
L is —O($C_{1-6}$ alkyl)- or —($C_{1-9}$ alkyl)-;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
m is 0-8; and
$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl.

In one embodiment, provided herein are compounds having the following formula (t):

(t)

or a pharmaceutically acceptable salt, tautomer, isotopolog, or stereoisomer thereof, where the variables are as described elsewhere herein.

In one embodiment, provided herein is a compound of formula (t), wherein
A is N, CH, or $CR^A$;
B is N, CH, or $CR^B$;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
b is 0-2
X is N;
L is —O($C_{1-6}$ alkyl)- or —($C_{1-9}$ alkyl)-;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
m is 0-8; and
$P^N$ is an amine protecting group.

In one embodiment, $P^N$ is tert-butyloxycarbonyl or carboxybenzyl.

In one embodiment, provided herein are compounds having the following formula (u):

(u)

or a pharmaceutically acceptable salt, tautomer, isotopolog, or stereoisomer thereof, where the variables are as described elsewhere herein.

In one embodiment, provided herein is a compound of formula (u), wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
b is 0-2
X is N;
L is —O($C_{1-6}$ alkyl)- or —($C_{1-9}$ alkyl)-;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
m is 0-8; and
$P^N$ is an amine protecting group.

In one embodiment, $P^N$ is tert-butyloxycarbonyl or carboxybenzyl.

In one embodiment, provided herein are compounds having the following formula (ab):

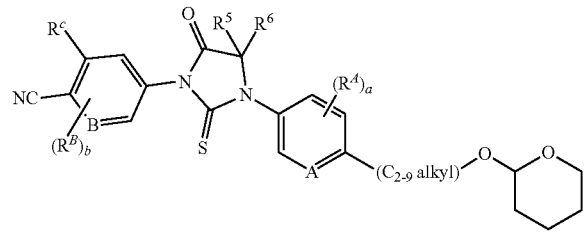

(ab)

or a pharmaceutically acceptable salt, tautomer, isotopolog, or stereoisomer thereof, where the variables are as described elsewhere herein.

In one embodiment, provided herein is a compound of formula (ab),
wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3; and
b is 0-2.

In one embodiment, provided herein are compounds having the following formula (ac):

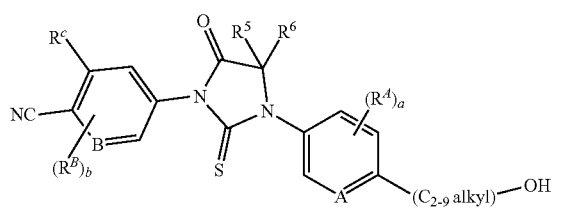

(ac)

or a pharmaceutically acceptable salt, tautomer, isotopolog, or stereoisomer thereof, where the variables are as described elsewhere herein.

In one embodiment, provided herein is a compound of formula (ac),
wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3; and
b is 0-2.

In one embodiment, provided herein are compounds having the following formula (ad):

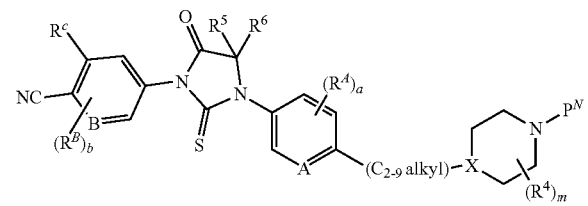

(ad)

or a pharmaceutically acceptable salt, tautomer, isotopolog, or stereoisomer thereof, where the variables are as described elsewhere herein.

In one embodiment, provided herein is a compound of formula (ad), wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3;
b is 0-2
X is N;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
m is 0-8; and
$P^N$ is an amine protecting group.

In one embodiment, $P^N$ is tert-butyloxycarbonyl or carboxybenzyl.

Methods of Use

In one embodiment, the compounds described herein have utility as pharmaceuticals to treat, prevent or improve conditions in animals or humans. The Piperidine Dione Compounds described herein have utility as pharmaceuticals to treat, prevent or improve conditions in animals or humans. Accordingly, provided herein are many uses of Piperidine Dione Compounds, including the treatment or prevention of those diseases set forth below. In one embodiment, the methods provided herein comprise the administration of an effective amount of a compound to a subject in need thereof.

The methods provided herein comprise the administration of an effective amount of one or more Piperidine Dione Compound(s) to a subject in need thereof.

Provided herein are methods for treating or preventing an androgen receptor (AR) mediated disease in a subject, the method comprising administering to a subject in need thereof an effective amount of a compound as described herein.

Provided herein are methods for treating or preventing an AR mediated disease in a subject, the method comprising administering to a subject in need thereof an effective amount of a Piperidine Dione Compound as described herein.

In another aspect, provided herein are compounds for use in the treatment or prevention of an AR mediated disease in a subject, comprising administering to a subject in need thereof an effective amount of a Piperidine Dione Compound as described herein. In some embodiments, provided herein are compounds for use in the treatment of an AR mediated disease in a subject, comprising administering to a subject in need thereof an effective amount of a Piperidine Dione Compound as described herein. In some embodiments, provided herein are compounds for use in the prevention of an AR mediated disease in a subject, comprising administering to a subject in need thereof an effective amount of a Piperidine Dione Compound as described herein.

In some embodiments, the compound used in the methods herein is a Piperidine Dione Compound as described herein. In some embodiments, the compound is a compound of formula (I). In some embodiments, the compound is a compound of formula (II). In some embodiments, the compound is a compound of formula (III). In some embodiments, the compound is a compound of formula (IV). In some embodiments, the compound is a compound of formula (V). In some embodiments, the compound is a compound of formula (VI). In some embodiments, the compound is a compound of formula (VII). In some embodiments, the compound is a compound of formula (VIII). In some embodiments, the compound is a compound of formula (IX). In some embodiments, the compound is a compound of formula (X). In some embodiments, the compound is a compound of formula (a). In some embodiments, the compound is a compound of formula (b). In some embodiments, the compound is a compound of formula (c). In some embodiments, the compound is a compound of formula (d). In some embodiments, the compound is a compound of formula (t). In some embodiments, the compound is a compound of formula (u). In some embodiments, the compound is a compound of formula (ab). In some embodiments, the compound is a compound of formula (ac). In some embodiments, the compound is a compound of formula (ad). In some embodiments, the compound is a compound from Table 1.

In some embodiments, the AR mediated disease is AR wild-type mediated disease. In other embodiments, the AR mediated disease is the result of AR amplification.

In certain embodiments, the AR mediated disease is prostate cancer. In some such embodiments, the prostate cancer is castration resistant prostate cancer (CRPC). In some such embodiments, the prostate cancer is metastatic castration resistant prostate cancer (mCRPC). In still another embodiment, the prostate cancer is non-metastatic CRPC (nmCRPC). In some embodiments, the prostate cancer is hormone refractory. In some embodiments, the prostate cancer is resistant to treatment with an AR antagonist. For example, the prostate cancer is resistant to treatment with enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, or spironolactone.

Provided herein are methods of reducing AR levels, the method comprising administering to a subject an effective amount of a Piperidine Dione Compound. Also provided herein are Piperidine Dione Compounds for use in methods of reducing AR levels in a cell in vivo, ex vivo or in vitro, comprising contacting the cell with an effective amount of a Piperidine Dione Compound. In one embodiment, the cell is in a patient. In one embodiment, the cell is not in a patient. In one embodiment, provided herein are methods of reducing levels of wild-type AR within a tumor, the method comprising administering a therapeutically effective amount of a Piperidine Dione Compound, to reduce the level of wild-type AR within the tumor. In one embodiment, provided herein are methods of reducing levels of AR-full length (AR-FL) within a tumor, the method comprising administering a therapeutically effective amount of a Piperidine Dione Compound, to reduce the level of AR-full length (AR-FL) within the tumor. In some embodiments, the AR levels are reduced compared to the AR levels prior to Piperidine Dione Compound administration. In some embodiments, the AR levels are reduced by 20%, 30%, 40%, 50%, 60%, 70%, 80%, 90%, 95%, or 99% compared to the AR levels prior to Piperidine Dione Compound administration.

Also provided herein are methods for regulating protein activity of AR in a patient in need thereof, comprising administering to said patient an amount of a Piperidine Dione Compound. In some such embodiments, provided herein are methods for decreasing protein activity of AR in a patient in need thereof, comprising administering to said patient an amount of a Piperidine Dione Compound. In some embodiments, the protein activity of AR is reduced compared to the protein activity of AR prior to Piperidine Dione Compound administration. In some embodiments, the protein activity of AR is reduced by 20%, 30%, 40%, 50%, 60%, 70%, 80%, 90%, 95%, or 99% compared to the protein activity of AR prior to Piperidine Dione Compound administration.

In some embodiments of the methods described herein, the methods additionally comprise administering one or more second agents selected from an AR antagonist (such as cyproterone acetate, spironolactone, bicalutamide, and enzalutamide), a 5α-reductase inhibitor (such as finasteride and dutasteride), a CYP17A1 inhibitor (such as abiraterone acetate), a gonadotropin-releasing hormone (GnRH) analog (such as leuprorelin and cetrorelix), and an anti-gonadotropin (such as megestrol acetate and medroxyprogesterone acetate).

In some embodiments, the compounds provided herein may be used in any of the above-mentioned methods.

In some embodiments, the Piperidine Dione Compound provided herein may be used in any of the above-mentioned methods.

Pharmaceutical Compositions and Routes of Administration

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The Piperidine Dione Compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Piperidine Dione Compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a Piperidine Dione Compound to be administered to a subject is rather widely variable and can be subject to the judgment of a health-care practitioner. In general, the Piperidine Dione Compounds can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the Piperidine Dione Compound administered will depend on such factors as the solubility of the active component, the formulation used and the route of administration.

In another embodiment, provided herein are methods for the treatment or prevention of a disease or disorder comprising the administration of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day of a Piperidine Dione Compound to a subject in need thereof.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a Piperidine Dione Compound.

In a particular embodiment, provided herein are unit dosage formulations comprising about 0.1 mg or 100 mg of a Piperidine Dione Compound.

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Piperidine Dione Compound.

An Piperidine Dione Compound can be administered once, twice, three, four or more times daily. In a particular embodiment, doses of 100 mg or less are administered as a once daily dose and doses of more than 100 mg are administered twice daily in an amount equal to one half of the total daily dose.

An Piperidine Dione Compound can be administered orally for reasons of convenience. In one embodiment, when administered orally, a Piperidine Dione Compound is administered with a meal and water. In another embodiment, the Piperidine Dione Compound is dispersed in water or juice (e.g., apple juice or orange juice) or any other liquid and administered orally as a solution or a suspension.

The Piperidine Dione Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Piperidine Dione Compound without an additional carrier, excipient or vehicle.

In another embodiment, provided herein are compositions comprising an effective amount of a Piperidine Dione Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Piperidine Dione Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Piperidine Dione Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Piperidine Dione Compound can be delayed or prolonged by proper formulation. For example, a slowly soluble pellet of the Piperidine Dione Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Piperidine Dione Compound in oily or emulsified vehicles that allow it to disperse slowly in the serum.

Examples

The following Examples are presented by way of illustration, not limitation. Compounds are named using the automatic name generating tool provided in Chemfliodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

Abbreviations Used:

| | |
|---|---|
| Boc | tert-Butyloxycarbonyl |
| $Boc_2O$ | di-tert-Butyl dicarbonate |
| nBuLi | n-Butyllithium |
| CataCXium ® A Palladacycle | Methanesulfonato(diadamantyl-n-butylphosphino)-2'-amino-1,1'-biphenyl-2-yl)palladium(II) dichloromethane adduct |
| Gen. 3 | |
| Cbz | Carboxybenzyl |
| CPhos | 2-(2-Dicyclohexylphosphanylphenyl)-$N^1,N^1,N^3,N^3$-tetramethyl-benzene-1,3-diamine |
| CPhosPdG3 | [(2-Dicyclohexylphosphino-2',6'-bis(N,N-dimethylamino)-1',1'-biphenyl)-2-(2'-amino-1,1'-biphenyl)] palladium(II) methanesulfonate |
| DCM | Dichloromethane |
| DIAD | Diisopropyl azodicarboxylate |
| DEAD | Diethyl azodicarboxylate |
| DIEA | N,N-Diisopropylethylamine |
| DMA | N,N-Dimethylacetamide |
| DMF | N,N-Dimethylformamide |
| DMSO | Dimethylsulfoxide |
| ESI | Electrospray ionization |
| EtOH | Ethanol |
| EtOAc | Ethyl acetate |
| $FeCl_2$ | Iron(II) chloride |
| HATU | 1-[Bis(dimethylamino)methylene]-1H-1,2,3-triazolo[4,5-b]pyridinium 3-oxide hexafluorophosphate |
| HPLC | High performance liquid chromatography |
| HTRF | Homogeneous time resolved fluorescence |
| LCMS | Liquid chromatography mass spectrometry |
| MeOH | Methanol |
| MS | Mass spectrometry |
| MTBE | Methyl tert-butyl ether |
| NMP | N-Methylpyrrolidone |
| NMR | Nuclear magnetic resonance |
| OMs | Mesylate |
| OTs | Tosylate |
| Pd/C | Palladium on carbon |
| $Pd(dppf)_2Cl_2$ | [1,1'-Bis(diphenylphosphino)ferrocene] dichloropalladium(II) |
| $PPh_3$ | Triphenylphosphine |
| TEA | Triethylamine |
| TFA | Trifluoroacetic acid |
| $Tf_2O$ | Triflic anhydride |
| THF | Tetrahydrofuran |
| THP | Tetrahydropyrane |
| TLC | Thin layer chromatography |
| TMSCl | Trimethylsilyl chloride |
| TMSCN | Trimethylsilyl cyanide |
| TMSOTf | Trimethylsilyl trifluoromethanesulfonate |
| TsOH | p-Toluenesulfonic acid |

Compound Synthesis

Example 1: 2-(4-(2-(4-(3-(6-Cyano-5-(trifluoromethyl)pyridin-3-yl)-5,5-dimethyl-4-oxo-2-thioxoimidazolidin-1-yl)phenoxy)ethyl)piperazin-1-yl)-N-(3-((2,6-dioxopiperidin-3-yl)amino)phenyl)acetamide formate

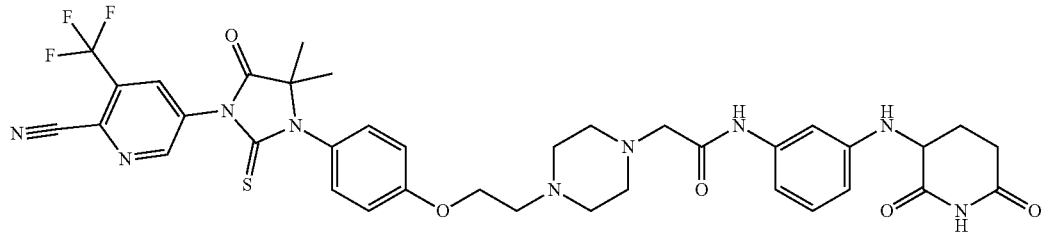 [SMILES: CC1(C)C(=O)N(c2cnc(C#N)c(C(F)(F)F)c2)C(=S)N1c1ccc(OCCN2CCN(CC(=O)Nc3cccc(NC4CCC(=O)NC4=O)c3)CC2)cc1]

5-Isothiocyanato-3-(trifluoromethyl)pyridine-2-carbonitrile To a solution of thiocarbonyl dichloride (75.9 g, 0.66 mol) in water (1000 mL) was added 5-amino-3-(trifluoromethyl)pyridine-2-carbonitrile (95.0 g, 0.508 mol) slowly in portions. The reaction mixture was stirred at 25° C. for 4 h. The reaction mixture was extracted with EtOAc (1000 mL×2). The combined organic layers were dried over anhydrous sodium sulfate, filtered, and concentrated. The residue was purified by silica gel column chromatography (0-10% EtOAc in petroleum ether) to give 5-isothiocyanato-3-(trifluoromethyl)pyridine-2-carbonitrile (86.0 g, 73.9% yield) as yellow oil. $^1$H NMR (400 MHz, CDCl$_3$) δ ppm 8.66 (d, J=2.0 Hz, 1H), 7.79 (d, J=2.0 Hz, 1H).

2-(4-Hydroxyanilino)-2-methyl-propanenitrile. To a solution of 4-aminophenol (80.0 g, 0.733 mmol) in DCM (1600 mL) and acetone (400 mL) was added trimethylsilyl trifluoromethanesulfonate (8.15 g, 36.7 mmol) and trimethylsilyl-formonitrile (102 g, 1.03 mol). The reaction mixture was stirred at 25° C. for 16 h. The reaction solution was concentrated under reduced pressure and the residue was purified by recrystallization from MTBE (500 mL) and dried to give 2-(4-hydroxyanilino)-2-methyl-propanenitrile (85.0 g, 65.8% yield) as an off-white solid. $^1$H NMR (400 MHz, DMSO-d$_6$) δ ppm 8.90 (s, 1H), 6.78-6.77 (m, 2H), 6.66-6.63 (m, 2H), 5.20 (s, 1H), 1.51 (s, 6H).

5-[3-(4-Hydroxyphenyl)-4,4-dimethyl-5-oxo-2-thioxoimidazolidin-1-yl]-3-(trifluoromethyl)pyridine-2-carbonitrile. To a solution of 2-(4-hydroxyanilino)-2-methyl-propanenitrile (53.0 g, 0.301 mol) in DMA (500 mL) was added 5-isothiocyanato-3-(trifluoromethyl)pyridine-2-carbonitrile (72.4 g, 0.316 mol) at 28° C. The reaction mixture was stirred at 28° C. for 2 h. The reaction solution was mixed with MeOH (500 mL) and aqueous HCl (2 M, 500 mL), and warmed up to 70° C. After stirring for 2 h, the reaction solution was cooled down to 30° C., mixed with water (500 mL) and extracted with EtOAc (1000 mL×2). The combined organic phases were washed with saturated sodium chloride solution (500 mL×2), dried over anhydrous sodium sulfate, and filtered. The filtrate was concentrated under reduced pressure and the residue was recrystallized from EtOAc (100 mL) to give 5-[3-(4-hydroxyphenyl)-4,4-dimethyl-5-oxo-2-thioxo-imidazolidin-1-yl]-3-(trifluoromethyl)pyridine-2-carbonitrile (41.5 g, 33.9% yield) as a white solid. $^1$H NMR (400 MHz, CDCl$_3$) δ ppm 9.10 (s, 1H), 8.37 (d, J=2.4 Hz, 1H), 7.17 (dd, J=2.0, 6.4 Hz, 2H), 6.97 (dd, J=2.0, 6.4 Hz, 2H), 5.23 (s, 1H), 1.59 (s, 6H).

tert-butyl 4-(2-(4-(3-(6-Cyano-5-(trifluoromethyl)pyridin-3-yl)-5,5-dimethyl-4-oxo-2-thioxoimidazolidin-1-yl)phenoxy)ethyl)piperazine-1-carboxylate. 5-(3-(4-Hydroxyphenyl)-4,4-dimethyl-5-oxo-2-thioxoimidazolidin-1-yl)-3-(trifluoromethyl)picolinonitrile (2.00 g, 4.92 mmol), tert-butyl 4-(2-bromoethyl)piperazine-1-carboxylate (1.44 g, 4.92 mmol) and cesium carbonate (2.40 g, 7.38 mmol) were combined in DMF (12 mL) and the mixture was heated to 45° C. in a screw capped scintillation vial. After 48 h, the solution was filtered, the solid washed with additional MeOH in DCM, and the combined filtrate was concentrated under reduced pressure to afford a yellow oil that partially solidified. The solid was purified by silica gel column chromatography (0-100% EtOAc in hexanes) to afford the title compound as an off-white solid (0.971 g, 1.57 mmol, 31.9% yield). MS (ESI) m/z 619 [M+1]$^+$.

5-(4,4-Dimethyl-5-oxo-3-(4-(2-(piperazin-1-yl)ethoxy)phenyl)-2-thioxoimidazolidin-1-yl)-3-(trifluoromethyl)picolinonitrile trihydrochloride. tert-butyl 4-(2-(4-(3-(6-Cyano-5-(trifluoromethyl)pyridin-3-yl)-5,5-dimethyl-4-oxo-2-thioxoimidazolidin-1-yl)phenoxy)ethyl)piperazine-1-carboxylate (0.971 g, 1.57 mmol) was dissolved in DCM (4 mL), and a 4.0 M solution of HCl in dioxane (0.572 mL, 18.8 mmol) was added. After 90 min, the solution was concentrated under reduced pressure to afford the title compound as a yellow solid (1.07 g, 1.7 mmol, quant. yield). MS (ESI) m/z 519 [M+1]$^+$.

Methyl 2-(4-(2-(4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)acetate. 5-(4,4-Dimethyl-5-oxo-3-(4-(2-(piperazin-1-yl)ethoxy)phenyl)-2-thioxoimidazolidin-1-yl)-3-(trifluoromethyl)picolinonitrile trihydrochloride (0.400 g, 0.637 mmol) and TEA (0.444 mL, 3.19 mmol) were combined in THF (3 mL). After stirring for 2 min, methyl 2-bromoacetate (0.065 mL, 0.637 mmol) was added and the mixture was stirred at ambient temperature in a screw-capped flask. After 30 min, the solution was loaded on a silica gel column for chromatographic purification (0-100% EtOAc in hexanes followed by 10% MeOH in EtOAc) to afford the title compound (0.273 g, 0.462 mmol, 72.6% yield). MS (ESI) m/z 591 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)phenoxy)ethyl)piperazin-1-yl)acetic acid. Methyl 2-(4-(2-(4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)

acetate (0.273 g, 0.462 mmol) was dissolved in THF (1 mL) and treated with a solution of lithium hydroxide hydrate (0.213 g, 5.08 mmol) in water (1.000 mL). The mixture was stirred at ambient temperature for 16 h, and then concentrated under reduced pressure. To the resulting yellow oil were added water (3 mL) and a 3.0 M aqueous solution of HCl to lower the pH to 4-5. The material was partitioned between 15% MeOH in DCM and water (75 mL). The aqueous phase was extracted with DCM and the combined organic layers were dried over magnesium sulfate, filtered, and concentrated under reduced pressure to afford the title compound as an off-white solid (0.135 g, 0.234 mmol, 51.0% yield). MS (ESI) m/z 577 [M+1]$^+$.

tert-Butyl N-[3-[(2,6-dioxo-3-piperidyl)amino]phenyl] carbamate. To a solution of 3-bromopiperidine-2,6-dione (120 g, 0.470 mol) in DMF (1 L) was added tert-butyl N-(3-aminophenyl)carbamate (81.4 g, 0.390 mol) and the mixture was stirred at 80° C. for 12 h, then was poured into water (2500 mL) slowly, and filtered. The solid was washed with EtOAc (200 mL) and dried to give tert-butyl N-[3-[(2,6-dioxo-3-piperidyl)amino]phenyl]carbamate (56.0 g, crude) as a blue solid. $^1$H NMR (400 MHz, DMSO-d$_6$) δ ppm 10.78 (s, 1H), 9.04 (s, 1H), 6.96-6.92 (m, 1H), 6.87 (s, 1H), 6.67 (d, J=8.0 Hz, 1H), 6.31 (dd, J=1.6 Hz, 8.0 Hz, 1H), 5.79 (s, 1H), 4.23-4.21 (m, 1H), 2.74-2.62 (m, 1H), 2.61-2.58 (m, 1H), 2.10-2.08 (m, 1H), 1.91-1.87 (m, 1H), 1.47 (s, 9H).

3-(3-Aminoanilino)piperidine-2,6-dione. To a solution of tert-butyl N-[3-[(2,6-dioxo-3-piperidyl)amino]phenyl]carbamate (55.6 g, 0.17 mol) in DCM (550 mL) was added TFA (385 g, 3.38 mol, 250 mL) at 0-5° C. The reaction mixture was stirred at 25° C. for 10 h then was concentrated to a residue. To the residue was added MTBE (600 mL) resulting in the precipitation of a blue solid. 3-(3-Aminoanilino)piperidine-2,6-dione trifluoroacetate (52.0 g, 89.6% yield) was collected by filtration. $^1$H NMR (400 MHz, DMSO-d$_6$) δ ppm 10.83 (s, 1H), 7.12 (t, J=8.0 Hz, 1H), 6.60 (d, J=8.0 Hz, 1H), 6.53 (s, 1H), 6.50-6.43 (m, 1H), 4.33 (dd, J=5.2 Hz, 11.6 Hz, 1H), 2.76-2.73 (m, 1H), 2.63-2.58 (m, 1H), 2.13-2.07 (m, 1H), 1.97-1.93 (m, 1H).

2-(4-(2-(4-(3-(6-Cyano-5-(trifluoromethyl)pyridin-3-yl)-5,5-dimethyl-4-oxo-2-thioxoimidazolidin-1-yl)phenoxy) ethyl)piperazin-1-yl)-N-(3-((2,6-dioxopiperidin-3-yl)amino)phenyl)acetamide formate. In a scintillation vial was added 2-(4-(2-(4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)acetic acid (0.135 g, 0.234 mmol), 3-((3-aminophenyl)amino)piperidine-2,6-dione (0.074 g, 0.234 mmol) and DIEA (0.123 mL, 0.702 mmol) in DMF (1 mL). HATU (0.089 g, 0.234 mmol) was added last and the solution was stirred at ambient temperature. After 30 min, the solution was diluted with DMSO (0.5 mL) and the mixture was purified by standard methods to afford the title compound (0.050 g, 0.064 mmol, 27.5% yield). MS (ESI) m/z 778 [M+1]$^+$; $^1$H NMR (400 MHz, DMSO-d$_6$) δ ppm 10.78 (s, 1H), 9.36-9.44 (m, 1H), 9.24 (d, J=1.22 Hz, 1H), 8.82 (d, J=1.83 Hz, 1H), 8.13 (s, 1H), 7.28 (m, J=8.68 Hz, 2H), 7.12 (m, J=8.56 Hz, 2H), 6.96-7.03 (m, 2H), 6.81 (br d, J=8.07 Hz, 1H), 6.52 (s, 1H), 6.39 (d, J=7.35 Hz, 1H), 5.88 (br d, J=8.68 Hz, 1H), 4.25 (dt, J=7.15, 5.35 Hz, 1H), 4.08-4.20 (m, 2H), 3.37 (br s, 1H), 3.24 (br s, 1H), 2.95-3.19 (m, 3H), 2.58-2.87 (m, 1H), 2.54-2.81 (m, 10H), 2.37-2.44 (m, 1H), 2.33 (br s, 1H), 2.04-2.14 (m, 1H), 1.82-1.95 (m, 1H), 1.46-1.54 (m, 7H), 1.25 (br d, J=1.47 Hz, 1H), 0.04 (br s, 1H), −0.04 (br d, J=3.18 Hz, 1H).

Example 2: (2S)-2-(4-(2-(2-Chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-((2,6-dioxopiperidin-3-yl)amino)phenyl) propanamide hydrochloride

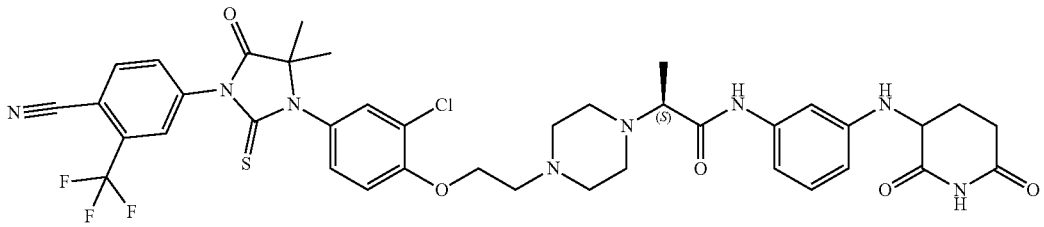

2-(3-chloro-4-hydroxy-anilino)-2-methyl-propanenitrile. To a solution of 4-amino-2-chloro-phenol (45.0 g, 0.310 mol) in DCM (450 mL) and acetone (225 mL) was added trimethylsilyl trifluoromethanesulfonate (3.48 g, 16.0 mmol) and trimethylsilylformonitrile (43.5 g, 0.440 mol) at 10° C. After addition, the reaction was stirred at 25° C. for 16 h then was concentrated to a residue that was purified by silica gel column chromatography (petroleum ether and EtOAc, 15:1-7:1) to afford 2-(3-chloro-4-hydroxy-anilino)-2-methyl-propanenitrile (41.5 g, 62.8% yield) as an off-white solid. $^1$H NMR (400 MHz, DMSO-d$_6$) δ ppm 9.52 (s, 1H), 6.89-6.84 (m, 2H), 6.76-6.73 (m, 1H), 5.52 (s, 1H), 1.54 (s, 6H).

4-[3-(3-Chloro-4-hydroxy-phenyl)-4,4-dimethyl-5-oxo-2-thioxo-imidazolidin-1-yl]-2-(trifluoromethyl)benzonitrile. To a solution of 2-(3-chloro-4-hydroxy-anilino)-2-methyl-propanenitrile (14.6 g, 69.0 mmol) in DMA (150 mL) was added 4-isothiocyanato-2-(trifluoromethyl)benzonitrile (19.0 g, 83.0 mmol) at 20° C. After stirring at 20° C. for 2 h, the reaction mixture was diluted with MeOH (150 mL) and aqueous HCl (2 M, 150 mL) at 20° C., and stirred at 70° C. for 5 h. The reaction mixture was cooled to 10° C. and filtered. The filter cake was washed with water (200 mL) and dried to afford 4-[3-(3-chloro-4-hydroxy-phenyl)-4,4-dimethyl-5-oxo-2-thioxo-imidazolidin-1-yl]-2-(trifluoromethyl) benzonitrile (20.0 g, 65.6% yield) as a white solid. $^1$H NMR (400 MHz, DMSO-d$_6$) δ ppm 10.72 (s, 1H), 8.38 (d, J=8.4 Hz, 1H), 8.27 (d, J=1.6 Hz, 1H), 8.07 (dd, J=1.6 Hz, 8.0 Hz, 1H), 7.39 (d, J=2.4 Hz, 1H), 7.15-7.10 (m, 2H), 1.49 (s, 6H).

tert-Butyl 4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazine-1-carboxylate. tert-Butyl 4-(2-chloroethyl)piperazine-1-carboxylate (0.424 g, 1.70 mmol, 1.50 eq) was dissolved in DMF (8.42 mL, 0.135 molar). Cesium carbonate (0.556 g, 1.70 mmol, 1.50 eq) and 4-(3-(3-chloro-4-hydroxyphenyl)-4,4-dimethyl-5-oxo-2-thioxoimidazolidin-1-yl)-2-(trifluoromethyl)benzonitrile (0.500 g, 1.14 mmol, 1 eq) were added and the reaction was warmed to 60° C. for 18 h. The reaction was quenched with water and diluted with EtOAc, and the organic phase was washed with brine, dried over sodium sulfate, filtered, and concentrated. The crude residue was purified by silica gel column chromatography (0-10% MeOH in DCM), and the corresponding fractions were combined and concentrated to afford tert-butyl4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazine-1-carboxylate (0.792 g, 1.07 mmol, 95% yield) as a yellow oil. MS (ESI) m/z 652.2 [M]$^+$.

4-(3-(3-Chloro-4-(2-(piperazin-1-yl)ethoxy)phenyl)-4,4-dimethyl-5-oxo-2-thioxoimidazolidin-1-yl)-2-(trifluoromethyl)benzonitrile hydrochloride. tert-Butyl 4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazine-1-carboxylate (0.701 g, 1.07 mmol, 1 eq) was suspended in DCM (4.75 mL, 0.226 molar), and treated with a solution of HCl in dioxane (4.03 mL, 16.1 mmol, 15 eq). The reaction was stirred at room temperature for 3 h, then concentrated to afford 4-(3-(3-chloro-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.633 g, 1.08 mmol, 100% yield) as a white solid. MS (ESI) m/z 552.2 [M]$^+$.

(S)-Methyl 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoate. (R)-Methyl 2-chloropropanoate (0.033 mL, 0.31 mmol, 1.2 eq) was added to a stirred mixture of 4-(3-(3-chloro-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.150 g, 0.255 mmol, 1 eq), THF (2.179 mL, 0.117 molar), and TEA (0.142 mL, 1.02 mmol, 4 eq). The reaction mixture was stirred for 18 h at 60° C., then was heated to 80° C. for 36 h. The reaction mixture was concentrated under reduced pressure and the crude was purified by silica gel column chromatography (0-80% EtOAc in hexanes) to give (S)-methyl 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoate (0.078 g, 0.122 mmol, 48.0% yield) as a yellow solid. MS (ESI) m/z 638.2 [M]$^+$.

(S)-2-(4-(2-(2-Chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoic acid. To (S)-Methyl 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoate (0.078 g, 0.12 mmol, 1 eq), suspended in a 3:1 mixture of THF (0.811 mL) and water (0.270 mL)(0.113 molar) was added lithium hydroxide (0.031 g, 1.30 mmol, 10. eq). The reaction was stirred at room temperature for 4 h, then diluted with EtOAc and water. The pH was lowered to ~3 with the addition of a 6 M aqueous solution of HCl. The organic layer was extracted with EtOAc, dried over sodium sulfate, filtered, and concentrated to afford (S)-2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoic acid (0.117 g, 0.127 mmol, 104% yield) as a beige solid. MS (ESI) m/z 624.2 [M]$^+$.

(2S)-2-(4-(2-(2-Chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-((2,6-dioxopiperidin-3-yl)amino)phenyl)propanamide hydrochloride. (S)-2-(4-(2-(2-Chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoic acid (0.076 g, 0.12 mmol, 1 eq) was combined with 3-((3-aminophenyl)amino)piperidine-2,6-dione trifluoroacetate salt (0.041 g, 0.12 mmol, 1 eq), HATU (0.051 g, 0.134 mmol, 1.1 eq), DIEA (0.085 mL, 0.49 mmol, 4 eq), and DMF (0.609 mL, 0.2 M), and the reaction was stirred at 25° C. for 2 h. The reaction was quenched with water and diluted with EtOAc, and the aqueous layer was extracted by EtOAc. The combined extracts were concentrated, and the residue was purified by standard methods to afford (2S)-2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-((2,6-dioxopiperidin-3-yl)amino)phenyl)propanamide hydrochloride (0.022 g, 0.027 mmol, 22% yield). MS (ESI) m/z 825.2 [M]$^+$; $^1$H NMR (400 MHz, DMSO-d$_6$) δ ppm 10.79 (s, 1H), 10.12 (br s, 1H), 8.40 (d, J=8.31 Hz, 1H), 8.27 (d, J=1.83 Hz, 1H), 8.06 (dd, J=1.59, 8.19 Hz, 1H), 7.54-7.57 (m, 1H), 7.38 (s, 3H), 6.96-7.06 (m, 2H), 6.85 (br d, J=7.83 Hz, 1H), 6.45 (dd, J=1.47, 8.19 Hz, 1H), 4.55 (br s, 2H), 4.26 (br dd, J=4.34, 11.19 Hz, 1H), 3.23-3.46 (m, 9H), 2.69-2.80 (m, 1H), 2.55-2.64 (m, 1H), 2.54 (s, 2H), 2.08-2.14 (m, 1H), 1.90 (br dq, J=4.46, 12.08 Hz, 1H), 1.52 (s, 6H), 1.39 (br s, 3H).

Example 3: 2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)-N-(5-((2,6-dioxopiperidin-3-yl)amino)-2-fluorophenyl)acetamide hydrochloride

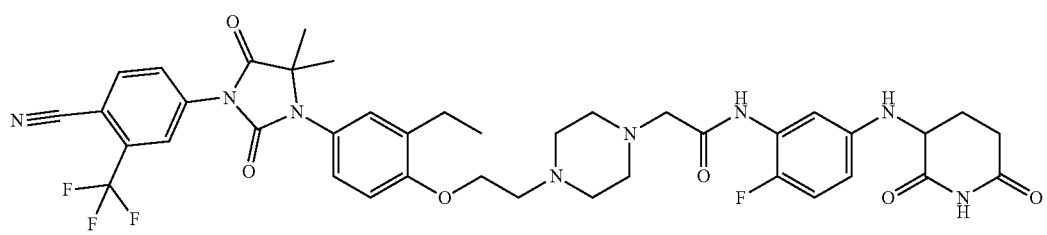 [SMILES: CCc1cc(N2C(=O)N(c3ccc(C#N)c(C(F)(F)F)c3)C(=O)C2(C)C)ccc1OCCN1CCN(CC(=O)Nc2cc(NC3CCC(=O)NC3=O)ccc2F)CC1]

tert-Butyl (2-fluoro-5-nitrophenyl)carbamate, tert-Butyl N-tert-butoxycarbonyl-N-(2-fluoro-5-nitro-phenyl)carbamate. To a solution of 2-fluoro-5-nitroaniline (100.0 g, 640.6 mmol, 1.00 eq) and Boc$_2$O (279.6 g, 1.28 mol, 294 mL, 2.00 eq) in THF (600 mL) was added 4-dimethylaminopyridine (7.83 g, 64.1 mmol, 0.10 eq) in one portion. The mixture was stirred at 50° C. under nitrogen for 12 h. The mixture was cooled to 15° C. and concentrated under reduced pressure to get a residue. The residue was diluted with water (1500 mL) and extracted with EtOAc (500 mL×3). The combined organic layers were washed with brine (500 mL), dried over anhydrous sodium sulfate, filtered and concentrated under reduced pressure to give a residue that was purified by silica gel column chromatography (petroleum ether). A mixture of tert-butyl (2-fluoro-5-nitrophenyl)carbamate and tert-butyl N-tert-butoxycarbonyl-N-(2-fluoro-5-nitro-phenyl)carbamate (200 g) was obtained as a colorless oil.

tert-Butyl (5-amino-2-fluorophenyl)carbamate, tert-Butyl N-(5-amino-2-fluoro-phenyl)-N-tert-butoxycarbonyl-carbamate. To a mixture of tert-butyl (2-fluoro-5-nitrophenyl)carbamate and tert-butyl N-tert-butoxycarbonyl-N-(2-fluoro-5-nitro-phenyl)carbamate (80.0 g, 224.5 mmol, 1.00 eq) in MeOH (800 mL) was added palladium on alumina (10.0 g, 224.5 mmol, 5% purity) under nitrogen. The suspension was degassed under vacuum and purged with hydrogen several times. The mixture was stirred under hydrogen (50 psi) at 15° C. for 2 h. The catalyst was removed by filtration and the filtrate was concentrated to get a residue. A mixture of tert-butyl (5-amino-2-fluorophenyl)carbamate and tert-butyl N-(5-amino-2-fluoro-phenyl)-N-tert-butoxycarbonyl-carbamate (70 g) was obtained as a white solid. The mixture was used in the next step without further purification. MS (ESI) m/z 171.1 [M−55]$^+$.

tert-Butyl (5-((2,6-dioxopiperidin-3-yl)amino)-2-fluorophenyl)carbamate, tert-Butyl N-tert-butoxycarbonyl-N-[5-[(2,6-dioxo-3-piperidyl)amino]-2-fluoro-phenyl]carbamate. To a mixture of tert-butyl (5-amino-2-fluorophenyl)carbamate and tert-butyl N-(5-amino-2-fluoro-phenyl)-N-tert-butoxycarbonyl-carbamate (30.00 g, 132.6 mmol, 1.00 eq) and sodium bicarbonate (22.28 g, 265.2 mmol, 2.00 eq) in DMF (250 mL) was added 3-bromopiperidine-2,6-dione (30.00 g, 156.2 mmol, 1.18 eq) in one portion. The mixture was stirred at 50° C. under nitrogen for 12 h. then was diluted with water (1000 mL) and extracted with EtOAc (300 mL×4). The combined organic layers were washed with brine (400 mL×3), dried over anhydrous sodium sulfate, filtered and concentrated under reduced pressure to give a residue that was purified by silica gel column chromatography (10~35% EtOAc in petroleum ether). A mixture of tert-butyl (5-((2,6-dioxopiperidin-3-yl)amino)-2-fluorophenyl)carbamate and tert-butyl N-tert-butoxycarbonyl-N-[5-[(2,6-dioxo-3-piperidyl)amino]-2-fluoro-phenyl]carbamate (43.00 g) was obtained as a light yellow solid. MS (ESI) m/z 282.1 [M−55]$^+$.

3-(3-Amino-4-fluorophenylamino)piperidine-2,6-dione. To a mixture of tert-butyl (5-((2,6-dioxopiperidin-3-yl)amino)-2-fluorophenyl)carbamate and tert-butyl N-tert-butoxycarbonyl-N-[5-[(2,6-dioxo-3-piperidyl)amino]-2-fluoro-phenyl]carbamate (30.00 g, 68.58 mmol, 1.00 eq) in DCM (300 mL) was added TFA (60.0 mL, 11.8 eq) in one portion at 0° C. The mixture was stirred at 0° C. for 0.5 h and then stirred at 20° C. for 2 h. TLC showed the reaction was complete. The reaction mixture was concentrated under reduced pressure at 40° C. to remove DCM. Then, saturated sodium bicarbonate solution (500 mL) and solid sodium bicarbonate was added to the mixture to adjust the pH to 7. The suspension was filtered and the filter cake was collected. The filter cake was washed with EtOAc (200×5), and dried under reduced pressure to get a gray solid. Compound 3-(3-amino-4-fluorophenylamino)piperidine-2,6-dione (10.02 g, 41.53 mmol, 60.6% yield) was obtained as a grey solid. MS (ESI) m/z 238.2 [M+1]$^+$; $^1$H NMR (400 MHz, DMSO-d$_6$) δ ppm 10.76 (s, 1H), 6.69 (dd, J=8.7, 11.2 Hz, 1H), 6.08 (dd, J=2.7, 7.9 Hz, 1H), 5.84 (td, J=3.1, 8.7 Hz, 1H), 5.40 (d, J=7.3 Hz, 1H), 4.81 (s, 2H), 4.16-4.07 (m, 1H), 2.76-2.65 (m, 1H), 2.61-2.53 (m, 1H), 2.13-2.04 (m, 1H), 1.83 (dq, J=4.7, 12.0 Hz, 1H).

4-(2-(4-((1-Methoxy-2-methyl-1-oxopropan-2-yl)amino)-2-vinylphenoxy)ethyl)piperazine-1-carboxylate. A mixture of tert-butyl 4-(2-(2-bromo-4-((1-methoxy-2-methyl-1-oxopropan-2-yl)amino)phenoxy)ethyl)piperazine-1-carboxylate (1.00 g, 2.00 mmol, 1 eq), 4,4,5,5-tetramethyl-2-vinyl-1,3,2-dioxaborolane (0.616 g, 4.00 mmol, 2 eq), potassium phosphate (2.12 g, 9.99 mmol, 5 eq), (1,1'-bis(diphenylphosphino)ferrocene)-dichloropalladium(II) (0.292 g, 0.399 mmol, 0.2 eq) in dioxane (1 mL) and water (0.5 mL) was degassed and purged with nitrogen 3 times. The mixture was stirred at 120° C. for 12 h under nitrogen atmosphere, then concentrated under reduced pressure at 40° C. The residue was poured into ice-water (50 mL). The aqueous phase was extracted with EtOAc (50 mL×3). The combined organic phase was washed with brine (100 mL×2), dried with anhydrous sodium sulfate, filtered, and concentrated under vacuum. The residue was purified by silica gel column chromatography (20-33% EtOAc in petroleum ether) to give tert-butyl 4-(2-(4-((1-methoxy-2-methyl-1-oxopropan-2-yl)amino)-2-vinylphenoxy)ethyl)piperazine-1-carboxylate (0.500 g, 1.12 mmol, 55.9% yield) was obtained as a yellow oil. MS (ESI) m/z 448.1 [M+1]$^+$.

tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazine-1-carboxylate. To a solution of tert-butyl 4-(2-(4-((1-methoxy-2-methyl-1-oxopropan-2-yl)amino)-2-vinylphenoxy)ethyl)piperazine-1-carboxylate (0.500 g, 1.12 mmol, 1 eq) in MeOH (10 mL) was added Pd—C (10%, 0.200 g) under nitrogen. The suspension was degassed under vacuum and purged with hydrogen several times. The mixture was stirred under hydrogen (50 psi) at 40° C. for 12 h. The reaction mixture was filtered and the filtrate was concentrated to give tert-butyl 4-(2-(2-ethyl-4-((1-methoxy-2-methyl-1-oxopropan-2-yl)amino)phenoxy)ethyl)piperazine-1-carboxylate (0.320 g, 0.712 mmol, 63.7% yield) as a yellow oil. MS (ESI) m/z 450.3 [M+1]$^+$.

tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazine-1-carboxylate. To a mixture of tert-butyl 4-(2-(2-ethyl-4-((1-methoxy-2-methyl-1-oxopropan-2-yl)amino)phenoxy)ethyl)piperazine-1-carboxylate (0.319 g, 0.710 mmol, 1 eq) and 4-isothiocyanato-2-(trifluoromethyl)benzonitrile (0.486 g, 2.130 mmol, 3 eq) in EtOAc (2 mL) was added TEA (0.359 g, 3.550 mmol, 5 eq). The mixture was stirred at 80° C. for 12 h, then concentrated under reduced pressure. The residue was purified by preparative TLC (67% EtOAc in petroleum ether) to afford tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazine-1-carboxylate (0.315 g, 0.488 mmol, 68.8% yield) as a yellow solid. MS (ESI) m/z 646.4 [M+1]$^+$.

4-(3-(3-Ethyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride. A solution of tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazine-1-carboxylate (0.315 g, 0.488 mmol, 1 eq)

in EtOAc (2 mL) was added HCl in dioxane (4 M, 10 mL). The mixture was stirred at 25° C. for 30 min, then was concentrated under reduced pressure to afford 4-(3-(3-ethyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.300 g, crude) as a yellow solid. MS (ESI) m/z 546.1 [M+1]⁺.

2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)acetic acid hydrochloride. To a solution of 4-(3-(3-ethyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride (1.00 g, 1.72 mmol) in THF (10 mL) was added DIEA (1.20 mL, 6.87 mmol) followed by tert-butyl 2-bromoacetate (0.266 mL, 1.80 mmol). The resulting mixture was stirred overnight at ambient temperature, then was diluted with EtOAc (125 mL), water (20 mL), and brine (20 mL). The solvent layers were separated and the combined organic extracts were dried over anhydrous magnesium sulfate, filtered, and concentrated to an oil. The oil was dissolved in DCM (25 mL), treated with TFA (2.65 mL, 34.4 mmol) and the solution was stirred overnight at ambient temperature. A 4.0 M solution of HCl in dioxane (5 mL) was added and stirring at room temperature resumed overnight. The reaction mixture was then concentrated under reduced pressure and the residual oil was treated with a 4.0 M solution of HCl in dioxane (5 mL). The resulting precipitate was collected by filtration and suspended and triturated in diethyl ether for 3 h. The material was collected by filtration, washed with hexanes, and dried in a vacuum oven overnight at 45° C., affording 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)acetic acid hydrochloride (0.989 g, 1.54 mmol, 90.0% yield). MS (ESI) m/z 604.2 [M+1]⁺.

2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)-N-(5-((2,6-dioxopiperidin-3-yl)amino)-2-fluorophenyl)acetamide hydrochloride. 2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)acetic acid hydrochloride (0.100 g, 0.156 mmol), 3-((3-amino-4-fluorophenyl)amino)piperidine-2,6-dione 2,2,2-trifluoroacetate (0.055 g, 0.156 mmol), DIEA (0.164 mL, 0.937 mmol), and DMF (1 mL) were combined and stirred for 5 min. HATU (0.065 g, 0.17 mmol) was added and the resulting mixture was stirred at ambient temperature. After 6 h, the reaction mixture was filtered and purified by standard methods to provide 2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)-N-(5-((2,6-dioxopiperidin-3-yl)amino)-2-fluorophenyl)acetamide hydrochloride (0.011 g, 0.013 mmol, 8.2% yield). MS (ESI) m/z 823.2 [M+1]⁺; ¹H NMR (400 MHz, DMSO-d₆) δ ppm 10.67-10.89 (m, 1H), 8.35-8.47 (m, 1H), 8.24-8.35 (m, 1H), 8.02-8.14 (m, 1H), 7.10-7.28 (m, 4H), 6.90-7.10 (m, 1H), 6.38-6.55 (m, 1H), 4.40-4.55 (m, 3H), 4.18-4.29 (m, 2H), 3.49-3.81 (m, 5H), 2.56-2.79 (m, 4H), 2.01-2.15 (m, 1H), 1.81-1.98 (m, 1H), 1.40-1.57 (m, 6H), 1.00-1.25 (m, 4H).

Example 4: 2-(4-(2-(4-(3-(4-Cyano-3-(trifluoromethyl)phenyl)-5,5-dimethyl-4-oxo-2-thioxoimidazolidin-1-yl)-2-fluorophenoxy)ethyl)piperazin-1-yl)-N-(3-cyano-5-((2,6-dioxopiperidin-3-yl)amino)phenyl)acetamide hydrochloride

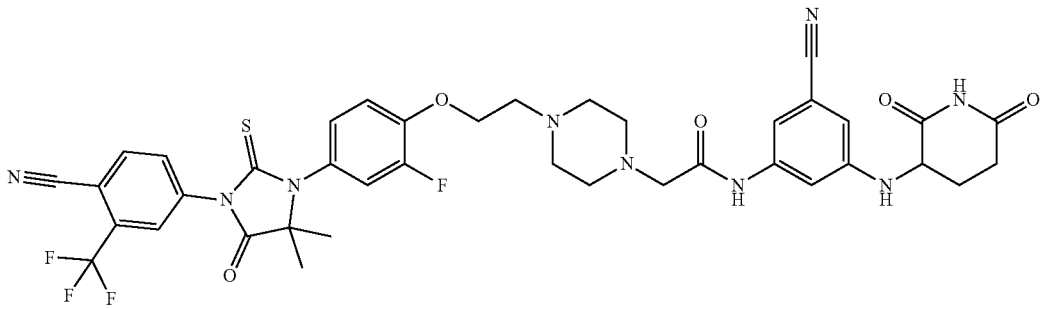 [SMILES: CC1(C)C(=O)N(c2ccc(C#N)c(C(F)(F)F)c2)C(=S)N1c1ccc(OCCN2CCN(CC(=O)Nc3cc(C#N)cc(NC4CCC(=O)NC4=O)c3)CC2)c(F)c1]

tert-Butyl N-(3-bromo-5-nitrophenyl)-N-tert-butoxycarbonyl-carbamate. To a solution of 3-bromo-5-nitro-aniline (5.50 g, 25.3 mmol, 1.00 eq) in pyridine (50 mL) was added Boc₂O (27.66 g, 126.7 mmol, 5.00 eq). The mixture was stirred at 25° C. for 12 h, then diluted with water (30 mL) and EtOAc (60 mL×3). The combined organic extracts were washed with brine (20 mL×2), dried with anhydrous sodium sulfate, filtered, and concentrated under vacuum. The residue was purified by silica gel column chromatography (3% EtOAc in petroleum ether) to afford tert-butyl N-(3-bromo-5-nitro-phenyl)-N-tert-butoxycarbonyl-carbamate (8.00 g, 19.2 mmol, 76.0% yield) as a yellow solid. ¹H NMR (400 MHz, DMSO-d₆) δ ppm 8.37 (t, J=1.8 Hz, 1H), 8.20 (t, J=1.8 Hz, 1H), 8.12 (t, J=1.6 Hz, 1H), 1.40 (s, 18H).

tert-Butyl (3-cyano-5-nitrophenyl)carbamate. To a mixture of tert-butyl N-(3-bromo-5-nitro-phenyl)-N-tert-butoxycarbonyl-carbamate (4.30 g, 10.31 mmol, 1.00 eq) in DMF (5 mL) was added zinc cyanide (2.42 g, 20.61 mmol, 2.00 eq), tetrakis[triphenylphosphine]palladium(0) (2.38 g, 2.06 mmol, 0.20 eq), and the mixture was stirred at 100° C. for 10 h under nitrogen. The reaction mixture was diluted with water (25 mL) and the product extracted with EtOAc (30 mL×3). The combined organic extracts were washed with brine (15 mL×2), dried with anhydrous sodium sulfate, filtered, and concentrated under vacuum. The residue was purified by silica gel column chromatography (4% EtOAc in petroleum ether) to afford tert-butyl (3-cyano-5-nitrophenyl)carbamate (1.10 g, 4.09 mmol, 30.0% yield) as a yellow solid. ¹H NMR (400 MHz, DMSO-d₆) δ ppm 10.24 (s, 1H), 8.64 (s, 1H), 8.31 (s, 1H), 8.13 (s, 1H), 1.50 (s, 9H).

tert-Butyl (3-amino-5-cyanophenyl)carbamate. To a mixture of tert-butyl N-(3-cyano-5-nitro-phenyl)carbamate (1.10 g, 4.2 mmol, 1.00 eq) in EtOH (30 mL) and water (10 mL) was added ferric nitrate (1.40 g, 25.1 mmol, 6.00 eq) and ammonium chloride (2.24 g, 41.8 mmol, 10.00 eq) at 25° C. The mixture was heated to 80° C., stirred for 10 h under nitrogen, and filtered. The filtrate was concentrated under reduced pressure to afford tert-butyl (3-amino-5-cyanophenyl)carbamate (0.95 g, 4.07 mmol, 97.0% yield) as a black brown oil. MS (ESI) m/z 178.1 [M−55]+.

3,5-Diaminobenzonitrile. To a solution of tert-butyl (3-amino-5-cyanophenyl)carbamate (0.200 g, 0.857 mmol, 1.00 eq) in EtOAc (2 mL) was added a 4.0 M solution of HCl in 1,4-dioxane (2.14 mL, 10.00 eq). The mixture was stirred at 25° C. for 1 h, then poured into a saturated aqueous solution of sodium bicarbonate (50 mL) and the mixture was extracted with EtOAc (50 mL×3). The combine organic extracts were washed with brine (50 mL×3), dried over anhydrous sodium sulfate, filtered, and concentrated under vacuum to afford 3,5-diaminobenzonitrile (0.100 g, 0.751 mmol, 88.0% yield) as a white solid. MS (ESI) m/z 134.2 [M+1]+.

3-Amino-5-((2,6-dioxopiperidin-3-yl)amino)benzonitrile. To a solution of 3,5-diaminobenzonitrile (0.100 g, 0.75 mmol, 1.00 eq) and 3-bromopiperidine-2,6-dione (0.288 g, 1.50 mmol, 2.00 eq) in DMF (1 mL) was added sodium hydrogen carbonate (0.094 g, 1.13 mmol, 1.50 eq). The mixture was stirred at 50° C. for 12 h. The mixture was poured into ice-water (20 mL), and the aqueous phase was extracted with EtOAc (20 mL×3). The combined organic extracts were washed with brine (20 mL), dried with anhydrous sodium sulfate, filtered, and concentrated under vacuum. The mixture was purified by preparative TLC (50% EtOAc in petroleum ether) to afford 3-amino-5-((2,6-dioxopiperidin-3-yl)amino)benzonitrile (0.050 g, 0.204 mmol, 27.0% yield) was obtained as a white solid. MS (ESI) m/z 245.2 [M+1]+.

2-(Difluoromethyl-fluoranyl)-4-isothiocyanato-benzonitrile. To a solution of thiocarbonyl dichloride (44.2 g, 385 mmol, 29.5 mL) in water (500 mL) was added 4-amino-2-(difluoromethyl-fluoranyl)benzonitrile (48.0 g, 256 mmol) at 15° C. After addition, the reaction was stirred at 28° C. for 12 h. The material was then extracted with DCM (3×300 mL). The combined organic layers were concentrated in vacuum and purified by silica gel column chromatography (0-5% EtOAc in petroleum ether) to afford 2-(difluoromethyl-fluoranyl)-4-isothiocyanato-benzonitrile (52.0 g, 88.4% yield) as a brown solid. 1H NMR (400 MHz, CDCl3) δ ppm 7.87 (d, J=8.0 Hz, 1H), 7.59 (s, 1H), 7.51-7.48 (m, 1H).

2-(3-Fluoro-4-hydroxy-anilino)-2-methyl-propanenitrile. To a solution of 4-amino-2-fluoro-phenol (25.0 g, 197 mmol) in DCM (250 mL) and acetone (125 mL) was added trimethylsilylformonitrile (27.3 g, 275 mmol, 34.57 mL) and trimethylsilyl trifluoromethanesulfonate (2.19 g, 9.83 mmol, 1.78 mL) at 0-5° C. After addition, the reaction was stirred at 20° C. for 16 h, then was concentrated under reduced pressure and the residue was purified by silica gel column chromatography (5% EtOAc in petroleum) to give 2-(3-fluoro-4-hydroxy-anilino)-2-methyl-propanenitrile (20.0 g, 53.4% yield) as a white solid. 1H NMR (400 MHz, CDCl3) δ ppm 6.93 (t, J=8.8 Hz, 1H), 6.82 (dd, J=2.8 Hz, 12.0 Hz, 1H), 6.78-6.71 (m, 1H), 4.99 (s, 1H), 3.41 (s, 1H), 1.62 (s, 6H).

4-[3-(3-Fluoro-4-hydroxy-phenyl)-4,4-dimethyl-5-oxo-2-thioxo-imidazolidin-1-yl]-2-(trifluoromethyl)benzonitrile. A solution of 2-(3-fluoro-4-hydroxy-anilino)-2-methyl-propanenitrile (20.0 g, 103 mmol) and 4-isothiocyanato-2-(trifluoromethyl)benzonitrile (31 g, 134 mmol) in DMA (300 mL) was stirred for 3 h at 18° C., then diluted with MeOH (200 mL) and aqueous HCl (2 M, 200 mL), and warmed to 70° C. After 2 h, the reaction mixture was cooled to room temperature (18° C.), mixed with water (150 mL) and extracted with EtOAc (200 mL×3). The organic phases were combined, washed with brine (100 mL×2), dried over anhydrous sodium sulfate, and filtered. The filtrate was concentrated under the reduced pressure and the residue was purified by silica gel column chromatography (11-16% EtOAc in petroleum ether) to give 4-[3-(3-fluoro-4-hydroxy-phenyl)-4,4-dimethyl-5-oxo-2-thioxo-imidazolidin-1-yl]-2-(trifluoromethyl)benzonitrile (19 g, 43.6% yield) as a light yellow solid. 1H NMR (400 MHz, CDCl3) δ ppm 8.00-7.96 (m, 2H), 7.85-7.82 (m, 1H), 7.16 (t, J=8.8 Hz, 1H), 7.09-7.06 (m, 1H), 7.02-7.00 (m, 1H), 5.84 (s, 1H), 1.60 (s, 6H).

tert-Butyl 4-[2-[4-[3-[4-cyano-3-(trifluoromethyl)phenyl]-5,5-dimethyl-4-oxo-2-thioxo-imidazolidin-1-yl]-2-fluoro-phenoxy]ethyl]piperazine-1-carboxylate. To a solution of 4-[3-(3-fluoro-4-hydroxy-phenyl)-4,4-dimethyl-5-oxo-2-thioxo-imidazolidin-1-yl]-2-(trifluoromethyl)benzonitrile (11.4 g, 26.9 mmol) and cesium carbonate (13.1 g, 40.3 mmol) in DMF (330 mL) was added tert-butyl 4-(2-chloroethyl)piperazine-1-carboxylate (10 g, 40.3 mmol) at 18° C. The reaction mixture was stirred at 60° C. for 10 h, then was diluted with water (500 mL) and extracted with EtOAc (300 mL×3). The combined organic phases were washed with brine (300 mL), dried over sodium sulfate, filtered, and concentrated under vacuum. The resulting crude product (20 g) was purified by preparative HPLC to give tert-butyl 4-[2-[4-[3-[4-cyano-3-(trifluoromethyl)phenyl]-5,5-dimethyl-4-oxo-2-thioxo-imidazolidin-1-yl]-2-fluoro-phenoxy]ethyl]piperazine-1-carboxylate (12.4 g, 72.6% yield) as a light yellow solid. 1H NMR (400 MHz, CDCl3) δ ppm 7.99-7.96 (m, 2H), 7.85-7.82 (m, 1H), 7.10-7.05 (m, 3H), 4.24 (t, J=5.6 Hz, 2H), 3.46 (t, J=4.4 Hz, 4H), 2.89 (t, J=5.2 Hz, 2H), 2.56 (t, J=4.8 Hz, 4H), 1.59 (s, 6H), 1.47 (s, 9H).

4-[3-[3-Fluoro-4-(2-piperazin-1-ylethoxy)phenyl]-4,4-dimethyl-5-oxo-2-thioxo-imidazolidin-1-yl]-2-(trifluoromethyl)benzonitrile. To a solution of tert-butyl 4-[2-[4-[3-[4-cyano-3-(trifluoromethyl)phenyl]-5,5-dimethyl-4-oxo-2-thioxo-imidazolidin-1-yl]-2-fluoro-phenoxy]ethyl]piperazine-1-carboxylate (16.4 g, 25.8 mmol) in DCM (100 mL) was added TFA (26.5 g, 232 mmol, 17.2 mL) at 0° C. The reaction mixture was stirred at 20° C. for 10 h, then was concentrated under vacuum. The resulting oil was dissolved in acetonitrile (20 mL) and the pH was adjusted to pH 8-9 with a saturated aqueous solution of sodium bicarbonate and the resulting solution was concentrated under vacuum. The aqueous phase was extracted with DCM (100 mL×2). The combined organic phases were washed with water (100 mL×2), dried over sodium sulfate, filtered, and concentrated to light yellow oil. The residue was lyophilized to give 4-[3-[3-fluoro-4-(2-piperazin-1-ylethoxy)phenyl]-4,4-dimethyl-5-oxo-2-thioxo-imidazolidin-1-yl]-2-(trifluoromethyl)benzonitrile (12.1 g, 87.5% yield) as a light yellow solid. 1H NMR (400 MHz, CDCl3) δ ppm 7.99-7.96 (m, 2H), 7.84-7.82 (m, 1H), 7.10-7.04 (m, 3H), 4.24 (t, J=5.6 Hz, 2H), 2.94-2.86 (m, 6H), 2.59 (s, 4H), 1.59 (s, 6H).

Methyl 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)acetate. 4-(3-(3-Fluoro-4-(2-(piperazin-1-yl)ethoxy)phenyl)-4,4-dimethyl-5-oxo-2-thioxoimidazolidin-1-yl)-2-(trifluoromethyl)benzonitrile (0.250 g, 0.467 mmol) was combined with methyl 2-bromoacetate (0.047 mL, 0.47 mmol) in THF (4 mL). The solution was stirred at ambient temperature in a screw cap vial for 30 min. The reaction mixture was diluted with DCM and the organic layers were washed with water and brine.

The organic extracts were dried over magnesium sulfate, filtered, and concentrated under reduced pressure. The resulting solid was purified via silica gel column chromatography (0-100% EtOAc in hexanes, followed by 5% MeOH in EtOAc (500 mL)) to afford the title compound (0.230 g, 0.379 mmol, 81.0% yield). MS (ESI) m/z 608 [M+1]$^+$.

2-(4-(2-(4-(3-(4-Cyano-3-(trifluoromethyl)phenyl)-5,5-dimethyl-4-oxo-2-thioxoimidazolidin-1-yl)-2-fluorophenoxy)ethyl)piperazin-1-yl)acetic acid. A solution of methyl 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)acetate (0.230 g, 0.379 mmol) in THF (2 mL) was treated with a solution of lithium hydroxide hydrate (0.159 g, 3.79 mmol) in water (2.00 mL). After 30 min, the pH was adjusted to 5 with a 2.0 M aqueous solution of HCl and the mixture diluted with DCM (100 mL) and water (30 mL). The organic phase was separated and the aqueous phase was extracted with DCM. The combined organic extracts were washed with brine, dried over magnesium sulfate, filtered, and concentrated under reduced pressure to afford the title compound as a white solid (0.183 g, 0.308 mmol, 81% yield). MS (ESI) m/z 594 [M+1]$^+$.

2-(4-(2-(4-(3-(4-Cyano-3-(trifluoromethyl)phenyl)-5,5-dimethyl-4-oxo-2-thioxoimidazolidin-1-yl)-2-fluorophenoxy)ethyl)piperazin-1-yl)-N-(3-cyano-5-((2,6-dioxopiperidin-3-yl)amino)phenyl)acetamide hydrochloride. To a solution of 3-amino-5-((2,6-dioxopiperidin-3-yl)amino)benzonitrile (0.040 g, 0.16 mmol, 1.0 eq) and 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)acetic acid (0.097 g, 0.16 mmol, 1.0 eq) in DMF (1 mL) was added HATU (0.093 g, 0.24 mmol, 1.5 eq) and DIEA (0.064 g, 0.49 mmol, 3.0 eq), and the mixture was stirred at 25° C. for 1 h under nitrogen and filtered. The filtrate was concentrated under reduced pressure and the residue was purified by standard methods to afford 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)-N-(3-cyano-5-((2,6-dioxopiperidin-3-yl)amino)phenyl)acetamide hydrochloride (0.050 g, 0.060 mmol, 37.0% yield). MS (ESI) m/z 820.2 [M+1]$^+$; $^1$H NMR (400 MHz, DMSO-d$_6$) δ ppm 10.82 (s, 1H), 10.51 (br s, 1H), 8.40 (d, J=8.2 Hz, 1H), 8.27 (d, J=1.6 Hz, 1H), 8.07 (d, J=8.2 Hz, 1H), 7.45-7.35 (m, 2H), 7.29-7.20 (m, 3H), 6.82 (s, 1H), 4.57 (br s, 2H), 4.40 (br dd, J=4.8, 11.8 Hz, 1H), 4.19-3.76 (m, 7H), 3.60 (br s, 5H), 3.40 (br s, 2H), 2.81-2.69 (m, 1H), 2.64-2.54 (m, 1H), 2.14-2.03 (m, 1H), 2.00-1.86 (m, 1H), 1.52 (s, 6H).

Example 5: N-(3-Chloro-5-((2,6-dioxopiperidin-3-yl)amino)phenyl)-2-(4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetamide hydrochloride

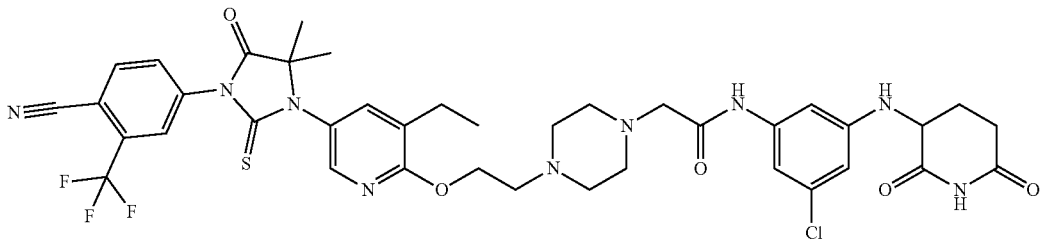 [SMILES: CCc1cc(N2C(=S)N(c3ccc(C#N)c(C(F)(F)F)c3)C(=O)C2(C)C)cnc1OCCN1CCN(CC(=O)Nc2cc(Cl)cc(NC3CCC(=O)NC3=O)c2)CC1]

6-Chloro-5-vinylpyridin-3-amine. A mixture of 5-bromo-6-chloropyridin-3-amine (0.750 g, 3.62 mmol, 1 eq), tributylstannylethylene (1.52 mL, 5.19 mmol, 1.43 eq), tetrakis(triphenylphosphine)palladium(0) (0.209 g, 0.181 mmol, 5 mol %) and lithium chloride (0.476 g, 11.2 mmol, 3.10 eq) in dioxane (19.0 mL, 0.190 molar) was heated under reflux for 24 h, then cooled to room temperature, diluted with water, and extracted with DCM. The organic layer was concentrated under reduced pressure, and the resulting residue was purified by column chromatography (0-15% MeOH in DCM) to afford 6-chloro-5-vinylpyridin-3-amine (0.804 g, 3.20 mmol, 89.0% yield) as a yellow solid MS (ESI) m/z 155.0 [M+1]$^+$.

6-Chloro-5-ethylpyridin-3-amine hydrochloride. A solution of 6-chloro-5-vinylpyridin-3-amine (0.194 g, 1.25 mmol, 1 eq) in EtOH (12.5 mL, 0.1 molar) was purged with nitrogen gas, and treated with 10% Pd/C (0.099 g, 0.094 mmol, 7.5 mol %). The suspension was purged with hydrogen gas and stirred for 30 min at room temperature under an atmosphere of hydrogen. The reaction mixture was filtered through celite and concentrated to afford a pale yellow oil that was suspended in DCM (5.17 mL, 0.226 molar), and treated with a solution of HCl in dioxane (4.38 mL, 17.53 mmol, 15 eq), and allowed to stir at room temperature for 6 h. The reaction was concentrated to afford 6-chloro-5-ethylpyridin-3-amine hydrochloride (0.226 g, 1.171 mmol, 93.7% yield) as a pale yellow solid. MS (ESI) m/z 157.0 [M+1]$^+$.

2-((6-Chloro-5-ethylpyridin-3-yl)amino)-2-methylpropanenitril. Acetone cyanohydrin (0.307 mL, 3.36 mmol, 2.87 eq) and magnesium sulfate (0.324 g, 2.69 mmol, 2.3 eq) were added to 6-chloro-5-ethylpyridin-3-amine hydrochloride (0.226 g, 1.17 mmol, 1 eq), TEA (0.280 mL, 1.17 mmol, 1 eq) and the mixture was stirred at 80° C. for 18 h. The reaction mixture was quenched with a saturated aqueous solution of sodium chloride and the aqueous phase was washed with EtOAc. The combined organic extracts were washed with saturated sodium bicarbonate, dried with sodium sulfate, filtered, and concentrated. The crude was purified by silica gel column chromatography (0-80% EtOAc in hexanes) to afford 2-((6-chloro-5-ethylpyridin-3-yl)amino)-2-methylpropanenitrile (0.232 g, 1.04 mmol, 30.9% yield) as a yellow residue. MS (ESI) m/z 224.2 [M+1]$^+$.

4-(3-(6-Chloro-5-ethylpyridin-3-yl)-4,4-dimethyl-5-oxo-2-thioxoimidazolidin-1-yl)-2-(trifluoromethyl)benzonitrile. To a solution of 2-((6-chloro-5-ethylpyridin-3-yl)amino)-2-methylpropanenitrile (0.232 g, 1.04 mmol, 1 eq) in DMA (2.19 mL) was added 4-isothiocyanato-2-(trifluoromethyl)benzonitrile (0.284 g, 1.24 mmol, 1.19 eq) at 25° C., and the reaction mixture was stirred at room temperature 18 h, then 70° C. for 4 h. To the reaction solution were added MeOH (2.188 mL, 0.474 molar) and an aqueous 3 M solution of HCl (1.46 mL, 4.38 mmol, 4.22 eq), and heating to 70° C. was resumed. After 18 h, the reaction was quenched with water and diluted with EtOAc, and the organic phase was washed with brine, dried over sodium sulfate, filtered, and concentrated. The crude residue was purified by silica gel column chromatography (0-10% MeOH in DCM). The corresponding fractions were combined and concentrated to give 4-(3-(6-chloro-5-ethylpyridin-3-yl)-4,4-dimethyl-5-oxo-2-thioxoimidazolidin-1-yl)-2-(trifluoromethyl)benzonitrile (0.117 g, 0.258 mmol, 24.91% yield) as an orange solid. MS (ESI) m/z 453.2 [M+1]$^+$.

tert-Butyl 4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazine-1-carboxylate. Tert-Butyl 4-(2-hydroxyethyl)piperazine-1-carboxylate (0.028 g, 0.12 mmol, 1 eq) and 4-(3-(6-chloro-5-ethylpyridin-3-yl)-4,4-dimethyl-5-oxo-2-thioxoimidazolidin-1-yl)-2-(trifluoromethyl)benzonitrile (0.056 g, 0.12 mmol, 1 eq) were dissolved in THE (2.86 mL, 0.043 molar). A 1.0 M solution of potassium tert-butoxide in THF (0.618 mL, 0.62 mmol, 5 eq) was added, and the reaction was warmed to 60° C. for 36 h, resulting in a partial deprotection of the product. The reaction was cooled to 25° C., and Boc$_2$O (0.034 mL, 0.15 mmol, 1.2 eq) was added. After 4 h, the reaction was quenched with water, diluted with DCM, and the aqueous phase was extracted with DCM. The combined organic extracts were dried over sodium sulfate, filtered, and concentrated, and the crude material was purified by silica gel column chromatography (04% MeOH in DCM). The corresponding fractions were combined and concentrated to afford tert-butyl 4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazine-1-carboxylate (0.033 g, 0.051 mmol, 41.3% yield) as a pale yellow solid. MS (ESI) m/z 647.2 [M+1]$^+$.

4-(3-(5-Ethyl-6-(2-(piperazin-1-yl)ethoxy)pyridin-3-yl)-4,4-dimethyl-5-oxo-2-thioxoimidazolidin-1-yl)-2-(trifluoromethyl)benzonitrile hydrochloride. A suspension of tert-butyl 4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazine-1-carboxylate (0.033 g, 0.051 mmol, 1 eq) in DCM (0.226 mL, 0.226 molar) was treated with a solution of HCl in dioxane (0.191 mL, 0.765 mmol, 15 eq), and stirred at room temperature for 2 h. The reaction was concentrated under reduced pressure to afford 4-(3-(5-ethyl-6-(2-(piperazin-1-yl)ethoxy)pyridin-3-yl)-4,4-dim-ethyl-5-oxo-2-thioxoimidazolidin-1-yl)-2-(trifluoromethyl)benzonitrile hydrochloride (0.030 g, 0.051 mmol, 101% yield) as a beige solid. MS (ESI) m/z 547.2 [M+1]$^+$.

tert-Butyl 2-(4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetate. Tert-Butyl 2-bromoacetate (9.97 µl, 0.062 mmol, 1.2 eq) was added to a stirred mixture of 4-(3-(5-ethyl-6-(2-(piperazin-1-yl)ethoxy)pyridin-3-yl)-4,4-dimethyl-5-oxo-2-thioxoimidazolidin-1-yl)-2-(trifluoromethyl)benzonitrile hydrochloride (0.030 g, 0.051 mmol, 1 eq), THE (0.440 mL, 0.117 molar) and TEA (0.029 mL, 0.206 mmol, 4 eq). The reaction mixture was stirred for 18 h at 60° C. The reaction was then concentrated under reduced pressure and purified by silica gel column chromatography (0-4% MeOH in DCM) to give tert-butyl 2-(4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetate (0.014.2 g, 0.021 mmol, 41.8% yield) as a pale yellow solid. MS (ESI) m/z 661.4 [M+1]$^+$.

2-(4-(2-((5-(3-(4-Cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetic acid hydrochloride. A suspension of tert-butyl 2-(4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetate (0.014 g, 0.021 mmol, 1 eq) in DCM (0.500 mL) was treated with a solution of hydrochloric acid in dioxane (0.081 mL, 0.322 mmol, 15 eq), and stirred at room temperature for 4 h. The reaction was concentrated under reduced pressure to afford 2-(4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetic acid hydrochloride (0.014 g, 0.022 mmol, 102% yield) as a beige solid. MS (ESI) m/z 605.2 [M+1]$^+$.

N-(3-Chloro-5-((2,6-dioxopiperidin-3-yl)amino)phenyl)-2-(4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetamide hydrochloride. 2-(4-(2-((5-(3-(4-Cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetic acid hydrochloride (14 mg, 0.023 mmol, 1 eq) was combined with 3-((3-amino-5-chlorophenyl)amino)piperidine-2,6-dione trifluoroacetate salt (8.51 mg, 0.023 mmol, 1 eq), HATU (9.68 mg, 0.025 mmol, 1.1 eq), DIEA (0.016 mL, 0.093 mmol, 4 eq), and DMF (0.116 mL), and the reaction was stirred at 25° C. for 2 h. The reaction mixture was quenched with water, diluted with EtOAc, and the aqueous layer was extracted with EtOAc. The combined organic extracts were concentrated, and the residue was purified by standard methods to afford N-(3-chloro-5-((2,6-dioxopiperidin-3-yl)amino)phenyl)-2-(4-(2-((5-(3-(4-cyano-3-(trifluoromethyl)phenyl)-5,5-dimethyl-4-oxo-2-thioxoimidazolidin-1-yl)-3-ethylpyridin-2-yl)oxy)ethyl)piperazin-1-yl)acetamide hydrochloride (5 mg, 5.47 µmol, 23.6% yield). MS (ESI) m/z 840.2 [M+1]$^+$; $^1$H NMR (500 MHz, acetonitrile-d$_3$) δ ppm 9.12 (br s, 1H), 8.7-8.8 (m, 1H), 8.1-8.2 (m, 3H), 7.9-8.0 (m, 2H), 7.50 (d, 1H, J=2.5 Hz), 7.03 (s, 1H), 6.95 (s, 1H), 6.49 (s, 1H), 5.04 (br d, 1H, J=6.6 Hz), 4.54 (t, 2H, J=5.5 Hz), 4.24 (ddd, 1H, J=5.2, 6.7, 12.1 Hz), 3.06 (s, 2H), 2.86 (br t, 2H, J=5.7 Hz), 2.77 (ddd, 2H, J=5.4, 12.6, 17.3 Hz), 2.7-2.7 (m, 4H), 2.67 (q, 4H, J=7.3 Hz), 2.60 (br s, 4H), 1.57 (s, 6H), 1.25 (t, 3H, J=7.6 Hz).

Example 6: 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)-N-(5-((2,6-dioxopiperidin-3-yl)amino)-2,3-difluorophenyl)acetamide

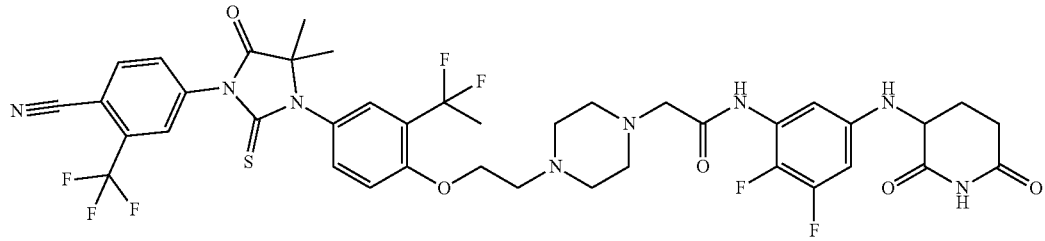 [SMILES: CC(F)(F)c1cc(N2C(=S)N(c3ccc(C#N)c(C(F)(F)F)c3)C(=O)C2(C)C)ccc1OCCN1CCN(CC(=O)Nc2cc(NC3CCC(=O)NC3=O)cc(F)c2F)CC1]

2-(1,1-Difluoroethyl)-4-nitrophenol. A solution of 1-(2-hydroxy-5-nitrophenyl)ethanone (1.27 g, 7.00 mmol) in DCM (18 mL) was cooled to 0° C. and bis(2-methoxyethyl)aminosulfur trifluoride (Deoxo-Fluor®, 2.58 mL, 14.0 mmol) was added dropwise over 2 min. The mixture was stirred for 2.5 h during which time the temperature gradually rose to 20° C. The mixture was poured into ice water (30 mL) and mixed for 5 min. The organic layer was removed, the aqueous layer extracted with DCM, and the combined organic extracts dried over sodium sulfate and activated carbon. The solution was filtered, concentrated, and the residual solid purified by silica gel column chromatography (10-40% EtOAc in hexanes) to provide the title compound as a light beige solid (1.23 g, 86.0% yield). $^1$H NMR (400 MHz, CDCl$_3$) δ ppm 8.33 (d, J=2.57 Hz, 1H), 8.24 (dd, J=8.99, 2.63 Hz, 1H), 7.06 (d, J=9.05 Hz, 1H), 6.51-6.92 (br s, 1H), 2.08 (t, J=18.9 Hz, 3H).

tert-Butyl 4-(2-(2-(1,1-difluoroethyl)-4-nitrophenoxy)ethyl)piperazine-1-carboxylate. To a solution of 2-(1,1-difluoroethyl)-4-nitrophenol (1.20 g, 5.91 mmol) and tert-butyl 4-(2-bromoethyl)piperazine-1-carboxylate (2.08 g, 7.09 mmol) in dry DMF (12 mL) was added cesium carbonate (3.85 g, 11.81 mmol) and the mixture was stirred under a nitrogen atmosphere at 65° C. for 4 h. The mixture was cooled to ambient temperature, poured into ice-water (60 mL), and mixed. The mixture was extracted with EtOAc and the combined extracts were washed with water, brine, and dried over magnesium sulfate with activated carbon. The solution was filtered through a silica gel plug, eluted with EtOAc elution, concentrated, and the residue dried under vacuum to give tert-butyl 4-(2-(2-(1,1-difluoroethyl)-4-nitrophenoxy)ethyl)piperazine-1-carboxylate as light tan solid (2.33 g, 95% yield). MS (ESI) m/z 416.2 [M+1]$^+$; $^1$H NMR (400 MHz, CDCl$_3$) δ ppm 8.44 (d, J=2.81 Hz, 1H), 8.30 (dd, J=9.11, 2.75 Hz, 1H), 7.03 (d, J=9.17 Hz, 1H), 4.26 (t, J=5.56 Hz, 2H), 3.40-3.47 (m, 4H), 2.88 (t, J=5.56 Hz, 2H), 2.49-2.58 (m, 4H), 2.00 (t, J=18.8 Hz, 3H), 1.46 (s, 9H).

tert-Butyl 4-(2-(4-amino-2-(1,1-difluoroethyl)phenoxy)ethyl)piperazine-1-carboxylate. To a solution of tert-butyl 4-(2-(2-(1,1-difluoroethyl)-4-nitrophenoxy)ethyl)piperazine-1-carboxylate (2.30 g, 5.54 mmol) in MeOH (20 mL) was added 10% Pd/C with 50% wt. water (1.18 g, 0.554 mmol) and the mixture was purged with H$_2$ gas. The reaction mixture was stirred under a H$_2$ atmosphere (balloon) for 3 h at ambient temperature. The mixture was purged with nitrogen gas, filtered through packed celite and concentrated. The residual syrup was dissolved in diethyl ether, dried over magnesium sulfate, filtered, and concentrated. The crude product was purified by silica gel column chromatography (25-100% EtOAc in hexanes) to provide tert-butyl 4-(2-(4-amino-2-(1,1-difluoroethyl)phenoxy)ethyl)piperazine-1-carboxylate as a light gold syrup (1.85 g, 87.0% yield). MS (ESI) m/z 386.2 [M+1]$^+$; $^1$H NMR (400 MHz, CDCl$_3$) δ ppm 6.87 (d, J=2.81 Hz, 1H), 6.78 (d, J=8.68 Hz, 1H), 6.68 (d, J=8.61 Hz, 1H), 4.05 (t, J=5.69 Hz, 2H), 3.51 (br s, 2H), 3.38-3.46 (m, 4H), 2.78 (t, J=5.69 Hz, 2H), 2.44-2.58 (m, 4H), 1.99 (t, J=18.8 Hz, 3H), 1.46 (s, 9H).

tert-Butyl 4-(2-(4-((2-cyanopropan-2-yl)amino)-2-(1,1-difluoroethyl)phenoxy)ethyl)piperazine-1-carboxylate. A solution of tert-butyl 4-(2-(4-amino-2-(1,1-difluoroethyl)phenoxy)ethyl)piperazine-1-carboxylate (1.59 g, 4.13 mmol) in acetone (15 mL) was cooled to 0° C. and trimethylsilyl cyanide (0.774 mL, 6.19 mmol) was added followed by trimethylsilyl trifluormethylsulfonate (0.037 mL, 0.21 mmol). The mixture was stirred for 7 h during which time the reaction mixture reached ambient temperature after approximately 2 h. The mixture was concentrated and the residue partitioned into saturated aqueous sodium bicarbonate and EtOAc and mixed. The organic layer was removed and the aqueous layer extracted with EtOAc. The combined EtOAc extracts were washed with brine, dried over magnesium sulfate with activated carbon, and filtered through a silica gel plug with EtOAc elution. The solution was concentrated and the residue dried under vacuum to provide tert-butyl 4-(2-(4-((2-cyanopropan-2-yl)amino)-2-(1,1-difluoroethyl)phenoxy)ethyl)piperazine-1-carboxylate as a faint pink solid (1.77 g, 95.0% yield). MS (ESI) m/z 453.4 [M+1]$^+$. $^1$H NMR (400 MHz, CDCl$_3$) δ ppm 7.02-7.19 (m, 2H), 6.89 (d, J=8.68 Hz, 1H), 4.11 (t, J=5.56 Hz, 2H), 3.35-3.52 (m, 4H), 2.82 (t, J=5.62 Hz, 2H), 2.44-2.60 (m, 4H), 2.01 (t, J=18.8 Hz, 3H), 1.64 (s, 6H), 1.46 (s, 9H).

4-(3-(3-(1,1-Difluoroethyl)-4-(2-(piperazin-1-yl)ethoxy)phenyl)-4,4-dimethyl-5-oxo-2-thioxoimidazolidin-1-yl)-2-(trifluoromethyl)benzonitrile. To a solution of tert-butyl 4-(2-(4-((2-cyanopropan-2-yl)amino)-2-(1,1-difluoroethyl)phenoxy)ethyl)piperazine-1-carboxylate (0.200 g, 0.442 mmol) in DMF (1.0 mL) was added 4-isothiocyanato-2-(trifluoromethyl)benzonitrile (0.121 g, 0.530 mmol) and the mixture was stirred at 60° C. for 3 h. Additional 4-isothiocyanato-2-(trifluoromethyl)benzonitrile (0.020 g) was added and the mixture was heated at 60° C. for 30 min. The reaction mixture was cooled to ambient temperature and diluted with MeOH (3 mL). A 2.0 M aqueous solution of HCl (1.11 mL, 2.21 mmol) was added and the mixture was stirred at 60° C. for 23 h. The mixture was concentrated, the residual syrup was dissolved in 5.0 M aqueous HCl in isopropyl alcohol (3 mL) and stirred for 90 min at ambient temperature. The mixture was concentrated, the residue partitioned into EtOAc and water and cooled to 0° C. The mixture was treated with 1.0 M aqueous solution of sodium hydroxide to pH=9-10, the organic layer was removed, and the aqueous layer extracted with EtOAc. The organic fractions were combined, dried over magnesium sulfate, filtered, and concentrated. The crude product was purified by silica gel column chromatography (20-100% EtOAc in hexanes then 5-50% MeOH in DCM) to furnish 4-(3-(3-(1,1-difluoroethyl)-4-(2-(piperazin-1-yl)ethoxy)phenyl)-4,4-dimethyl-5-oxo-2-thioxoimidazolidin-1-yl)-2-(trifluoromethyl)benzonitrile as a white solid (0.112 g, 44.0% yield). MS (ESI) m/z 582.2 [M+1]$^+$.

tert-Butyl 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)acetate. To a solution of 5-(3-(3-(1,1-difluoroethyl)-4-(2-(piperazin-1-yl)ethoxy)phenyl)-4,4-dimethyl-5-oxo-2-thioxoimidazolidin-1-yl)-3-(trifluoromethyl)picolinonitrile (0.140 g, 0.240 mmol) and DIEA (0.092 mL, 0.529 mmol) in dry THF (2 mL) was added tert-butyl 2-bromoacetate (0.039 mL, 0.264 mmol) and the mixture was stirred at ambient temperature for 6 h. The mixture was diluted with EtOAc (4 mL), added to water (10 mL), and mixed. The organic layer was removed and the aqueous layer was extracted with EtOAc. The organic fractions were combined, washed with brine, dried over magnesium sulfate, filtered, and concentrated. The residue was purified by silica gel column chromatography (0-10% of a 10% solution of ammonium hydroxide in MeOH in DCM) to provide tert-butyl 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)acetate as a colorless foam (0.085 g, 51.0% yield). MS (ESI) m/z 697.2 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)acetic acid trifluoroacetate. To a solution of tert-butyl 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)acetate (0.083 g, 0.12 mmol) in DCM (1 mL) was added TFA (2 mL) and the mixture was stirred at ambient temperature for 3 h. The reaction mixture was concentrated and the residual glass was sonicated in diethyl ether to give a granular solid. The solid was collected, washed with diethyl ether and dried under vacuum to afford 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)acetic acid trifluoroacetate as a white solid (0.083 g, 92.0% yield). MS (ESI) m/z 641.2 [M+1]$^+$.

bis-tert-Butyl (N-3-nitro-5,6-difluorophenyl)iminodicarbonate. 2,3-Difluoro-5-nitroaniline (1.0 g, 5.74 mmol) was placed in a vial with Boc$_2$O (3.33 mL, 14.36 mmol), (I)-2,2'-bis(diphenylphosphino)-1,1'-binaphthalene (0.351 g, 2.87 mmol), TEA (1.60 mL, 11.49 mmol), and THF (50.0 mL). The reaction mixture was stirred at 25° C. for 18 h. Volatile organics were removed under reduced pressure to give a dark orange oil. The oil was dissolved in EtOAc and purified by silica gel column chromatography (0-100% EtOAc in hexanes). Fractions containing the desired product were combined and volatile organics were removed under reduced pressure to give bis-tert-butyl (N-3-nitro-5,6-difluorophenyl)iminodicarbonate (1.29 g, 3.45 mmol, 60.0% yield) as a white solid. $^1$H NMR (400 MHz, DMSO-d$_6$) δ ppm 8.53 (ddd, J=2.81, 6.72, 9.78 Hz, 1H), 8.42 (td, J=2.34, 5.84 Hz, 1H), 1.34-1.46 (m, 18H); MS (ESI) m/z 397.0 [M+Na]$^+$.

bis-tert-Butyl (5-((2,6-dioxopiperidin-3-yl)amino)-2,3-difluorophenyl)iminodicarbonate. bis-tert-Butyl (N-3-nitro-5,6-difluorophenyl)iminodicarbonate (0.200 g, 0.534 mmol), 3-bromopiperidine-2,6-dione (0.513 g, 2.67 mmol), zinc (0.175 g, 2.67 mmol), and iron(II) chloride tetrahydrate (0.032 g, 0.16 mmol) were combined in NMP (1.5 mL). After degassing for a few minutes with argon and treatment with trimethylsilyl chloride (0.171 mL, 1.34 mmol), the reaction mixture was stirred sealed overnight at 90° C., then diluted with EtOAc (100 mL) and water (15 mL). The biphasic mixture was filtered through celite. The layers were separated and the organic layer was washed with a saturated aqueous sodium bicarbonate solution (50 mL) followed by brine (2×50 mL). The organic layer was dried over sodium sulfate, filtered, and concentrated to a dark green oil. The oil was dissolved in EtOAc and purified by silica gel column chromatography (0-80% EtOAc in hexanes). Fractions containing the desired product were combined and concentrated under reduced pressure to give bis-tert-butyl (5-((2,6-dioxopiperidin-3-yl)amino)-2,3-difluorophenyl)iminodicarbonate (0.075 g, 0.16 mmol, 30.8% yield) as a yellow oil. MS (ESI) m/z 300.0 [M−(Boc+t-butyl)]$^+$.

3-((3-Amino-4,5-difluorophenyl)amino)piperidine-2,6-dione dihydrochloride. bis-tert-Butyl (5-((2,6-dioxopiperidin-3-yl)amino)-2,3-difluorophenyl)iminodicarbonate (0.075 g, 0.165 mmol) in solution in DCM (1.0 mL) was treated with a 4.0 M solution of HCl in dioxane (1.0 mL, 4.00 mmol). The reaction mixture was stirred at 25° C. for 18 h. Volatile organics were removed under reduced pressure to give 3-((3-amino-4,5-difluorophenyl)amino)piperidine-2,6-dione dihydrochloride (0.074 g, 0.23 mmol, 137% yield) as a light orange solid. MS (ESI) m/z 256.0 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)-N-(5-((2,6-dioxopiperidin-3-yl)amino)-2,3-difluorophenyl)acetamide. To a solution of 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)acetic acid trifluoro acetate (0.113 g, 0.150 mmol) and 3-((3-amino-4,5-difluorophenyl)amino)piperidine-2,6-dione di-hydrochloride (0.054 g, 0.165 mmol) in dry DMF (1.0 mL) were sequentially added HATU (0.068 g, 0.180 mmol) and DIEA (0.131 mL, 0.749 mmol) and the mixture was stirred at ambient temperature for 16 h. Additional 3-((3-amino-4,5-difluorophenyl)amino)piperidine-2,6-dione di-hydrochloride (0.025 g), HATU (0.035 g) and DIEA (0.070 mL) were used and the mixture stirred for an additional 3 h. The reaction mixture was slowly poured into ice water (10 mL) with stirring and the resulting suspension was filtered. The collected solid was washed with water and diethyl ether and was dissolved in a 25% solution of formic acid in DMSO (2 mL). The solution was filtered (45 μm nylon membrane) and purified by standard methods to furnish 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)-N-(5-((2,6-dioxopiperidin-3-yl)amino)-2,3-difluorophenyl)acetamide (0.010 g, 8.0% yield). MS (ESI) m/z 878.0 [M+1]$^+$; $^1$H NMR (400 MHz, DMSO-d$_6$) δ ppm 10.82 (br s, 1H), 9.81 (br s, 1H), 9.26 (br s, 1H), 8.83 (br s, 1H), 7.17-7.65 (m, 4H), 6.98 (br s, 1H), 6.22 (br s, 1H), 4.48 (br s, 2H), 4.28 (br s, 1H), 3.08-3.16 (m, 4H), 2.67-2.77 (m, 4H), 2.02-2.16 (m, 5H), 1.90 (br s, 3H), 1.55 (br s, 9H).

Example 7: 2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(3-((2,6-dioxopiperidin-3-yl)amino)phenyl)acetamide hydrochloride

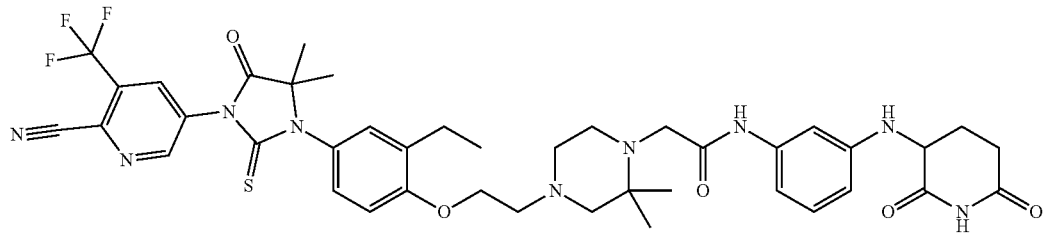 [SMILES: CCc1cc(N2C(=S)N(c3cnc(C#N)c(C(F)(F)F)c3)C(=O)C2(C)C)ccc1OCCN1CCN(CC(=O)Nc2cccc(NC3CCC(=O)NC3=O)c2)C(C)(C)C1]

1-(Benzyloxy)-2-bromo-4-nitrobenzene. To mixture of 2-bromo-4-nitrophenol (30.00 g, 137.61 mmol, 1 eq) and potassium carbonate (57.06 g, 412.8 mmol, 3 eq) in acetonitrile (300 mL) was added (bromomethyl)benzene (25.89 g, 151.4 mmol, 17.98 mL, 1.1 eq) under nitrogen. The reaction mixture was stirred at 80° C. for 2 h, filtered, and the filtrate was concentrated under vacuum. The residue was purified by silica gel column chromatography (5-20% EtOAc in petroleum ether) to give the product, 1-(benzyloxy)-2-bromo-4-nitrobenzene (35.80 g, 116.2 mmol, 84.4% yield) was obtained as a yellow solid. MS (ESI) m/z 332.0 [M+Na]$^+$; $^1$H NMR (400 MHz, DMSO-d$_6$) δ ppm 8.44 (d, J=2.7 Hz, 1H), 8.27 (dd, J=2.8, 9.2 Hz, 1H), 7.52-7.46 (m, 2H), 7.45-7.40 (m, 3H), 7.38-7.34 (m, 1H), 5.37 (s, 2H).

1-(Benzyloxy)-4-nitro-2-vinylbenzene. To a mixture of 1-(benzyloxy)-2-bromo-4-nitrobenzene (20.00 g, 64.91 mmol, 1 eq), 4,4,5,5-tetramethyl-2-vinyl-1,3,2-dioxaborolane (19.99 g, 129.82 mmol, 22.02 mL, 2.0 eq) and potassium phosphate (41.33 g, 194.72 mmol, 3 eq) in dioxane (300 mL) and water (150 mL) was added [1,1'-bis(diphenylphosphino)-ferrocene]dichloropalladium(II) (4.75 g, 6.49 mmol, 0.1 eq) at room temperature (25° C.). The reaction mixture was de-gassed and then heated to 100° C. for 12 h under nitrogen, filtered and the filtrate concentrated under vacuum. The residue was purified by silica gel column chromatography (0-1% EtOAc in petroleum ether) to give the product, 1-(benzyloxy)-4-nitro-2-vinylbenzene (12.50 g, 48.97 mmol, 75.4% yield) was obtained as a yellow solid. MS (ESI) m/z 278.1 [M+Na]$^+$.

4-Amino-2-ethylphenol. To a solution of 1-(benzyloxy)-4-nitro-2-vinylbenzene (12.50 g, 48.97 mmol, 1 eq) in MeOH (50 mL) and THF (50 mL) was added Pd/C (2.00 g, 10% purity) under nitrogen. The suspension was degassed under vacuum and purged with hydrogen. The mixture was stirred under hydrogen (50 psi) at 50° C. for 12 h, filtered, and the filtrate was concentrated under vacuum. The residue was purified by silica gel column chromatography (0-2% EtOAc in petroleum ether) to give the product, 4-amino-2-ethylphenol (6.40 g, 46.65 mmol, 95.3% yield) was obtained as a brown solid. MS (ESI) m/z 170.2 [M+Na]$^+$; $^1$H NMR (400 MHz, DMSO-d$_6$) δ ppm 8.13 (s, 1H), 6.46 (d, J=8.3 Hz, 1H), 6.34 (d, J=2.6 Hz, 1H), 6.23 (dd, J=2.8, 8.3 Hz, 1H), 4.28 (s, 1H), 2.41 (q, J=7.5 Hz, 2H), 1.07 (t, J=7.5 Hz, 3H).

5-Isothiocyanato-3-(trifluoromethyl)picolinonitrile. To a solution of 5-amino-3-(trifluoromethyl)picolinonitrile (20.00 g, 106.88 mmol, 1 eq) in toluene (200 mL) was added thiocarbonyl dichloride (24.58 g, 213.76 mmol, 16.39 mL, 2 eq). The reaction mixture was stirred at 110° C. for 12 h, then concentrated under reduced pressure. The residue was purified by silica gel column chromatography (0-5% EtOAc in petroleum ether) to give the product, 5-isothiocyanato-3-(trifluoromethyl)picolinonitrile (18.90 g, 82.47 mmol, 77.2% yield) which was obtained as a yellow liquid. MS (ESI) m/z 230.1 [M+1]$^+$.

2-((3-Ethyl-4-hydroxyphenyl)amino)-2-methylpropanenitrile. To a solution of 2-hydroxy-2-methylpropanenitrile (18.64 g, 219.00 mmol, 20 mL, 4.69 eq) in 4-amino-2-ethylphenol (6.400 g, 46.65 mmol, 1 eq) was added magnesium sulfate (14.04 g, 116.62 mmol, 2.5 eq). The reaction mixture was stirred at 60° C. for 12 h, then poured into EtOAc-water (v/v=1/1, 100 mL) and stirred for 15 min. The organic phase was separated and the aqueous phase was extracted with EtOAc (100 mL×2). The combined organic extracts were washed with brine (200 mL×5), dried with anhydrous sodium sulfate, filtered, and concentrated under vacuum. 2-((3-Ethyl-4-hydroxyphenyl)amino)-2-methylpropanenitrile (12.00 g, crude) was obtained as a brown solid. MS (ESI) m/z 205.1 [M+1]$^+$.

5-(3-(3-Ethyl-4-hydroxyphenyl)-4,4-dimethyl-5-oxo-2-thioxoimidazolidin-1-yl)-3-(trifluoromethyl)picolinonitrile. A solution of 2-((3-ethyl-4-hydroxyphenyl)amino)-2-methylpropanenitrile (9.50 g, 46.51 mmol, 1 eq) and 5-isothiocyanato-3-(trifluoromethyl)picolinonitrile (8.53 g, 37.21 mmol, 0.8 eq) in DMF (100 mL) was stirred at 20° C. for 1 h. Then, a 4.0 M solution of HCl/MeOH (100 mL, 2.15 eq) was added. The resulting mixture was stirred at 70° C. for 12 h, then was concentrated under vacuum to remove MeOH. The resulting mixture was diluted with water (200 mL) and extracted with EtOAc (200 mL×2). The combined organic extracts were washed with brine (50 mL×2), dried with anhydrous sodium sulfate, and concentrated under reduced pressure. The residue was purified by silica gel column chromatography (5-30% EtOAc in petroleum ether) to give the product, 5-(3-(3-ethyl-4-hydroxyphenyl)-4,4-dimethyl-5-oxo-2-thioxoimidazolidin-1-yl)-3-(trifluoromethyl)picolinonitrile (13.30 g, 30.61 mmol, 65.8% yield) was obtained as a brown solid. MS (ESI) m/z 457.2 [M+Na]$^+$.

tert-Butyl 4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazine-1-carboxylate. 5-(3-(3-Ethyl-4-hydroxyphenyl)-4,4-dimethyl-5-oxo-2-thioxoimidazolidin-1-yl)-3-(trifluoromethyl)picolinonitrile (0.800 g, 1.84 mmol), tert-butyl 4-(2-bromoethyl)-2,2-dimethylpiperazine-1-carboxylate (0.887 g, 2.76 mmol), sodium iodide (0.276 g, 1.84 mmol) and cesium carbonate (0.900 g, 2.76 mmol) were combined in DMF (7.366 mL) and heated to 60° C. for 1.5 h. The reaction mixture was cooled to room temperature and diluted with EtOAc (150 mL) and water (50 mL). After separation, the organic layer was washed with brine, dried over anhydrous magnesium sulfate, filtered, and concentrated to an oil. The crude material was purified by silica gel column chromatography (0-50% EtOAc in hexanes). Fractions were combined and concentrated under reduced pressure to afford tert-butyl 4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazine-1-carboxylate (1.45 g, 2.15 mmol, 117% yield) as an oil. MS (ESI) m/z 675.4 [M+1]$^+$.

tert-Butyl 4-(2-bromoethyl)-2,2-dimethylpiperazine-1-carboxylate. tert-Butyl 2,2-dimethylpiperazine-1-carboxylate (3.60 g, 16.8 mmol) and phosphoric acid, potassium salt (10.70 g, 50.4 mmol) were combined in THF (168 mL). To this mixture was added 1,2-dibromoethane (21.7 mL, 252 mmol). The reaction mixture was stirred at 60° C. for 48 h, filtered, and concentrated under reduced pressure to an oil that was dissolved in a minimum of DCM and purified by silica gel column chromatography (0-70% EtOAc in hexanes). Product containing fractions were combined and concentrated to afford tert-butyl 4-(2-bromoethyl)-2,2-dimethylpiperazine-1-carboxylate (2.93 g, 9.12 mmol, 54.3% yield) as an oil that was dried overnight under vacuum. MS (ESI) m/z 321.2, 323.2 [M+1, M+3]$^+$.

5-(3-(4-(2-(3,3-Dimethylpiperazin-1-yl)ethoxy)-3-ethylphenyl)-4,4-dimethyl-5-oxo-2-thioxoimidazolidin-1-yl)-3-(trifluoromethyl)picolinonitrile hydrochloride. tert-Butyl 4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazine-1-carboxylate (1.456 g, 2.158 mmol) was dissolved in DCM (40 mL) and treated with a 4.0 M solution of HCl in dioxane (10.8 mL, 43.2 mmol). The mixture was stirred at ambient temperature for 2 h, then concentrated to an oil under reduced pressure, that was then triturated in diethyl ether at ambient temperature overnight. The resulting solid, 5-(3-(4-(2-(3,3-dimethylpiperazin-1-yl)ethoxy)-3-ethylphenyl)-4,4-dimethyl-5-oxo-2-thioxoimidazolidin-1-yl)-3-(trifluoromethyl)picolinonitrile hydrochloride (1.24 g, 2.02 mmol, 94.0% yield), was collected by filtration and dried in a vacuum oven for 1.5 h. MS (ESI) m/z 575.2 [M+1]$^+$.

tert-Butyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)acetate. 5-(3-(4-(2-(3,3-Dimethylpiperazin-1-yl)ethoxy)-3-ethylphenyl)-4,4-dimethyl-5-oxo-2-thioxoimidazolidin-1-yl)-3-(trifluoromethyl)picolinonitrile hydrochloride (1.24 g, 2.02 mmol) was dissolved in THF (15 mL) and treated with DIEA (1.77 mL, 10.11 mmol) followed by tert-butyl 2-bromoacetate (0.314 mL, 2.12 mmol). The reaction mixture was stirred overnight at 50° C. To this mixture was added sodium iodide (0.303 g, 2.02 mmol, 1 eq), DMF (1 mL), and 0.75 equivalents of DIEA and tert-butyl 2-bromoacetate, and heating to 50° C. was resumed overnight. After cooling to room temperature, the reaction mixture was concentrated to dryness under reduced pressure. The residue was dissolved in EtOAc, washed with water and brine, dried over anhydrous magnesium sulfate, filtered, and concentrated to give tert-butyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)acetate (1.32 g, 1.92 mmol, 95.0% yield) as an oil that was used without further purification. MS (ESI) m/z 689.3 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)acetic acid trihydrochloride. A solution of tert-butyl 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)acetate (1.32 g, 1.92 mmol) in DCM (10 mL) with treated with a 4.0 M solution of HCl in dioxane (15.6 mL, 62.3 mmol). After 6 h, the temperature was increased to 45-50° C. for 12 h. The reaction mixture was concentrated under reduced pressure affording 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)acetic acid trihydrochloride as a tan solid (1.37 g, 1.84 mmol, 96.0% yield). MS(ESI) m/z 633 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(3-((2,6-dioxopiperidin-3-yl)amino)phenyl)acetamide hydrochloride. 2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)acetic acid tri-hydrochloride (0.125 g, 0.168 mmol, 1 eq) was combined with 3-((3-aminophenyl)amino)piperidine-2,6-dione trifluoroacetate salt (0.056 g, 0.17 mmol, 1 eq), HATU (0.070 g, 0.18 mmol, 1.1 eq), DIEA (0.177 mL, 1.01 mmol, 6 eq), and DMF (0.842 mL, 0.2 M), and the reaction was stirred at 25° C. for 1 h. The reaction was quenched with water and the mixture was diluted with EtOAc. The aqueous layer was extracted by EtOAc, and the combined organic extracts were concentrated under reduced pressure. The residue was purified by standard methods to afford 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(3-((2,6-dioxopiperidin-3-yl)amino)phenyl)acetamide hydrochloride (0.063 g, 0.076 mmol, 45.1% yield). MS (ESI) m/z 834.4 [M+1]$^+$; $^1$H NMR (400 MHz, DMSO-d$_6$) δ ppm 10.80 (s, 1H), 10.14 (br s, 1H), 9.25 (d, 1H, J=1.7 Hz), 8.82 (d, 1H, J=2.1 Hz), 7.1-7.2 (m, 3H), 7.04 (t, 1H, J=8.1 Hz), 7.01 (br s, 1H), 6.83 (br d, 1H, J=8.3 Hz), 6.45 (dd, 1H, J=1.8, 8.0 Hz), 4.42 (br s, 2H), 4.27 (br dd, 1H, J=4.8, 11.4 Hz), 3.3-3.5 (m, 6H), 3.2-3.3 (m, 4H), 2.6-2.8 (m, 5H), 2.10 (td, 1H, J=4.1, 8.5 Hz), 1.91 (dq, 1H, J=4.8, 12.1 Hz), 1.52 (s, 6H), 1.41 (br s, 3H), 1.35 (br s, 3H), 1.18 (t, 3H, J=7.5 Hz).

Example 8: N-(3-Chloro-5-((2,6-dioxopiperidin-3-yl)amino)phenyl)-2-(7-(2-(4-(3-(4-cyano-3-(trifluoromethyl)phenyl)-5,5-dimethyl-4-oxo-2-thioxoimidazolidin-1-yl)-2-ethylphenoxy)ethyl)-4,7-diazaspiro[2.5]octan-4-yl)acetamide hydrochloride

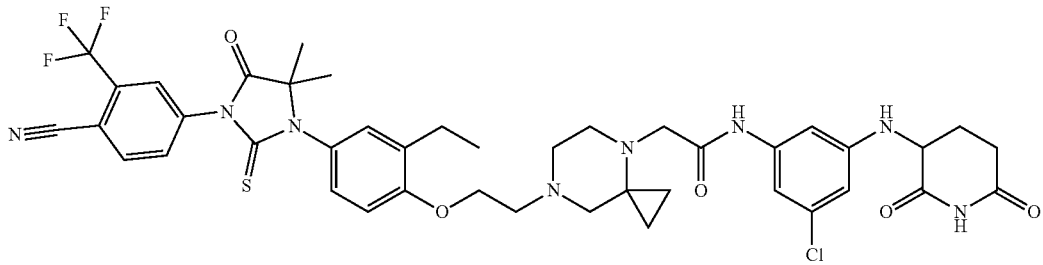 [SMILES: CCc1cc(N2C(=S)N(c3ccc(C#N)c(C(F)(F)F)c3)C(=O)C2(C)C)ccc1OCCN1CCN(CC(=O)Nc2cc(Cl)cc(NC3CCC(=O)NC3=O)c2)C2(CC2)C1]

2-Bromo-1-(2-bromoethoxy)-4-nitrobenzene. To a solution of 2-bromo-4-nitrophenol (10 g, 45.9 mmol) in DMF (115 mL) was added cesium carbonate (29.9 g, 92 mmol) followed by 1,2-dibromoethane (39.5 mL, 460 mmol), and the mixture was stirred overnight at 70° C. The reaction was diluted with EtOAc (400 mL), water (75 mL), and brine (75 mL). The layers were separated and the organic layer was washed with brine (3×100 mL), dried over anhydrous magnesium sulfate, filtered, and concentrated to dryness. The resulting oil was purified by silica gel column chromatography (0-30% EtOAc in hexanes) to afford the title compound (9.20 g, 28.3 mmol, 61.7% yield). MS (ESI) m/z 325.9 [M+1]$^+$.

tert-Butyl 7-(2-(2-bromo-4-nitrophenoxy)ethyl)-4,7-diazaspiro[2.5]octane-4-carboxylate. To a solution of 2-bromo-1-(2-bromoethoxy)-4-nitrobenzene (6.20 g, 19.08 mmol) in DMF (47.7 mL) were added DIEA (6.66 mL, 38.2 mmol) and tert-butyl 4,7-diazaspiro[2.5]octane-4-carboxylate (4.86 g, 22.90 mmol), and the mixture was stirred at 60° C. for 5 h. The reaction mixture was then cooled to ambient temperature and diluted with EtOAc (400 mL), water (75 mL), and brine (75 mL). The layers were separated and the organic layer was washed with brine (3×100 mL), dried over anhydrous magnesium sulfate, filtered, and was concentrated under reduced pressure to afford the title compound that was used without further purification (8.29 g, 18.18 mmol, 95.0% yield). MS (ESI) m/z 456.2 [M+1]$^+$.

tert-Butyl 7-(2-(4-nitro-2-vinylphenoxy)ethyl)-4,7-diazaspiro[2.5]octane-4-carboxylate. tert-Butyl 7-(2-(2-bromo-4-nitrophenoxy)ethyl)-4,7-diazaspiro[2.5]octane-4-carboxylate (8.71 g, 19.1 mmol), potassium trifluoro(vinyl)borate (7.67 g, 57.3 mmol), [1,1'-bis(diphenylphosphino)ferrocene]dichloropalladium(II) (3.12 g, 3.82 mmol) and cesium carbonate (18.66 g, 57.3 mmol) were combined in a 4:1 mixture of THF (100 mL) and water (25 mL), and heated for 6 h at 70° C. under a nitrogen atmosphere and then allowed to cool to ambient temperature overnight. The reaction mixture was diluted with EtOAc (500 mL), water (100 mL), and brine (100 mL). The solvent layers was separated, and the organic layer was washed with brine (100 mL), dried over anhydrous magnesium sulfate, filtered, and concentrated to an oil under reduced pressure. The crude material was purified using silica gel chromatography [0-70% EtOAc (containing 10% of a 7 N ammonia in MeOH solution) in hexanes] to afford the title compound assuming theoretical yield. MS (ESI) m/z 404.2 [M+1]$^+$.

tert-Butyl 7-(2-(4-amino-2-ethylphenoxy)ethyl)-4,7-diazaspiro[2.5]octane-4-carboxylate. A solution of tert-butyl 7-(2-(4-nitro-2-vinylphenoxy)ethyl)-4,7-diazaspiro[2.5]octane-4-carboxylate (7.92 g, 19.63 mmol in MeOH (196 mL) was purged with nitrogen, and treated with wetted 10% Pd/C (2.09 g, 1.96 mmol). The reaction mixture was stirred under a hydrogen atmosphere at ambient temperature overnight. Additional wetted 10% palladium (2 g) and 12 h of stirring at room temperature under an atmosphere of hydrogen were necessary to reach complete conversion. The reaction mixture was filtered through celite, the filtrate was concentrated under reduced pressure to afford tert-butyl 7-(2-(4-amino-2-ethylphenoxy)ethyl)-4,7-diazaspiro[2.5]octane-4-carboxylate (6.52 g, 17.36 mmol, 88% yield). MS (ESI) m/z 376.2 [M+1]$^+$.

4-(3-(4-(2-(4,7-Diazaspiro[2.5]octan-7-yl)ethoxy)-3-ethylphenyl)-4,4-dimethyl-5-oxo-2-thioxoimidazolidin-1-yl)-2-(trifluoromethyl)benzonitrile hydrochloride. tert-Butyl 7-(2-(4-((2-cyanopropan-2-yl)amino)-2-ethylphenoxy)ethyl)-4,7-diazaspiro[2.5]octane-4-carboxylate (3.50 g, 7.91 mmol) and 4-isothiocyanato-2-(trifluoromethyl)benzonitrile (1.80 g, 7.91 mmol) were combined in DMA (26.4 mL) and mixed at ambient temperature. The reaction mixture was treated with MeOH (10 mL) and a 3 N aqueous HCl solution (10 mL), and was stirred at 70° C. for 6 h, then diluted with EtOAc (400 mL) and water (50 mL), and a saturated aqueous solution of sodium bicarbonate (50 mL). The solvent layers were separated and the pH of the aqueous layer checked to insure its basicity. The organic layer was washed with brine (2×75 mL), dried over anhydrous magnesium sulfate, filtered, and concentrated to an oil under reduced pressure. This oil was dissolved in DCM (30 mL) and a 4 N solution of HCl in dioxane (29.6 mL, 119 mmol) was added. The mixture was stirred at ambient temperature for 1 h and concentrated to dryness under reduced pressure. The material was triturated with diethyl ether overnight at ambient temperature. The resulting solid was collected by filtration and dried under reduced pressure to afford the title compound (3.193 g, 5.25 mmol, 66.5% yield). MS (ESI) m/z 572.2 [M+1]$^+$.

5-Chlorobenzene-1,3-diamine. 1,3-Dibromo-5-chlorobenzene (30.00 g, 111 mmol, 1 eq), diphenylmethanimine (44.7 mL, 266 mmol, 2.4 eq), tris(dibenzylideneacetone)dipalladium(0) (2.03 g, 2.22 mmol, 2 mol %), (±)-2,2'-bis(diphenylphosphino)-1,1'-binaphthalene (4.15 g, 6.66 mmol, 6 mol %) and sodium t-butoxide (27.7 g, 289 mmol, 2.6 eq) in toluene (556 mL, 0.067 M) were heated to 80° C. for 18 h. The reaction was quenched with a saturated aqueous solution of sodium bicarbonate and extracted with EtOAc. The combined organic layers were washed with brine, dried over sodium sulfate, filtered, and concentrated to dryness. The residue was dissolved in THF (444 mL, 0.049 molar), treated with a 1.0 N aqueous solution of HCl (388 mL, 388 mmol, 3.5 eq), and stirred for 5 min. The reaction mixture was diluted with a 3:1 mixture of EtOAc and hexane and the aqueous layer was washed with a 3:1 mixture of EtOAc and hexane. The pH of the aqueous layer was adjusted to 11 with a 1.0 N aqueous solution of NaOH and extracted with DCM. The combined organic extracts were dried over sodium sulfate, filtered, and concentrated to give 5-chlorobenzene-1,3-diamine (13.48 g, 95 mmol, 85.0% yield) as a beige solid. MS (ESI) m/z 143.0 [M+1]+.

3-((3-Amino-5-chlorophenyl)amino)piperidine-2,6-dione. 5-Chlorobenzene-1,3-diamine (13.48 g, 95 mmol, 1 eq), 3-bromopiperidine-2,6-dione (18.15 g, 95 mmol, 1 eq), and sodium bicarbonate (9.53 g, 113 mmol, 1.2 eq) were combined in DMF (95 mL, 1 molar) and heated at 50° C. for 3 days. The reaction mixture was partitioned between EtOAc and brine. The organic layer was washed twice with brine, dried over sodium sulfate, filtered, and concentrated under reduced pressure. The crude material was purified by silica gel column chromatography (0-100% EtOAc in hexanes, followed by 20% MeOH in EtOAc) to afford 3-((3-amino-5-chlorophenyl)amino)piperidine-2,6-dione (2.38 g, 9.37 mmol, 9.9% yield) as a blue-green solid. MS (ESI) m/z 254.0 [M+1]+.

2-Chloro-N-(3-chloro-5-((2,6-dioxopiperidin-3-yl)amino)phenyl)acetamide. 3-((3-Amino-5-chlorophenyl)amino)piperidine-2,6-dione (3.74 g, 14.74 mmol, 1 eq), 2-chloroacetic acid (1.06 mL, 17.69 mmol, 1.2 eq), HATU (8.41 g, 22.11 mmol, 1.5 eq), and DIEA (7.72 mL, 44.2 mmol, 3 eq) were combined in DMF (42.1 mL, 0.350 molar) and stirred at room temperature. After 10 min, the reaction mixture was partitioned between EtOAc and brine. The combined organic layers were dried over sodium sulfate, filtered, and concentrated. The crude material was purified by silica gel column chromatography (50-100% EtOAc in hexanes) to afford a green oil, which was triturated in DCM and hexanes. Following the removal of the solvents under reduced pressure and further drying under high vacuum, 2-chloro-N-(3-chloro-5-((2,6-dioxopiperidin-3-yl)amino)phenyl)acetamide (3.25 g, 9.84 mmol, 66.7% yield) was isolated as a light green solid. MS (ESI) m/z 330.0 [M]+; 1H NMR (400 MHz, DMSO-d6) δ ppm 10.80 (s, 1H), 10.19 (s, 1H), 6.92 (t, 1H, J=1.7 Hz), 6.82 (t, 1H, J=1.8 Hz), 6.47 (t, 1H, J=1.9 Hz), 6.32 (d, 1H, J=8.1 Hz), 4.3-4.4 (m, 1H), 4.22 (s, 2H), 2.7-2.8 (m, 1H), 2.5-2.6 (m, 1H), 2.0-2.1 (m, 1H), 1.90 (dq, 1H, J=4.7, 12.4 Hz).

N-(3-Chloro-5-((2,6-dioxopiperidin-3-yl)amino)phenyl)-2-(7-(2-(4-(3-(4-cyano-3-(trifluoromethyl)phenyl)-5,5-dimethyl-4-oxo-2-thioxoimidazolidin-1-yl)-2-ethylphenoxy)ethyl)-4,7-diazaspiro[2.5]octan-4-yl)acetamide hydrochloride. 2-Chloro-N-(3-chloro-5-((2,6-dioxopiperidin-3-yl)amino)phenyl)acetamide (0.285 g, 0.863 mmol, 1.5 eq) was added to a stirred mixture of 4-(3-(4-(2-(4,7-diazaspiro[2.5]octan-7-yl)ethoxy)-3-ethylphenyl)-4,4-dimethyl-5-oxo-2-thioxoimidazolidin-1-yl)-2-(trifluoromethyl)benzonitrile hydrochloride (0.350 g, 0.576 mmol, 1 eq), sodium iodide (0.129 g, 0.863 mmol, 1.5 eq), DMF (4.80 mL, 0.12 molar) and DIEA (0.402 mL, 2.302 mmol, 4 eq). The reaction mixture was stirred for 20 min at 60° C. The solution was then cooled to room temperature, filtered, concentrated under reduced pressure, and the crude material was purified by standard methods to afford N-(3-chloro-5-((2,6-dioxopiperidin-3-yl)amino)phenyl)-2-(7-(2-(4-(3-(4-cyano-3-(trifluoromethyl)phenyl)-5,5-dimethyl-4-oxo-2-thioxoimidazolidin-1-yl)-2-ethylphenoxy)ethyl)-4,7-diazaspiro[2.5]octan-4-yl)acetamide hydrochloride (0.122 g, 0.141 mmol, 24.5% yield). MS (ESI) m/z 865.3 [M+1]+; 1H NMR (400 MHz, DMSO-d6) δ ppm 10.79 (s, 1H), 10.58 (br s, 1H), 9.49 (s, 1H), 8.39 (d, 1H, J=8.3 Hz), 8.29 (d, 1H, J=1.7 Hz), 8.08 (dd, 1H, J=1.6, 8.2 Hz), 7.1-7.2 (m, 3H), 6.9-7.0 (m, 2H), 6.45 (t, 1H, J=1.8 Hz), 4.4-4.6 (m, 2H), 4.32 (dd, 1H, J=4.8, 11.7 Hz), 3.3-3.5 (m, 6H), 3.11 (br d, 1H, J=12.8 Hz), 2.92 (br d, 1H, J=12.1 Hz), 2.5-2.8 (m, 4H), 2.5-2.5 (m, 2H), 2.0-2.1 (m, 1H), 1.90 (dq, 1H, J=4.9, 12.3 Hz), 1.50 (s, 6H), 1.17 (t, 3H, J=7.5 Hz), 1.02 (br s, 1H), 0.87 (br s, 2H), 0.6-0.7 (m, 1H).

Example 9: N-(3-Chloro-5-((2,6-dioxopiperidin-3-yl)amino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanamide hydrochloride

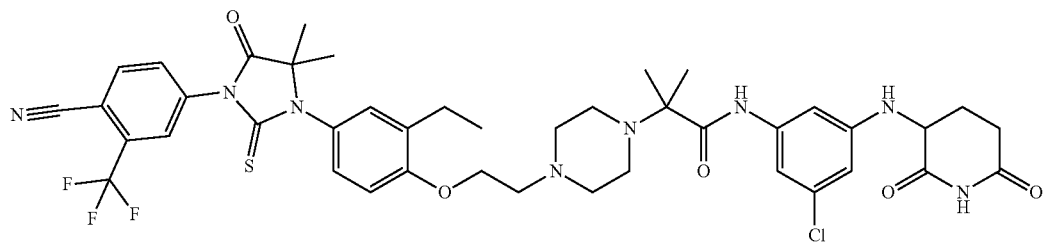 [SMILES: CCc1cc(N2C(=S)N(c3ccc(C#N)c(C(F)(F)F)c3)C(=O)C2(C)C)ccc1OCCN1CCN(C(C)(C)C(=O)Nc2cc(Cl)cc(NC3CCC(=O)NC3=O)c2)CC1]

4-(2-(4-((1-Methoxy-2-methyl-1-oxopropan-2-yl)amino)-2-vinylphenoxy)ethyl)piperazine-1-carboxylate. A mixture of tert-butyl 4-(2-(2-bromo-4-((1-methoxy-2-methyl-1-oxopropan-2-yl)amino)phenoxy)ethyl)piperazine-1-carboxylate (1.00 g, 2.00 mmol, 1 eq) (prepared as described herein), 4,4,5,5-tetramethyl-2-vinyl-1,3,2-dioxaborolane (0.62 g, 4.00 mmol, 2 eq), potassium phosphate (2.12 g, 9.99 mmol, 5 eq), (1,1'-bis(diphenylphosphino)ferrocene)-dichloropalladium(II) (0.29 g, 0.40 mmol, 0.2 eq) in dioxane (1 mL) and water (0.5 mL) was degassed and purged with nitrogen 3 times. The mixture was stirred at 120° C. for 12 h under nitrogen atmosphere, then concentrated under reduced pressure at 40° C. The residue was poured into ice-water (50 mL). The aqueous phase was extracted with EtOAc (50 mL×3). The combined organic phases were washed with brine (100 mL×2), dried with anhydrous sodium sulfate, filtered and concentrated under vacuum. The residue was purified by silica gel column chromatography (20%-33% EtOAc in petroleum ether) to provide tert-butyl 4-(2-(4-((1-methoxy-2-methyl-1-oxopropan-2-yl)amino)-2-vinylphenoxy)ethyl)piperazine-1-carboxylate (0.50 g, 1.12 mmol, 55.9% yield) was obtained as a yellow oil. MS (ESI) m/z 448.1 [M+1]$^+$.

tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazine-1-carboxylate. To a solution of tert-butyl 4-(2-(4-((1-methoxy-2-methyl-1-oxopropan-2-yl)amino)-2-vinylphenoxy)ethyl)piperazine-1-carboxylate (0.500 g, 1.120 mmol, 1 eq) in MeOH (10 mL) was added Pd—C (10%, 0.2 g) under nitrogen. The suspension was degassed under vacuum and purged with hydrogen several times. The mixture was stirred under hydrogen (50 psi) at 40° C. for 12 h. The reaction mixture was filtered and the filter was concentrated to afford tert-butyl 4-(2-(2-ethyl-4-((1-methoxy-2-methyl-1-oxopropan-2-yl)amino)phenoxy)ethyl)piperazine-1-carboxylate (0.320 g, 0.712 mmol, 63.7% yield) was obtained as a yellow oil. MS (ESI) m/z 450.3 [M+1]$^+$.

tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazine-1-carboxylate. To a mixture of tert-butyl 4-(2-(2-ethyl-4-((1-methoxy-2-methyl-1-oxopropan-2-yl)amino)phenoxy)ethyl)piperazine-1-carboxylate (0.319 g, 0.71 mmol, 1 eq) and 4-isothiocyanato-2-(trifluoromethyl)benzonitrile (0.486 g, 2.13 mmol, 3 eq) in EtOAc (2 mL) was added TEA (0.359 g, 3.55 mmol, 5 eq). The mixture was stirred at 80° C. for 12 h, then concentrated under reduced pressure. The residue was purified by preparative TLC (66.7% EtOAc in petroleum ether). tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazine-1-carboxylate (0.315 g, 0.488 mmol, 68.8% yield) was obtained as a yellow solid. MS (ESI) m/z 646.4 [M+1]$^+$.

4-(3-(3-Ethyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride. To a solution of tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazine-1-carboxylate (0.315 g, 0.488 mmol, 1 eq) in EtOAc (2 mL) was added HCl/dioxane (4 M, 10 mL). The mixture was stirred at 25° C. for 30 min, then was concentrated under reduced pressure. The crude material was used without further purification affording 4-(3-(3-ethyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.300 g, crude) as a yellow solid. MS (ESI) m/z 546.1 [M+1]$^+$.

tert-Butyl 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanoate. tert-Butyl 2-bromo-2-methylpropanoate (0.077 mL, 0.41 mmol, 1.2 eq) was added to a stirred mixture of 4-(3-(3-ethyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.200 g, 0.34 mmol, 1 eq), THF (2.94 mL, 0.12 molar) and TEA (0.192 mL, 1.37 mmol, 4 eq). The reaction mixture was stirred for 4 days at 85° C. An additional 4.8 eq of tert-butyl 2-bromo-2-methylpropanoate was added to the reaction, and the reaction was stirred at 85° C. for an additional 4 days. The reaction was concentrated and purified by silica gel column chromatography (20-100% EtOAc in hexanes followed by 0-5% MeOH in DCM) to give tert-butyl 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanoate (0.026 g, 0.038 mmol, 11.0% yield) as a beige solid contaminated with some hydantoin product. MS (ESI) m/z 688.2 [M+1]$^+$.

2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanoic acid trihydrochloride. A suspension of tert-butyl 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanoate (0.026 g, 0.038 mmol, 1 eq) in DCM (0.170 mL, 0.226 M), was treated with a solution of HCl in dioxane (142 µL, 0.567 mmol, 15 eq), and stirred at room temperature for 4 days. The reaction was concentrated to afford 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanoic acid trihydrochloride (0.028 g, 0.038 mmol, 100% yield) as a brown solid. MS (ESI) m/z 632.2 [M+1]$^+$.

N-(3-Chloro-5-((2,6-dioxopiperidin-3-yl)amino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanamide hydrochloride. A mixture of 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanoic acid trihydrochloride (0.028 g, 0.038 mmol, 1 eq) combined with 3-((3-amino-5-chlorophenyl)amino)piperidine-2,6-dione (0.011 g, 0.038 mmol, 1 eq), HATU (0.016 g, 0.042 mmol, 1.1 eq), DIEA (0.040 mL, 0.23 mmol, 6 eq), and DMF (0.189 mL, 0.2 molar) was stirred at 25° C. for 4 days. The reaction was quenched with water and the mixture was diluted with EtOAc. The aqueous layer was extracted with EtOAc and the combined organic extracts were concentrated. The material was purified standard methods to afford N-(3-chloro-5-((2,6-dioxopiperidin-3-yl)amino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanamide hydrochloride (0.002 g, 0.002 mmol, 5.2% yield). MS (ESI) m/z 867.2 [M+1]$^+$; $^1$H NMR (400 MHz, DMSO-d$_6$) δ ppm 10.80 (s, 1H), 10.40 (br s, 1H), 9.48 (br s, 1H), 8.39 (d, 1H, J=8.2 Hz), 8.29 (d, 1H, J=1.6 Hz), 8.07 (dd, 1H, J=1.8, 8.3 Hz), 7.1-7.2 (m, 4H), 6.86 (s, 1H), 6.46 (s, 1H), 4.48 (br s, 2H), 4.35 (br dd, 1H, J=4.7, 11.7 Hz), 3.6-3.6 (m, 4H), 3.2-3.3 (m, 4H), 2.9-3.0 (m, 2H), 2.7-2.8 (m, 1H), 2.67 (q, 2H, J=7.5 Hz), 2.62 (td, 1H, J=4.0, 13.6 Hz), 2.07 (tt, 1H, J=3.9, 8.1 Hz), 1.90 (dq, 1H, J=4.0, 11.9 Hz), 1.50 (s, 6H), 1.2-1.2 (m, 6H), 1.17 (br t, 3H, J=7.5 Hz).

Example 10: 1-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)-N-(3-((2,6-dioxopiperidin-3-yl)amino)phenyl)cyclopropanecarboxamide hydrochloride

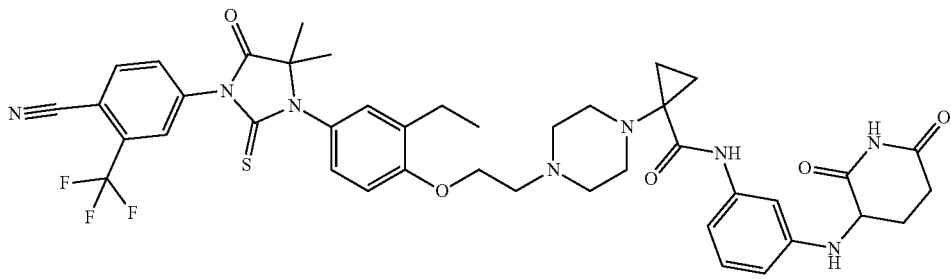 [SMILES: CCc1cc(N2C(=S)N(c3ccc(C#N)c(C(F)(F)F)c3)C(=O)C2(C)C)ccc1OCCN1CCN(C2(C(=O)Nc3cccc(NC4CCC(=O)NC4=O)c3)CC2)CC1]

Ethyl 1-(4-benzylpiperazin-1-yl)cyclopropanecarboxylate. Ethyl 1-aminocyclopropanecarboxylate hydrochloride (0.500 g, 3.02 mmol, 1 eq) was added to a stirred mixture of N-benzyl-2-chloro-N-(2-chloroethyl)ethanamine hydrochloride (0.886 g, 3.30 mmol, 1.09 eq), EtOH (6.66 mL, 0.453 molar) and DIEA (5.30 mL, 30.3 mmol, 10.05 eq). The reaction mixture was stirred for 18 h at 78° C., then concentrated under reduced pressure. The crude material was partitioned between DCM and water. The layers were separated, and the aqueous layer was extracted with DCM. The combined organic extracts were concentrated under reduced pressure and the crude material was purified by silica gel column chromatography (5-10% EtOAc in hexanes) to give ethyl 1-(4-benzylpiperazin-1-yl)cyclopropanecarboxylate (0.409 g, 1.42 mmol, 47.0% yield) as a yellow oil. MS (ESI) m/z 289.2 [M+1]$^+$.

Ethyl 1-(piperazin-1-yl)cyclopropanecarboxylate hydrochloride. To a solution of ethyl 1-(4-benzylpiperazin-1-yl)cyclopropanecarboxylate (0.200 g, 0.694 mmol, 1 eq) in anhydrous DCM (1.692 mL, 0.410 molar) cooled to 0° C., 1-chloroethyl carbonochloridate (0.110 mL, 1.02 mmol, 1.465 eq) was slowly added to maintain the temperature below 0° C. The mixture was stirred at 18° C. for 1 h. The reaction was concentrated to dryness and the residue was dissolved in EtOH (1.69 mL, 0.410 M). The resulting solution was stirred at 78° C. for 18 h. The reaction mixture was concentrated to dryness. The residue was then stirred in a 5:1 mixture of EtOH and MTBE, and the precipitate was collected by filtration to give ethyl 1-(piperazin-1-yl)cyclopropanecarboxylate hydrochloride (0.107 g, 0.456 mmol, 65.7% yield) as a beige solid. MS (ESI) m/z 199.2 [M+1]$^+$.

2-((3-Bromo-4-hydroxyphenyl)amino)-2-methylpropanenitrile. To a solution of 4-amino-2-bromophenol (5.00 g, 26.6 mmol) in DCM (177 mL) and acetone (89 mL) were added trimethylsilyl cyanide (4.66 mL, 37.2 mmol) and trimethylsilyl trifluoromethylsulphonate (0.241 mL, 1.33 mmol). The reaction mixture was stirred at room temperature for 1 h, then was concentrated to remove the solvent. The crude material was purified by silica gel column chromatography (0-100% EtOAc in hexanes) to afford 2-((3-bromo-4-hydroxyphenyl)amino)-2-methylpropanenitrile (4.56 g, 17.87 mmol, 67.2% yield) as a brown solid. MS (ESI) m/z 256.2 [M+1]$^+$; $^1$H NMR (400 MHz, DMSO-d$_6$) δ ppm 9.55-9.66 (m, 1H), 7.05 (d, J=2.69 Hz, 1H), 6.83-6.87 (m, 1H), 6.77-6.81 (m, 1H), 5.51 (s, 1H), 1.55 (s, 6H).

4-(3-(3-Bromo-4-hydroxyphenyl)-4,4-dimethyl-5-oxo-2-thioxoimidazolidin-1-yl)-2-(trifluoromethyl)benzonitrile. 2-((3-Bromo-4-hydroxyphenyl)amino)-2-methylpropanenitrile (1.00 g, 3.92 mmol) and 4-isothiocyanato-2-(trifluoromethyl)benzonitrile (0.894 g, 3.92 mmol) were combined in DMA (13.07 mL) and stirred at room temperature overnight. MeOH (5 mL) and a 3.0 N aqueous solution of HCl (5 mL) were added and the reaction was heated at 70° C. After 2 h, the reaction mixture was partitioned between EtOAc and water. The aqueous layer was extracted with EtOAc before the combined organic layers were dried over magnesium sulfate, filtered, and concentrated under reduced pressure. The crude material was purified by silica gel column chromatography (0-100% EtOAc in hexanes) to afford 4-(3-(3-bromo-4-hydroxyphenyl)-4,4-dimethyl-5-oxo-2-thioxoimidazolidin-1-yl)-2-(trifluoromethyl)benzonitrile (1.23 g, 2.423 mmol, 62.0% yield) as a white solid. MS (ESI) m/z 484.0 [M+1]$^+$.

2-Bromo-4-(3-(4-cyano-3-(trifluoromethyl)phenyl)-5,5-dimethyl-4-oxo-2-thioxoimidazolidin-1-yl)phenyl acetate. A solution of 4-(3-(3-bromo-4-hydroxyphenyl)-4,4-dimethyl-5-oxo-2-thioxoimidazolidin-1-yl)-2-(trifluoromethyl)benzonitrile (0.75 g, 1.55 mmol) in DCM (7.74 mL) treated with DIEA (0.541 mL, 3.10 mmol) and acetyl chloride (0.132 mL, 1.86 mmol) was stirred at room temperature. After 12 h, the reaction was diluted with EtOAc (100 mL) and the organic layer was washed with a saturated aqueous solution of sodium bicarbonate (2×100 mL) and brine (100 mL). The organic layer was dried over magnesium sulfate and concentrated to provide a colorless oil which was purified by silica gel column chromatography (20-50% EtOAc in hexanes) to give the title compound (0.766 g, 1.455 mmol, 94% yield). MS (ESI) m/z 526.0 [M+1]$^+$; $^1$H NMR (400 MHz, CDCl$_3$) δ ppm 7.97 (s, 1H), 7.94 (s, 1H), 7.82 (dd, J=2.1, 8.2 Hz, 1H), 7.58 (d, J=2.3 Hz, 1H), 7.36-7.27 (m, 2H), 2.40 (s, 3H), 1.61 (s, 6H).

4-(3-(4-Cyano-3-(trifluoromethyl)phenyl)-5,5-dimethyl-4-oxo-2-thioxoimidazolidin-1-yl)-2-ethylphenyl acetate. To a mixture of 2-bromo-4-(3-(4-cyano-3-(trifluoromethyl)

phenyl)-5,5-dimethyl-4-oxo-2-thioxoimidazolidin-1-yl) phenyl acetate (2 g, 3.80 mmol), [(2-dicyclohexylphosphino-2',6'-bis(N,N-dimethylamino)-1,1'-biphenyl)-2-(2'-amino-1,1'-biphenyl)] palladium(II) methanesulfonate (0.311 g, 0.380 mmol) and 2-(2-dicyclohexylphosphanylphenyl)-$N^1,N^1,N^3,N^3$-tetramethyl-benzene-1,3-diamine (0.166 g, 0.38 mmol) combined in a schlenk flask and purged with argon, was added toluene (15.20 mL). The reaction mixture was placed in an ice bath for 5 min, then treated with a 0.5 M solution of ethylzinc(II) bromide in THF (6.08 mL, 3.04 mmol, 0.8 equiv). After 30 min, an additional 0.5 equivalent of ethylzinc(II) bromide solution was used (3.80 mL, 1.90 mmol) at 0° C. for 30 min, the reaction was quenched with the addition of a 2.0 M aqueous solution of HCl (2.470 mL, 4.94 mmol) and the mixture was diluted with EtOAc (350 mL). The organic layer was washed twice with a saturated aqueous solution of sodium bicarbonate, dried over magnesium sulfate, filtered, and concentrated under reduced pressure to afford a brown solid. The crude material was purified by silica gel column chromatography (0-45% EtOAc in hexanes) to afford 4-(3-(4-cyano-3-(trifluoromethyl)phenyl)-5,5-dimethyl-4-oxo-2-thioxoimidazolidin-1-yl)-2-ethylphenyl acetate (0.986 g, 2.07 mmol, 55.0% yield). MS(ESI) m/z 476 [M+1]$^+$.

4-(3-(3-Ethyl-4-hydroxyphenyl)-4,4-dimethyl-5-oxo-2-thioxoimidazolidin-1-yl)-2-(trifluoromethyl)benzonitrile. A suspension of 4-(3-(4-cyano-3-(trifluoromethyl)phenyl)-5,5-dimethyl-4-oxo-2-thioxoimidazolidin-1-yl)-2-ethylphenyl acetate (0.876 g, 1.84 mmol) and potassium carbonate (0.255 g, 1.84 mmol) in MeOH (20 mL) was stirred at ambient temperature. After 40 min, the solution diluted with EtOAc (200 mL) and partitioned with water (50 mL). The combined organic layers were dried over magnesium sulfate, filtered, and concentrated under reduced pressure to afford the title compound (0.766 g, 1.76 mmol, 96.0% yield). MS(ESI) m/z 434 [M+1]$^+$.

4-(3-(4-(2-Bromoethoxy)-3-ethylphenyl)-4,4-dimethyl-5-oxo-2-thioxoimidazolidin-1-yl)-2-(trifluoromethyl)benzonitrile. 1,2-Dibromoethane (2.99 mL, 34.6 mmol, 20.0 eq), cesium carbonate (1.97 g, 6.06 mmol, 3.5 eq) and 4-(3-(3-ethyl-4-hydroxyphenyl)-4,4-dimethyl-5-oxo-2-thioxoimidazolidin-1-yl)-2-(trifluoromethyl)benzonitrile (0.750 g, 1.73 mmol, 1 eq) were dissolved in DMF (20.36 mL, 0.085 M) in a preheated flask, and the reaction was stirred at 60° C. for 18 h under a nitrogen atmosphere. The reaction was quenched with water and the mixture was diluted with EtOAc. The aqueous phase was extracted with EtOAc and the combined organic extracts were washed with brine, dried over sodium sulfate, filtered, and concentrated. The crude residue was purified by silica gel column chromatography (0-100% EtOAc in hexane). Fractions were concentrated to a residue that was triturated with DCM and hexane to afford 4-(3-(4-(2-bromoethoxy)-3-ethylphenyl)-4,4-dimethyl-5-oxo-2-thioxoimidazolidin-1-yl)-2-(trifluoromethyl)benzonitrile (0.296 g, 0.548 mmol, 31.7% yield) as a beige solid. MS (ESI) m/z 540.0 [M]$^+$.

Ethyl 1-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)cyclopropanecarboxylate. To a solution of ethyl 1-(piperazin-1-yl)cyclopropanecarboxylate hydrochloride (0.107 g, 0.456 mmol, 1 eq) in DMF (4.56 mL, 0.1 molar) was added 4-(3-(4-(2-bromoethoxy)-3-ethylphenyl)-4,4-dimethyl-5-oxo-2-thioxoimidazolidin-1-yl)-2-(trifluoromethyl)benzonitrile (0.296 g, 0.547 mmol, 1.2 eq) and DIEA (0.279 mL, 1.596 mmol, 3.5 eq). The vessel was sealed and the mixture was heated to 60° C. with stirring for 18 h. The reaction was concentrated and purified by silica gel column chromatography (0-10% MeOH in DCM) to give ethyl 1-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)cyclopropanecarboxylate (0.090 g, 0.137 mmol, 30.0% yield) as an orange oil. MS (ESI) m/z 658.2 [M+1]$^+$.

(S)-2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperidin-1-yl)propanoic acid tetrahydrochloride. To ethyl 1-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)cyclopropanecarboxylate (0.090 g, 0.137 mmol) was added a 6 M aqueous solution of HCl (1.140 mL, 6.84 mmol) slowly at 0° C. The reaction was gradually warmed to 100° C. and stirred for 18 h. The reaction mixture was concentrated to afford 1-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)cyclopropanecarboxylic acid, tetrahydrochloride (0.108 g, 0.139 mmol, 102% yield) as a pale yellow solid. MS (ESI) m/z 630.2 [M+1]$^+$.

1-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)-N-(3-((2,6-dioxopiperidin-3-yl)amino)phenyl)cyclopropanecarboxamide hydrochloride. 1-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)cyclopropanecarboxylic acid tetrahydrochloride (0.108 g, 0.139 mmol, 1 eq) was combined with 3-((3-aminophenyl)amino)piperidine-2,6-dione trifluoroacetate salt (0.046 g, 0.139 mmol, 1 eq), HATU (0.058 g, 0.153 mmol, 1.1 eq), DIEA (0.170 mL, 0.975 mmol, 7 eq) in DMF (0.696 mL, 0.2 molar), and the reaction was stirred at 25° C. for 15 min. The reaction was quenched with water and the mixture was diluted with EtOAc. The aqueous layer was extracted with EtOAc and the combined organic extracts were concentrated. The crude material was purified by standard methods to afford 1-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-((2,6-dioxopiperidin-3-yl)amino)phenyl)cyclopropanecarboxamide hydrochloride (0.027 g, 0.032 mmol, 22.7% yield). MS (ESI) m/z 831.6 [M+1]$^+$; $^1$H NMR (400 MHz, DMSO-$d_6$) δ ppm 10.78 (s, 1H), 10.49 (br s, 1H), 9.48 (s, 1H), 8.39 (d, 1H, J=8.3 Hz), 8.29 (d, 1H, J=1.7 Hz), 8.07 (dd, 1H, J=1.7, 8.3 Hz), 7.1-7.2 (m, 4H), 7.02 (t, 1H, J=8.0 Hz), 6.79 (dd, 1H, J=1.0, 8.1 Hz), 6.43 (dd, 1H, J=1.7, 8.1 Hz), 4.49 (t, 2H, J=4.4 Hz), 4.30 (dd, 1H, J=4.8, 11.3 Hz), 3.58 (br s, 2H), 3.44 (t, 4H, J=10.6 Hz), 2.97 (br d, 2H, J=12.2 Hz), 2.7-2.9 (m, 3H), 2.66 (q, 2H, J=7.4 Hz), 2.59 (td, 1H, J=4.3, 17.2 Hz), 2.1-2.1 (m, 1H), 1.89 (dq, 1H, J=4.5, 12.2 Hz), 1.50 (s, 6H), 1.17 (t, 3H, J=7.5 Hz), 1.1-1.2 (m, 2H), 1.0-1.1 (m, 2H).

Example 11: N-(3-Chloro-5-((2,6-dioxopiperidin-3-yl)amino)phenyl)-1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)cyclopropane-1-carboxamide hydrochloride

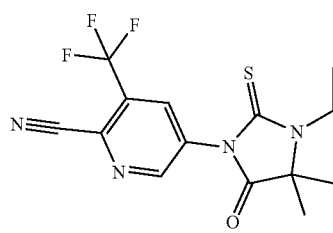
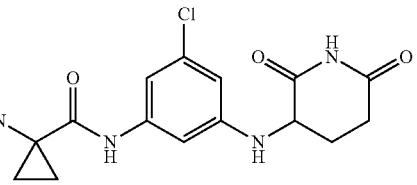

5-(3-(4-(2-Bromoethoxy)-3-ethylphenyl)-4,4-dimethyl-5-oxo-2-thioxoimidazolidin-1-yl)-3-(trifluoromethyl)picolinonitrile. 1,2-Dibromoethane (2.39 mL, 27.6 mmol, 20 eq), cesium carbonate (1.57 g, 4.83 mmol, 3.5 eq) and 5-[3-(3-ethyl-4-hydroxy-phenyl)-4,4-dimethyl-5-oxo-2-thioxo-imidazolidin-1-yl]-3-(trifluoromethyl)pyridine-2-carbonitrile (0.600 g, 1.38 mmol, 1 eq) were dissolved in DMF (16.2 mL, 0.085 molar) in a preheated flask, and the reaction was stirred at 60° C. for 18 h under a nitrogen atmosphere. The reaction was quenched with water and diluted with EtOAc, and the aqueous phase was extracted with EtOAc. The combined organic phases were washed with brine, dried over sodium sulfate, filtered, and concentrated under reduced pressure. The crude product was purified by silica gel column chromatography (0-100% EtOAc in hexanes). The fractions were concentrated, and the residue was triturated in DCM and hexanes to afford 5-[3-[4-(2-bromoethoxy)-3-ethyl-phenyl]-4,4-dimethyl-5-oxo-2-thioxo-imidazolidin-1-yl]-3-(trifluoromethyl)pyridine-2-carbonitrile (0.324 g, 0.60 mmol, 43.3% yield) as a pale pink solid. MS (ESI) m/z 539.8 [M]$^+$.

Ethyl 1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)cyclopropane-1-carboxylate. To a solution of ethyl 1-piperazin-1-ylcyclopropanecarboxylate hydrochloride (0.181 g, 0.69 mmol, 1.15 eq) in DMF (6.00 mL, 0.100 molar) was added 5-[3-[4-(2-bromoethoxy)-3-ethyl-phenyl]-4,4-dimethyl-5-oxo-2-thioxo-imidazolidin-1-yl]-3-(trifluoromethyl)pyridine-2-carbonitrile (0.324 g, 0.60 mmol, 1 eq) and DIEA (0.36 mL, 2.09 mmol, 3.5 eq). The reaction was sealed and heated to 60° C. with stirring for 18 h. The solution was concentrated under reduced pressure and the residue was purified by silica gel column chromatography (0-100% EtOAc in hexanes) to give ethyl 1-[4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]piperazin-1-yl]cyclopropanecarboxylate (0.036 g, 0.05 mmol, 9.1% yield) as a light yellow semi-solid. MS (ESI) m/z 496.0 [M+1]$^+$.

1-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)piperazin-1-yl)cyclopropane-1-carboxylic acid trihydrochloride. To ethyl 1-[4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]piperazin-1-yl]cyclopropanecarboxylate (0.036 g, 0.05 mmol, 1 eq) was slowly added a 6.0 N aqueous solution of HCl (0.46 mL, 2.73 mmol, 50 eq) at 0° C. The reaction mixture was gradually warmed to 100° C. and stirred for 18 h, then concentrated to afford 1-[4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]piperazin-1-yl]cyclopropanecarboxylic acid trihydrochloride (0.040 g, 0.05 mmol, 99.9% yield) as a pale yellow solid. MS (ESI) m/z 629.8 [M+1]$^+$.

N-(3-Chloro-5-((2,6-dioxopiperidin-3-yl)amino)phenyl)-1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)cyclopropane-1-carboxamide hydrochloride. 1-[4-[2-[4-[3-[6-Cyano-5-(trifluoromethyl)-3-pyridyl]-5,5-dimethyl-4-oxo-2-thioxo-imidazolidin-1-yl]-2-ethyl-phenoxy]ethyl]piperazin-1-yl]cyclopropanecarboxylic acid trihydrochloride (0.040 g, 0.050 mmol, 1 eq) was combined with 3-(3-amino-5-chloro-anilino)piperidine-2,6-dione (13.8 mg, 0.050 mmol, 1 eq), HATU (22.8 mg, 0.060 mmol, 1.1 eq), DIEA (0.05 mL, 0.270 mmol, 5 eq), and DMF (0.273 mL, 0.200 M), and the reaction was stirred at 25° C. for 18 h. The reaction was quenched with water and diluted with EtOAc, and the aqueous layer was extracted with EtOAc. The combined organic layers were concentrated and purified by standard methods to afford N-[3-chloro-5-[(2,6-dioxo-3-piperidyl)amino]phenyl]-1-[4-[2-[4-[3-[6-cyano-5-(trifluoromethyl)-3-pyridyl]-5,5-dimethyl-4-oxo-2-thioxo-imidazolidin-1-yl]-2-ethyl-phenoxy]ethyl]piperazin-1-yl]cyclopropanecarboxamide hydrochloride (0.005 g, 5.8×10$^{-2}$ mmol, 10.6% yield). MS (ESI) m/z 866.7 [M+1]$^+$; $^1$H NMR (400 MHz, DMSO-d$_6$) δ ppm 10.81 (s, 1H), 10.53 (s, 1H), 10.45 (br s, 1H), 9.22 (d, 1H, J=1.8 Hz), 8.76 (d, 1H, J=2.1 Hz), 7.2-7.3 (m, 3H), 7.02 (s, 1H), 6.98 (s, 1H), 6.57 (t, 1H, J=1.8 Hz), 6.36 (br s, 1H), 4.4-4.5 (m, 2H), 4.34 (br dd, 1H, J=4.8, 11.9 Hz), 3.69 (br d, 2H, J=10.8 Hz), 3.58 (br dd, 2H, J=4.4, 7.7 Hz), 3.22 (q, 2H, J=9.8 Hz), 2.5-2.8 (m, 7H), 2.4-2.5 (m, 2H), 2.0-2.1 (m, 1H), 1.8-2.0 (m, 6H), 1.5-1.6 (m, 1H), 1.18 (t, 3H, J=7.5 Hz).

Example 12: 2-(4-(2-(2-Chloro-4-(7-(4-cyano-3-(trifluoromethyl)phenyl)-8-oxo-6-thioxo-5,7-diazaspiro[3.4]octan-5-yl)phenoxy)ethyl)piperazin-1-yl)-N-(3-((2,6-dioxopiperidin-3-yl)amino)phenyl)acetamide hydrochloride

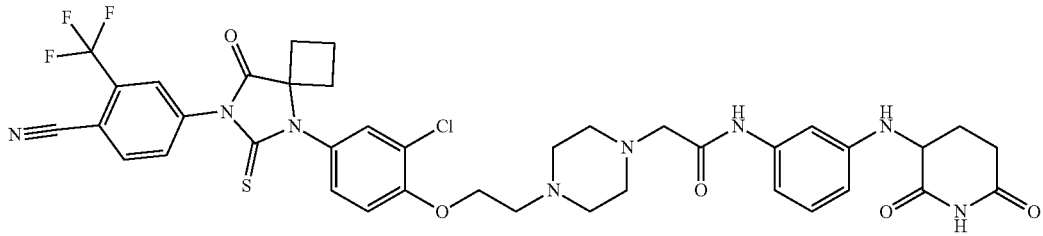 [SMILES: N#Cc1ccc(N2C(=O)C3(CCC3)N(c3ccc(OCCN4CCN(CC(=O)Nc5cccc(NC6CCC(=O)NC6=O)c5)CC4)c(Cl)c3)C2=S)cc1C(F)(F)F]

(3-((2,6-Dioxopiperidin-3-yl)amino)phenyl)carbamate To a solution of tert-butyl (3-((2,6-dioxopiperidin-3-yl)amino)phenyl)carbamate (10.00 g, 48.02 mmol, 1 eq) and 3-bromopiperidine-2,6-dione (9.22 g, 48.02 mmol, 1 eq) in DMF (100 mL) was added sodium bicarbonate (4.03 g, 48.02 mmol, 1 eq). The reaction mixture was stirred at 50° C. for 10 h then filtered. The filtrate was purified by preparative reverse phase HPLC (25%-55% acetonitrile in water+0.225% formic acid, 30 min) to give the tert-butyl (3-((2,6-dioxopiperidin-3-yl)amino)phenyl)carbamate (6.04 g, 18.91 mmol, 39.4% yield) as a green solid. $^1$H NMR (400 MHz, DMSO-$d_6$) δ ppm 10.76 (s, 1H), 9.02 (s, 1H), 6.92 (t, J=8.0 Hz, 1H), 6.85 (s, 1H), 6.65 (d, J=8.4 Hz, 1H), 6.29 (d, J=7.6 Hz, 1H), 5.78 (d, J=7.2 Hz, 1H), 2.76-2.59 (m, 2H), 2.11-2.07 (m, 1H), 1.92-1.82 (m, 1H).

3-((3-Aminophenyl)amino)piperidine-2,6-dione. To a solution of tert-butyl (3-((2,6-dioxopiperidin-3-yl)amino)phenyl)carbamate (6.04 g, 18.91 mmol, 1 eq) in DCM (50 mL) was added a 4.0 M solution of HCl in dioxane (28.37 mL, 6 eq), and the reaction mixture was stirred at 20° C. for 2 h. The reaction mixture was concentrated to dryness. 3-((3-Aminophenyl)amino)piperidine-2,6-dione hydrochloride (4.50 g, 17.60 mmol, 93.1% yield) was isolated as a light green solid and used in the next step without purification. $^1$H NMR (400 MHz, DMSO-$d_6$) δ ppm 10.81 (s, 1H), 10.12 (s, 3H), 7.16 (t, J=8.0 Hz, 1H), 6.70-6.68 (m, 1H), 6.64-6.63 (m, 1H), 6.55-6.53 (m, 1H), 4.36-4.32 (m, 1H), 2.79-2.70 (m, 1H), 2.67-2.56 (m, 1H), 2.11-2.05 (m, 1H), 1.95-1.86 (m, 1H).

tert-Butyl 4-(2-((3-((2,6-dioxopiperidin-3-yl)amino)phenyl)amino)-2-oxoethyl)piperazine-1-carboxylate. To a solution of 2-(4-(tert-butoxycarbonyl)piperazin-1-yl)acetic acid (1.05 g, 4.30 mmol, 1.1 eq), HATU (1.78 g, 4.69 mmol, 1.2 eq), and DIEA (1.26 g, 9.78 mmol, 2.5 eq) in DMF (10 mL) was added 3-(3-aminoanilino)piperidine-2,6-dione hydrochloride (1.00 g, 3.91 mmol, 1 eq) at 0° C. The mixture was stirred at 15° C. for 10 h. To the mixture was added water (60 mL) and the resulting suspension was extracted with EtOAc (40 mL×2). The combined organic extracts were washed with brine (50 mL×5), dried, filtered, and concentrated to give tert-butyl 4-(2-((3-((2,6-dioxopiperidin-3-yl)amino)phenyl)amino)-2-oxoethyl)piperazine-1-carboxylate (1.37 g, 3.08 mmol, 78.6% yield) as a white solid. $^1$H NMR (400 MHz, DMSO-$d_6$) δ ppm 10.78 (s, 1H), 9.84 (br, 1H), 7.01 (t, J=8.0 Hz, 1H), 6.95 (s, 1H), 6.82 (d, J=7.6 Hz, 1H), 6.42 (d, J=8.0 Hz, 1H), 5.92 (d, J=7.2 Hz, 1H), 4.28-4.22 (m, 1H), 3.63-3.33 (m, 10H), 2.72-2.70 (m, 1H), 2.62-2.56 (m, 1H), 2.13-2.07 (m, 1H), 1.95-1.84 (m, 1H), 1.40 (s, 9H).

N-(3-((2,6-Dioxopiperidin-3-yl)amino)phenyl)-2-(piperazin-1-yl)acetamide. To a solution of tert-butyl 4-(2-((3-((2,6-dioxopiperidin-3-yl)amino)phenyl)amino)-2-oxoethyl)piperazine-1-carboxylate (1.35 g, 3.03 mmol, 1 eq) in DCM (10 mL) was added a 4.0 M solution of HCl in dioxane (3.79 mL, 5 eq). The reaction was stirred at 15° C. for 12 h. To the suspension was added EtOAc (20 mL) and the resulting suspension was filtered. The filter cake was washed with EtOAc (20 mL) and dried under reduced pressure to give N-(3-((2,6-dioxopiperidin-3-yl)amino)phenyl)-2-(piperazin-1-yl)acetamide hydrochloride (1.26 g, crude) as a light yellow solid. $^1$H NMR (400 MHz, DMSO-$d_6$) δ ppm 10.82 (s, 1H), 10.67 (s, 1H), 10.01 (br, 1H), 7.05 (t, J=8.0 Hz, 1H), 7.01 (s, 1H), 6.89 (d, J=7.6 Hz, 1H), 6.50 (d, J=7.6 Hz, 1H), 4.29-4.26 (m, 3H), 3.73-3.57 (m, 4H), 3.44-3.35 (m, 4H), 2.77-2.69 (m, 1H), 2.61-2.57 (m, 1H), 2.11-2.09 (m, 1H), 1.98-1.89 (m, 1H).

1-((3-Chloro-4-hydroxyphenyl)amino)cyclobutanecarbonitrile. Trimethylsilylformonitrile (0.249 g, 2.51 mmol, 1.20 eq) was added dropwise to a mixture of 4-amino-2-chlorophenol (0.300 g, 2.09 mmol, 1 eq) and cyclobutanone (0.293 g, 4.18 mmol, 2 eq) in DCM (3 mL). The mixture was stirred at 25° C. for 10 h. At the end of the dropwise addition of a saturated aqueous solution of sodium bicarbonate (0.5 mL), the mixture was concentrated to a residue that was purified by column chromatography (0-50% EtOAc in petroleum ether) to yield 1-((3-chloro-4-hydroxyphenyl)amino)cyclobutanecarbonitrile (0.320 g, 1.44 mmol, 68.8% yield) as a red solid. MS (ESI) m/z 223.2 [M+1]$^+$; $^1$H NMR (400 MHz, DMSO-$d_6$) δ ppm 9.34 (s, 1H), 6.84 (d, J=8.7 Hz, 1H), 6.55 (d, J=2.8 Hz, 1H), 6.47-6.40 (m, 1H), 6.27 (s, 1H), 2.72-2.61 (m, 2H), 2.29 (br d, J=10.5 Hz, 2H), 2.12-2.00 (m, 2H).

4-(5-(3-Chloro-4-hydroxyphenyl)-8-oxo-6-thioxo-5,7-diazaspiro[3.4]octan-7-yl)-2-(trifluoromethyl)benzonitrile. Thiocarbonyl dichloride (0.108 g, 0.943 mmol, 1 eq) was added dropwise to a mixture of 1-((3-chloro-4-hydroxyphenyl)amino)cyclobutanecarbonitrile (0.210 g, 0.943 mmol, 1 eq) and 4-amino-2-(trifluoromethyl)benzonitrile (0.176 g, 0.943 mmol, 1 eq) in DMA (3 mL). The mixture was stirred at 60° C. for 12 h, then diluted with MeOH (0.6 mL) and an aqueous solution of HCl (2M, 0.4 mL), and stirred at 15° C. for 2 h. The mixture was poured into water (10 mL), and the aqueous phase was extracted with EtOAc (15 mL×3). The combined organic phases were washed with brine (10 mL×2), dried with anhydrous sodium sulfate, filtered, and concentrated under vacuum to get the crude product. The material was purified by preparative TLC followed by flash silica gel chromatography (0-50% EtOAc in petroleum ether) to get 4-(5-(3-chloro-4-hydroxyphenyl)-8-oxo-6-thioxo-5,7-diazaspiro[3.4]octan-7-yl)-2-(trifluoromethyl)benzonitrile (0.208 g, 0.460 mmol, 48.8% yield) as a brown solid. MS (ESI) m/z 451.9 [M+1]⁺; ¹H NMR (400 MHz, DMSO-d₆) δ ppm 10.76 (s, 1H), 8.37 (d, J=8.3 Hz, 1H), 8.22 (d, J=1.8 Hz, 1H), 8.09-7.97 (m, 1H), 7.42 (d, J=2.4 Hz, 1H), 7.23-7.18 (m, 1H), 7.15 (s, 1H), 2.64-2.55 (m, 2H), 2.47-2.37 (m, 2H), 1.95-1.89 (m, 1H), 1.60-1.49 (m, 1H).

4-(5-(4-(2-Bromoethoxy)-3-chlorophenyl)-8-oxo-6-thioxo-5,7-diazaspiro[3.4]octan-7-yl)-2-(trifluoromethyl)benzonitrile. To a mixture of 4-(5-(3-chloro-4-hydroxyphenyl)-8-oxo-6-thioxo-5,7-diazaspiro[3.4]octan-7-yl)-2-

1H), 6.97 (s, 1H), 6.84 (br d, J=7.9 Hz, 1H), 6.50-6.38 (m, 1H), 4.60 (br s, 2H), 4.31-4.22 (m, 1H), 3.93 (br s, 13H), 2.82-2.68 (m, 1H), 2.62 (br s, 2H), 2.43 (br d, J=10.3 Hz, 3H), 2.15-2.05 (m, 1H), 2.02-1.83 (m, 2H), 1.61-1.50 (m, 1H).

Example 13: 2-(4-(2-(4-(3-(4-Cyano-3-(trifluoromethyl)phenyl)-5,5-dimethyl-4-oxo-2-thioxoimidazolidin-1-yl)-2-cyclopropylphenoxy)ethyl)piperazin-1-yl)-N-(3-((2,6-dioxopiperidin-3-yl)amino)phenyl) acetamide hydrochloride

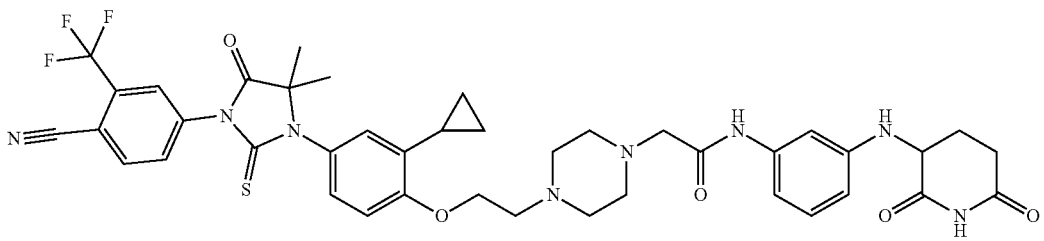 [SMILES: CC1(C)C(=O)N(c2ccc(C#N)c(C(F)(F)F)c2)C(=S)N1c1ccc(OCCN2CCN(CC(=O)Nc3cccc(NC4CCC(=O)NC4=O)c3)CC2)c(C2CC2)c1]

(trifluoromethyl)benzonitrile (0.200 g, 0.44 mmol, 1 eq) in acetonitrile (7 mL) was added potassium carbonate (0.245 g, 1.77 mmol, 4 eq) and 1,2-dibromoethane (0.416 g, 2.21 mmol, 5 eq). The mixture was stirred at 80° C. for 12 h, then was concentrated and poured into water (10 mL). The aqueous phase was extracted with EtOAc (15 mL×3). The combined organic phases were washed with brine (10 mL×2), dried with anhydrous sodium sulfate, filtered, and concentrated under vacuum to get the crude product. The material was purified by silica gel column chromatography (0-50% EtOAc in petroleum ether) to get 4-(5-(4-(2-bromoethoxy)-3-chlorophenyl)-8-oxo-6-thioxo-5,7-diazaspiro[3.4]octan-7-yl)-2-(trifluoromethyl)benzonitrile (0.170 g, 0.285 mmol, 64.4% yield) as a light yellow oil. MS (ESI) m/z 558.1 559.1 [M+1, M+2]⁺; ¹H NMR (400 MHz, CDCl₃) δ ppm 8.01-7.95 (m, 2H), 7.84 (dd, J=1.9, 8.2 Hz, 1H), 7.39 (d, J=2.5 Hz, 1H), 7.21 (dd, J=2.5, 8.7 Hz, 1H), 7.10 (d, J=8.8 Hz, 1H), 4.44 (t, J=6.3 Hz, 2H), 3.75 (t, J=6.3 Hz, 2H), 2.74-2.64 (m, 2H), 2.61-2.50 (m, 2H), 2.33-2.17 (m, 1H), 1.74-1.67 (m, 1H).

2-(4-(2-(2-Chloro-4-(7-(4-cyano-3-(trifluoromethyl)phenyl)-8-oxo-6-thioxo-5,7-diazaspiro[3.4]octan-5-yl)phenoxy)ethyl)piperazin-1-yl)-N-(3-((2,6-dioxopiperidin-3-yl)amino)phenyl)acetamide hydrochloride. To a solution of 4-(5-(4-(2-bromoethoxy)-3-chlorophenyl)-8-oxo-6-thioxo-5,7-diazaspiro[3.4]octan-7-yl)-2-(trifluoromethyl)benzonitrile (0.161 g, 0.288 mmol, 1.1 eq) and N-(3-((2,6-dioxopiperidin-3-yl)amino)phenyl)-2-(piperazin-1-yl)acetamide hydrochloride (0.100 g, 0.262 mmol, 1.00 eq) in DMF (1 mL) was added DIEA (0.169 g, 1.310 mmol, 5 eq). The mixture was stirred at 60° C. for 12 h, then treated with potassium iodide (0.087 g, 0.524 mmol, 2 eq) and stirred at 80° C. for 8 h. The material was purified by standard methods to get 2-(4-(2-(2-chloro-4-(7-(4-cyano-3-(trifluoromethyl)phenyl)-8-oxo-6-thioxo-5,7-diazaspiro[3.4]octan-5-yl)phenoxy)ethyl)piperazin-1-yl)-N-(3-((2,6-dioxopiperidin-3-yl)amino)phenyl)acetamide hydrochloride (0.046 g, 0.052 mmol, 20.0% yield). MS (ESI) m/z 823.4 [M+1]⁺; ¹H NMR (400 MHz, DMSO-d₆) δ ppm 10.80 (s, 1H), 10.46-10.03 (m, 1H), 8.39 (d, J=8.3 Hz, 1H), 8.22 (d, J=1.5 Hz, 1H), 8.10-7.97 (m, 1H), 7.60 (s, 1H), 7.43 (s, 2H), 7.03 (s, tert-Butyl 4-(2-(2-bromo-4-nitrophenoxy)ethyl)piperazine-1-carboxylate. To a mixture of tert-butyl 4-(2-chloroethyl)piperazine-1-carboxylate (5.71 g, 22.94 mmol, 1 eq) and 2-bromo-4-nitrophenol (5.00 g, 22.94 mmol, 1 eq) in acetonitrile (50 mL) was added potassium carbonate (15.85 g, 114.68 mmol, 5 eq). The mixture was stirred at 60° C. for 2 h. The mixture was concentrated under reduced pressure, and the residue was partitioned between EtOAc (30 mL) and water (20 mL). The aqueous phase was extracted with EtOAc (15 mL×1). The combined organic phases were washed with water (20 mL×3) and brine (10 mL×1), dried with anhydrous sodium sulfate, filtered and concentrated in vacuum. tert-Butyl 4-(2-(2-bromo-4-nitrophenoxy)ethyl)piperazine-1-carboxylate (8.22 g, 19.10 mmol, 83.3% yield) was obtained as a yellow solid and was used without further purification. MS (ESI) m/z 432.0 [M+3]⁺.

tert-Butyl 4-(2-(4-amino-2-bromophenoxy)ethyl)piperazine-1-carboxylate. To tert-butyl 4-(2-(2-bromo-4-nitrophenoxy)ethyl)piperazine-1-carboxylate (6.00 g, 13.94 mmol, 1 eq) in MeOH (60 mL) was added zinc (4.56 g, 69.72 mmol, 5 eq) and ammonium chloride (14.92 g, 278.88 mmol, 20 eq). The mixture was stirred at 50° C. for 48 h then filtered, and the filtrate was concentrated under reduced pressure. The residue was purified by semi-preparative reverse phase HPLC (5%-35% acetonitrile+0.225% formic acid in water). The collected fractions were concentrated to remove most of the acetonitrile, and treated with a saturated aqueous solution of sodium bicarbonate to adjust the pH to 7. The aqueous phase was extracted with EtOAc (200 mL×3). The combined organic phase was washed with brine (100 mL×1), dried with anhydrous sodium sulfate, filtered and concentrated under vacuum. tert-Butyl 4-(2-(4-amino-2-bromophenoxy)ethyl)piperazine-1-carboxylate (3.02 g, 7.55 mmol, 54.2% yield) was obtained as a yellow solid. MS (ESI) m/z 400.1 [M+1]⁺; ¹H NMR (400 MHz, DMSO-d₆) δ ppm 6.83 (d, J=8.8 Hz, 1H), 6.79 (d, J=2.8 Hz, 1H), 6.51 (dd, J=2.4, 8.8 Hz, 1H), 4.90 (br s, 2H), 3.97 (t, J=5.6 Hz, 2H), 3.29 (br s, 4H), 2.67 (t, J=5.6 Hz, 2H), 2.47-2.41 (m, 4H), 1.39 (s, 9H)

tert-Butyl 4-(2-(2-bromo-4-((1-methoxy-2-methyl-1-oxopropan-2-yl)amino)phenoxy)ethyl)piperazine-1-carboxylate. To tert-butyl 4-(2-(4-amino-2-bromophenoxy)ethyl)piperazine-1-carboxylate (1.90 g, 4.13 mmol, 1 eq) in DIEA (15 mL) was added methyl 2-bromo-2-methylpropanoate (2.24 g, 12.39 mmol, 3 eq). The mixture was stirred at 120° C. for 12 h. The mixture was concentrated under reduced pressure and diluted with water (20 mL). The aqueous phase was extracted with EtOAc (20 mL×2). The combined organic phase was washed with brine (10 mL×1), dried with anhydrous sodium sulfate, filtered, and concentrated in vacuum. The residue was purified by silica gel column chromatography (30-60% EtOAc in petroleum ether). tert-Butyl 4-(2-(2-bromo-4-((1-methoxy-2-methyl-1-oxopropan-2-yl)amino)phenoxy)ethyl)piperazine-1-carboxylate (1.90 g, 3.80 mmol, 92.0% yield) was obtained as a yellow solid. $^1$H NMR (400 MHz, DMSO-d$_6$) δ ppm 6.89 (d, J=8.8 Hz, 1H), 6.75-6.66 (m, 1H), 6.36 (dd, J=2.8, 8.8 Hz, 1H), 5.83-5.78 (m, 1H), 5.81 (s, 1H), 3.99 (t, J=5.6 Hz, 2H), 3.59 (s, 3H), 3.29 (br s, 4H), 2.72-2.65 (m, 2H), 2.46-2.39 (m, 4H), 1.41-1.37 (m, 15H).

tert-Butyl 4-(2-(2-cyclopropyl-4-((1-methoxy-2-methyl-1-oxopropan-2-yl)amino)phenoxy)ethyl)piperazine-1-carboxylate. To a mixture of tert-butyl 4-(2-(2-bromo-4-((1-methoxy-2-methyl-1-oxopropan-2-yl)amino)phenoxy)ethyl)piperazine-1-carboxylate (0.300 g, 0.599 mmol, 1 eq) and 2-cyclopropyl-4,4,5,5-tetramethyl-1,3,2-dioxaborolane (0.201 g, 1.200 mmol, 2 eq) in dioxane (5 mL) and water (0.5 mL) was added potassium phosphate (0.636 g, 3.000 mmol, 5 eq) and [1,1'-bis(diphenylphosphino)ferrocene]dichloropalladium(II) (0.088 g, 0.120 mmol, 0.2 eq) under nitrogen. The mixture was stirred at 120° C. for 12 h. The mixture was concentrated under reduced pressure. The residue was purified by preparative TLC (50% EtOAc in petroleum ether) followed by semi-preparative reverse phase HPLC (10%-40% acetonitrile+0.225% formic acid in water, 10 min). Then the collected fractions were concentrated to remove most of the acetonitrile, and lyophilized. tert-Butyl 4-(2-(2-cyclopropyl-4-((1-methoxy-2-methyl-1-oxopropan-2-yl)amino)phenoxy)ethyl)piperazine-1-carboxylate (0.108 g, 0.234 mmol, 39.0% yield) was obtained as a yellow oil. MS (ESI) m/z 462.2 [M+1]$^+$; $^1$H NMR (400 MHz, DMSO-d$_6$) δ ppm 8.15 (s, 1H), 6.68 (d, J=8.8 Hz, 1H), 6.16 (dd, J=2.8, 8.6 Hz, 1H), 5.95 (d, J=2.8 Hz, 1H), 5.37 (br s, 1H), 3.96 (t, J=5.6 Hz, 2H), 3.57 (s, 3H), 3.38 (br s, 4H), 2.69 (t, J=5.6 Hz, 2H), 2.47-2.40 (m, 4H), 2.12-2.00 (m, 1H), 1.45-1.31 (m, 15H), 0.90-0.75 (m, 1H), 0.79 (s, 1H), 0.50-0.36 (m, 1H), 0.50 (s, 1H).

tert-Butyl 4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)piperazine-1-carboxylate. To a mixture of tert-butyl 4-(2-(2-cyclopropyl-4-((1-methoxy-2-methyl-1-oxopropan-2-yl)amino)phenoxy)ethyl)piperazine-1-carboxylate (0.108 g, 0.234 mmol, 1 eq) and 4-isothiocyanato-2-(trifluoromethyl)benzonitrile (0.160 g, 0.702 mmol, 3 eq) in EtOAc (1 mL) was added TEA (0.118 g, 1.170 mmol, 5 eq). The mixture was stirred at 80° C. for 2 h. The mixture was concentrated under reduced pressure and the residue was purified by preparative TLC (66.7% EtOAc in petroleum ether). tert-Butyl 4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)piperazine-1-carboxylate (0.090 g, 0.137 mmol, 58.5% yield) was obtained as a yellow solid. MS (ESI) m/z 658.1 [M+1]$^+$.

4-(3-(3-Cyclopropyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride. To a solution of tert-butyl 4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)piperazine-1-carboxylate (0.09 g, 0.1374 mmol, 1 eq) in EtOAc (2 mL) was added a solution of HCl in dioxane (4 M, 5 mL). The mixture was stirred at 25° C. for 30 min. The mixture was concentrated under reduced pressure. 4-(3-(3-Cyclopropyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.10 g, crude) was obtained as a yellow oil and was used without further purification. MS (ESI) m/z 558.1 [M+1]$^+$.

2-Chloro-N-(3-((2,6-dioxopiperidin-3-yl)amino)phenyl)acetamide. To a mixture of 2-chloroacetic acid (1.39 g, 14.66 mmol, 1.1 eq), HATU (5.57 g, 14.66 mmol, 1.1 eq), and DMF (40 mL), stirred at 15° C. for 2 h, was added 3-((3-aminophenyl)amino)piperidine-2,6-dione hydrobromide (4.00 g, 13.33 mmol, 1 eq) and DIEA (5.17 g, 39.98 mmol, 6.96 mL, 3 eq), The reaction mixture was stirred at 15° C. for 1 h, diluted with brine (150 mL) and EtOAc (150 mL), and the layers were separated. The aqueous layer was extracted with EtOAc (100 mL×2). The combined organic extracts were concentrated and the resulting suspension was filtered. The filtrate was purified by reverse phase semi-preparative HPLC (10-40% acetonitrile in water+0.05% HCl, 26 min) to give 2-chloro-N-(3-((2,6-dioxopiperidin-3-yl)amino)phenyl)acetamide (2.60 g, 8.79 mmol, 66.0% yield) as a grey solid. $^1$H NMR (400 MHz, DMSO-d$_6$) δ ppm 10.81 (s, 1H), 10.17 (s, 1H), 7.06-7.02 (m, 2H), 6.86 (d, J=8.0 Hz, 1H), 6.48 (dd, J=8.0, 1.6 Hz, 1H), 4.36-4.26 (m, 1H), 4.22 (s, 2H), 2.77-2.68 (m, 1H), 2.59 (dt, J=17.6, 4.0 Hz, 1H), 2.12-2.05 (m, 1H), 1.91 (qd, J=12.4, 4.8 Hz, 1H).

2-(4-(2-(4-(3-(4-Cyano-3-(trifluoromethyl)phenyl)-5,5-dimethyl-4-oxo-2-thioxoimidazolidin-1-yl)-2-cyclopropylphenoxy)ethyl)piperazin-1-yl)-N-(3-((2,6-dioxopiperidin-3-yl)amino)phenyl)acetamide hydrochloride. To a mixture of 4-(3-(3-cyclopropyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.100 g, 0.168 mmol, 1 eq) and 2-chloro-N-(3-((2,6-dioxopiperidin-3-yl)amino)phenyl)acetamide (0.060 g, 0.202 mmol, 1.2 eq) in DMF (2 mL) was added DIEA (0.109 g, 0.842 mmol, 5 eq). The mixture was stirred at 50° C. for 10 h. The mixture was filtered and the filtrate was purified by standard methods to afford 2-(4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)piperazin-1-yl)-N-(3-((2,6-dioxopiperidin-3-yl)amino)phenyl)acetamide hydrochloride (0.079 g, 0.095 mmol, 56.5% yield). MS (ESI) m/z 817.2 [M+1]$^+$; $^1$H NMR (400 MHz, DMSO-d$_6$) δ ppm 10.80 (s, 1H), 10.38 (br s, 1H), 8.39 (d, J=8.4 Hz, 1H), 8.27 (d, J=1.6 Hz, 1H), 8.06 (dd, J=1.6, 8.2 Hz, 1H), 7.19-7.11 (m, 2H), 7.07-7.00 (m, 1H), 6.97 (s, 1H), 6.86 (br s, 2H), 6.46 (br d, J=8.0 Hz, 1H), 4.53 (br s, 2H), 4.25 (br dd, J=4.8, 11.2 Hz, 1H), 4.09 (br s, 4H), 3.83 (br s, 8H), 2.79-2.68 (m, 1H), 2.64-2.51 (m, 2H), 2.29-2.17 (m, 1H), 2.10 (td, J=4.4, 8.5 Hz, 1H), 1.91 (dq, J=4.8, 12.4 Hz, 1H), 1.47 (s, 6H), 1.00-0.88 (m, 2H), 0.66-0.54 (m, 2H).

Example 14: 2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)-N-(3-((2,6-dioxopiperidin-3-yl)amino)phenyl) acetamide hydrochloride

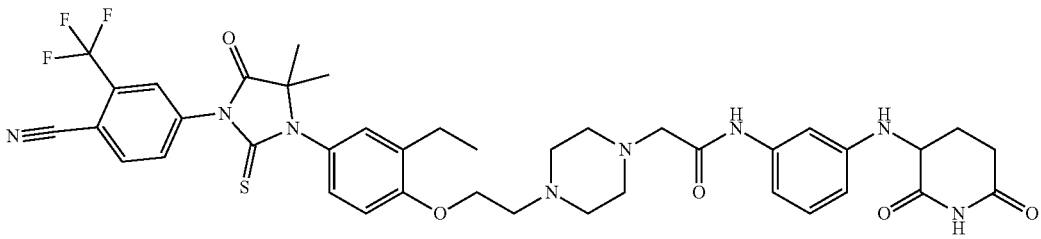 [SMILES: CCc1cc(N2C(=S)N(c3ccc(C#N)c(C(F)(F)F)c3)C(=O)C2(C)C)ccc1OCCN1CCN(CC(=O)Nc2cccc(NC3CCC(=O)NC3=O)c2)CC1]

2-(4-(2-(4-(3-(4-Cyano-3-(trifluoromethyl)phenyl)-5,5-dimethyl-4-oxo-2-thioxoimidazolidin-1-yl)-2-ethylphenoxy)ethyl)piperazin-1-yl)-N-(3-((2,6-dioxopiperidin-3-yl)amino)phenyl)acetamide hydrochloride. To a mixture of 4-(3-(3-ethyl-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.150 g, 0.258 mmol, 1 eq) and 2-chloro-N-(3-((2,6-dioxopiperidin-3-yl)amino)phenyl)acetamide (0.091 g, 0.309 mmol, 1.2 eq) in DMF (2 mL), (prepared as described herein), was added DIEA (0.167 g, 1.29 mmol, 5 eq). The mixture was stirred at 50° C. for 10 h then was filtered. The filtrate was purified by standard methods to afford 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-((2,6-dioxopiperidin-3-yl)amino)phenyl)acetamide hydrochloride (0.106 g, 0.131 mmol, 50.8% yield). MS (ESI) m/z 805.2 [M+1]$^+$; $^1$H NMR (400 MHz, DMSO-$d_6$) δ ppm 10.80 (s, 1H), 10.48 (br s, 1H), 8.39 (d, J=8.4 Hz, 1H), 8.29 (d, J=1.2 Hz, 1H), 8.08 (d, J=8.4 Hz, 1H), 7.24-7.11 (m, 3H), 7.09-7.01 (m, 1H), 7.09-7.01 (m, 1H), 6.98 (s, 1H), 6.87 (d, J=8.0 Hz, 1H), 6.47 (br d, J=7.6 Hz, 1H), 4.52 (br s, 2H), 4.26 (br dd, J=4.8, 11.4 Hz, 1H), 4.16 (br s, 4H), 3.70 (br s, 8H), 2.80-2.66 (m, 3H), 2.66-2.52 (m, 2H), 2.10 (td, J=4.0, 8.8 Hz, 1H), 1.91 (dq, J=4.0, 12.0 Hz, 1H), 1.53-1.47 (m, 1H), 1.50 (s, 5H), 1.17 (t, J=7.6 Hz, 3H).

Example 15: (2R)-2-(4-(2-(2-Chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-((2,6-dioxopiperidin-3-yl)amino)phenyl) propanamide hydrochloride

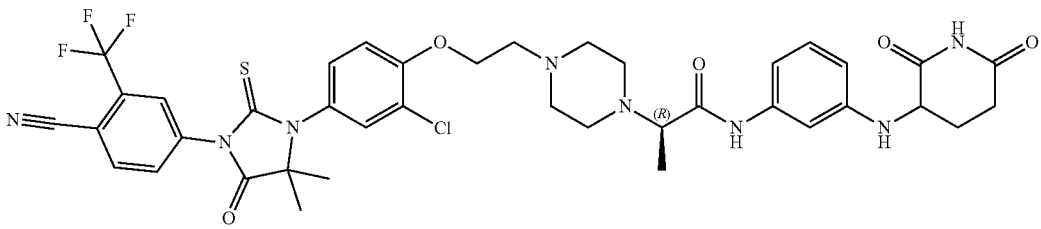

2-(3-chloro-4-hydroxy-anilino)-2-methyl-propanenitrile. To a solution of 4-amino-2-chloro-phenol (45 g, 0.31 mol) in DCM (450 mL) and acetone (225 mL) was added trimethylsilyl trifluoromethanesulfonate (3.48 g, 16 mmol) and trimethylsilylformonitrile (43.5 g, 440 mmol) at 10° C. After addition, the reaction was stirred at 25° C. for 16 h, then was concentrated to a residue that was purified by silica gel column chromatography (petroleum ether and EtOAc, 15:1-7:1) to afford 2-(3-chloro-4-hydroxy-anilino)-2-methyl-propanenitrile (41.5 g, 62.8% yield) as an off-white solid. $^1$H NMR (400 MHz, DMSO-$d_6$) δ ppm 9.52 (s, 1H), 6.89-6.84 (m, 2H), 6.76-6.73 (m, 1H), 5.52 (s, 1H), 1.54 (s, 6H).

4-[3-(3-Chloro-4-hydroxy-phenyl)-4,4-dimethyl-5-oxo-2-thioxo-imidazolidin-1-yl]-2-(trifluoromethyl)benzonitrile. To a solution of 2-(3-chloro-4-hydroxy-anilino)-2-methyl-propanenitrile (14.6 g, 69 mmol) in DMA (150 mL) was added 4-isothiocyanato-2-(trifluoromethyl)benzonitrile (19.0 g, 83 mmol) at 20° C. After stirring at 20° C. for 2 h, the reaction mixture was diluted with MeOH (150 mL) and aqueous HCl (2 M, 150 mL) at 20° C., and stirred at 70° C. for 5 h. The reaction mixture was cooled to 10° C. and filtered. The filter cake was washed with water (200 mL) and dried to afford 4-[3-(3-chloro-4-hydroxy-phenyl)-4,4-dimethyl-5-oxo-2-thioxo-imidazolidin-1-yl]-2-(trifluoromethyl)benzonitrile (20.0 g, 65.6% yield) as a white solid. $^1$H NMR (400 MHz, DMSO-$d_6$) δ ppm 10.72 (s, 1H), 8.38 (d, J=8.4 Hz, 1H), 8.27 (d, J=1.6 Hz, 1H), 8.07 (dd, J=1.6 Hz, 8.0 Hz, 1H), 7.39 (d, J=2.4 Hz, 1H), 7.15-7.10 (m, 2H), 1.49 (s, 6H).

tert-Butyl 4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazine-1-carboxylate. tert-Butyl 4-(2-chloroethyl)piperazine-1-carboxylate (0.424 g, 1.705 mmol, 1.5 eq) was dissolved in DMF (8.42 mL, 0.135 molar). Cesium carbonate (0.556 g, 1.705 mmol, 1.5 eq) and 4-(3-(3-chloro-4-hydroxyphenyl)-4,4-dimethyl-5-oxo-2-thioxoimidazolidin-1-yl)-2-(trifluoromethyl)benzonitrile (0.500 g, 1.137 mmol, 1 eq) were added and the reaction was warmed to 60° C. for 18 h. The reaction was quenched with water, diluted with EtOAc, and the organic phase was washed with brine, dried over anhydrous sodium sulfate, filtered, and concentrated. The crude residue was purified by silica gel column chromatography (0-10% MeOH in DCM), and the pure fractions were combined and concentrated to afford tert-butyl 4-(2-(2-chloro-4-(3-(4-cyano-3-(trifluoromethyl)

phenyl)-5,5-dimethyl-4-oxo-2-thioxoimidazolidin-1-yl)phenoxy)ethyl)piperazine-1-carboxylate (0.792 g, 1.075 mmol, 95.0% yield) as a yellow oil. MS (ESI) m/z 652.2 [M]+.

4-(3-(3-Chloro-4-(2-(piperazin-1-yl)ethoxy)phenyl)-4,4-dimethyl-5-oxo-2-thioxoimidazolidin-1-yl)-2-(trifluoromethyl)benzonitrile hydrochloride. tert-Butyl 4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazine-1-carboxylate (0.701 g, 1.075 mmol, 1 eq) was suspended in DCM (4.75 mL, 0.226 M), and was treated with a solution of HCl in dioxane (4.03 mL, 16.13 mmol, 15 eq). The reaction mixture was stirred at room temperature for 3 h and then concentrated to afford 4-(3-(3-chloro-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.633 g, 1.076 mmol, 100% yield) as a white solid. MS (ESI) m/z 552.2 [M]+.

(R)-Methyl 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoate. (S)-Methyl 2-chloropropanoate (0.044 mL, 0.408 mmol, 1.2 eq) was added to a stirred mixture of 4-(3-(3-chloro-4-(2-(piperazin-1-yl)ethoxy)phenyl)-4,4-dimethyl-5-oxo-2-thioxoimidazolidin-1-yl)-2-(trifluoromethyl)benzonitrile hydrochloride (0.200 g, 0.340 mmol, 1 eq), THF (2.90 mL, 0.117 M) and TEA (0.189 mL, 1.359 mmol, 4 eq). The reaction mixture was stirred for 60 h at 80° C. The reaction was concentrated and purified by silica gel column chromatography (20-40% EtOAc/hexanes) to give (R)-methyl 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoate (0.105 g, 0.165 mmol, 48.4% yield) as a yellow solid. MS (ESI) m/z 638.2 [M]+.

(R)-2-(4-(2-(2-Chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoic acid. (R)-Methyl 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoate (0.105 g, 0.165 mmol, 1 eq) was suspended in a 3:1 mixture of THF (1.592 mL) and water (0.531 mL)(0.078 molar), treated with lithium hydroxide (0.041 g, 1.715 mmol, 10.42 eq), and stirred at room temperature for 4 h. The reaction was diluted with EtOAc and water, and the pH was adjusted to ~3 with a 6 M aqueous solution of HCl. The aqueous layer was extracted with EtOAc, and the extracts were dried over sodium sulfate, filtered, and concentrated to afford (R)-2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoic acid (0.120 g, 0.133 mmol, 81.0% yield) as a beige solid. MS (ESI) m/z 624.2 [M]+.

(2R)-2-(4-(2-(2-Chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-((2,6-dioxopiperidin-3-yl)amino)phenyl)propanamide hydrochloride. (R)-2-(4-(2-(2-Chloro-4-(3-(4-cyano-3-(trifluoromethyl)phenyl)-5,5-dimethyl-4-oxo-2-thioxoimidazolidin-1-yl)phenoxy)ethyl)piperazin-1-yl)propanoic acid (0.103 g, 0.165 mmol, 1 eq) was combined with 3-((3-aminophenyl)amino)piperidine-2,6-dione trifluoroacetate salt (0.055 g, 0.165 mmol, 1 eq), HATU (0.069 g, 0.182 mmol, 1.1 eq), DIEA (0.115 mL, 0.660 mmol, 4 eq), and DMF (0.825 mL, 0.2 molar). The reaction mixture was stirred at 25° C. for 2 h and quenched with water and diluted with EtOAc. The aqueous layer was extracted with EtOAc. The combined organic layers were concentrated, and the residue was purified by standard methods to afford (2R)-2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-((2,6-dioxopiperidin-3-yl)amino)phenyl)propanamide hydrochloride (0.041 g, 0.049 mmol, 29.9% yield). MS (ESI) m/z 825.2 [M]+; $^1$H NMR (400 MHz, DMSO-$d_6$) δ ppm 10.79 (s, 1H), 9.97 (s, 1H), 8.40 (d, J=8.31 Hz, 1H), 8.27 (d, J=1.71 Hz, 1H), 8.06 (dd, J=1.59, 8.31 Hz, 1H), 7.55 (t, J=1.16 Hz, 1H), 7.37 (d, J=0.98 Hz, 2H), 6.99-7.05 (m, 2H), 6.84 (br d, J=7.95 Hz, 1H), 6.43 (dd, J=1.28, 8.13 Hz, 1H), 4.51 (br s, 2H), 4.26 (br dd, J=4.71, 11.55 Hz, 1H), 3.40 (br s, 4H), 3.14-3.34 (m, 8H), 2.74 (br ddd, J=5.62, 11.98, 17.85 Hz, 1H), 2.55-2.63 (m, 1H), 2.08-2.13 (m, 1H), 1.90 (br dq, J=4.65, 12.19 Hz, 1H), 1.51 (s, 6H), 1.35 (br s, 3H).

Example 16: 2-((S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-3-methylpiperazin-1-yl)-N-(3-((2,6-dioxopiperidin-3-yl)amino)phenyl)acetamide

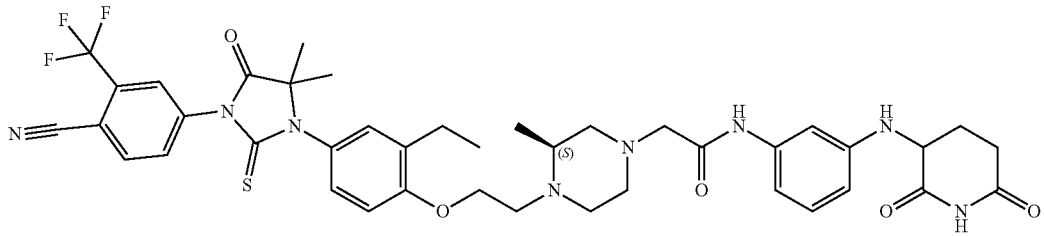

tert-Butyl (S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-3-methylpiperazine-1-carboxylate. 4-(3-(4-(2-Bromoethoxy)-3-ethylphenyl)-4,4-dimethyl-5-oxo-2-thioxoimidazolidin-1-yl)-2-(trifluoromethyl)benzonitrile (0.09 g, 0.167 mmol) (prepared as described herein), (S)-tert-butyl 3-methylpiperazine-1-carboxylate (0.040 g, 0.200 mmol) and DIEA (0.073 mL, 0.416 mmol) were combined in DMF (1.25 mL) and the mixture was heated to 70° C. in a sealed vessel. After 16 h, the solution was concentrated under reduced pressure to afford an orange residue. The residue was purified via column chromatography (0-90% EtOAc in hexanes) to afford tert-butyl (S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-3-methylpiperazine-1-carboxylate (0.084 g, 0.127 mmol, 69.0% yield). MS (ESI) m/z 660 [M+1]+.

(S)-4-(3-(3-Ethyl-4-(2-(2-methylpiperazin-1-yl)ethoxy)phenyl)-4,4-dimethyl-5-oxo-2-thioxoimidazolidin-1-yl)-2-(trifluoromethyl)benzonitrile dihydrochloride. (S)-tert-butyl 4-(2-(4-(3-(4-Cyano-3-(trifluoromethyl)phenyl)-5,5-dimethyl-4-oxo-2-thioxoimidazolidin-1-yl)-2-ethylphenoxy)ethyl)-3-methylpiperazine-1-carboxylate (0.084 g, 0.13 mmol) was dissolved in DCM (0.5 mL). To the solution was added a 4.0 M solution of HCl in dioxane (0.637 mL, 2.55 mmol). The mixture was stirred at ambient temperature in a sealed vial. After 45 min, the solution was concentrated under reduced pressure to afford (S)-4-(3-(3-ethyl-4-(2-(2-methylpiperazin-1-yl)ethoxy)phenyl)-4,4-dimethyl-5-oxo-2-thioxoimidazolidin-1-yl)-2-(trifluoromethyl)benzonitrile dihydrochloride as a white solid (0.085 g, 0.13 mmol, 106% yield). MS (ESI) m/z 560 [M+1]$^+$.

2-((S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-3-methylpiperazin-1-yl)-N-(3-((2,6-dioxopiperidin-3-yl)amino)phenyl)acetamide. To a mixture of (S)-4-(3-(3-ethyl-4-(2-(2-methylpiperazin-1-yl)ethoxy)phenyl)-4,4-dimethyl-5-oxo-2-thioxoimidazolidin-1-yl)-2-(trifluoromethyl)benzonitrile dihydrochloride (0.086 g, 0.136 mmol) and 2-chloro-N-(3-((2,6-dioxopiperidin-3-yl)amino)phenyl)acetamide (0.040 g, 0.136 mmol) in DMF (0.340 mL) was added DIEA (0.071 mL, 0.408 mmol). The reaction solution was heated to 45° C. After 3 h, the solution was diluted with DMSO and purified by standard methods to afford the title compound (0.073 g, 0.076 mmol, 56.0% yield). MS (ESI) m/z 819.2 [M+1]$^+$; $^1$H NMR (400 MHz, DMSO-d$_6$) δ ppm 10.77 (s, 1H), 9.37 (s, 1H), 8.38 (d, J=8.19 Hz, 1H), 8.29 (s, 1H), 8.15 (s, 1H), 8.07 (dd, J=8.25, 1.65 Hz, 1H), 7.08-7.18 (m, 3H), 6.96-7.03 (m, 2H), 6.80 (br d, J=7.95 Hz, 1H), 6.36-6.42 (m, 1H), 5.88 (d, J=7.82 Hz, 1H), 4.26 (br s, 1H), 4.12 (br t, J=5.14 Hz, 2H), 3.33 (br dd, J=2.45, 1.59 Hz, 4H), 3.00-3.22 (m, 4H), 2.92 (br d, J=11.62 Hz, 1H), 2.53-2.78 (m, 10H), 2.25-2.46 (m, 1H), 1.99-2.14 (m, 2H), 1.89 (td, J=12.07, 7.64 Hz, 1H), 1.49 (s, 6H), 1.24 (br s, 2H), 1.16 (t, J=7.46 Hz, 3H), 1.06 (d, J=6.11 Hz, 3H), 0.95 (d, J=6.60 Hz, 1H), 0.80-0.90 (m, 2H).

Example 17: 2-((R)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide hydrochloride

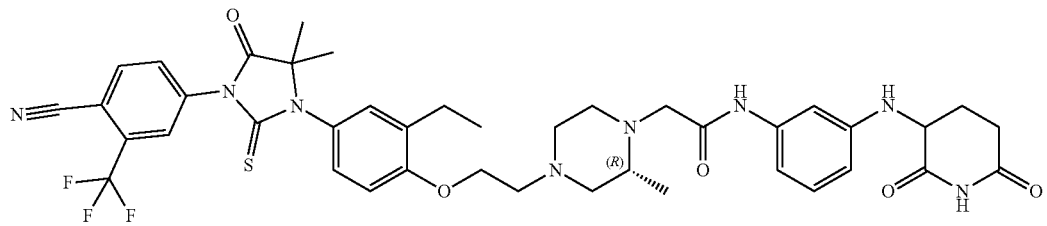

(R)-tert-Butyl 4-(2-(2-bromo-4-nitrophenoxy)ethyl)-2-methylpiperazine-1-carboxylate. To a solution of 2-bromo-1-(2-bromoethoxy)-4-nitrobenzene (9.00 g, 27.70 mmol, 1 eq) (prepared as described herein), and (R)-tert-butyl 2-methylpiperazine-1-carboxylate (5.55 g, 27.70 mmol, 1 eq) in DMF (70 mL) was added DIEA (7.16 g, 55.39 mmol, 2 eq). The reaction was stirred at 60° C. for 12 h, then diluted with water (300 mL) and EtOAc (200 mL), and the layers were separated. The aqueous layer was extracted with EtOAc (10 mL). The combined organic extracts were washed with brine (100 mL×4), dried, filtered and concentrated. The residue was purified by silica gel column chromatography (0-30% EtOAc in petroleum ether) to give (R)-tert-butyl 4-(2-(2-bromo-4-nitrophenoxy)ethyl)-2-methylpiperazine-1-carboxylate (10.97 g, 24.69 mmol, 89.1% yield) as a yellow oil. $^1$H NMR (400 MHz, CDCl$_3$) δ ppm 8.47 (d, J=2.8 Hz, 1H), 8.20 (dd, J=8.8, 2.4 Hz, 1H), 6.96 (d, J=9.2 Hz, 1H), 4.27-4.21 (m, 3H), 3.82 (d, J=13.2 Hz, 1H), 3.08 (td, J=12.4, 3.2 Hz, 1H), 2.91-2.85 (m, 3H), 2.75 (d, J=11.2 Hz, 1H), 2.39 (dd, J=10.8, 3.6 Hz, 1H), 2.20 (td, J=12.0, 3.6 Hz, 1H), 1.46 (s, 9H), 1.22 (d, J=6.4 Hz, 3H).

(R)-tert-Butyl 2-methyl-4-(2-(4-nitro-2-vinylphenoxy)ethyl)piperazine-1-carboxylate. A mixture of (R)-tert-butyl 4-(2-(2-bromo-4-nitrophenoxy)ethyl)-2-methylpiperazine-1-carboxylate (10.96 g, 24.67 mmol, 1 eq), 4,4,5,5-tetramethyl-2-vinyl-1,3,2-dioxaborolane (7.60 g, 49.33 mmol, 2 eq), [1,1'-bis(diphenylphosphino)ferrocene]-dichloropalladium(II) (0.90 g, 1.23 mmol, 0.05 eq), potassium phosphate (15.71 g, 74.00 mmol, 3 eq), dioxane (100 mL) and water (50 mL) was stirred at 90° C. under nitrogen for 12 h. To the mixture was added brine (100 mL) and the layers were separated. The aqueous layer was extracted with EtOAc (50 mL). The combined organic extracts were washed with brine (100 mL), dried, filtered, and concentrated. The crude product was purified by silica gel column chromatography (0-20% EtOAc in petroleum ether) to give (R)-tert-butyl 2-methyl-4-(2-(4-nitro-2-vinylphenoxy)ethyl)piperazine-1-carboxylate (9.62 g, 24.57 mmol, 99.6% yield) as a yellow oil. $^1$H NMR (400 MHz, CDCl$_3$) δ ppm 8.36 (d, J=2.8 Hz, 1H), 8.14 (dd, J=9.2, 2.8 Hz, 1H), 7.01-6.92 (m, 2H), 5.91 (dd, J=17.6, 0.8 Hz, 1H), 5.43 (dd, J=11.2, 0.8 Hz, 1H), 4.23-4.20 (m, 3H), 3.82 (d, J=13.2 Hz, 1H), 3.09 (td, J=12.8, 3.6 Hz, 1H), 2.85-2.81 (m, 3H), 2.69 (d, J=11.2 Hz, 1H), 2.35 (dd, J=11.2, 4.0 Hz, 1H), 2.16 (td, J=11.6, 3.6 Hz, 1H), 1.46 (s, 9H), 1.22 (d, J=6.8 Hz, 3H).

(R)-tert-Butyl 4-(2-(4-amino-2-ethylphenoxy)ethyl)-2-methylpiperazine-1-carboxylate. A mixture of (R)-tert-butyl 2-methyl-4-(2-(4-nitro-2-vinylphenoxy)ethyl)piperazine-1-carboxylate (11.60 g, 29.63 mmol, 1 eq), palladium on activated carbon (1.00 g, 10% purity) and MeOH (120 mL) was stirred at 30° C. under hydrogen (50 psi) for 12 h. The suspension was filtered and the filtrate was concentrated. The crude product (R)-tert-butyl 4-(2-(4-amino-2-ethylphenoxy)ethyl)-2-methylpiperazine-1-carboxylate (10.75 g, 29.57 mmol, 99.8% yield) was isolated as a brown oil and used to next step without further purification. $^1$H NMR (400 MHz, CDCl$_3$) δ ppm 6.68 (d, J=8.4 Hz, 1H), 6.55 (d, J=2.8 Hz, 1H), 6.49 (dd, J=8.4, 2.8 Hz, 1H), 4.21-4.20 (m, 1H), 4.01 (t, J=5.6 Hz, 1H), 3.81 (d, J=13.2 Hz, 1H), 3.10 (td, J=12.8, 3.2 Hz, 1H), 2.87 (d, J=11.2 Hz, 1H), 2.79-2.68 (m, 3H), 2.57 (q, J=7.6 Hz, 1H), 2.31 (dd, J=11.2, 3.6 Hz, 1H), 2.12 (td, J=12.0, 3.2 Hz, 1H), 1.46 (s, 9H), 1.23 (s, 3H), 1.17 (t, J=7.6 Hz, 1H).

(R)-tert-Butyl 4-(2-(4-((2-cyanopropan-2-yl)amino)-2-ethylphenoxy)ethyl)-2-methylpiperazine-1-carboxylate. A mixture of (R)-tert-butyl 4-(2-(4-amino-2-ethylphenoxy)

ethyl)-2-methylpiperazine-1-carboxylate (5.00 g, 13.76 mmol, 1 eq), magnesium sulfate (4.140 g, 34.39 mmol, 2.5 eq) and 2-hydroxy-2-methylpropanenitrile (13.98 g, 164.27 mmol, 15.00 mL, 11.94 eq) was stirred at 60° C. for 12 h. To the mixture were added water (60 mL) and EtOAc (40 mL) and the layers were separated. The aqueous layer was extracted with EtOAc (30 mL). The combined organic extracts were washed with brine (50 mL×4), dried, filtered and concentrated. The crude product (R)-tert-butyl 4-(2-(4-((2-cyanopropan-2-yl)amino)-2-ethylphenoxy)ethyl)-2-methylpiperazine-1-carboxylate (5.92 g, crude) isolated as a yellow oil, was used in the next step without additional purification. MS (ESI) m/z 431.3 [M+1]⁺.

(R)-4-(3-(3-Ethyl-4-(2-(3-methylpiperazin-1-yl)ethoxy)phenyl)-4,4-dimethyl-5-oxo-2-thioxoimidazolidin-1-yl)-2-(trifluoromethyl)benzonitrile. A mixture of (R)-tert-butyl 4-(2-(4-((2-cyanopropan-2-yl)amino)-2-ethylphenoxy)ethyl)-2-methylpiperazine-1-carboxylate (5.92 g, 13.75 mmol, 1 eq), 4-isothiocyanato-2-(trifluoromethyl)benzonitrile (3.14 g, 13.75 mmol, 1 eq) and DMF (50 mL) was stirred at 20° C. for 1 h. To the mixture was added a solution of HCl in MeOH (4 M, 17.19 mL, 5 eq) and the reaction was stirred at 80° C. for 1 h. The solvents were removed under reduced pressure. The remaining solution was purified by semi-preparative reverse phase HPLC (10-45% acetonitrile in water+0.05% HCl, 29 min). The collected fractions were concentrated to remove most of the organic volatiles. To the aqueous solution was added sodium bicarbonate to adjust the pH to 8. The aqueous layer was extracted with EtOAc (200 mL×2). The combined organic extracts were washed with brine (200 mL), dried, filtered, and concentrated to give (R)-4-(3-(3-ethyl-4-(2-(3-methylpiperazin-1-yl)ethoxy)phenyl)-4,4-dimethyl-5-oxo-2-thioxoimidazolidin-1-yl)-2-(trifluoromethyl)benzonitrile (3.71 g, 6.560 mmol, 47.7% yield) as a light yellow solid. MS (ESI) m/z 560.1 [M+1]⁺; ¹H NMR (400 MHz, CDCl₃) δ ppm 7.99-7.96 (m, 2H), 7.85 (dd, J=8.0, 2.0 Hz, 1H), 7.09-7.05 (m, 2H), 6.93 (d, J=8.4 Hz, 1H), 4.16 (t, J=5.6 Hz, 2H), 3.07-3.03 (m, 1H), 2.98-2.90 (m, 3H), 2.87 (t, J=5.6 Hz, 2H), 2.68 (q, J=7.6 Hz, 1H), 2.32-2.28 (m, 1H), 1.96 (t, J=10.8 Hz, 1H), 1.57 (s, 6H), 1.22 (t, J=7.6 Hz, 3H), 1.12 (d, J=6.4 Hz, 3H).

2-((R)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide hydrochloride. A mixture of (R)-4-(3-(3-ethyl-4-(2-(3-methylpiperazin-1-yl)ethoxy)phenyl)-4,4-dimethyl-5-oxo-2-thioxoimidazolidin-1-yl)-2-(trifluoromethyl)benzonitrile (3.50 g, 6.25 mmol, 1 eq), 2-chloro-N-(3-((2,6-dioxopiperidin-3-yl)amino)phenyl)acetamide (2.07 g, 7.00 mmol, 1.12 eq), DIEA (2.02 g, 15.63 mmol, 2.72 mL, 2.5 eq) and DMF (15 mL) was stirred at 60° C. for 8 h. The solution was filtered and the filtrate was purified by standard methods to give 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide hydrochloride (2.61 g, 3.03 mmol, 48.5% yield). MS (ESI) m/z 819.3 [M+1]⁺; ¹H NMR (400 MHz, DMSO-d₆) δ ppm 10.78 (s, 1H), 10.37 (br, 1H), 8.38 (d, J=8.4 Hz, 1H), 8.29 (d, J=1.6 Hz, 1H), 8.08-8.06 (m, 1H), 7.22-7.13 (m, 3H), 7.05-7.00 (m, 2H), 6.86 (d, J=7.6 Hz, 1H), 6.46 (d, J=8.0 Hz, 1H), 4.50 (br, 2H), 4.27 (dd, J=11.2, 5.6 Hz, 1H), 4.14-3.84 (m, 5H), 3.49-3.20 (m, 6H), 2.75-2.57 (m, 4H), 2.12-2.06 (m, 1H), 1.90 (qd, J=12.4, 4.8 Hz, 1H), 1.49 (s, 6H), 1.32 (br, 3H), 1.17 (t, J=7.2 Hz, 3H).

Example 18: 2-((S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide

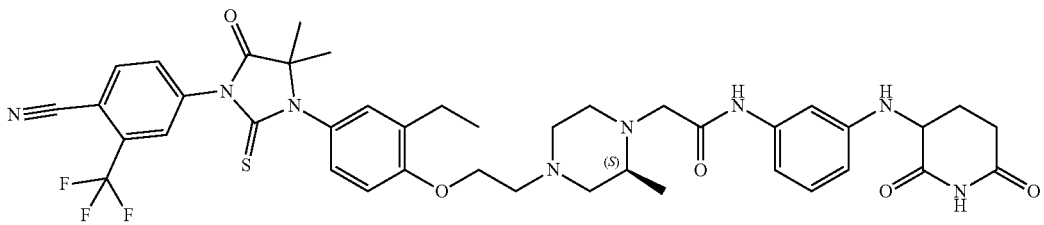

tert-Butyl (S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2-methylpiperazine-1-carboxylate. 4-(3-(4-(2-Bromoethoxy)-3-ethylphenyl)-4,4-dimethyl-5-oxo-2-thioxoimidazolidin-1-yl)-2-(trifluoromethyl)benzonitrile (0.100 g, 0.185 mmol), (S)-tert-butyl 2-methylpiperazine-1-carboxylate (0.044 g, 0.222 mmol) and DIEA (0.081 mL, 0.463 mmol) were combined in DMF (1.5 mL) and the mixture was heated to 70° C. in a screw cap scintillation vial. After 16 h, the solution was concentrated under reduced pressure to afford an orange residue. The residue was purified by silica gel column chromatography (0-100% EtOAc in hexanes) to afford the title compound (0.087 g, 0.132 mmol, 71% yield). MS (ESI) m/z 660 [M+1]⁺.

(S)-4-(3-(3-Ethyl-4-(2-(3-ethylpiperazin-1-yl)ethoxy)phenyl)-4,4-dimethyl-5-oxo-2-thioxoimidazolidin-1-yl)-2-(trifluoromethyl)benzonitrile dihydrochloride. (S)-tert-butyl 4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2-methylpiperazine-1-carboxylate (0.087 g, 0.132 mmol) was dissolved in DCM (0.5 mL). To the solution was added a 4.0 M solution of HCl in dioxane (0.659 mL, 2.64 mmol). The mixture was stirred at ambient temperature in a screw cap scintillation vial. After 45 min, the solution was concentrated under reduced pressure to afford the title compound (0.085 g, 0.134 mmol, 102% yield). MS (ESI) m/z 560 [M+1]⁺.

2-((S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide. To a 1-dram vial containing (S)-4-(3-(3-ethyl-4-(2-(3-methylpiperazin-1-yl)ethoxy)phenyl)-4,4-dimethyl-5-oxo-2-thioxoimidazolidin-1-yl)-2-(trifluoromethyl)benzonitrile dihydrochloride (0.085 g, 0.134 mmol) and 2-chloro-N-(3-((2,6-dioxopiperidin-3-yl)amino)phenyl)acetamide (0.040 g, 0.134 mmol) was added DMF (0.336 mL) followed by DIEA (0.070 mL, 0.403 mmol). The reaction solution was heated to 45° C., then to 60° C. after 45 min. After 16 h, the solution was diluted with DMSO and purified by standard methods to afford the title compound (0.084 g, 0.088 mmol, 65.0% yield). MS (ESI) m/z 819.2 [M+1]$^+$; $^1$H NMR (400 MHz, DMSO-d$_6$) δ ppm 10.77 (s, 1H), 9.36 (s, 1H), 8.38 (d, J=8.19 Hz, 1H), 8.27-8.31 (m, 1H), 8.16 (s, 1H), 8.07 (d, J=7.74 Hz, 1H), 7.06-7.20 (m, 3H), 6.97-7.03 (m, 2H), 6.80 (br d, J=8.31 Hz, 1H), 6.39 (d, J=8.52 Hz, 1H), 5.88 (d, J=7.70 Hz, 1H), 4.27 (br s, 1H), 4.16 (br t, J=5.26 Hz, 2H), 3.16-3.30 (m, 2H), 3.00 (br d, J=16.02 Hz, 2H), 2.67-2.88 (m, 6H), 2.53-2.66 (m, 5H), 2.27-2.46 (m, 1H), 1.99-2.19 (m, 2H), 1.90 (br s, 1H), 1.49 (s, 6H), 1.24 (br s, 1H), 1.16 (t, J=7.46 Hz, 3H), 0.93-1.06 (m, 3H), 0.85 (br d, J=10.76 Hz, 1H); MS(ESI) m/z 819 [M+1]$^+$.

Example 19: 2-((R)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-3-(hydroxymethyl)piperazin-1-yl)-N-(3-((2,6-dioxopiperidin-3-yl)amino)phenyl)acetamide formate din-1-yl)-2-(trifluoromethyl)benzonitrile dihydrochloride. (R)-tert-butyl 4-(2-(4-(3-(4-Cyano-3-(trifluoromethyl)phenyl)-5,5-dimethyl-4-oxo-2-thioxoimidazolidin-1-yl)-2-ethylphenoxy)ethyl)-3-(hydroxymethyl)piperazine-1-carboxylate (0.063 g, 0.093 mmol) was dissolved in DCM (0.5 mL) and to the solution was added a 4.0 M solution of HCl in dioxane (0.466 mL, 1.865 mmol). The solution was stirred at ambient temperature. After 90 min, the solution was concentrated under reduced pressure to afford the title compound as the hydrochloride salt (0.065 g, 0.095 mmol, quant. yield). MS (ESI) m/z 576 [M+1]$^+$.

2-((R)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-3-(hydroxymethyl)piperazin-1-yl)-N-(3-((2,6-dioxopiperidin-3-yl)amino)phenyl)acetamide formate. (R)-4-(3-(3-Ethyl-4-(2-(2-(hydroxymethyl)piperazin-1-yl)ethoxy)phenyl)-4,4-dimethyl-5-oxo-2-thioxoimidazolidin-1-yl)-2-(trifluoromethyl)benzonitrile dihydrochloride (0.068 g, 0.105 mmol) and DIEA (0.092 mL, 0.524 mmol) were combined in DMF (0.262 mL). To the solution was then added 2-chloro-N-(3-((2,6-dioxopiperidin-3-yl)amino)phenyl)acetamide (0.031 g, 0.105 mmol) and the mixture was

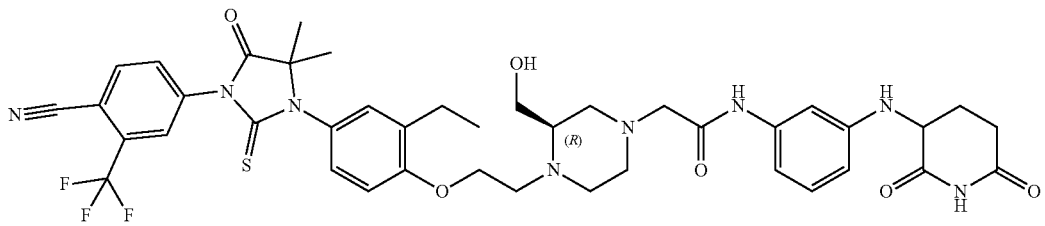

tert-Butyl (R)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-3-(hydroxymethyl)piperazine-1-carboxylate. 4-(3-(4-(2-Bromoethoxy)-3-ethylphenyl)-4,4-dimethyl-5-oxo-2-thioxoimidazolidin-1-yl)-2-(trifluoromethyl)benzonitrile (0.095 g, 0.176 mmol), (R)-tert-butyl-(hydroxymethyl)piperazine-1-carboxylate (0.046 g, 0.211 mmol) and DIEA (0.077 mL, 0.439 mmol) were combined in DMF (1.25 mL) and the mixture heated to 70° C. in a screw cap scintillation vial. After 16 h, the solution was concentrated under reduced pressure to afford a yellow oil. The oil was purified via column chromatography (0-100% EtOAc in hexanes) to afford the title compound (0.063 g, 0.093 mmol, 53.0% yield). MS (ESI) m/z 676 [M+1]$^+$.

(R)-4-(3-(3-Ethyl-4-(2-(2-(hydroxymethyl)piperazin-1-yl)ethoxy)phenyl)-4,4-dimethyl-5-oxo-2-thioxoimidazoliheated to 45° C. in a screw cap scintillation vial. After 3 h, the solution was diluted with DMSO (1 mL) and purified by standard methods to afford the title compound (0.033 g, 0.034 mmol, 32.3% yield). MS (ESI) m/z 835.2 [M+1]$^+$; $^1$H NMR (400 MHz, DMSO-d$_6$) δ ppm 10.78 (s, 1H), 9.36 (s, 1H), 8.38 (d, J=8.19 Hz, 1H), 8.29 (d, J=1.71 Hz, 1H), 8.07 (dd, J=8.25, 1.65 Hz, 1H), 7.07-7.17 (m, 3H), 6.96-7.03 (m, 2H), 6.81 (d, J=7.95 Hz, 1H), 6.39 (dd, J=8.13, 1.53 Hz, 1H), 5.87 (d, J=7.82 Hz, 1H), 4.43-4.63 (m, 1H), 4.20-4.30 (m, 1H), 4.12 (br t, J=5.38 Hz, 2H), 3.68 (br dd, J=10.64, 3.91 Hz, 1H), 3.39-3.54 (m, 2H), 3.11-3.26 (m, 2H), 3.06 (s, 2H), 2.94 (br dd, J=11.19, 4.10 Hz, 1H), 2.56-2.84 (m, 9H), 2.30-2.47 (m, 2H), 2.21 (br t, J=9.41 Hz, 1H), 2.02-2.15 (m, 1H), 1.88 (br dd, J=12.29, 4.34 Hz, 1H), 1.49 (s, 6H), 1.24 (br s, 1H), 1.16 (t, J=7.52 Hz, 3H), 0.95 (d, J=6.60 Hz, 1H), 0.81-0.89 (m, 1H).

Example 20: 2-(4-(2-(4-(3-(6-Cyano-5-(trifluoromethyl)pyridin-3-yl)-5,5-dimethyl-4-oxo-2-thioxoimidazolidin-1-yl)-2-isopropylphenoxy)ethyl)piperazin-1-yl)-N-(3-((2,6-dioxopiperidin-3-yl)amino)phenyl) acetamide hydrochloride

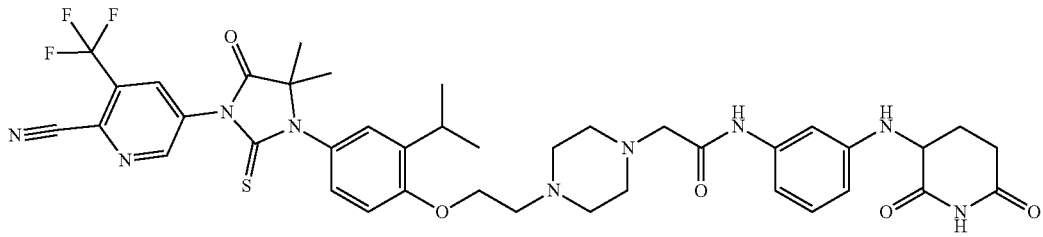 [SMILES: CC(C)c1cc(N2C(=S)N(c3cnc(C#N)c(C(F)(F)F)c3)C(=O)C2(C)C)ccc1OCCN1CCN(CC(=O)Nc2cccc(NC3CCC(=O)NC3=O)c2)CC1]

2-((3-Bromo-4-hydroxyphenyl)amino)-2-methylpropanenitrile. To a solution of 4-amino-2-bromophenol (5.00 g, 26.6 mmol) in DCM (177 mL) and acetone (89 mL) were added trimethylsilyl cyanide (4.66 mL, 37.2 mmol) and trimethylsilyl trifluoromethylsulphonate (0.241 mL, 1.33 mmol). The reaction mixture was stirred at room temperature for 1 h and concentrated to remove solvent. The crude material was purified by silica gel column chromatography (0-100% EtOAc in hexane) to afford 2-((3-bromo-4-hydroxyphenyl)amino)-2-methylpropanenitrile (4.56 g, 17.9 mmol, 67.2% yield) as a brown solid. MS (ESI) m/z 256.2 [M+1]$^+$; $^1$H NMR (400 MHz, DMSO-$d_6$) δ ppm 9.55-9.66 (m, 1H), 7.05 (d, J=2.69 Hz, 1H), 6.83-6.87 (m, 1H), 6.77-6.81 (m, 1H), 5.51 (s, 1H), 1.55 (s, 6H).

5-(3-(3-Bromo-4-hydroxyphenyl)-4,4-dimethyl-5-oxo-2-thioxoimidazolidin-1-yl)-3-(trifluoromethyl)picolinonitrile. 2-((3-Bromo-4-hydroxyphenyl)amino)-2-methylpropanenitrile (1 g, 3.92 mmol) and 5-isothiocyanato-3-(trifluoromethyl)picolinonitrile (0.898 g, 3.92 mmol) were combined in DMA (13.07 mL) and stirred at room temperature overnight. MeOH (5 mL) and a 3.0 N aqueous solution of HCl were added and the reaction was heated at 70° C. for 4 h. The reaction mixture was partitioned between EtOAc and water. The aqueous layer was extracted with EtOAc and the combined organic extracts were dried over magnesium sulfate, filtered, and concentrated. The crude material was purified by silica gel column chromatography (0-100% EtOAc in hexanes) to afford 5-(3-(3-bromo-4-hydroxyphenyl)-4,4-dimethyl-5-oxo-2-thioxoimidazolidin-1-yl)-3-(trifluoromethyl)picolinonitrile (1.2 g, 2.40 mmol, 61.4% yield) as a white solid. MS (ESI) m/z 484.0 [M+1]$^+$.

tert-Butyl 4-(2-(2-bromo-4-(3-(6-cyano-5-(trifluoromethyl)pyridin-3-yl)-5,5-dimethyl-4-oxo-2-thioxoimidazolidin-1-yl)phenoxy)ethyl)piperazine-1-carboxylate. 5-(3-(3-Bromo-4-hydroxyphenyl)-4,4-dimethyl-5-oxo-2-thioxoimidazolidin-1-yl)-3-(trifluoromethyl)picolinonitrile (1.20 g, 2.47 mmol), tert-butyl 4-(2-bromoethyl)piperazine-1-carboxylate (0.725 g, 2.47 mmol), sodium iodide (0.371 g, 2.47 mmol), and cesium carbonate (1.611 g, 4.95 mmol) were combined in DMF (12.36 mL) and heated at 50° C. for 3 h. The reaction mixture was partitioned between EtOAc and water. The organic layer was washed with brine (3×) and the combined extracts were dried over magnesium sulfate, filtered, and concentrated to dryness. The crude material was purified by silica gel column chromatography (0-15% MeOH in DCM) to afford tert-butyl 4-(2-(2-bromo-4-(3-(6-cyano-5-(trifluoromethyl)pyridin-3-yl)-5,5-dimethyl-4-oxo-2-thioxoimidazolidin-1-yl)phenoxy)ethyl)piperazine-1-carboxylate (1.31 g, 1.60 mmol, 64.6% yield) as a yellow powder. MS (ESI) m/z 697.8 [M+1]$^+$.

tert-Butyl 4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)piperazine-1-carboxylate. A mixture of tert-butyl 4-(2-(2-bromo-4-(3-(6-cyano-5-(trifluoromethyl)pyridin-3-yl)-5,5-dimethyl-4-oxo-2-thioxoimidazolidin-1-yl)phenoxy)ethyl)piperazine-1-carboxylate (0.250 g, 0.358 mmol), [(2-dicyclohexylphosphino-2',6'-bis(N,N-dimethylamino)-1,1'-biphenyl)-2-(2'-amino-1,1'-biphenyl)] palladium(II) methanesulfonate (0.088 g, 0.108 mmol) and 2-(2-dicyclohexylphosphanylphenyl)-$N^1$,$N^1$,$N^3$,$N^3$-tetramethyl-benzene-1,3-diamine (0.047 g, 0.108 mmol) was purged with nitrogen, suspended in toluene (1.434 mL), and purged with argon. The reaction was cooled in an ice bath for 10 min, before a solution of isopropylzinc(II) bromide in THF (1.075 mL, 0.538 mmol) was added dropwise. The reaction solution was stirred at 0° C. for 20 min then warmed to room temperature. After a total of 2 h, an additional 1.5 eq of isopropylzinc bromide was added, and the reaction was stirred at room temperature, leading to complete conversion after a total of 5 h. A 1.0 M aqueous solution of HCl (1 mL) was added, followed by EtOAc (60 mL). The organic layer was washed with saturated aqueous sodium bicarbonate (2×50 mL) and brine (50 mL). The organic layer was dried over magnesium sulfate and concentrated to provide a dark amber oil, which was purified by silica gel column chromatography (0.7-1.5% MeOH in DCM with 0.2% triethyl amine) to give tert-butyl 4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)piperazine-1-carboxylate (0.190 g, 0.224 mmol, 62.6% yield), contaminated with some of the oxidized 2-(2-dicyclohexylphosphanylphenyl)-$N^1$,$N^1$,$N^3$,$N^3$-tetramethyl-benzene-1,3-diamine ligand. MS (ESI) m/z 661.2 [M+1]$^+$; $^1$H NMR (400 MHz, CDCl$_3$) δ ppm 9.14-9.04 (m, 1H), 8.37 (s, 1H), 7.09-7.04 (m, 2H), 6.88-6.79 (m, 1H), 4.19-4.15 (m, 2H), 3.49-3.44 (m, 4H), 3.38-3.28 (m, 1H), 2.89 (t, J=5.6 Hz, 2H), 2.57 (br s, 4H), 1.59 (s, 6H), 1.47 (s, 9H), 1.24 (d, J=7.0 Hz, 6H).

5-(3-(3-Isopropyl-4-(2-(piperazin-1-yl)ethoxy)phenyl)-4,4-dimethyl-5-oxo-2-thioxoimidazolidin-1-yl)-3-(trifluoromethyl)picolinonitrile. To a solution of tert-butyl 4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)piperazine-1-carboxylate (0.12 g, 0.18 mmol) in DCM (0.908 mL) was added TFA (0.420 mL, 5.45 mmol). After stirring at room temperature for 90 min, the reaction was diluted with EtOAc (50 mL) and the organic layer was washed with saturated aqueous sodium bicarbonate (2×50 mL) and brine (50 mL). The organic layer was dried over magnesium sulfate and concentrated to provide 5-(3-(3-isopropyl-4-(2-(piperazin-1-yl)ethoxy)phenyl)-4,4-dimethyl-5-oxo-2-thioxoimidazolidin-1-yl)-3-(trifluoromethyl)picolinonitrile (0.094 g, 0.17 mmol, 92.0% yield) as a yellow oil. The material was carried forward without further purification. MS (ESI) m/z 561.2 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-isopropylphenoxy)ethyl)piperazin-1-yl)-N-(3-((2,6-dioxopiperidin-3-yl)amino)phenyl)acetamide hydrochloride. A mixture of 5-(3-(3-isopropyl-4-(2-(piperazin-1-yl)ethoxy)phenyl)-4,4-dimethyl-5-oxo-2-thioxoimidazolidin-1-yl)-3-(trifluoromethyl)picolinonitrile (0.098 g, 0.175 mmol) and 2-chloro-N-(3-((2,6-dioxopiperidin-3-yl)amino)phenyl)acetamide (0.052 g, 0.175 mmol) in DMF (0.438 mL) was treated with DIEA (0.122 mL, 0.700 mmol) and heated to 45° C. After 18 h, the reaction solution was diluted with DMSO to a total volume of 2 mL, filtered, and purified by standard methods to afford 2-(4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)piperazin-1-yl)-N-(3-((2,6-dioxopiperidin-3-yl)amino)phenyl)acetamide hydrochloride (0.057 g, 0.069 mmol, 40.0%). MS (ESI) m/z 820.2 [M+1]$^+$; $^1$H NMR (400 MHz, DMSO-d$_6$) δ ppm 10.80 (s, 1H), 10.37-10.18 (m, 1H), 9.26 (d, J=2.1 Hz, 1H), 8.83 (d, J=2.1 Hz, 1H), 7.24-7.14 (m, 3H), 7.08-7.02 (m, 1H), 7.00-6.96 (m, 1H), 6.88-6.82 (m, 1H), 6.46 (dd, J=1.9, 8.1 Hz, 1H), 4.55-4.45 (m, 3H), 4.31-4.22 (m, 3H), 4.06-3.55 (m, 10H), 3.40-3.31 (m, 1H), 2.79-2.60 (m, 2H), 2.16-2.03 (m, 1H), 1.99-1.84 (m, 1H), 1.52 (s, 6H), 1.20 (d, J=6.8 Hz, 6H).

Example 21: N-(3-Chloro-5-((2,6-dioxopiperidin-3-yl)amino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetamide hydrochloride

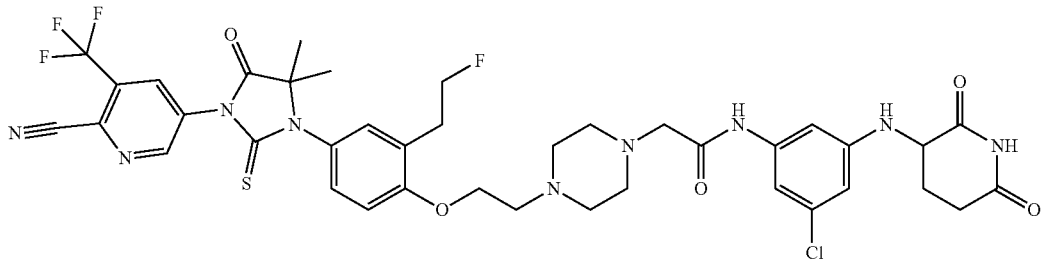 [SMILES: CC1(C)C(=O)N(c2cnc(C#N)c(C(F)(F)F)c2)C(=S)N1c1ccc(OCCN2CCN(CC(=O)Nc3cc(Cl)cc(NC4CCC(=O)NC4=O)c3)CC2)c(CCF)c1]

2-(2-(Benzyloxy)-5-nitrophenyl)ethan-1-ol. 1-(Benzyloxy)-4-nitro-2-vinylbenzene (3.12 g, 12.22 mmol) was dissolved in THF (61.1 mL), placed under nitrogen and cooled to 0° C. before adding 9-borabicyclo[3.3.1]nonane (26.9 mL, 13.44 mmol). After stirring at room temperature overnight, the reaction mixture was cooled to 0° C. before adding NaOH (2.69 mL, 13.44 mmol) and hydrogen peroxide (1.37 mL, 13.44 mmol). The ice bath was removed. After 1 h, the reaction was partitioned between EtOAc and a 1.0 N aqueous solution of HCl. The organic layer was washed with brine, and the combined organic extracts were dried over magnesium sulfate, filtered, and condensed. The crude material was purified by silica gel column chromatography (0-80% EtOAc in hexanes) to afford 2-(2-(benzyloxy)-5-nitrophenyl)ethan-1-ol (1.33 g, 4.87 mmol, 39.8% yield) as a yellow oil. MS (ESI) m/z 274.2 [M+1]$^+$; $^1$H NMR (400 MHz, DMSO-d$_6$) δ ppm 8.10-8.16 (m, 2H) 7.47-7.52 (m, 2H) 7.40-7.45 (m, 2H) 7.33-7.39 (m, 1H) 7.27 (d, J=8.93 Hz, 1H) 5.30 (s, 2H) 4.69 (t, J=5.26 Hz, 1H) 3.61-3.70 (m, 2H) 2.84 (t, J=6.60 Hz, 2H).

1-(Benzyloxy)-2-(2-fluoroethyl)-4-nitrobenzene. 2-(2-(Benzyloxy)-5-nitrophenyl)EtOH (1.16 g, 4.24 mmol) was dissolved in DCM (21.22 mL), placed under nitrogen, and cooled to 0° C., before adding dropwise a 1.0 M solution in DCM of diethylaminosulfur trifluoride (DAST, 8.49 mL, 8.49 mmol). After 30 min, the reaction was poured into ice water, stirred for 2 min, and phases were separated. The aqueous layer was extracted with DCM and the combined organic extracts were dried over magnesium sulfate, filtered, and concentrated under reduced pressure. The crude material was purified by silica gel column chromatography (0-30% EtOAc in hexanes) to afford 1-(benzyloxy)-2-(2-fluoroethyl)-4-nitrobenzene (0.560 g, 2.03 mmol, 47.9% yield) as a white solid. $^1$H NMR (400 MHz, CDCl$_3$) δ ppm 8.11-8.19 (m, 2H) 7.36-7.46 (m, 5H) 6.96-7.02 (m, 1H) 5.20 (s, 2H) 4.58-4.75 (m, 2H) 3.06-3.21 (m, 2H).

4-Amino-2-(2-fluoroethyl)phenol. 1-(Benzyloxy)-2-(2-fluoroethyl)-4-nitrobenzene (0.560 g, 2.04 mmol) was dissolved in MeOH (20.3 mL), treated with a catalytic amount of 10% Pd/C. The reaction vessel was sealed and purged with hydrogen. An atmosphere of hydrogen was maintained over the reaction with a balloon. After 2 h, the reaction was degassed with nitrogen and the catalyst was removed by filtration through a pad of celite. The filtrate was concentrated under reduced pressure to afford 4-amino-2-(2-fluoroethyl)phenol (0.316 g, 2.04 mmol, 100% yield) as a light purple solid. MS (ESI) m/z 156.2 [M+1]$^+$.

2-((3-(2-Fluoroethyl)-4-hydroxyphenyl)amino)-2-methylpropanenitrile. 4-Amino-2-(2-fluoroethyl)phenol (0.316 g, 2.04 mmol) was dissolved in DCM (10.20 mL) and acetone (10.20 mL), and treated with trimethylsilyl cyanide (0.357 mL, 2.85 mmol) and trimethylsilyl trifluoromethylsulphonate (0.018 mL, 0.10 mmol). Stirring was maintained for 1 h at room temperature. The reaction mixture was concentrated to an oil under reduced pressure and the crude material was purified by silica gel column chromatography (0-100% EtOAc in hexanes) to afford 2-((3-(2-fluoroethyl)-4-hydroxyphenyl)amino)-2-methylpropanenitrile (0.209 g, 0.94 mmol, 46.2% yield) as a brown solid. MS (ESI) m/z 241.2 [M+1]$^+$.

5-(3-(3-(2-Fluoroethyl)-4-hydroxyphenyl)-4,4-dimethyl-5-oxo-2-thioxoimidazolidin-1-yl)-3-(trifluoromethyl)picolinonitrile. 2-((3-(2-Fluoroethyl)-4-hydroxyphenyl)amino)-2-methylpropanenitrile (0.209 g, 0.940 mmol) and 5-isothiocyanato-3-(trifluoromethyl)picolinonitrile (0.216 g, 0.94 mmol) were combined in DMA (3.13 mL) and stirred at room temperature. After 1 h, a 3.0 N aqueous solution of HCl (0.628 mL, 1.88 mmol) and MeOH (0.6 mL) were added and the solution was heated to 70° C. After 2 h, the reaction mixture was partitioned between EtOAc and water. The aqueous layer was extracted with EtOAc and the combined organic extracts were dried over magnesium sulfate, filtered, and concentrated under reduced pressure. The crude material was purified by silica gel column chromatography (0-100% EtOAc in hexanes) to afford 5-(3-(3-(2-fluoroethyl)-4-hydroxyphenyl)-4,4-dimethyl-5-oxo-2-thioxoimidazolidin-1-yl)-3-(trifluoromethyl)picolinonitrile (0.193 g, 0.427 mmol, 45.3% yield) as an off-white solid. MS (ESI) m/z 453.2 [M+1]$^+$.

tert-Butyl 4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazine-1-carboxylate. 5-(3-(3-(2-Fluoroethyl)-4-hydroxyphenyl)-4,4-dimethyl-5-oxo-2-thioxoimidazolidin-1-yl)-3-(trifluoromethyl)picolinonitrile (0.180 g, 0.398 mmol), tert-butyl 4-(2-bromoethyl)piperazine-1-carboxylate (0.117 g, 0.398 mmol), and cesium carbonate (0.156 g, 0.477 mmol) were combined in DMF (2.65 mL) and heated at 70° C. After 90 min, an additional 0.1 eq of tert-butyl 4-(2-bromoethyl)piperazine-1-carboxylate was used. After 30 min, the reaction was partitioned between EtOAc and brine. The organic layer was washed with brine and the combined organic extracts were dried over magnesium sulfate, filtered, and condensed. The crude material was purified by silica gel column chromatography (0-10% EtOAc in hexanes) to afford tert-butyl 4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazine-1-carboxylate (0.100 g, 0.150 mmol, 37.8% yield) as an off-white solid. MS (ESI) m/z 665.3 [M+1]$^+$.

5-(3-(3-(2-Fluoroethyl)-4-(2-(piperazin-1-yl)ethoxy)phenyl)-4,4-dimethyl-5-oxo-2-thioxoimidazolidin-1-yl)-3-(trifluoromethyl)picolinonitrile hydrochloride. tert-Butyl 4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazine-1-carboxylate (0.100 g, 0.150 mmol) was dissolved in DCM (3 mL) and was treated with a 4.0 M aqueous solution of HCl (0.752 mL) in dioxane. After stirring at room temperature for 90 min, solvents were evaporated to afford 5-(3-(3-(2-fluoroethyl)-4-(2-(piperazin-1-yl)ethoxy)phenyl)-4,4-dimethyl-5-oxo-2-thioxoimidazolidin-1-yl)-3-(trifluoromethyl)picolinonitrile dihydrochloride (0.096 g, 0.151 mmol, 100% yield) as a white solid. MS (ESI) m/z 565.2 [M+1]$^+$.

tert-Butyl 2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetate. A solution of 5-(3-(3-(2-fluoroethyl)-4-(2-(piperazin-1-yl)ethoxy)phenyl)-4,4-dimethyl-5-oxo-2-thioxoimidazolidin-1-yl)-3-(trifluoromethyl)picolinonitrile dihydrochloride (0.096 g, 0.151 mmol) in THF (1.5 mL) was treated with tert-butyl 2-bromoacetate (0.025 mL, 0.166 mmol) and DIEA (0.105 mL, 0.602 mmol). After stirring at room temperature for 90 min, the reaction was partitioned between EtOAc and water. The organic layer was washed with brine and the combined organic extracts were dried over magnesium sulfate, filtered, and concentrated to afford crude tert-butyl 2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetate (0.101 g, 0.149 mmol, 99.0% yield) as an off-white solid. MS (ESI) m/z 679.3 [M+1]$^+$.

2-(4-(2-(4-(3-(6-Cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetic acid. To a solution of tert-butyl 2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetate (0.101 g, 0.149 mmol) in THF (0.992 mL) was added a 4.0 M solution of HCl in dioxane (0.744 mL, 2.98 mmol). After stirring at 50° C. overnight, solvents were removed under reduced pressure to give a colorless oil. Diethyl ether was added to induce the formation of a white precipitate. After trituration, solvents were removed and 2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetic acid dihydrochloride (0.104 g, 0.150 mmol, 100% yield) was isolated as a colorless oil. MS (ESI) m/z 623.2 [M+1]$^+$.

N-(3-chloro-5-((2,6-dioxopiperidin-3-yl)amino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetamide hydrochloride. 2-(4-(2-(4-(3-(6-Cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetic acid dihydrochloride (0.050 g, 0.072 mmol), 3-((3-amino-5-chlorophenyl)amino)piperidine-2,6-dione hydrochloride (0.023 g, 0.079 mmol), HATU (0.041 g, 0.108 mmol), and DIEA (0.046 g, 0.359 mmol) were combined in DMF (1 mL) and stirred at room temperature. After 90 min, the reaction mixture was diluted with DMSO (1 mL), filtered, and purified by standard methods to afford N-(3-chloro-5-((2,6-dioxopiperidin-3-yl)amino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)acetamide hydrochloride (0.020 g, 0.021 mmol, 29.9% yield). MS (ESI) m/z 858.6 [M+1]$^+$; $^1$H NMR (400 MHz, DMSO-d$_6$) δ ppm 10.81 (s, 1H) 9.20-9.31 (m, 1H) 8.83 (d, J=1.96 Hz, 1H) 7.15-7.33 (m, 3H) 6.97 (s, 1H) 6.89 (br s, 1H) 6.48 (s, 1H) 4.54-4.78 (m, 4H) 4.26-4.39 (m, 2H) 3.65-3.83 (m, 6H) 3.42-3.53 (m, 4H) 3.00-3.15 (m, 3H) 2.62-2.82 (m, 2H) 2.02-2.14 (m, 1H) 1.84-1.96 (m, 1H) 1.52 (s, 6H).

Example 22: N-(3-Chloro-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)acetamide hydrochloride

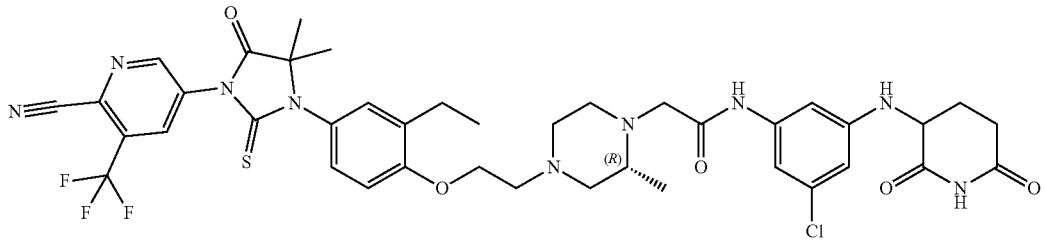

(R)-tert-Butyl 4-(2-(2-ethyl-4-((1-methoxy-2-methyl-1-oxopropan-2-yl)amino)phenoxy)ethyl)-2-methylpiperazine-1-carboxylate. To a solution of (R)-tert-butyl 4-(2-(4-amino-2-ethylphenoxy)ethyl)-2-methylpiperazine-1-carboxylate (5.00 g, 13.76 mmol, 1.00 eq) (prepared as described herein), and methyl 2-bromo-2-methylpropanoate (5.04 g, 27.84 mmol, 3.6 mL, 2.02 eq) was added DIEA (17.81 g, 137.79 mmol, 24 mL, 10.02 eq) in one portion. The mixture was stirred at 127° C. under nitrogen for 12 h, then diluted with water (800 mL) and extracted with EtOAc (200 mL×3). The combined organic layers were washed with brine (300 mL×2), dried over anhydrous sodium sulfate, filtered and concentrated under reduced pressure to give a residue. The residue was purified by silica gel column chromatography (10-25% EtOAc in petroleum ether). Compound (R)-tert-butyl 4-(2-(2-ethyl-4-((1-methoxy-2-methyl-1-oxopropan-2-yl)amino)phenoxy)ethyl)-2-methylpiperazine-1-carboxylate (6.40 g, 13.80 mmol, 50.2% yield) was obtained as a dark brown oil. MS (ESI) m/z 464.3 [M+1]+.

5-Isothiocyanato-3-(trifluoromethyl)picolinonitrile. To a solution of 5-amino-3-(trifluoromethyl)picolinonitrile (10.00 g, 53.44 mmol, 1.00 eq) in toluene (100 mL) was added thiophosgene (9.22 g, 80.16 mmol, 6 mL, 1.50 eq) in one portion under nitrogen. The mixture was stirred at 110° C. for 2 h, concentrated under reduced pressure at 60° C. to get a residue that was purified by silica gel column chromatography (0-5% EtOAc in petroleum ether). Compound 5-isothiocyanato-3-(trifluoromethyl)picolinonitrile (14.00 g, 61.09 mmol, 57.2% yield) was obtained as a colorless oil.

(R)-tert-Butyl 4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazine-1-carboxylate. To a solution of (R)-tert-butyl 4-(2-(2-ethyl-4-((1-methoxy-2-methyl-1-oxopropan-2-yl)amino)phenoxy)ethyl)-2-methylpiperazine-1-carboxylate (8.00 g, 17.26 mmol, 1.00 eq) and 5-isothiocyanato-3-(trifluoromethyl)picolinonitrile (7.91 g, 34.51 mmol, 2.00 eq) in EtOAc (20 mL) was added TEA (10.91 g, 107.77 mmol, 15 mL, 6.25 eq) in one portion under nitrogen. The mixture was stirred at 80° C. for 12 h, and diluted with water (800 mL) and extracted with EtOAc (300 mL×4). The combined organic extracts were washed with brine (300 mL×2), dried over anhydrous sodium sulfate, filtered, and concentrated under reduced pressure to give a residue. The residue was purified by flash silica gel chromatography (15-20% EtOAc in petroleum ether). Compound (R)-tert-butyl 4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazine-1-carboxylate (9.500 g, 12.39 mmol, 71.8% yield, 86.2% purity) was obtained as a dark brown oil. MS (ESI) m/z 661.3 [M+1]+.

(R)-5-(3-(3-Ethyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile. To a solution of (R)-tert-butyl 4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazine-1-carboxylate (9.50 g, 14.38 mmol, 1.00 eq) in DCM (10 mL) was added a 4.0 M solution of HCl in dioxane (95 mL, 26.43 eq) in one portion. The mixture was stirred at 20° C. for 2 h, then treated with a saturated solution of sodium bicarbonate (250 mL) and sodium bicarbonate as a solid, added to adjust the pH to 7. Then, the mixture was extracted with DCM (50 mL×5). The combined organic layers were washed with brine (100 mL), dried over anhydrous sodium sulfate, filtered, and concentrated under reduced pressure to give a residue. The residue was purified by silica gel column chromatography (0-10% MeOH in DCM). Compound (R)-5-(3-(3-Ethyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile (7.100 g, 11.70 mmol, 81.4% yield, 92.4% purity) was obtained as a dark red solid. MS (ESI) m/z 561.1 [M+1]+.

N-(3-Chloro-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)acetamide. To a solution of (R)-5-(3-(3-ethyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile (3.00 g, 5.35 mmol, 1.00 eq) and 2-chloro-N-(3-chloro-5-((2,6-dioxopiperidin-3-yl)amino)phenyl)acetamide (1.86 g, 5.62 mmol, 1.05 eq) in DMF (30 mL) was added DIEA (2.07 g, 16.05 mmol, 2.80 mL, 3.00 eq) in one portion. The mixture was stirred at 50° C. under nitrogen for 12 h, then cooled to 20° C. Water (200 mL) was poured into the mixture. The resulting suspension was filtered, and the filter cake was dried under reduced pressure and purified by standard methods to afford N-(3-chloro-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)acetamide hydrochloride (2.73 g, 3.05 mmol, 57.0% yield). MS (ESI) m/z 854.3 [M+1]+; 1H NMR (400 MHz, DMSO-$d_6$) δ ppm 10.80 (s, 1H), 10.42 (br s, 1H), 9.24 (d, J=1.6 Hz, 1H), 8.82 (d, J=1.7 Hz, 1H), 7.23-7.19 (m, 1H), 7.18-7.13 (m, 2H), 6.98 (s, 1H), 6.89 (s, 1H), 6.49 (s, 1H), 4.50 (br s, 2H), 4.33 (dd, J=4.8, 11.5 Hz, 1H), 4.03 (br s, 10H), 2.80-2.66 (m, 3H), 2.65-2.52 (m, 2H), 2.10-2.03 (m, 1H), 1.91 (dq, J=4.7, 12.5 Hz, 1H), 1.52 (s, 6H), 1.27 (br s, 3H), 1.17 (t, J=7.5 Hz, 3H).

Example 23: 2-((R)-4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)-5-fluorophenyl)acetamide hydrochloride

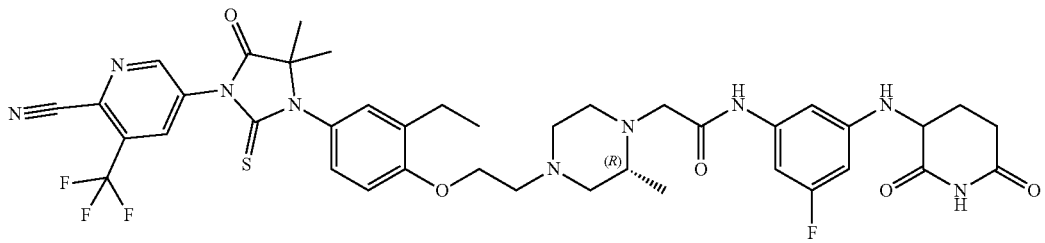

5-Fluorobenzene-1,3-diamine. To a solution of 3-fluoro-5-nitro-aniline (10.00 g, 64.06 mmol, 1 eq) in MeOH (200 mL) was added Pd/C (10%, 1.00 g) under nitrogen. The suspension was degassed under vacuum and purged with hydrogen several times. The mixture was stirred under hydrogen (50 psi) at 25° C. for 12 h, filtered, and concentrated under reduced pressure to afford 5-fluorobenzene-1,3-diamine (6.50 g, 51.53 mmol, 80.4% yield) as a brown oil. $^1$HNMR (400 MHz, CDCl$_3$) δ 5.59 (d, J=2.0 Hz, 1H), 5.53-5.50 (m, 2H), 4.96 (m, 4H).

3-(3-Amino-5-fluoro-anilino)piperidine-2,6-dione. To a solution of 5-fluorobenzene-1,3-diamine (0.10 g, 0.793 mmol, 1 eq) in DMF (2 mL) was added 3-bromopiperidine-2,6-dione (0.137 g, 0.713 mmol, 0.9 eq). The mixture was stirred at 70° C. for 3 h, then poured into ice-water (20 mL). The aqueous phase was extracted with EtOAc (20 mL×3). The combined organic extracts were washed with brine (20 mL×3), dried with anhydrous sodium sulfate, filtered, and concentrated under vacuum. The residue was purified by preparative TLC (50% EtOAc in petroleum ether) to afford 3-(3-amino-5-fluoro-anilino)piperidine-2,6-dione (0.067 g, 0.282 mmol, 35.6% yield) as a white solid. MS (ESI) m/z 238.1 [M+1]$^+$.

2-Chloro-N-(3-((2,6-dioxopiperidin-3-yl)amino)-5-fluorophenyl)acetamide. To a solution of 3-((3-amino-5-fluorophenyl)amino)piperidine-2,6-dione (18.00 g, 75.88 mmol, 1 eq) and 2-chloroacetic acid (7.17 g, 75.88 mmol, 1 eq) in DMF (200 mL) were added HATU (57.70 g, 151.75 mmol, 2 eq) and DIEA (49.03 g, 379.4 mmol, 5 eq). The mixture was stirred at 25° C. for 2 h. The reaction mixture was poured into ice-water (500 mL). The aqueous phase was extracted with EtOAc (500 mL×3). The combined organic extracts were washed with brine (500 mL×3), dried with anhydrous sodium sulfate, filtered, and concentrated under vacuum. The residue was purified by silica gel column chromatography (33-50% EtOAc in petroleum ether) to afford 2-chloro-N-(3-((2,6-dioxopiperidin-3-yl)amino)-5-fluorophenyl)acetamide (12.00 g, 38.25 mmol, 50.4% yield) was obtained as a white solid. $^1$H NMR (400 MHz, DMSO-d$_6$) δ ppm 10.81 (s, 1H), 10.20 (s, 1H), 6.77-6.66 (m, 2H), 6.33 (d, J=7.96 Hz, 1H), 6.29-6.21 (m, 1H), 4.39-4.26 (m, 1H), 4.22 (s, 2H), 2.78 (d, J=5.36 Hz, 1H), 2.65-2.55 (m, 1H), 2.18-2.04 (m, 1H), 1.97-1.82 (m, 1H).

2-((R)-4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)-5-fluorophenyl)acetamide hydrochloride. To a solution of (R)-5-(3-(3-ethyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile (3.00 g, 5.35 mmol, 1 eq) (prepared as described herein) in DMF (30 mL) was added DIEA (2.07 g, 16.05 mmol, 2.80 mL, 3 eq) and 2-chloro-N-(3-((2,6-dioxopiperidin-3-yl)amino)-5-fluorophenyl)acetamide (2.52 g, 5.62 mmol, 1.05 eq). The mixture was stirred at 50° C. for 12 h then purified by standard methods to afford 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)-5-fluorophenyl)acetamide hydrochloride (1.53 g, 1.82 mmol, 34.0% yield). MS (ESI) m/z 838.2 [M+1]$^+$; $^1$HNMR (400 MHz, DMSO-d$_6$) δ ppm 10.81 (s, 1H), 10.52 (s, 1H), 9.25 (d, J=2.0 Hz, 1H), 8.83 (d, J=2.0 Hz, 1H), 7.22-7.14 (m, 3H), 6.79-6.74 (m, 2H), 6.29 (d, J=12.4 Hz, 1H), 4.31 (d, J=11.6 Hz, 4.8 Hz, 1H), 3.56-3.52 (m, 11H), 2.74-2.60 (m, 6H), 2.07-2.06 (m, 1H), 1.93-1.91 (m, 1H), 1.52 (s, 6H), 1.27 (s, 3H), 1.18 (d, J=7.2 Hz, 3H).

Example 24: 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(3-((2,6-dioxopiperidin-3-yl)amino)-5-fluorophenyl)acetamide hydrochoride

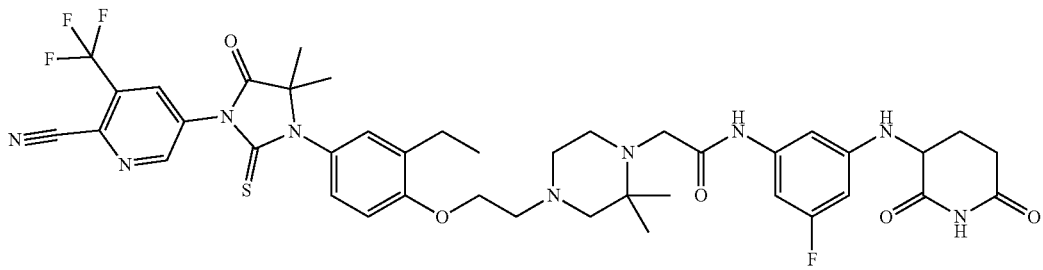 [SMILES: CCc1cc(N2C(=S)N(c3cnc(C#N)c(C(F)(F)F)c3)C(=O)C2(C)C)ccc1OCCN1CCN(CC(=O)Nc2cc(F)cc(NC3CCC(=O)NC3=O)c2)C(C)(C)C1]

2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(3-((2,6-dioxopiperidin-3-yl)amino)-5-fluorophenyl)acetamide hydrochloride. To a solution of 5-(3-(4-(2-(3,3-dimethylpiperazin-1-yl)ethoxy)-3-ethylphenyl)-4,4-dimethyl-5-oxo-2-thioxoimidazolidin-1-yl)-3-(trifluoromethyl)picolinonitrile hydrochloride (3.60 g, 5.89 mmol, 1.0 eq) (prepared as described herein) and 2-chloro-N-(3-((2,6-dioxopiperidin-3-yl)amino)-5-fluorophenyl)acetamide (4.62 g, 14.73 mmol, 2.5 eq), (prepared as described herein), in DMF (30 mL) was added DIEA (3.81 g, 29.45 mmol, 5.13 mL, 5.0 eq) under nitrogen. The reaction mixture was stirred at 60° C. for 16 h. The reaction mixture was diluted with water (150 mL) and extracted with EtOAc (200 mL×3). The combined organic layers were concentrated under reduced pressure to give a residue that was purified by standard methods to yield 2-(4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(3-((2,6-dioxopiperidin-3-yl)amino)-5-fluorophenyl)acetamide hydrochloride (2.63 g, 2.92 mmol, 49.5% yield). MS (ESI) m/z 852.3 [M+1]$^+$; $^1$H NMR (400 MHz, DMSO-d$_6$) δ ppm 10.79 (s, 1H), 10.67-9.66 (m, 1H), 9.24 (d, J=1.6 Hz, 1H), 8.82 (d, J=1.6 Hz, 1H), 7.31-7.04 (m, 3H), 6.89-6.63 (m, 2H), 6.27 (br d, J=12.0 Hz, 1H), 4.48 (br s, 2H), 4.34-4.30 (br dd, J=4.8, 11.6 Hz, 1H), 4.01 (br s, 2H), 3.40-3.33 (m, 7H), 2.82-2.54 (m, 5H), 2.14-2.03 (m, 1H), 1.90 (m, 1H), 1.52 (s, 6H), 1.39 (br s, 6H), 1.18 (t, J=7.6 Hz, 3H).

Example 25: 2-((R)-4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide hydrochloride

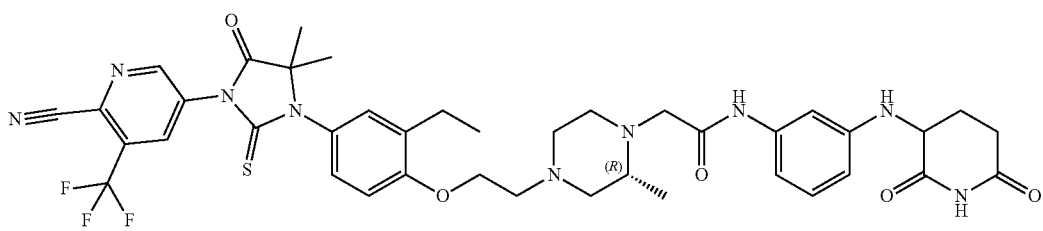

2-((R)-4-(2-(4-(3-(6-Cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide. A mixture of (R)-5-(3-(3-ethyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile (3.00 g, 5.35 mmol, 1 eq), 2-chloro-N-(3-((2,6-dioxopiperidin-3-yl)amino)phenyl)acetamide hydrochloride (1.78 g, 5.35 mmol, 1 eq), (prepared as described herein), DIEA (1.73 g, 13.38 mmol, 2.33 mL, 2.5 eq) and DMF (15 mL) was stirred at 60° C. for 8 h. The solution was filtered. The filtrate was purified by standard methods to give 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide hydrochloride (2.97 g, 3.44 mmol, 64.3% yield). MS (ESI) m/z 820.3 [M+1]$^+$; $^1$H NMR (400 MHz, DMSO-d$_6$) δ ppm 10.80 (s, 1H), 10.66 (br, 1H), 9.24 (d, J=2.0 Hz, 1H), 8.82 (d, J=2.0 Hz, 1H), 7.22-7.14 (m, 3H), 7.08-7.03 (m, 2H), 6.90 (d, J=8.0 Hz, 1H), 6.50 (d, J=8.4 Hz, 1H), 4.53 (br, 2H), 4.38-4.25 (m, 5H), 3.69-3.51 (m, 7H), 2.78-2.65 (m, 3H), 2.61-2.56 (m, 1H), 2.11-2.07 (m, 1H), 1.91 (qd, J=12.4, 4.8 Hz, 1H), 1.51 (s, 6H), 1.39 (d, J=5.2 Hz, 3H), 1.17 (t, J=7.2 Hz, 3H).

Example 26: N-(3-Chloro-5-((2,6-dioxopiperidin-3-yl)amino)phenyl)-2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)acetamide hydrochloride

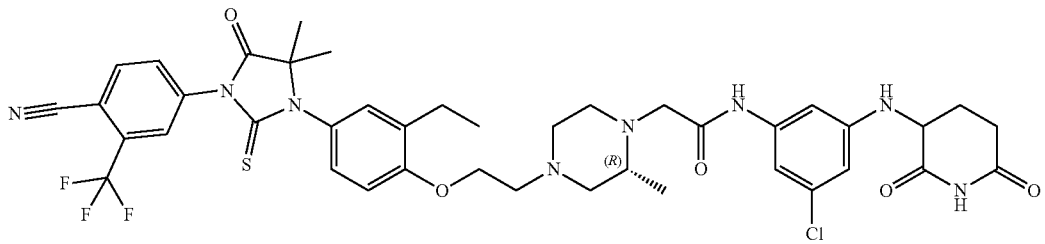

(R)-tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazine-1-carboxylate. A solution of 4-(3-(4-(2-bromoethoxy)-3-ethylphenyl)-4,4-dimethyl-5-oxo-2-thioxoimidazolidin-1-yl)-2-(trifluoromethyl)benzonitrile (3.50 g, 6.48 mmol, 1 eq), (prepared as described herein), (R)-tert-butyl 2-methylpiperazine-1-carboxylate (1.43 g, 7.12 mmol, 1.1 eq) and DIEA (2.51 g, 19.43 mmol, 3.38 mL, 3 eq) in DMF (10 mL) was stirred at 60° C. for 12 h. The mixture was diluted water (50 mL) and extracted with EtOAc (50 mL×2). The combined organic phases were washed with water (30 mL×3) and brine (50 mL), dried over anhydrous sodium sulfate, and concentrated. The residue was purified by silica gel chromatography column (10-16% EtOAc in petroleum ether) to provide (R)-tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazine-1-carboxylate (3.20 g, 4.85 mmol, 74.9% yield) was obtained as a white solid. MS (ESI) m/z [M+1]$^+$; $^1$H NMR (400 MHz, CDCl$_3$) δ ppm 8.03-7.94 (m, 2H), 7.85 (dd, J=1.7, 8.2 Hz, 1H), 7.12-7.03 (m, 2H), 6.95 (d, J=8.6 Hz, 1H), 4.24 (br s, 2H), 3.84 (br d, J=12.2 Hz, 1H), 3.12 (br s, 1H), 3.01-2.71 (m, 4H), 2.68 (q, J=7.5 Hz, 2H), 2.49-2.09 (m, 2H), 1.58 (s, 6H), 1.52-1.42 (m, 9H), 1.27-1.18 (m, 6H).

(R)-4-(3-(3-Ethyl-4-(2-(3-methylpiperazin-1-yl)ethoxy)phenyl)-4,4-dimethyl-5-oxo-2-thioxoimidazolidin-1-yl)-2-(trifluoromethyl)benzonitrile. To a solution of (R)-tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazine-1-carboxylate (3.20 g, 4.85 mmol, 1 eq) in DCM (10 mL) was added a 4.0 M solution of HCl in dioxane (10 mL, 8.25 eq) and the resulting solution was stirred at 20° C. for 2 h. The mixture was concentrated to afford (R)-4-(3-(3-ethyl-4-(2-(3-methylpiperazin-1-yl)ethoxy)phenyl)-4,4-dimethyl-5-oxo-2-thioxoimidazolidin-1-yl)-2-(trifluoromethyl)benzonitrile hydrochloride (3.50 g, crude) as a white solid that was used in the next step without purification. MS (ESI) m/z 560.2 [M+1]$^+$.

N-(3-Chloro-5-((2,6-dioxopiperidin-3-yl)amino)phenyl)-2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)acetamide hydrochloride. To a solution of (R)-4-(3-(3-ethyl-4-(2-(3-methylpiperazin-1-yl)ethoxy)phenyl)-4,4-dimethyl-5-oxo-2-thioxoimidazolidin-1-yl)-2-(trifluoromethyl)benzonitrile hydrochloride (3.50 g, 5.87 mmol, 1 eq) and 2-chloro-N-(3-chloro-5-((2,6-dioxopiperidin-3-yl)amino)phenyl)acetamide (1.94 g, 5.87 mmol, 1 eq) in DMF (20 mL) was added DIEA (3.79 g, 29.36 mmol, 5.11 mL, 5 eq), and the resulting solution was stirred at 60° C. for 12 h. The reaction mixture was diluted with water (50 mL) and extracted with EtOAc (50 mL×2), and the combined organic phases were washed with water (30 mL×3) and brine (50 mL), dried over anhydrous sodium sulfate, and concentrated. The residue was purified by standard methods to afford N-(3-chloro-5-((2,6-dioxopiperidin-3-yl)amino)phenyl)-2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)acetamide hydrochloride (2.16 g, 2.39 mmol, 40.7% yield). MS (ESI) m/z 853.2 [M+1]$^+$; $^1$H NMR (400 MHz, DMSO-d$_6$+D$_2$O) δ ppm 10.77 (s, 1H), 10.41 (br s, 1H), 8.35 (d, J=8.3 Hz, 1H), 8.27 (d, J=1.6 Hz, 1H), 8.05 (dd, J=1.7, 8.3 Hz, 1H), 7.25-7.06 (m, 3H), 6.97 (t, J=1.6 Hz, 1H), 6.85 (s, 1H), 6.49 (t, J=1.8 Hz, 1H), 4.46 (br s, 2H), 4.31 (dd, J=5.0, 11.7 Hz, 1H), 4.05 (br d, J=15.9 Hz, 1H), 3.83 (br d, J=15.8 Hz, 1H), 3.75-3.68 (m, 4H), 3.59-3.42 (m, 4H), 3.32 (br t, J=11.1 Hz, 1H), 2.79-2.55 (m, 4H), 2.12-2.04 (m, 1H), 1.90 (dq, J=4.6, 12.3 Hz, 1H), 1.48 (s, 6H), 1.26 (br d, J=6.0 Hz, 3H), 1.16 (t, J=7.5 Hz, 3H).

Example 27: 2-(4-(3-(4-(3-(4-Cyano-3-(trifluoromethyl)phenyl)-5,5-dimethyl-4-oxo-2-thioxoimidazolidin-1-yl)-2-ethylphenyl)propyl)piperazin-1-yl)-N-(3-((2,6-dioxopiperidin-3-yl)amino)-5-fluorophenyl)acetamide hydrochloride

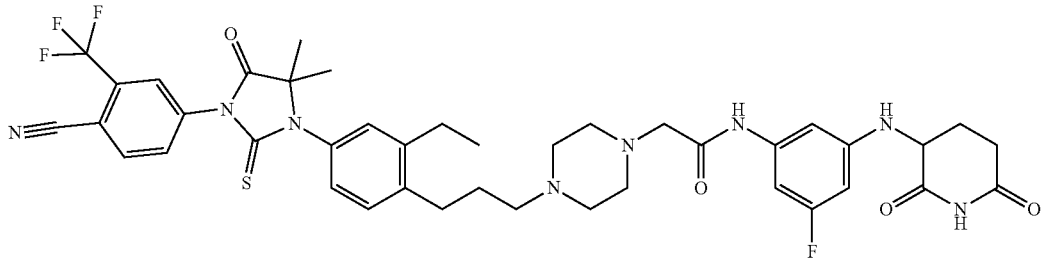 [SMILES: CCc1cc(N2C(=S)N(c3ccc(C#N)c(C(F)(F)F)c3)C(=O)C2(C)C)ccc1CCCN1CCN(CC(=O)Nc2cc(F)cc(NC3CCC(=O)NC3=O)c2)CC1]

4-(3-(4-Cyano-3-(trifluoromethyl)phenyl)-5,5-dimethyl-4-oxo-2-thioxoimidazolidin-1-yl)-2-ethylphenyl trifluoromethanesulfonate. A solution of 4-(3-(3-ethyl-4-hydroxyphenyl)-4,4-dimethyl-5-oxo-2-thioxoimidazolidin-1-yl)-2-(trifluoromethyl)benzonitrile (0.45 g, 1.04 mmol) (prepared as described herein), in DCM (10.4 mL) was treated with DIEA (0.91 mL, 5.19 mmol), then cooled to 0° C. before trifluoromethanesulfonic anhydride (0.193 mL, 1.14 mmol) was added. After 2 h, the reaction was diluted with EtOAc (75 mL) and the organic layer was washed with a saturated aqueous solution of sodium bicarbonate (2×100 mL) and brine (100 mL). The organic layer was dried over magnesium sulfate and concentrated to provide an amber glassy oil that was purified by silica gel column chromatography (15-30% EtOAc in hexanes) to give 4-(3-(3-ethyl-4-hydroxyphenyl)-4,4-dimethyl-5-oxo-2-thioxoimidazolidin-1-yl)-2-(trifluoromethyl)benzonitrile (0.45 g, 1.04 mmol) as a pale yellow solid. MS (ESI) m/z 566.0 [M+1]$^+$; $^1$H NMR (400 MHz, CDCl$_3$) δ ppm 7.99 (d, J=8.3 Hz, 1H), 7.96 (d, J=2.1 Hz, 1H), 7.83 (dd, J=2.1, 8.3 Hz, 1H), 7.44 (d, J=8.7 Hz, 1H), 7.30 (d, J=2.6 Hz, 1H), 7.23 (dd, J=2.6, 8.7 Hz, 1H), 2.82 (q, J=7.5 Hz, 2H), 1.61 (s, 6H), 1.31 (t, J=7.5 Hz, 3H).

4-(3-(3-Ethyl-4-(3-((tetrahydro-2H-pyran-2-yl)oxy)propyl)phenyl)-4,4-dimethyl-5-oxo-2-thioxoimidazolidin-1-yl)-2-(trifluoromethyl)benzonitrile. A mixture of 4-(3-(4-cyano-3-(trifluoromethyl)phenyl)-5,5-dimethyl-4-oxo-2-thioxoimidazolidin-1-yl)-2-ethylphenyl trifluoromethanesulfonate (0.400 g, 0.707 mmol), [(2-dicyclohexylphosphino-2',6'-bis(N,N-dimethylamino)-1,1'-biphenyl)-2-(2'-amino-1,1'-biphenyl)] palladium(II) methanesulfonate (0.077 g, 0.177 mmol), and [(2-dicyclohexylphosphino-2',6'-bis(N,N-dimethylamino)-1,1'-biphenyl)-2-(2'-amino-1,1'-biphenyl)] palladium(II) methanesulfonate (0.143 g, 0.177 mmol) was suspended in toluene (2.021 mL), purged with argon, and cooled to 0° C. before a 0.5 M solution of (3-((tetrahydro-2H-pyran-2-yl)oxy)propyl)zinc(II) bromide in THF (2.122 mL, 1.061 mmol) was added. After 1.5 h, a 0.5 equivalent of 3-((tetrahydro-2H-pyran-2-yl)oxy)propyl)zinc(II) bromide in THF (0.353 mmol, 0.707 mL) was added and the reaction allowed to warm to room temperature over 3 h. The reaction was quenched with the addition of a saturated aqueous solution of ammonium chloride (1 mL), then diluted with EtOAc (50 mL) and the organic layer was washed with a saturated aqueous solution of sodium bicarbonate (2×50 mL) and brine (50 mL). The organic layer was dried over magnesium sulfate and concentrated to provide a brown oil which was purified by silica gel column chromatography (10-30% EtOAc in hexanes) to give 4-(3-(3-ethyl-4-(3-((tetrahydro-2H-pyran-2-yl)oxy)propyl)phenyl)-4,4-dimethyl-5-oxo-2-thioxoimidazolidin-1-yl)-2-(trifluoromethyl)benzonitrile (0.36 g, 0.64 mmol, 91.0% yield). MS (ESI) m/z 582.2 [M+Na]$^+$; $^1$H NMR (400 MHz, CDCl$_3$) δ ppm 8.01-7.95 (m, 2H), 7.85 (dd, J=2.0, 8.3 Hz, 1H), 7.32 (d, J=8.1 Hz, 1H), 7.11-7.02 (m, 2H), 4.62 (dd, J=2.7, 4.4 Hz, 1H), 3.94-3.80 (m, 2H), 3.57-3.45 (m, 2H), 2.83-2.76 (m, 2H), 2.72 (q, J=7.7 Hz, 3H), 1.99-1.69 (m, 5H), 1.64-1.59 (m, 2H), 1.58 (s, 6H), 1.26 (t, J=7.5 Hz, 3H).

4-(3-(3-Ethyl-4-(3-hydroxypropyl)phenyl)-4,4-dimethyl-5-oxo-2-thioxoimidazolidin-1-yl)-2-(trifluoromethyl)benzonitrile. To a solution of 4-(3-(3-ethyl-4-(3-((tetrahydro-2H-pyran-2-yl)oxy)propyl)phenyl)-4,4-dimethyl-5-oxo-2-thioxoimidazolidin-1-yl)-2-(trifluoromethyl)benzonitrile (0.400 g, 0.715 mmol) in DCM (3.57 mL) and EtOH (3.57 mL) was added p-toluenesulfonic acid (0.014 g, 0.071 mmol). The reaction solution was stirred at room temperature for 16 h. The reaction was diluted with EtOAc (100 mL) and the organic layer was washed with a saturated aqueous solution of sodium bicarbonate (2×100 mL) and brine (100 mL). The organic layer was dried over magnesium sulfate and concentrated to provide a light yellow oil that was carried forward without further purification. MS (ESI) m/z 476.2 [M+1]$^+$; $^1$H NMR (400 MHz, CDCl$_3$) δ ppm 8.02-7.93 (m, 2H), 7.85 (dd, J=2.0, 8.4 Hz, 1H), 7.32 (d, J=7.9 Hz, 1H), 7.11-7.03 (m, 2H), 3.76 (br t, J=6.2 Hz, 2H), 2.82-2.67 (m, 4H), 1.96-1.85 (m, 2H), 1.58 (s, 6H), 1.42 (br d, J=1.3 Hz, 1H), 1.26 (t, J=7.6 Hz, 3H).

tert-Butyl 4-(3-(4-(3-(4-cyano-3-(trifluoromethyl)phenyl)-5,5-dimethyl-4-oxo-2-thioxoimidazolidin-1-yl)-2-ethylphenyl)propyl)piperazine-1-carboxylate. To a vessel containing 1,1,1-triacetoxy-1,1-dihydro-1,2-benziodoxol-3(1H)-one (Dess-Martin Periodinane, 0.177 g, 0.416 mmol) was added a solution of 4-(3-(3-ethyl-4-(3-hydroxypropyl)phenyl)-4,4-dimethyl-5-oxo-2-thioxoimidazolidin-1-yl)-2-(trifluoromethyl)benzonitrile (0.180 g, 0.379 mmol) in DCM (3.79 mL). After 1 h at 0° C., sodium triacetoxyborohydride (0.241 g, 1.136 mmol) was added, followed by a solution of tert-butyl piperazine-1-carboxylate (0.210 g, 0.326 mmol) in MeOH (2 mL), and the reaction mixture was stirred at room temperature. After 1 h, the reaction was diluted with EtOAc (50 mL) and the organic layer was washed with a saturated aqueous solution of sodium bicarbonate (2×50 mL) and brine (50 mL). The organic phase was dried over magnesium sulfate, concentrated under reduced pressure and the crude material was purified by silica gel column chromatography (1-3% MeOH in DCM with 0.2% triethyl amine) to give tert-butyl 4-(3-(4-(3-(4-cyano-3-(trifluoromethyl)phenyl)-5,5-dimethyl-4-oxo-2-thioxoimidazolidin-1-yl)-2-ethylphenyl)propyl)piperazine-1-carboxylate (0.210 g, 0.326 mmol, 86.0% yield). MS (ESI) m/z 643.8 [M+1]$^+$; $^1$H NMR (400 MHz, CDCl$_3$) δ ppm 8.00-7.92 (m, 2H), 7.88-7.80 (m, 1H), 7.31 (d, J=8.1 Hz, 1H), 7.10-7.00 (m, 2H), 3.49-3.39 (m, 4H), 2.75-2.65 (m, 4H), 2.50-2.37 (m, 6H), 1.89-1.78 (m, 2H), 1.58 (s, 6H), 1.46 (s, 9H), 1.25 (t, J=7.6 Hz, 3H).

4-(3-(3-Ethyl-4-(3-(piperazin-1-yl)propyl)phenyl)-4,4-dimethyl-5-oxo-2-thioxoimidazolidin-1-yl)-2-(trifluoromethyl)benzonitrile hydrochloride. To a solution of tert-butyl 4-(3-(4-(3-(4-cyano-3-(trifluoromethyl)phenyl)-5,5-dimethyl-4-oxo-2-thioxoimidazolidin-1-yl)-2-ethylphenyl)propyl)piperazine-1-carboxylate (0.210 g, 0.326 mmol) in DCM (3.26 mL) was added TFA (0.754 mL, 9.79 mmol). The reaction solution was stirred at room temperature for 3 h, then diluted with EtOAc (50 mL) and the organic layer was washed with a saturated aqueous solution of sodium bicarbonate (2×100 mL) and brine (100 mL). The organic layer was dried over magnesium sulfate and concentrated to provide 4-(3-(3-ethyl-4-(3-(piperazin-1-yl)propyl)phenyl)-4,4-dimethyl-5-oxo-2-thioxoimidazolidin-1-yl)-2-(trifluoromethyl)benzonitrile (0.167 g, 0.307 mmol, 94.0% yield) as an amber oil that was carried forward without further purification. MS (ESI) m/z 544.0 [M+1]$^+$.

2-(4-(3-(4-(3-(4-Cyano-3-(trifluoromethyl)phenyl)-5,5-dimethyl-4-oxo-2-thioxoimidazolidin-1-yl)-2-ethylphenyl)propyl)piperazin-1-yl)-N-(3-((2,6-dioxopiperidin-3-yl)amino)-5-fluorophenyl)acetamide hydrochloride. To a mixture of 4-(3-(3-ethyl-4-(3-(piperazin-1-yl)propyl)phenyl)-4,4-dimethyl-5-oxo-2-thioxoimidazolidin-1-yl)-2-(trifluoromethyl)benzonitrile (0.080 g, 0.147 mmol) and 2-chloro-N-(3-((2,6-dioxopiperidin-3-yl)amino)-5-fluorophenyl)acetamide (0.046 g, 0.147 mmol) in DMF (0.368 mL) was added DIEA (0.129 mL, 0.736 mmol). The reaction solution was stirred at 45° C. for 18 h, then diluted with DMSO to a total volume of 2 mL, filtered, and purified by standard methods to give 2-(4-(3-(4-(3-(4-cyano-3-(trifluoromethyl)phenyl)-5,5-dimethyl-4-oxo-2-thioxoimidazolidin-1-yl)-2-ethylphenyl)propyl)piperazin-1-yl)-N-(3-((2,6-dioxopiperidin-3-yl)amino)-5-fluorophenyl)acetamide hydrochloride (0.039 g, 0.047 mmol, 32.0%). MS (ESI) m/z 821.4 [M+1]$^+$; $^1$H NMR (400 MHz, DMSO-d$_6$) δ ppm 10.82 (s, 1H), 10.36-10.19 (m, 1H), 8.40 (d, J=8.3 Hz, 1H), 8.09 (dd, J=1.9, 8.3 Hz, 1H), 7.39 (d, J=7.9 Hz, 1H), 7.19 (s, 2H), 6.77 (dd, J=2.1, 11.0 Hz, 1H), 6.72 (s, 1H), 6.34-6.19 (m, 1H), 4.62-4.38 (m, 3H), 4.35-4.25 (m, 3H), 4.18-3.62 (m, 6H), 3.48-3.12 (m, 6H), 2.71 (br d, J=7.3 Hz, 4H), 2.64-2.54 (m, 1H), 2.14-2.00 (m, 3H), 1.91 (dq, J=4.8, 12.3 Hz, 1H), 1.51 (s, 5H), 1.21 (t, J=7.5 Hz, 3H).

Example 28: N-(3-Chloro-5-(2,6-dioxopiperidin-3-ylamino)phenyl)-2-((R)-4-(2-(4-(7-(4-cyano-3-(trifluoromethyl)phenyl)-8-oxo-6-thioxo-5,7-diazaspiro[3.4]octan-5-yl)-2-ethylphenoxy)ethyl)-2-methylpiperazin-1-yl)acetamide hydrochloride

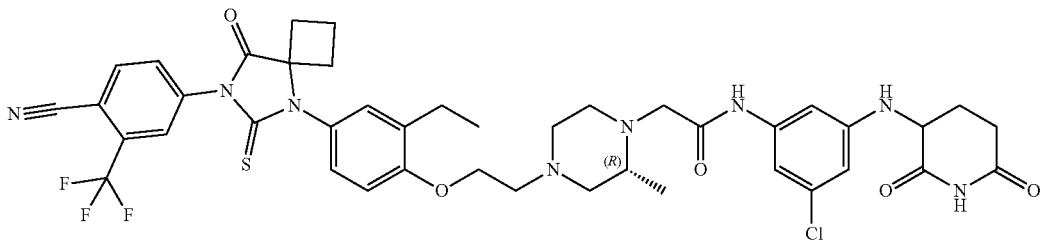

(R)-tert-Butyl 4-(2-(4-((1-cyanocyclobutyl)amino)-2-ethylphenoxy)ethyl)-2-methylpiperazine-1-carboxylate. To a solution of (R)-tert-butyl 4-(2-(4-amino-2-ethylphenoxy)ethyl)-2-methylpiperazine-1-carboxylate (6.00 g, 16.51 mmol, 1.00 eq), (prepared as described herein) and cyclobutanone (4.69 g, 66.91 mmol, 5 mL, 4.05 eq) in DCM (60 mL) was added trimethylsilyl cyanide (4.76 g, 47.96 mmol, 6 mL, 2.91 eq) in one portion drop-wise at 0° C. under nitrogen. The mixture was stirred at 20° C. for 48 h, then was diluted with water (150 mL) and extracted with DCM (60 mL×3). The combined organic layers were washed with brine (100 mL), dried over anhydrous sodium sulfate, filtered and concentrated under reduced pressure. The resulting residue was purified by silica gel column chromatography (10-23% EtOAc in petroleum ether). Compound (R)-tert-butyl 4-(2-(4-((1-cyanocyclobutyl)amino)-2-ethylphenoxy)ethyl)-2-methylpiperazine-1-carboxylate (5.70 g, 12.54 mmol, 76.0% yield) was obtained as a light yellow oil. MS (ESI) m/z 443.4 [M+1]$^+$.

(R)-4-(5-(3-Ethyl-4-(2-(3-methylpiperazin-1-yl)ethoxy)phenyl)-8-oxo-6-thioxo-5,7-diazaspiro[3.4]octan-7-yl)-2-(trifluoromethyl)benzonitrile. A solution of (R)-tert-butyl 4-(2-(4-((1-cyanocyclobutyl)amino)-2-ethylphenoxy)ethyl)-2-methylpiperazine-1-carboxylate (2.50 g, 5.65 mmol, 1.00 eq) and 4-isothiocyanato-2-(trifluoromethyl)benzonitrile (1.93 g, 8.47 mmol, 1.50 eq) in DMF (20 mL) was stirred at 20° C. under nitrogen for 1 h, then treated with a 4.0 M solution of HCl in MeOH (15.0 mL, 10.62 eq) and MeOH (10 mL) at 70° C. for 12 h. The reaction mixture was diluted with water (200 mL) and extracted with EtOAc (50 mL×3). The combined organic layers were washed with brine (50 mL×3), dried over anhydrous sodium sulfate, filtered, and concentrated under reduced pressure. The residue was purified by silica gel column chromatography (0-10% MeOH in DCM) to afford (R)-4-(5-(3-ethyl-4-(2-(3-methylpiperazin-1-yl)ethoxy)phenyl)-8-oxo-6-thioxo-5,7-diazaspiro[3.4]octan-7-yl)-2-(trifluoromethyl)benzonitrile (2.75 g, 4.77 mmol, 84.4% yield) isolated as a light yellow solid. MS (ESI) m/z 572.1 [M+1]$^+$.

N-(3-Chloro-5-(2,6-dioxopiperidin-3-ylamino)phenyl)-2-((R)-4-(2-(4-(7-(4-cyano-3-(trifluoromethyl)phenyl)-8-oxo-6-thioxo-5,7-diazaspiro[3.4]octan-5-yl)-2-ethylphenoxy)ethyl)-2-methylpiperazin-1-yl)acetamide hydrochloride. To a solution of (R)-4-(5-(3-ethyl-4-(2-(3-methylpiperazin-1-yl)ethoxy)phenyl)-8-oxo-6-thioxo-5,7-diazaspiro[3.4]octan-7-yl)-2-(trifluoromethyl)benzonitrile (0.100 g, 0.175 mmol, 1.00 eq) and 2-chloro-N-(3-chloro-5-((2,6-dioxopiperidin-3-yl)amino)phenyl)acetamide (0.064 g, 0.192 mmol, 1.10 eq) in DMF (3 mL) was added DIEA (0.074 g, 0.574 mmol, 0.100 mL, 3.28 eq) in one portion. The mixture was stirred at 50° C. under nitrogen for 12 h, then was diluted with water (100 mL) and extracted with DCM (40 mL×4). The combined organic layers were washed with brine (80 mL), dried over anhydrous sodium sulfate, filtered, and concentrated under reduced pressure to give a residue. The residue was purified by standard methods give N-(3-chloro-5-(2,6-dioxopiperidin-3-ylamino)phenyl)-2-((R)-4-(2-(4-(7-(4-cyano-3-(trifluoromethyl)phenyl)-8-oxo-6-thioxo-5,7-diazaspiro[3.4]octan-5-yl)-2-ethylphenoxy)ethyl)-2-methylpiperazin-1-yl)acetamide hydrochloride (0.128 g, 0.142 mmol, 81.0% yield). MS (ESI) m/z 865.4 [M+1]$^+$; $^1$H NMR (400 MHz, DMSO-d$_6$) δ ppm 10.80 (s, 1H), 10.24 (br s, 1H), 8.37 (d, J=8.3 Hz, 1H), 8.26-8.24 (m, 1H), 8.05 (d, J=8.2 Hz, 1H), 7.27-7.23 (m, 1H), 7.22-7.16 (m, 2H), 6.97 (s, 1H), 6.91 (br s, 1H), 6.48 (s, 1H), 4.50 (br s, 2H), 4.33 (br dd, J=4.8, 11.7 Hz, 1H), 3.18 (br s, 10H), 2.81-2.65 (m, 4H), 2.63-2.55 (m, 3H), 2.45-2.37 (m, 2H), 2.11-2.03 (m, 1H), 2.00-1.87 (m, 2H), 1.58-1.47 (m, 1H), 1.27-1.16 (m, 6H).

Example 29: 2-((R)-4-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-2-methylpiperazin-1-yl)-N-(3-((2,6-dioxopiperidin-3-yl)amino)phenyl)acetamide hydrochloride (R)-5-(5-(3-Ethyl-4-(2-(3-methylpiperazin-1-yl)ethoxy)phenyl)-8-oxo-6-thioxo-5,7-diazaspiro[3.4]octan-7-yl)-3-(trifluoromethyl)picolinonitrile. A mixture of (R)-tert-butyl 4-(2-(4-((1-cyanocyclobutyl)amino)-2-ethylphenoxy)ethyl)-2-methylpiperazine-1-carboxylate (3.00 g, 6.78 mmol, 1 eq), intermediate prepared as described herein and 5-isothiocyanato-3-(trifluoromethyl)picolinonitrile (2.33 g, 10.17 mmol, 1.5 eq) in DMF (15 mL) was stirred at 20° C. under nitrogen for 2 h, then treated with MeOH (5 mL) and a 4.0 M aqueous solution of HCl in MeOH (20 mL, 11.80 eq). The reaction mixture was stirred at 70° C. for 11 h then concentrated under reduced pressure. The residue was neutralized with a saturated aqueous solution of sodium bicarbonate, then diluted with water (50 mL) and extracted with EtOAc (40 mL×3). The combined organic extracts were washed with brine (50 mL), dried over anhydrous sodium sulfate, filtered, and concentrated under reduced pressure. The residue was purified by silica gel column chromatography (0-50% EtOAc in petroleum ether followed by 0-20% MeOH in DCM). (R)-5-(5-(3-Ethyl-4-(2-(3-methylpiperazin-1-yl)ethoxy)phenyl)-8-oxo-6-thioxo-5,7-diazaspiro[3.4]octan-7-yl)-3-(trifluoromethyl)picolinonitrile (3.90 g, 6.69 mmol, 98.7% yield) was obtained as a white solid after concentration of the fractions. MS (ESI) m/z 573.3 [M+1]$^+$.

2-((R)-4-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-2-methylpiperazin-1-yl)-N-(3-((2,6-dioxopiperidin-3-yl)amino)phenyl)acetamide hydrochloride. A mixture of (R)-5-(5-(3-ethyl-4-(2-(3-methylpiperazin-1-yl)ethoxy)phenyl)-8-oxo-6-thioxo-5,7-diazaspiro[3.4]octan-7-yl)-3-(trifluoromethyl)picolinonitrile (0.070 g, 0.122 mmol, 1 eq) and 2-chloro-N-(3-((2,6-dioxopiperidin-3-yl)amino)phenyl)acetamide (0.038 g, 0.128 mmol, 1.05 eq) in DMF (2 mL) was treated with DIEA (0.047 g, 0.367 mmol, 0.064 mL, 3 eq), and stirred at 50° C. for 8 h. The reaction mixture was then filtered and the filtrate was purified by standard methods to afford 2-((R)-4-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-2-methylpiperazin-1-yl)-N-(3-((2,6-dioxopiperidin-3-yl)amino)phenyl)acetamide hydrochloride (0.076 g, 0.086 mmol, 70.6% yield). MS (ESI) m/z 832.3 [M+1]$^+$; $^1$H NMR (400 MHz, DMSO-d$_6$) δ ppm 10.79 (s, 1H), 10.26 (br s, 1H), 9.23 (d,

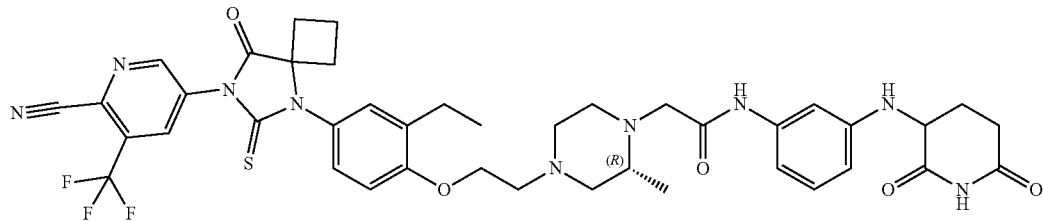

J=1.8 Hz, 1H), 8.77 (d, J=1.8 Hz, 1H), 7.27-7.24 (m, 1H), 7.22-7.19 (m, 2H), 7.07-7.02 (m, 1H), 7.00 (s, 1H), 6.86 (br d, J=7.8 Hz, 1H), 6.46 (br d, J=8.3 Hz, 1H), 4.52 (br s, 2H), 4.27 (br dd, J=4.9, 11.2 Hz, 1H), 3.73 (br s, 3H), 3.62 (br s, 4H), 3.30 (br s, 1H), 2.79-2.73 (m, 1H), 2.71 (d, J=7.3 Hz, 2H), 2.68 (br s, 1H), 2.65-2.56 (m, 3H), 2.55-2.52 (m, 2H), 2.46 (br d, J=9.9 Hz, 2H), 2.11 (br dd, J=4.8, 12.8 Hz, 1H), 2.02-1.89 (m, 2H), 1.58-1.51 (m, 1H), 1.30 (br s, 3H), 1.20 (t, J=7.5 Hz, 3H).

Example 30: N-(3-chloro-5-((2,6-dioxopiperidin-3-yl)amino)phenyl)-2-((1S,4S)-5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.1]heptan-2-yl)acetamide hydrochloride

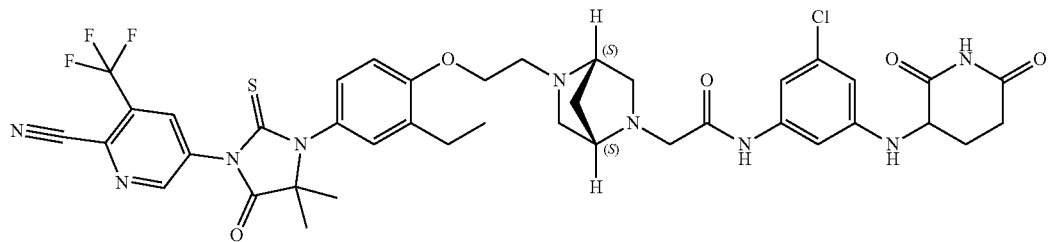

(1S,4S)-tert-butyl 5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.1]heptane-2-carboxylate. To a solution of 5-(3-(4-(2-bromoethoxy)-3-ethylphenyl)-4,4-dimethyl-5-oxo-2-thioxoimidazolidin-1-yl)-3-(trifluoromethyl)picolinonitrile (0.300 g, 0.554 mmol, 1 eq) (prepared as described herein) in acetonitrile (5 mL) was added (1S,4S)-tert-butyl 2,5-diazabicyclo[2.2.1]heptane-2-carboxylate (0.110 g, 0.554 mmol, 1 eq) and potassium carbonate (0.230 g, 1.660 mmol, 3 eq). The reaction mixture was stirred at 80° C. for 12 h then was filtered and the filtrate concentrated under vacuum. The residue was purified by silica gel column chromatography (0-4% MeOH in DCM) to give (1S,4S)-tert-butyl 5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.1]heptane-2-carboxylate (0.320 g, 0.486 mmol, 87.7% yield) as a brown oil. MS (ESI) m/z 659.4 [M+1]$^+$.

5-(3-(4-(2-((1S,4S)-2,5-diazabicyclo[2.2.1]heptan-2-yl)ethoxy)-3-ethylphenyl)-4,4-dimethyl-5-oxo-2-thioxoimidazolidin-1-yl)-3-(trifluoromethyl)picolinonitrile. A solution of (1S,4S)-tert-butyl 5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.1]heptane-2-carboxylate (0.320 g, 0.486 mmol, 1 eq) in dioxane (10 mL) was treated with a 4.0 solution of HCl in dioxane (20.0 mL, 165 eq) and was stirred at 20° C. for 0.5 h. The reaction mixture was concentrated under reduced pressure to give a residue. The residue was purified by semi-preparative reverse phase HPLC (17-37% acetonitrile+ 0.05% HCl in water, 9 min). The selected fraction was concentrated to remove most of the acetonitrile and the resultant suspension was lyophilized to afford 5-(3-(4-(2-((1S,4S)-2,5-diazabicyclo[2.2.1]heptan-2-yl)ethoxy)-3-ethylphenyl)-4,4-dimethyl-5-oxo-2-thioxoimidazolidin-1-yl)-3-(trifluoromethyl)picolinonitrile dihydrochloride (0.227 g, 0.376 mmol, 77.4% yield) obtained as a white solid. MS (ESI) m/z=559.1 [M+1]$^+$; $^1$H NMR (400 MHz, DMSO-d$_6$) δ ppm 12.79-11.87 (m, 1H), 10.55-9.53 (m, 2H), 9.26 (d, J=1.8 Hz, 1H), 8.84 (d, J=2.0 Hz, 1H), 7.26-7.13 (m, 3H), 4.73-4.44 (m, 4H), 3.93-3.66 (m, 4H), 3.39 (s, 2H), 2.67 (q, J=7.3 Hz, 2H), 2.38 (d, J=7.8 Hz, 1H), 2.16 (d, J=11.9 Hz, 1H), 1.53 (s, 6H), 1.19 (t, J=7.5 Hz, 3H).

N-(3-chloro-5-((2,6-dioxopiperidin-3-yl)amino)phenyl)-2-((1S,4S)-5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.1]heptan-2-yl)acetamide hydrochloride. To a solution of 2-chloro-N-(3-chloro-5-((2,6-dioxopiperidin-3-yl)amino)phenyl)acetamide (0.111 g, 0.336 mmol, 1 eq) in DMF (2 mL) was added 5-(3-(4-(2-((1S,4S)-2,5-diazabicyclo[2.2.1]heptan-2-yl)ethoxy)-3-ethylphenyl)-4,4-dimethyl-5-oxo-2-thioxoimidazolidin-1-yl)-3-(trifluoromethyl)picolinonitrile (0.200 g, 0.336 mmol, 1 eq, HCl) and DIEA (0.130 g, 1.010 mmol, 175.62 μL, 3 eq). The reaction mixture was stirred at 60° C. for 12 h. The pH of the reaction was then adjusted to pH=6 with the addition of formic acid (0.3 mL). The mixture was purified by standard methods to afford N-(3-chloro-5-((2,6-dioxopiperidin-3-yl)amino)phenyl)-2-((1S,4S)-5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.1]heptan-2-yl)acetamide hydrochloride (0.163 g, 0.173 mmol, 51.5% yield). MS (ESI) m/z 852.3 [M+1]$^+$; $^1$H NMR (400 MHz, DMSO-d$_6$) δ ppm 13.19-11.24 (m, 1H), 10.80 (s, 2H), 9.25 (d, J=1.8 Hz, 1H), 8.83 (d, J=1.8 Hz, 1H), 7.29-7.11 (m, 3H), 7.09-6.75 (m, 2H), 6.50 (s, 1H), 4.56 (s, 6H), 4.32 (dd, J=4.9, 11.7 Hz, 1H), 4.21 (s, 2H), 3.83 (s, 4H), 3.39 (s, 2H), 2.82-2.70 (m, 1H), 2.70-2.64 (m, 2H), 2.62-2.57 (m, 1H), 2.08 (td, J=4.0, 8.4 Hz, 1H), 1.91 (dq, J=4.7, 12.3 Hz, 1H), 1.52 (s, 6H), 1.19 (t, J=7.5 Hz, 3H).

Example 31: N-(3-Chloro-5-((2,6-dioxopiperidin-3-yl)amino)phenyl)-2-((2R,5R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)acetamide trifluoroacetate

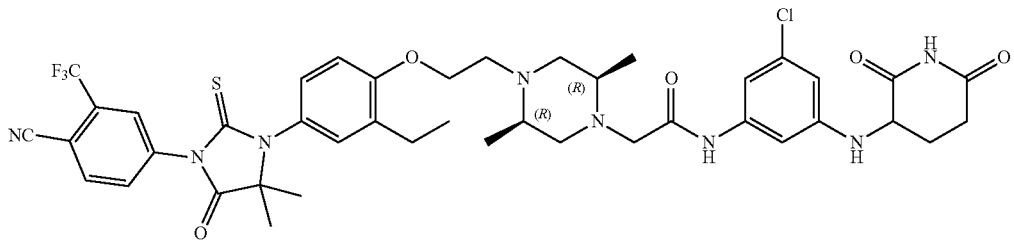

A. tert-Butyl (2R,5R)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,5-dimethylpiperazine-1-carboxylate. 4-(3-(4-(2-Bromoethoxy)-3-ethylphenyl)-4,4-dimethyl-5-oxo-2-thioxoimidazolidin-1-yl)-2-(trifluoromethyl)benzonitrile (0.200 g, 0.370 mmol) (prepared as described herein), (2R,5R)-tert-butyl 2,5-dimethylpiperazine-1-carboxylate (0.095 g, 0.444 mmol) and DIEA (0.162 mL, 0.925 mmol) were combined in DMF (1.5 mL) and the mixture was heated to 70° C. in a screw cap vial. After 16 h, the solution was concentrated under reduced pressure to afford an orange residue that was purified by silica gel column chromatography (0-80% EtOAc in hexanes) to afford the title compound (0.204 g, 0.299 mmol, 81.0% yield). MS (ESI) m/z 674 [M+1]⁺.

4-(3-(4-(2-((2R,5R)-2,5-Dimethylpiperazin-1-yl)ethoxy)-3-ethylphenyl)-4,4-dimethyl-5-oxo-2-thioxoimidazolidin-1-yl)-2-(trifluoromethyl)benzonitrile dihydrochloride. (2R,5R)-tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazine-1-carboxylate (0.204 g, 0.303 mmol) was dissolved in DCM (1.5 mL). To the solution was added a 4.0 M solution of HCl in dioxane (1.89 mL, 7.57 mmol) and the mixture was stirred at ambient temperature. After 45 min, the solution was concentrated under reduced pressure to afford the title compound (0.200 g, 0.309 mmol, quant. yield). MS (ESI) m/z 574 [M+1]⁺.

N-(3-Chloro-5-((2,6-dioxopiperidin-3-yl)amino)phenyl)-2-((2R,5R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)acetamide trifluoroacetate. 4-(3-(4-(2-((2R,5R)-2,5-Dimethylpiperazin-1-yl)ethoxy)-3-ethylphenyl)-4,4-dimethyl-5-oxo-2-thioxoimidazolidin-1-yl)-2-(trifluoromethyl)benzonitrile dihydrochloride (0.110 g, 0.170 mmol), 2-chloro-N-(3-chloro-5-((2,6-dioxopiperidin-3-yl)amino)phenyl)acetamide (0.067 g, 0.204 mmol), sodium iodide (0.026 g, 0.170 mmol) and DIEA (0.149 mL, 0.851 mmol) were combined in DMF (0.5 mL) and the mixture was stirred at 60° C. in a screw cap scintillation vial. After 2 h, the solution was diluted with DMSO (1 mL) and purified by standard methods to afford N-(3-Chloro-5-((2,6-dioxopiperidin-3-yl)amino)phenyl)-2-((2R,5R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)acetamide trifluoroacetate (0.058 g, 0.060 mmol, 40.2% yield). MS (ESI) m/z 867 [M]⁺ 869 [M+2]⁺; ¹H NMR (400 MHz, DMSO-d₆) δ ppm 10.78-10.82 (m, 1H), 9.80-10.09 (m, 1H), 9.53-9.74 (m, 1H), 8.39 (d, J=8.31 Hz, 1H), 8.29 (d, J=1.71 Hz, 1H), 8.07 (dd, J=8.31, 1.71 Hz, 1H), 7.12-7.24 (m, 3H), 6.95 (br d, J=4.89 Hz, 1H), 6.89 (br s, 1H), 6.47 (br s, 1H), 6.12-6.42 (m, 1H), 4.40 (br s, 2H), 4.32 (br dd, J=11.43, 4.34 Hz, 2H), 3.26-3.42 (m, 3H), 3.00-3.26 (m, 4H), 2.55-2.78 (m, 4H), 2.02-2.11 (m, 1H), 1.92 (br s, 1H), 1.50 (s, 8H), 1.40 (br s, 1H), 1.07-1.29 (m, 8H), 0.95 (d, J=6.60 Hz, 1H), 0.81-0.89 (m, 1H).

Example 32: 2-((2R,6R)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-((2,6-dioxopiperidin-3-yl)amino)phenyl)acetamide trifluoroacetate

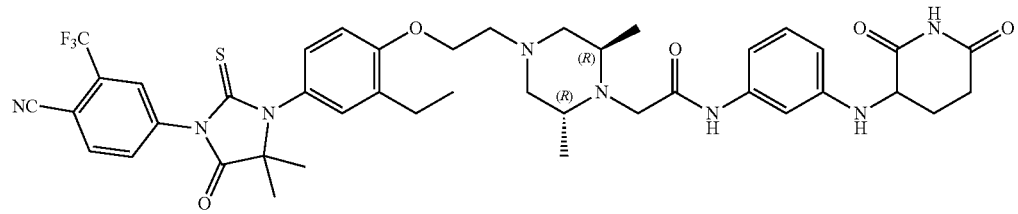

tert-Butyl (2R,6R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazine-1-carboxylate. 4-(3-(4-(2-Bromoethoxy)-3-ethylphenyl)-4,4-dimethyl-5-oxo-2-thioxoimidazolidin-1-yl)-2-(trifluoromethyl)benzonitrile (0.210 g, 0.389 mmol) (prepared as described herein), (2R,6R)-tert-butyl 2,6-dimethylpiperazine-1-carboxylate (0.100 g, 0.466 mmol) and DIEA (0.170 mL, 0.972 mmol) were combined in DMF (3 mL) and the mixture was heated to 70° C. in a screw cap vial. After 90 min, the solution was condensed under reduced pressure to afford an orange residue, which was purified by silica gel column chromatography (0-70% EtOAc in hexanes) to afford the title compound (0.206 g, 0.306 mmol, 79.0% yield). MS (ESI) m/z 674 [M+1]⁺.

4-(3-(4-(2-((3R,5R)-3,5-Dimethylpiperazin-1-yl)ethoxy)-3-ethylphenyl)-4,4-dimethyl-5-oxo-2-thioxoimidazolidin-1-yl)-2-(trifluoromethyl)benzonitrile dihydrochloride. (2R,6R)-tert-butyl 4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,6-dimethylpiperazine-1-carboxylate (0.206 g, 0.306 mmol) was dissolved in DCM (1.5 mL). To the solution was added a 4.0 M solution of HCl in dioxane (1.91 mL, 7.64 mmol) and the mixture was stirred at ambient temperature. After 45 min, the solution was condensed under reduced pressure to afford the title compound (0.210 g, 0.325 mmol, quant. yield). MS (ESI) m/z 574 [M+1]⁺.

N-(3-Chloro-5-((2,6-dioxopiperidin-3-yl)amino)phenyl)-2-((2R,6R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetamide trifluoroacetate. 4-(3-(4-(2-((3R,5R)-3,5-Dimethylpiperazin-1-yl)ethoxy)-3-ethylphenyl)-4,4-dimethyl-5-oxo-2-thioxoimidazolidin-1-yl)-2-(trifluoromethyl)benzonitrile dihydrochloride (0.105 g, 0.162 mmol), 2-chloro-N-(3-((2,6-dioxopiperidin-3-yl)amino)phenyl)acetamide (0.053 g, 0.179 mmol), sodium iodide (0.024 g, 0.162 mmol) and DIEA (0.142 mL, 0.812 mmol) were combined in DMF (0.5 mL) and the mixture was stirred at 60° C. in a screw cap vial. After 48 h, the solution was diluted with DMSO (1 mL) and purified by standard methods to afford N-(3-Chloro-5-((2,6-dioxopiperidin-3-yl)amino)phenyl)-2-((2R,6R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetamide trifluoroacetate (0.033 g, 0.035 mmol, 22.0% yield). MS (ESI) m/z 833 [M+1]⁺; ¹H NMR (400 MHz, DMSO-d₆) δ ppm 10.79 (s, 1H), 10.23-10.43 (m, 1H), 9.59-9.81 (m, 1H), 9.22-9.48 (m, 1H), 8.39 (d, J=8.19 Hz, 1H), 8.29 (d, J=1.71 Hz, 1H), 8.07 (dd, J=8.13, 1.77 Hz, 1H), 7.11-7.22 (m, 3H), 6.89-7.11 (m, 2H), 6.39-6.49 (m, 1H), 4.07-4.29 (m, 4H), 3.74-4.00 (m, 6H), 3.58-3.70 (m, 3H), 3.44-3.52 (m, 2H), 3.06-3.35 (m, 2H), 2.83 (br d, J=3.18 Hz, 2H), 2.57-2.79 (m, 5H), 2.37-2.44 (m, 1H), 2.33 (dt, J=3.67, 1.83 Hz, 2H), 2.03-2.16 (m, 2H), 1.82-1.98 (m, 1H), 1.50 (s, 7H), 1.40 (s, 1H), 1.22-1.36 (m, 7H), 1.17 (t, J=7.46 Hz, 4H), 0.98-1.09 (m, 2H), 0.81-0.88 (m, 3H), 0.01-0.01 (m, 1H), −0.03−−0.01 (m, 2H).

Example 33: 2-(4-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperazin-1-yl)-N-(3-((2,6-dioxopiperidin-3-yl)amino)phenyl)acetamide hydrochloride

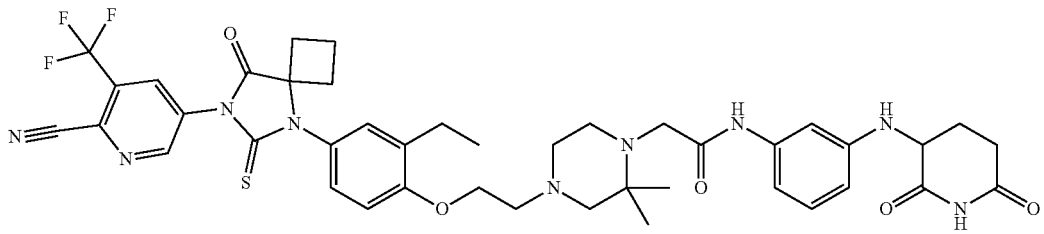 [SMILES: CCc1cc(N2C(=S)N(c3cnc(C#N)c(C(F)(F)F)c3)C(=O)C23CCC3)ccc1OCCN1CCN(CC(=O)Nc2cccc(NC3CCC(=O)NC3=O)c2)C(C)(C)C1]

1-((3-Ethyl-4-hydroxyphenyl)amino)cyclobutanecarbonitrile. To a mixture of 4-amino-2-ethyl-phenol (0.700 g, 5.10 mmol, 1 eq) and cyclobutanone (0.715 g, 10.21 mmol, 0.762 mL, 2 eq) in THF (7 mL) was added trimethylsilyl cyanide (0.607 g, 6.12 mmol, 0.766 mL, 1.2 eq), and the solution was stirred at 20° C. for 6 h. Tetrabutylammonium fluoride (1.02 mL, 0.2 eq) was added and the solution was stirred for 30 min. The reaction mixture was concentrated and diluted with EtOAc (200 mL), washed with brine (100 mL), dried, filtered, and concentrated under reduced. The residue was purified by flash silica gel chromatography (0-50% EtOAc in petroleum ether) to afford 1-((3-ethyl-4-hydroxyphenyl)amino)cyclobutanecarbonitrile (0.778 g, 3.60 mmol, 70.4% yield) as a brown solid. MS (ESI) m/z 217.1 [M+1]⁺.

5-(5-(3-Ethyl-4-hydroxyphenyl)-8-oxo-6-thioxo-5,7-diazaspiro[3.4]octan-7-yl)-3-(trifluoromethyl)picolinonitrile. Thiophosgene (0.239 g, 2.08 mmol, 0.159 mL, 1 eq) was added dropwise into a mixture of 1-(3-ethyl-4-hydroxyanilino)cyclobutanecarbonitrile (0.450 g, 2.08 mmol, 1 eq) and 5-amino-3-(trifluoromethyl)pyridine-2-carbonitrile (0.389 g, 2.08 mmol, 1 eq) in DMA (18 mL). The mixture was stirred at 60° C. for 12 h, then MeOH (2.7 mL) and a 2.0 M aqueous solution of HCl (1.8 mL, 1.73 eq) were added. After 2 h at 15° C., the reaction mixture was diluted with EtOAc (200 mL), washed with brine (100 mL×3), dried, filtered, and concentrated under reduced pressure. 5-(5-(3-Ethyl-4-hydroxyphenyl)-8-oxo-6-thioxo-5,7-diazaspiro[3.4]octan-7-yl)-3-(trifluoromethyl)picolinonitrile (1.160 g, crude) was obtained as brown solid and was used in the next step without further purification. MS (ESI) m/z 447.0 [M+1]⁺.

5-(5-(4-(2-Bromoethoxy)-3-ethylphenyl)-8-oxo-6-thioxo-5,7-diazaspiro[3.4]octan-7-yl)-3-(trifluoromethyl)picolinonitrile. To a solution of 5-(5-(3-ethyl-4-hydroxyphenyl)-8-oxo-6-thioxo-5,7-diazaspiro[3.4]octan-7-yl)-3-(trifluoromethyl)picolinonitrile (0.400 g, 0.896 mmol, 1 eq) in acetonitrile (10 mL) was added potassium carbonate (0.371 g, 2.69 mmol, 3 eq) and 1,2-dibromoethane (3.370 g, 17.92 mmol, 1.35 mL, 20 eq). The mixture was stirred at 80° C. for 12 h, filtered, and the filtrate was concentrated. The residue was purified by silica gel chromatography (20-33% EtOAc in petroleum ether). Compound 5-(5-(4-(2-bromoethoxy)-3-ethylphenyl)-8-oxo-6-thioxo-5,7-diazaspiro[3.4]octan-7-yl)-3-(trifluoromethyl)picolinonitrile (0.400 g, 0.723 mmol, 80.7% yield) was obtained as a yellow solid. MS (ESI) m/z 553.0 [M+1]⁺.

tert-Butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperazine-1-carboxylate. To a solution of 5-(5-(4-(2-bromoethoxy)-3-ethylphenyl)-8-oxo-6-thioxo-5,7-diazaspiro[3.4]octan-7-yl)-3-(trifluoromethyl)picolinonitrile (0.400 g, 0.723 mmol, 1 eq) in DMF (8 mL) was added DIEA (0.280 g, 2.17 mmol, 3 eq) and tert-butyl 2,2-dimethylpiperazine-1-carboxylate (0.232 g, 1.08 mmol, 1.5 eq). The mixture was stirred at 60° C. for 12 h. The mixture was purified by preparative HPLC (36-66% acetonitrile+0.05% formic acid in water, 10 min). Compound tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperazine-1-carboxylate (0.400 g, 0.582 mmol, 80.6% yield) was obtained as a white solid. MS (ESI) m/z 687.3 [M+1]⁺.

5-(5-(4-(2-(3,3-Dimethylpiperazin-1-yl)ethoxy)-3-ethylphenyl)-8-oxo-6-thioxo-5,7-diazaspiro[3.4]octan-7-yl)-3-(trifluoromethyl)picolinonitrile. To a solution of tert-butyl 4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperazine-1-carboxylate (0.350 g, 0.509 mmol, 1 eq) in EtOAc (3 mL) was added a 4.0 M solution of HCl in EtOAc (3.75 mL, 29.4 eq). The mixture was stirred at 25° C. for 12 h, then concentrated under reduced pressure at 40° C. Compound 5-(5-(4-(2-(3,3-dimethylpiperazin-1-yl)ethoxy)-3-ethylphenyl)-8-oxo-6-thioxo-5,7-diazaspiro[3.4]octan-7-yl)-3-(trifluoromethyl)picolinonitrile hydrochloride (0.300 g, 0.481 mmol, 94.4% yield) was obtained as a white solid. MS (ESI) m/z 587.2 [M+1]⁺.

2-(4-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperazin-1-yl)-N-(3-((2,6-dioxopiperidin-3-yl)amino)phenyl)acetamide hydrochloride. To a solution of 5-(5-(4-(2-(3,3-dimethylpiperazin-1-yl)ethoxy)-3-ethylphenyl)-8-oxo-6-thioxo-5,7-diazaspiro[3.4]octan-7-yl)-3-(trifluoromethyl)picolinonitrile hydrochloride (0.300 g, 0.481 mmol, 1 eq) in DMF (5 mL) was added DIEA (0.311 g, 2.41 mmol, 5 eq) and 2-chloro-N-(3-((2,6-dioxopiperidin-3-yl)amino)phenyl)acetamide (0.157 g, 0.529 mmol, 1.1 eq). The mixture was stirred at 50° C. for 12 h, then purified by standard methods to afford 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperazin-1-yl)-N-(3-((2,6-dioxopiperidin-3-yl)amino)phenyl)acetamide hydrochloride (0.120 g, 0.134 mmol, 27.8% yield). MS (ESI) m/z 846.3 [M+1]⁺; ¹H NMR (400 MHz, DMSO-d₆) δ ppm 10.81 (s, 1H), 10.27 (s, 1H), 9.22 (d, J=1.60 Hz, 1H), 8.77 (s, 1H), 7.26-7.19 (m, 3H), 7.05-7.01 (m, 2H), 6.87 (d, J=8.40 Hz, 1H), 6.47 (d, J=8.40 Hz, 1H), 4.49 (s, 2H), 4.28 (dd, J=11.6 Hz, 4.8 Hz, 1H), 2.70-2.61 (m, 6H), 2.50-2.49 (m, 10H), 2.48-2.46 (m, 2H), 2.11-2.08 (m, 1H), 1.96-1.88 (m, 2H), 1.53-1.39 (m, 7H), 1.20 (t, J=7.60 Hz, 3H).

Example 34: 2-((2R,6S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-((2,6-dioxopiperidin-3-yl)amino)phenyl)acetamide hydrochloride

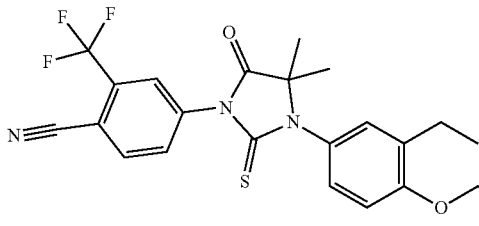
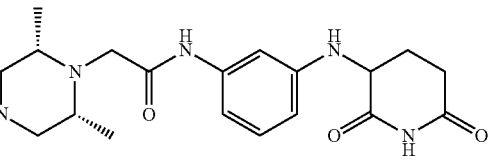

(2R,6S)-tert-Butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazine-1-carboxylate. A mixture of cesium carbonate (0.395 g, 1.211 mmol), 4-(3-(3-ethyl-4-hydroxyphenyl)-4,4-dimethyl-5-oxo-2-thioxoimidazolidin-1-yl)-2-(trifluoromethyl)benzonitrile (0.350 g, 0.807 mmol) (prepared as described herein), and (2R,6S)-tert-butyl 4-(2-bromoethyl)-2,6-dimethylpiperazine-1-carboxylate (0.311 g, 0.969 mmol) in DMF (4.04 mL) was stirred at 60° C. for 12 h. The reaction was diluted with EtOAc (75 mL) and the organic layer was washed with a saturated aqueous solution of sodium bicarbonate (2×100 mL) and brine (100 mL). The organic layer was dried over magnesium sulfate and concentrated to provide a brown oil which was purified by column chromatography (20-40% EtOAc in hexanes) to give (2R,6S)-tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazine-1-carboxylate (0.366, 0.543 mmol, 67.3% yield). MS (ESI) m/z 674.2 [M+1]⁺; ¹H NMR (400 MHz, CDCl₃) δ ppm 8.00-7.94 (m, 2H), 7.89-7.78 (m, 1H), 7.12-7.04 (m, 2H), 6.95 (d, J=8.6 Hz, 1H), 4.17-4.08 (m, 4H), 2.82 (t, J=5.6 Hz, 2H), 2.76-2.64 (m, 4H), 2.32 (dd, J=4.5, 11.3 Hz, 2H), 1.58 (s, 6H), 1.47 (s, 9H), 1.29 (d, J=6.7 Hz, 6H), 1.23 (t, J=7.5 Hz, 3H).

4-(3-(4-(2-((3R,5S)-3,5-Dimethylpiperazin-1-yl)ethoxy)-3-ethylphenyl)-4,4-dimethyl-5-oxo-2-thioxoimidazolidin-1-yl)-2-(trifluoromethyl)benzonitrile. A solution of (2R,6S)-tert-butyl 4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazine-1-carboxylate (0.366 g, 0.543 mmol) in DCM (2.72 mL) was treated with TFA (1.255 mL, 16.30 mmol). The reaction solution was stirred at room temperature overnight, then diluted with EtOAc (75 mL) and the organic layer was washed with a saturated aqueous solution of sodium bicarbonate (2×100 mL) and brine (100 mL). The organic layer was dried over magnesium sulfate and concentrated to provide 4-(3-(4-(2-((3R,5S)-3,5-dimethylpiperazin-1-yl)ethoxy)-3-ethylphenyl)-4,4-dimethyl-5-oxo-2-thioxoimidazolidin-1-yl)-2-(trifluoromethyl)benzonitrile as a glassy solid that was carried forward without further purification. MS (ESI) m/z 574.2 [M+1]⁺.

2-((2R,6S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-((2,6-dioxopiperidin-3-yl)amino)phenyl)acetamide hydrochloride. A mixture of 4-(3-(4-(2-((3R,5S)-3,5-dimethylpiperazin-1-yl)ethoxy)-3-ethylphenyl)-4,4-dimethyl-5-oxo-2-thioxoimidazolidin-1-yl)-2-(trifluoromethyl)benzonitrile (0.100 g, 0.174 mmol) and 2-chloro-N-(3-((2,6-dioxopiperidin-3-yl)amino)phenyl)acetamide (0.052 g, 0.174 mmol) in DMF (0.349 mL) was treated with DIEA (0.122 mL, 0.697 mmol). The reaction solution was stirred at 45° C. After 16 h, 30% conversion was observed. Sodium iodide (0.013 g, 0.087 mmol) was added and the temperature was increased to 60° C. After 36 h, the reaction solution was diluted with DMSO to a total volume of 2 mL, filtered, and purified by standard methods to give 2-((2R,6S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-((2,6-dioxopiperidin-3-yl)amino)phenyl)acetamide hydrochloride (0.012 g, 0.014 mmol, 8.0%). MS (ESI) m/z 833.0 [M+1]$^+$; $^1$H NMR (400 MHz, DMSO-d$_6$) δ ppm 10.79 (s, 1H), 8.40 (d, J=8.3 Hz, 1H), 8.30 (d, J=2.0 Hz, 1H), 8.11-8.02 (m, 1H), 7.26-7.12 (m, 3H), 7.07-6.96 (m, 2H), 6.84-6.78 (m, 1H), 6.47-6.40 (m, 1H), 4.49-4.38 (m, 2H), 4.30-4.24 (m, 1H), 3.54-3.49 (m, 9H), 2.73-2.62 (m, 3H), 2.13-2.05 (m, 1H), 1.97-1.85 (m, 1H), 1.50 (s, 6H), 1.24-1.10 (m, 9H).

Example 35: N-(3-Chloro-5-(2,6-dioxopiperidin-3-ylamino)phenyl)-2-((R)-4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazin-1-yl)acetamide hydrochloride ethoxy)-5-nitrobenzaldehyde (9.00 g, 32.84 mmol, 1 eq), tert-butyl (R)-tert-butyl 2-methylpiperazine-1-carboxylate (7.89 g, 39.41 mmol, 1.20 eq) and sodium bicarbonate (8.28 g, 98.52 mmol, 3 eq) in acetonitrile (45 mL) was stirred at 85° C. for 12 h. The reaction mixture was filtered, and the filtrate was concentrated under reduced pressure. The residue was purified by silica gel column chromatography (10-20% EtOAc in petroleum ether). Impure fractions were purified by preparative reverse phase HPLC (15-45% acetonitrile in water+0.225% formic acid, over 25 min). The pure fraction was concentrated under reduced pressure to remove most of the acetonitrile, and the pH was adjusted to pH=8 with saturate aqueous sodium bicarbonate, and extracted with EtOAc (50 mL×3). The combined organic phases were dried over sodium sulfate, filtered, and concentrated under reduced pressure. (R)-tert-Butyl 4-(2-(2-formyl-4-nitrophenoxy)ethyl)-2-methylpiperazine-1-carboxylate (2.10 g, 5.34 mmol, 16.3% yield) was obtained as a light yellow oil following purification by silica gel column chromatography followed by reverse phase preparative HPLC and was obtained as a light yellow oil. MS (ESI) m/z 394.2 [M+1]$^+$; $^1$H NMR (400 MHz, CDCl$_3$) δ ppm 10.46 (s, 1H), 8.71 (d, J=2.8 Hz, 1H), 8.43 (dd, J=2.9, 9.2 Hz, 1H), 7.14 (d, J=9.3 Hz, 1H), 4.34 (t, J=5.6 Hz, 2H), 4.23 (br s, 1H), 3.83 (br d, J=13.2 Hz, 1H), 3.08 (dt, J=3.3, 12.8 Hz, 1H), 2.96-2.79 (m, 3H), 2.68 (br d, J=11.0 Hz, 1H), 2.37 (dd, J=3.9, 11.1 Hz, 1H), 2.17 (dt, J=3.5, 11.6 Hz, 1H), 1.46 (s, 9H), 1.21 (d, J=6.8 Hz, 3H).

(R)-tert-Butyl 4-(2-(2-(2,2-difluorovinyl)-4-nitrophenoxy)ethyl)-2-methylpiperazine-1-carboxylate. A mixture of (R)-tert-butyl 4-(2-(2-formyl-4-nitrophenoxy)ethyl)-2-methylpiperazine-1-carboxylate (11.00 g, 27.96 mmol, 1.00 eq), sodium 2-chloro-2,2-difluoroacetate (6.39 g, 41.94 mmol, 1.50 eq) and PPh$_3$ (11.00 g, 41.94 mmol, 1.50 eq) in

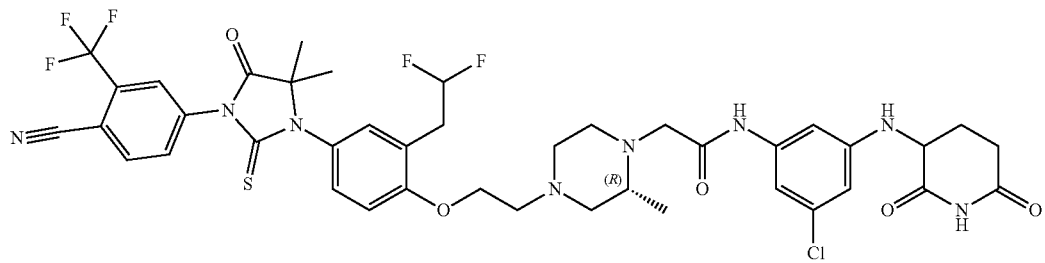

DMF (50 mL) was stirred at 120° C. for 6 h. The reaction mixture was diluted with EtOAc (200 mL) and washed with water (500 mL×4). The organic phase was dried over anhydrous sodium sulfate, filtered, and concentrated under reduce pressure. The residue was purified by silica gel column chromatography followed by preparative reverse phase HPLC (20-50% acetonitrile in water+0.1% TFA, over 33 min). The selected fraction was concentrated under reduced pressure, and the pH adjusted to 8 with sodium bicarbonate (aqueous, saturated) and extracted by EtOAc (100 mL×5). The combined organic phase was dried over anhydrous sodium sulfate, filtered, and concentrated under reduced pressure. (R)-tert-Butyl 4-(2-(2-(2,2-difluorovinyl)-4-nitrophenoxy)ethyl)-2-methylpiperazine-1-carboxylate (7.62 g, 17.65 mmol, 63.1% yield) was obtained as a yellow semi-solid material. MS (ESI) m/z 428.2 [M+1]$^+$; $^1$H NMR (400 MHz, CDCl$_3$) δ ppm 8.37 (d, J=2.7 Hz, 1H), 8.13 (dd, 2-(2-Bromoethoxy)-5-nitrobenzaldehyde. A mixture of 2-hydroxy-5-nitrobenzaldehyde (10.00 g, 59.84 mmol, 1.00 eq), 1,2-dibromoethane (112.41 g, 598.38 mmol, 45.15 mL, 10 eq), potassium carbonate (24.81 g, 179.51 mmol, 3 eq) and 18-crown-6 (1.580 g, 5.980 mmol, 0.10 eq) in acetonitrile (100 mL) was heated to reflux 85° C. for 5 h. The reaction mixture was cooled to room temperature and filtered. The filtrate was concentrated under reduced pressure to give an oily residue, which was washed by petroleum ether (300 mL×2). The crude product was purified by silica gel column chromatography (0-15% EtOAc in petroleum ether) to afford 2-(2-bromoethoxy)-5-nitrobenzaldehyde (10.32 g, 37.65 mmol, 62.9% yield) was obtained as a white solid. MS (ESI) m/z 558.1; $^1$H NMR (400 MHz, CDCl$_3$) δ ppm 10.52 (s, 1H), 8.73 (d, J=2.9 Hz, 1H), 8.44 (dd, J=2.9, 9.2 Hz, 1H), 7.11 (d, J=9.2 Hz, 1H), 4.56 (t, J=5.9 Hz, 2H), 3.77 (t, J=5.9 Hz, 2H).

(R)-tert-Butyl 4-(2-(2-formyl-4-nitrophenoxy)ethyl)-2-methylpiperazine-1-carboxylate. A mixture of 2-(2-bromo- J=2.7, 9.0 Hz, 1H), 6.95 (d, J=9.0 Hz, 1H), 5.76-5.53 (m, 1H), 4.21 (t, J=5.7 Hz, 3H), 3.83 (br d, J=13.2 Hz, 1H), 3.09 (dt, J=3.3, 12.7 Hz, 1H), 2.91-2.75 (m, 3H), 2.67 (br d, J=11.1 Hz, 1H), 2.35 (dd, J=3.9, 11.1 Hz, 1H), 2.15 (dt, J=3.4, 11.6 Hz, 1H), 1.46 (s, 9H), 1.22 (d, J=6.8 Hz, 3H).

(R)-tert-Butyl 4-(2-(4-amino-2-(2,2-difluoroethyl)phenoxy)ethyl)-2-methylpiperazine-1-carboxylate. To a solution of (R)-tert-butyl 4-(2-(2-(2,2-difluorovinyl)-4-nitrophenoxy)ethyl)-2-methylpiperazine-1-carboxylate (6.00 g, 14.04 mmol, 1.00 eq) in MeOH (60 mL) and TFA (1 mL) was added Pd/C (0.60 g, 10% purity) under nitrogen. The suspension was degassed under vacuum and purged with hydrogen several times. The mixture was stirred under hydrogen (50 psi) at 25° C. for 12 h. The mixture was filtered and the filtrate was concentrated under reduced pressure to afford (R)-tert-butyl 4-(2-(4-amino-2-(2,2-difluoroethyl)phenoxy)ethyl)-2-methylpiperazine-1-carboxylate (8.40 g, crude, trifluoroacetate) obtained as a light yellow solid. MS (ESI) m/z 400.2 [M+1]$^+$; $^1$H NMR (400 MHz, DMSO-d$_6$) δ ppm 7.01-6.83 (m, 3H), 4.34-4.15 (m, 3H), 3.89 (br d, J=14.3 Hz, 1H), 3.27-3.05 (m, 8H), 2.57 (q, J=7.6 Hz, 1H), 1.41 (s, 9H), 1.23-1.18 (m, 3H).

(R)-tert-Butyl 4-(2-(2-(2,2-difluoroethyl)-4-((1-ethoxy-2-methyl-1-oxopropan-2-yl)amino)phenoxy)ethyl)-2-methylpiperazine-1-carboxylate. To a mixture of (R)-tert-butyl 4-(2-(4-amino-2-(2,2-difluoroethyl)phenoxy)ethyl)-2-methylpiperazine-1-carboxylate (8.00 g, 20.03 mmol, 1 eq) and ethyl 2-bromo-2-methylpropanoate (7.81 g, 40.05 mmol, 5.87 mL, 2 eq) was added DIEA (30 mL) in one portion under nitrogen. The mixture was stirred at 127° C. for 12 h. The reaction mixture was diluted with water (600 mL) and extracted with EtOAc (200 mL×3). The combined organic extracts were washed with brine (200 mL×2), dried over anhydrous sodium sulfate, filtered and concentrated under reduced pressure to give a residue. The residue was purified by silica gel column chromatography (0-25% EtOAc in petroleum ether). Compound (R)-tert-butyl 4-(2-(2-(2,2-difluoroethyl)-4-((1-ethoxy-2-methyl-1-oxopropan-2-yl)amino)phenoxy)ethyl)-2-methylpiperazine-1-carboxylate (4.60 g, 6.78 mmol, 33.8% yield) was obtained as a light yellow oil. MS (ESI) m/z 514.3 [M+1]$^+$.

(R)-tert-Butyl 4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazine-1-carboxylate. To a solution of (R)-tert-butyl 4-(2-(2-(2,2-difluoroethyl)-4-((1-ethoxy-2-methyl-1-oxopropan-2-yl)amino)phenoxy)ethyl)-2-methylpiperazine-1-carboxylate (4.50 g, 8.76 mmol, 1 eq) and 4-isothiocyanato-2-(trifluoromethyl)benzonitrile (2.20 g, 9.64 mmol, 1.1 eq) in EtOAc (10 mL) was added TEA (7.27 g, 71.85 mmol, 10 mL, 8.2 eq) in one portion under nitrogen. The mixture was stirred at 80° C. for 12 h. The reaction mixture was diluted with water (150 mL) and extracted with EtOAc (50 mL×3). The combined organic extracts were washed with brine (50 mL×2), dried over anhydrous sodium sulfate, filtered, and concentrated under reduced pressure to give a residue. The residue was purified by silica gel column chromatography (10-30% EtOAc in petroleum ether). Compound (R)-tert-butyl 4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazine-1-carboxylate (3.11 g, 4.42 mmol, 50.5% yield) was obtained as a light yellow solid. MS (ESI) m/z 696.3 [M+1]$^+$.

(R)-4-(3-(3-(2,2-Difluoroethyl)-4-(2-(3-methylpiperazin-1-yl)ethoxy)phenyl)-4,4-dimethyl-5-oxo-2-thioxoimidazolidin-1-yl)-2-(trifluoromethyl)benzonitrile. To a solution of (R)-tert-butyl 4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazine-1-carboxylate (0.10 g, 0.14 mmol, eq) in DCM (1 mL) was added a 4.0 M solution of HCl in dioxane (5 mL, 139.15 eq) in one portion. The mixture was stirred at 25° C. for 12 h, then was concentrated under reduced pressure at 60° C. The residue was purified by semi-preparative reverse phase HPLC (17-47% acetonitrile+0.225% formic acid in water, over 12 min). The collected fraction was concentrated to remove most of the acetonitrile, then treated with a 1.0 M aqueous solution of HCl. Following lyophilization, (R)-4-(3-(3-(2,2-difluoroethyl)-4-(2-(3-methylpiperazin-1-yl)ethoxy)phenyl)-4,4-dimethyl-5-oxo-2-thioxoimidazolidin-1-yl)-2-(trifluoromethyl)benzonitrile hydrochloride (0.084 g, 0.133 mmol, 92.8% yield) was isolated as a white solid. MS (ESI) m/z 596.2 [M+1]$^+$; $^1$H NMR (400 MHz, DMSO-d$_6$) δ ppm 9.94 (br s, 2H), 8.39 (d, J=8.3 Hz, 1H), 8.29 (d, J=1.5 Hz, 1H), 8.08 (dd, J=1.7, 8.3 Hz, 1H), 7.37-7.31 (m, 1H), 7.28 (d, J=2.4 Hz, 1H), 7.22 (d, J=8.8 Hz, 1H), 6.54-6.15 (m, 1H), 4.51 (br s, 2H), 3.94-3.58 (m, 6H), 3.34-3.22 (m, 4H), 1.49 (s, 6H), 1.32 (br d, J=6.4 Hz, 3H). N-(3-Chloro-5-(2,6-dioxopiperidin-3-ylamino)phenyl)-2-((R)-4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazin-1-yl)acetamide hydrochloride. To a solution of (R)-4-(3-(3-(2,2-difluoroethyl)-4-(2-(3-methylpiperazin-1-yl)ethoxy)phenyl)-4,4-dimethyl-5-oxo-2-thioxoimidazolidin-1-yl)-2-(trifluoromethyl)benzonitrile (0.150 g, 0.252 mmol, 1 eq) and 2-chloro-N-(3-chloro-5-((2,6-dioxopiperidin-3-yl)amino)phenyl)acetamide (0.089 g, 0.271 mmol, 1.07 eq) in DMF (3 mL) was added DIEA (0.098 g, 0.756 mmol, 0.131 mL, 3.00 eq) in one portion under nitrogen. The mixture was stirred at 50° C. for 12 h. The reaction mixture was diluted with water (80 mL) and extracted with DCM (40 mL×3). The combined organic extracts were washed with brine (50 mL), dried over anhydrous sodium sulfate, filtered and concentrated under reduced pressure. The residue was purified by standard methods to afford N-(3-Chloro-5-(2,6-dioxopiperidin-3-ylamino)phenyl)-2-((R)-4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazin-1-yl)acetamide hydrochloride (0.092 g, 0.098 mmol, 38.8% yield). MS (ESI) m/z 889.0 [M+1]$^+$; H NMR (400 MHz, DMSO-d$_6$) δ ppm 10.79 (s, 1H), 10.74-10.51 (m, 1H), 8.38 (d, J=8.3 Hz, 1H), 8.29 (s, 1H), 8.07 (dd, J=1.5, 8.3 Hz, 1H), 7.36-7.13 (m, 3H), 6.99 (s, 1H), 6.89 (s, 1H), 6.54-6.49 (m, 1H), 6.48-6.17 (m, 1H), 4.53 (br s, 2H), 4.33 (br dd, J=4.9, 11.6 Hz, 1H), 4.19 (br s, 2H), 3.91 (br s, 5H), 3.39-3.23 (m, 5H), 3.16 (s, 1H), 2.80-2.69 (m, 1H), 2.63-2.54 (m, 1H), 2.12-2.03 (m, 1H), 1.91 (dq, J=4.5, 12.3 Hz, 1H), 1.49 (s, 6H), 1.32 (br d, J=5.0 Hz, 3H).

Example 36: 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-cyano-5-((2,6-dioxopiperidin-3-yl)amino)phenyl)acetamide trifluoroacetate

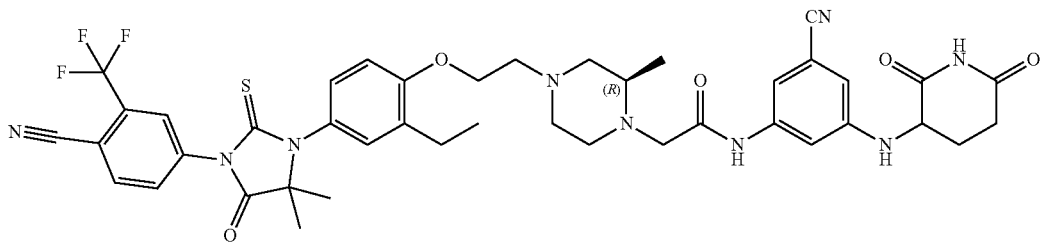

2-((3H-[1,2,3]Triazolo[4,5-b]pyridin-3-yl)oxy)-N-(3-cyano-5-((2,6-dioxopiperidin-3-yl)amino)phenyl)acetamide. 3-Amino-5-((2,6-dioxopiperidin-3-yl)amino)benzonitrile (0.290 g, 1.19 mmol), 2-chloroacetic acid (0.112 g, 1.19 mmol) (prepared as described herein), HATU (0.587 g, 1.54 mmol), and DIEA (0.622 mL, 3.56 mmol) were combined in DMF (3 mL) and stirred at room temperature. After 45 min, the solution was concentrated under reduced pressure to afford a dark oil. The oil was purified by silica gel column chromatography (0-90% EtOAc in hexanes). The resulting material was dissolved in 80% EtOAc in hexanes and the solution was washed with water and then dried over magnesium sulfate, filtered, and concentrated under reduced pressure to afford the title compound as a yellow solid (0.250 g, 0.56 mmol, 50.0% yield). MS (ESI) m/z 421 [M+1]+.

2-((R)-4-(2-((6-(3-(4-Cyano-3-(trifluoromethyl)phenyl)-5,5-dimethyl-4-oxo-2-thioxoimidazolidin-1-yl)-4-ethylpyridin-3-yl)oxy)ethyl)-2-methylpiperazin-1-yl)-N-(3-cyano-5-((2,6-dioxopiperidin-3-yl)amino)phenyl)acetamide trifluoroacetate. (R)-5-(3-(3-Ethyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile dihydrochloride (0.121 g, 0.190 mmol), 2-((3H-[1,2,3]triazolo[4,5-b]pyridin-3-yl)oxy)-N-(3-cyano-5-((2,6-dioxopiperidin-3-yl)amino)phenyl)acetamide (0.08 g, 0.190 mmol), sodium iodide (0.029 g, 0.190 mmol) and DIEA (0.133 mL, 0.761 mmol) were combined in DMF (0.5 mL) and the mixture was stirred at 80° C. in a screw cap vial. After 16 h, the solution was diluted with DMSO (1 mL) and purified by standard methods to afford the title compound (0.008 g, 0.009 mmol, 5.0% yield). MS (ESI) m/z 845 [M+1]+; 1H NMR (400 MHz, DMSO-$d_6$) δ ppm 10.82 (s, 1H), 9.58-10.06 (m, 1H), 9.23-9.26 (m, 1H), 8.81-8.84 (m, 1H), 7.24 (br s, 2H), 7.09-7.20 (m, 3H), 6.78 (br s, 1H), 6.53 (s, 2H), 4.39 (br s, 2H), 2.57-2.78 (m, 6H), 2.02-2.14 (m, 1H), 1.92 (qd, J=12.19, 4.16 Hz, 1H), 1.51 (s, 7H), 1.24 (br s, 1H), 1.17 (br t, J=7.46 Hz, 4H), 0.95-1.10 (m, 3H).

Example 37: 2-((R)-4-(2-(4-(3-(6-Cyano-5-(trifluoromethyl)pyridin-3-yl)-5,5-dimethyl-4-oxo-2-thioxoimidazolidin-1-yl)-2-isopropylphenoxy)ethyl)-2-methylpiperazin-1-yl)-N-(3-((2,6-dioxopiperidin-3-yl)amino)phenyl)acetamide hydrochloride

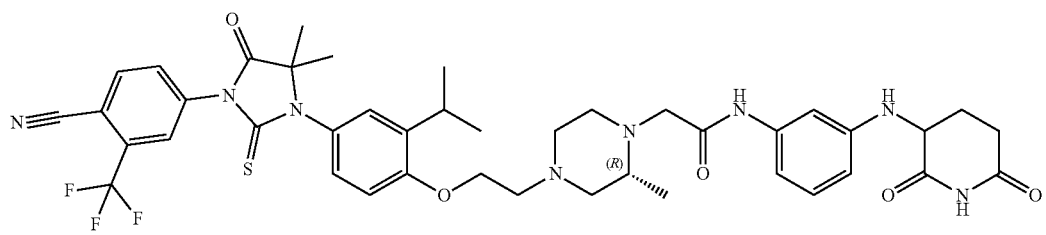

(R)-tert-Butyl 2-methyl-4-(2-(4-nitro-2-(prop-1-en-2-yl)phenoxy)ethyl)piperazine-1-carboxylate. To a mixture of (R)-tert-butyl 4-(2-(2-bromo-4-nitrophenoxy)ethyl)-2-methylpiperazine-1-carboxylate (4.10 g, 9.23 mmol, 1 eq) (prepared as described herein), and 4,4,5,5-tetramethyl-2-(prop-1-en-2-yl)-1,3,2-dioxaborolane (0.98 g, 5.830 mmol, 0.63 eq) in dioxane (40 mL) and water (20 mL) was added [1,1'-bis(diphenylphosphino)ferrocene]dichloropalladium (II) (0.338 g, 0.46 mmol, 0.050 eq), and potassium phosphate (5.88 g, 27.69 mmol, 3 eq) in one portion at 25° C. under nitrogen. The mixture was heated to 90° C. and stirred for 12 h, then cooled to 25° C. and poured into ice-water (60 mL). The aqueous phase was extracted with EtOAc (80 mL×3). The combined organic phases were washed with brine (60 mL×2), dried with anhydrous sodium sulfate, filtered and concentrated under vacuum. The residue was purified by silica gel chromatography (9% EtOAc in petroleum ether) to afford (R)-tert-butyl 2-methyl-4-(2-(4-nitro-2-(prop-1-en-2-yl)phenoxy)ethyl)piperazine-1-carboxylate (1.69 g, 4.17 mmol, 45.2% yield) as yellow oil. $^1$H NMR (400 MHz, CDCl$_3$) δ ppm 8.16 (dd, J=8.8, 2.8 Hz, 1H), 8.11 (d, J=2.8 Hz, 1H), 6.92 (d, J=9.2 Hz, 1H), 5.23 (t, J=1.2 Hz, 1H), 5.17 (d, J=0.8 Hz, 1H), 4.19 (t, J=6.4 Hz, 3H), 3.81 (d, J=14.0 Hz, 1H), 3.11-3.04 (m, 1H), 2.84 (d, J=11.2 Hz, 1H), 2.79 (t, J=6.4 Hz, 2H), 2.69 (d, J=11.2 Hz, 1H), 2.32 (dd, J=11.2, 4.0 Hz, 1H), 2.14-2.12 (m, 4H), 1.47 (s, 9H), 1.21 (d, J=6.8 Hz, 3H).

(R)-tert-Butyl 4-(2-(4-amino-2-isopropylphenoxy)ethyl)-2-methylpiperazine-1-carboxylate. To a solution of (R)-tert-butyl 2-methyl-4-(2-(4-nitro-2-(prop-1-en-2-yl)phenoxy)ethyl)piperazine-1-carboxylate (1.69 g, 4.17 mmol, 1 eq) in MeOH (15 mL) was added palladium on activated carbon (0.15 g, 10% purity) under nitrogen. The suspension was degassed under vacuum and purged with hydrogen several times. The mixture was stirred under hydrogen (50 psi) at 30° C. for 12 h, filtered, and the filtrate was concentrated. The residue was poured into ice-water (50 mL). The aqueous phase was extracted with EtOAc (60 mL×2). The combined organic phases were washed with brine (40 mL), dried with anhydrous sodium sulfate, filtered, and concentrated under vacuum. The crude product was purified by silica gel column chromatography (0-60% EtOAc in petroleum ether). Compound (R)-tert-butyl 4-(2-(4-amino-2-isopropylphenoxy)ethyl)-2-methylpiperazine-1-carboxylate (1.33 g, 3.52 mmol, 84.5% yield) was isolated as brown oil. $^1$H NMR (400 MHz, CDCl$_3$) δ ppm 6.69 (d, J=8.4 Hz, 1H), 6.60 (d, J=2.4 Hz, 1H), 6.49 (dd, J=8.4, 2.8 Hz, 1H), 4.13 (q, J=7.2 Hz, 1H), 4.01 (t, J=4.8 Hz, 2H), 3.81 (d, J=12.8 Hz, 1H), 3.29-3.26 (m, 1H), 3.10 (m, 1H), 2.86 (d, J=11.6 Hz, 1H), 2.76-2.71 (m, 3H), 2.30 (dd, J=11.2, 4.0 Hz, 1H), 2.11 (m, 1H), 1.47 (s, 9H), 1.24 (d, J=6.8 Hz, 3H), 1.19 (d, J=6.8 Hz, 6H)

(R)-tert-Butyl 4-(2-(4-((2-cyanopropan-2-yl)amino)-2-isopropylphenoxy)ethyl)-2-methylpiperazine-1-carboxylate. To a mixture of (R)-tert-butyl 4-(2-(4-amino-2-isopropylphenoxy)ethyl)-2-methylpiperazine-1-carboxylate (1.33 g, 3.52 mmol, 1 eq) in 2-hydroxy-2-methylpropanenitrile (3.26 g, 38.33 mmol, 10.88 eq) was added magnesium sulfate (1.06 g, 8.81 mmol, 2.5 eq) in one portion at 20° C. under nitrogen. The mixture was heated to 60° C. and stirred for 2 h, cooled to 25° C., then poured into ice-water (60 mL). The aqueous phase was extracted with EtOAc (80 mL×2). The combined organic extracts were washed with brine (50 mL), dried with anhydrous sodium sulfate, filtered, and concentrated under vacuum, to afford (R)-tert-butyl 4-(2-(4-((2-cyanopropan-2-yl)amino)-2-isopropylphenoxy)ethyl)-2-methylpiperazine-1-carboxylate (2.70 g, crude) as brown oil. MS (ESI) m/z 445.3 [M+1]$^+$.

(R)-4-(3-(3-Isopropyl-4-(2-(3-methylpiperazin-1-yl)ethoxy)phenyl)-4,4-dimethyl-5-oxo-2-thioxoimidazolidin-1-yl)-2-(trifluoromethyl)benzonitrile. A mixture of (R)-tert-butyl 4-(2-(4-((2-cyanopropan-2-yl)amino)-2-isopropylphenoxy)ethyl)-2-methylpiperazine-1-carboxylate (1.30 g, 2.34 mmol, 1 eq) and 4-isothiocyanato-2-(trifluoromethyl)benzonitrile (0.534 g, 2.34 mmol, 1 eq) in DMF (10 mL) in was stirred at 25° C. for 1 h, then treated with a 4.0 M solution of HCl in MeOH (2.92 mL, 5 eq) and heated to 80° C. for 17 h. The mixture was cooled to 25° C., and poured into ice-water (40 mL). The aqueous phase was extracted with EtOAc (50 mL×2). The combined organic extracts were washed with brine (40 mL), dried with anhydrous sodium sulfate, filtered, and concentrated under vacuum. The residue was purified by semi-preparative reverse phase HPLC (25-55% acetonitrile in water+0.05% HCl, 25 min), to afford (R)-4-(3-(3-isopropyl-4-(2-(3-methylpiperazin-1-yl)ethoxy)phenyl)-4,4-dimethyl-5-oxo-2-thioxoimidazolidin-1-yl)-2-(trifluoromethyl)benzonitrile hydrochloride (0.486 g, 0.797 mmol, 34.0% yield) as yellow foam. $^1$H NMR (400 MHz, CDCl$_3$) δ ppm 7.95-8.01 (m, 2H) 7.87-7.84 (m, 1H), 7.08-7.06 (m, 2H), 6.94 (d, J=8.0 Hz, 1H), 4.19-4.10 (m, 3H), 3.39-3.32 (m, 1H), 3.04-2.97 (m, 2H), 2.92-2.82 (m, 4H), 2.25-2.22 (m, 1H), 1.92 (t, J=10.4 Hz, 1H), 1.58 (s, 6H), 1.24 (d, J=6.8 Hz, 6H), 1.08 (d, J=6.4 Hz, 3H).

2-((R)-4-(2-(4-(3-(4-Cyano-3-(trifluoromethyl)phenyl)-5,5-dimethyl-4-oxo-2-thioxoimidazolidin-1-yl)-2-isopropylphenoxy)ethyl)-2-methylpiperazin-1-yl)-N-(3-((2,6-dioxopiperidin-3-yl)amino)phenyl)acetamide hydrochloride. To a mixture of (R)-4-(3-(3-isopropyl-4-(2-(3-methylpiperazin-1-yl)ethoxy)phenyl)-4,4-dimethyl-5-oxo-2-thioxoimidazolidin-1-yl)-2-(trifluoromethyl)benzonitrile hydrochloride (0.300 g, 0.491 mmol) and 2-chloro-N-(3-((2,6-dioxopiperidin-3-yl)amino)phenyl)acetamide hydrochloride (0.195 g, 0.586 mmol, 1.19 eq) in DMF (1.5 mL) was added DIEA (0.170 g, 1.310 mmol, 2.7 eq) in one portion at 25° C. under nitrogen. The mixture was heated to 60° C. for 12 h, then concentrated to dryness. The residue was purified by standard methods to afford 2-((R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2-methylpiperazin-1-yl)-N-(3-((2,6-dioxopiperidin-3-yl)amino)phenyl)acetamide hydrochloride (0.174 g, 0.198 mmol, 40.3% yield). MS (ESI) m/z 833.4 [M+1]$^+$; $^1$H NMR (400 MHz, DMSO-d$_6$) δ ppm 10.80 (s, 1H), 10.51-10.26 (m, 1H), 8.39 (d, J=8.0 Hz, 1H), 8.29 (d, J=1.6 Hz, 1H), 8.07 (dd, J=8.4, 1.6 Hz, 1H), 7.21-7.14 (m, 3H), 7.06-6.98 (m, 2H), 6.85 (d, J=7.6 Hz, 1H), 6.46 (d, J=8.0 Hz, 1H), 4.50 (br, 2H), 4.28-4.19 (m, 2H), 4.02-3.83 (m, 5H), 3.38-3.29 (m, 6H), 2.79-2.69 (m, 1H), 2.62-2.56 (m, 1H), 2.11-2.07 (m, 1H), 1.98-1.85 (m, 1H), 1.49 (s, 6H), 1.32 (br, 3H), 1.18 (d, J=6.8 Hz, 6H).

Example 38: 2-((R)-4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)-2-methylpiperazin-1-yl)-N-(3-((2,6-dioxopiperidin-3-yl)amino)phenyl)acetamide hydrochloride

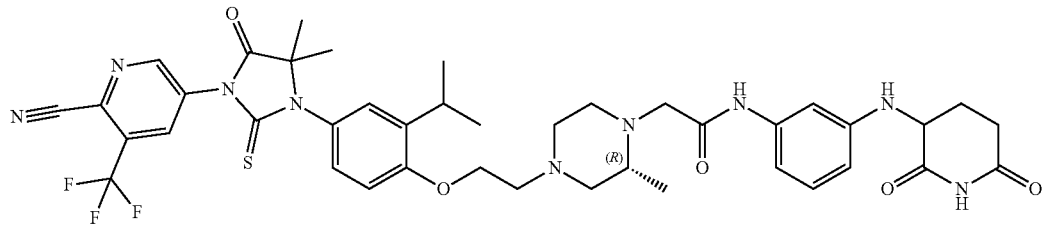

(R)-5-(3-(3-Isopropyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile. To a mixture of (R)-tert-butyl 4-(2-(4-((2-cyanopropan-2-yl)amino)-2-isopropylphenoxy)ethyl)-2-methylpiperazine-1-carboxylate (0.780 g, 1.40 mmol, 1 eq) and 5-isothiocyanato-3-(trifluoromethyl)picolinonitrile (0.322 g, 1.40 mmol, 1 eq) (prepared as described herein) in DMF (3 mL) was added a 4.0 M solution of HCl in MeOH (4 M, 1.75 mL, 5 eq). The mixture was stirred at 25° C. for 1 h, then heated to 80° C. for 12 h. The mixture was cooled to 30° C. and concentrated under reduced pressure at 50° C. The residue was purified by semi-preparative reverse phase HPLC (25-55% acetonitrile in water+0.05% HCl, 40 min) to afford (R)-5-(3-(3-isopropyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile hydrochloride (0.330 g, 0.540 mmol, 38.48% yield) as light yellow solid. MS (ESI) m/z 575.3[M+1]$^+$; $^1$H NMR (400 MHz, DMSO-d$_6$) δ ppm 10.04-9.56 (m, 2H), 9.25 (d, J=2 Hz, 1H), 8.82 (d, J=2 Hz, 1H), 7.21-7.14 (m, 3H), 4.47 (br, 2H), 3.75-3.49 (m, 10H), 1.51 (s, 6H), 1.30 (br, J=5.2 Hz, 3H), 1.19 (dd, J=6.8, 1.6 Hz, 6H).

2-((R)-4-(2-(4-(3-(6-Cyano-5-(trifluoromethyl)pyridin-3-yl)-5,5-dimethyl-4-oxo-2-thioxoimidazolidin-1-yl)-2-isopropylphenoxy)ethyl)-2-methylpiperazin-1-yl)-N-(3-((2,6-dioxopiperidin-3-yl)amino)phenyl)acetamide hydrochloride. To a mixture of (R)-5-(3-(3-isopropyl-4-(2-(3-methylpiperazin-1-yl)ethoxy)phenyl)-4,4-dimethyl-5-oxo-2-thioxoimidazolidin-1-yl)-3-(trifluoromethyl)picolinonitrile hydrochloride (0.150 g, 0.245 mmol, 1 eq) and 2-chloro-N-(3-((2,6-dioxopiperidin-3-yl)amino)phenyl)acetamide (0.091 mg, 0.275 mmol, 1.12 eq) in DMF (1 mL) was added DIEA (0.952 mg, 0.736 mmol, 3.00 eq) and the mixture was heated to 60° C. for 12 h and concentrated to dryness. The residue was purified by standard methods to afford 2-((R)-4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)-2-methylpiperazin-1-yl)-N-(3-((2,6-dioxopiperidin-3-yl)amino)phenyl)acetamide hydrochloride (0.131 mg, 0.148 mmol, 60.3% yield). MS (ESI) m/z 834.3 [M+1]$^+$; $^1$H NMR (400 MHz, DMSO-d$_6$) δ ppm 9.21 (d, J=2.0 Hz, 1H), 8.78 (d, J=2.0 Hz, 1H), 7.20-7.12 (m, 3H), 7.06-7.02 (m, 1H), 6.92 (m, 1H), 6.82 (d, J=7.60 Hz, 1H), 6.44 (dd, J=8.0, 2.0 Hz, 1H), 4.41 (br, 2H), 4.24 (dd, J=11.2, 4.8 Hz, 1H), 4.01-3.97 (m, 1H), 3.74-3.23 (m, 11H), 2.76-2.67 (m, 1H), 2.61-2.57 (m, 1H), 2.10-2.05 (m, 1H), 1.94-1.85 (m, 1H), 1.47 (s, 6H), 1.23 (d, J=6.4 Hz, 3H), 1.16 (d, J=6.8 Hz, 6H).

Example 39: 2-((R)-4-(2-(4-(3-(4-Cyano-3-(trifluoromethyl)phenyl)-5,5-dimethyl-4-oxo-2-thioxoimidazolidin-1-yl)-2-(2-fluoroethyl)phenoxy)ethyl)-2-methylpiperazin-1-yl)-N-(3-((2,6-dioxopiperidin-3-yl)amino)phenyl)acetamide hydrochloride

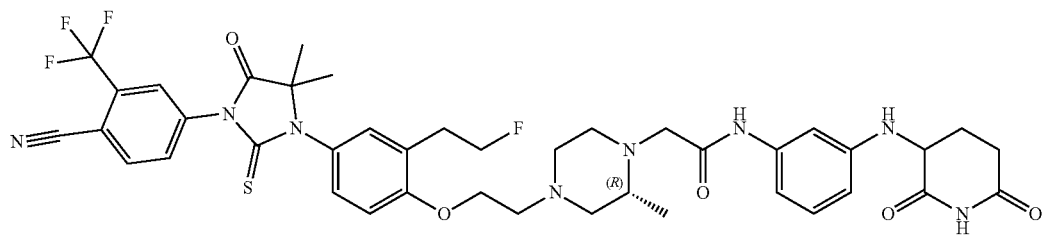

4-(3-(3-(2-fluoroethyl)-4-hydroxyphenyl)-4,4-dimethyl-5-oxo-2-thioxoimidazolidin-1-yl)-2-(trifluoromethyl)benzonitrile. To a solution of 2-((3-(2-fluoroethyl)-4-hydroxyphenyl)amino)-2-methylpropanenitrile (1.50 g, 6.75 mmol, 1 eq) (prepared as described herein), in DMF (15 mL) was added 4-isothiocyanato-2-(trifluoromethyl)benzonitrile (1.08 g, 4.72 mmol, 0.7 eq). The mixture was stirred at 20° C. for 1 h, then treated with a 4.0 M solution of HCl in MeOH (8.44 mL, 5 eq) and stirred at 70° C. for 12 h under nitrogen atmosphere. The reaction mixture was concentrated under reduced pressure. The residue was suspended in water (50 mL) and extracted with EtOAc (30 mL×5). The combined organic extracts were washed with brine (20 mL×3), dried over anhydrous sodium sulfate, filtered, and concentrated under reduced pressure. The residue was purified by silica gel column chromatography (5-20% EtOAc in petroleum ether) to afford 4-(3-(3-(2-fluoroethyl)-4-hydroxyphenyl)-4,4-dimethyl-5-oxo-2-thioxoimidazolidin-1-yl)-2-(trifluoromethyl)benzonitrile (1.47 g, 3.26 mmol, 48.2% yield) obtained as a yellow gum. MS (ESI) m/z 452.1 [M+1]$^+$; $^1$H NMR (400 MHz, CH$_3$OD) δ ppm 8.16-8.12 (m, 2H), 7.98 (br d, J=2.0 Hz, 1H), 7.14 (d, J=2.6 Hz, 1H), 7.07 (dd, J=2.6, 8.4 Hz, 1H), 6.91 (d, J=8.4 Hz, 1H), 4.68 (t, J=6.5 Hz, 1H), 4.56 (t, J=6.5 Hz, 1H), 3.09-3.00 (m, 2H), 1.53 (s, 6H), 1.56-1.50 (m, 1H).

(R)-tert-Butyl 4-(2-hydroxyethyl)-2-methylpiperazine-1-carboxylate. A solution of tert-butyl (2R)-2-methylpiperazine-1-carboxylate (3.00 g, 14.98 mmol, 1 eq), 2-bromoethanol (2.25 g, 17.98 mmol, 1.28 mL, 1.2 eq) and potassium carbonate (4.14 g, 29.96 mmol, 2 eq) in acetonitrile (30 mL) was stirred at 90° C. for 12 h. The reaction mixture was filtered and concentrated under reduced pressure. The residue was purified by silica gel column chromatography (0-30% of EtOAc in petroleum ether). The organic layers were combined and concentrated under reduced pressure to afford tert-butyl (2R)-4-(2-hydroxyethyl)-2-methyl-piperazine-1-carboxylate (1.50 g, 6.14 mmol, 40.9% yield) as a yellow oil. $^1$H NMR (400 MHz, CDCl$_3$) δ ppm 4.21 (s, 1H), 3.81 (d, J=13.2 Hz, 1H), 3.59 (t, J=5.6 Hz, 2H), 3.06 (t, J=3.2, 12.8 Hz, 1H), 2.77 (dd, J=1.6, 11.2 Hz, 1H), 2.63 (d, J=11.2 Hz, 1H), 2.57-2.39 (m, 3H), 2.23 (dd, J=4.0, 11.2 Hz, 1H), 2.12-1.99 (m, 1H), 1.43 (s, 9H), 1.21 (d, J=6.8 Hz, 3H).

(R)-tert-Butyl 4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)-2-methylpiperazine-1-carboxylate. A mixture of 4-(3-(3-(2-fluoroethyl)-4-hydroxyphenyl)-4,4-dimethyl-5-oxo-2-thioxoimidazolidin-1-yl)-2-(trifluoromethyl)benzonitrile (0.200 g, 0.443 mmol, 1 eq), tert-butyl (2R)-4-(2-hydroxyethyl)-2-methyl-piperazine-1-carboxylate (0.140 g, 0.575 mmol, 1.3 eq) and PPh$_3$ (0.174 g, 0.664 mmol, 1.5 eq) in THF (2 mL) was cooled to 0° C. DIAD (0.134 g, 0.664 mmol, 0.129 mL, 1.5 eq) was added to the solution, and the solution was stirred at 50° C. for 10 h. The reaction mixture was diluted with water (100 mL), extracted with EtOAc (100 mL×3), the organic layers were combined and washed with brine (50 mL×3), dried, filtered, and concentrated under reduced pressure. The residue was purified by preparative TLC (50% EtOAc in petroleum ether) to afford (R)-tert-butyl 4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)-2-methylpiperazine-1-carboxylate (0.340 g, crude) as a brown oil. MS (ESI) m/z 678.1 [M+1]$^+$.

(R)-4-(3-(3-(2-Fluoroethyl)-4-(2-(3-methylpiperazin-1-yl)ethoxy)phenyl)-4,4-dimethyl-5-oxo-2-thioxoimidazolidin-1-yl)-2-(trifluoromethyl)benzonitrile. A solution of (R)-tert-butyl 4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)-2-methylpiperazine-1-carboxylate (0.300 g, 0.442 mmol, 1 eq) in a 4.0 M solution of HCl in dioxane (2.77 mL, 25 eq) was stirred at 25° C. for 2 h. The reaction mixture was concentrated under reduced pressure. The residue, (R)-4-(3-(3-(2-fluoroethyl)-4-(2-(3-methylpiperazin-1-yl)ethoxy)phenyl)-4,4-dimethyl-5-oxo-2-thioxoimidazolidin-1-yl)-2-(trifluoromethyl)benzonitrile (0.330 g, crude, hydrochloride acid), obtained as light yellow solid, was used directly to the next step. MS (ESI) m/z 578.1 [M+1]$^+$.

2-((R)-4-(2-(4-(3-(4-Cyano-3-(trifluoromethyl)phenyl)-5,5-dimethyl-4-oxo-2-thioxoimidazolidin-1-yl)-2-(2-fluoroethyl)phenoxy)ethyl)-2-methylpiperazin-1-yl)-N-(3-((2,6-dioxopiperidin-3-yl)amino)phenyl)acetamide hydrochloride. To a mixture of (R)-4-(3-(3-(2-fluoroethyl)-4-(2-(3-methylpiperazin-1-yl)ethoxy)phenyl)-4,4-dimethyl-5-oxo-2-thioxoimidazolidin-1-yl)-2-(trifluoromethyl)benzonitrile (0.200 g, 0.325 mmol, 1 eq, hydrochloride), 2-chloro-N-(3-((2,6-dioxopiperidin-3-yl)amino)phenyl)acetamide hydrochloride (0.075 g, 0.227 mmol, 0.7 eq) and DIEA (0.147 g, 1.140 mmol, 0.198 mL, 3.5 eq) in DMF (1 mL) was stirred at 50° C. for 10 h. The reaction mixture was filtered and the filtrate was purified by standard methods to afford 2-((R)-4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)-2-methylpiperazin-1-yl)-N-(3-((2,6-dioxopiperidin-3-yl)amino)phenyl)acetamide hydrochloride (0.070 g, 0.080 mmol, 24.7% yield). MS (ESI) m/z 837.3 [M+1]$^+$; $^1$H NMR (400 MHz, DMSO-d$_6$) δ ppm 10.78 (s, 1H), 10.35 (s, 1H), 8.37 (d, J=8.4 Hz, 1H), 8.28 (d, J=1.6 Hz, 1H), 8.06 (dd, J=1.6, 8.4 Hz, 1H), 7.29-7.23 (m, 1H), 7.23-7.20 (m, 1H), 7.20-7.14 (m, 1H), 7.06-6.99 (m, 1H), 6.97 (s, 1H), 6.84 (d, J=8.0 Hz, 1H), 6.44 (d, J=8.0 Hz, 1H), 4.71 (t, J=6.0 Hz, 1H), 4.59 (t, J=6.4 Hz, 1H), 4.49 (s, 2H), 4.25 (dd, J=4.8, 11.4 Hz, 1H), 4.17 (s, 6H), 3.35 (d, J=16.4 Hz, 6H), 3.14-2.98 (m, 2H), 2.77-2.67 (m, 1H), 2.62-2.53 (m, 1H), 2.42 (dd, J=2.0, 4.0 Hz, 1H), 2.08 (td, J=4.6, 8.8 Hz, 1H), 1.96-1.82 (m, 1H), 1.47 (s, 6H), 1.34-1.18 (m, 3H).

Example 40: 2-((R)-4-(2-(4-(3-(3-Chloro-4-cyano-phenyl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide hydrochloride

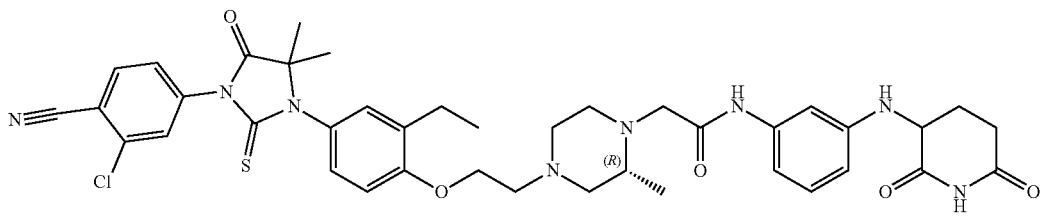

2-Chloro-4-isothiocyanatobenzonitrile. To a mixture of 4-amino-2-chlorobenzonitrile (0.50 g, 3.28 mmol, 1 eq) in water (5 mL) was added thiocarbonyl dichloride (0.754 g, 6.550 mmol, 0.502 mL, 2 eq). The mixture was stirred at 25° C. for 2 h, then was diluted with water (30 mL) and extracted with EtOAc (30 mL×3). The combined organic layers were washed with brine (40 mL), dried over anhydrous sodium sulfate, filtered, and concentrated under reduced pressure. The residue was purified by silica gel column chromatography (0-1% EtOAc in petroleum ether) to afford 2-chloro-4-isothiocyanatobenzonitrile (0.60 g, 3.08 mmol, 94.1% yield) as a white solid. MS (ESI) m/z 236.9 [M+1]$^+$; $^1$HNMR (400 MHz, DMSO-d$_6$) δ ppm 7.61-7.67 (m, 1H), 7.91-7.96 (m, 1H), 8.02-8.06 (m, 1H).

(R)-tert-Butyl 4-(2-(4-(3-(3-chloro-4-cyanophenyl)-5,5-dimethyl-4-oxo-2-thioxoimidazolidin-1-yl)-2-ethylphenoxy)ethyl)-2-methylpiperazine-1-carboxylate. To a mixture of (R)-tert-butyl 4-(2-(2-ethyl-4-((1-methoxy-2-methyl-1-oxopropan-2-yl)amino)phenoxy)ethyl)-2-methylpiperazine-1-carboxylate (0.450 g, 0.971 mmol, 1 eq) and 2-chloro-4-isothiocyanatobenzonitrile (0.378 g, 1.940 mmol, 2 eq) in EtOAc (3 mL) was added TEA (0.295 g, 2.910 mmol, 0.405 mL, 3 eq). The reaction mixture was stirred at 80° C. for 8 h, then was diluted with water (80 mL) and extracted with EtOAc (30 mL×3). The combined organic layers were washed with brine (40 mL), dried over anhydrous sodium sulfate, filtered, and concentrated under reduced pressure. The residue was purified by silica gel preparative TLC (33% EtOAc in petroleum ether) to afford (R)-tert-butyl 4-(2-(4-(3-(3-chloro-4-cyanophenyl)-5,5-dimethyl-4-oxo-2-thioxoimidazolidin-1-yl)-2-ethylphenoxy)ethyl)-2-methylpiperazine-1-carboxylate (0.600 g, 0.932 mmol, 96.0% yield) as a yellow oil. MS (ESI) m/z 626.3 [M+1]$^+$.

(R)-2-Chloro-4-(3-(3-ethyl-4-(2-(3-methylpiperazin-1-yl)ethoxy)phenyl)-4,4-dimethyl-5-oxo-2-thioxoimidazolidin-1-yl)benzonitrile hydrochloride. To a mixture of (R)-tert-butyl 4-(2-(4-(3-(3-chloro-4-cyanophenyl)-5,5-dimethyl-4-oxo-2-thioxoimidazolidin-1-yl)-2-ethylphenoxy)ethyl)-2-methylpiperazine-1-carboxylate (0.200 g, 0.319 mmol, 1 eq) in DCM (2 mL) was added a 4.0 M solution of HCl in dioxane (0.08 mL, 1 eq). The reaction mixture was stirred at 25° C. for 1.5 h, then was concentrated under reduced pressure to give (R)-2-chloro-4-(3-(3-ethyl-4-(2-(3-methylpiperazin-1-yl)ethoxy)phenyl)-4,4-dimethyl-5-oxo-2-thioxoimidazolidin-1-yl)benzonitrile hydrochloride (0.168 g, crude), was obtained as a yellow solid. MS (ESI) m/z 526.0 [M+1]$^+$.

2-((R)-4-(2-(4-(3-(3-Chloro-4-cyanophenyl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide hydrochloride. To a mixture of (R)-2-chloro-4-(3-(3-ethyl-4-(2-(3-methylpiperazin-1-yl)ethoxy)phenyl)-4,4-dimethyl-5-oxo-2-thioxoimidazolidin-1-yl)benzonitrile hydrochloride (0.168 g, 0.299 mmol, 1 eq) and 2-chloro-N-(3-((2,6-dioxopiperidin-3-yl)amino)phenyl)acetamide (0.106 g, 0.358 mmol, 1.2 eq) in DMF (1.5 mL) was added DIEA (0.116 g, 0.896 mmol, 0.156 mL, 3 eq). The mixture was stirred at 50° C. for 8 h, filtered, and the filtrate was purified by standard methods to afford 2-((R)-4-(2-(4-(3-(3-chloro-4-cyanophenyl)-5,5-dimethyl-4-oxo-2-thioxoimidazolidin-1-yl)-2-ethylphenoxy)ethyl)-2-methylpiperazin-1-yl)-N-(3-((2,6-dioxopiperidin-3-yl)amino)phenyl)acetamide hydrochloride (0.095 g, 0.115 mmol, 38.5% yield). MS (ESI) m/z 785.1 [M+1]$^+$; $^1$H NMR (400 MHz, DMSO-d$_6$) δ ppm 1.18 (t, J=7.46 Hz, 3H), 1.33 (br s, 3H), 1.49 (s, 6H), 1.86-1.96 (m, 1H), 2.07-2.14 (m, 1H), 2.53-2.65 (m, 2H), 2.65-2.71 (m, 2H), 2.71-2.81 (m, 1H), 3.74-3.82 (m, 4H), 3.86-4.07 (m, 4H), 4.27 (br dd, J=11.31, 4.83 Hz, 2H), 4.51 (br s, 2H), 6.47 (dd, J=8.25, 1.28 Hz, 1H), 6.87 (d, J=8.44 Hz, 1H), 6.97-7.09 (m, 2H), 7.12-7.23 (m, 3H), 7.72 (dd, J=8.31, 1.83 Hz, 1H), 8.03 (d, J=1.83 Hz, 1H), 8.18 (d, J=8.31 Hz, 1H), 10.21-10.57 (m, 1H), 10.80 (s, 1H).

Example 41: 2-((2S,6R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,6-dimethylpiperazin-1-yl)-N-(3-((2,6-dioxopiperidin-3-yl)amino)phenyl)acetamide hydrochloride

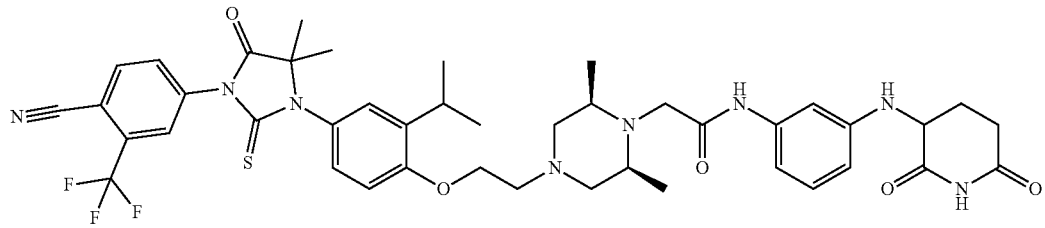 [SMILES: CC(C)c1cc(N2C(=S)N(c3ccc(C#N)c(C(F)(F)F)c3)C(=O)C2(C)C)ccc1OCCN1C[C@@H](C)N(CC(=O)Nc2cccc(NC3CCC(=O)NC3=O)c2)[C@@H](C)C1]

1-(Benzyloxy)-4-nitro-2-(prop-1-en-2-yl)benzene. To a mixture of 1-(benzyloxy)-2-bromo-4-nitrobenzene (10.00 g, 32.45 mmol, 1 eq) (prepared as described herein), and 4,4,5,5-tetramethyl-2-(prop-1-en-2-yl)-1,3,2-dioxaborolane (10.91 g, 64.91 mmol, 2 eq) in dioxane (100 mL), water (50 mL) were added potassium phosphate (20.67 g, 97.36 mmol, 3 eq) and diphenyl phosphorus di ferrocene palladium dichloride (1.190 g, 1.62 mmol, 0.05 eq) in one portion at 25° C. under nitrogen. The mixture was heated to 90° C. and stirred for 12 h, then concentrated under reduced pressure at 60° C., and filtered. The residue was poured into ice-water (300 mL). The aqueous phase was extracted with EtOAc (500 mL×3). The combined organic phases were washed with brine (200 mL), dried with anhydrous sodium sulfate, filtered and concentrated under vacuum. The residue was purified by silica gel column chromatography (9% EtOAc in petroleum ether) to afford 1-(benzyloxy)-4-nitro-2-(prop-1-en-2-yl)benzene (13.26 g, 49.20 mmol, 75.9% yield) as yellow solid. $^1$H NMR (400 MHz, CDCl$_3$) δ ppm 8.07-8.19 (m, 2H), 7.42-7.34 (m, 5H), 6.99-6.97 (m, 1H), 5.27-5.19 (m, 4H), 2.15 (d, J=0.8 Hz, 3H).

4-Amino-2-isopropylphenol. To a solution of 1-(benzyloxy)-4-nitro-2-(prop-1-en-2-yl)benzene (11.90 g, 44.19 mmol, 1 eq) in EtOAc (120 mL) was added palladium on activated carbon (3.00 g, 10% purity) under nitrogen. The suspension was degassed under vacuum and purged with hydrogen several times. The mixture was stirred under hydrogen (50 psi) at 30° C. for 3 h, then filtered and the filtrate was concentrated. The crude product was purified by reverse phase silica gel column chromatography (0.1% FA condition) to afford 4-amino-2-isopropylphenol (5.00 g, 33.07 mmol, 74.8% yield) as brown solid. $^1$H NMR (400 MHz, CDCl$_3$) δ ppm 6.60-6.58 (m, 2H), 6.44 (dd, J=8.4, 2.8 Hz, 1H), 1.23 (d, J=7.2 Hz, 6H).

2-((4-Hydroxy-3-isopropylphenyl)amino)-2-methylpropanenitrile. To a mixture of 4-amino-2-isopropylphenol (0.400 g, 2.65 mmol, 1 eq) in 2-hydroxy-2-methylpropanenitrile (0.675 g, 7.94 mmol, 3 eq) was added magnesium sulfate (0.796 g, 6.61 mmol, 2.5 eq) in one portion at 25° C. The reaction mixture was heated to 60° C. for 12 h, then concentrated under reduced pressure at 40° C. The residue was poured into ice-water (40 mL) and the aqueous phase was extracted with EtOAc (60 mL×2). The combined organic phases were washed with brine (40 mL), dried with anhydrous sodium sulfate, filtered, and concentrated under vacuum to afford 2-((4-hydroxy-3-isopropylphenyl)amino)-2-methylpropanenitrile (0.730 g, crude) as dark red solid. MS (ESI) m/z 192.1 [M−26]$^+$.

4-(3-(4-Hydroxy-3-isopropylphenyl)-4,4-dimethyl-5-oxo-2-thioxoimidazolidin-1-yl)-2-(trifluoromethyl)benzonitrile. A mixture of 2-((4-hydroxy-3-isopropylphenyl)amino)-2-methylpropanenitrile (0.730 g, 3.34 mmol, 1 eq) and 4-isothiocyanato-2-(trifluoromethyl)benzonitrile (0.530 g, 2.34 mmol, 0.7 eq) in DMF (7.5 mL) was stirred at 25° C. for 1 h, then treated with a 4.0 M solution of HCl in MeOH (2 mL, 2.39 eq). The solution was stirred at 70° C. for 12 h, cooled, and concentrated under reduced pressure at 40° C. The residue was poured into ice-water (50 mL) and the aqueous phase was extracted with EtOAc (60 mL×2). The combined organic phases were washed with brine (40 mL), dried with anhydrous sodium sulfate, filtered, and concentrated under vacuum. The residue was purified by silica gel column chromatography (30-35% EtOAc in petroleum ether) to afford 4-(3-(4-hydroxy-3-isopropylphenyl)-4,4-dimethyl-5-oxo-2-thioxoimidazolidin-1-yl)-2-(trifluoromethyl)benzonitrile (1.110 g, 2.48 mmol, 74.2% yield) as dark red oil. $^1$H NMR (400 MHz, CDCl$_3$) δ ppm 7.99-7.97 (m, 2H), 7.85 (dd, J=8.0, 1.2 Hz, 1H), 7.08 (d, J=2.8 Hz, 1H), 7.00-6.97 (m, 1H), 6.88 (d, J=8.4 Hz, 1H), 5.48-5.37 (m, 1H), 3.26 (m, 1H), 1.58 (s, 6H), 1.27-1.29 (d, J=7.4 Hz, 6H).

4-(3-(4-(2-Bromoethoxy)-3-isopropylphenyl)-4,4-dimethyl-5-oxo-2-thioxoimidazolidin-1-yl)-2-(trifluoromethyl)benzonitrile. To a mixture of 4-(3-(4-hydroxy-3-isopropylphenyl)-4,4-dimethyl-5-oxo-2-thioxoimidazolidin-1-yl)-2-(trifluoromethyl)benzonitrile (1.11 g, 2.48 mmol, 1 eq) and 1,2-dibromoethane (4.66 g, 24.80 mmol, 10 eq) in acetonitrile (15 mL) was added potassium carbonate (1.03 g, 7.44 mmol, 3 eq) in one portion at 25° C. The mixture was heated to 90° C. and stirred for 24 h, then cooled and concentrated under reduced pressure at 40° C. The residue was poured into ice-water (50 mL) and the aqueous phase was extracted with EtOAc (70 mL×2). The combined organic phases were washed with brine (60 mL), dried with anhydrous sodium sulfate, filtered, and concentrated under vacuum. The residue was purified by silica gel column chromatography (0-45% EtOAc in petroleum ether) to afford 4-(3-(4-(2-bromoethoxy)-3-isopropylphenyl)-4,4-dimethyl-5-oxo-2- thioxoimidazolidin-1-yl)-2-(trifluoromethyl)benzonitrile (0.66 g, 1.19 mmol, 48.0% yield) as yellow oil. $^1$H NMR (400 MHz, CDCl$_3$) δ ppm 8.00-7.98 (m, 2H), 7.86 (dd, J=8.4, 1.6 Hz, 1H), 7.12-7.07 (m, 2H), 6.92 (d, J=8.8 Hz, 1H), 4.37 (t, J=6.0 Hz, 2H), 3.72 (t, J=6.0 Hz, 2H), 3.44-3.37 (m, 1H), 1.58 (s, 6H), 1.26-1.28 (d, J=6.8 Hz, 6H).

(3S,5R)-tert-Butyl 4-(2-((3-((2,6-dioxopiperidin-3-yl)amino)phenyl)amino)-2-oxoethyl)-3,5-dimethylpiperazine-1-carboxylate. To a solution of 2-chloro-N-(3-((2,6-dioxopiperidin-3-yl)amino)phenyl)acetamide (0.950 g, 3.21 mmol, 1.00 eq) and (3S,5R)-tert-butyl 3,5-dimethylpiperazine-1-carboxylate (0.688 g, 3.21 mmol, 1.00 eq) in DMF (10 mL) was added DIEA (1.250 g, 9.64 mmol, 1.7 mL, 3.00 eq) and sodium iodide (0.144 g, 0.964 mmol, 0.30 eq) in one portion under nitrogen. The mixture was stirred at 70° C. for 12 h, and then filtered. The filtrate was concentrated under reduced pressure, and purified by semi-preparative reverse phase HPLC (10-40% acetonitrile+0.225% formic acid in water, over 30 min). The collected fractions were extracted with EtOAc (100 mL×4). The combined organic layers were washed with brine (200 mL), dried over anhydrous sodium sulfate, filtered, and concentrated under reduced pressure to give (3S,5R)-tert-butyl 4-(2-((3-((2,6-dioxopiperidin-3-yl)amino)phenyl)amino)-2-oxoethyl)-3,5-dimethylpiperazine-1-carboxylate (1.20 g, 2.52 mmol, 78.4% yield) as a light yellow solid. MS (ESI) m/z 474.3 [M+1]$^+$; $^1$H NMR (400 MHz, DMSO-d$_6$) δ ppm 10.77 (s, 1H), 9.41 (s, 1H), 7.05-6.96 (m, 2H), 6.83-6.75 (m, 1H), 6.40 (dd, J=1.6, 8.1 Hz, 1H), 5.87 (d, J=7.9 Hz, 1H), 4.33-4.22 (m, 1H), 3.74 (br s, 2H), 3.27 (s, 2H), 2.80-2.53 (m, 6H), 2.15-2.04 (m, 1H), 1.89 (dq, J=4.8, 12.1 Hz, 1H), 1.40 (s, 9H), 1.00 (d, J=5.6 Hz, 6H).

2-((2S,6R)-2,6-Dimethylpiperazin-1-yl)-N-(3-((2,6-dioxopiperidin-3-yl)amino)phenyl)acetamide. To a solution of (3S,5R)-tert-butyl 4-(2-((3-((2,6-dioxopiperidin-3-yl)amino)phenyl)amino)-2-oxoethyl)-3,5-dimethylpiperazine-1-carboxylate (1.70 g, 3.59 mmol, 1 eq) in dioxane (10 mL) was added hydrobromic acid (8.89 M, 10 mL, 24.8 eq) in one portion. The mixture was stirred at 25° C. for 1 h, then diluted with water (150 mL) and lyophilized to give 2-((2S,6R)-2,6-dimethylpiperazin-1-yl)-N-(3-((2,6-dioxopiperidin-3-yl)amino)phenyl)acetamide hydrobromide (2.70 g, crude) as a red solid. MS (ESI) m/z 374.2 [M+1]$^+$; $^1$H NMR (400 MHz, DMSO-d$_6$) δ ppm 10.82-10.76 (m, 1H), 11.04-10.74 (m, 1H), 10.38-9.99 (m, 1H), 9.79-9.30 (m, 2H), 7.47-7.25 (m, 1H), 7.14 (s, 1H), 7.03-6.88 (m, 1H), 6.57 (dd, J=2.5, 8.9 Hz, 1H), 4.53-4.21 (m, 3H), 3.99 (br s, 2H), 3.68-3.55 (m, 2H), 3.24 (br s, 2H), 2.92-2.69 (m, 1H), 2.65-2.54 (m, 1H), 2.44-2.28 (m, 1H), 2.15-1.82 (m, 2H), 1.37 (br s, 6H).

2-((2S,6R)-4-(2-(4-(3-(4-Cyano-3-(trifluoromethyl)phenyl)-5,5-dimethyl-4-oxo-2-thioxoimidazolidin-1-yl)-2-isopropylphenoxy)ethyl)-2,6-dimethylpiperazin-1-yl)-N-(3-((2,6-dioxopiperidin-3-yl)amino)phenyl)acetamide hydrochloride. To a mixture of 4-(3-(4-(2-bromoethoxy)-3-isopropylphenyl)-4,4-dimethyl-5-oxo-2-thioxoimidazolidin-1-yl)-2-(trifluoromethyl)benzonitrile (0.150 g, 0.271 mmol, 1 eq) and 2-((2S,6R)-2,6-dimethylpiperazin-1-yl)-N-(3-((2,6-dioxopiperidin-3-yl)amino)phenyl)acetamide hydrobromide (0.202 g, 0.445 mmol, 1.64 eq) in DMF (1.5 mL) was added DIEA (0.105 g, 0.817 mmol, 3 eq), sodium iodide (0.020 g, 0.135 mmol, 0.5 eq) in one portion at 25° C. under nitrogen. The mixture was heated to 60° C. and stirred for 12 h, then cooled to 30° C., and filtered. The filtrated was concentrated under reduced pressure and the residue was purified by standard methods to afford 2-((2S,6R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,6-dimethylpiperazin-1-yl)-N-(3-((2,6-dioxopiperidin-3-yl)amino)phenyl)acetamide hydrochloride (0.072 g, 0.081 mmol, 29.8% yield). MS (ESI) m/z 847.3 [M+1]$^+$; $^1$H NMR (400 MHz, DMSO-d$_6$) δ ppm 10.79 (s, 1H), 10.65-9.98 (m, 1H), 8.39 (d, J=8.4 Hz, 1H), 8.29 (d, J=1.2 Hz, 1H), 8.08 (dd, J=8.4, 1.6 Hz, 1H), 7.23-7.18 (m, 2H), 7.17-7.11 (m, 1H), 7.07-6.96 (m, 2H), 6.83 (d, J=8.0 Hz, 1H), 6.45 (d, J=7.2 Hz, 1H), 4.48 (s, 2H), 4.26 (dd, J=11.2, 4.8 Hz, 1H), 4.18-3.90 (m, 6H), 3.75-3.64 (m, 5H), 2.80-2.69 (m, 1H), 2.64-2.56 (m, 1H), 2.13-2.05 (m, 1H), 1.97-1.85 (m, 1H), 1.49 (s, 6H), 1.29 (s, 6H), 1.19 (d, J=6.8 Hz, 6H).

Example 42: 2-(3-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-3,8-diazabicyclo[3.2.1]octan-8-yl)-N-(3-((2,6-dioxopiperidin-3-yl)amino)phenyl)acetamide hydrochloride

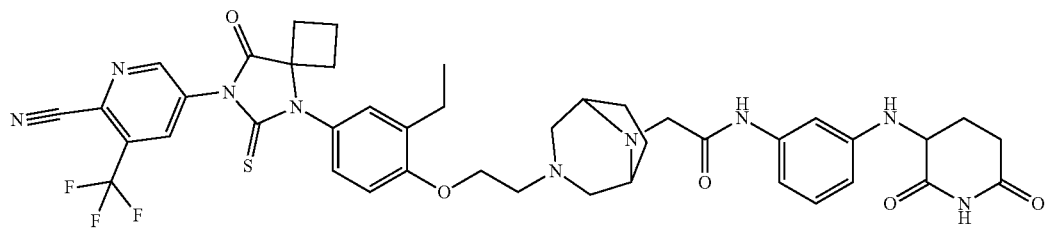 [SMILES: CCc1cc(N2C(=S)N(c3cnc(C#N)c(C(F)(F)F)c3)C(=O)C23CCC3)ccc1OCCN1CC2CCC(C1)N2CC(=O)Nc1cccc(NC2CCC(=O)NC2=O)c1]

5-[5-[4-(2-bromoethoxy)-3-ethyl-phenyl]-8-oxo-6-thioxo-5,7-diazaspiro[3.4]octan-7-yl]-3-(trifluoromethyl)pyridine-2-carbonitrile. To a solution of 5-[5-(3-ethyl-4-hydroxy-phenyl)-8-oxo-6-thioxo-5,7-diazaspiro[3.4]octan-7-yl]-3-(trifluoromethyl)pyridine-2-carbonitrile (1.23 g, 2.75 mmol, 1 eq) (prepared as described herein), in acetonitrile (30.8 mL, 0.09 M) were added potassium carbonate (1.16 g, 8.28 mmol, 3 eq) and 1,2-dibromoethane (4.77 mL, 55.1 mmol, 20 eq). The mixture was stirred at 80° C. for 18 h, filtered, and the filtrate was concentrated. The crude residue was purified by silica gel column chromatography (0-33% EtOAc in hexanes) to afford 5-[5-[4-(2-bromoethoxy)-3-ethyl-phenyl]-8-oxo-6-thioxo-5,7-diazaspiro[3.4]octan-7-yl]-3-(trifluoromethyl)pyridine-2-carbonitrile (0.867 g, 1.56 mmol, 56.7% yield) as a light pink solid. MS (ESI) m/z 553.0 [M+1]$^+$.

tert-Butyl 3-[2-[4-[7-[6-cyano-5-(trifluoromethyl)-3-pyridyl]-8-oxo-6-thioxo-5,7-diazaspiro[3.4]octan-5-yl]-2-ethyl-phenoxy]ethyl]-3,8-diazabicyclo[3.2.1]octane-8-carboxylate. To a solution of tert-butyl 3,8-diazabicyclo[3.2.1]octane-8-carboxylate (0.057 g, 0.27 mmol, 1.2 eq) in DMF (2.25 mL, 0.100 M) was added 5-[5-[4-(2-bromoethoxy)-3-ethyl-phenyl]-8-oxo-6-thioxo-5,7-diazaspiro[3.4]octan-7-yl]-3-(trifluoromethyl)pyridine-2-carbonitrile (0.125 g, 0.23 mmol, 1 eq) and DIEA (0.14 mL, 0.79 mmol, 3.5 eq). The mixture was heated to 60° C. with stirring for 18 h, concentrated under reduced pressure and the residue was purified by silica gel column chromatography (0-100% hexane/EtOAc) to give tert-butyl 3-[2-[4-[7-[6-cyano-5-(trifluoromethyl)-3-pyridyl]-8-oxo-6-thioxo-5,7-diazaspiro[3.4]octan-5-yl]-2-ethyl-phenoxy]ethyl]-3,8-diazabicyclo[3.2.1]octane-8-carboxylate (0.129 g, 0.19 mmol, 83.4% yield) as an off-white solid. MS (ESI) m/z 685.2 [M+1]$^+$.

5-[5-[4-[2-(3,8-Diazabicyclo[3.2.1]octan-3-yl)ethoxy]-3-ethyl-phenyl]-8-oxo-6-thioxo-5,7-diazaspiro[3.4]octan-7-yl]-3-(trifluoromethyl)pyridine-2-carbonitrile dihydrochloride. tert-Butyl 3-[2-[4-[7-[6-cyano-5-(trifluoromethyl)-3-pyridyl]-8-oxo-6-thioxo-5,7-diazaspiro[3.4]octan-5-yl]-2-ethyl-phenoxy]ethyl]-3,8-diazabicyclo[3.2.1]octane-8-carboxylate (0.129 g, 0.19 mmol, 1 eq) was suspended in DCM (0.83 mL, 0.23 M), treated with a 4.0 M solution of HCl in dioxane (0.71 mL, 2.83 mmol, 15 eq), and stirred at room temperature for 2 h. The reaction was concentrated to afford 5-[5-[4-[2-(3,8-diazabicyclo[3.2.1]octan-3-yl)ethoxy]-3-ethyl-phenyl]-8-oxo-6-thioxo-5,7-diazaspiro[3.4]octan-7-yl]-3-(trifluoromethyl)pyridine-2-carbonitrile dihydrochloride (0.123 g, 0.19 mmol, 99.3% yield) as a beige solid. MS (ESI) m/z 585.2 [M+1]$^+$.

2-(3-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-3,8-diazabicyclo[3.2.1]octan-8-yl)-N-(3-((2,6-dioxopiperidin-3-yl)amino)phenyl)acetamide hydrochloride. 2-Chloro-N-[3-[(2,6-dioxo-3-piperidyl)amino]phenyl]acetamide (0.083 g, 0.28 mmol, 1.5 eq) was added to a stirred mixture of 5-[5-[4-[2-(3,8-diazabicyclo[3.2.1]octan-3-yl)ethoxy]-3-ethyl-phenyl]-8-oxo-6-thioxo-5,7-diazaspiro[3.4]octan-7-yl]-3-(trifluoromethyl)pyridine-2-carbonitrile dihydrochloride (0.123 g, 0.19 mmol, 1 eq), sodium iodide (0.042 g, 0.28 mmol, 1.5 eq), DMF (1.55 mL, 1.2 molar) and DIEA (0.16 mL, 0.94 mmol, 5 eq). After stirring for 1 h at 60° C., the solution was filtered and purified by standard methods to afford 2-[3-[2-[4-[7-[6-cyano-5-(trifluoromethyl)-3-pyridyl]-8-oxo-6-thioxo-5,7-diazaspiro[3.4]octan-5-yl]-2-ethyl-phenoxy]ethyl]-3,8-diazabicyclo[3.2.1]octan-8-yl]-N-[3-[(2,6-dioxo-3-piperidyl)amino]phenyl]acetamide hydrochloride (0.106 g, 0.11 mmol, 61.5% yield). MS (ESI) m/z 844.4 [M+1]$^+$; $^1$H NMR (400 MHz, DMSO-d$_6$) δ ppm 10.80 (s, 1H), 10.48 (br s, 1H), 9.22 (d, 1H, J=1.7 Hz), 8.76 (d, 1H, J=2.0 Hz), 7.1-7.3 (m, 3H), 7.05 (t, 1H, J=8.0 Hz), 6.98 (s, 1H), 6.86 (d, 1H, J=8.9 Hz), 6.46 (dd, 1H, J=1.5, 8.1 Hz), 4.47 (br s, 2H), 4.25 (br dd, 1H, J=4.8, 11.4 Hz), 4.20 (br s, 3H), 3.7-3.8 (m, 2H), 3.2-3.6 (m, 6H), 2.6-2.8 (m, 6H), 2.3-2.5 (m, 4H), 2.22 (br s, 2H), 2.1-2.1 (m, 1H), 1.9-2.0 (m, 2H), 1.5-1.6 (m, 1H), 1.20 (t, 3H, J=7.5 Hz).

Example 43: 2-((1S,4S)-5-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-2,5-diazabicyclo[2.2.2]octan-2-yl)-N-(3-((2,6-dioxopiperidin-3-yl)amino)phenyl)acetamide hydrochloride

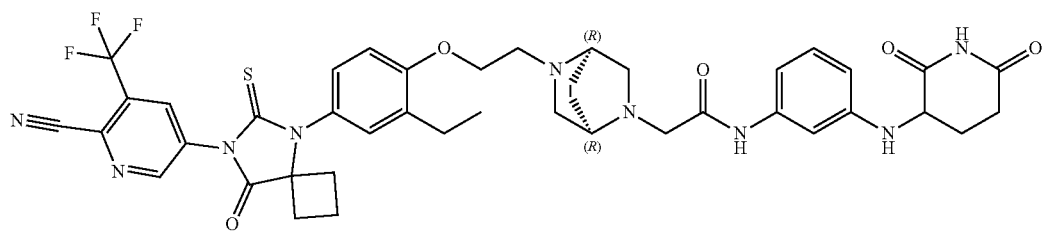

tert-Butyl (1S,4S)-5-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,5-diazabicyclo[2.2.2]octane-2-carboxylate. To a solution of tert-butyl (1S,4S)-2,5-diazabicyclo[2.2.2]octane-2-carboxylate (0.057 g, 0.27 mmol, 1.2 eq) in DMF (2.26 mL, 0.100 M) was added 5-[5-[4-(2-bromoethoxy)-3-ethyl-phenyl]-8-oxo-6-thioxo-5,7-diazaspiro[3.4]octan-7-yl]-3-(trifluoromethyl)pyridine-2-carbonitrile (0.125 g, 0.23 mmol, 1 eq), (prepared as described herein), and DIEA (0.14 mL, 0.79 mmol, 3.5 eq). The mixture was heated to 60° C., while stirring for 18 h. After concentration under reduced pressure, the reaction mixture was purified by silica gel column chromatography (0-100% hexane/EtOAc) to give tert-butyl (1S,4S)-5-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,5-diazabicyclo[2.2.2]octane-2-carboxylate (0.130 g, 0.19 mmol, 84.0% yield) as a beige solid. MS (ESI) m/z 685.2 [M+1]$^+$.

acetamide hydrochloride (0.102 g, 0.11 mmol, 58.3% yield). MS (ESI) m/z 844.4 [M+1]$^+$; $^1$H NMR (400 MHz, DMSO-d$_6$) δ ppm 10.80 (s, 1H), 10.54 (br s, 1H), 9.22 (d, 1H, J=1.8 Hz), 8.76 (d, 1H, J=2.0 Hz), 7.2-7.3 (m, 3H), 7.05 (t, 1H, J=7.9 Hz), 6.99 (br s, 1H), 6.88 (br d, 1H, J=7.9 Hz), 6.46 (br d, 1H, J=8.3 Hz), 4.57 (br s, 1H), 4.37 (br s, 2H), 4.26 (br dd, 1H, J=4.8, 11.2 Hz), 4.04 (br s, 2H), 3.96 (br s, 2H), 3.86 (br s, 5H), 2.5-2.8 (m, 7H), 2.4-2.5 (m, 3H), 2.2-2.4 (m, 2H), 1.9-2.2 (m, 5H), 1.5-1.6 (m, 1H), 1.20 (t, 3H, J=7.5 Hz).

Example 44: 2-((S)-4-(2-(4-(3-(6-Cyano-5-(trifluoromethyl)pyridin-3-yl)-5,5-dimethyl-4-oxo-2-thioxoimidazolidin-1-yl)-2-cyclopropylphenoxy)ethyl)-2-(trifluoromethyl)piperazin-1-yl)-N-(3-((2,6-dioxopiperidin-3-yl)amino)phenyl)acetamide

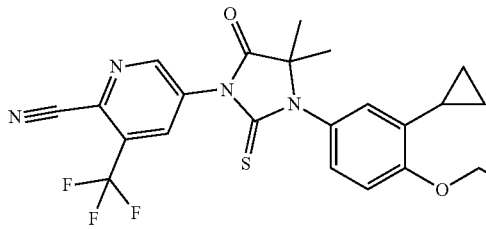
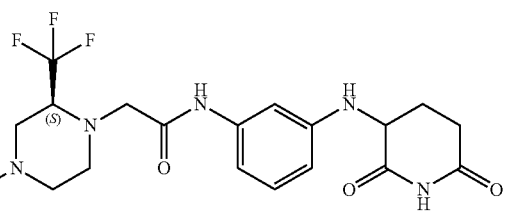

5-(5-(4-(2-((1S,4S)-2,5-Diazabicyclo[2.2.2]octan-2-yl)ethoxy)-3-ethylphenyl)-8-oxo-6-thioxo-5,7-diazaspiro[3.4]octan-7-yl)-3-(trifluoromethyl)picolinonitrile dihydrochloride. tert-Butyl (1S,4S)-5-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,5-diazabicyclo[2.2.2]octane-2-carboxylate (0.130 g, 0.19 mmol, 1 eq) was suspended in DCM (0.84 mL, 0.226 molar) and treated with a 4.0 M solution of HCl in dioxane (0.71 mL, 2.85 mmol, 15 eq). The reaction mixture was stirred at room temperature for 6 h, and concentrated to afford 5-(5-(4-(2-((1S,4S)-2,5-diazabicyclo[2.2.2]octan-2-yl)ethoxy)-3-ethylphenyl)-8-oxo-6-thioxo-5,7-diazaspiro[3.4]octan-7-yl)-3-(trifluoromethyl)picolinonitrile dihydrochloride (0.124 g, 0.19 mmol, 99.3% yield) as a beige solid. MS (ESI) m/z 585.2 [M+1]$^+$.

2-((1S,4S)-5-(2-(4-(7-(6-Cyano-5-(trifluoromethyl)pyridin-3-yl)-8-oxo-6-thioxo-5,7-diazaspiro[3.4]octan-5-yl)-2-ethylphenoxy)ethyl)-2,5-diazabicyclo[2.2.2]octan-2-yl)-N-(3-((2,6-dioxopiperidin-3-yl)amino)phenyl)acetamide hydrochloride. 2-Chloro-N-[3-[(2,6-dioxo-3-piperidyl)amino]phenyl]acetamide (0.084 g, 0.28 mmol, 1.5 eq) was added to a stirred mixture of 5-(5-(4-(2-((1S,4S)-2,5-diazabicyclo[2.2.2]octan-2-yl)ethoxy)-3-ethylphenyl)-8-oxo-6-thioxo-5,7-diazaspiro[3.4]octan-7-yl)-3-(trifluoromethyl)picolinonitrile dihydrochloride (0.124 g, 0.19 mmol, 1 eq), sodium iodide (0.043 g, 0.28 mmol, 1.5 eq), DMF (1.57 mL, 0.120 molar) and DIEA (0.16 mL, 0.94 mmol, 5 eq). The reaction mixture was stirred for 1 h at 60° C., and then the solution was filtered and purified by standard methods to afford 2-((1S,4S)-5-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,5-diazabicyclo[2.2.2]octan-2-yl)-N-(3-((2,6-dioxopiperidin-3-yl)amino)phenyl)

1-(Benzyloxy)-2-cyclopropyl-4-nitrobenzene. To a mixture of 1-benzyloxy-2-bromo-4-nitro-benzene (15.0 g, 48.7 mmol, 1 eq) and cyclopropylboronic acid (4.60 g, 53.5 mmol, 1.1 eq) in toluene (120 mL) was added palladium(II) acetate (1.09 g, 4.87 mmol, 0.1 eq), tricyclohexylphosphine (4.10 g, 16.4 mmol, 0.3 eq), potassium phosphate (31.0 g, 146 mmol, 3 eq) and water (15 mL). The reaction was stirred at 120° C. for 12 h. The reaction was concentrated under vacuum and water (100 mL) was added to the residue. The mixture was extracted with EtOAc (100 mL×3), and the combined organic layers were washed with brine (50 mL×2), dried over anhydrous sodium sulfate, filtered and concentrated under reduced pressure to give a residue. The residue was purified by silica gel column chromatography (9-17% EtOAc/petroleum ether) to give 1-(benzyloxy)-2-cyclopropyl-4-nitrobenzene (10.60 g, 39.36 mmol, 80.7% yield) as a red oil. MS (ESI) m/z 270.5 [M+1]$^+$.

4-Amino-2-cyclopropylphenol. To a solution of 1-benzyloxy-2-cyclopropyl-4-nitro-benzene (10.6 g, 39.3 mmol, 1 eq) in MeoH (150 mL) was added palladium on activated carbon (3.00 g, 3.94 mmol, 10% wt, 0.1 eq) and ammonium hydroxide (1 mL). The reaction was stirred for 3 h under a hydrogen atmosphere (50 psi) at 40° C. The mixture was filtered and concentrated under vacuum. The crude product was stirred in 4% EtOAc/petroleum ether at 25° C. for 0.5 h. The mixture was then filtered to afford the desired product (4.60 g, 30.8 mmol, 78.3% yield) was obtained as a yellow solid. MS (ESI) m/z 150.1 [M+1]$^+$.

2-((3-Cyclopropyl-4-hydroxyphenyl)amino)-2-methylpropanenitrile. To a mixture of 4-amino-2-cyclopropyl-phenol (4.50 g, 30.1 mmol, 1 eq) in 2-hydroxy-2-methylpropanenitrile (28.2 g, 332 mmol, 30.3 mL, 11 eq) was added magnesium sulfate (18.1 g, 151 mmol, 5 eq). The reaction was stirred at 60° C. for 3 h. The reaction was concentrated under vacuum and poured into water (50 mL), and the mixture was extracted with ethyl ether (30 mL×3)

and concentrated under vacuum to afford crude 2-((3-cyclopropyl-4-hydroxyphenyl)amino)-2-methylpropanenitrile (10.0 g) as a red oil. MS (ESI) m/z 217.6 [M+1]⁺.

5-(3-(3-Cyclopropyl-4-hydroxyphenyl)-4,4-dimethyl-5-oxo-2-thioxoimidazolidin-1-yl)-3-(trifluoromethyl)picolinonitrile. A mixture of 2-((3-cyclopropyl-4-hydroxyphenyl)amino)-2-methylpropanenitrile (5.00 g, 23.1 mmol, 1 eq) and 5-isothiocyanato-3-(trifluoromethyl)picolinonitrile (5.83 g, 25.4 mmol, 1.1 eq) in DMF (30 mL) was stirred at 25° C. for 1 h. After that time, hydrochloride acid/MeOH (4 M, 11.5 mL, 2 eq) was added, and the reaction was stirred at 80° C. for 12 h. The mixture was concentrated under vacuum. The residue was purified by preparative, reverse-phase liquid chromatography (40-70% acetonitrile+0.05% hydrochloric acid in water, 25 min), the collected fractions were concentrated under vacuum, and the pH was adjusted to 8 with saturated sodium bicarbonate solution. The aqueous phase was extracted with ethyl ether (300 mL×3), and the combine organic phases were dried over anhydrous sodium sulfate, filtered and concentrated under vacuum. Compound 5-(3-(3-cyclopropyl-4-hydroxyphenyl)-4,4-dimethyl-5-oxo-2-thioxoimidazolidin-1-yl)-3-(trifluoromethyl)picolinonitrile (5.20 g, 11.6 mmol, 50.4% yield) was obtained as a white solid. MS (ESI) m/z 447.1 [M+1]⁺.

5-(3-(4-(2-Bromoethoxy)-3-cyclopropylphenyl)-4,4-dimethyl-5-oxo-2-thioxoimidaz olidin-1-yl)-3-(trifluoromethyl)picolinonitrile. To a mixture of 5-(3-(3-cyclopropyl-4-hydroxyphenyl)-4,4-dimethyl-5-oxo-2-thioxoimidazolidin-1-yl)-3-(trifluoromethyl)picolino nitrile (1.00 g, 2.24 mmol, 1 eq) and 1,2-dibromoethane (8.42 g, 44.8 mmol, 3.38 mL, 20 eq) in acetonitrile (10 mL) was added potassium carbonate (0.93 g, 6.72 mmol, 3 eq). The reaction was stirred at 80° C. for 48 h. The mixture was filtered and concentrated under vacuum, and the residue was purified by preparative, reverse-phase liquid chromatography (57-87% acetonitrile+ 0.05% hydrochloric acid in water, 20 min). Compound 5-(3-(4-(2-bromoethoxy)-3-cyclopropylphenyl)-4,4-dimethyl-5-oxo-2-thioxoimida zolidin-1-yl)-3-(trifluoromethyl)picolinonitrile (0.30 g, 0.51 mmol, 22.7% yield, hydrochloric acid) was obtained as a white solid. MS (ESI) m/z 555.0 [M+1]⁺.

(3S)-tert-Butyl 4-(2-((3-((2,6-dioxopiperidin-3-yl)amino) phenyl)amino)-2-oxoethyl)-3-(trifluoromethyl)piperazine-1-carboxylate. To a mixture of tert-butyl (3S)-3-(trifluoromethyl)piperazine-1-carboxylate (0.08 g, 0.31 mmol, 1 eq) and 2-chloro-N-(3-((2,6-dioxopiperidin-3-yl)amino)phenyl) acetamide (0.12 g, 0.41 mmol, 1.3 eq) in DMF (2 mL) was added DIEA (0.20 g, 1.57 mmol, 0.27 mL, 5 eq) and sodium iodide (14.1 mg, 0.09 mmol, 0.3 eq). The reaction was stirred at 80° C. for 12 h. The mixture was poured into water and extracted with ethyl ether (20 mL×2), and the combined organic phases were concentrated under vacuum. The residue was purified by preparative TLC (5% MeOH/DCM) to give (3S)-tert-butyl 4-(2-((3-((2,6-dioxopiperidin-3-yl) amino)phenyl)amino)-2-oxoethyl)-3-(trifluoromethyl)piperazine-1-carboxylate (0.04 g, 77.9 μmol, 24.7% yield) as a yellow oil. MS (ESI) m/z 536.3 [M+Na]⁺.

N-(3-((2,6-Dioxopiperidin-3-yl)amino)phenyl)-2-((S)-2-(trifluoromethyl)piperazin-1-yl)acetamide. To a mixture of (3S)-tert-butyl 4-(2-((3-((2,6-dioxopiperidin-3-yl)amino) phenyl)amino)-2-oxoethyl)-3-(trifluoromethyl)piperazine-1-carboxylate (0.07 g, 0.13 mmol, 1 eq) in DCM (5 mL) was added hydrobromic acid/acetic acid (0.5 mL, 33% v/v). The reaction was stirred at 25° C. for 1 h. The mixture was concentrated under vacuum to afford N-(3-((2,6-dioxopiperidin-3-yl)amino)phenyl)-2-((S)-2-(trifluoromethyl)piperazin-1-yl)acetamide (0.10 g, crude, hydrobromic acid) as a white solid.

2-((S)-4-(2-(4-(3-(6-Cyano-5-(trifluoromethyl)pyridin-3-yl)-5,5-dimethyl-4-oxo-2-thioxoimidazolidin-1-yl)-2-cyclopropylphenoxy)ethyl)-2-(trifluoromethyl)piperazin-1-yl)-N-(3-((2,6-dioxopiperidin-3-yl)amino)phenyl)acetamide. To a mixture of N-(3-((2,6-dioxopiperidin-3-yl)amino)phenyl)-2-((S)-2-(trifluoromethyl)piperazin-1-yl)acetamide (0.10 g, 0.20 mmol, 1 eq, hydrobromic acid) and 5-(3-(4-(2-bromoethoxy)-3-cyclopropylphenyl)-4,4-dimethyl-5-oxo-2-thioxoimidazolidin-1-yl)-3-(trifluoromethyl)picolinonitrile (0.13 g, 0.24 mmol, 1.2 eq) in DMF (2 mL) was added DIEA (0.61 mmol, 0.11 mL, 3 eq) and sodium iodide (0.01 g, 0.06 mmol, 0.3 eq). The reaction was stirred at 50° C. for 12 h. The mixture was filtered, and the residue was purified by standard methods to afford 2-((S)-4-(2-(4-(3-(6-cyano-5-(trifluoromethyl) pyridin-3-yl)-5,5-dimethyl-4-oxo-2-thioxoimidazolidin-1-yl)-2-cyclopropylphenoxy) ethyl)-2-(trifluoromethyl)piperazin-1-yl)-N-(3-((2,6-dioxopiperidin-3-yl)amino)phenyl)acetamide (45.3 mg, 47.90 μmol, 23.7% yield, 97% purity, hydrochloric acid). MS (ESI) m/z 886.2 [M+1]⁺; ¹H NMR (400 MHz, DMSO-d₆) δ 10.79 (s, 1H), 9.69 (br d, J=2.4 Hz, 1H), 9.23 (d, J=2.0 Hz, 1H), 8.80 (d, J=2.0 Hz, 1H), 7.19-7.12 (m, 1H), 7.16 (s, 1H), 7.02-6.97 (m, 1H), 6.97-6.91 (m, 1H), 6.83 (s, 1H), 6.82-6.76 (m, 1H), 6.40 (br d, J=7.6 Hz, 1H), 4.52 (s, 2H), 4.24 (dd, J=4.8, 11.2 Hz, 1H), 3.91-3.54 (m, 7H), 3.24-3.12 (m, 2H), 2.79-2.69 (m, 1H), 2.63-2.56 (m, 1H), 2.24-2.03 (m, 3H), 1.95-1.81 (m, 1H), 1.49 (s, 6H), 0.99-0.89 (m, 2H), 0.61 (d, J=4.4 Hz, 2H).

Example 45: 2-((S)-4-(2-(4-(3-(4-Cyano-3-(trifluoromethyl)phenyl)-5,5-dimethyl-4-oxo-2-thioxoimidazolidin-1-yl)-2-cyclopropylphenoxy)ethyl)-2-(trifluoromethyl)piperazin-1-yl)-N-(3-((2,6-dioxopiperidin-3-yl)amino)phenyl)acetamide

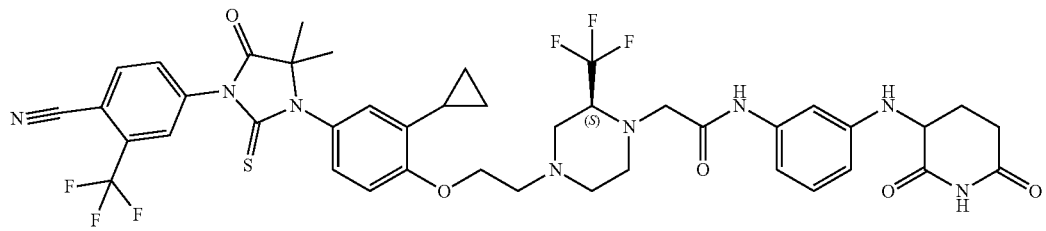

Benzyl (3-(2-chloroacetamido)phenyl)carbamate. A mixture of 2-chloroacetic acid (3.02 mL, 26.8 mmol) and HATU (11.7 g, 30.9 mmol) in DMF (20 mL) was stirred at 25° C. for 12 h. Benzyl (3-aminophenyl)carbamate (5.00 g, 20.6 mmol) and DIEA (10.7 mL, 61.9 mmol) were them added subsequently. The reaction was stirred at 25° C. for 4 h. The mixture was concentrated under vacuum, and the residue was purified by preparative, reverse-phase, liquid chromatography (40-70% acetonitrile+0.05% hydrochloric acid in water, over 20 min). The collected fractions were concentrated, and the pH was adjusted to 8 with saturated sodium bicarbonate solution and extracted with EtOAc (100 mL×3). The organic phase was dried over anhydrous sodium sulfate and concentrated under vacuum to give benzyl (3-(2-chloroacetamido)phenyl)carbamate (3.50 g, 10.9 mmol, 53.2% yield) as a white solid. MS (ESI) m/z 319.1 [M+1]+

(S)-tert-Butyl 4-(2-((3-(((benzyloxy)carbonyl)amino)phenyl)amino)-2-oxoethyl)-3-(trifluoromethyl)piperazine-1-carboxylate. To a mixture of tert-butyl (3S)-3-(trifluoromethyl)piperazine-1-carboxylate (0.40 g, 1.57 mmol) and benzyl (3-(2-chloroacetamido)phenyl)carbamate (0.70 g, 2.20 mmol) in DMF (5 mL) was added sodium iodide (71.0 mg, 0.47 mmol) and DIEA (0.82 mL, 4.72 mmol). The reaction was stirred at 90° C. for 12 h. The mixture was poured into water and extracted with EtOAc (20 mL×3). The organic phase was dried over anhydrous sodium sulfate, concentrated under vacuum, and purified by flash silica gel chromatography (0-15% EtOAc/petroleum ether). (S)-tert-butyl 4-(2-((3-(((benzyloxy)carbonyl)amino)phenyl)amino)-2-oxoethyl)-3-(trifluoromethyl)piperazine-1-carboxylate (0.44 g, crude) was obtained as a yellow oil. MS (ESI) m/z 559.2 [M+Na]+.

(S)-tert-Butyl 4-(2-((3-aminophenyl)amino)-2-oxoethyl)-3-(trifluoromethyl)piperazine-1-carboxylate. A mixture of (S)-tert-butyl 4-(2-((3-(((benzyloxy)carbonyl)amino)phenyl)amino)-2-oxoethyl)-3-(trifluoromethyl)piperazine-1-carboxylate (0.44 g, 0.83 mmol) and palladium on activated carbon (0.10 g, 10% wt) in MeOH (10 mL) was stirred at 25° C. under hydrogen for 12 h. The mixture was filtered and concentrated under vacuum to provide (S)-tert-butyl 4-(2-((3-aminophenyl)amino)-2-oxoethyl)-3-(trifluoromethyl)piperazine-1-carboxylate (0.28 g, 0.69 mmol, 83.9% yield) as a crude colorless oil. MS (ESI) m/z 347.1 [M+1]+.

(3S)-tert-Butyl 4-(2-((3-((2,6-dioxopiperidin-3-yl)amino)phenyl)amino)-2-oxoethyl)-3-(trifluoromethyl)piperazine-1-carboxylate. To a mixture of (S)-tert-butyl 4-(2-((3-aminophenyl)amino)-2-oxoethyl)-3-(trifluoromethyl)piperazine-1-carboxylate (0.28 g, 0.69 mmol) and 3-bromopiperidine-2,6-dione (0.40 g, 2.09 mmol) in DMF (5 mL) was added sodium bicarbonate (0.17 g, 2.09 mmol). The reaction was stirred at 60° C. for 48 h, and then the mixture was poured into water and extracted with EtOAc (30 mL×3). The combined organic phases were dried with anhydrous sodium sulfate, filtered and concentrated under vacuum. The residue was purified by preparative-TLC (60% EtOAc/petroleum ether) to give (3S)-tert-butyl 4-(2-((3-((2,6-dioxopiperidin-3-yl)amino)phenyl)amino)-2-oxoethyl)-3-(trifluoromethyl)piperazine-1-carboxylate (0.18 g, 0.35 mmol, 51.2% yield) as a light-yellow oil. MS (ESI) m/z 514.2 [M+1]+.

N-(3-((2,6-Dioxopiperidin-3-yl)amino)phenyl)-2-((S)-2-(trifluoromethyl)piperazin-1-yl)acetamide. To a mixture of (3S)-tert-butyl 4-(2-((3-((2,6-dioxopiperidin-3-yl)amino)phenyl)amino)-2-oxoethyl)-3-(trifluoromethyl)piperazine-1-carboxylate (0.18 g, 0.13 mmol, 1 eq) in DCM (5 mL) was added hydrobromic acid/acetic acid (0.48 mL, 33% purity). The reaction was stirred at 25° C. for 1 h. The mixture was concentrated under vacuum to give crude N-(3-((2,6-dioxopiperidin-3-yl)amino)phenyl)-2-((S)-2-(trifluoromethyl)piperazin-1-yl)acetamide (0.30 g, hydrobromic acid) as a red solid.

4-(3-(3-Cyclopropyl-4-hydroxyphenyl)-4,4-dimethyl-5-oxo-2-thioxoimidazolidin-1-yl)-2-(trifluoromethyl)benzonitrile. A mixture of 2-((3-cyclopropyl-4-hydroxyphenyl)amino)-2-methylpropanenitrile (5.00 g, 23.1 mmol, 1 eq) and 4-isothiocyanato-2-(trifluoromethyl)benzonitrile (5.80 g, 25.4 mmol, 1.1 eq) in DMF (30 mL) was stirred at 25° C. for 1 h. Hydrochloric acid/MeOH (4 M, 11.56 mL, 2 eq) was then added, and the reaction was stirred at 80° C. for 12 h. The residue was purified by preparative, reverse-phase chromatography (40-70% acetonitrile+0.05% hydrochloric acid in water, 25 min). The collected fractions were concentrated under vacuum and the pH was adjusted to 8 with saturated sodium bicarbonate. The aqueous layer was extracted with ethyl ether (300 mL×3), and the combine organic phases were dried over anhydrous sodium sulfate, filtered and concentrated under vacuum to give 4-(3-(3-cyclopropyl-4-hydroxyphenyl)-4,4-dimethyl-5-oxo-2-thioxoimidazolidin-1-yl)-2-(trifluoromethyl)benzonitrile (4.90 g, 11.0 mmol, 47.6% yield) as a white solid. MS (ESI) m/z 446.2 [M+1]+.

4-(3-(4-(2-Bromoethoxy)-3-cyclopropylphenyl)-4,4-dimethyl-5-oxo-2-thioxoimidazolidin-1-yl)-2-(trifluoromethyl)benzonitrile. To a mixture of 4-(3-(3-cyclopropyl-4-hydroxyphenyl)-4,4-dimethyl-5-oxo-2-thioxoimidazolidin-1-yl)-2-(trifluoromethyl)benzonitrile (1.00 g, 2.24 mmol, 1 eq) and 1,2-dibromoethane (8.43 g, 44.9 mmol, 3.39 mL, 20 eq) in acetonitrile (10 mL) was added potassium carbonate (0.93 g, 6.73 mmol, 3 eq). The reaction was stirred at 80° C. for 24 h. The mixture was filtered and concentrated under vacuum, and the residue was purified by preparative, reverse-phase chromatography (57-87% acetonitrile+0.05% hydrochloric acid in water, 20 min) to afford 4-(3-(4-(2-bromoethoxy)-3-cyclopropylphenyl)-4,4-dimethyl-5-oxo-2-thioxoimidazolidin-1-yl)-2-(trifluoromethyl)benzonitrile (0.650 g, 1.10 mmol, 49.2% yield, hydrochloride) as a white solid. MS (ESI) m/z 554.0 [M+1]+.

2-((S)-4-(2-(4-(3-(4-Cyano-3-(trifluoromethyl)phenyl)-5,5-dimethyl-4-oxo-2-thioxoimidazolidin-1-yl)-2-cyclopropylphenoxy)ethyl)-2-(trifluoromethyl)piperazin-1-yl)-N-(3-((2,6-dioxopiperidin-3-yl)amino)phenyl)acetamide. To a mixture of N-(3-((2,6-dioxopiperidin-3-yl)amino)phenyl)-2-((S)-2-(trifluoromethyl)piperazin-1-yl)acetamide (0.12 g, 0.25 mmol, 1 eq, hydrobromic acid) and 4-(3-(4-(2-bromoethoxy)-3-cyclopropylphenyl)-4,4-dimethyl-5-oxo-2-thioxoimidazolidin-1-yl)-2-(trifluoromethyl)benzonitrile (0.16 g, 0.28 mmol, 1.13 eq, Hydrochloride) in DMF (2 mL) was added DIEA (0.13 mL, 3 eq) and sodium iodide (0.01 g, 0.76 mmol, 0.3 eq). The reaction was stirred at 60° C. for 12 h. The mixture was filtered and purified by standard methods to afford 2-((S)-4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)-2-(trifluoromethyl)piperazin-1-yl)-N-(3-((2,6-dioxopiperidin-3-yl)amino)phenyl)acetamide (0.09 g, 90.5 µmol, 35.8% yield, 97% purity, hydrochloride). MS (ESI) m/z 885.3 [M+1]+; 1H NMR (400 MHz, DMSO-$d_6$) δ 11.10 (s, 1H), 10.79 (s, 1H), 9.70 (br s, 1H), 8.39 (d, J=8.4 Hz, 1H), 8.27 (d, J=1.6 Hz, 1H), 8.06 (dd, J=1.6, 8.4 Hz, 1H), 7.15 (s, 2H), 7.04-6.93 (m, 2H), 6.84 (s, 1H), 6.82-6.76 (m, 1H), 6.40 (d, J=7.6 Hz, 1H), 4.54 (s, 3H), 4.24 (dd, J=4.4, 11.2 Hz, 1H), 3.66-3.44 (m, 6H), 3.41-3.24 (m, 2H), 3.23-3.14 (m, 1H), 2.79-2.68 (m, 1H), 2.64-2.56 (m, 1H), 2.25-2.01 (m, 3H), 1.97-1.81 (m, 1H), 1.47 (s, 6H), 1.00-0.89 (m, 2H), 0.61 (d, J=3.6 Hz, 2H).

Example 46: 2-((2S,6R)-4-((S)-1-(4-(3-(4-Cyano-3-(trifluoromethyl)phenyl)-5,5-dimethyl-4-oxo-2-thioxoimidazolidin-1-yl)-2-ethylphenoxy)propan-2-yl)-2,6-dimethylpiperazin-1-yl)-N-(3-((2,6-dioxopiperidin-3-yl)amino)phenyl)acetamide and 2-((2S,6R)-4-((R)-1-(4-(3-(4-cyano-3-(trifluoromethyl)phenyl)-5,5-dimethyl-4-oxo-2-thioxoimidazolidin-1-yl)-2-ethylphenoxy)propan-2-yl)-2,6-dimethylpiperazin-1-yl)-N-(3-((2,6-dioxopiperidin-3-yl)amino)phenyl)acetamide

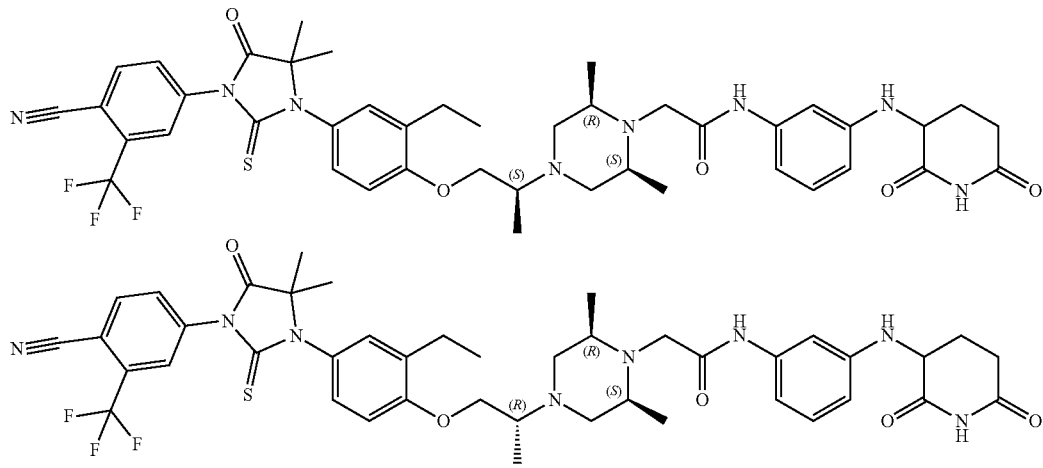

(2S,6R)-tert-Butyl 4-((S)-1-methoxy-1-oxopropan-2-yl)-2,6-dimethylpiperazine-1-carboxylate and (2S,6R)-tert-butyl 4-((R)-1-methoxy-1-oxopropan-2-yl)-2,6-dimethylpiperazine-1-carboxylate. To a mixture of (2S,6R)-tert-butyl 2,6-dimethylpiperazine-1-carboxylate (1.20 g, 5.60 mmol) and (R)-methyl 2-chloropropanoate (0.9 mL, 8.40 mmol) in DMF (10 mL) was added DIEA (2.9 mL, 16.8 mmol) in one portion at 25° C. The mixture was heated to 60° C. and stirred for 12 h. The mixture was poured into water (20 mL), and the aqueous phase was extracted with EtOAc (30 mL×3). The combined organic layers were washed with brine (30 mL×3), dried over anhydrous sodium sulfate, filtered and concentrated in vacuo. The residue was purified by silica gel chromatography (3:1 petroleum ether/EtOAc) to afford a mixture of (2S,6R)-tert-butyl 4-((S)-1-methoxy-1-oxopropan-2-yl)-2,6-dimethylpiperazine-1-carboxylate and (2S,6R)-tert-butyl 4-((R)-1-methoxy-1-oxopropan-2-yl)-2,6-dimethylpiperazine-1-carboxylate (0.70 g, 2.33 mmol, 41.6% yield) as a light yellow oil. $^1$H NMR (400 MHz, CDCl$_3$) δ 4.04-4.12 (m, 2H), 3.70 (s, 3H), 3.36 (q, J=7.2 Hz, 1H), 2.54-2.67 (m, 3H), 2.38 (dd, J=11.6, 4.4 Hz, 1H), 1.47 (s, 9H), 1.25-1.31 (m, 9H).

(2S,6R)-tert-Butyl 4-((S)-1-hydroxypropan-2-yl)-2,6-dimethylpiperazine-1-carboxylate and (2S,6R)-tert-butyl 4-((R)-1-hydroxypropan-2-yl)-2,6-dimethylpiperazine-1-carboxylate. To a solution of the mixture obtained above (0.68 g, 2.26 mmol) in THF (10 mL) was added lithium aluminum hydride (0.13 g, 3.40 mmol) portionwise at 0° C. The reaction was stirred at 0° C. for 1 h. To the reaction was added THF (12 mL) and anhydrous sodium sulfate (10 g). To the stirred mixture was then added water (2 mL) dropwise at 0° C., and the mixture was stirred at 25° C. for 0.5 h. The suspension was filtered, and the filter cake was washed with EtOAc (20 mL). The filtrate was concentrated under reduced pressure, and the residue was purified by silica gel chromatography (1:1 petroleum ether/EtOAc) to afford a mixture of (2S,6R)-tert-butyl 4-((S)-1-hydroxypropan-2-yl)-2,6-dimethylpiperazine-1-carboxylate and (2S,6R)-tert-butyl 4-((R)-1-hydroxypropan-2-yl)-2,6-dimethylpiperazine-1-carboxylate (0.56 g, 2.04 mmol, 90.2% yield) as a colorless oil. $^1$H NMR (400 MHz, CDCl$_3$) δ 4.15 (q, J=6.0 Hz, 2H), 3.43-3.51 (m, 1H), 3.33-3.42 (m, 1H), 3.25 (s, 1H), 2.82-2.92 (m, 1H), 2.77 (dd, J=11.2, 4.4 Hz, 1H), 2.40-2.58 (m, 2H), 2.29 (dd, J=11.2, 4.4 Hz, 1H), 1.58 (s, 1H), 1.48 (s, 9H), 1.23-1.36 (m, 6H), 0.88 (d, J=6.8 Hz, 3H)

(2S,6R)-tert-Butyl 4-((S)-1-(4-(3-(4-cyano-3-(trifluoromethyl)phenyl)-5,5-dimethyl-4-oxo-2-thioxoimidazolidin-1-yl)-2-ethylphenoxy)propan-2-yl)-2,6-dimethylpiperazine-1-carboxylate and (2S,6R)-tert-butyl 4-((R)-1-(4-(3-(4-cyano-3-(trifluoromethyl)phenyl)-5,5-dimethyl-4-oxo-2-thioxoimidazolidin-1-yl)-2-ethylphenoxy)propan-2-yl)-2,6-dimethylpiperazine-1-carboxylate. To a mixture of 4-(3-(3-ethyl-4-hydroxyphenyl)-4,4-dimethyl-5-oxo-2-thioxoimidazolidin-1-yl)-2-(trifluoromethyl)benzonitrile (0.50 g, 1.15 mmol) and the mixture obtained above (0.47 g, 1.73 mmol) in toluene (4 mL) was added (E)-diazene-1,2-diylbis(piperidin-1-ylmethanone) (0.58 g, 2.31 mmol) at 25° C. under nitrogen. The mixture was cooled to 0° C., and tributylphosphine (0.57 mL, 2.31 mmol) was added dropwise. The mixture was then heated to 110° C. and stirred for 12 h. The mixture was concentrated under reduced pressure at 45° C. The residue was purified by silica gel chromatography (2:1 petroleum ether/EtOAc) to afford a mixture of (2S,6R)-tert-butyl 4-((S)-1-(4-(3-(4-cyano-3-(trifluoromethyl)phenyl)-5,5-dimethyl-4-oxo-2-thioxoimidazolidin-1-yl)-2-ethylphenoxy)propan-2-yl)-2,6-dimethylpiperazine-1-carboxylate and (2S,6R)-tert-butyl 4-((R)-1-(4-(3-(4-cyano-3-(trifluoromethyl)phenyl)-5,5-dimethyl-4-oxo-2-thioxoimidazolidin-1-yl)-2-ethylphenoxy)propan-2-yl)-2,6- dimethylpiperazine-1-carboxylate (0.70 g, 1.02 mmol, 88.2% yield) as a light yellow solid. MS (ESI) m/z 688.2 [M+1]$^+$; $^1$H NMR (400 MHz, CDCl$_3$) δ 7.95-8.01 (m, 2H), 7.85 (dd, J=8.4, 2.0 Hz, 1H), 7.03-7.11 (m, 2H), 6.93 (d, J=8.4 Hz, 1H), 4.05-4.11 (m, 3H), 3.85-3.96 (m, 1H), 3.05-3.19 (m, 1H), 2.62-2.74 (m, 5H), 1.58 (s, 6H), 1.47 (s, 9H), 1.27-1.32 (m, 9H), 1.21-1.25 (m, 3H)

4-(3-(4-((S)-2-((3S,5R)-3,5-Dimethylpiperazin-1-yl)propoxy)-3-ethylphenyl)-4,4-dimethyl-5-oxo-2-thioxoimidazolidin-1-yl)-2-(trifluoromethyl)benzonitrile and 4-(3-(4-((R)-2-((3S,5R)-3,5-dimethylpiperazin-1-yl)propoxy)-3-ethylphenyl)-4,4-dimethyl-5-oxo-2-thioxoimidazolidin-1-yl)-2-(trifluoromethyl)benzonitrile. To a solution of the mixture obtained above (0.70 g, 1.02 mmol, 1 eq) in DCM (15 mL) was added TFA (7.70 g, 67.5 mmol, 5 mL, 66.4 eq) in one portion at 0° C. under N$_2$. The mixture was stirred at 25° C. for 1 h. The mixture was purified by semi-preparative, reverse-phase HPLC (29-49% acetonitrile in water+ 0.1% TFA, 10 min). The mixture was concentrated under reduced pressure at 45° C. to remove the acetonitrile, and the aqueous phase was adjusted to pH 8 by a saturated aqueous solution of sodium bicarbonate. The aqueous phase was extracted with DCM (50 mL×3), and the combined organic phases were washed with brine (50 mL×3), dried over anhydrous sodium sulfate, filtered and concentrated in vacuo. The desired mixture of products 4-(3-(4-((S)-2-((3S,5R)-3,5-dimethylpiperazin-1-yl)propoxy)-3-ethylphenyl)-4,4-dimethyl-5-oxo-2-thioxoimidazolidin-1-yl)-2-(trifluoromethyl)benzonitrile and 4-(3-(4-((R)-2-((3S,5R)-3,5-dimethylpiperazin-1-yl)propoxy)-3-ethylphenyl)-4,4-dimethyl-5-oxo-2-thioxoimidazolidin-1-yl)-2-(trifluoromethyl)benzonitrile (0.48 g, 0.81 mmol, 79.4% yield, 99% purity) was isolated as a light yellow oil. MS (ESI) m/z 588.2 [M+1]$^+$ Enantiomer 1 and 2 of 4-(3-(4-((S or R)-2-((3S,5R)-3,5-Dimethylpiperazin-1-yl)propoxy)-3-ethylphenyl)-4,4-dimethyl-5-oxo-2-thioxoimidazolidin-1-yl)-2-(trifluoromethyl)benzonitrile. The mixture obtained above (0.48 g, 0.81 mmol) was purified by chiral SFC (column: Phenomenex-Cellulose-2 (250 mm×30 mm, 10 μm); mobile phase: 50% 0.1% ammonia in 2-propanol, 3.7 min) to afford 2 peaks for which the chirality was not determined.

Enantiomer 2 (0.27 g, 0.46 mmol, 55.8% yield, 99.6% purity) was obtained as a light yellow oil. $^1$H NMR (400 MHz, CDCl$_3$) δ 7.95-8.01 (m, 2H), 7.85 (d, J=8.4 Hz, 1H), 7.03-7.11 (m, 2H), 6.93 (d, J=8.4 Hz, 1H), 4.09-4.14 (m, 1H), 3.89-3.99 (m, 1H), 3.01-3.14 (m, 1H), 2.87-2.98 (m, 2H), 2.75-2.85 (m, 2H), 2.70 (q, J=7.2 Hz, 2H), 2.02-2.09 (m, 2H), 1.58 (s, 6H), 1.22-1.26 (m, 6H), 1.08 (d, J=6.0 Hz, 6H)

Enantiomer 1 (0.14 g, 0.24 mmol, 28.8% yield, 96.1% purity) was obtained as a light yellow oil. $^1$H NMR (400 MHz, CDCl$_3$) δ 7.95-8.02 (m, 2H), 7.85 (d, J=8.4 Hz, 1H), 7.03-7.12 (m, 2H), 6.93 (d, J=8.4 Hz, 1H), 4.10-4.13 (m, 1H), 3.91-3.97 (m, 1H), 3.03-3.15 (m, 1H), 2.89-3.00 (m, 2H), 2.81 (t, J=12.4 Hz, 2H), 2.70 (q, J=7.60 Hz, 2H), 2.05-2.18 (m, 2H), 1.58 (s, 6H), 1.21-1.26 (m, 6H), 1.09 (d, J=6.0 Hz, 6H);

Enantiomer 2 of 2-((2S,6R)-4-((S or R)-1-(4-(3-(4-Cyano-3-(trifluoromethyl)phenyl)-5,5-dimethyl-4-oxo-2-thioxoimidazolidin-1-yl)-2-ethylphenoxy)propan-2-yl)-2,6-dimethylpiperazin-1-yl)-N-(3-((2,6-dioxopiperidin-3-yl)amino)phenyl)acetamide. To a mixture of enantiomer 2 obtained above (0.22 g, 0.37 mmol, 1 eq) and 2-chloro-N-(3-((2,6-dioxopiperidin-3-yl)amino)phenyl)acetamide (0.17 g, 0.56 mmol, 1.5 eq) in DMF (5 mL) was added DIEA (0.15 g, 1.12 mmol, 0.2 mL, 3 eq) and potassium iodide (0.03 g, 0.19 mmol, 0.5 eq) in one portion at 25° C. The mixture was heated to 50° C. and stirred for 12 h. The mixture was cooled to 25° C., and the residue was poured into water (10 mL). The aqueous phase was extracted with EtOAc (10 mL×3), and the combined organic phases were washed with brine (10 mL×3), dried over anhydrous sodium sulfate, filtered and concentrated in vacuo. The residue was purified by standard methods to afford enantiomer 2 of 2-((2S,6R)-4-((S or R)-1-(4-(3-(4-cyano-3-(trifluoromethyl)phenyl)-5,5-dimethyl-4-oxo-2-thioxoimidazolidin-1-yl)-2-ethylphenoxy)propan-2-yl)-2,6-dimethylpiperazin-1-yl)-N-(3-((2,6-dioxopiperidin-3-yl)amino)phenyl)acetamide (0.12 g, 0.13 mmol, 34.9% yield, 99.0% purity, hydrochloride). MS (ESI) m/z 847.3 [M+1]$^+$; $^1$H NMR (400 MHz, DMSO-d$_6$+D$_2$O) δ 8.37 (d, J=8.4 Hz, 1H), 8.28 (d, J=1.6 Hz, 1H), 8.06 (dd, J=8.0, 1.6 Hz, 1H), 7.10-7.26 (m, 3H), 7.00-7.08 (m, 1H), 6.90-6.95 (m, 1H), 6.78-6.87 (m, 1H), 6.46 (dd, J=8.0, 2.0 Hz, 1H), 4.40-4.47 (m, 1H), 4.30-4.38 (m, 1H), 4.25 (dd, J=11.2, 4.8 Hz, 1H), 4.10-4.22 (m, 2H), 3.86-4.08 (m, 3H), 3.55-3.80 (m, 4H), 2.68-2.79 (m, 2H), 2.54-2.65 (m, 2H), 2.03-2.13 (m, 1H), 1.84-1.96 (m, 1H), 1.51 (d, J=6.8 Hz, 3H), 1.49 (s, 6H), 1.32 (d, J=4.8 Hz, 6H), 1.17 (t, J=7.6 Hz, 3H).

Enantiomer 1 was prepared via the same method (0.058 g, 0.063 mmol, 16.82% yield, 95.29% purity, hydrochloride). MS (ESI) m/z 847.4 [M+1]$^+$; 1H NMR (400 MHz, DMSO-d$_6$) δ 10.79 (s, 1H), 8.38-8.40 (d, J=8.0 Hz, 1H), 8.29 (d, J=1.6 Hz, 1H), 8.06-8.08 (d, J=8.4 Hz, 1H), 7.17-7.23 (m, 3H), 7.02-7.06 (m, 1H), 6.96 (br, s, 1H), 6.81-6.83 (d, J=8.0 Hz, 1H), 6.44-6.46 (d, J=8.8 Hz, 1H), 4.36-4.43 (m, 2H), 4.24-4.28 (m, 1H), 3.85 (m, 2H), 3.66 (m, 7H), 2.69-2.78 (m, 3H), 2.57-2.61 (m, 1H), 2.08-2.11 (m, H), 1.86-1.95 (m, 1H), 1.50 (s, 9H), 1.30 (m, 6H), 1.16-1.20 (d, J=7.6 Hz, 3H).

Example 47: 2-((2S,6R)-4-((R)-2-(4-(3-(6-Cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazin-1-yl)-N-(3-((2,6-dioxopiperidin-3-yl)amino)phenyl)acetamide and 2-((2S,6R)-4-((S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazin-1-yl)-N-(3-((2,6-dioxopiperidin-3-yl)amino)phenyl)acetamide

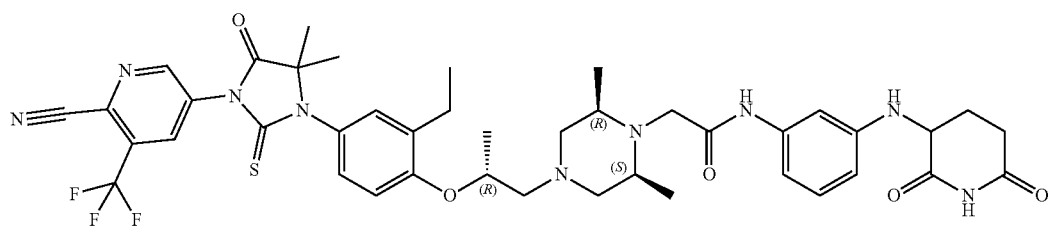

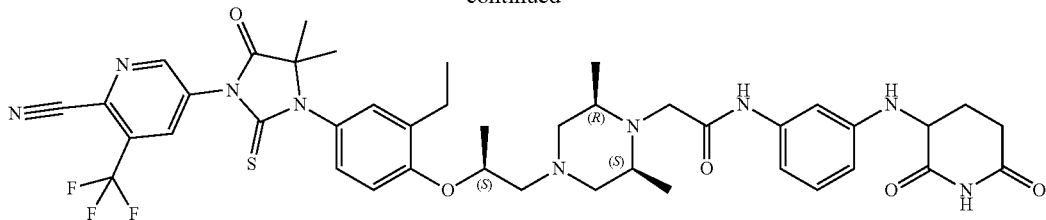

(2S,6R)-tert-Butyl 4-((S)-2-hydroxypropyl)-2,6-dimethylpiperazine-1-carboxylate and (2S,6R)-tert-butyl 4-((R)-2-hydroxypropyl)-2,6-dimethylpiperazine-1-carboxylate. A mixture of (2S,6R)-tert-butyl 2,6-dimethylpiperazine-1-carboxylate (1.50 g, 7.00 mmol) and (S)-2-methyloxirane (588 uL, 8.40 mmol) in water (10 mL) was stirred for 20 h at 70° C. Water (10 mL) was added to the reaction mixture, which was then extracted with DCM (10 mL×2). The combined organic layers were dried over anhydrous sodium sulfate, filtered and concentrated under reduced pressure to give a mixture of (2S,6R)-tert-butyl 4-((S)-2-hydroxypropyl)-2,6-dimethylpiperazine-1-carboxylate and (2S,6R)-tert-butyl 4-((R)-2-hydroxypropyl)-2,6-dimethylpiperazine-1-carboxylate (1.80 g, 6.61 mmol, 94.4% yield) as crude colorless oil. $^1$H NMR (400 MHz, CDCl$_3$) δ 4.08-4.14 (m, 2H), 3.79-3.88 (m, 1H), 3.40 (s, 1H), 2.73-2.76 (d, J=11.2 Hz, 1H), 2.56-2.58 (m, 1H), 2.43-2.46 (m, 1H), 2.21-2.30 (m, 2H), 2.08-2.12 (d, J=11.2, 4.4 Hz, 1H), 1.46 (s, 9H), 1.27-1.31 (m, 6H), 1.14-1.16 (d, J=6.0 Hz, 3H).

(2S,6R)-tert-Butyl 4-((R)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazine-1-carboxylate and (2S,6R)-tert-butyl 4-((S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazine-1-carboxylate. To a solution of the mixture obtained above (0.60 g, 2.20 mmol, 1 eq) and 5-(3-(3-ethyl-4-hydroxyphenyl)-4,4-dimethyl-5-oxo-2-thioxoimidazolidin-1-yl)-3-(trifluoromethyl)picolinonitrile (0.96 g, 2.20 mmol, 1 eq) in anhydrous THF (1 mL) was added PPh$_3$ (0.69 g, 2.64 mmol, 1.2 eq), followed by (E)-diisopropyl diazene-1,2-dicarboxylate (1.34 g, 6.61 mmol, 1.28 mL, 3 eq) at 0° C., and then the reaction mixture was warmed to 20° C. for 12 h under a nitrogen atmosphere. The mixture was concentrated under reduced pressure to give a residue. The residue was purified by semi-preparative, reverse-phase HPLC (48-68% acetonitrile in water+0.1% TFA, 10 min) and repurified by semi-preparative, reverse phase HPLC (43-63% acetonitrile in water+0.1% TFA, 10 min). The pH of the collected fractions was adjusted to 7-8 with saturated sodium bicarbonate, and the fractions were concentrated to removed organic volatiles. The aqueous solution was extracted with EtOAc (30 mL×3), and the combined organic layers were dried over anhydrous sodium sulfate, filtered and concentrated under reduced pressure to give a mixture of (2S,6R)-tert-butyl 4-((R)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazine-1-carboxylate and (2S,6R)-tert-butyl 4-((S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazine-1-carboxylate (0.45 g, 0.65 mmol, 29.6% yield) as a brown solid and chiral SFC showed 31% ee. MS (ESI) m/z 689.2 [M+1]$^+$; $^1$H NMR (400 MHz, CDCl$_3$) δ 9.10 (s, 1H), 8.37 (s, 1H), 6.99-7.06 (m, 3H), 4.57-4.62 (m, 1H), 4.07-4.10 (m, 2H), 2.65-2.73 (m, 5H), 2.51-2.56 (m, 1H), 2.27-2.33 (m, 2H), 1.60 (s, 6H), 1.47 (s, 9H), 1.44-1.45 (d, J=6.0 Hz, 1H), 1.26-1.27 (m, 6H), 1.20-1.24 (m, 3H).

Enantiomers 1 and 2 of (2S,6R)-tert-butyl 4-((R or S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazine-1-carboxylate. The two enantiomers of (2S,6R)-tert-butyl 4-((R)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazine-1-carboxylate (0.45 g, 0.65 mmol, 1 eq) and (2S,6R)-tert-butyl 4-((S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazine-1-carboxylate (0.20 g, 0.29 mmol, 0.44 eq) were separated by chiral SFC (column: Chiralpak AD-3 (50×4.6 mm ID, 3 μm); mobile phase: phase A carbon dioxide, and phase B isopropanol (0.05% diisopropylamine); gradient elution: 5-40% IP (0.05% DIEA) in carbon dioxide; flow rate: 3 mL/min; wavelength: 220 nm; column temp: 35° C.; back pressure: 100 bar). The two enantiomers were then further purified by chiral HPLC (column: DAICEL CHIRALPAK AD (250 mm×30 mm, 10 μm); mobile phase: 20% 0.1% ammonia in isopropanol, 4.5 min, 60 min). The chirality of the two products was not determined.

Enantiomer 1 (0.34 g, 0.49 mmol, 75.4% yield, 99.7% purity) was obtained as a brown solid with 100% ee. $^1$H NMR (400 MHz, CDCl$_3$) δ 9.10 (d, J=2.0 Hz, 1H), 8.37 (d, J=2.0 Hz, 1H), 7.05-7.07 (m, 2H), 6.99-7.01 (m, 1H), 4.56-4.63 (m, 1H), 4.05-4.11 (m, 2H), 2.61-2.73 (m, 5H), 2.51-2.56 (m, 1H), 2.27-2.33 (m, 2H), 1.60 (s, 6H), 1.47 (s, 9H), 1.44-1.45 (d, J=6.0 Hz, 3H), 1.25-1.27 (m, 6H), 1.22-1.23 (m, 3H);

Enantiomer 2 (0.18 g, 0.26 mmol, 39.8% yield, 99.4% purity) was obtained as a brown solid with 100% ee. $^1$H NMR (400 MHz, CDCl$_3$) δ 9.10 (d, J=2.0 Hz, 1H), 8.37 (d, J=2.0 Hz, 1H), 7.05-7.07 (m, 2H), 6.99-7.01 (m, 1H), 4.56-4.63 (m, 1H), 4.07-4.10 (m, 2H), 2.65-2.73 (m, 5H), 2.51-2.56 (m, 1H), 2.27-2.33 (m, 2H), 1.60 (s, 6H), 1.47 (s, 9H), 1.44-1.45 (d, J=6.0 Hz, 3H), 1.25-1.27 (m, 6H), 1.22-1.23 (m, 3H).

Enantiomers 1 and 2 of 5-(3-(4-(((R or S)-1-((3S,5R)-3,5-Dimethylpiperazin-1-yl)propan-2-yl)oxy)-3-ethylphenyl)-4,4-dimethyl-5-oxo-2-thioxoimidazolidin-1-yl)-3-(trifluoromethyl)picolinonitrile. To a solution of enantiomer 1, (2S,6R)-tert-butyl 4-((R or S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazine-1-carboxylate (0.34 g, 0.49 mmol, 1 eq), in DCM (6 mL) was added TFA (3.08 g, 27.0 mmol, 2 mL, 54.7 eq), and the mixture was stirred for 2 h at 20° C. The reaction mixture was poured into saturated ammonium chloride (10 mL) and extracted with DCM (10 mL×2). The combined organic layers were dried over anhydrous sodium sulfate, filtered and concentrated under reduced pressure to give crude enantiomer 1 of 5-(3-(4-(((R or S)-1-((3S,5R)-3,5-dimethylpiperazin-1-yl)propan-2-yl)oxy)-3-ethylphenyl)-4,4-dimethyl-5-oxo-2-thioxoimidazolidin-1-yl)-3-(trifluoromethyl)picolinonitrile (0.24 g, 0.41 mmol, 82.6% yield) as a brown solid. MS (ESI) m/z 589.2 [M+1]⁺.

Enantiomer 2 of 5-(3-(4-(((R or S)-1-((3S,5R)-3,5-dimethylpiperazin-1-yl)propan-2-yl)oxy)-3-ethylphenyl)-4,4-dimethyl-5-oxo-2-thioxoimidazolidin-1-yl)-3-(trifluoromethyl)picolinonitrile was prepared using the same methods and gave a yellow oil. (130 mg, crude) MS (ESI) m/z 589.3 [M+1]⁺.

Enantiomers 1 and 2 of 2-((2S,6R)-4-((R or S)-2-(4-(3-(6-Cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazin-1-yl)-N-(3-((2,6-dioxopiperidin-3-yl)amino)phenyl)acetamide. To a solution of enantiomer 1, 5-(3-(4-(((R or S)-1-((3S,5R)-3,5-dimethylpiperazin-1-yl)propan-2-yl)oxy)-3-ethylphenyl)-4,4-dimethyl-5-oxo-2-thioxoimidazolidin-1-yl)-3-(trifluoromethyl)picolinonitrile (0.24 g, 0.41 mmol, 1 eq), and 2-chloro-N-[3-[(2,6-dioxo-3-piperidyl)amino]phenyl]acetamide (0.12 g, 0.41 mmol, 1 eq) in DMF (2.5 mL) was added DIEA (0.16 g, 1.22 mmol, 213 μL, 3 eq), followed by potassium iodide (0.03 g, 0.20 mmol, 0.5 eq). The reaction mixture was stirred for 12 h at 60° C., and then concentrated under reduced pressure to give a residue. The residue was purified by standard methods to afford enantiomer 1 of 2-((2S,6R)-4-((R or S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazin-1-yl)-N-(3-((2,6-dioxopiperidin-3-yl)amino)phenyl)acetamide (0.14 g, 0.15 mol, 38.4% yield, 97.0% purity, hydrochloride). MS (ESI) m/z 848.4 [M+1]⁺; ¹H NMR (400 MHz, DMSO-d₆) δ 10.81 (s, 1H), 9.25-9.26 (d, J=2.0 Hz, 1H), 8.83-8.84 (d, J=2.0 Hz, 1H), 7.27-7.29 (m, 1H), 7.16-7.21 (m, 2H), 7.03-7.07 (m, 1H), 6.98 (s, 1H), 6.86-6.88 (d, J=8.0 Hz, 1H), 6.46-6.48 (d, J=6.8 Hz, 1H), 5.19 (s, 1H), 4.25-4.29 (m, 5H), 3.73 (m, 3H), 3.48 (m, 3H), 2.67-2.79 (m, 3H), 2.57-2.63 (m, 1H), 2.07-2.11 (m, 1H), 1.86-1.96 (m, 1H), 1.53 (s, 6H), 1.30-1.38 (m, 9H), 1.15-1.19 (t, J=7.8 Hz, 3H).

Enantiomer 2 of 2-((2S,6R)-4-((R or S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazin-1-yl)-N-(3-((2,6-dioxopiperidin-3-yl)amino)phenyl)acetamide (0.088 g, 0.104 mmol, 45.20% yield, 100% purity, hydrochloride) was obtained using the same method. MS (ESI) m/z 848.3 [M+1]⁺; ¹H NMR (400 MHz, DMSO-d₆) δ 11.05-10.35 (m, 2H), 9.25 (d, J=2.0 Hz, 1H), 8.83 (d, J=2.0 Hz, 1H), 7.31-7.23 (m, 1H), 7.23-7.13 (m, 2H), 7.09-6.95 (m, 2H), 6.87 (d, J=8.0 Hz, 1H), 6.47 (d, J=7.2 Hz, 1H), 5.20 (s, 1H), 4.45-4.00 (m, 5H), 3.94-3.25 (m, 6H), 2.79-2.54 (m, 4H), 2.14-2.03 (m, 1H), 1.97-1.83 (m, 1H), 1.52 (s, 6H), 1.34-1.24 (m, 9H), 1.16 (t, J=7.6 Hz, 3H).

Example 48: 2-((2R,6S)-4-(2-(4-(3-(6-Cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)-N-(3-((2,6-dioxopiperidin-3-yl)amino)phenyl)acetamide

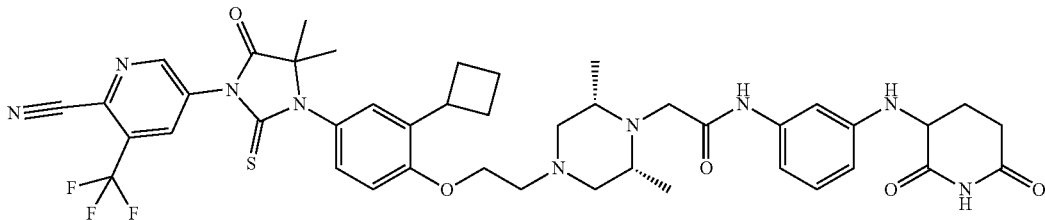 [SMILES: C[C@@H]1CN(CCOc2ccc(N3C(=S)N(c4cnc(C#N)c(C(F)(F)F)c4)C(=O)C3(C)C)cc2C2CCC2)C[C@H](C)N1CC(=O)Nc1cccc(NC2CCC(=O)NC2=O)c1]

1-(Benzyloxy)-2-bromo-4-nitrobenzene. To a mixture of 2-bromo-4-nitrophenol (50.0 g, 0.229 mol, 1 eq) and bromomethylbenzene (47.0 g, 0.27 mol, 1.2 eq) in acetonitrile (500 mL) was added potassium carbonate (63.4 g, 0.46 mol, 2 eq), and the reaction mixture was stirred for 12 h at 80° C. The reaction mixture was concentrated under reduced pressure to remove the acetonitrile. Water was added, the mixture was filtered, and the filter cake was washed with water. The crude product was triturated with 20:1 petroleum ether/EtOAc, stirring at 25° C. for 30 min and then filtering to afford 1-(benzyloxy)-2-bromo-4-nitrobenzene (68.0 g, 0.22 mol, 96.2% yield) as yellow solid. ¹H NMR (400 MHz, CDCl₃) δ 8.48-8.49 (d, J=2.8 Hz, 1H), 8.16-819 (dd, J=9.2 Hz, 2.8 Hz, 1H), 7.35-7.48 (m, 5H), 6.99-7.02 (d, J=9.2 Hz, 1H), 5.28 (s, 2H).

1-(Benzyloxy)-2-cyclobutyl-4-nitrobenzene. To a solution of 1-(benzyloxy)-2-bromo-4-nitrobenzene (5.00 g, 16.2 mmol, 1 eq) and cyclobutylboronic acid (2.43 g, 24.3 mmol, 1.5 eq) in toluene (50 mL) and water (10 mL) was added cesium carbonate (15.8 g, 48.6 mmol, 3 eq), followed by Pd(dppf)₂Cl₂ (1.19 g, 1.62 mmol, 10 mol %). The reaction mixture was stirred for 48 h at 100° C. under nitrogen atmosphere. The reaction mixture was poured into water and extracted with EtOAc. The combined organic layers were dried over anhydrous sodium sulfate, filtered and concentrated under reduced pressure to give a residue. The residue was purified by semi-preparative, reverse-phase HPLC (55-85% acetonitrile in water+0.1% TFA, 25 min). The pH value of the collected fractions was adjusted to 7-8 with saturated sodium bicarbonate and the fractions were concentrated to remove the organic volatiles, and the aqueous solution was extracted with EtOAc. The combined organic layers were dried over anhydrous sodium sulfate, filtered and concentrated under reduced pressure to give 1-(benzyloxy)-2-cyclobutyl-4-nitrobenzene (2.50 g, 8.82 mmol, 13.6% yield) as a white solid. MS (ESI) m/z: 284.1 [M+1]⁺; ¹H NMR (400 MHz, CDCl₃) δ 8.07-8.13 (m, 2H), 7.36-7.45 (m, 5H), 6.90-6.92 (d, J=8.8 Hz, 1H), 5.17 (s, 2H), 3.72-3.83 (m, 1H), 2.35-2.42 (m, 2H), 2.12-2.22 (m, 2H), 2.01-2.09 (m, 1H), 1.83-1.91 (m, 1H).

4-(Benzyloxy)-3-cyclobutylaniline. To a solution of 1-(benzyloxy)-2-cyclobutyl-4-nitro benzene (2.50 g, 8.82 mmol, 1 eq) in EtOH (20 mL) and water (20 mL) was added ammonium chloride (2.36 g, 44.1 mmol, 5 eq), followed by iron (1.48 g, 26.4 mmol, 3 eq). The reaction mixture was stirred for 1 h at 60° C. The reaction mixture was poured into water and extracted with EtOAc. The combined organic layers were dried over anhydrous sodium sulfate, filtered and concentrated under reduced pressure to give a residue. The residue was purified by silica gel column chromatography (8:1-3:1 petroleum ether/EtOAc) to give 4-(benzyloxy)-3-cyclobutylaniline (1.90 g, 7.50 mmol, 84.9% yield) as a brown oil. MS (ESI) m/z: 254.1 [M+1]$^+$.

2-((4-(Benzyloxy)-3-cyclobutylphenyl)amino)-2-methylpropanenitrile. To a mixture of 4-(benzyloxy)-3-cyclobutylaniline (1.10 g, 4.34 mmol) in 2-hydroxy-2-methylpropanenitrile (4.0 mL, 43.8 mmol) was added magnesium sulfate (1.31 g, 10.8 mmol). The mixture was heated to 60° C. and stirred for 12 h. The reaction was concentrated in vacuo and the residue was poured into water (30 mL). The aqueous phase was extracted with EtOAc, and the combined organic layers were washed with brine, dried over anhydrous sodium sulfate, filtered and concentrated in vacuo. The reaction was used directly in the next step without further purification. The compound 2-(4-benzyloxy-3-cyclobutyl-anilino)-2-methyl-propanenitrile (1.50 g, crude) was obtained as a yellow oil. MS (ESI) m/z 294.2 [M+1-CN]$^+$.

5-(3-(4-(Benzyloxy)-3-cyclobutylphenyl)-4,4-dimethyl-5-oxo-2-thioxoimidazolidin-1-yl)-3-(trifluoromethyl)picolinonitrile. A solution of 2-(4-benzyloxy-3-cyclobutyl-anilino)-2-methyl-propanenitrile (1.50 g, 4.68 mmol) and 5-isothiocyanato-3-(trifluoromethyl)picolinonitrile (1.29 g, 5.62 mmol) in DMF (10 mL) was stirred at 25° C. for 1 h. To the solution was added hydrochloric acid in MeOH (4 M, 5.85 mL), and the reaction was stirred at 80° C. for 1 h. The residue was poured into water (50 mL), and the aqueous phase was extracted with EtOAc. The combined organic layers were washed with brine, dried over anhydrous sodium sulfate, filtered and concentrated in vacuo. The crude product was purified by semi-preparative reverse phase HPLC (85-98% acetonitrile in water+0.2% hydrochloric acid, over 12 min). The residue was poured into a saturated aqueous solution of sodium bicarbonate (30 mL), and the aqueous phase was extracted with EtOAc, which was dried over anhydrous sodium sulfate, filtered and concentrated in vacuo. The compound 5-(3-(4-(benzyloxy)-3-cyclobutylphenyl)-4,4-dimethyl-5-oxo-2-thioxoimidazolidin-1-yl)-3-(trifluoromethyl)picolinonitrile (1.18 g, 2.14 mmol, 45.8% yield) was obtained as a yellow oil. MS (ESI) m/z 551.3 [M+1]$^+$; $^1$H NMR (400 MHz, CDCl$_3$) δ 9.09-9.14 (d, J=2.4 Hz, 1H), 8.37-8.40 (d, J=2.4 Hz, 1H), 7.34-7.48 (m, 5H), 7.05-7.12 (m, 2H), 6.96-7.02 (m, 1H), 5.11 (s, 2H), 3.75-3.88 (m, 1H), 2.31-2.43 (m, 2H), 2.06-2.19 (m, 3H), 1.78-1.87 (m, 1H), 1.62 (s, 6H).

5-(3-(3-Cyclobutyl-4-hydroxyphenyl)-4,4-dimethyl-5-oxo-2-thioxoimidazolidin-1-yl)-3-(trifluoromethyl)picolinonitrile. To a solution of 5-(3-(4-(benzyloxy)-3-cyclobutylphenyl)-4,4-dimethyl-5-oxo-2-thioxoimidazolidin-1-yl)-3-(trifluoromethyl)picolinonitrile (1.18 g, 2.14 mmol) in DCM (15 mL) was added tribromoborane (1.61 g, 6.43 mmol) at −70° C. under nitrogen. The reaction mixture was stirred at −70° C. for 1 h. The reaction mixture was quenched by addition of saturated sodium bicarbonate solution (30 mL) at −20° C. and further dilution with water (20 mL). The organic phase was separated, and the aqueous phase was extracted with EtOAc. The combined organic layers were dried over anhydrous sodium sulfate, filtered and concentrated under reduced pressure to give a residue. The crude product was purified by silica gel chromatography (0-25% EtOAc/petroleum ether) to give 5-(3-(3-cyclobutyl-4-hydroxyphenyl)-4,4-dimethyl-5-oxo-2-thioxoimidazolidin-1-yl)-3-(trifluoromethyl)picolinonitrile (0.53 g, 1.15 mmol, 53.7% yield) as a yellow solid. MS (ESI) m/z 461.2 [M+1]$^+$; $^1$H NMR (400 MHz, CDCl$_3$) δ 9.09-9.12 (d, J=2.4 Hz, 1H), 8.37-8.39 (d, J=2.0 Hz, 1H), 7.03-7.06 (d, J=2.4 Hz, 1H), 6.98-7.02 (m, 1H), 6.87-6.91 (d, J=8.4 Hz, 1H), 5.08 (s, 1H), 3.65-3.75 (m, 1H), 2.38-2.47 (m, 2H), 2.08-2.23 (m, 3H), 1.86-1.94 (m, 1H), 1.62 (s, 6H).

tert-Butyl 2-((2R,6S)-4-(2-(4-(3-(6-cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)acetate. To a solution of 5-(3-(3-cyclobutyl-4-hydroxyphenyl)-4,4-dimethyl-5-oxo-2-thioxoimidazolidin-1-yl)-3-(trifluoromethyl)picolinonitrile (0.33 g, 0.71 mmol, 1 eq), tert-butyl 2-((2R,6S)-4-(2-hydroxyethyl)-2,6-dimethylpiperazin-1-yl)acetate (0.39 g, 1.43 mmol, 2 eq), and PPh$_3$ (0.37 g, 1.43 mmol, 2 eq) in THF (2 mL) was added (E)-diisopropyldiazene-1,2-dicarboxylate (0.28 g, 1.43 mmol, 2 eq) at 0° C. The reaction was stirred at 50° C. for 16 h. The reaction mixture was concentrated under reduced pressure to give a residue, and the crude product was purified by semi-preparative, reverse phase HPLC (50-70% acetonitrile in water+0.1% TFA, 10 min). The residue was poured into saturated aqueous solution of sodium bicarbonate, and the aqueous phase was extracted with EtOAc, dried over anhydrous sodium sulfate, filtered and concentrated in vacuo. The compound tert-butyl 2-((2R,6S)-4-(2-(4-(3-(6-cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)acetate (0.16 g, 0.22 mmol, 32.0% yield) was obtained as a yellow solid. MS (ESI) m/z 715.5 [M+1]$^+$; $^1$H NMR (400 MHz, CDCl$_3$) δ 9.12-9.19 (d, J=2.0 Hz, 1H), 8.64-8.68 (d, J=2.0 Hz, 1H), 7.11-7.19 (m, 2H), 7.00-7.06 (d, J=8.8 Hz, 1H), 4.15-4.23 (t, J=5.2 Hz, 2H), 3.72-3.82 (m, 1H), 3.44 (s, 2H), 2.97-3.09 (m, 2H), 2.88-2.96 (m, 2H), 2.80-2.86 (t, J=5.6 Hz, 2H), 2.31-2.42 (m, 2H), 2.02-2.16 (m, 5H), 1.80-1.89 (m, 1H), 1.57 (s, 6H), 1.47 (s, 9H), 1.06-1.13 (d, J=6.4 Hz, 6H).

2-((2R,6S)-4-(2-(4-(3-(6-Cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)acetic acid. A solution of tert-butyl 2-((2R,6S)-4-(2-(4-(3-(6-cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)acetate (0.16 g, 0.23 mmol, 1 eq) was treated with hydrochloric acid in dioxane (4 M, 3.32 mL, 57.1 eq) and stirred at 25° C. for 10 h. The reaction mixture was concentrated under reduced pressure to give crude 2-((2R,6S)-4-(2-(4-(3-(6-cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)acetic acid (0.16 g, crude, Hydrochloride) as a white solid. MS (ESI) m/z 659.1 [M+1]$^+$.

2-((2R,6S)-4-(2-(4-(3-(6-Cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)-N-(3-((2,6-dioxopiperidin-3-yl)amino)phenyl)acetamide. To a mixture of 3-((3-aminophenyl)amino)piperidine-2,6-dione (0.08 g, 0.34 mmol, 1.5 eq, Hydrochloride), 2-((2R,6S)-4-(2-(4-(3-(6-cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)acetic acid (0.15 g, 0.22 mmol, 1 eq), HATU (0.13 g, 0.34 mmol, 1.5 eq) in DMF (1 mL) was added DIEA (0.14 g, 1.14 mmol, 5 eq), and the reaction was stirred at 25° C. for 12 h. The mixture was poured into water (50 mL), the aqueous phase was extracted with EtOAc, and the combined organic layers were washed with brine (30 mL×5), dried over anhydrous sodium sulfate, filtered and concentrated in vacuo. The residue was purified by standard methods to afford 2-((2R,6S)-4-(2-(4-

(3-(6-cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)-N-(3-((2,6-dioxopiperidin-3-yl)amino)phenyl)acetamide (72.0 mg, 0.08 mmol, 36.0% yield, 98% purity). MS (ESI) m/z 860.3 [M+1]$^+$; $^1$H NMR (400 MHz, DMSO-d$_6$) δ 10.76 (s, 1H), 9.34 (s, 1H), 9.25 (s, 1H), 8.82 (s, 1H), 7.07-7.17 (m, 3H), 6.96-7.04 (m, 2H), 6.76-6.82 (d, J=8.0 Hz, 1H), 6.37-6.44 (d, J=8.0 Hz, 1H), 5.84-5.92 (d, J=7.6 Hz, 1H), 4.28 (br s, 1H), 4.14 (s, 2H), 3.64-3.75 (m, 1H), 3.21 (s, 2H), 2.85-2.95 (d, J=10.8 Hz, 2H), 2.73 (br s, 5H), 2.54-2.64 (m, 1H), 2.29-2.36 (m, 2H), 1.76-2.09 (m, 8H), 1.52 (s, 6H), 0.96-1.02 (d, J=5.6 Hz, 6H).

Example 49: 2-((2R,6S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-((2,6-dioxopiperidin-3-yl)amino)phenyl)acetamide

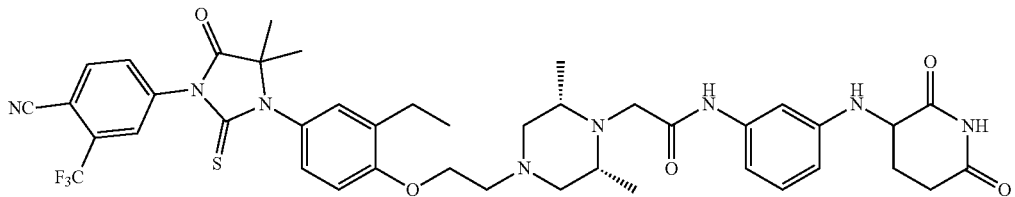 [SMILES: CCc1cc(N2C(=S)N(c3ccc(C#N)c(C(F)(F)F)c3)C(=O)C2(C)C)ccc1OCCN1C[C@@H](C)N(CC(=O)Nc2cccc(NC3CCC(=O)NC3=O)c2)[C@@H](C)C1]

tert-Butyl (3S,5R)-4-(2-(tert-butoxy)-2-oxoethyl)-3,5-dimethylpiperazine-1-carboxylate. To a solution of tert-butyl (3S,5R)-3,5-dimethylpiperazine-1-carboxylate (1.20 g, 5.60 mmol, 1.00 eq) in DMF (7.2 mL) was added tert-butyl 2-bromoacetate (1.31 g, 6.72 mmol, 0.993 mL, 1.20 eq), sodium iodide (0.25 g, 1.68 mmol, 0.30 eq) and DIEA (2.17 g, 16.8 mmol, 2.93 mL, 3.00 eq) at 15° C. The resulting mixture was stirred at 60° C. for 12 h. The mixture was diluted with water (21.0 mL) and extracted with EtOAc (5.0 mL×2), and the combined organic layers were washed with brine (5.0 mL), dried over anhydrous sodium sulfate, filtered and concentrated under reduced pressure to give a residue. The residue was purified by silica gel column chromatography (100:1-0:1 petroleum ether/EtOAc) to give tert-Butyl (3S,5R)-4-(2-(tert-butoxy)-2-oxoethyl)-3,5-dimethylpiperazine-1-carboxylate (1.80 g, crude) as a yellow oil.

tert-Butyl 2-((2S,6R)-2,6-dimethylpiperazin-1-yl)acetate. To a solution of tert-butyl (3S,5R)-4-(2-(tert-butoxy)-2-oxoethyl)-3,5-dimethylpiperazine-1-carboxylate (1.80 g, 5.42 mmol, 1.00 eq) in MeOH (18.0 mL) was added hydrochloric acid/MeOH (18.0 mL) at 10° C. The resulting mixture was stirred at 10° C. for 12 h. The mixture was quenched with saturated sodium bicarbonate to a pH of 8, concentrated under reduced pressure, and then extracted with EtOAc (10.0 mL×2). The combined organic layers were washed with brine (10.0 mL), dried over anhydrous sodium sulfate, filtered and concentrated under reduced pressure. tert-Butyl 2-((2S,6R)-2,6-dimethylpiperazin-1-yl)acetate (1.08 g, 4.73 mmol, 86.3% yield) was obtained as a yellow oil. $^1$H NMR (400 MHz, MeOD) δ 3.44 (s, 2H), 2.81-2.89 (m, 4H), 2.44 (t, J=1.6 Hz, 2H), 1.477 (s, 9H), 1.05 (d, J=3.0 Hz, 6H).

2-Bromo-1-(2-bromoethoxy)-4-nitrobenzene. To a solution of 2-bromo-4-nitrophenol (1.60 g, 7.34 mmol, 1.0 eq) in acetonitrile (12.8 mL) was added potassium carbonate (2.03 g, 14.7 mmol, 2.0 eq) and 1,2-dibromoethane (13.8 g, 73.4 mmol, 5.54 mL, 10.0 eq) at 15° C. The mixture was stirred at 90° C. for 12 h. The reaction mixture was filtered, and the filtrate was concentrated to give a yellow oil. Petroleum ether (10.0 mL) was added to the oil while stirring, and a yellow solid formed, filtered and purified by silica gel column chromatography (50:1-0:1 petroleum ether/EtOAc). 2-Bromo-1-(2-bromoethoxy)-4-nitrobenzene (1.93 g, 5.94 mmol, 80.9% yield) was obtained as a yellow solid. $^1$H NMR (400 MHz, CDCl$_3$) δ 8.48 (d, J=2.8 Hz, 1H), 8.19-8.22 (dd, J=9.2 Hz, J=2.8 Hz, 1H), 6.94 (d, J=9.2 Hz, 1H), 4.45 (t, J=6.4 Hz, 2H), 3.73 (t, J=6.4 Hz, 2H)

tert-Butyl 2-((2S,6R)-4-(2-(2-bromo-4-nitrophenoxy)ethyl)-2,6-dimethylpiperazin-1-yl)acetate. To a solution of tert-butyl 2-((2S,6R)-2,6-dimethylpiperazin-1-yl)acetate (1.08 g, 4.73 mmol, 1.0 eq) in acetonitrile (7.7 mL) was added potassium carbonate (1.31 g, 9.46 mmol, 2.0 eq) and 2-bromo-1-(2-bromoethoxy)-4-nitrobenzene (1.54 g, 4.73 mmol, 1.0 eq) at 15° C. The resulting mixture was stirred at 90° C. for 12 h. The reaction mixture was filtered, the filter cake was washed with acetonitrile (2.0 mL×2), and the filtrate was concentrated under reduced pressure to give a residue. The residue was purified by silica gel column chromatography (100:1-0:1 petroleum ether/EtOAc) to give tert-butyl 2-((2S,6R)-4-(2-(2-bromo-4-nitrophenoxy)ethyl)-2,6-dimethylpiperazin-1-yl)acetate (2.08 g, 4.40 mmol, 93.1% yield) as a yellow solid. $^1$H NMR (400 MHz, CDCl$_3$) δ 8.46 (d, J=2.4 Hz, 1H), 8.17-8.20 (m, 1H), 6.94 (d, J=9.2 Hz, 1H), 4.25 (t, J=5.6 Hz, 2H), 3.43 (s, 1H), 2.97-3.00 (m, 2H), 2.84-2.88 (m, 4H), 2.09 (t, J=10.4 Hz, 2H), 1.46 (s, 9H), 1.09 (d, J=6.4 Hz, 6H).

tert-Butyl 2-((2S,6R)-2,6-dimethyl-4-(2-(4-nitro-2-vinylphenoxy)ethyl)piperazin-1-yl)acetate. A mixture of tert-butyl 2-((2S,6R)-4-(2-(2-bromo-4-nitrophenoxy)ethyl)-2,6-dimethylpiperazin-1-yl)acetate (2.07 g, 4.38 mmol, 1.0 eq), 4,4,5,5-tetramethyl-2-vinyl-1,3,2-dioxaborolane (1.35 g, 8.76 mmol, 1.49 mL, 2.0 eq), potassium carbonate (2.79 g, 13.1 mmol, 3.0 eq), and Pd(dppf)Cl$_2$—CH$_2$Cl$_2$ (0.18 g, 0.22 mmol, 0.05 eq) in dioxane (12.4 mL) and water (6.20 mL) was stirred at 90° C. under N$_2$ for 12 h. The mixture was diluted with water (5.00 mL) and extracted with EtOAc (10.0 mL×2). The combined organic layers were washed with brine (5.00 mL), dried over anhydrous sodium sulfate, filtered and concentrated under reduced pressure to give a residue. The residue was purified by silica gel column chromatography (100:1-0:1 petroleum ether/EtOAc) to afford tert-butyl 2-((2S,6R)-2,6-dimethyl-4-(2-(4-nitro-2-vinylphenoxy)ethyl)piperazin-1-yl)acetate (1.80 g, crude) as a brown oil. MS (ESI) m/z 420.2 [M+1]$^+$; $^1$H NMR (400 MHz, CDCl$_3$) δ 8.35 (d, J=2.8 Hz, 1H), 8.11-8.14 (m, 1H), 6.90-7.26 (m, 2H), 5.86 (d, J=0.8 Hz, 1H), 5.40 (d, J=0.8 Hz, 1H), 4.21 (t, J=6.0 Hz, 2H), 3.44 (s, 2H), 2.97-3.00 (m, 2H), 2.80-2.84 (m, 4H), 2.04 (t, J=10.4 Hz, 2H), 1.46 (s, 9H), 1.09 (d, J=6.4 Hz, 6H).

tert-Butyl 2-((2R,6S)-4-(2-(4-amino-2-ethylphenoxy)ethyl)-2,6-dimethylpiperazin-1-yl)acetate. To a solution of tert-butyl 2-((2S,6R)-2,6-dimethyl-4-(2-(4-nitro-2-vinylphenoxy)ethyl)piperazin-1-yl)acetate (1.80 g, 4.30 mmol, 1.0 eq) in MeOH (18.0 mL) was added palladium on activated carbon (0.18 g, 10% wt, 1.0 eq). The suspension was degassed under vacuum and purged with $H_2$ several times. The mixture was then stirred under $H_2$ (50 psi) at 30° C. for 12 h. The reaction mixture was filtered, washed with MeOH (3.0 mL×3), and concentrated under reduced pressure to give crude tert-butyl 2-((2R,6S)-4-(2-(4-amino-2-ethylphenoxy)ethyl)-2,6-dimethylpiperazin-1-yl)acetate (1.68 g) as a black oil. MS (ESI) m/z 392.2 [M+1]$^+$; $^1$H NMR (400 MHz, CDCl$_3$) δ 6.66 (d, J=8.4 Hz, 1H), 6.54 (d, J=2.8 Hz, 1H), 6.47-6.50 (m, 1H), 4.01 (t, J=6.0 Hz, 2H), 2.83-2.86 (m, 2H), 2.74 (d, J=4.0 Hz, 2H), 2.72 (t, J=5.6 Hz, 2H), 2.55-2.57 (m, 2H), 2.01 (t, J=10.8 Hz, 2H), 1.46 (s, 9H), 1.16 (t, J=7.2 Hz, 2H), 1.15 (d, J=7.6 Hz, 6H).

Methyl 2-((4-(2-((3R,5S)-4-(2-(tert-butoxy)-2-oxoethyl)-3,5-dimethylpiperazin-1-yl)ethoxy)-3-ethylphenyl)amino)-2-methylpropanoate. To a solution of tert-butyl 2-((2R,6S)-4-(2-(4-amino-2-ethylphenoxy)ethyl)-2,6-dimethylpiperazin-1-yl)acetate (1.68 g, 4.29 mmol, 1.0 eq) in methyl 2-bromo-2-methylpropanoate (4.19 g, 23.2 mmol, 3.0 mL, 5.4 eq) was added sodium bicarbonate (1.08 g, 12.9 mmol, 0.50 mL, 3.0 eq), and the resulting mixture was stirred at 90° C. for 48 h. The reaction mixture was filtered and washed with EtOAc (3.0 mL×2), and the filtrate was concentrated under reduced pressure to give a residue that was purified by silica gel column chromatography (10:1-0:1 petroleum ether/EtOAc). Methyl 2-((4-(2-((3R,5S)-4-(2-(tert-butoxy)-2-oxoethyl)-3,5-dimethylpiperazin-1-yl)ethoxy)-3-ethylphenyl)amino)-2-methylpropanoate (1.05 g, 2.14 mmol, 50.0% yield) was obtained as a brown oil. MS (ESI) m/z 492.2 [M+1]$^+$; $^1$H NMR (400 MHz, CDCl$_3$) δ 6.65 (d, J=8.8 Hz, 1H), 6.53 (d, J=2.8 Hz, 1H), 6.43-6.46 (m, 1H), 4.01 (t, J=5.6 Hz, 2H), 3.69 (s, 3H), 3.42 (s, 2H), 2.94-2.98 (m, 2H), 2.84 (d, J=10.4 Hz, 2H), 2.73 (t, J=5.6 Hz, 2H), 2.54-2.56 (m, 2H), 2.01-2.04 (m, 3H), 1.49 (s, 6H), 1.46 (s, 9H), 1.14 (t, J=7.6 Hz, 3H), 1.08 (d, J=6.4 Hz, 6H).

tert-Butyl 2-((2R,6S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetate. To a solution of methyl 2-((4-(2-((3R,5S)-4-(2-(tert-butoxy)-2-oxoethyl)-3,5-dimethylpiperazin-1-yl)ethoxy)-3-ethylphenyl)amino)-2-methylpropanoate (1.05 g, 2.14 mmol, 1.0 eq) in EtOAc (8.4 mL) was added 4-isothiocyanato-2-(trifluoromethyl)benzonitrile (0.97 g, 4.27 mmol, 2.0 eq) and TEA (0.65 g, 6.41 mmol, 0.89 mL, 3.0 eq). The resulting mixture was stirred at 70° C. for 12 h. The reaction suspension was concentrated under reduced pressure to give a residue that was purified by silica gel column chromatography (100:1-0:1 petroleum ether/EtOAc). tert-Butyl 2-((2R, 6S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetate (0.71 g, 1.04 mmol, 48.5% yield) was obtained as a brown oil. $^1$H NMR (400 MHz, CDCl$_3$) δ 7.96-7.98 (m, 2H), 7.83-7.85 (m, 1H), 7.05-7.08 (m, 2H), 6.92 (d, J=8.4 Hz, 1H), 4.11-4.15 (m, 3H), 3.44 (s, 2H), 2.96-2.98 (m, 2H), 2.80-2.87 (m, 4H), 2.65-2.70 (m, 2H), 2.03-2.08 (m, 3H), 1.91 (s, 2H), 1.57 (s, 6H), 1.46 (s, 9H), 1.10 (d, J=6.0 Hz, 6H).

2-((2R,6S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetic acid hydrochloride. To a solution of tert-butyl 2-((2R,6S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetate (0.70 g, 1.02 mmol, 1.0 eq) in DCM (4.9 mL) was added hydrochloric acid/dioxane (4 M, 4.90 mL, 19.3 eq) dropwise at 0° C. The resulting mixture was stirred at 20° C. for 12 h. The mixture was concentrated under reduced pressure, treated with petroleum ether (5.00 mL), and stirred for 10 min. The slurry was filtered, and the filter cake was dried to give 2-((2R,6S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetic acid hydrochloride (0.56 g, 0.80 mmol, 82.7% yield) as a yellow solid. MS (ESI) m/z 632.2 [M+1]$^+$; $^1$H NMR (400 MHz, DMSO-d$_6$) δ 8.39 (d, J=8.0 Hz, 1H), 8.29 (d, J=1.2 Hz, 1H), 8.08 (d, J=6.8 Hz, 1H), 7.12-7.21 (m, 3H), 4.50 (m, 2H), 4.00-4.05 (m, 2H), 3.67-3.75 (m, 2H), 3.58-3.59 (m, 2H), 2.63-2.69 (m, 2H), 1.50 (s, 6H), 1.24-1.25 (m, 6H), 1.15-1.20 (m, 4H), 0.81-0.87 (m, 2H).

2-((2R,6S)-4-(2-(4-(3-(4-Cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-((2,6-dioxopiperidin-3-yl)amino)phenyl)acetamide. To a solution of 2-((2R,6S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetic acid hydrochloride (550 mg, 0.82 mmol, 1.0 eq) in DMF (3.3 mL) was added HATU (378 mg, 0.99 mmol, 1.2 eq), 3-((3-aminophenyl)amino)piperidine-2,6-dione (199 mg, 0.91 mmol, 1.1 eq) and DIEA (63.8 mg, 4.94 mmol, 86.0 µL, 6.0 eq), and the resulting mixture was stirred at 25° C. for 4 h. The reaction mixture was quenched by water (10.0 mL) at 0° C. and then filtered. The filter cake was dissolved in EtOAc (20.0 mL), dried over anhydrous sodium sulfate, filtered and concentrated to give a residue. The residue was purified by standard methods to provide. 2-((2R,6S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-((2,6-dioxopiperidin-3-yl)amino)phenyl)acetamide (160 mg, 0.19 mmol, 23.3% yield). MS (ESI) m/z 833.2 [M+1]$^+$; $^1$H NMR (400 MHz, DMSO-d$_6$) δ 10.8 (s, 1H), 9.34 (s, 1H), 8.38 (d, J=8.4 Hz, 1H), 8.29 (s, 1H), 8.08 (d, J=7.6 Hz, 1H), 7.10-7.17 (m, 3H), 7.00-7.03 (m, 3H), 6.79 (d, J=8.4 Hz, 1H), 6.40 (d, J=8.0 Hz, 1H), 4.27-4.30 (m, 1H), 4.15-4.17 (m, 2H), 3.20 (s, 2H), 2.90 (d, J=10.4 Hz, 2H), 2.59-2.74 (m, 10H), 1.89-2.07 (m, 4H), 1.49 (s, 6H), 1.16 (t, J=7.6 Hz, 3H), 0.98 (d, J=6.0 Hz, 6H).

Example 50: 2-((2S,6R)-4-(2-(4-(3-(4-Cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl)-N-(3-((2,6-dioxopiperidin-3-yl)amino)phenyl)acetamide

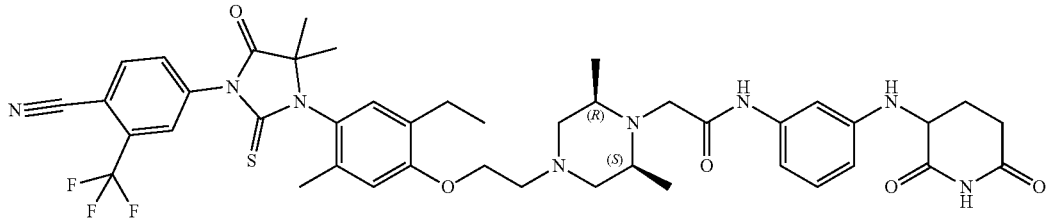

(3R,5S)-1-(2-(Benzyloxy)ethyl)-3,5-dimethylpiperazine. To a mixture (2S,6R)-2,6-dimethylpiperazine (8.00 g, 70.1 mmol, 1 eq) and ((2-bromoethoxy)methyl)benzene (15.1 g, 70.1 mmol, 1 eq) in DMF (80 mL) was added DIEA (27.1 g, 210 mmol, 3 eq), and the mixture was stirred at 60° C. for 4 h. The residue was poured into water (100 mL). The aqueous phase was extracted with EtOAc (100 mL×3), and the combined organic layers were washed with brine (100 mL×5), dried over anhydrous sodium sulfate, filtered and concentrated in vacuo. The crude product was purified by silica gel chromatography (0-60% EtOAc/petroleum ether) to afford (3R,5S)-1-(2-(benzyloxy)ethyl)-3,5-dimethylpiperazine (10.1 g, 40.8 mmol, 58.2% yield) as a yellow oil. MS (ESI) m/z 249.2 [M+1]$^+$; $^1$H NMR (400 MHz, CDCl$_3$) δ 7.38-7.28 (m, 5H), 4.55 (s, 2H), 3.62-3.56 (t, J=6.0 Hz, 2H), 2.99-2.90 (m, 2H), 2.85-2.82 (m, 1H), 2.81-2.78 (m, 1H), 2.63-2.57 (t, J=6.0 Hz, 2H), 1.67-1.60 (t, J=10.8 Hz, 2H), 1.06-1.00 (d, J=6.4 Hz, 6H).

tert-Butyl 2-((2S,6R)-4-(2-(benzyloxy)ethyl)-2,6-dimethylpiperazin-1-yl)acetate. To a mixture of tert-butyl 2-bromoacetate (7.97 g, 40.8 mmol, 1 eq) and (3R,5S)-1-(2-(benzyloxy)ethyl)-3,5-dimethylpiperazine (10.1 g, 40.8 mmol, 1 eq) in DMF (100 mL) was added potassium iodide (6.78 g, 40.8 mmol, 1 eq), and DIEA (15.8 g, 122 mmol, 3 eq) in one portion at 25° C. under nitrogen. The mixture was heated to 25° C. and stirred for 5 h. The residue was poured into water (200 mL), and the aqueous phase was extracted with EtOAc (100 mL×3). The combined organic layers were washed with brine (100 mL×5), dried with anhydrous sodium sulfate, filtered and concentrated in vacuo. The residue was purified by silica gel chromatography (0-50% EtOAc/petroleum ether) to afford tert-butyl 2-((2S,6R)-4-(2-(benzyloxy)ethyl)-2,6-dimethylpiperazin-1-yl)acetate (12.2 g, 33.6 mmol, 82.5% yield) as a colorless oil. MS (ESI) m/z 363.3 [M+1]$^+$; $^1$H NMR (400 MHz, CDCl$_3$) δ 7.36-7.28 (m, J=5H), 4.54 (s, 2H), 3.60-3.55 (t, J=6.0 Hz, 2H), 3.42 (s, 2H), 3.02-2.92 (m, 2H), 2.80-2.74 (m, 2H), 2.59-2.53 (t, J=6.0 Hz, 2H), 1.94-1.85 (t, J=10.8 Hz, 2H), 1.46 (s, 9H), 1.11-1.05 (d, J=6.4 Hz, 6H).

tert-Butyl 2-((2S,6R)-4-(2-hydroxyethyl)-2,6-dimethylpiperazin-1-yl)acetate. To a solution of tert-butyl 2-((2S,6R)-4-(2-(benzyloxy)ethyl)-2,6-dimethylpiperazin-1-yl)acetate (6.00 g, 16.5 mmol, 1 eq) in MeOH (120 mL) was added Pd/C (1.20 g, 10% wt) and palladium hydroxide (1.20 g, 20% wt) under nitrogen. The suspension was degassed under vacuum and purged with hydrogen several times, and then the mixture was stirred under hydrogen (15 psi) at 25° C. for 24 h. The reaction mixture was filtered, and the filtrate was concentrated to give crude tert-butyl 2-((2S,6R)-4-(2-hydroxyethyl)-2,6-dimethylpiperazin-1-yl)acetate (8.06 g, 29.6 mmol, 89.4% yield) as a yellow oil. $^1$H NMR (400 MHz, CDCl$_3$) δ 3.62-3.56 (t, J=5.2 Hz, 2H), 3.46 (s, 2H), 3.07-2.95 (m, 2H), 2.77-2.71 (d, J=9.6 Hz, 2H), 2.50-2.45 (m, 2H), 1.98-1.90 (t, J=10.8 Hz, 2H), 1.47 (s, 9H), 1.12-1.06 (d, J=6.4 Hz, 6H).

tert-Butyl 2-((2S,6R)-4-(2-(2-bromo-5-methyl-4-nitrophenoxy)ethyl)-2,6-dimethylpiperazin-1-yl)acetate. To a solution of tert-butyl 2-((2S,6R)-4-(2-hydroxyethyl)-2,6-dimethylpiperazin-1-yl)acetate (4.00 g, 14.7 mmol, 1 eq) in anhydrous THF (40 mL) was added sodium 2-methylpropan-2-olate (2.12 g, 22.0 mmol, 1.5 eq) under nitrogen at 0° C., and the reaction mixture was stirred at 25° C. for 1 h. After that time, 1-bromo-2-fluoro-4-methyl-5-nitrobenzene (5.16 g, 22.0 mmol, 1.5 eq) in anhydrous THF (10 mL) was added, and the reaction was stirred for another 12 h at 25° C. The residue was poured into a saturated ammonium chloride solution (80 mL) and stirred for 10 min. The aqueous phase was extracted with EtOAc (50 mL×3), and the combined organic layers were washed with brine (50 mL×1), dried over anhydrous sodium sulfate, filtered and concentrated in vacuo. The crude product was purified by semi-preparative, reverse phase HPLC (30-45% acetonitrile in water+0.05% hydrochloric acid, 15 min) to afford tert-butyl 2-((2S,6R)-4-(2-(2-bromo-5-methyl-4-nitrophenoxy)ethyl)-2,6-dimethylpiperazin-1-yl)acetate (2.20 g, 4.52 mmol, 30.8% yield) as a yellow oil. MS (ESI) m/z 486.2 [M+1]$^+$; $^1$H NMR (400 MHz, CDCl$_3$) δ 8.34 (s, 1H), 6.76 (s, 1H), 4.26-4.20 (t, J=5.6 Hz, 2H), 3.45 (s, 2H), 3.05-2.94 (m, 2H), 2.91-2.83 (m, 4H), 2.63 (s, 3H), 2.14-2.06 (t, J=10.8 Hz, 2H), 1.47 (s, 9H), 1.13-1.08 (d, J=6.0 Hz, 6H).

tert-Butyl 2-((2S,6R)-2,6-dimethyl-4-(2-(5-methyl-4-nitro-2-vinylphenoxy)ethyl)piperazin-1-yl)acetate. To a mixture of tert-butyl 2-((2S,6R)-4-(2-(2-bromo-5-methyl-4-nitrophenoxy)ethyl)-2,6-dimethylpiperazin-1-yl)acetate (1.78 g, 3.66 mmol, 1 eq) in dioxane (10 mL) and water (5 mL) was added 4,4,5,5-tetramethyl-2-vinyl-1,3,2-dioxaborolane (1.13 g, 7.32 mmol, 2 eq), sodium carbonate (0.77 g, 7.32 mmol, 2 eq) and Pd(dppf)Cl$_2$ (0.27 g, 0.36 mmol, 0.1 eq) in one portion at 25° C. under nitrogen. The mixture was heated to 100° C. and stirred for 12 h. The residue was poured into water (50 mL), and the aqueous phase was extracted with EtOAc (50 mL×3). The combined organic layers were washed with brine (50 mL×1), dried with anhydrous sodium sulfate, filtered and concentrated in vacuo, and the residue was purified by silica gel chromatography (0-50% EtOAc/petroleum ether). Compound tert-butyl 2-((2S,6R)-2,6-dimethyl-4-(2-(5-methyl-4-nitro-2-vinylphenoxy)ethyl)piperazin-1-yl)acetate (1.50 g, 3.46 mmol, 94.5% yield) was obtained as a yellow oil. MS (ESI) m/z 434.4 [M+1]$^+$; $^1$H NMR (400 MHz, CDCl$_3$) δ 8.23 (s, 1H), 6.98-6.86 (m, 1H), 6.73 (s, 1H), 5.89-5.80 (dd, J=18.0, 1.2 Hz, 1H), 5.40-5.33 (dd, J=11.2, 0.8 Hz, 1H), 4.22-4.17 (t, J=6.0 Hz, 2H), 3.45 (s, 2H), 3.04-2.95 (m, 2H), 2.86-2.79 (m, 4H), 2.64 (s, 3H), 2.10-2.05 (m, 2H), 1.47 (s, 9H), 1.12-1.08 (d, J=6.4 Hz, 6H).

tert-Butyl 2-((2S,6R)-4-(2-(4-amino-2-ethyl-5-methylphenoxy)ethyl)-2,6-dimethylpiperazin-1-yl)acetate. To a solution of tert-butyl 2-((2S,6R)-2,6-dimethyl-4-(2-(5-methyl-4-nitro-2-vinylphenoxy)ethyl)piperazin-1-yl)acetate (1.50 g, 3.46 mmol, 1 eq) in THF (20 mL) was added Pd/C (0.45 g, 10% wt) under nitrogen. The suspension was degassed under vacuum and purged with hydrogen three times, and the mixture was stirred under hydrogen atmosphere (50 psi) at 25° C. for 24 h. The reaction mixture was filtered, and the filtrate was concentrated. The crude product was purified by semi-preparative, reverse-phase HPLC (1-28% acetonitrile in water+0.2% formic acid, 11 min), and the desired fractions were poured into a saturated aqueous solution of sodium bicarbonate (30 mL). The aqueous phase was extracted with EtOAc (30 mL), and the organic phase was dried over anhydrous sodium sulfate, filtered and concentrated in vacuo. Compound tert-butyl 2-((2S,6R)-4-(2-(4-amino-2-ethyl-5-methylphenoxy)ethyl)-2,6-dimethylpiperazin-1-yl)acetate (0.88 g, 2.17 mmol, 62.7% yield) was obtained as a colorless oil. $^1$H NMR (400 MHz, CDCl$_3$) δ 6.59 (s, 1H), 6.52 (s, 1H), 4.05-3.99 (t, J=6.0 Hz, 2H), 3.44 (s, 2H), 3.04-2.93 (m, 2H), 2.89-2.82 (br d, J=10.4 Hz, 2H), 2.76-2.71 (t, J=5.6 Hz, 1H), 2.60-2.50 (q, J=7.6 Hz, 2H), 2.14 (s, 3H), 2.05-1.96 (t, J=6.8 Hz, 2H), 1.47 (s, 9H), 1.19-1.13 (t, J=7.6 Hz, 3H), 1.12-1.07 (d, J=6.4 Hz, 6H).

Methyl 2-((4-(2-((3S,5R)-4-(2-(tert-butoxy)-2-oxoethyl)-3,5-dimethylpiperazin-1-yl)ethoxy)-5-ethyl-2-methylphenyl)amino)-2-methylpropanoate. A mixture of tert-butyl 2-((2S,6R)-4-(2-(4-amino-2-ethyl-5-methylphenoxy)ethyl)-2,6-dimethylpiperazin-1-yl)acetate (0.88 g, 2.17 mmol, 1 eq), methyl 2-bromo-2-methylpropanoate (1.96 g, 10.8 mmol, 5 eq) and DIEA (1.40 g, 10.8 mmol, 5 eq) was stirred at 100° C. for 24 h. The residue was poured into water (30 mL). The aqueous phase was extracted with EtOAc (20 mL×3), and the combined organic layers were washed with brine (20 mL), dried over anhydrous sodium sulfate, filtered and concentrated in vacuo. The crude product was purified by semi-preparative, reverse-phase HPLC (20-50% acetonitrile in water+0.2% formic acid, 11 min), and the desired fractions were poured into a saturated aqueous solution of sodium bicarbonate (30 mL). The aqueous phase was extracted with EtOAc (30 mL), and the organic phase was dried over anhydrous sodium sulfate, filtered and concentrated in vacuo to afford methyl 2-((4-(2-((3S,5R)-4-(2-(tert-butoxy)-2-oxoethyl)-3,5-dimethylpiperazin-1-yl)ethoxy)-5-ethyl-2-methylphenyl)amino)-2-methylpropanoate (0.38 g, 0.76 mmol, 35.2% yield) as a yellow oil. MS (ESI) m/z 560.4 [M+1]$^+$; $^1$H NMR (400 MHz, CDCl$_3$) δ 6.62 (s, 1H), 6.36 (s, 1H), 4.04-3.98 (t, J=6.0 Hz, 2H), 3.71 (s, 3H), 3.44 (s, 2H), 3.02-2.92 (m, 2H), 2.88-2.82 (d, J=10.0 Hz, 2H), 2.76-2.71 (t, J=5.6 Hz, 2H), 2.59-2.51 (q, J=7.2 Hz, 2H), 2.16 (s, 3H), 2.05-1.96 (t, J=10.8, 2H), 1.54 (s, 6H), 1.47 (s, 9H), 1.16-1.11 (t, J=7.6 Hz, 3H), 1.11-1.06 (d, J=6.0 Hz, 6H).

tert-Butyl 2-((2S,6R)-4-(2-(4-(3-(4-cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl) acetate. A mixture of 4-isothiocyanato-2-(trifluoromethyl)benzonitrile (0.26 g, 1.13 mmol, 1.5 eq), methyl 2-((4-(2-((3S,5R)-4-(2-(tert-butoxy)-2-oxoethyl)-3,5-dimethylpiperazin-1-yl)ethoxy)-5-ethyl-2-methylphenyl)amino)-2-methylpropanoate (0.38 g, 0.75 mmol, 1 eq), TEA (0.23 g, 2.25 mmol, 3 eq) and EtOAc (3 mL) was stirred at 60° C. for 10 h. The residue was poured into water (50 mL). The aqueous phase was extracted with EtOAc (30 mL×3), and the combined organic phases were washed with brine (50 mL), dried over anhydrous sodium sulfate, filtered and concentrated in vacuo. The crude product was purified by preparative TLC (1:1 petroleum ether/EtOAc) to give tert-butyl 2-((2S,6R)-4-(2-(4-(3-(4-cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl) acetate (0.21 g, 0.30 mmol, 39.8% yield) as a yellow oil. MS (ESI) m/z 702.5 [M+1]$^+$; $^1$H NMR (400 MHz, CDCl$_3$) δ 8.01-7.95 (m, 2H), 7.90-7.85 (dd, J=8.4, 2.0 Hz, 1H), 6.93 (s, 1H), 6.79 (s, 1H), 4.16-4.13 (m, 2H), 3.50 (s, 2H), 3.02-2.96 (m, 2H), 2.91-2.84 (m, 2H), 2.83-2.78 (m, 2H), 2.70-2.56 (m, 2H), 2.28 (s, 3H), 2.10-2.06 (m, 2H), 1.69 (s, 3H), 1.51 (s, 3H), 1.48 (s, 9H), 1.23-1.18 (t, J=7.6 Hz, 3H), 1.12-1.10 (d, J=6.0 Hz, 6H).

2-((2S,6R)-4-(2-(4-(3-(4-Cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl) acetic acid. To a mixture of tert-butyl 2-((2S,6R)-4-(2-(4-(3-(4-cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl)acetate (0.21 g, 0.30 mmol, 1 eq) in DCM (0.5 mL) was added hydrochloric acid in dioxane (4 M, 0.3 mL, 4 eq). The mixture was stirred at 25° C. for 1 h. The reaction was concentrated to give crude 2-((2S,6R)-4-(2-(4-(3-(4-cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl)acetic acid (0.26 g, HCl) as a brown solid. MS (ESI) m/z 646.3 [M+1]$^+$.

2-((2S,6R)-4-(2-(4-(3-(4-Cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl)-N-(3-((2,6-dioxopiperidin-3-yl)amino)phenyl)acetamide. To a mixture of 3-((3-aminophenyl)amino)piperidine-2,6-dione (0.11 g, 0.43 mmol, 1.27 eq, HCl), 2-((2S,6R)-4-(2-(4-(3-(4-cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl)acetic acid (0.26 g, 0.34 mmol, 1 eq, HCl), HATU (0.21 g, 0.54 mmol, 1.58 eq) in DMF (2 mL) was added DIEA (0.23 g, 1.81 mmol, 5.28 eq), and the reaction was stirred at 25° C. for 12 h. The reaction was filtered. The residue was purified by standard methods to afford Compound 2-((2S,6R)-4-(2-(4-(3-(4-cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl)-N-(3-((2,6-dioxopiperidin-3-yl)amino)phenyl)acetamide (0.12 g, 0.14 mmol, 39.7% yield, 98% purity). MS (ESI) m/z 847.3 [M+1]$^+$; $^1$H NMR (400 MHz, DMSO-d$_6$) δ 10.76 (s, 1H), 9.34 (s, 1H), 8.42-8.36 (d, J=8.0 Hz, 1H), 8.34-8.29 (d, J=1.2 Hz, 1H), 8.13-8.07 (m, 1H), 7.04-6.95 (m, 4H), 6.82-6.75 (d, J=9.2 Hz, 1H), 6.44-6.37 (m, 1H), 5.92-5.84 (d, J=7.6 Hz, 1H), 4.33-4.23 (m, 1H), 4.19-4.08 (m, 2H), 3.02 (s, 2H), 2.94-2.85 (d, J=10.0 Hz, 2H), 2.79-2.68 (m, 5H), 2.64-2.53 (m, 3H), 2.23 (s, 3H), 2.14-2.07 (m, 1H), 2.05-1.97 (t, J=10.8 Hz, 2H), 1.95-1.82 (m, 1H), 1.60 (s, 3H), 1.42 (s, 3H), 1.18-1.11 (t, J=7.6 Hz, 3H), 1.02-0.93 (d, J=6.0 Hz, 6H).

Example 51: 2-((2S,6R)-4-(2-(4-(3-(4-Cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)-N-(3-((2,6-dioxopiperidin-3-yl)amino)phenyl)acetamide

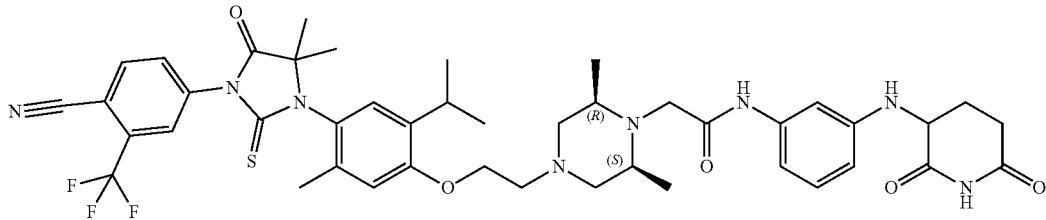

2-((2S,6R)-4-(2-(2-Bromo-5-methyl-4-nitrophenoxy)ethyl)-2,6-dimethylpiperazin-1-yl)acetate. To a mixture of sodium tert-butoxide (0.79 g, 8.26 mmol, 1.5 eq) in THF (5 mL) was added tert-butyl 2-((2S,6R)-4-(2-hydroxyethyl)-2,6-dimethylpiperazin-1-yl)acetate (1.50 g, 5.51 mmol, 1 eq), and the mixture was stirred at 0° C. for 1 h. After that time, 1-bromo-2-fluoro-4-methyl-5-nitrobenzene (1.93 g, 8.26 mmol, 1.5 eq) in THF (10 mL) was added, and the mixture was stirred at 15° C. for another 1 h. The residue was poured into a saturated ammonium chloride solution (30 mL) and stirred for 10 min. The aqueous phase was extracted with EtOAc (30 mL×3), and the combined organic phases were washed with saturated brine (40 mL), dried with anhydrous sodium sulfate, filtered and concentrated in vacuo. The residue was purified by semi-preparative, reverse-phase HPLC (30-43% acetonitrile+0.225% formic acid in water, 10 min), and the collected fractions were adjusted to pH 7 with a saturated sodium bicarbonate solution and then extracted with EtOAc (50 mL×3). The combined organic layers were washed with saturated brine (40 mL), dried over anhydrous sodium sulfate, filtered and concentrated under reduced pressure to give tert-butyl 2-((2S,6R)-4-(2-(2-bromo-5-methyl-4-nitrophenoxy)ethyl)-2,6-dimethylpiperazin-1-yl) acetate (1.19 g, 2.45 mmol, 44.4% yield) as a yellow solid. MS (ESI) m/z 486.0 [M+H]$^+$; $^1$H NMR (400 MHz, DMSO-d$_6$) δ=8.28 (s, 1H), 7.28 (s, 1H), 4.31 (br s, 2H), 2.85 (br s, 4H), 2.72 (br s, 2H), 2.56 (s, 5H), 1.96-1.68 (m, 2H), 1.41 (s, 9H), 0.97 (d, J=6.1 Hz, 6H).

tert-Butyl 2-((2S,6R)-2,6-dimethyl-4-(2-(5-methyl-4-nitro-2-(prop-1-en-2-yl)phenoxy)ethyl)piperazin-1-yl)acetate. To a mixture of tert-butyl 2-((2S,6R)-4-(2-(2-bromo-5-methyl-4-nitrophenoxy)ethyl)-2,6-dimethylpiperazin-1-yl) acetate (1.19 g, 2.45 mmol, 1 eq) and 4,4,5,5-tetramethyl-2-(prop-1-en-2-yl)-1,3,2-dioxaborolane (0.62 g, 3.67 mmol, 1.5 eq) in dioxane (12 mL) and water (1.2 mL) was added Pd(dppf)Cl$_2$ (0.09 g, 0.12 mmol, 0.05 eq) and sodium carbonate (0.78 g, 7.34 mmol, 3 eq), and the mixture was stirred at 100° C. for 8 h. The reaction mixture was filtered, and the filtrate was diluted with water (50 mL) and extracted with EtOAc (30 mL×3). The combined organic phases were washed with brine (40 mL), dried over anhydrous sodium sulfate, filtered and concentrated under reduced pressure to give a residue. The residue was purified by preparative TLC (25% EtOAc/petroleum ether) to give tert-butyl 2-((2S,6R)-2,6-dimethyl-4-(2-(5-methyl-4-nitro-2-(prop-1-en-2-yl)phenoxy)ethyl)piperazin-1-yl) acetate (1.20 g, 2.35 mmol, 95.9% yield, 87.5% purity) as a yellow oil. MS (ESI) m/z 448.2 [M+H]$^+$.

tert-Butyl 2-((2S,6R)-4-(2-(4-amino-2-isopropyl-5-methylphenoxy)ethyl)-2,6-dimethylpiperazin-1-yl)acetate. To a mixture of tert-butyl 2-((2S,6R)-2,6-dimethyl-4-(2-(5-methyl-4-nitro-2-(prop-1-en-2-yl)phenoxy)ethyl)piperazin-1-yl)acetate (0.95 g, 1.86 mmol, 1 eq) in MeOH (20 mL) was added palladium on activated carbon (0.20 g, 10% wt) under hydrogen atmosphere (50 psi). The mixture was stirred at 25° C. for 6 h. The reaction mixture was filtered and concentrated under reduced pressure to give a residue that was purified by preparative TLC (100% EtOAc/petroleum ether). tert-butyl 2-((2S,6R)-4-(2-(4-amino-2-isopropyl-5-methylphenoxy)ethyl)-2,6-dimethylpiperazin-1-yl) acetate (0.50 g, 1.11 mmol, 59.9% yield, 93.3% purity) was obtained as a white solid. MS (ESI) m/z 420.4 [M+H]$^+$.

Methyl 2-((4-(2-((3S,5R)-4-(2-(tert-butoxy)-2-oxoethyl)-3,5-dimethylpiperazin-1-yl)ethoxy)-5-isopropyl-2-methylphenyl)amino)-2-methylpropanoate. A mixture of tert-butyl 2-((2S,6R)-4-(2-(4-amino-2-isopropyl-5-methylphenoxy)ethyl)-2,6-dimethylpiperazin-1-yl)acetate (0.50 g, 1.19 mmol, 1 eq) and methyl 2-bromo-2-methylpropanoate (0.43 g, 2.38 mmol, 0.31 mL, 2 eq) in DIEA (1.5 mL) was stirred at 130° C. for 8 h. The reaction mixture was diluted with water (100 mL) and extracted with EtOAc (30 mL×3). The combined organic layers were washed with brine (40 mL), dried over anhydrous sodium sulfate, filtered and concentrated under reduced pressure to give a residue. The residue was purified by preparative TLC (67% EtOAc/petroleum ether) to give methyl 2-((4-(2-((3S,5R)-4-(2-(tert-butoxy)-2-oxoethyl)-3,5-dimethylpiperazin-1-yl)ethoxy)-5-isopropyl-2-methylphenyl)amino)-2-methylpropanoate (0.30 g, 0.52 mmol, 43.8% yield, 90.4% purity) as a red oil. MS (ESI) m/z 520.5 [M+H]$^+$.

tert-Butyl 2-((2S,6R)-4-(2-(4-(3-(4-cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)acetate. To a mixture of methyl 2-((4-(2-((3S,5R)-4-(2-(tert-butoxy)-2-oxoethyl)-3,5-dimethylpiperazin-1-yl) ethoxy)-5-isopropyl-2-methylphenyl)amino)-2-methylpropanoate (0.25 g, 0.48 mmol, 1 eq) and 4-isothiocyanato-2-(trifluoromethyl)benzonitrile (0.22 g, 0.96 mmol, 2 eq) in EtOAc (0.5 mL) was added TEA (0.14 g, 1.44 mmol, 0.20 mL, 3 eq), and the mixture was stirred at 80° C. for 8 h. The reaction mixture was diluted with water (100 mL) and extracted with EtOAc (30 mL×3). The combined organic layers were washed with brine (40 mL), dried over anhydrous sodium sulfate, filtered and concentrated under reduced pressure to give a residue that was purified by preparative TLC (50% EtOAc/petroleum ether). tert-Butyl 2-((2S,6R)-4-(2-(4-(3-(4-cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)acetate (0.25 g, 0.29 mmol, 61.5% yield, 84.7% purity) was obtained as a yellow oil. MS (ESI) m/z 716.5 [M+H]$^+$.

2-((2S,6R)-4-(2-(4-(3-(4-Cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)acetic acid. To a mixture of tert-butyl 2-((2S,6R)-4-(2-(4-(3-(4-cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)acetate (0.25 g, 0.29 mmol, 1 eq) in DCM (1 mL) was added TFA (1.54 g, 13.5 mmol, 1 mL, 45.6 eq), and the mixture was stirred at 15° C. for 2 h. The reaction mixture was concentrated under reduced pressure. The residue was diluted with saturated sodium bicarbonate (30 mL), extracted with EtOAc (30 mL×3), and the combined organic layers were washed with brine (40 mL), dried with anhydrous sodium sulfate, filtered and concentrated under reduced pressure to give crude 2-((2S,6R)-4-(2-(4-(3-(4-cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)acetic acid (0.19 g) as a white solid. MS (ESI) m/z 660.2 [M+H]$^+$.

2-((2S,6R)-4-(2-(4-(3-(4-Cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)-N-(3-((2,6-dioxopiperidin-3-yl)amino)phenyl)acetamide. To a mixture of 2-((2S,6R)-4-(2-(4-(3-(4-cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)acetic acid (0.19 g, 0.29 mmol, 1 eq) and 3-((3-aminophenyl)amino)piperidine-2,6-dione (0.06 g, 0.25 mmol, 0.85 eq, hydrochloride) in DMF (2 mL) was added HATU (0.12 g, 0.32 mmol, 1.1 eq) and DIEA (0.11 g, 0.88 mmol, 0.15 mL, 3 eq), and the mixture was stirred at 15° C. for 8 h. The reaction mixture was diluted with water (60 mL) and extracted with EtOAc (30 mL×3). The combined organic layers were washed with brine (40 mL), dried with anhydrous sodium sulfate, filtered and concentrated under reduced pressure to give a residue that was purified by standard methods to afford 2-((2S,6R)-4-(2-(4-(3-(4-cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)-N-(3-((2,6-dioxopiperidin-3-yl)amino)phenyl)acetamide (0.07 g, 0.08 mmol, 26.7% yield, 95.6% purity, hydrochloride). MS (ESI) m/z 861.3 [M+H]$^+$; $^1$H NMR (400 MHz, DMSO-d$_6$) δ 10.79 (s, 1H), 8.40 (d, J=8.3 Hz, 1H), 8.33 (d, J=1.5 Hz, 1H), 8.15-8.08 (m, 1H), 7.06 (s, 1H), 7.05-7.02 (m, 1H), 7.02-6.98 (m, 2H), 6.84 (br d, J=8.0 Hz, 1H), 6.46 (br d, J=7.8 Hz, 1H), 4.48 (br s, 2H), 4.27 (br dd, J=4.9, 11.5 Hz, 1H), 3.68-3.64 (m, 2H), 3.63-3.51 (m, 4H), 3.37-3.21 (m, 3H), 2.75 (br s, 2H), 2.62 (br s, 2H), 2.27 (s, 3H), 2.10 (td, J=4.4, 8.8 Hz, 1H), 1.95-1.86 (m, 1H), 1.61 (s, 3H), 1.42 (s, 3H), 1.29 (br s, 6H), 1.19 (dd, J=7.0, 8.6 Hz, 6H).

Example 52: 2-((2S,6R)-4-(2-(4-(3-(4-Cyano-3-(trifluoromethyl)phenyl)-5,5-dimethyl-4-oxo-2-thioxoimidazolidin-1-yl)-2-ethyl-6-fluorophenoxy)ethyl)-2,6-dimethylpiperazin-1-yl)-N-(3-(2,6-dioxopiperidin-3-ylamino)phenyl)acetamide

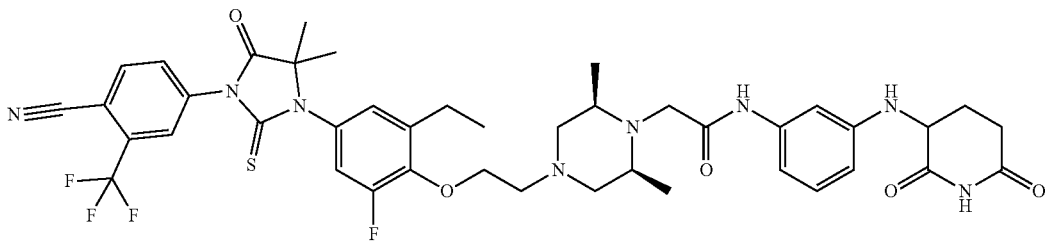 [SMILES: CCc1cc(N2C(=S)N(c3ccc(C#N)c(C(F)(F)F)c3)C(=O)C2(C)C)cc(F)c1OCCN1C[C@@H](C)N(CC(=O)Nc2cccc(NC3CCC(=O)NC3=O)c2)[C@@H](C)C1]

2-Bromo-6-fluoro-4-nitrophenol. To a solution of 2-fluoro-4-nitrophenol (8.00 g, 50.9 mmol, 1 eq) in acetic acid (25 mL) was added bromine (8.95 g, 56.0 mmol, 1.1 eq). The reaction was stirred at 15° C. for 3 h. The reaction solution was poured into water (100 mL) to form a yellow suspension. The suspension was filtered, and the filter cake was washed with water (50 mL). The collected filter cake was dried under reduced pressure to give crude 2-bromo-6-fluoro-4-nitrophenol (9.80 g, 41.5 mmol, 81.5% yield) as an off-white solid. $^1$H NMR (400 MHz, DMSO-d$_6$) δ 8.26 (dd, J=2.8, 1.2 Hz, 1H), 8.17 (dd, J=10.4, 2.4 Hz, 1H).

2-(Benzyloxy)-1-bromo-3-fluoro-5-nitrobenzene. A mixture of 2-bromo-6-fluoro-4-nitrophenol (9.80 g, 41.5 mmol, 1 eq), (bromomethyl)benzene (8.52 g, 49.8 mmol, 1.2 eq), potassium carbonate (11.5 g, 83.0 mmol, 2 eq) and acetonitrile (100 mL) was stirred at 90° C. for 2 h. The suspension was filtered, and the filtrate was concentrated. The crude product was purified by flash silica gel column chromatography (5% EtOAc/petroleum ether) to give 2-(benzyloxy)-1-bromo-3-fluoro-5-nitrobenzene (12.0 g, 36.8 mmol, 88.6% yield) as a light-yellow solid. $^1$H NMR (400 MHz, DMSO-d$_6$) δ 8.32 (dd, J=2.4, 1.2 Hz, 1H), 8.31-8.21 (m, 1H), 7.55-7.45 (m, 2H), 7.44-7.33 (m, 3H), 5.35 (d, J=1.59 Hz, 2H).

2-Fluoro-4-nitro-6-vinylphenol. To a solution of 2-(benzyloxy)-1-bromo-3-fluoro-5-nitrobenzene (5.0 g, 15.3 mmol, 1 eq) and 4,4,5,5-tetramethyl-2-vinyl-1,3,2-dioxaborolane (4.72 g, 30.6 mmol, 2 eq) in dioxane (50 mL) and water (10 mL) was added Pd(dppf)Cl$_2$ (1.12 g, 1.53 mmol, 0.1 eq) and potassium phosphate (9.76 g, 46.0 mmol, 3 eq). The mixture was stirred at 90° C. for 12 h under nitrogen. To the reaction mixture was added water (100 mL), and the mixture was extracted with EtOAc (200 mL×3). The combined organic layers were washed with brine (200 mL), dried over anhydrous sodium sulfate, filtered and concentrated in vacuo. The residue was purified by flash silica gel column chromatography (0-4% EtOAc/petroleum ether) to afford 2-fluoro-4-nitro-6-vinylphenol (2.00 g, 10.9 mmol, 71.2% yield) as a yellow solid. $^1$H NMR (400 MHz, CDCl$_3$) δ 8.24-8.19 (m, 1H), 7.93 (dd, J=9.6, 2.4 Hz, 1H), 7.03-6.93 (m, 1H), 6.35-5.94 (m, 2H), 5.55 (d, J=10.8 Hz, 1H).

tert-Butyl 2-((2S,6R)-4-(2-(2-fluoro-4-nitro-6-vinylphenoxy)ethyl)-2,6-dimethylpiperazin-1-yl)acetate. To a solution of 2-fluoro-4-nitro-6-vinylphenol (1.80 g, 9.83 mmol, 1 eq), tert-butyl 2-((2S,6R)-4-(2-hydroxyethyl)-2,6-dimethylpiperazin-1-yl)acetate (2.94 g, 10.8 mmol, 1.1 eq) and ammonium di-n-hexadecyldithiophosphate (4.96 g, 19.6 mmol, 2 eq) in toluene (5 mL) was added tributylphosphane (3.98 g, 19.6 mmol, 2 eq) at 0° C. under nitrogen. The mixture was stirred at 110° C. for 12 h under nitrogen. The reaction mixture was concentrated in vacuo, and the crude product was purified by semi-preparative, reverse-phase HPLC (35-65% acetonitrile in water+0.225% formic acid, 8 min). The pH of the aqueous phase was adjusted to 7 by addition of a saturation aqueous sodium bicarbonate solution. The mixture was extracted with EtOAc (100 mL×3), and the combined organic phases were washed with brine (200 mL), dried over anhydrous sodium sulfate, filtered and concentrated in vacuo to afford tert-butyl 2-((2S,6R)-4-(2-(2-fluoro-4-nitro-6-vinylphenoxy)ethyl)-2,6-dimethylpiperazin-1-yl)acetate (1.90 g, 4.34 mmol, 44.2% yield) as a yellow oil. $^1$H NMR (400 MHz, DMSO-d$_6$) δ 8.27-8.22 (m, 1H), 8.10 (dd, J=11.6, 2.8 Hz, 1H), 7.11 (dd, J=17.6, 11.2 Hz, 1H), 6.10 (d, J=17.6 Hz, 1H), 5.51 (d, J=11.2 Hz, 1H), 4.28 (t, J=4.8 Hz, 2H), 3.31 (s, 2H), 2.75-2.65 (m, 4H), 2.59 (t, J=5.2 Hz, 2H), 1.71 (t, J=10.4 Hz, 2H), 1.39 (s, 9H), 0.92 (d, J=6.4 Hz, 6H).

tert-Butyl 2-((2S,6R)-4-(2-(4-amino-2-ethyl-6-fluorophenoxy)ethyl)-2,6-dimethylpiperazin-1-yl)acetate. To a solution of tert-butyl 2-((2S,6R)-4-(2-(2-fluoro-4-nitro-6-vinylphenoxy) ethyl)-2,6-dimethylpiperazin-1-yl)acetate (1.90 g, 4.34 mmol, 1 eq) in MeOH (20 mL) was added Pd/C (0.20 g, 10% wt) under nitrogen. The suspension was degassed under vacuum and purged with hydrogen three times, and then the mixture was stirred under hydrogen (15 psi) at 30° C. for 12 h. The reaction mixture was filtered through a pad of celite, and the filtrate was concentrated in vacuo to give the crude product. The residue was purified by flash silica gel column chromatography (0-25% EtOAc/petroleum ether) to afford tert-butyl 2-((2S,6R)-4-(2-(4-amino-2-ethyl-6-fluoro phenoxy)ethyl)-2,6-dimethylpiperazin-1-yl)acetate (1.30 g, 3.17 mmol, 73.1% yield) as a colorless oil. $^1$H NMR (400 MHz, DMSO-d$_6$) δ 6.24-6.15 (m, 2H), 4.98 (s, 2H), 3.84 (t, J=5.6 Hz, 2H), 3.34 (s, 2H), 2.90-2.80 (m, 2H), 2.76 (d, J=10.0 Hz, 2H), 2.54-2.51 (m, 4H), 1.75 (t, J=10.4 Hz, 2H), 1.41 (s, 9H), 1.09 (t, J=7.6 Hz, 3H), 0.96 (d, J=6.0 Hz, 6H).

tert-Butyl 2-((2S,6R)-4-(2-(4-((2-cyanopropan-2-yl)amino)-2-ethyl-6-fluorophenoxy)ethyl)-2,6-dimethylpiperazin-1-yl)acetate. A mixture of tert-butyl 2-((2S,6R)-4-(2-(4-amino-2-ethyl-6-fluorophenoxy)ethyl)-2,6-dimethylpiperazin-1-yl)acetate (0.80 g, 1.95 mmol, 1 eq), 2-hydroxy-2-methylpropanenitrile (4.66 g, 54.7 mmol, 5 mL, 28.1 eq) and magnesium sulfate (0.59 mg, 4.88 mmol, 2.5 eq) was stirred at 60° C. for 12 h. To the reaction mixture was added water (30 mL), and the mixture was extracted with EtOAc (30 mL×3). The combined organic layers were washed with brine (20 mL), dried over anhydrous sulfate, filtered and concentrated in vacuo to afford crude tert-butyl 2-((2S,6R)-4-(2-(4-((2-cyanopropan-2-yl)amino)-2-ethyl-6-fluorophenoxy)ethyl)-2,6-dimethylpiperazin-1-yl)acetate (1 g) as a yellow oil. MS (ESI) m/z 477.4 [M+1]$^+$.

2-((2S,6R)-4-(2-(4-(3-(4-Cyano-3-(trifluoromethyl)phenyl)-5,5-dimethyl-4-oxo-2-thioxoimidazolidin-1-yl)-2-ethyl-6-fluorophenoxy)ethyl)-2,6-dimethylpiperazin-1-yl) acetic acid. To a solution of tert-butyl 2-((2S,6R)-4-(2-(4-((2-cyanopropan-2-yl)amino)-2-ethyl-6-fluorophenoxy) ethyl)-2,6-dimethylpiperazin-1-yl)acetate (1.00 g, 2.10 mmol, 1 eq) in DMF (5 mL) was added 4-isothiocyanato-2-(trifluoromethyl)benzonitrile (0.48 g, 2.10 mmol, 1 eq), and the mixture was stirred at 25° C. for 1 h. Hydrochloric acid in MeOH (4 M, 5.56 mL, 10.6 eq) was then added, and the mixture was stirred at 80° C. for 12 h. The reaction mixture was concentrated in vacuo, and the crude product was purified by semi-preparative, reverse-phase HPLC (30-60% acetonitrile in water+0.225% hydrochloric acid, 20 min) to afford 2-((2S,6R)-4-(2-(4-(3-(4-cyano-3-(trifluoromethyl) phenyl)-5,5-dimethyl-4-oxo-2-thioxoimidazolidin-1-yl)-2-ethyl-6-fluorophenoxy)ethyl)-2,6-dim ethylpiperazin-1-yl)acetic acid (0.18 g, 0.28 mmol, 13.2% yield) as a yellow solid. $^1$H NMR (400 MHz, DMSO-d$_6$) δ 8.40 (d, J=8.4 Hz, 1H), 8.27 (d, J=1.6 Hz, 1H), 8.07 (dd, J=8.4, 1.6 Hz, 1H), 7.27 (dd, J=11.6, 2.0 Hz, 1H), 7.10 (s, 1H), 4.54 (s, 2H), 4.02-3.77 (m, 3H), 3.66 (s, 1H), 3.53 (s, 2H), 3.29-3.08 (m, 2H), 2.74 (q, J=7.6 Hz, 2H), 1.52 (s, 6H), 1.35 (s, 2H), 1.28-1.15 (m, 9H).

2-((2S,6R)-4-(2-(4-(3-(4-Cyano-3-(trifluoromethyl)phenyl)-5,5-dimethyl-4-oxo-2-thioxoimidazolidin-1-yl)-2-ethyl-6-fluorophenoxy)ethyl)-2,6-dimethylpiperazin-1-yl)-N-(3-(2,6-dioxopiperidin-3-ylamino)phenyl)acetamide. To a solution of 2-((2S,6R)-4-(2-(4-(3-(4-cyano-3-(trifluoromethyl)phenyl)-5,5-dimethyl-4-oxo-2-thioxoimidazolidin-1-yl)-2-ethyl-6-fluorophenoxy)ethyl)-2,6-dimethylpiperazin-1-yl)acetic acid (0.17 g, 0.26 mmol, 1 eq) and 3-((3-amino phenyl)amino)piperidine-2,6-dione (0.074 g, 0.29 mmol, 1.1 eq, hydrochloride) in DMF (2 mL) was added HATU (0.11 g, 0.29 mmol, 1.1 eq) and DIEA (0.17 g, 1.31 mmol, 5 eq). The mixture was stirred at 25° C. for 12 h. The reaction mixture was filtered, and the filtrate was concentrated and purified by standard methods to afford 2-((2S,6R)-4-(2-(4-(3-(4-cyano-3-(trifluoromethyl)phenyl)-5,5-dimethyl-4-oxo-2-thioxoimidazolidin-1-yl)-2-ethyl-6-fluorophenoxy) ethyl)-2,6-dimethylpiperazin-1-yl)-N-(3-(2,6-dioxopiperidin-3-ylamino)phenyl)acetamide (0.08 g, 0.09 mmol, 35.9% yield). MS (ESI) m/z 851.4 [M+1]$^+$; $^1$H NMR (400 MHz, DMSO-d$_6$) δ 10.80 (s, 1H), 10.56 (s, 1H), 8.40 (d, J=8.0 Hz, 1H), 8.28 (d, J=1.2 Hz, 1H), 8.10-8.03 (m, 1H), 7.27 (dd, J=12.0, 2.4 Hz, 1H), 7.12-6.99 (m, 3H), 6.88 (d, J=8.0 Hz, 1H), 6.48 (d, J=8.0 Hz, 1H), 4.60-4.51 (s, 2H), 4.28 (dd, J=11.2, 4.8 Hz, 5H), 3.80 (d, J=10.4 Hz, 2H), 3.65-3.37 (m, 4H), 2.80-2.69 (m, 3H), 2.64-2.55 (m, 1H), 2.09 (m, 1H), 1.91 (m, 1H), 1.52 (s, 6H), 1.38 (d, J=5.2 Hz, 6H), 1.19 (t, J=7.2 Hz, 3H).

Assays

Cell Based Assays

VCAP AR Degradation Assay. Test compounds were pre-dispensed into a Corning CellBind 96-well clear bottom plate (Cat #3300) using an acoustic dispenser to make a 10-point concentration series at 1:3 dilution for each compound. The final top concentration of each compound was 5 µM. DMSO at a final concentration of 0.1% was used as a control. VCaP cells cultured in DMEM with 8% fetal bovine serum (FBS) were seeded at 50K cells per well in a 200 μL volume into the compound plate and incubated at 37° C. in a CO$_2$ incubator for 24 h. The medium was carefully removed from the cells and the plate was placed on ice. One hundred μL of ice-cold 1× cell lysis buffer from Cell Signaling Technologies (Cat #9803) was added to each well of the cells and the plate was incubated at 4° C. on a shaker for 1 h. Fifteen μL of cell lysate was used for AR ELISA detection using a PathScan Total Sandwich AR ELISA kit (Cell Signaling Technology, Cat #12580). AR levels in compound-treated wells were normalized to that of DMSO control and expressed as percent of control (PoC) (y). A Four Parameter Logistic Model (Sigmoidal Dose-Response Model) was used to determine the compound's DC$_{50}$, and EC$_{50}$, using the following equation:

$$y=(A+((B-A)/(1+((C/x)^{\wedge}D))))$$

A=Y$_{Min}$ (lowest AR level normalized to DMSO control in response to compound treatment, as determined by curve fit)
B=Y$_{Max}$ (maximum AR level as determined by curve fit)
C=EC$_{50}$
D=Hill Slope
x=compound concentration
EC$_{50}$=the concentration of compound when y=(Y$_{Max}$−Y$_{Min}$)/2
DC$_{50}$=the concentration of the compound when y=50% of DMSO control (50% AR degradation)
y=AR protein level normalized to DMSO control The lowest measured AR level normalized to DMSO control in response to compound treatment, termed Y value, was used to characterize the compound-mediated AR degradation efficiency.

Each of the Piperidine Dione Compounds in Table 1, was tested in the VCAP AR degradation assay, and was found to have activity therein. All of the compounds in Table 1 were shown to have an DC$_{50}$<1 μM and Y<50% of DMSO control.

Prostate Cancer Cell Proliferation Assay. VCAP or ENZR cells were plated at 10K cells per well in 96-well CellBind (Costar) plates using DMEM+8% FBS media. Cells were incubated overnight at 37° C. and test compound was serially diluted and added to the well. Following seven-day incubation, the assay media was removed by inversion and the plate was frozen overnight at −80° C. Plates were thawed at room temperature and 100 μL deionized water (ddH$_2$O) was added to each well. Plates were incubated at 37° C. in non-CO$_2$ incubator for 1 h and then frozen at −80° C. overnight. Plates were thawed to room temperature and 100-μL TNE buffer (NaCl, Tris, EDTA)+Hoescht dye (1.0 mg/ml, 1:400) was added to each well. Fluorescent signal was measured at 460 nm. All data were normalized as a percentage of the DMSO control. A Four Parameter Logistic Model (Sigmoidal Dose-Response Model) was used to determine the compound's GI$_{50}$ value, using the following equation:

$$y=(A+((B-A)/(1+((C/x)^{\wedge}D))))$$

A=Y$_{Min}$ (lowest cell viability in luminescence unit normalized to DMSO control in response to compound treatment determined by curve fit)
B=Y$_{Max}$ (maximum cell viability measured as luminescence unit normalized to DMSO control as determined by curve fit)
C=EC$_{50}$
D=Hill Slope
GI$_{50}$=the concentration of the compound when Y=(Y$_{Max}$+Y$_{t_0}$)/2
EC$_{50}$=the concentration of compound when y=(Y$_{Max}$−Y$_{Min}$)/2
IC$_{50}$=the concentration of the compound when Y=50% of DMSO control
y=cell viability measured as luminescence unit and normalized as percentage of the DMSO control
t$_0$=time when compound was added
Y$_{t_0}$=value of y at t0

Piperidine Dione Compounds have been, or will be tested in the prostate cancer cell proliferation assay, and have shown, or will be shown, to have activity therein.

In Vivo Assays

AR Degradation Assay. In vivo AR degradation assays were performed in uuNSG mice bearing VCaP prostate cancer xenograft tumors. Male NSG mice were inoculated with VCaP cells in the flank region above the right leg. Following inoculation of the animals, the tumors were allowed to grow to approximately 500 mm$^3$ prior to randomization. The randomized animals were administered with test compounds formulated in 20% Labrasol, 80% 25 mM citrate buffer pH 3. The compounds were administered orally once daily for 3 days. After the last dose of compound administration, the plasma and tumors were collected and processed for AR degradation assays. Intratumoral AR levels were measured using western blot analysis. Statistical analysis was performed using a one-way analysis of variance (ANOVA).

Piperidine Dione Compounds have been, or will be tested in the in vivo AR degradation assay, and have shown, or will be shown, to have activity therein.

VCaP Prostate Cancer Xenograft model. The xenograft study was conducted with male NSG mice bearing VCaP prostate cancer xenograft tumors. Male NSG mice were inoculated subcutaneously with VCaP cells in the flank region above the right hind leg. Following inoculation of the animals, the tumors were allowed to grow to approximately 200 mm$^3$ prior to randomization. During randomization, the mice bearing VCaP tumors ranging between 75 and 250 mm$^3$ were pooled together and randomized into various treatment groups. Test compounds formulated in 20% Labrasol, 80% 25 mM citrate buffer pH 3 were administered in a dose volume of 5 mL/kg. The compounds were administered orally once daily for the duration of the study. Tumors were measured twice a week using calipers and tumor volumes were calculated using the formula W$^2$×L/2. Statistical analysis was performed using a one-way or two-way analysis of variance (ANOVA).

Piperidine Dione Compounds have been, or will be tested in the VCAP prostate cancer xenograft model and have shown, or will be shown, to be effective as treatments of prostate cancer in the models.

Activity Tables

Each of the Piperidine Dione Compounds in Table 1, was tested in one or more of the AR degradation assays shown above, for example, the VCAP AR Degradation Assay, and was found to have activity therein.

All of the compounds in Table 1 were shown to have a DC$_{50}$<1 μM and Y<50% of DMSO control, with some compounds having a DC$_{50}$ value C: DC$_{50}$≤0.10 μM, some a DC$_{50}$ value B: 0.10 μM<DC$_{50}$≤0.50 μM, and others a DC$_{50}$ value A: 0.50 μM<DC$_{50}$≤1.0 μM.

Additionally the compounds were shown to have an AR degradation efficiency Y value<50% of DMSO control, with some compounds having 0<Y<=25% (shown as *), some compounds having 25%<Y<=35% (shown as ), and others having 35%<Y<50% (shown as *).

TABLE 1

| Cmpd No. | Cmpd Structure | Cmpd Name | MH+ Obs. | DC50 | Y |
|---|---|---|---|---|---|
| 1 | | 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)-N-(3-(2,6-dioxopiperidin-3-ylamino)phenyl)acetamide | 795.2 | C | *** |
| 2 | | 2-(4-(2-(4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)-N-(3-(2,6-dioxopiperidin-3-ylamino)phenyl)acetamide | 778.0 | C | ** |
| 3 | | 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-(2,6-dioxopiperidin-3-ylamino)phenyl)acetamide | 811.3 | C | * |
| 4 | | N-(3-chloro-5-(2,6-dioxopiperidin-3-ylamino)-2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)acetamide | 829.6 | C | * |

TABLE 1-continued

| Cmpd No. | Cmpd Name | Cmpd Structure | MH+ Obs. | DC50 | Y |
|---|---|---|---|---|---|
| 5 | 2-(4-(2-(2-chloro-4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)-N-(3-(2,6-dioxopiperidin-3-ylamino)phenyl)acetamide | | 812.1 | C | * |
| 6 | 2-(4-(2-(4-(7-(6-cyano-5-(trifluoromethyl)pyridin-3-yl)-8-oxo-6-thioxo-5,7-diazaspiro[3.4]octan-5-yl)-2-fluorophenoxy)ethyl)piperazin-1-yl)-N-(3-(2,6-dioxopiperidin-3-ylamino)phenyl)acetamide | | 808.4 | C | ** |
| 7 | 2-(4-(2-(2-chloro-4-(7-(4-cyano-3-(trifluoromethyl)phenyl)-8-oxo-6-thioxo-5,7-diazaspiro[3.4]octan-5-yl)phenoxy)ethyl)piperazin-1-yl)-N-(3-(2,6-dioxopiperidin-3-ylamino)phenyl)acetamide | | 823.4 | C | * |
| 8 | 2-(4-(2-(4-(7-(4-cyano-3-(trifluoromethyl)phenyl)-8-oxo-6-thioxo-5,7-diazaspiro[3.4]octan-5-yl)-2-fluorophenoxy)ethyl)piperazin-1-yl)-N-(3-(2,6-dioxopiperidin-3-ylamino)phenyl)acetamide | | 807.4 | C | ** |

TABLE 1-continued

| Cmpd No. | Cmpd Structure | Cmpd Name | MH+ Obs. | DC50 | Y |
|---|---|---|---|---|---|
| 9 | | 2-(4-(2-(4-(3-(4-cyano-3-(trifluoromethyl)phenyl)-5,5-dimethyl-4-oxo-2-thioxoimidazolidin-1-yl)-2-cyclopropyl)phenoxy)ethyl)piperazin-1-yl)-N-(3-(2,6-dioxopiperidin-3-ylamino)phenyl)acetamide | 817.2 | C | * |
| 10 | | 2-(4-(2-(4-(3-(4-cyano-3-(trifluoromethyl)phenyl)-5,5-dimethyl-4-oxo-2-thioxoimidazolidin-1-yl)-2-ethyl)phenoxy)ethyl)piperazin-1-yl)-N-(3-(2,6-dioxopiperidin-3-ylamino)phenyl)acetamide | 805.2 | C | * |
| 11 | | 2-(4-(2-(2-bromo-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-(2,6-dioxopiperidin-3-ylamino)phenyl)acetamide | 855.0 | C | ** |
| 12 | | 2-(4-(2-(4-(3-(4-cyano-3-(trifluoromethyl)phenyl)-5,5-dimethyl-4-oxo-2-thioxoimidazolidin-1-yl)-2-(trifluoromethyl)phenoxy)ethyl)piperazin-1-yl)-N-(3-(2,6-dioxopiperidin-3-ylamino)phenyl)acetamide | 845.3 | B | *** |

TABLE 1-continued

| Cmpd No. | Cmpd Structure | Cmpd Name | MH+ Obs. | DC50 | Y |
|---|---|---|---|---|---|
| 13 | | 2-(4-(2-(4-(3-(4-cyano-3-(trifluoromethyl)phenyl)-5,5-dimethyl-4-oxo-2-thioxoimidazolidin-1-yl)-2-fluoro-5-methylphenoxy)ethyl)piperazin-1-yl)-N-(3-(2,6-dioxopiperidin-3-ylamino)phenyl)acetamide | 809.2 | C | *** |
| 14 | | 2-(4-(2-(2-chloro-4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)-N-(3-chloro-5-(2,6-dioxopiperidin-3-ylamino)phenyl)acetamide | 846.2 | C | * |
| 15 | | 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)-N-(3-(2,6-dioxopiperidin-3-ylamino)-5-methylphenyl)acetamide | 809.3 | C | ** |
| 16 | | 2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-chloro-5-(2,6-dioxopiperidin-3-ylamino)phenyl)acetamide | 846.2 | C | * |

TABLE 1-continued

| Cmpd No. | Cmpd Structure | Cmpd Name | MH+ Obs. | DC50 | Y |
|---|---|---|---|---|---|
| 17 | | 2-(4-(2-(4-(3-(4-cyano-3-(trifluoromethyl)phenyl)-5,5-dimethyl-4-oxo-2-thioxoimidazolidin-1-yl)-2-isopropylphenoxy)ethyl)piperazin-1-yl)-N-(3-(2,6-dioxopiperidin-3-ylamino)phenyl)acetamide | 819.4 | C | * |
| 18 | | 2-(4-(2-(4-(3-(4-cyano-3-(trifluoromethyl)phenyl)-5,5-dimethyl-4-oxo-2-thioxoimidazolidin-1-yl)-2-isobutylphenoxy)ethyl)piperazin-1-yl)-N-(3-(2,6-dioxopiperidin-3-ylamino)phenyl)acetamide | 833.4 | C | * |
| 19 | | 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)-N-(3-(2,6-dioxopiperidin-3-ylamino)-5-fluorophenyl)acetamide | 813.3 | C | * |

TABLE 1-continued

| Cmpd No. | Cmpd Structure | Cmpd Name | MH+ Obs. | DC50 | Y |
|---|---|---|---|---|---|
| 20 | | 2-(4-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(2-chloro-5-(2,6-dioxopiperidin-3-ylamino)phenyl)acetamide | 845.2 | C | * |
| 21 | | (2S)-2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-(2,6-dioxopiperidin-3-ylamino)phenyl)propanamide | 825.2 | C | * |
| 22 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)acetamide | 806.4 | C | * |
| 23 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)phenoxy)ethyl)piperazin-1-yl)acetamide | 811.2 | C | * |

TABLE 1-continued

| Cmpd No. | Cmpd Name | MH+ Obs. | DC50 | Y |
|---|---|---|---|---|
| 24 | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)acetamide | 812.2 | C | * |
| 25 | (2R)-2-(4-(2-(2-chloro-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-(2,6-dioxopiperidin-3-ylamino)phenyl)propanamide | 825.2 | C | *** |
| 26 | 2-(4-(2-(4-(3-(6-cyano-5-(trifluoromethyl)pyridin-3-yl)-5,5-dimethyl-4-oxo-2-thioxoimidazolidin-1-yl)-2-fluoro-5-methylphenoxy)ethyl)piperazin-1-yl)-N-(3-(2,6-dioxopiperidin-3-ylamino)phenyl)acetamide | 810.2 | C | ** |
| 27 | (S)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)acetamide | 805.0 | C | * |

TABLE 1-continued

| Cmpd No. | Cmpd Structure | Cmpd Name | MH+ Obs. | DC50 | Y |
|---|---|---|---|---|---|
| 28 | | (R)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)acetamide | 805.0 | C | * |
| 29 | | 2-(4-(2-(2-sec-butyl-4-(3-(4-cyano-3-(trifluoromethyl)phenyl)-5,5-dimethyl-4-oxo-2-thioxoimidazolidin-1-yl)phenoxy)ethyl)piperazin-1-yl)-N-(3-(2,6-dioxopiperidin-3-ylamino)phenyl)acetamide | 833.2 | A | ** |
| 30 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)piperazin-1-yl)acetamide | 851.2 | C | * |
| 31 | | 2-(4-(2-(4-(3-(4-cyano-3-(trifluoromethyl)phenyl)-5,5-dimethyl-4-oxo-2-thioxoimidazolidin-1-yl)-2-cyclobutylphenoxy)ethyl)piperazin-1-yl)-N-(3-(2,6-dioxopiperidin-3-ylamino)phenyl)acetamide | 831.2 | C | * |

TABLE 1-continued

| Cmpd No. | Cmpd Structure | Cmpd Name | MH+ Obs. | DC50 | Y |
|---|---|---|---|---|---|
| 32 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)acetamide | 840.2 | C | * |
| 33 | | 2-(4-(2-(4-(3-(6-cyano-5-(trifluoromethyl)pyridin-3-yl)-5,5-dimethyl-4-oxo-2-thioxoimidazolidin-1-yl)-2-cyclopropylphenoxy)ethyl)piperazin-1-yl)-N-(3-(2,6-dioxopiperidin-3-ylamino)phenyl)acetamide | 818.2 | C | * |
| 34 | | 2-(4-(2-(4-(3-(4-cyano-3-(trifluoromethyl)phenyl)-5,5-dimethyl-4-oxo-2-thioxoimidazolidin-1-yl)-2-propylphenoxy)ethyl)piperazin-1-yl)-N-(3-(2,6-dioxopiperidin-3-ylamino)phenyl)acetamide | 819.4 | C | * |
| 35 | | N-(2-chloro-3-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)acetamide | 839.2 | B | ** |

TABLE 1-continued

| Cmpd No. | Cmpd Structure | Cmpd Name | MH⁺ Obs. | DC$_{50}$ | Y |
|---|---|---|---|---|---|
| 36 | | 2-(4-(2-(4-(3-(6-cyano-5-(trifluoromethyl)pyridin-3-yl)-5,5-dimethyl-4-oxo-2-thioxoimidazolidin-1-yl)-2-cyclobutylphenoxy)ethyl)piperazin-1-yl)-N-(3-(2,6-dioxopiperidin-3-ylamino)phenyl)acetamide | 832.6 | C | * |
| 37 | | 2-(4-(2-(2-sec-butyl-4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)-N-(3-(2,6-dioxopiperidin-3-ylamino)phenyl)acetamide | 834.6 | A | *** |
| 38 | | 2-(4-(2-(4-(3-(6-cyano-5-(trifluoromethyl)pyridin-3-yl)-5,5-dimethyl-4-oxo-2-thioxoimidazolidin-1-yl)-2-propylphenoxy)ethyl)piperazin-1-yl)-N-(3-(2,6-dioxopiperidin-3-ylamino)phenyl)acetamide | 820.6 | C | * |
| 39 | | 2-(4-(2-(4-(3-(4-cyano-3-(trifluoromethyl)phenyl)-5,5-dimethyl-4-oxo-2-thioxoimidazolidin-1-yl)-2-cyclopentylphenoxy)ethyl)piperazin-1-yl)-N-(3-(2,6-dioxopiperidin-3-ylamino)phenyl)acetamide | 845.2 | B | ** |

TABLE 1-continued

| Cmpd No. | Cmpd Structure | Cmpd Name | MH+ Obs. | DC50 | Y |
|---|---|---|---|---|---|
| 40 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)acetamide | 839.2 | C | * |
| 41 | | N-(2-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)acetamide | 839.2 | C | * |
| 42 | | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(5-(2,6-dioxopiperidin-3-ylamino)-2-fluorophenyl)acetamide | 823.2 | C | * |
| 43 | | 2-((S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-3-methylpiperazin-1-yl)-N-(3-(2,6-dioxopiperidin-3-ylamino)phenyl)acetamide | 819.2 | C | * |

TABLE 1-continued

| Cmpd No. | Cmpd Structure | Cmpd Name | MH+ Obs. | DC50 | Y |
|---|---|---|---|---|---|
| 44 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-3-methylpiperazin-1-yl)-N-(3-(2,6-dioxopiperidin-3-ylamino)phenyl)acetamide | 819.0 | C | * |
| 45 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)phenyl)acetamide | 819.3 | C | * |
| 46 | | 2-((S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)phenyl)acetamide | 819.2 | C | * |
| 47 | | N-(2-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)acetamide | 840.2 | C | * |

TABLE 1-continued

| Cmpd No. | Cmpd Structure | Cmpd Name | MH+ Obs. | DC50 | Y |
|---|---|---|---|---|---|
| 48 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-3-(hydroxymethyl)piperazin-1-yl)-N-(3-(2,6-dioxopiperidin-3-ylamino)phenyl)acetamide | 835.2 | C | * |
| 49 | | 2-((S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-3-(hydroxymethyl)piperazin-1-yl)-N-(3-(2,6-dioxopiperidin-3-ylamino)phenyl)acetamide | 835.0 | C | ** |
| 50 | | 2-((S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-3-(hydroxymethyl)piperazin-1-yl)-N-(3-(2,6-dioxopiperidin-3-ylamino)phenyl)acetamide | 835.0 | A | *** |
| 51 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-3-(hydroxymethyl)piperazin-1-yl)-N-(3-(2,6-dioxopiperidin-3-ylamino)phenyl)acetamide | 835.0 | B | *** |

TABLE 1-continued

| Cmpd No. | Cmpd Structure | Cmpd Name | MH+ Obs. | DC50 | Y |
|---|---|---|---|---|---|
| 52 | | 2-(4-(2-(4-(3-(4-cyano-3-(trifluoromethyl)phenyl)-5,5-dimethyl-2,4-dioxoimidazolidin-1-yl)-2-ethylphenoxy)ethyl)piperazin-1-yl)-N-(3-(2,6-dioxopiperidin-3-ylamino)phenyl)acetamide | 789.4 | C | ** |
| 53 | | 2-(4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)piperazin-1-yl)-N-(3-(2,6-dioxopiperidin-3-ylamino)phenyl)acetamide | 820.2 | C | * |
| 54 | | N-(3-chloro-5-(2,6-dioxopiperidin-3-ylamino)phenyl)-2-(4-(2-(4-(3-(4-cyano-3-(trifluoromethyl)phenyl)-4-oxo-2-thioxo-7-oxa-1,3-diazaspiro[4.4]nonan-1-yl)-2-fluorophenoxy)ethyl)piperazin-1-yl)acetamide (THP-enantiomer 1) | 857.2 | C | * |
| 55 | | N-(3-chloro-5-(2,6-dioxopiperidin-3-ylamino)phenyl)-2-(4-(2-(4-(3-(4-cyano-3-(trifluoromethyl)phenyl)-4-oxo-2-thioxo-7-oxa-1,3-diazaspiro[4.4]nonan-1-yl)-2-fluorophenoxy)ethyl)piperazin-1-yl)acetamide (THP-enantiomer 2) | 857.2 | B | ** |

TABLE 1-continued

| Cmpd No. | Cmpd Structure | Cmpd Name | MH+ Obs. | DC50 | Y |
|---|---|---|---|---|---|
| 56 | | 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperazin-1-yl)-N-(3-(2,6-dioxopiperidin-3-ylamino)phenyl)acetamide | 818.3 | C | * |
| 57 | | (2S)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)propanamide | 819.4 | C | * |
| 58 | | (2R)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)propanamide | 819.4 | C | * |
| 59 | | 2-(4-(2-(4-(3-(4-cyano-3-(trifluoromethyl)phenyl)-5,5-dimethyl-4-oxo-2-thioxoimidazolidin-1-yl)-2-(1,1-difluoroethyl)phenoxy)ethyl)piperazin-1-yl)-N-(3-(2,6-dioxopiperidin-3-ylamino)phenyl)acetamide | 841.2 | C | * |

| Cmpd No. | Cmpd Structure | Cmpd Name | MH+ Obs. | DC50 | Y |
|---|---|---|---|---|---|
| 60 | | 2-(4-(2-(4-(3-(6-cyano-5-(trifluoromethyl)pyridin-3-yl)-5,5-dimethyl-4-oxo-2-thioxoimidazolidin-1-yl)-N-(3-(2,6-dioxopiperidin-3-ylamino)phenyl)acetamide | 842.2 | C | * |
| 61 | | 2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)-5-fluorophenyl)acetamide | 823.0 | C | * |
| 62 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)acetamide | 876.2 | C | * |
| 63 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)-5-fluorophenyl)acetamide | 824.8 | C | * |

TABLE 1-continued

| Cmpd No. | Cmpd Structure | Cmpd Name | MH+ Obs. | DC50 | Y |
|---|---|---|---|---|---|
| 64 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)-N-(5-(2,6-dioxopiperidin-3-ylamino)-2-fluorophenyl)acetamide | 824.2 | C | * |
| 65 | | 2-(4-(2-(4-(3-(4-cyano-3-(trifluoromethyl)phenyl)-5,5-dimethyl-4-oxo-2-thioxoimidazolidin-1-yl)-2-fluorophenoxy)ethyl)piperazin-1-yl)-N-(3-cyano-5-(2,6-dioxopiperidin-3-ylamino)phenyl)acetamide | 820.2 | B | ** |
| 66 | | 2-(4-(2-(4-(3-(6-cyano-5-(trifluoromethyl)pyridin-3-yl)-5,5-dimethyl-4-oxo-2-thioxoimidazolidin-1-yl)-2-(2,2-difluoroethyl)phenoxy)ethyl)piperazin-1-yl)-N-(5-(2,6-dioxopiperidin-3-ylamino)-2-fluorophenyl)acetamide | 860.5 | C | * |

TABLE 1-continued

| Cmpd No. | Cmpd Structure | Cmpd Name | MH+ Obs. | DC50 | Y |
|---|---|---|---|---|---|
| 67 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(2,2-difluoroethyl)phenoxy)ethyl)piperazin-1-yl)acetamide | 876.5 | C | * |
| 68 | | 2-(4-(2-(4-(3-(6-cyano-5-(trifluoromethyl)pyridin-3-yl)-5,5-dimethyl-4-oxo-2-thioxoimidazolidin-1-yl)-2-(2,2-difluoroethyl)phenoxy)ethyl)piperazin-1-yl)-N-(3-(2,6-dioxopiperidin-3-ylamino)-5-fluorophenyl)acetamide | 860.5 | C | * |
| 69 | | N-(3-chloro-5-(2,6-dioxopiperidin-3-ylamino)phenyl)-2-(4-(2-(5-(3-(4-cyano-3-(trifluoromethyl)phenyl)-5,5-dimethyl-4-oxo-2-thioxoimidazolidin-1-yl)-3-ethylpyridin-2-yloxy)ethyl)piperazin-1-yl)acetamide | 840.2 | C | * |

TABLE 1-continued

| Cmpd No. | Cmpd Structure | Cmpd Name | MH+ Obs. | DC50 | Y |
|---|---|---|---|---|---|
| 70 | | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(5-(2,6-dioxopiperidin-3-ylamino)-2,3-difluorophenyl)acetamide | 841.2 | C | * |
| 71 | | 2-(4-(2-(4-(3-(6-cyano-5-(trifluoromethyl)pyridin-3-yl)-5,5-dimethyl-4-oxo-2-thioxoimidazolidin-1-yl)-2-fluorophenoxy)ethyl)piperazin-1-yl)-N-(5-(2,6-dioxopiperidin-3-ylamino)-2-fluorophenyl)acetamide | 842.5 | C | * |
| 72 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-fluorophenoxy)ethyl)piperazin-1-yl)acetamide | 858.6 | C | * |
| 73 | | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,2-dimethylpiperidin-1-yl)-N-(3-(2,6-dioxopiperidin-3-ylamino)-5-fluorophenyl)acetamide | 851.3 | C | * |

| Cmpd No. | Cmpd Structure | Cmpd Name | MH+ Obs. | DC50 | Y |
|---|---|---|---|---|---|
| 74 | | N-(3-chloro-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)acetamide | 854.3 | C | * |
| 75 | | 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)-5-fluorophenyl)acetamide | 838.2 | C | * |
| 76 | | 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(5-(2,6-dioxopiperidin-3-ylamino)-2-fluorophenyl)acetamide | 838.2 | C | * |
| 77 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(3-(2,6-dioxopiperidin-3-ylamino)-5-fluorophenyl)acetamide | 852.3 | C | * |

TABLE 1-continued

| Cmpd No. | Cmpd Structure | Cmpd Name | MH+ Obs. | DC50 | Y |
|---|---|---|---|---|---|
| 78 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)acetamide | | C | * |
| 79 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,2-dimethylpiperazin-1-yl)acetamide | 867.3 | C | ** |
| 80 | | 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)-N-(3-(2,6-dioxopiperidin-3-ylamino)-5-fluorophenyl)acetamide | 860.0 | C | * |
| 81 | | 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)phenyl)acetamide | 820.3 | C | * |

TABLE 1-continued

| Cmpd No. | Cmpd Structure | Cmpd Name | MH+ Obs. | DC50 | Y |
|---|---|---|---|---|---|
| 82 | | 2-(4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)piperazin-1-yl)-N-(5-(2,6-dioxopiperidin-3-ylamino)-2,3-difluorophenyl)acetamide | 878.0 | C | * |
| 83 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(5-(2,6-dioxopiperidin-3-ylamino)-2,3-difluorophenyl)acetamide | 870.2 | C | * |
| 84 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-cyclopropylphenoxy)ethyl)piperazin-1-yl)acetamide | 852.2 | C | * |

TABLE 1-continued

| Cmpd No. | Cmpd Structure | Cmpd Name | MH+ Obs. | DC50 | Y |
|---|---|---|---|---|---|
| 85 | | N-(3-chloro-5-(2,6-dioxopiperidin-3-ylamino)phenyl)-2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperazin-1-yl)acetamide | 852.4 | C | * |
| 86 | | 2-(4-(2-(4-(3-(6-cyano-5-(trifluoromethyl)pyridin-3-yl)-5,5-dimethyl-4-oxo-2-thioxoimidazolidin-1-yl)phenoxy)ethyl)piperazin-1-yl)-N-(5-(2,6-dioxopiperidin-3-ylamino)-2-fluorophenyl)acetamide | 796.2 | C | ** |
| 87 | | N-(3-chloro-5-(2,6-dioxopiperidin-3-ylamino)phenyl)-2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)acetamide | 853.2 | C | * |
| 88 | | 2-(4-(3-(4-(3-(4-cyano-3-(trifluoromethyl)phenyl)-5,5-dimethyl-4-oxo-2-thioxoimidazolidin-1-yl)-2-ethylphenyl)propyl)piperazin-1-yl)-N-(3-(2,6-dioxopiperidin-3-ylamino)-5-fluorophenyl)acetamide | 821.4 | C | * |

TABLE 1-continued

| Cmpd No. | Cmpd Structure | Cmpd Name | MH+ Obs. | DC50 | Y |
|---|---|---|---|---|---|
| 89 | | N-(3-chloro-5-(2,6-dioxopiperidin-3-ylamino)phenyl)-2-(4-(3-(4-(3-(4-cyano-3-(trifluoromethyl)phenyl)-5,5-dimethyl-4-oxo-2-thioxoimidazolidin-1-yl)-2-ethylphenyl)propyl)piperazin-1-yl)acetamide | 838.2 | C | * |
| 90 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)-5-fluorophenyl)acetamide | 837.4 | C | * |
| 91 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(hydroxymethyl)phenoxy)ethyl)piperazin-1-yl)acetamide | 842.0 | C | *** |

TABLE 1-continued

| Cmpd No. | Cmpd Structure | Cmpd Name | MH+ Obs. | DC50 | Y |
|---|---|---|---|---|---|
| 92 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-(1-hydroxyethyl)phenoxy)ethyl)piperazin-1-yl)acetamide | 856.3 | B | *** |
| 93 | | N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)piperazin-1-yl)acetamide | 854.1 | C | * |
| 94 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-isopropylphenoxy)ethyl)piperazin-1-yl)acetamide | 853.2 | B | ** |
| 95 | | 2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,2-dimethylpiperazin-1-yl)-N-(3-(2,6-dioxopiperidin-3-ylamino)phenyl)acetamide | 833.4 | C | * |

TABLE 1-continued

| Cmpd No. | Cmpd Structure | Cmpd Name | MH+ Obs. | DC50 | Y |
|---|---|---|---|---|---|
| 96 | | 2-(4-(2-(4-(3-(4-cyano-2-methyl-3-(trifluoromethyl)phenyl)-5,5-dimethyl-4-oxo-2-thioxoimidazolidin-1-yl)-2-fluorophenoxy)ethyl)piperazin-1-yl)-N-(3-(2,6-dioxopiperidin-3-ylamino)phenyl)acetamide | 809.4 | C | *** |
| 97 | | 2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,2-dimethylpiperazin-1-yl)-N-(3-(2,6-dioxopiperidin-3-ylamino)phenyl)acetamide | 834.4 | C | * |
| 98 | | 2-(7-(2-(4-(3-(4-cyano-3-(trifluoromethyl)phenyl)-5,5-dimethyl-4-oxo-2-thioxoimidazolidin-1-yl)-2-ethylphenoxy)ethyl)-4,7-diazaspiro[2.5]octan-4-yl)-N-(3-(2,6-dioxopiperidin-3-ylamino)phenyl)acetamide | 831.4 | C | ** |
| 99 | | 2-(7-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4,7-diazaspiro[2.5]octan-4-yl)-N-(3-(2,6-dioxopiperidin-3-ylamino)phenyl)acetamide | 832.4 | C | * |

TABLE 1-continued

| Cmpd No. | Cmpd Structure | Cmpd Name | MH+ Obs. | DC50 | Y |
|---|---|---|---|---|---|
| 100 | | 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(5-(2,6-dioxopiperidin-3-ylamino)-2,3-difluorophenyl)acetamide | 856.4 | C | * |
| 101 | | N-(3-chloro-5-(2,6-dioxopiperidin-3-ylamino)phenyl)-2-(7-(2-(4-(3-(4-cyano-3-(trifluoromethyl)phenyl)-5,5-dimethyl-4-oxo-2-thioxoimidazolidin-1-yl)-2-ethylphenoxy)ethyl)-4,7-diazaspiro[2.5]octan-4-yl)acetamide | 865.3 | C | * |
| 102 | | N-(3-chloro-5-(2,6-dioxopiperidin-3-ylamino)phenyl)-2-(7-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4,7-diazaspiro[2.5]octan-4-yl)acetamide | 866.2 | C | * |
| 103 | | N-(3-chloro-5-(2,6-dioxopiperidin-3-ylamino)phenyl)-2-((R)-4-(2-(4-(7-(4-cyano-3-(trifluoromethyl)phenyl)-8-oxo-6-thioxo-5,7-diazaspiro[3.4]octan-5-yl)-2-ethylphenoxy)ethyl)-2-methylpiperazin-1-yl)acetamide | 865.4 | C | * |

TABLE 1-continued

| Cmpd No. | Cmpd Structure | Cmpd Name | MH+ Obs. | DC50 | Y |
|---|---|---|---|---|---|
| 104 | | 2-((R)-4-(2-(4-(7-(4-cyano-3-(trifluoromethyl)phenyl)-8-oxo-6-thioxo-5,7-diazaspiro[3.4]octan-5-yl)-2-ethylphenoxy)ethyl)-2-methylpiperazin-1-yl)-N-(3-(2,6-dioxopiperidin-3-ylamino)-5-fluorophenyl)acetamide | 849.4 | C | * |
| 105 | | 2-((R)-4-(2-(4-(7-(4-cyano-3-(trifluoromethyl)phenyl)-8-oxo-6-thioxo-5,7-diazaspiro[3.4]octan-5-yl)-2-ethylphenoxy)ethyl)-2-methylpiperazin-1-yl)-N-(3-(2,6-dioxopiperidin-3-ylamino)phenyl)acetamide | 831.4 | C | * |
| 106 | | N-(3-chloro-5-(2,6-dioxopiperidin-3-ylamino)phenyl)-2-((R)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2-methylpiperazin-1-yl)acetamide | 866.3 | C | * |
| 107 | | 2-((R)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2-methylpiperazin-1-yl)-N-(3-(2,6-dioxopiperidin-3-ylamino)-5-fluorophenyl)acetamide | 850.2 | C | * |

| Cmpd No. | Cmpd Structure | Cmpd Name | MH+ Obs. | DC50 | Y |
|---|---|---|---|---|---|
| 108 | | 2-((R)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2-methylpiperazin-1-yl)-N-(3-(2,6-dioxopiperidin-3-ylamino)phenyl)acetamide | 832.31 | C | * |
| 109 | | 2-(7-(2-(4-(3-(4-cyano-3-(trifluoromethyl)phenyl)-5,5-dimethyl-4-oxo-2-thioxoimidazolidin-1-yl)-2-ethylphenoxy)ethyl)-4,7-diazaspiro[2.5]octan-4-yl)-N-(3-(2,6-dioxopiperidin-3-ylamino)-5-fluorophenyl)acetamide | 849.3 | C | * |
| 110 | | 2-(7-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-4,7-diazaspiro[2.5]octan-4-yl)-N-(3-(2,6-dioxopiperidin-3-ylamino)-5-fluorophenyl)acetamide | 850.3 | C | * |
| 111 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-((S)-2,6-dioxopiperidin-3-ylamino)phenyl)acetamide | 819.0 | C | * |

TABLE 1-continued

| Cmpd No. | Cmpd Structure | Cmpd Name | MH+ Obs. | DC50 | Y |
|---|---|---|---|---|---|
| 112 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-((R)-2,6-dioxopiperidin-3-ylamino)phenyl)acetamide | 819.0 | C | * |
| 113 (peak 1) | | (2R)-N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)propanamide or | 854.2 | C | * |
| 114 (peak 2) | | (2S)-N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)propanamide | 854.0 | C | * |
| 115 | | N-(3-chloro-5-(2,6-dioxopiperidin-3-ylamino)phenyl)-2-(1S,4S)-5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.1]heptan-2-yl)acetamide | 852.3 | B | ** |

TABLE 1-continued

| Cmpd No. | Cmpd Structure | Cmpd Name | MH+ Obs. | DC50 | Y |
|---|---|---|---|---|---|
| 116 | | (2S)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)-5-fluorophenyl)propanamide | 838.2 | C | * |
| 117 | | (2R)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)-5-fluorophenyl)propanamide | 838.2 | C | * |
| 118 | | (2S)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)propanamide | 820.7 | C | * |
| 119 | | (2R)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)propanamide | 820.4 | C | * |

TABLE 1-continued

| Cmpd No. | Cmpd Structure | Cmpd Name | MH+ Obs. | DC50 | Y |
|---|---|---|---|---|---|
| 120 | | N-(3-chloro-5-(2,6-dioxopiperidin-3-ylamino)phenyl)-2-((1R,4R)-5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.1]heptan-2-yl)acetamide | 852.0 | B | ** |
| 121 | | 2-((2R,5S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)-N-(3-(2,6-dioxopiperidin-3-ylamino)phenyl)acetamide | 833.0 | C | * |
| 122 | | 2-((2S,5R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)-N-(3-(2,6-dioxopiperidin-3-ylamino)phenyl)acetamide | 833.0 | B | ** |
| 123 | | N-(3-chloro-5-(2,6-dioxopiperidin-3-ylamino)phenyl)-2-((2R,5S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)acetamide | 868.0 | C | * |

| Cmpd No. | Cmpd Structure | Cmpd Name | MH+ Obs. | DC50 | Y |
|---|---|---|---|---|---|
| 124 | | N-(3-chloro-5-(2,6-dioxopiperidin-3-ylamino)phenyl)-2-((2S,5R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)acetamide | 867.0 | B | * |
| 125 | | 2-((2S,5S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)-N-(3-(2,6-dioxopiperidin-3-ylamino)phenyl)acetamide | 833.0 | B | * |
| 126 | | N-(3-chloro-5-(2,6-dioxopiperidin-3-ylamino)phenyl)-2-((2S,5S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)acetamide | 867.0 | C | * |
| 127 | | 2-((2R,5R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)-N-(3-(2,6-dioxopiperidin-3-ylamino)phenyl)acetamide | 833.0 | C | * |

TABLE 1-continued

| Cmpd No. | Cmpd Structure | Cmpd Name | MH+ Obs. | DC50 | Y |
|---|---|---|---|---|---|
| 128 | | N-(3-chloro-5-(2,6-dioxopiperidin-3-ylamino)phenyl)-2-((2R,5R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)acetamide | 867.0 | C | * |
| 129 | | 2-((2R,6R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-(2,6-dioxopiperidin-3-ylamino)phenyl)acetamide | 833.0 | C | * |
| 130 | | N-(3-chloro-5-(2,6-dioxopiperidin-3-ylamino)phenyl)-2-((2R,6R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetamide | 867.0 | C | * |
| 131 | | N-(3-chloro-5-(2,6-dioxopiperidin-3-ylamino)phenyl)-2-((S)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)acetamide | 854.1 | C | * |

TABLE 1-continued

| Cmpd No. | Cmpd Structure | Cmpd Name | MH+ Obs. | DC50 | Y |
|---|---|---|---|---|---|
| 132 | | 2-(4-(2-(4-(7-(4-cyano-3-(trifluoromethyl)phenyl)-8-oxo-6-thioxo-5,7-diazaspiro[3.4]octan-5-yl)-2-ethylphenoxy)ethyl)piperazin-1-yl)-N-(3-(2,6-dioxopiperidin-3-ylamino)phenyl)acetamide | 817.0 | C | * |
| 133 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-2-methylpropanamide | 867.2 | B | ** |
| 134 | | 2-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,2-dimethylpiperazin-1-yl)-N-(3-(2,6-dioxopiperidin-3-ylamino)phenyl)acetamide | 846.3 | C | * |
| 135 | | N-(3-chloro-5-(2,6-dioxopiperidin-3-ylamino)phenyl)-2-((R)-4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)-2-methylpiperazin-1-yl)acetamide | 871.2 | C | * |

TABLE 1-continued

| Cmpd No. | Cmpd Structure | Cmpd Name | MH+ Obs. | DC50 | Y |
|---|---|---|---|---|---|
| 136 |  | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperazin-1-yl)acetamide | 857.3 | C | * |
| 137 |  | 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-((S)-2,6-dioxopiperidin-3-ylamino)phenyl)acetamide | 820.0 | C | * |
| 138 |  | 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)-N-(3-((R)-2,6-dioxopiperidin-3-ylamino)phenyl)acetamide | 820.0 | C | * |
| 139 |  | 1-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)cyclopropanecarboxamide | 831.6 | C | * |

TABLE 1-continued

| Cmpd No. | Cmpd Structure | Cmpd Name | MH+ Obs. | DC50 | Y |
|---|---|---|---|---|---|
| 140 | | N-(3-chloro-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)-2-methylpiperazin-1-yl)acetamide | 872.1 | C | * |
| 141 | | 2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperazin-1-yl)-N-(5-(2,6-dioxopiperidin-3-ylamino)-2-fluorophenyl)acetamide | 841.2 | C | * |
| 142 | | N-(3-chloro-5-(2,6-dioxopiperidin-3-ylamino)phenyl)-2-((R)-4-(2-(4-(7-(6-cyano-5-(trifluoromethyl)pyridin-3-yl)-8-oxo-6-thioxo-5,7-diazaspiro[3.4]octan-5-yl)-2-(2-fluoroethyl)phenoxy)ethyl)-2-methylpiperazin-1-yl)acetamide | 884.2 | C | * |
| 143 | | N-(3-chloro-5-(2,6-dioxopiperidin-3-ylamino)phenyl)-2-((R)-4-(2-(4-(7-(4-cyano-3-(trifluoromethyl)phenyl)-8-oxo-6-thioxo-5,7-diazaspiro[3.4]octan-5-yl)-2-(2-fluoroethyl)phenoxy)ethyl)-2-methylpiperazin-1-yl)acetamide | 883.2 | C | * |

TABLE 1-continued

| Cmpd No. | Cmpd Structure | Cmpd Name | MH+ Obs. | DC50 | Y |
|---|---|---|---|---|---|
| 144 | | N-(3-chloro-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)acetamide | 854.0 | C | * |
| 145 | | N-(3-chloro-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)acetamide | 854.0 | C | * |
| 146 | | 2-((2S,6S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-(2,6-dioxopiperidin-3-ylamino)phenyl)acetamide | 833.0 | C | * |
| 147 | | N-(3-chloro-5-(2,6-dioxopiperidin-3-ylamino)phenyl)-2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)acetamide | 867.0 | C | * |

TABLE 1-continued

| Cmpd No. | Cmpd Structure | Cmpd Name | MH+ Obs. | DC50 | Y |
|---|---|---|---|---|---|
| 148 | | N-(3-chloro-5-(2,6-dioxopiperidin-3-ylamino)phenyl)-2-((R)-4-(2-(4-(3-(4-cyano-3-(trifluoromethyl)phenyl)-5,5-dimethyl-4-oxo-2-thioxoimidazolidin-1-yl)-2-(1,1-difluoroethyl)phenoxy)ethyl)-2-methylpiperazin-1-yl)acetamide | 889.2 | C | * |
| 149 | | N-(3-chloro-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)-2-methylpiperazin-1-yl)acetamide | 890.3 | C | * |
| 150 | | 2-((2S,6R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-(2,6-dioxopiperidin-3-ylamino)phenyl)acetamide | 833.0 | C | * |
| 151 | | 2-((2R,6S)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,6-dimethylpiperazin-1-yl)-N-(3-(2,6-dioxopiperidin-3-ylamino)phenyl)acetamide | 834.0 | C | * |

TABLE 1-continued

| Cmpd No. | Cmpd Structure | Cmpd Name | MH+ Obs. | DC50 | Y |
|---|---|---|---|---|---|
| 152 | | N-(3-chloro-5-(2,6-dioxopiperidin-3-ylamino)phenyl)-2-((R)-4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazin-1-yl)acetamide | 889.0 | C | * |
| 153 | | 2-((R)-4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazin-1-yl)-N-(3-(2,6-dioxopiperidin-3-ylamino)phenyl)acetamide | 855.0 | C | * |
| 154 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-cyano-5-(2,6-dioxopiperidin-3-ylamino)phenyl)acetamide | 844.0 | C | * |

TABLE 1-continued

| Cmpd No. | Cmpd Structure | Cmpd Name | MH+ Obs. | DC50 | Y |
|---|---|---|---|---|---|
| 155 | | N-(3-cyano-5-(2,6-dioxopiperidin-3-ylamino)phenyl)-2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-methylpiperazin-1-yl)acetamide | 845.0 | C | * |
| 156 | | 2-((R)-4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazin-1-yl)-N-(5-(2,6-dioxopiperidin-3-ylamino)-2-fluorophenyl)acetamide | 873.3 | C | * |
| 157 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-(1,1-difluoroethyl)phenoxy)ethyl)piperazin-1-yl)acetamide | 875.3 | C | * |

TABLE 1-continued

| Cmpd No. | Cmpd Structure | Cmpd Name | MH+ Obs. | DC50 | Y |
|---|---|---|---|---|---|
| 158 | | 2-((R)-4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)-2-methylpiperazin-1-yl)-N-(3-(2,6-dioxopiperidin-3-ylamino)-5-fluorophenyl)acetamide | 873.3 | C | * |
| 159 | | N-(3-chloro-5-(2,6-dioxopiperidin-3-ylamino)phenyl)-2-(4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)piperazin-1-yl)acetamide | 875.3 | C | * |
| 160 | | 2-(4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)piperazin-1-yl)-N-(3-(2,6-dioxopiperidin-3-ylamino)phenyl)acetamide | 823.3 | C | * |

| Cmpd No. | Cmpd Structure | Cmpd Name | MH+ Obs. | DC50 | Y |
|---|---|---|---|---|---|
| 161 | | 2-(4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)piperazin-1-yl)-N-(3-(2,6-dioxopiperidin-3-ylamino)phenyl)acetamide | 824.3 | C | * |
| 162 | | 2-((R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2-methylpiperazin-1-yl)-N-(3-(2,6-dioxopiperidin-3-ylamino)phenyl)acetamide | 833.4 | B | ** |
| 163 | | 2-((R)-4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)-2-methylpiperazin-1-yl)-N-(3-(2,6-dioxopiperidin-3-ylamino)phenyl)acetamide | 834.3 | B | * |
| 164 | | 2-((R)-4-(2-(4-(3-(4-cyano-3-(trifluoromethyl)phenyl)-5,5-dimethyl-4-oxo-2-thioxoimidazolidin-1-yl)-2-(2-fluoroethyl)phenoxy)ethyl)-2-methylpiperazin-1-yl)-N-(3-(2,6-dioxopiperidin-3-ylamino)phenyl)acetamide | 837.3 | C | * |

| Cmpd No. | Cmpd Structure | Cmpd Name | MH+ Obs. | DC50 | Y |
|---|---|---|---|---|---|
| 165 | | N-(3-chloro-5-(2,6-dioxopiperidin-3-ylamino)phenyl)-1-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)cyclopropanecarboxamide | 866.71 | C | * |
| 166 | | 2-((R)-4-(2-(4-(3-(6-cyano-5-(trifluoromethyl)pyridin-3-yl)-5,5-dimethyl-4-oxo-2-thioxoimidazolidin-1-yl)-2-(2-fluoroethyl)phenoxy)ethyl)-2-methylpiperazin-1-yl)-N-(3-(2,6-dioxopiperidin-3-ylamino)phenyl)acetamide | 838.2 | C | * |
| 167 | | 2-((R)-4-(2-(4-(3-(5-chloro-6-cyanopyridin-3-yl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)phenyl)acetamide | 786.3 | C | * |
| 168 | | 2-((R)-4-(2-(4-(3-(3-chloro-4-cyanophenyl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)phenyl)acetamide | 785.1 | C | * |

| Cmpd No. | Cmpd Structure | Cmpd Name | MH+ Obs. | DC50 | Y |
|---|---|---|---|---|---|
| 169 | | N-(3-chloro-5-(2,6-dioxopiperidin-3-ylamino)phenyl)-2-((2R,5R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-dimethylpiperazin-1-yl)acetamide | 868.2 | C | * |
| 170 | | 2-((2S,6R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,6-dimethylpiperazin-1-yl)-N-(3-(2,6-dioxopiperidin-3-ylamino)phenyl)acetamide | 847.3 | C | * |
| 171 | | 2-(3-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-3,8-diazabicyclo[3.2.1]octan-8-yl)-N-(3-(2,6-dioxopiperidin-3-ylamino)phenyl)acetamide | 844.4 | C | * |
| 172 | | 2-((1S,4S)-5-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,5-diazabicyclo[2.2.2]octan-2-yl)-N-(3-(2,6-dioxopiperidin-3-ylamino)phenyl)acetamide | 844.41 | B | *** |

TABLE 1-continued

| Cmpd No. | Cmpd Structure | Cmpd Name | MH+ Obs. | DC50 | Y |
|---|---|---|---|---|---|
| 173 | | N-(3-chloro-5-(2,6-dioxopiperidin-3-ylamino)phenyl)-2-(3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-3,8-diazabicyclo[3.2.1]octan-8-yl)acetamide | 866.2 | C | * |
| 174 | | 2-(4-(2-(4-(3-(4-cyano-3-(trifluoromethyl)phenyl)-5,5-dimethyl-4-oxo-2-thioxoimidazolidin-1-yl)-2-(2,2-difluoroethyl)phenoxy)ethyl)piperazin-1-yl)-N-(5-(2,6-dioxopiperidin-3-ylamino)-2-fluorophenyl)acetamide | 859.2 | C | * |
| 175 | | N-(3-chloro-5-(2,6-dioxopiperidin-3-ylamino)phenyl)-2-((2R,5R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,5-dimethylpiperazin-1-yl)acetamide | 881.3 | B | * |

TABLE 1-continued

| Cmpd No. | Cmpd Structure | Cmpd Name | MH+ Obs. | DC50 | Y |
|---|---|---|---|---|---|
| 176 | | 2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-isopropylphenoxy)ethyl)-2,6-dimethylpiperazin-1-yl)-N-(3-(2,6-dioxopiperidin-3-ylamino)phenyl)acetamide | 860.4 | C | * |
| 177 | | 2-(3-(2-(4-(3-(4-cyano-3-(trifluoromethyl)phenyl)-5,5-dimethyl-4-oxo-2-thioxoimidazolidin-1-yl)-2-ethylphenoxy)ethyl)-3,8-diazabicyclo[3.2.1]octan-8-yl)-N-(3-(2,6-dioxopiperidin-3-ylamino)phenyl)acetamide | 831.4 | B | * |
| 178 | | 2-(3-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-3,8-diazabicyclo[3.2.1]octan-8-yl)-N-(3-(2,6-dioxopiperidin-3-ylamino)phenyl)acetamide | 832.4 | C | ** |
| 179 | | N-(3-chloro-5-(2,6-dioxopiperidin-3-ylamino)phenyl)-2-((1S,4S)-5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.2]octan-2-yl)acetamide | 866.2 | B | ** |

TABLE 1-continued

| Cmpd No. | Cmpd Structure | Cmpd Name | MH+ Obs. | DC50 | Y |
|---|---|---|---|---|---|
| 180 | | 2-((2S,6R)-4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)-2,6-dimethylpiperazin-1-yl)-N-(3-(2,6-dioxopiperidin-3-ylamino)phenyl)acetamide | 848.3 | C | * |
| 181 | | 2-((2R,5R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,5-dimethylpiperazin-1-yl)-N-(3-cyano-5-(2,6-dioxopiperidin-3-ylamino)phenyl)acetamide | 858.3 | C | * |
| 182 | | 2-((1R,4R)-5-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,5-diazabicyclo[2.2.2]octan-2-yl)-N-(3-(2,6-dioxopiperidin-3-ylamino)phenyl)acetamide | 844.4 | B | ** |
| 183 | | 2-((1R,4R)-5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.2]octan-2-yl)-N-(3-(2,6-dioxopiperidin-3-ylamino)phenyl)acetamide | 832.4 | B | ** |

TABLE 1-continued

| Cmpd No. | Cmpd Structure | Cmpd Name | MH+ Obs. | DC50 | Y |
|---|---|---|---|---|---|
| 184 | | N-(3-chloro-5-(2,6-dioxopiperidin-3-ylamino)phenyl)-2-((1R,4R)-5-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2,5-diazabicyclo[2.2.2]octan-2-yl)acetamide | 866.2 | B | ** |
| 185 | | N-(3-chloro-5-(2,6-dioxopiperidin-3-ylamino)phenyl)-2-((2R,5R)-4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)-2,5-dimethylpiperazin-1-yl)acetamide | 882.2 | B | * |
| 186 | | 2-((2S,6R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-cyano-5-(2,6-dioxopiperidin-3-ylamino)phenyl)acetamide | 858.3 | C | * |
| 187 | | 2-((R)-4-(2-(5-(3-(4-cyano-3-(trifluoromethyl)phenyl)-5,5-dimethyl-4-oxo-2-thioxoimidazolidin-1-yl)-3-ethylpyridin-2-yloxy)ethyl)-2-methylpiperazin-1-yl)-N-(3-(2,6-dioxopiperidin-3-ylamino)phenyl)acetamide | 820.3 | C | * |

TABLE 1-continued

| Cmpd No. | Cmpd Structure | Cmpd Name | MH+ Obs. | DC50 | Y |
|---|---|---|---|---|---|
| 188 | | 1-(4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)piperazin-1-yl)-N-(3-(2,6-dioxopiperidin-3-ylamino)phenyl)cyclopropanecarboxamide | 844.3 | C | * |
| 189 | | N-(3-chloro-5-(2,6-dioxopiperidin-3-ylamino)phenyl)-2-((2R,5R)-4-(2-(5-(3-(4-cyano-3-(trifluoromethyl)phenyl)-5,5-dimethyl-4-oxo-2-thioxoimidazolidin-1-yl)-3-ethylpyridin-2-yloxy)ethyl)-2,5-dimethylpiperazin-1-yl)acetamide | 868.2 | C | * |
| 190 | | 2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-ethylphenoxy)ethyl)-2,6-dimethylpiperazin-1-yl)-N-(5-(2,6-dioxopiperidin-3-ylamino)-2-fluorophenyl)acetamide | 864.3 | C | * |
| 191 | | (2R)-N-(3-chloro-5-(2,6-dioxopiperidin-3-ylamino)phenyl)-2-(4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)piperazin-1-yl)propanamide | 854.3 | C | * |

TABLE 1-continued

| Cmpd No. | Cmpd Structure | Cmpd Name | MH+ Obs. | DC50 | Y |
|---|---|---|---|---|---|
| 192 | | 2-((2R,5R)-4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)-2,5-dimethylpiperazin-1-yl)-N-(3-(2,6-dioxopiperidin-3-ylamino)phenyl)acetamide | 848.0 | B | ** |
| 193 | | 2-((2R,5R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,5-dimethylpiperazin-1-yl)-N-(3-(2,6-dioxopiperidin-3-ylamino)phenyl)acetamide | 847.0 | B | ** |
| 194 | | 2-((2S,6R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,6-dimethylpiperazin-1-yl)-N-(3-cyano-5-(2,6-dioxopiperidin-3-ylamino)phenyl)acetamide | 872.3 | C | * |
| 195 | | N-(3-chloro-5-(2,6-dioxopiperidin-3-ylamino)phenyl)-2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-isopropylphenoxy)ethyl)-2,6-dimethylpiperazin-1-yl)acetamide | 894.3 | C | * |

TABLE 1-continued

| Cmpd No. | Cmpd Structure | Cmpd Name | MH+ Obs. | DC50 | Y |
|---|---|---|---|---|---|
| 196 | | 2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-cyclopropylphenoxy)ethyl)-2,6-dimethylpiperazin-1-yl)-N-(3-(2,6-dioxopiperidin-3-ylamino)phenyl)acetamide | 858.3 | C | * |
| 197 | | 1-(4-(2-(4-(3-(4-cyano-3-(trifluoromethyl)phenyl)-5,5-dimethyl-4-oxo-2-thioxoimidazolidin-1-yl)-2-isopropylphenoxy)ethyl)piperazin-1-yl)-N-(3-(2,6-dioxopiperidin-3-ylamino)phenyl)cyclopropanecarboxamide | 845.3 | B | *** |
| 198 | | 2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-cyclopropylphenoxy)ethyl)-2,6-dimethylpiperazin-1-yl)-N-(5-(2,6-dioxopiperidin-3-ylamino)-2-fluorophenyl)acetamide | 876.3 | C | * |
| 199 | | (2R)-2-(4-(2-(4-(3-(4-cyano-3-(trifluoromethyl)phenyl)-5,5-dimethyl-4-oxo-2-thioxoimidazolidin-1-yl)-2-ethylphenoxy)ethyl)piperazin-1-yl)-N-(3-(2,6-dioxopiperidin-3-ylamino)phenyl)propanamide | 819.3 | C | ** |

TABLE 1-continued

| Cmpd No. | Cmpd Structure | Cmpd Name | MH+ Obs. | DC50 | Y |
|---|---|---|---|---|---|
| 200 | | 2-((R)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-(trifluoromethyl)piperazin-1-yl)-N-(3-(2,6-dioxopiperidin-3-ylamino)phenyl)acetamide | 874.0 | C | * |
| 201 | | 2-((S)-4-(2-(4-(3-(6-cyano-5-(trifluoromethyl)pyridin-3-yl)-5,5-dimethyl-4-oxo-2-thioxoimidazolidin-1-yl)-2-ethylphenoxy)ethyl)-2-(trifluoromethyl)piperazin-1-yl)-N-(3-(2,6-dioxopiperidin-3-ylamino)phenyl)acetamide | 874.0 | C | * |
| 202 | | 2-((2S,6R)-4-(2-(4-(3-(3-chloro-4-cyanophenyl)-5,5-dimethyl-4-oxo-2-thioxoimidazolidin-1-yl)-2-isopropylphenoxy)ethyl)-2,6-dimethylpiperazin-1-yl)-N-(3-(2,6-dioxopiperidin-3-ylamino)phenyl)acetamide | 813.4 | C | * |
| 203 | | 2-((2R,5R)-4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)-2,5-dimethylpiperazin-1-yl)-N-(3-(2,6-dioxopiperidin-3-ylamino)phenyl)acetamide | 845.0 | C | * |

| Cmpd No. | Cmpd Structure | Cmpd Name | MH+ Obs. | DC50 | Y |
|---|---|---|---|---|---|
| 204 | | 2-((2S,6R)-4-(2-(4-(4-cyano-3-(trifluoromethyl)phenyl)-5,5-dimethyl-4-oxo-2-thioxoimidazolidin-1-yl)-2-cyclopropylphenoxy)ethyl)-2,6-dimethylpiperazin-1-yl)-N-(3-(2,6-dioxopiperidin-3-ylamino)phenyl)acetamide | 845.0 | C | * |
| 205 | | 2-((2R,5R)-4-(2-(4-(3-chloro-4-cyanophenyl)-5,5-dimethyl-4-oxo-2-thioxoimidazolidin-1-yl)-2-cyclopropylphenoxy)ethyl)-2,5-dimethylpiperazin-1-yl)-N-(3-(2,6-dioxopiperidin-3-ylamino)phenyl)acetamide | 811.4 | C | * |
| 206 | | 2-((2S,6R)-4-(2-(4-(3-chloro-4-cyanophenyl)-5,5-dimethyl-4-oxo-2-thioxoimidazolidin-1-yl)-2-cyclopropylphenoxy)ethyl)-2,6-dimethylpiperazin-1-yl)-N-(3-(2,6-dioxopiperidin-3-ylamino)phenyl)acetamide | 811.4 | C | * |
| 207 | | 2-((2R,5R)-4-(2-(4-(3-chloro-4-cyanophenyl)-5,5-dimethyl-4-oxo-2-thioxoimidazolidin-1-yl)-2-isopropylphenoxy)ethyl)-2,5-dimethylpiperazin-1-yl)-N-(3-(2,6-dioxopiperidin-3-ylamino)phenyl)acetamide | 813.4 | B | ** |

| Cmpd No. | Cmpd Structure | Cmpd Name | MH+ Obs. | DC50 | Y |
|---|---|---|---|---|---|
| 208 | | N-(3-chloro-5-(2,6-dioxopiperidin-3-ylamino)phenyl)-2-((2S,6R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,6-dimethylpiperazin-1-yl)acetamide | 881.3 | B | * |
| 209 | | 2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-isopropylphenoxy)ethyl)-2,6-dimethylpiperazin-1-yl)-N-(5-(2,6-dioxopiperidin-3-ylamino)-2-fluorophenyl)acetamide | 878.3 | B | ** |
| 210 | | N-(3-cyano-5-(2,6-dioxopiperidin-3-ylamino)phenyl)-2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-isopropylphenoxy)ethyl)-2,6-dimethylpiperazin-1-yl)acetamide | 885.3 | C | * |
| 211 | | 2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-isopropylphenoxy)ethyl)-2,6-dimethylpiperazin-1-yl)-N-(3-(2,6-dioxopiperidin-3-ylamino)-5-fluorophenyl)acetamide | 878.3 | C | * |

TABLE 1-continued

| Cmpd No. | Cmpd Structure | Cmpd Name | MH+ Obs. | DC50 | Y |
|---|---|---|---|---|---|
| 212 | | N-(3-cyano-5-(2,6-dioxopiperidin-3-ylamino)phenyl)-2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-cyclopropylphenoxy)ethyl)-2,6-dimethylpiperazin-1-yl)acetamide | 883.3 | C | * |
| 213 | | 2-((2S,6R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,6-dimethylpiperazin-1-yl)-N-(3-(2,6-dioxopiperidin-3-ylamino)-5-fluorophenyl)acetamide | 865.2 | C | * |
| 214 | | N-(3-chloro-5-(2,6-dioxopiperidin-3-ylamino)phenyl)-2-((2R,5R)-4-(2-(5-(3-(4-cyano-3-(trifluoromethyl)phenyl)-5,5-dimethyl-4-oxo-2-thioxoimidazolidin-1-yl)-3-isopropylpyridin-2-yloxy)ethyl)-2,5-dimethylpiperazin-1-yl)acetamide | 882.3 | B | ** |

TABLE 1-continued

| Cmpd No. | Cmpd Structure | Cmpd Name | MH+ Obs. | DC50 | Y |
|---|---|---|---|---|---|
| 215 | | N-(3-chloro-5-(2,6-dioxopiperidin-3-ylamino)phenyl)-2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-cyclopropylphenoxy)ethyl)-2,6-dimethylpiperazin-1-yl)acetamide | 892.3 | C | * |
| 216 | | 2-((2R,6S)-4-(2-(5-(3-(4-cyano-3-(trifluoromethyl)phenyl)-5,5-dimethyl-4-oxo-2-thioxoimidazolidin-1-yl)-3-ethylpyridin-2-yloxy)ethyl)-2,6-dimethylpiperazin-1-yl)-N-(3-(2,6-dioxopiperidin-3-ylamino)phenyl)acetamide | 834.3 | C | ** |
| 217 | | 2-((2S,6R)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2,6-dimethylpiperazin-1-yl)-N-(5-(2,6-dioxopiperidin-3-ylamino)-2-fluorophenyl)acetamide | 865.3 | A | * |
| 218 | | 2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-cyclopropylphenoxy)ethyl)-2,6-dimethylpiperazin-1-yl)-N-(3-(2,6-dioxopiperidin-3-ylamino)-5-fluorophenyl)acetamide | 876.3 | C | * |

TABLE 1-continued

| Cmpd No. | Cmpd Structure | Cmpd Name | MH+ Obs. | DC50 | Y |
|---|---|---|---|---|---|
| 219 | | 2-((2S,6R)-4-(2-(4-(3-(3-chloro-4-cyanophenyl)-5,5-dimethyl-4-oxo-2-thioxoimidazolidin-1-yl)-2-cyclopropylphenoxy)ethyl)-2,6-dimethylpiperazin-1-yl)-N-(3-cyano-5-(2,6-dioxopiperidin-3-ylamino)phenyl)acetamide | 836.4 | C | ** |
| 220 | | 2-((2S,6R)-4-(2-(4-(3-(3-chloro-4-cyanophenyl)-5,5-dimethyl-4-oxo-2-thioxoimidazolidin-1-yl)-2-cyclopropylphenoxy)ethyl)-2,6-dimethylpiperazin-1-yl)-N-(3-chloro-5-(2,6-dioxopiperidin-3-ylamino)phenyl)acetamide | 845.2 | C | ** |
| 221 | | 2-((2S,6R)-4-(2-(4-(3-(3-chloro-4-cyanophenyl)-5,5-dimethyl-4-oxo-2-thioxoimidazolidin-1-yl)-2-cyclopropylphenoxy)ethyl)-2,6-dimethylpiperazin-1-yl)-N-(5-(2,6-dioxopiperidin-3-ylamino)-2-fluorophenyl)acetamide | 829.2 | C | ** |
| 222 | | 2-((2S,6R)-4-(2-(4-(3-(3-chloro-4-cyanophenyl)-5,5-dimethyl-4-oxo-2-thioxoimidazolidin-1-yl)-2-isopropylphenoxy)ethyl)-2,6-dimethylpiperazin-1-yl)-N-(5-(2,6-dioxopiperidin-3-ylamino)-2-fluorophenyl)acetamide | 831.2 | B | * |

TABLE 1-continued

| Cmpd No. | Cmpd Structure | Cmpd Name | MH+ Obs. | DC50 | Y |
|---|---|---|---|---|---|
| 223 | | 2-((2S,6R)-4-(2-(4-(3-chloro-4-cyanophenyl)-5,5-dimethyl-4-oxo-2-thioxoimidazolidin-1-yl)-2-isopropylphenoxy)ethyl)-2,6-dimethylpiperazin-1-yl)-N-(3-chloro-5-(2,6-dioxopiperidin-3-ylamino)phenyl)acetamide | 847.2 | B | ** |
| 224 | | 2-((2R,6S)-4-(2-(5-(3-(4-cyano-3-(trifluoromethyl)phenyl)-5,5-dimethyl-4-oxo-2-thioxoimidazolidin-1-yl)-3-isopropylpyridin-2-yloxy)ethyl)-2,6-dimethylpiperazin-1-yl)-N-(3-(2,6-dioxopiperidin-3-ylamino)phenyl)acetamide | 847.8 | B | ** |
| 225 | | 2-((2R,6S)-4-(2-(4-(7-(4-cyano-3-(trifluoromethyl)phenyl)-8-oxo-6-thioxo-5,7-diazaspiro[3.4]octan-5-yl)-2-cyclopropylphenoxy)ethyl)-2,6-dimethylpiperazin-1-yl)-N-(3-(2,6-dioxopiperidin-3-ylamino)phenyl)acetamide | 857.3 | C | * |
| 226 | | 2-((2S,6R)-4-(2-(4-(3-chloro-4-cyanophenyl)-5,5-dimethyl-4-oxo-2-thioxoimidazolidin-1-yl)-2-cyclopropylphenoxy)ethyl)-2,6-dimethylpiperazin-1-yl)-N-(3-(2,6-dioxopiperidin-3-ylamino)-5-fluorophenyl)acetamide | 828.6 | C | * |

TABLE 1-continued

| Cmpd No. | Cmpd Structure | Cmpd Name | MH+ Obs. | DC50 | Y |
|---|---|---|---|---|---|
| 227 | | 2-((2S,6R)-4-(2-(5-(7-(4-cyano-3-(trifluoromethyl)phenyl)-8-oxo-6-thioxo-5,7-diazaspiro[3.4]octan-5-yl)-3-isopropylpyridin-2-yloxy)ethyl)-2,6-dimethylpiperazin-1-yl)-N-(3-(2,6-dioxopiperidin-3-ylamino)phenyl)acetamide | 860.3 | C | * |
| 228 | | 2-((2S,6R)-4-(2-(5-(3-(4-cyano-3-(trifluoromethyl)phenyl)-5,5-dimethyl-4-oxo-2-thioxoimidazolidin-1-yl)-3-cyclopropylpyridin-2-yloxy)ethyl)-2,6-dimethylpiperazin-1-yl)-N-(3-(2,6-dioxopiperidin-3-ylamino)phenyl)acetamide | 846.5 | C | * |
| 229 | | 2-((2S,6R)-4-(2-(5-(7-(4-cyano-3-(trifluoromethyl)phenyl)-8-oxo-6-thioxo-5,7-diazaspiro[3.4]octan-5-yl)-3-cyclopropylpyridin-2-yloxy)ethyl)-2,6-dimethylpiperazin-1-yl)-N-(3-(2,6-dioxopiperidin-3-ylamino)phenyl)acetamide | 858.5 | C | * |
| 230 | | 2-((2R,5R)-4-(2-(5-(3-(4-cyano-3-(trifluoromethyl)phenyl)-5,5-dimethyl-4-oxo-2-thioxoimidazolidin-1-yl)-3-isopropylpyridin-2-yloxy)ethyl)-2,5-dimethylpiperazin-1-yl)-N-(3-(2,6-dioxopiperidin-3-ylamino)phenyl)acetamide | 848.4 | A | *** |

TABLE 1-continued

| Cmpd No. | Cmpd Structure | Cmpd Name | MH+ Obs. | DC50 | Y |
|---|---|---|---|---|---|
| 231 | | 2-((2R,5R)-4-(2-(5-(7-(4-cyano-3-(trifluoromethyl)phenyl)-8-oxo-6-thioxo-5,7-diazaspiro[3.4]octan-5-yl)-3-isopropylpyridin-2-yloxy)ethyl)-2,5-dimethylpiperazin-1-yl)-N-(3-cyano-5-(2,6-dioxopiperidin-3-ylamino)phenyl)acetamide | 885.3 | B | * |
| 232 | | 2-((2R,5R)-4-(2-(5-(3-(4-cyano-3-(trifluoromethyl)phenyl)-5,5-dimethyl-4-oxo-2-thioxoimidazolidin-1-yl)-3-isopropylpyridin-2-yloxy)ethyl)-2,5-dimethylpiperazin-1-yl)-N-(3-cyano-5-(2,6-dioxopiperidin-3-ylamino)phenyl)acetamide | 873.3 | B | * |
| 233 | | 2-((S)-4-(2-(4-(3-(6-cyano-5-(trifluoromethyl)pyridin-3-yl)-5,5-dimethyl-4-oxo-2-thioxoimidazolidin-1-yl)-2-cyclopropylphenoxy)ethyl)-2-(trifluoromethyl)piperazin-1-yl)-N-(3-(2,6-dioxopiperidin-3-ylamino)phenyl)acetamide | 886.2 | C | * |

TABLE 1-continued

| Cmpd No. | Cmpd Structure | Cmpd Name | MH+ Obs. | DC50 | Y |
|---|---|---|---|---|---|
| 234 | | 2-((2R,5R)-4-(2-(4-(3-(6-cyano-5-(trifluoromethyl)pyridin-3-yl)-5,5-dimethyl-4-oxo-2-thioxoimidazolidin-1-yl)-2-cyclopropylphenoxy)ethyl)-2,5-dimethylpiperazin-1-yl)-N-(3-(2,6-dioxopiperidin-3-ylamino)phenyl)acetamide | 845.8 | C | * |
| 235 | | 2-((2S,6R)-4-(2-(4-(3-(6-cyano-5-(trifluoromethyl)pyridin-3-yl)-5,5-dimethyl-4-oxo-2-thioxoimidazolidin-1-yl)-2-cyclopropylphenoxy)ethyl)-2,6-dimethylpiperazin-1-yl)-N-(3-(2,6-dioxopiperidin-3-ylamino)phenyl)acetamide | 845.8 | C | * |
| 236 (peak 1) | | 2-((2S,6R)-4-((S)-1-(4-(3-(4-cyano-3-(trifluoromethyl)phenyl)-5,5-dimethyl-4-oxo-2-thioxoimidazolidin-1-yl)-2-ethylphenoxy)propan-2-yl)-2,6-dimethylpiperazin-1-yl)-N-(3-(2,6-dioxopiperidin-3-ylamino)phenyl)acetamide or | 847.3 | B | ** |
| 237 (peak 2) | | 2-((2S,6R)-4-((R)-1-(4-(3-(4-cyano-3-(trifluoromethyl)phenyl)-5,5-dimethyl-4-oxo-2-thioxoimidazolidin-1-yl)-2-ethylphenoxy)propan-2-yl)-2,6-dimethylpiperazin-1-yl)-N-(3-(2,6-dioxopiperidin-3-ylamino)phenyl)acetamide | 847.3 | B | ** |

TABLE 1-continued

| Cmpd No. | Cmpd Structure | Cmpd Name | MH+ Obs. | DC50 | Y |
|---|---|---|---|---|---|
| 238 | | 2-(3-(2-(4-(3-(4-cyano-3-(trifluoromethyl)phenyl)-5,5-dimethyl-4-oxo-2-thioxoimidazolidin-1-yl)-2-cyclopropylphenoxy)ethyl)-3,8-diazabicyclo[3.2.1]octan-8-yl)-N-(3-(2,6-dioxopiperidin-3-ylamino)phenyl)acetamide | 843 | A | * |
| 239 (Peak 1) | | 2-((2S,6R)-4-((R)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazin-1-yl)-N-(3-(2,6-dioxopiperidin-3-ylamino)phenyl)acetamide or | 848.3 | C | * |
| 240 (Peak 2) | | 2-((2S,6R)-4-((S)-2-(4-(3-(6-cyano-5-(trifluoromethyl)pyridin-3-yl)-5,5-dimethyl-4-oxo-2-thioxoimidazolidin-1-yl)-2-ethylphenoxy)propyl)-2,6-dimethylpiperazin-1-yl)-N-(3-(2,6-dioxopiperidin-3-ylamino)phenyl)acetamide or | 848.4 | B | ** |
| 241 (Peak 1) | | 2-((2S,6R)-4-((R)-2-(4-(3-(4-cyano-3-(trifluoromethyl)phenyl)-5,5-dimethyl-4-oxo-2-thioxoimidazolidin-1-yl)-2-ethylphenoxy)propyl)-2,6-dimethylpiperazin-1-yl)-N-(3-(2,6-dioxopiperidin-3-ylamino)phenyl)acetamide or | 847.3 | B | * |

TABLE 1-continued

| Cmpd No. | Cmpd Structure | Cmpd Name | MH+ Obs. | DC50 | Y |
|---|---|---|---|---|---|
| 242 (Peak 2) | | 2-((2S,6R)-4-((S)-2-(4-(3-(4-cyano-3-(trifluoromethyl)phenyl)-5,5-dimethyl-4-oxo-2-thioimidazolidin-1-yl)-2-ethylphenoxy)propyl)-2,6-dimethylpiperazin-1-yl)-N-(3-(2,6-dioxopiperidin-3-ylamino)phenyl)acetamide | 847.3 | A | *** |
| 243 | | N-(3-cyano-5-(2,6-dioxopiperidin-3-ylamino)phenyl)-2-((2R,5R)-4-(2-(4-(3-(6-cyano-5-(trifluoromethyl)pyridin-3-yl)-5,5-dimethyl-4-oxo-2-thioimidazolidin-1-yl)-2-(1,1-difluoroethyl)phenoxy)ethyl)-2,5-dimethylpiperazin-1-yl)acetamide | 895.3 | C | * |
| 244 | | 2-((2R,5R)-4-(2-(4-(3-(6-cyano-5-(trifluoromethyl)pyridin-3-yl)-5,5-dimethyl-4-oxo-2-thioimidazolidin-1-yl)-2-(1,1-difluoroethyl)phenoxy)ethyl)-2,5-dimethylpiperazin-1-yl)-N-(3-(2,6-dioxopiperidin-3-ylamino)phenyl)acetamide | 870.3 | C | * |
| 245 | | 2-((S)-4-(2-(4-(3-(4-cyano-3-(trifluoromethyl)phenyl)-5,5-dimethyl-4-oxo-2-thioimidazolidin-1-yl)-2-cyclopropylphenoxy)ethyl)-2-(trifluoromethyl)piperazin-1-yl)-N-(3-(2,6-dioxopiperidin-3-ylamino)phenyl)acetamide | 885.3 | C | * |

| Cmpd No. | Cmpd Structure | Cmpd Name | MH⁺ Obs. | DC₅₀ | Y |
|---|---|---|---|---|---|
| 246 | | 2-((S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-(trifluoromethyl)piperazin-1-yl)-N-(3-(2,6-dioxopiperidin-3-ylamino)phenyl)acetamide | 873.3 | C | * |
| 247 | | 2-((2S,6R)-4-(2-(4-(3-(4-cyano-3-(trifluoromethyl)phenyl)-5,5-dimethyl-4-oxo-2-thioxoimidazolidin-1-yl)-2-ethyl-5-fluorophenoxy)ethyl)-2,6-dimethylpiperazin-1-yl)-N-(3-(2,6-dioxopiperidin-3-ylamino)phenyl)acetamide | 851.4 | C | * |
| 248 | | 2-((2S,6R)-4-(2-(4-(3-(4-cyano-3-(trifluoromethyl)phenyl)-5,5-dimethyl-4-oxo-2-thioxoimidazolidin-1-yl)-2-ethyl-6-fluorophenoxy)ethyl)-2,6-dimethylpiperazin-1-yl)-N-(3-(2,6-dioxopiperidin-3-ylamino)phenyl)acetamide | 851.4 | C | * |
| 249 | | 2-((2R,6S)-4-(2-(4-(3-(4-cyano-3-(trifluoromethyl)phenyl)-5,5-dimethyl-4-oxo-2-thioxoimidazolidin-1-yl)-2-ethyl-6-methylphenoxy)ethyl)-2,6-dimethylpiperazin-1-yl)-N-(3-(2,6-dioxopiperidin-3-ylamino)phenyl)acetamide | 847.3 | B | *** |

| Cmpd No. | Cmpd Structure | Cmpd Name | MH+ Obs. | DC50 | Y |
|---|---|---|---|---|---|
| 250 | | 2-((2S,6R)-4-(2-(4-(3-chloro-4-cyanophenyl)-5,5-dimethyl-4-oxo-2-thioxoimidazolidin-1-yl)-2-isopropylphenoxy)ethyl)-2,6-dimethylpiperazin-1-yl)-N-(3-cyano-5-(2,6-dioxopiperidin-3-ylamino)phenyl)acetamide | 837.8 | C | * |
| 251 | | 2-((2S,6R)-4-(2-(4-(3-chloro-4-cyanophenyl)-5,5-dimethyl-4-oxo-2-thioxoimidazolidin-1-yl)-2-isopropylphenoxy)ethyl)-2,6-dimethylpiperazin-1-yl)-N-(3-(2,6-dioxopiperidin-3-ylamino)-5-fluorophenyl)acetamide | 830.8 | C | * |
| 252 | | 2-((2S,6R)-4-(2-(4-(4-cyano-3-(trifluoromethyl)phenyl)-5,5-dimethyl-4-oxo-2-thioxoimidazolidin-1-yl)-2-(1,1-difluoroethyl)phenoxy)ethyl)-2,6-dimethylpiperazin-1-yl)-N-(3-(2,6-dioxopiperidin-3-ylamino)phenyl)acetamide | 868.6 | C | * |
| 253 | | 2-((2S,6R)-4-(2-(4-(3-(4-cyano-3-(trifluoromethyl)phenyl)-5,5-dimethyl-4-oxo-2-thioxoimidazolidin-1-yl)-2-isopropyl-5-methylphenoxy)ethyl)-2,6-dimethylpiperazin-1-yl)-N-(3-(2,6-dioxopiperidin-3-ylamino)phenyl)acetamide | 861.3 | B | * |

TABLE 1-continued

TABLE 1-continued

| Cmpd No. | Cmpd Name | MH+ Obs. | DC50 | Y |
|---|---|---|---|---|
| 254 | 2-((2S,6R)-4-(2-(4-(3-(4-cyano-3-(trifluoromethyl)phenyl)-5,5-dimethyl-4-oxo-2-thioxoimidazolidin-1-yl)-2-ethyl-5-methylphenoxy)ethyl)-2,6-dimethylpiperazin-1-yl)-N-(3-(2,6-dioxopiperidin-3-ylamino)phenyl)acetamide | 847.3 | C | * |
| 255 | 2-((2S,6R)-4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)-2,6-dimethylpiperazin-1-yl)-N-(3-(2,6-dioxopiperidin-3-ylamino)phenyl)acetamide | 870.3 | C | * |
| 256 | 2-((S)-4-(2-(4-(3-(6-cyano-5-(trifluoromethyl)pyridin-3-yl)-5,5-dimethyl-4-oxo-2-thioxoimidazolidin-1-yl)-2-isopropylphenoxy)ethyl)-2-(trifluoromethyl)piperazin-1-yl)-N-(3-(2,6-dioxopiperidin-3-ylamino)phenyl)acetamide | 888.3 | B | ** |
| 257 | 2-((S)-4-(2-(4-(3-(4-cyano-3-(trifluoromethyl)phenyl)-5,5-dimethyl-4-oxo-2-thioxoimidazolidin-1-yl)-2-isopropylphenoxy)ethyl)-2-(trifluoromethyl)piperazin-1-yl)-N-(3-(2,6-dioxopiperidin-3-ylamino)phenyl)acetamide | 885.5 | A | *** |

TABLE 1-continued

| Cmpd No. | Cmpd Structure | Cmpd Name | MH+ Obs. | DC50 | Y |
|---|---|---|---|---|---|
| 258 | | N-(3-cyano-5-(2,6-dioxopiperidin-3-ylamino)phenyl)-2-((2S,6R)-4-(2-(4-(3-(6-cyano-5-(trifluoromethyl)pyridin-3-yl)-5,5-dimethyl-4-oxo-2-thioxoimidazolidin-1-yl)-2-(1,1-difluoroethyl)phenoxy)ethyl)-2,6-dimethylpiperazin-1-yl)acetamide | 894.7 | C | * |
| 259 | | 2-((2R,6S)-4-(2-(4-(3-(4-cyano-3-(trifluoromethyl)phenyl)-5,5-dimethyl-4-oxo-2-thioxoimidazolidin-1-yl)-2-cyclobutylphenoxy)ethyl)-2,6-dimethylpiperazin-1-yl)-N-(3-(2,6-dioxopiperidin-3-ylamino)phenyl)acetamide | 859.3 | C | * |
| 260 | | 2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-ethylpiperazin-1-yl)-N-(3-(2,6-dioxopiperidin-3-ylamino)phenyl)acetamide | 833.4 | B | * |
| 261 | | 2-((R)-4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)-2-ethylpiperazin-1-yl)-N-(3-(2,6-dioxopiperidin-3-ylamino)phenyl)acetamide | 844.8 | B | ** |

| Cmpd No. | Cmpd Structure | Cmpd Name | MH+ Obs. | DC50 | Y |
|---|---|---|---|---|---|
| 262 | | 2-((R)-4-(2-(4-(7-(6-cyano-5-(trifluoromethyl)pyridin-3-yl)-8-oxo-6-thioxo-5,7-diazaspiro[3.4]octan-5-yl)-2-cyclopropyl)phenoxy)ethyl)-2-ethylpiperazin-1-yl)-N-(3-(2,6-dioxopiperidin-3-ylamino)phenyl)acetamide | 858.4 | B | * |
| 263 | | 2-((S)-4-(2-(4-(3-(4-cyano-3-(trifluoromethyl)phenyl)-5,5-dimethyl-4-oxo-2-thioxoimidazolidin-1-yl)-2-cyclopropyl)phenoxy)ethyl)-2-ethylpiperazin-1-yl)-N-(3-(2,6-dioxopiperidin-3-ylamino)phenyl)acetamide | 845.4 | C | * |
| 264 | | 2-((2S,6R)-4-(2-(4-(3-(4-cyano-3-(trifluoromethyl)phenyl)-4-oxo-2-thioxo-1,3-diazaspiro[4.5]decan-1-yl)-2-ethylphenoxy)ethyl)-2,6-dimethylpiperazin-1-yl)-N-(3-(2,6-dioxopiperidin-3-ylamino)phenyl)acetamide | 873.4 | C | * |
| 265 | | 2-((2S,6R)-4-(2-(4-(7-(6-cyano-5-(trifluoromethyl)pyridin-3-yl)-8-oxo-6-thioxo-5,7-diazaspiro[3.4]octan-5-yl)-2-(1,1-difluoroethyl)phenoxy)ethyl)-2,6-dimethylpiperazin-1-yl)-N-(3-(2,6-dioxopiperidin-3-ylamino)phenyl)acetamide | 881.8 | C | * |

TABLE 1-continued

| Cmpd No. | Cmpd Structure | Cmpd Name | MH+ Obs. | DC50 | Y |
|---|---|---|---|---|---|
| 266 | | 2-((2S,6R)-4-(2-(4-(3-(4-cyano-3-(trifluoromethyl)phenyl)-4-oxo-2-thioxo-1,3-diazaspiro[4.4]nonan-1-yl)-2-cyclopropylphenoxy)ethyl)-2,6-dimethylpiperazin-1-yl)-N-(3-(2,6-dioxopiperidin-3-ylamino)phenyl)acetamide | 871.8 | C | * |
| 267 | | 2-((2S,6R)-4-(2-(4-(3-(4-cyano-3-(trifluoromethyl)phenyl)-4-oxo-2-thioxo-1,3-diazaspiro[4.4]nonan-1-yl)-2-ethylphenoxy)ethyl)-2,6-dimethylpiperazin-1-yl)-N-(3-(2,6-dioxopiperidin-3-ylamino)phenyl)acetamide | 859.8 | C | * |
| 268 | | 2-((2R,6S)-4-(2-(4-(3-(6-cyano-5-(trifluoromethyl)pyridin-3-yl)-5,5-dimethyl-4-oxo-2-thioxoimidazolidin-1-yl)-2-cyclobutylphenoxy)ethyl)-2,6-dimethylpiperazin-1-yl)-N-(3-(2,6-dioxopiperidin-3-ylamino)phenyl)acetamide | 860.5 | C | ** |
| 269 | | 2-((2S,6R)-4-(2-(4-(3-chloro-4-cyanophenyl)-5,5-dimethyl-4-oxo-2-thioxoimidazolidin-1-yl)-2-(1,1-difluoroethyl)phenoxy)ethyl)-2,6-dimethylpiperazin-1-yl)-N-(3-(2,6-dioxopiperidin-3-ylamino)phenyl)acetamide | 834.8 | C | * |

TABLE 1-continued

| Cmpd No. | Cmpd Structure | Cmpd Name | MH+ Obs. | DC50 | Y |
|---|---|---|---|---|---|
| 270 | | 2-((2R,6S)-4-(2-(4-(3-(4-cyano-3-(trifluoromethyl)phenyl)-5,5-dimethyl-4-oxo-2-thioxoimidazolidin-1-yl)-2-ethyl-3-methylphenoxy)ethyl)-2,6-dimethylpiperazin-1-yl)-N-(3-(2,6-dioxopiperidin-3-ylamino)phenyl)acetamide | 847.3 | B | ** |
| 271 | | 2-((2S,6R)-4-(2-(4-(3-(4-cyano-3-(trifluoromethyl)phenyl)-5,5-dimethyl-4-oxo-2-thioxoimidazolidin-1-yl)-2-ethyl-3-fluorophenoxy)ethyl)-2,6-dimethylpiperazin-1-yl)-N-(3-(2,6-dioxopiperidin-3-ylamino)phenyl)acetamide | 851.3 | C | * |
| 272 | | 2-(R)-4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)-2-methylpiperazin-1-yl)-N-(3-(2,6-dioxopiperidin-3-ylamino)phenyl)acetamide | 831.3 | C | * |
| 273 | | 2-((2R,5R)-4-(3-(4-(3-(4-cyano-3-(trifluoromethyl)phenyl)-5,5-dimethyl-4-oxo-2-thioxoimidazolidin-1-yl)-2,5-dimethylphenyl)propyl)-2-ethylphenyl)piperazin-1-yl)-N-(3-(2,6-dioxopiperidin-3-ylamino)phenyl)acetamide | 831.3 | C | * |

TABLE 1-continued

| Cmpd No. | Cmpd Structure | Cmpd Name | MH+ Obs. | DC50 | Y |
|---|---|---|---|---|---|
| 274 | | (2R)-2-((S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-yl)aminophenyl)propanamide | 833.3 | C | * |
| 275 | | (2S)-2-((S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-yl)aminophenyl)propanamide | 833.3 | C | * |
| 276 | | 2-((R)-4-(2-(2-chloro-4-(3-(4-cyano-3-(trifluoromethyl)phenyl)-5,5-dimethyl-4-oxo-2-thioxoimidazolidin-1-yl)phenoxy)ethyl)-2-methylpiperazin-1-yl)-N-(3-(2,6-dioxopiperidin-3-yl)aminophenyl)acetamide | 825.3 | C | * |
| 277 | | 2-((R)-4-(2-(4-(3-(4-cyano-3-(trifluoromethyl)phenyl)-5,5-dimethyl-4-oxo-2-thioxoimidazolidin-1-yl)-2-fluorophenoxy)ethyl)-2-methylpiperazin-1-yl)-N-(3-(2,6-dioxopiperidin-3-yl)aminophenyl)acetamide | 809.3 | C | *** |

TABLE 1-continued

| Cmpd No. | Cmpd Structure | Cmpd Name | MH+ Obs. | DC50 | Y |
|---|---|---|---|---|---|
| 278 | | 2-((2S,6R)-4-(2-(4-(3-(4-cyano-3-(trifluoromethyl)phenyl)-5,5-dimethyl-4-oxo-2-thioxoimidazolidin-1-yl)-2-fluorophenoxy)ethyl)-2,6-dimethylpiperazin-1-yl)-N-(3-(2,6-dioxopiperidin-3-ylamino)phenyl)acetamide | 823.4 | C | * |
| 279 | | 2-((S)-4-(3-(4-(3-(4-cyano-3-(trifluoromethyl)phenyl)-5,5-dimethyl-4-oxo-2-thioxoimidazolidin-1-yl)-2-ethylphenyl)propyl)-2-methylpiperazin-1-yl)-N-(3-(2,6-dioxopiperidin-3-ylamino)phenyl)acetamide | 817.3 | C | * |
| 280 | | (2R)-2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)phenyl)propanamide | 833.3 | B | *** |
| 281 | | (2S)-2-((R)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2-methylpiperazin-1-yl)-N-(3-(2,6-dioxopiperidin-3-ylamino)phenyl)propanamide | 833.3 | C | * |

TABLE 1-continued

| Cmpd No. | Cmpd Structure | Cmpd Name | MH+ Obs. | DC50 | Y |
|---|---|---|---|---|---|
| 282 | | 2-((2S,6R)-4-(2-(2-chloro-4-(3-(4-cyano-3-(trifluoromethyl)phenyl)-5,5-dimethyl-4-oxo-2-thioimidazolidin-1-yl)phenoxy)ethyl)-2,6-dimethylpiperazin-1-yl)-N-(3-(2,6-dioxopiperidin-3-ylamino)phenyl)acetamide | 839.2 | C | * |
| 283 | | 2-((2R,6S)-4-(2-(4-(3-(4-cyano-3-(trifluoromethyl)phenyl)-5,5-dimethyl-4-oxo-2-thioimidazolidin-1-yl)-2,6-dimethylphenoxy)ethyl)-2,6-dimethylpiperazin-1-yl)-N-(3-(2,6-dioxopiperidin-3-ylamino)-5-fluorophenyl)acetamide | 852.2 | C | * |
| 284 | | 2-((2R,6S)-4-(3-(4-(3-(4-cyano-3-(trifluoromethyl)phenyl)-5,5-dimethyl-4-oxo-2-thioimidazolidin-1-yl)-2-ethylphenyl)propyl)-2,6-dimethylpiperazin-1-yl)-N-(3-(2,6-dioxopiperidin-3-ylamino)phenyl)acetamide | 831.3 | C | * |
| 285 | | 2-((2R,6S)-4-(2-(4-(3-(4-cyano-3-(trifluoromethyl)phenyl)-5,5-dimethyl-4-oxo-2-thioimidazolidin-1-yl)-2-ethylphenoxy)ethyl)-2,6-dimethylpiperazin-1-yl)-N-(3-((S)-2,6-dioxopiperidin-3-ylamino)phenyl)acetamide | 833.3 | C | * |

TABLE 1-continued

| Cmpd No. | Cmpd Structure | Cmpd Name | MH+ Obs. | DC50 | Y |
|---|---|---|---|---|---|
| 286 | | 2-((2R,6S)-4-(2-(4-(3-(4-cyano-3-(trifluoromethyl)phenyl)-5,5-dimethyl-4-oxo-2-thioxoimidazolidin-1-yl)-2-ethylphenoxy)ethyl)-2,6-dimethylpiperazin-1-yl)-N-(3-((R)-2,6-dioxopiperidin-3-ylamino)phenyl)acetamide | 833.3 | C | * |
| 287 | | 2-((2R,6S)-4-(3-(4-(3-(4-cyano-3-(trifluoromethyl)phenyl)-5,5-dimethyl-4-oxo-2-thioxoimidazolidin-1-yl)-2-fluorophenyl)propyl)-2,6-dimethylpiperazin-1-yl)-N-(3-(2,6-dioxopiperidin-3-ylamino)phenyl)acetamide | 821.3 | C | * |
| 288 | | 2-((2R,6S)-4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)-2,6-dimethylpiperazin-1-yl)-N-(3-((R)-2,6-dioxopiperidin-3-ylamino)phenyl)acetamide | 845.3 | C | * |
| 289 | | 2-((2R,6S)-4-(2-(4-(3-(4-cyano-3-(trifluoromethyl)phenyl)-5,5-dimethyl-4-oxo-2-thioxoimidazolidin-1-yl)-2-cyclopropylphenoxy)ethyl)-2,6-dimethylpiperazin-1-yl)-N-(3-((S)-2,6-dioxopiperidin-3-ylamino)phenyl)acetamide | 845.3 | C | * |

TABLE 1-continued

| Cmpd No. | Cmpd Structure | Cmpd Name | MH+ Obs. | DC50 | Y |
|---|---|---|---|---|---|
| 290 | | 2-((2S,6R)-4-(2-chloro-4-(3-(3-chloro-4-cyanophenyl)-5,5-dimethyl-4-oxo-2-thioxoimidazolidin-1-yl)phenoxy)ethyl)-2,6-dimethylpiperazin-1-yl)-N-(3-((2,6-dioxopiperidin-3-yl)amino)phenyl)acetamide | 806.6 | C | * |
| 291 | | 2-((2S,6R)-4-(2-(4-(3-(3-chloro-4-cyanophenyl)-5,5-dimethyl-4-oxo-2-thioxoimidazolidin-1-yl)-2-ethylphenoxy)ethyl)-2,6-dimethylpiperazin-1-yl)-N-(3-((2,6-dioxopiperidin-3-yl)amino)phenyl)acetamide | 799.3 | C | * |

A number of references have been cited, the disclosures of which are incorporated herein by reference in their entirety.

What is claimed is:

1. A compound of formula (I)

(I)

or a pharmaceutically acceptable salt, tautomer, or stereoisomer thereof, wherein
$R^N$ is H;
each $R^1$ is independently selected from halogen, CN, and $C_{1-3}$ alkyl;
$R^2$ and $R^3$ are each independently selected from H, and $C_{1-3}$ alkyl, or $R^2$ and $R^3$ and the carbon to which they are attached form a substituted or unsubstituted $C_{3-6}$ cycloalkyl;
each $R^4$ is independently substituted or unsubstituted $C_{1-3}$ alkyl, or two $R^4$ groups, together with the same carbon atom or adjacent carbon atoms to which they are attached, form a substituted or unsubstituted $C_{3-6}$ cycloalkyl, or two $R^4$ groups together with the non-adjacent carbon atoms to which they are attached form a substituted or unsubstituted 4-7-membered heterocyclyl;
X is N;
L is —O($C_{1-6}$ alkyl)- or —($C_{1-9}$ alkyl)-;
n is 0-4;
m is 0-8;
V is wherein
A is N, CH, or $CR^A$;
B is N, CH, or $CR^B$;
each $R^A$ is independently selected from halogen, substituted or unsubstituted $C_{1-6}$ alkyl, and substituted or unsubstituted $C_{3-6}$ cycloalkyl;
each $R^B$ is independently selected from halogen, and substituted or unsubstituted $C_{1-6}$ alkyl;
$R^C$ is halogen or $CF_3$;
$R^5$ and $R^6$ are $C_{1-3}$ alkyl, or $R^5$ and $R^6$, together with the carbon atom to which they are attached, form a substituted or unsubstituted $C_{3-6}$ cycloalkyl or a 3-6 membered heterocyclyl;
a is 0-3; and
b is 0-2.

2. The compound of claim 1, wherein L is —O($CH_2$)$_p$— or —($CH_2$)$_p$—, and p is 1-3.

3. The compound of claim 1, wherein each $R^1$ is independently selected from Cl, F, Br, CN, —$CH_3$, —$CH_2CH_3$, and isopropyl.

4. The compound of claim 1, wherein each $R^1$ is independently selected from Cl, F, CN, and —$CH_3$.

5. The compound of claim 1, wherein n is 0.

6. The compound of claim 1, wherein n is 1 or 2.

7. The compound of claim 1, wherein $R^2$ and $R^3$ are each independently selected from H, substituted or unsubstituted methyl, and ethyl, or wherein $R^2$ and $R^3$ and the carbon to which they are attached form a substituted or unsubstituted cyclopropyl, cyclobutyl or cyclopentyl.

8. The compound of claim 1, wherein $R^2$ and $R^3$ are each independently selected from H and methyl, or wherein $R^2$ and $R^3$ and the carbon to which they are attached form an unsubstituted cyclopropyl.

9. The compound of claim 1, wherein $R^2$ and $R^3$ are both H or methyl, or wherein $R^2$ and $R^3$ and the carbon to which they are attached form an unsubstituted cyclopropyl.

10. The compound of claim 1, wherein each $R^4$ is independently selected from substituted or unsubstituted methyl and ethyl, or wherein two $R^4$ groups, together with the same carbon atom to which they are attached, form a substituted or unsubstituted cyclopropyl or cyclobutyl.

11. The compound of claim 1, wherein each $R^4$ is independently selected from substituted or unsubstituted methyl, or wherein two $R^4$ groups, together with the same carbon atom to which they are attached, form an unsubstituted cyclopropyl.

12. The compound of claim 1, wherein each $R^4$ is independently selected from methyl, $CF_3$, and $CH_2OH$, or wherein two $R^4$ groups, together with the same carbon atom to which they are attached, form an unsubstituted cyclopropyl.

13. The compound of claim 1, wherein m is 0, 1, 2, 3 or 4.

14. The compound of claim 1, wherein m is 0, 1, or 2.

15. The compound of claim 1, wherein two $R^4$ groups together with the non-adjacent carbon atoms to which they are attached form an unsubstituted 4-7-membered heterocyclyl.

16. The compound of claim 1, wherein L is O($CH_2$)($CH_2$)—, —O($CH_2$)(CH($CH_3$))—, —O($CH_2$)(C($CH_3$)$_2$)—, —O(CH($CH_3$))($CH_2$)—, —O(C($CH_3$)$_2$)($CH_2$)—, —O(CH($CH_3$))(CH($CH_3$))—, —O(CH($CH_3$))(C($CH_3$)$_2$)—, —O(C($CH_3$)$_2$)(CH($CH_3$))—, —($CH_2$)—, —($CH_2$)($CH_2$)—, —($CH_2$)($CH_2$)($CH_2$)—, —(C($CH_3$)$_2$)(C($CH_3$)$_2$)—, —(CH($CH_3$))—, —(C($CH_3$)$_2$)—, —(CH($CH_3$))(CH($CH_3$))—, —(CH($CH_3$))(C($CH_3$)$_2$)—, —(C($CH_3$)$_2$)(CH($CH_3$))—, —(C($CH_3$)$_2$)(C($CH_3$)$_2$)—, —($CH_3$)($CH_3$)(CH($CH_3$))—, —($CH_2$)(CH($CH_3$))($CH_2$)—, —(CH($CH_3$))($CH_2$)($CH_2$)—, —($CH_2$)($CH_2$)(C($CH_2$)$_2$)—, —($CH_2$)(C($CH_2$)$_2$)($CH_2$)—, —(C($CH_2$)$_2$)($CH_2$)($CH_2$)—, —($CH_2$)(CH($CH_3$))(CH($CH_3$))—, —(CH($CH_3$))(CH($CH_3$))(CH($CH_3$))—, —(CH($CH_3$))(CH($CH_3$))($CH_2$)—, —(CH($CH_3$))($CH_2$)(CH($CH_3$))—, —($CH_2$)(CH($CH_3$))(C($CH_3$)$_2$)—, —(CH($CH_3$))($CH_2$)(C($CH_2$)$_2$)—, —(C($CH_3$)$_2$)($CH_2$)(C($CH_3$)$_2$)—, —($CH_2$)(C($CH_3$)$_2$)(C($CH_3$)$_2$)—, —($CH_2$)(C($CH_3$)$_2$)(CH($CH_3$))—, —(CH($CH_3$)(C($CH_3$)$_2$)($CH_2$)—, —(C($CH_3$)$_2$)($CH_2$)(CH($CH_3$))—, —(C($CH_3$)$_2$)(CH($CH_3$))($CH_2$)—, —(C($CH_3$)$_2$)(C($CH_3$)$_2$)($CH_2$)—, —(CH($CH_3$))(CH($CH_3$))(C($CH_3$)$_2$)—, —(CH($CH_3$))(C($CH_3$)$_2$)(C($CH_3$)$_2$)—, —(C($CH_3$)$_2$)(CH($CH_3$))(C($CH_3$)$_2$)—, —(CH($CH_3$))(C($CH_3$)$_2$)(CH($CH_3$))—, —(C($CH_3$)$_2$)(C($CH_3$)$_2$)(CH($CH_3$))—, —(C($CH_3$)$_2$)(CH($CH_3$))(CH($CH_3$))—, and —(C($CH_3$)$_2$)(C($CH_3$)$_2$)(C($CH_3$)$_2$)—.

17. The compound of claim 1, wherein L is —O(CH$_2$)(CH$_2$)—, —O(CH$_2$)(CH(CH$_3$))—, —O(CH$_2$)(C(CH$_3$)$_2$)—, —O(CH(CH$_3$))(CH$_2$)—, —O(C(CH$_3$)$_2$)(CH$_2$)—, —(CH$_2$)—, —(CH$_2$)(CH$_2$)—, or —(CH$_2$)(CH$_2$)(CH$_2$)—.

18. The compound of claim 1, wherein L is —O(CH$_2$)(CH$_2$)—, —O(CH$_2$)(CH(CH$_3$))—, —O(CH(CH$_3$))(CH$_2$)—, or —(CH$_2$)(CH$_2$)(CH$_2$)—.

19. The compound of claim 1, wherein A is CH.

20. The compound of claim 1, wherein B is CH.

21. The compound of claim 1, wherein B is N.

22. The compound of claim 1, wherein a is 0, 1 or 2.

23. The compound of claim 19, wherein each R$^A$ is independently selected from Cl, Br, F, methyl, ethyl, n-propyl, isopropyl, n-butyl, isobutyl, sec-butyl, tert-butyl, n-pentyl, CH$_2$CH$_2$CH(CH$_3$)$_2$, CH(CH$_3$)CH(CH$_3$)$_2$, CF$_3$, CF$_2$CH$_3$, CH$_2$CH$_2$F, CH$_2$CHF$_2$, CH$_2$CF$_3$, CH$_2$OH, CH(CH$_3$)OH, CH$_2$CH$_2$OH, CH(CH$_3$)CH$_2$OH, CH$_2$CH(CH$_3$)OH, cyclopropyl, cyclobutyl, and cyclopentyl.

24. The compound of claim 1, wherein each R$^A$ is independently selected from Cl, Br, F, methyl, ethyl, n-propyl, isopropyl, isobutyl, sec-butyl, CF$_3$, CF$_2$CH$_3$, CH$_2$CH$_2$F, CH$_2$CHF$_2$, CH$_2$OH, CH(CH$_3$)OH, cyclopropyl, cyclobutyl, and cyclopentyl.

25. The compound of claim 1, wherein each R$^A$ is independently selected from Cl, Br, F, methyl, ethyl, n-propyl, isopropyl, isobutyl, sec-butyl, CF$_3$, CF$_2$CH$_3$, CH$_2$CH$_2$F, CH$_2$CHF$_2$, cyclopropyl, cyclobutyl, and cyclopentyl.

26. The compound of claim 1, wherein each R$^A$ is independently selected from Cl, F, methyl, ethyl, n-propyl, isopropyl, sec-butyl, CF$_2$CH$_3$, CH$_2$CH$_2$F, CH$_2$CHF$_2$, CH$_2$OH, CH(CH$_3$)OH, cyclopropyl, and cyclobutyl.

27. The compound of claim 1, wherein b is 0 or 1.

28. The compound of claim 1, wherein R$^B$ is methyl.

29. The compound of claim 1, wherein R$^C$ is CF$_3$ or Cl.

30. The compound of claim 1, wherein R$^5$ and R$^6$ are methyl, or R$^5$ and R$^6$, together with the carbon atom to which they are attached, form a cyclopropyl, cyclobutyl, cyclopentyl, cyclohexyl, tetrahydrofuranyl, or tetrahydropyranyl.

31. The compound of claim 1, wherein R$^5$ and R$^6$ are methyl, or R$^5$ and R$^6$, together with the carbon atom to which they are attached, form a cyclobutyl, cyclopentyl, cyclohexyl, or tetrahydrofuranyl.

32. A pharmaceutical composition comprising an effective amount of a compound of claim 1, or a pharmaceutically acceptable salt, tautomer, or stereoisomer thereof, and a pharmaceutically acceptable carrier, excipient or vehicle.

33. A method for the treatment of an androgen receptor mediated disease, the method comprising administering to a subject in need thereof an effective amount of a compound of claim 1, wherein the androgen mediated disease is prostate cancer.

34. A method for the treatment of an androgen receptor mediated disease, the method comprising administering to a subject in need thereof an effective amount of the pharmaceutical composition of claim 32, wherein the androgen mediated disease is prostate cancer.

* * * * *

UNITED STATES PATENT AND TRADEMARK OFFICE
CERTIFICATE OF CORRECTION

| | | |
|---|---|---|
| PATENT NO. | : 11,873,283 B2 | Page 1 of 1 |
| APPLICATION NO. | : 17/403742 | |
| DATED | : January 16, 2024 | |
| INVENTOR(S) | : Ammirante et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 38 days.

Signed and Sealed this
Twelfth Day of August, 2025

Coke Morgan Stewart
*Acting Director of the United States Patent and Trademark Office*